US010036030B2

(12) United States Patent
Damude et al.

(10) Patent No.: US 10,036,030 B2
(45) Date of Patent: Jul. 31, 2018

(54) USE OF THE SOYBEAN SUCROSE SYNTHASE PROMOTER TO INCREASE PLANT SEED LIPID CONTENT

(71) Applicants: E I DU PONT DE NEMOURS AND COMPANY, Wilmington, DE (US); PIONEER HI-BRED INTERNATIONAL INC, Johnston, IA (US)

(72) Inventors: Howard Glenn Damude, Hockessin, DE (US); Bryce Daines, Johnston, IA (US); Knut Meyer, Wilmington, DE (US); Kevin G Ripp, Wilmington, DE (US); Kevin L Stecca, New Castle, DE (US)

(73) Assignees: E I DU PONT DE NEMOURS AND COMPANY, Wilmington, DE (US); PIONEER HI-BRED INTERNATIONAL, INC.IA (US)

( * ) Notice: Subject to any disclaimer, the term of this patent is extended or adjusted under 35 U.S.C. 154(b) by 880 days.

(21) Appl. No.: 14/367,454

(22) PCT Filed: Dec. 20, 2012

(86) PCT No.: PCT/US2012/070828

§ 371 (c)(1),
(2) Date: Jun. 20, 2014

(87) PCT Pub. No.: WO2013/096562

PCT Pub. Date: Jun. 27, 2013

(65) Prior Publication Data

US 2015/0143583 A1 May 21, 2015

Related U.S. Application Data

(60) Provisional application No. 61/578,903, filed on Dec. 22, 2011.

(51) Int. Cl.
*C12N 15/82* (2006.01)
*C12N 9/10* (2006.01)
*C07K 14/415* (2006.01)

(52) U.S. Cl.
CPC ........ *C12N 15/8247* (2013.01); *C07K 14/415* (2013.01); *C12N 9/1062* (2013.01); *C12N 15/8218* (2013.01); *C12N 15/8234* (2013.01)

(58) Field of Classification Search
None
See application file for complete search history.

(56) References Cited

U.S. PATENT DOCUMENTS

| | | | | |
|---|---|---|---|---|
| 5,004,863 | A | 4/1991 | Umbeck | |
| 5,107,065 | A | 4/1992 | Shewmaker et al. | |
| 5,159,135 | A | 10/1992 | Umbeck | |
| 5,416,011 | A | 5/1995 | Hinchee et al. | |
| 5,463,174 | A | 10/1995 | Moloney et al. | |
| 5,518,908 | A | 5/1996 | Corbin et al. | |
| 5,569,834 | A | 10/1996 | Hinchee et al. | |
| 5,631,152 | A | 5/1997 | Fry et al. | |
| 5,968,809 | A | 10/1999 | Knutzon et al. | |
| 6,072,050 | A | 6/2000 | Bowen et al. | |
| 6,512,165 | B1 | 1/2003 | Ross et al. | |
| 6,555,673 | B1 | 4/2003 | Bowen et al. | |
| 7,157,621 | B2 | 1/2007 | Allen et al. | |
| 7,294,759 | B2 | 11/2007 | Allen et al. | |
| 8,404,926 | B2 | 3/2013 | Meyer et al. | |
| 8,785,726 | B2 | 7/2014 | Allen et al. | |
| 9,284,571 | B2 | 3/2016 | Damude et al. | |
| 2003/0135889 | A1 | 7/2003 | Ross et al. | |
| 2003/0204870 | A1* | 10/2003 | Allen ................ | C12N 15/8247 800/281 |
| 2003/0226166 | A1 | 12/2003 | Falco et al. | |
| 2005/0257289 | A1 | 11/2005 | Gordon-Kamm et al. | |
| 2007/0022499 | A1 | 1/2007 | Allen et al. | |
| 2009/0249517 | A1 | 10/2009 | Allen et al. | |
| 2009/0293152 | A1* | 11/2009 | Roesler ................ | C12N 9/1029 800/281 |
| 2010/0242138 | A1* | 9/2010 | Allen ................ | C12N 15/8247 800/281 |
| 2010/0257635 | A1* | 10/2010 | Meyer ................ | C12N 15/8247 800/281 |
| 2014/0325704 | A1 | 10/2014 | Allen et al. | |

FOREIGN PATENT DOCUMENTS

| | | |
|---|---|---|
| EP | 0 301 749 | 2/1989 |
| WO | 1998/46776 | 10/1998 |
| WO | WO 99/67405 | 12/1999 |

(Continued)

OTHER PUBLICATIONS

Fourgoux-Nicol et al (1999, Plant Molecular Biology 40: 857-872).*

Turchetto-Zolet et al (Evolutionary view of acyl-CoA diacylglycerol acyltransferase (DGAT), a key enzyme in neutral lipid biosynthesis. BMC Evolutionary Biology 11:263, p. 1-14, 2011).*

Licausi et al (APETALA2/Ethylene Responsive Factor (AP2/ERF) transcription factors: mediators of stress responses and developmental programs. New Phytologist 199: 639-649, 2013).*

Paula P. Chee et al., Transformation of Soybean (Glycine max) by Infecting Germinating Seeds with Agrobacterium tumefaciens, Plant Phys., Vol. 91: 1212-1218, Jun. 12, 1989.

Maud A.W. Hinchee et al., Production of Transgenic Soybean Plants using Agrobacterium-Mediated DNA Transfer, Bio/Technology, vol. 6:915-922, Aug. 1988.

(Continued)

*Primary Examiner* — Medina A Ibrahim
*Assistant Examiner* — Wayne Zhong

(57) ABSTRACT

Recombinant DNA constructs comprising the soybean sucrose synthase promoter operably linked to polynucleotides encoding transcription factors such as ODP1, Lec1 and FUSCA3 are disclosed. These constructs are used for increasing oil content while maintaining normal germination in oilseed plants. Methods to increase oil content in the seeds of an oilseed plant using this construct are also disclosed herein.

13 Claims, 5 Drawing Sheets

(56) References Cited

FOREIGN PATENT DOCUMENTS

| | | | |
|---|---|---|---|
| WO | WO 00/00619 | | 1/2000 |
| WO | 2000/04761 | | 2/2000 |
| WO | WO 00/28058 | | 5/2000 |
| WO | 0200904 | A2 | 1/2002 |
| WO | 0208269 | A2 | 1/2002 |
| WO | 03001902 | A2 | 1/2003 |
| WO | 2004071467 | A2 | 8/2004 |
| WO | 2005075655 | A2 | 8/2005 |
| WO | 2006000732 | A1 | 1/2006 |
| WO | 2007061845 | A2 | 5/2007 |
| WO | 2010/114989 | A1 | 10/2010 |

OTHER PUBLICATIONS

Marc De Block et al., Transformation of *Brassica napus and Brassica oleracea* Using Agrobacterium tumefaciens and the Expression of the bar and neo Genes in the Transgenic Plants, Plant Phys., vol. 91:694-701, Apr. 3, 1989.
N.P. Everett et al., Genetic Engineering of Sunflower (*Helianthus Annuus* L.), Bio/Technology, vol. 5:1201-1204, 1987.
S.D. Tanksley et al., RFLP Mapping in Plant Breeding: New Tools for an Old Science, Bio/Technology, vol. 7:257-264, Mar. 1989.
Sebastien Baud et al., WRINKLED1 specifies the regulatory action of LEAFY COTYLEDON2 towards fatty acid metabolism during seed maturation in *Arabidopsis*, The Plant Journal, 2007, pp. 825-838. vol. 5.
Minou Nowrousian et al., Cell Differentiation during Sexual Development of the Fungus Sordaria macrospora Requires ATP Citrate Lyase Activity, Molecular and Cellular Biology, vol. 19(1):450-460, Jan. 1999.
David M. Braun et al., Plant transmembrane receptors: new pieces in the signaling puzzle, Trends Biochem., 21:70-73, 1996.
Xiaoquan Wang et al., The PR5K receptor protein kinase from *Arabidopsis thaliana* is structurally related to a family of plant defense proteins, PNAS, vol. 93:2598-2602, Mar. 1996.
John C. Walker, Structure and function of the receptor-like protein kinases of higher plants, Plant Molecular Biology, vol. 26:1599-1609, 1994.
Thomas M. Wahlund et al., The Reductive Tricarboxylic Acid Cycle of Carbon Dioxide Assimilation: Initial Studies and Purification of ATP-Citrate Lyase from the Green Sulfur Bacterium Chlorobium tepidum, Journal of Bacteriology, vol. 179(15):4859-4867, Aug. 1997.
Paul A. Srere, The Citrate Cleavage Enzyme, Journ. of Biol. Chem., vol. 234(10):2544-2547, Oct. 1959.
A. Guerritore et al., Presence and Adaptive Changes of Citrate Enzyme in the Yeast Rhodotorula gracilis, Experientia, vol. 26;28-30, 1970.
Oliver H. Lowry et al., Protein Measurement with the Folin Phenol Reagent, J. Biol. Chem., vol. 193:265-275, 1951.
Hansjorg Fritsch et al., ATP Citrate Lyase from Germinating Castor Bean Endosperm, Plant Phys., vol. 63:687-691, 1979.
Changguo Chen et al., Some Enzymes and Properties of the Reductive Carboxylic Acid Cycle Are Present in the Green Alga Chiamydomonas reinhardtii F-60, Plant Phys., vol. 98:535-539, Jun. 27, 1991.
Dhandapani Rangasamy et al., Compartmentation of ATP:Citrate Lyase in Plants, Plant Phys., vol. 122:1225-1230, Apr. 2000.
Colin Ratledge et al., Correlation of ATP/Citrate Lyase Activity with Lipid Accumulation in Developing Seeds of *Brassica napus* L., Lipids, vol. 32(1):7-12, 1997.
Christopher Thomas Evans et al., The Physiological Significance of Citric Acid in the Control of Metabolism in Lipid-Accumuafating Yeasts, Biotechnology and Genetic Engineering Reviews, vol. 3:349-375, 1985.
Dhandapani Rangasamy et al., Genetic Enhancement of Fatty Acid Synthesis by Targeting Rat Liver ATP:Citrate Lyase into Plastids of Tobacco, Plant Physiology, vol. 122:1231-1238, Apr. 2000.
Hendrik Naested et al., Caleosins: Ca2+-binding proteins associated with lipid bodies, Plant Molecular Biology, vol. 44:463-476, 2000.
Mitsuhiko Ikura, Calcium binding and conformational response in EF-hand proteins, Trends in Biochem. Science, vol. 21:14-17, 1996.
Ping Lin et al., The Mammalian Calcium-binding Protein, Nucleobindin (CALNUC), Is a Golgi Resident Protein, Journal of Cell Biology, vol. 141(7):1515-1527, Jun. 29, 1998.
Gitte Frandsen et al., Novel Plant Ca2+-binding Protein Expressed in Response to Abscisic Acid and Osmotic Stress, Journ. of Biological Chem., vol. 271(1):343-348, Jan. 5, 1996.
Emily C.F. Chen et al., Identification of Three Novel Unique Proteins in Seed Oil Bodies of Sesame, Plant Cell Phys., vol. 39(9):935-941, 1998.
Michael L. Nuccio et al., ATS1 and ATS3: two novel embryo-specific genes in *Arabidopsis thaliana*, Plant Molecular Biology, vol. 39:1153-1163, 1999.
Dennis E. McCabe et al., Stable Transformation of Soybean (Glycine Max) by Particle Acceleration, Bio/Technology, vol. 6:923-926, Aug. 1988.
Paul Christou et al., Stable Transformation of Soybean Callus by DNA-Coated Gold Particles, Plant Phys., vol. 87:671-674, 1988.
Ming Cheng et al., Production of fertile transgenic peanut (*Arachis hypogaea* L.) plants using Agrobacterium tumefaciens, Plant Cell Reports, vol. 15:653-657, 1996.
A. H. McKently et al., Agrobacterium-mediated transformation of peanut (*Arachis hypogaea* L.) embryo axes and the development of transgenic plants, Plant Cell Reports, vol. 14:699-703, 1995.
Jan E. Grant et al., Transformation of peas (*Pisum sativum* L.) using immature cotyledons, Plant Cell Reports, vol. 15:254-258, 1995.
Benny Bytebier et al., T-DNA organization in tumor cultures and transgenic plants of monocotyledon Asparagus officinalis, PNAS, vol. 84:5345-5349, Aug. 1987.
Yuechun Wan et al., Generation of Large Numbers of Independently Transformed Fertile Barley Plants, Plant Phys., vol. 104:37-48, 1994.
Carol A. Rhodes et al., Genetically Transformed Maize Plants form Protoplasts, Science, vol. 240:204-207, Apr. 8, 1988
William J. Gordon-Kamm et al., Transformation of Maize Cells and Regeneration of Fertile Transgenic Plants, The Plant Cell, vol. 2, 603-618, Jul. 1990.
Michael E. Fromm et al., Inheritance and Expression of Chimeric Genes in the Progeny of Transgenic Maize Plans, Bio/Technology, vol. 8:833-839, Sep. 1990.
Michael G. Koziel et al., Field Performance of Elite Transgenic Maize Plants Expressing an Insecticidal Protein Derived From Bacillus thuringiensis, Bio/Technology, vol. 11:194-199, Feb. 11, 1993.
Charles L. Armstrong et al., Field Evaluation of European Com Borer Control in Progeny of 173 Transgenic Corn Events Expressing an Insecticidal Protein from Bacillus thuringiensis, Crop Science, vol. 35:550-557, 1995.
David A. Somers et al., Fertile, Transgenic Oat Plants, Bio/Technolgy, vol. 10:1589-1594, Dec. 1992.
M.E. Horn et al., Transgenic plants of Orchardgrass(*Dactylis glomerata* L.) from protoplasts, Plant Cell Reports, vol. 7:469-472, 1988.
Kinya Toriyama et al., Haploid and diploid plant regeneration from protoplasts of anther callus in rice, Theor. Appl. Genet., vol. 73:16-19, 1986.
Sung Hun Park et al., T-DNA integration into genomic DNA of rice following Agrobacterium inoculation of isolated shoot apices, Plant Molecular Biology, vol. 32:1135-1148, 1996.
M. Abedinia et al., An Efficient Transformation System for the Australian Rice Cultivar, Jarrah, Aus. J. Plant Phys., vol. 24:133-141, 1997.
W. Zhang et al., Efficient regeneration of transgenic plants from rice protoplasts and correctly regulated expression of the foreign gene in the plants, Theor. Appl. Genet., vol. 76:835-840, 1988.
H. M. Zhang et al., Transgenic rice plants produced by electroporation-mediated plasmid uptake into protoplasts, Plant Cell Reports, vol. 7:379-384, 1988.

(56) References Cited

OTHER PUBLICATIONS

M. Battraw et al., Expression of a chimeric neomycin phosphotransferase II gene in first and second generation transgenic rice plants, Plant Science, vol. 86:191-202, 1992.
Paul Christou et al., Production of Transgenic Rice (*Oryza Sativa* L.) Plants from Agronomically Important Indica and Japonica Varieties Via Electric Discharge Particle Acceleration of Exogenous DNA Into Immature Zygotic Embryos, Bio/Technology, vol. 9:957-962, Oct. 1991.
A. De La Pena et al., Transgenic rye plants obtained by injecting DNA into young floral tillers, Nature, vol. 325:274-276, Jan. 15, 1987.
Robert Bower et al., Transgenic sugarcane plants via microprojectile bombardment, The Plant Journal, vol. 2(3):409-416, 1992.
Zeng-Yu Wang et al., Transgenic Plants of Tall Fescue (Festuca Arundinacea Schreb.) Obtained by direct Gene Transfer to Protoplasts, Bio/Technology, vol. 10:691-696, Jun. 1992.
Vimla Vasil et al., Herbicide Resistant Fertile Transgenic Wheat Plants Obtained by Microprojectile Bombardment of Regenerable Embryogenic Callus, Bio/Technology, vol. 10:667-674, Jun. 1992.
William R. Marcotte, Jr. et al., Regulation of a Wheat Promoter by Ascisic Acid in Rice Protoplasts, Nature, vol. 335:454-457, Sep. 29, 1988.
Donald R. McCarty et al., Molecular Analysis of viviparous-1: An Abscisic Acid-Insensitive Mutant of Maize, The Plant Cell, vol. 1:523-532, May 1989.
Donald R. McCarty et al., The Viviparous-1 Development Gene of Maize Encodes a Novel Transcriptional Activator, Cell, vol. 66:895-905, Sep. 6, 1991.
Tsukaho Hattori et al., The Viviparous-1 gene and abscisic acid activate the C1 regulatory gene for anthocyanin biosynthesis during seed maturation in maize, Genes & Development, vol. 6:609-618, 1992.
Stephen A. Goff et al., Transactivation of anthocyanin biosynthetic genes following transfer of B regulatory genes into maize tissues, The EMBO Journal, vol. 9(8):2517-2522, 1990.
National Center for Biotechnology Information General Identifier No. 1171429, Accession No. AAA86281, P. Vergani et al., Jan. 30, 1996.
Paul Christou et al., Inheritance and expression of foreign genes in transgenic soybean plants, Proc. Natl. Acad. Scie USA, vol. 86:7500-7504, 1989.
X. Zhang, Leucine-rich repeat receptor-kinases in plants, Plant Molecular Biology Reporter, vol. 16:301-311, 1998.
Jacqueline H. A. Barker et al., Evidence that barley 3-hydroxy-3-methylgfutaryl-coenzyme A reductase kinase is a member of the sucrose nonfermenting-1-related protein kinase family, Plant Phys., vol. 112(3):1141-1149, 1996.
Smith et al., The challenges of genome sequence annotation or "The devil is in the details", Nature Biotechnology, Nov. 1997, vol. 15, No. 12, pp. 1222-1223.
Brenner, S. E., Errors in genome annotation, Apr. 1999, Trends in Genetics 15(4):132-133.
Bork et al., Go hunting in sequence databases but watch out for traps, Trends in Genetics, Oct. 1996, vol. 12, No. 10: 425-427.
Broun et al., Catalytic Plasticity of Fatty Acid Modification Enzymes Underlying Chemical Diversity of Plant Lipids, Science, Nov. 13, 1998, Vo. 282:1315-1317.
Van De Loo, An oleate 12-hydroxylase from *Ricinus communis* L. is a fatty acyl desaturase homolog, Proc. Natl. Acad. Sci. USA, Jul. 1995, vol. 92:6743-6747.
Doerks et al., Protein annotation: detective work for function prediction, Trends in Genetics, Jun. 1998, vol. 14(6):248-250.
Johan Ericsson et al., Identification of Glycerol-3-phosphate Acyltransferase as an Adipocyte Determination and Differentiation Factor 1- and Sterol Regulatory Element-binding Protein-responsive Gene, The Journal of Biological Chemistry, 1997, pp. 7298-7305, vol. 272, No. 11.
Juan Gabriel Angeles-Nunez et al., Regulation of AtSUS2 and AtSUS3 by glucose and the transcription factor LEC2 in different tissues and at different stages of *Arabidopsis* seed development, Plant Mol Biol (2012) 78:377-392.
Boutilier, K., et al., "Ectopic Expression of Baby Boom Triggers a Conversion from Vegetative to Embryonic Growth," *The Plant Cell*14: 1737-1749, Aug. 2002.
Bowie, J.U., et al., "Deciphering the Message in Protein Sequences: Tolerance to Amino Acid Substitutions," *Science* 247:1306-1310, 1990.
Marsh-Martinez, N., eta!., Bolita, an *Arabidopsis* AP2/ERF-like transcription factor that affects cell expansion and proliferation/differentiation pathways,*Plant Mol. Bioi*. 62: 825-843, 2006.
McConnell, J.R., eta!., "Role ofPHABULOSA and PHAVOLUTA in determining radial patterning in shoots," *Nature 411* (6838):709-713, 2001.
Philip N. Benfey et al., The Cauliflower Mosaic Virus 35S Promoter: Combinatorial Regulation of Transcription in Plants, Science, 1990 pp. 959-966, vol. 250.
Philip N. Benfey et al., The CaMV 35S enhancer contains at least two domains which can confer different developmental and tissue-specific expression patterns, The EMBO Journal, 1989, pp. 2195-2202, vol. 8, No. 8.
Sebastian Baud et al., Regulation of de novo fatty acid synthesis in maturing oilseeds of *Arabidopsis*, Plant Physiology and Biochemistry, 2009, pp. 1-8.
Glycine max strain Williams 82 clone BM_WBc0099F23, Mar. 13, 2009, EBI Accession No. AC235472, XP002693656.
Medicago truncatula chromosome 8 clone mth2-13h21, Jun. 21, 2002, EBI Accession No. AC124967, XP002693657.
Cui-Ge Zhao et al., Advance in Research on Seed Oil Bosynthesis and Basal Metabolism, Seed, Apr. 30, 2010, vol. 29, No. 4, pp. 56-62 (English Translation not available).
Yasuaki Kagaya et al., The promoter from the rice nuclear gene encoding chloroplast aldolase confers mesophyll-specific and light-regulated expression in transgenic tobacco, Mol. Gen. Genet, 1995, pp. 668-674, 248.
Communication from China Patent Agent, CN Application No. 201280062933.2, dated Apr. 14, 2016.
International Search Report—PCT/US2012/070828, dated Apr. 3, 2013.
International Search Report—PCT/US02/20152, dated Apr. 3, 2003.
International Search Report—PCT/US02/22086, dated Feb. 25, 2003.
International Search Report—PCT/US2010/029609, dated Jul. 16, 2010.
Sebatien Baud et al., "A Spatiotemporal Analysis of Enzymatic Activities Associated with Carbon Metabolism in Wild-Type and Mutant Embryos of *Arabidopsis* Using in Situ Histochemistry", The Plant Journal, vol. 46:155-169, 2006.
Sebastien Baud et al., "Structure and Expression Profile of the Sucrose Synthase Multigene Family in *Arabidopsis*", Journal of Experimental Botany, vol. 55(396):397-409, 2004.
R.N. Beachy et al., "Accumulation and Assembly of Soybean B-Conglycinin in Seeds of Transformed Petunia Plants",The EMBO Journal, vol. 4(12):3047-3053, 1985.
Daniel M. Becker et al., "A CDNA Encoding a Human CCAAT-Binding Protein Cloned by Functional Complementation in Yeast", Proc. Natl. Acad. Sci. USA, vol. 88:1968-1972, 1991.
Alex Cernac et al "Wrinkled1 Encodes an AP2/EREB Domain Protein Involved in the Control of Storage Compound Biosynthesis in *Arabidopsis*", The Plant Journal, 40:575-585, 2004.
Gary N. Drews et al., "Negative Regulation of the *Arabidopsis homeotic* Gene Agamous by the Apetala2 Product", Cell, vol. 65(6):991-1002, 1991.
David Edwards et al., "Multiple Genes Encoding the Conserved CCAAT-Box Transcription Factor Complex Are Expressed in *Arabidopsis*", Plant Physiol., vol. 117:1015-1022, 1998.
Johan Ericsson et al., "Synergistic Binding of Sterol Regulatory Element-Binding Protein and NF-Y to the Farnesyl Diphosphate

(56) References Cited

OTHER PUBLICATIONS

Synthase Promoter Is Critical for Sterol-Regulated Expression of the Gene", The Journal of Biological Chemistry, Vol. 271(40):24359-24364, 1996.
Robert B. Goldberg et al., "Regulation of Gene Expression During Plant Embryogenesis", Cell, vol. 56(2):149-160, 1989.
National Center for Biotechnology Information General Identifier No. 32364685, Accession No. AAP80382, Aug. 23, 2004, A.Cernac et al., "Wrinkled1 [*Arabidopsis thaliana*]", Biochemistry and Molecular Biology, MSU, East Lansing, Michigan, USA.
Vivian F. Irish et al., "Function of the Apetala-1 Gene During *Arabidopsis* Floral Development", The Plant Cell, vol. 2:741-753, 1990.
Simon M. Jackson et al "NF-Y Has a Novel Role in Sterol-Dependent Transcription of Two Cholesterogenic Genes", The Journal of Biological Chemistry, vol. 270(37):21445-21448, 1995.
K. Diane Jofuku et al., "Control of *Arabidopsis* Flower and Seed Development by the Homeotic Gene Apetala2", The Plant Cell, vol. 6:1211-1225, 1994.
Xiao-Yan Li et al, "Evolutionary Variation of the CCAAT-Binding Transcription Factor NF-Y", Nucleic Acids Research, Vol. 20(5):1087-1091, 1991.
Yonghua Li et al., "Oil Content of *Arabidopsis* Seeds: The Influence of Seed Anatomy, Light and Plant-To-Plant Variation", Elsevier Phytochemistry, vol. 67:904-915, 2006.
Jose M. Lopez et al., "Sterol Regulation of Acetyl Coenzyme a Carboxylase: A Mechanism for Coordinate Control of Cellular Lipid", Proc. Natl. Acad. Sci. USA, vol. 93:1049-1053, 1996.
Tamar Lotan et al., "*Arabidopsis* Leafy Cotyledon1 Is Sufficient to Induce Embryo Development in Vegetative Cells", Cell, vol. 93:1195-1205, 1998.
S.L. McKnight et al, "Is CCAAT/Enhancer-Binding Protein a Central Regulator of Energy Metabolism?", Genes Dev. vol. 3:2021-2024, 1989.
Jack K. Okamuro et al., "The AP2 Domain of Apetala2 Defines a Large New Family of DNA Binding Proteins in *Arabidopsis*", Proc. Natl. Acad. Sci. USA, vol. 94:7076-7081, 1997.
Karim Roder et al., "NF-Y Binds to the Inverted CCAAT Box, An Essential Element for C Amp-Dependent Regulation of the Rat Fatty Acid Synthase (FAS) Gene", Gene, vol. 184:21-26, 1997.
Sari A. Ruuska et al, "Contrapuntal Networks of Gene Expression During Arabidopsis Seed Filling", The Plant Cell, Vol. 14:1191-1206, 2002.
Satrajit Sinha et al., "Recombinant Rat Cbf-C, The Third Subunit of Cbf/Nfy, Allows Formation of a Protein-DNA Complex With Cbf-A and Cbf-B and With Yeast HAP2 and HAP3", Proc. Natl. Acad. Sci. USA, vol. 92:1624-1628, 1995.
Masaru Ohme-Takagi et al., "Ethylene-Inducible DNA Binding Proteins That Interact with an Ethylene-Responsive Element", The Plant Cell, vol. 7:173-182, 1995.

* cited by examiner

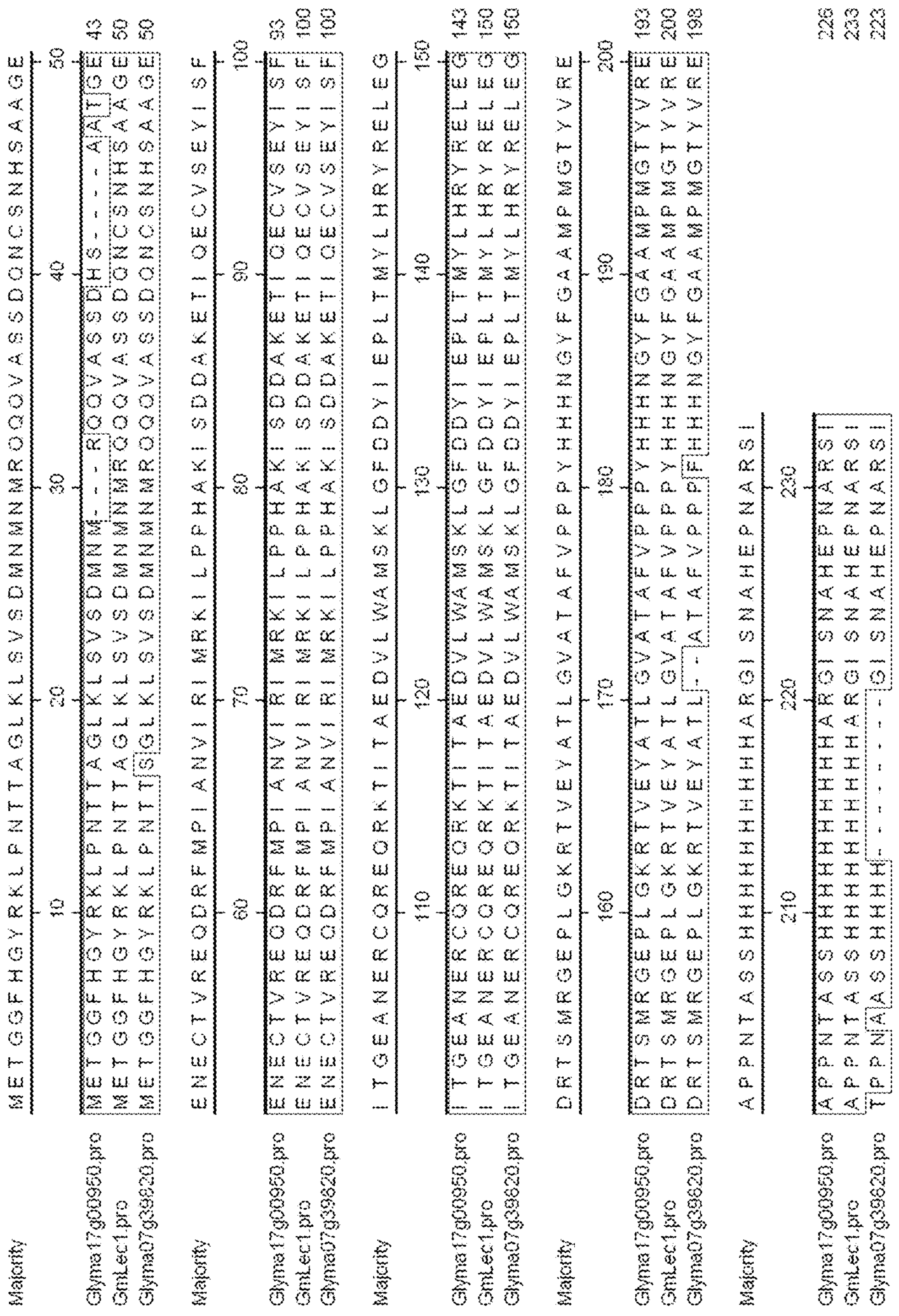

FIG. 2

| | | |
|---|---|---|
| Majority | METGGFHGYRKLPNTTAGLKLSVSDMNMNMRQQVASSDQNCSNHSAAGE | 50 |

| | | |
|---|---|---|
| Glyma17g00950.pro | METGGFHGYRKLPNTTAGLKLSVSDMNM---RQQVASSDHS----AATGE | 43 |
| GmLec1.pro | METGGFHGYRKLPNTTAGLKLSVSDMNMNMRQQVASSDQNCSNHSAAGE | 50 |
| Glyma07g39620.pro | METGGFHGYRKLPNTTSGLKLSVSDMNMNMRQQVASSDQNCSNHSAAGE | 50 |

| | | |
|---|---|---|
| Majority | ENECTVREQDRFMPIANVIRIMRKILPPHAKISDDAKETIQECVSEYISF | 100 |

| | | |
|---|---|---|
| Glyma17g00950.pro | ENECTVREQDRFMPIANVIRIMRKILPPHAKISDDAKETIQECVSEYISF | 93 |
| GmLec1.pro | ENECTVREQDRFMPIANVIRIMRKILPPHAKISDDAKETIQECVSEYISF | 100 |
| Glyma07g39620.pro | ENECTVREQDRFMPIANVIRIMRKILPPHAKISDDAKETIQECVSEYISF | 100 |

| | | |
|---|---|---|
| Majority | ITGEANERCQREQRKTITAEDVLWAMSKLGFDDYIEPLTMYLHRYRELEG | 150 |

| | | |
|---|---|---|
| Glyma17g00950.pro | ITGEANERCQREQRKTITAEDVLWAMSKLGFDDYIEPLTMYLHRYRELEG | 143 |
| GmLec1.pro | ITGEANERCQREQRKTITAEDVLWAMSKLGFDDYIEPLTMYLHRYRELEG | 150 |
| Glyma07g39620.pro | ITGEANERCQREQRKTITAEDVLWAMSKLGFDDYIEPLTMYLHRYRELEG | 150 |

| | | |
|---|---|---|
| Majority | DRTSMRGEPLGKRTVEYATLGVATAFVPPPYHHHNGYFGAAMPMGTYVRE | 200 |

| | | |
|---|---|---|
| Glyma17g00950.pro | DRTSMRGEPLGKRTVEYATLGVATAFVPPPYHHHNGYFGAAMPMGTYVRE | 193 |
| GmLec1.pro | DRTSMRGEPLGKRTVEYATLGVATAFVPPPYHHHNGYFGAAMPMGTYVRE | 200 |
| Glyma07g39620.pro | DRTSMRGEPLGKRTVEYATL--ATAFVPPPFHHHNGYFGAAMPMGTYVRE | 198 |

| | | |
|---|---|---|
| Majority | APPNTASSHHHHHHHHHHARGISNAHEPNARSI | |

| | | |
|---|---|---|
| Glyma17g00950.pro | APPNTASSHHHHHHHHHHARGISNAHEPNARSI | 226 |
| GmLec1.pro | APPNTASSHHHHHHHHHH--------ARGISNAHEPNARSI | 233 |
| Glyma07g39620.pro | TPPNASSHHHHH------------GISNAHEPNARSI | 223 |

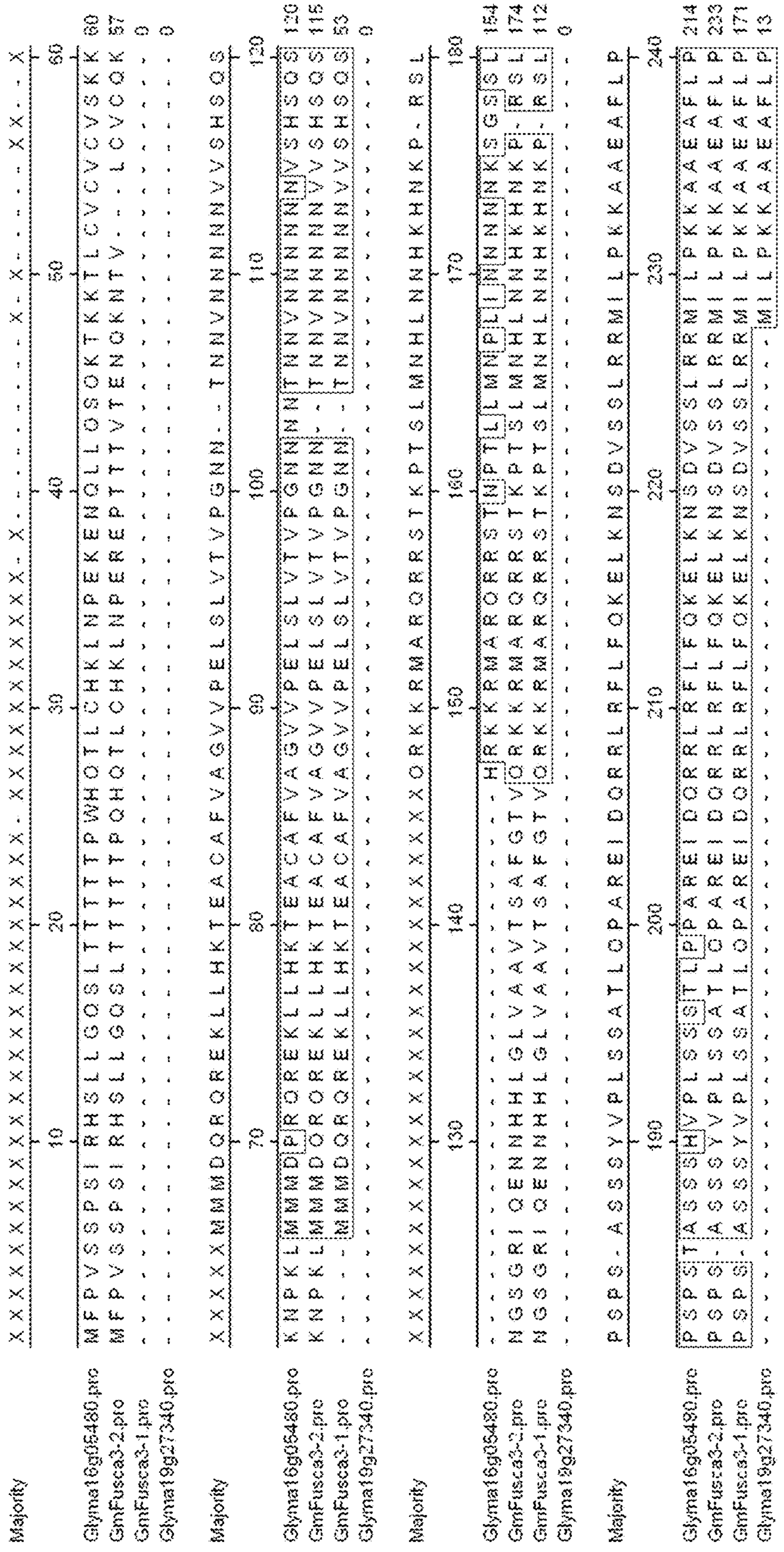

FIG. 3A

| Majority | XXXXXXXXXXXXXXXXXXXX.XXXXXXXXXX.XXXXXXXXXXX.X.....XX..X | X |
| --- | --- | --- |
| | 10 20 30 40 50 60 | |
| Glyma16g05480.pro | M F P V S S P S I R H S L L G Q S L T T T T T P W H Q T L C H K L N P E K E N Q L L Q S Q K T K K T L C V C V C V S K K | 60 |
| GmFusca3-2.pro | M F P V S S P S I R H S L L G Q S L T T T T T P Q H Q T L C H K L N P E R E P T T T V T E N Q K N T V . . . L C V C Q K | 57 |
| GmFusca3-1.pro | . . . . . . . . . . . . . . . . . . . . . . . . . . . . . . . . . . . . . . . . . . . . . . . . . . . . . . . . . . . . | 0 |
| Glyma19g27340.pro | . . . . . . . . . . . . . . . . . . . . . . . . . . . . . . . . . . . . . . . . . . . . . . . . . . . . . . . . . . . . | 0 |

| Majority | XXXXMMMDQRQREKLLHKTEACAFVAGVVPELSLVTVPGNN..TNNVNNNNNVVSHSQS | |
| --- | --- | --- |
| | 70 80 90 100 110 120 | |
| Glyma16g05480.pro | K N P K L M M M D P R Q R E K L L H K T E A C A F V A G V V P E L S L V T V P G N N N T N N V N N N N N V V S H S Q S | 120 |
| GmFusca3-2.pro | K N P K L M M M D Q R Q R E K L L H K T E A C A F V A G V V P E L S L V T V P G N N . . T N N V N N N N N V V S H S Q S | 115 |
| GmFusca3-1.pro | . . . . . M M M D Q R Q R E K L L H K T E A C A F V A G V V P E L S L V T V P G N N . . T N N V N N N N N V V S H S Q S | 53 |
| Glyma19g27340.pro | . . . . . . . . . . . . . . . . . . . . . . . . . . . . . . . . . . . . . . . . . . . . . . . . . . . . . . . . . . . . | 0 |

| Majority | XXXXXXXXXXXXXXXXXXXXXXXXXXXXXQRKKKRMARQRRSTKPTSLMNHLNNHKHNKP.RSL | |
| --- | --- | --- |
| | 130 140 150 160 170 180 | |
| Glyma16g05480.pro | . . . . . . . . . . . . . . . . . . . . . . . . . . . . . . H R K K R M A R Q R R S T N P T L L M N P L L N N K S G S L | 154 |
| GmFusca3-2.pro | . . . . . . . . . . . . . . . . . . . . . . . . . . . . . . Q R K K K R M A R Q R R S T K P T S L M N H L N N H K H N K P . R S L | 174 |
| GmFusca3-1.pro | . . . . . . . . . . . . . . . . . . . . . . . . . . . . . . Q R K K K R M A R Q R R S T K P T S L M N H L N N H K H N K P . R S L | 112 |
| Glyma19g27340.pro | . . . . . . . . . . . . . . . . . . . . . . . . . . . . . . . . . . . . . . . . . . . . . . . . . . . . . . . . . . . . | 0 |

| Majority | PSPS.ASSSYVPLSSATLQPAREIDQRRLRFLFQKELKNSDVSSLRRMILPKKAAEAFLP | |
| --- | --- | --- |
| | 190 200 210 220 230 240 | |
| Glyma16g05480.pro | N G S G R I Q E N N H H L G L V A A V T S A F G T V P A R E I D Q R R L R F L F Q K E L K N S D V S S L R R M I L P K K A A E A F L P | 214 |
| GmFusca3-2.pro | N G S G R I Q E N N H H L G L V A A V T S A F G T V Q R K K K R M A R Q R R S T K P T S L M N H L N N H K H N K P . R S L | 223 |
| GmFusca3-1.pro | . . . . . . . . . . . . . . . . . . . . . . . . . . . . . . . . . . . . . . . . . . . . . . . . . . . . . . . . . . . . | 171 |
| Glyma19g27340.pro | P S P S . A S S S Y V P L S S H V P L S S T L P P A R E I D Q R R L R F L F Q K E L K N S D V S S L R R M I L P K K A A E A F L P | 13 |

FIG. 3B

```
Majority           ALESKEGIVISMDDIDGLHVWSFKYRFWPNNNSRMYVLENTGDFVNTHGLRFGDSIMVYQ
                   250 260 270 280 290 300
Glyma16g05480.pro  ALESKEGIVISMDDIDGLHVWSFKYRFWPNNNSRMYVLENTGDFVNTHGLRFGDSILVYQ 274
GmFusca3-2.pro     ALESKEGIVISMDDIDGLHVWSFKYRFWPNNNSRMYVLENTGDFVNTHGLRFGDSIMVYQ 293
GmFusca3-1.pro     ALESKEGIVISMDDIDGLHVWSFKYRFWPNNNSRMYVLENTGDFVNTHGLRFGDSIMVYQ 231
Glyma19g27340.pro  ALESKEGIVISMDDIDGLHVWSFKYRFWPNNNSRMYVLENTGDFVNTHGLRFGDSIMVYQ 73

Majority           DSENNNYVIQAKKASDQDEFMEETSDTINDIFLNDYEVNKPGCFNVTNPAVNDTGMSFIY
                   310 320 330 340 350 360
Glyma16g05480.pro  DSENNNYVIQAKKASDQDEFMEETSDTINDIFLNDYEVNKPGCFNVTYPAVNDTGMSFIY 334
GmFusca3-2.pro     DSENNNYVIQAKKASDQDEFMEETSDTINDIFLNDYEVNKPGCFNVTNPAVNDTGMSFIY 353
GmFusca3-1.pro     DSENNNYVIQAKKASDQDEFMEETSDTINDIFLNDYEVNKPGCFNVTNPAVNDTGMSFIY 291
Glyma19g27340.pro  DSENNNYVIQAKKASDQDEFMEETSDTINDIFLNDYEVNKPGCFNVTNPAVNDTGMSFIY 133

Majority           ETTFSNDSPLDFLGGSMTNFSRIGPVETFGSVENLSLDDFY
                   370 380 390 400
Glyma16g05480.pro  ETTFSNDSPLDFLGGSMTNFSRIGPVETFGSVENLSLDDFY 375
GmFusca3-2.pro     ETTFSNDSPLDFLGGSMTNFSRIGPVETFGSVENLSLDDFY 394
GmFusca3-1.pro     ETTFSNDSPLDFLGGSMTNFSRIGPVETFGSVENLSLDDFY 332
Glyma19g27340.pro  ETTFSNDSPLDFLGGSMTNFSRIGPVETFGSVENLSLDDFY 174
```

FIG. 4

| Chromo-some | Position | Ref. Allele | Alternate Allele | Type | A | B | C | D | E | F | G | H |
|---|---|---|---|---|---|---|---|---|---|---|---|---|
| Gm13 | 21218639 | T | G | SNP | Ref | Het | Alt | Ref | Ref | Ref | Ref | Ref |
| Gm13 | 21218079 | T | A | SNP | Ref | Het | Alt | Ref | Ref | Ref | Ref | Het |
| Gm13 | 21219144 | A | AA | INDEL | Het | Het | Het | Ref | Ref | Ref | Ref | Ref |
| Gm13 | 21219096 | GT | GTCTAATTATT | INDEL | Het | Ref | Ref | Het | Het | Het | Ref | Ref |
| Gm13 | 21219095 | TGT | TGTCTAATTAGT | INDEL | Het | Ref | Ref | Het | Het | Het | Ref | Ref |
| Gm13 | 21219097 | T | TCTAATTATT | INDEL | Het | Ref | Ref | Het | Het | Het | Ref | Ref |
| Gm13 | 21216269 | C | CTAATTATTGTTT | INDEL | Het | Ref | Ref | Het | Ref | Ref | Het | Ref |
| Gm13 | 21216986 | GA | GAAA | INDEL | Ref | Ref | Ref | Het | Ref | Ref | Ref | Ref |
| Gm13 | 21216987 | A | AAA | INDEL | Ref | Ref | Ref | Het | Ref | Ref | Ref | Ref |
| Gm13 | 21219102 | AA | AAAGAA | INDEL | Het | Ref | Ref | Ref | Ref | Ref | Ref | Ref |
| Gm13 | 21216434 | G | GAATAAAG | INDEL | Ref | Ref | Ref | Het | Het | Het | Ref | Ref |
| Gm13 | 21217300 | A | AATATATAC | INDEL | Het | Ref | Ref | Ref | Ref | Ref | Ref | Ref |
| Gm13 | 21218374 | T | TTTTG | INDEL | Het | Ref | Ref | Ref | Ref | Ref | Ref | Ref |
| Gm13 | 21216174 | C | CTAGA | INDEL | Ref | Ref | Ref | Het | Ref | Ref | Ref | Ref |
| Gm13 | 21216433 | A | AATAAA | INDEL | Ref | Ref | Ref | Ref | Het | Het | Ref | Ref |

USE OF THE SOYBEAN SUCROSE SYNTHASE PROMOTER TO INCREASE PLANT SEED LIPID CONTENT

CROSS REFERENCE TO RELATED APPLICATIONS

This application is a 371 national stage filing of International Application No. PCT/US12/70828, filed Dec. 20, 2012, with claims the benefit of U.S. Provisional Application No. 61/578,903, filed Dec. 22, 2011, the entire content of each is herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named "20150202_BB1927USPCT_SubstituteSequenceListing" created on Feb. 2, 2015, and having a size of 587 kilobytes. The sequence listing contained in this ASCII formatted document is part of the specification and is herein incorporated by reference in its entirety.

FIELD OF THE INVENTION

This invention is in the field of biotechnology, in particular, this pertains to increasing oil content while maintaining normal germination in oilseed plants using the soybean sucrose synthase promoter to drive expression of transcription factors such as ODP1, Lec1 and FUSCA3.

BACKGROUND OF THE INVENTION

Plant oil is a valuable renewable resource. Plant lipids have a variety of industrial and nutritional uses and are central to plant membrane function and climatic adaptation. Besides the nutritional uses, vegetable oils are gaining increasing interest as substitutes for petroleum-derived materials in fuels, lubricants, and specialty chemicals, especially as crude oil supplies decline. Oilseeds provide a unique platform for the production of high-value fatty acids that can replace non-sustainable petroleum products. (Cahoon et al. (2007) *Curr. Opin. Plant Biol.* 10:236-244). Methods to increase the content and to improve and alter the composition of plant oils are therefore desired.

Triacylglycerol (TAG) is the primary component of vegetable oil in plants; it is used by the seed as a stored form of energy to be used during seed germination. The quality and content of plant oil can be altered by various methods, by impinging on the enzymes involved directly or indirectly in TAG biosynthesis.

There are limitations to using conventional plant breeding to alter fatty acid composition and content. Molecular and cellular biology techniques offer the potential for overcoming some of the limitations of the conventional breeding approach. Some of the particularly useful technologies are seed-specific expression of foreign genes in transgenic plants (Goldberg et al. (1989) *Cell* 56:149-160), and the use of antisense RNA to inhibit plant target genes in a dominant and tissue-specific manner (van der Krol et al. (1988) *Gene* 72:45-50]. Other advances include the transfer of foreign genes into elite commercial varieties of commercial oilseed crops, such as soybean (Chee et al. (1989) *Plant Physiol.* 91:1212-1218; Christou et al. (1989) *Proc. Natl. Acad. Sci. U.S.A.* 86:7500-7504; Hinchee et al. (1988) *Bio/Technology* 6:915-922; EPO publication 0 301 749 A2], rapeseed (De Block et al. (1989) *Plant Physiol.* 91:694-701), and sunflower (Everett et al. (1987) *Bio/Technology* 5:1201-1204), and the use of genes as restriction fragment length polymorphism (RFLP) markers in a breeding program, which makes introgression of recessive traits into elite lines rapid and less expensive (Tanksley et al. (1989) *Bio/Technology* 7:257-264). However, application of each of these technologies requires identification and isolation of commercially-important genes.

Transcription factors regulate transcription and orchestrate gene expression in plants and other organisms; control of transcription factor gene expression provides a powerful means for altering plant phenotype. The transformation of plants with transcription factors, however, can result in aberrant development based on the overexpression and/or ectopic expression of the transcription factor, and thus, tight control of timing, strength and location of transcription factor expression is crucial for optimal phenotype. Using strong seed-specific promoters or strong constitutive promoters can lead to aberrant phenotypes.

SUMMARY OF THE INVENTION

The present invention relates to the use of a seed-specific promoter of a soybean sucrose synthase gene or a *Medicago truncatula* sucrose synthase gene to drive expression of transcription factors such as soybean ODP1, Lec1 or FUSCA3 in the seeds of an oilseed plant, to increase oil content.

In one embodiment, a recombinant DNA construct comprising at least one heterologous polynucleotide encoding a polypeptide selected from the group consisting of: an ODP1 polypeptide, a Lec1 polypeptide and a FUSCA3 polypeptide, wherein the at least one polynucleotide is operably linked to a soybean sucrose synthase promoter or a *Medicago truncatula* sucrose synthase promoter, wherein expression of said polypeptide in a transgenic soybean seed comprising the recombinant DNA construct results in an increased oil content in the transgenic soybean seed, when compared to a control soybean seed not comprising the recombinant DNA construct. The transgenic soybean seed comprising said recombinant DNA construct may have normal germination, when compared to a control soybean seed not comprising the recombinant DNA construct.

In another embodiment, a recombinant DNA construct as described herein, wherein the at least one polynucleotide is operably linked to a soybean sucrose synthase promoter, wherein the soybean sucrose synthase promoter comprises a nucleic acid sequence selected from the group consisting of: (a) the nucleic acid sequence of SEQ ID NO: 8; (b) a nucleic acid sequence with at least 95% sequence identity to the nucleic acid sequence of SEQ ID NO: 8; (c) a nucleic acid sequence that hybridizes to SEQ ID NO: 8 under stringent conditions; (d) a nucleic acid sequence that differs from SEQ ID NO: 8 in at least one way as described in FIG. 4; and (e) a nucleic acid sequence comprising a functional fragment of (a), (b), (c) or (d).

In another embodiment, a recombinant DNA construct as described herein, wherein the at least one polynucleotide is operably linked to a *Medicago truncatula* sucrose synthase promoter, wherein the *Medicago truncatula* sucrose synthase promoter comprises a nucleic acid sequence selected from the group consisting of: (a) the nucleic acid sequence of SEQ ID NO: 81 or SEQ ID NO: 85; (b) a nucleic acid sequence with at least 95% sequence identity to the nucleic acid sequence of SEQ ID NO: 81 or SEQ ID NO: 85; (c) a nucleic acid sequence that hybridizes to SEQ ID NO: 81 or SEQ ID NO: 85 under stringent conditions; and (d) a nucleic acid sequence comprising a functional fragment of (a), (b) or (c).

In another embodiment, a recombinant DNA construct as described herein, wherein the at least one heterologous polynucleotide encodes an ODP1 polypeptide, wherein the ODP1 polypeptide comprises an amino acid sequence with at least 80%, 85%, 90%, 95% or 100% identity to SEQ ID NO: 30 or SEQ ID NO: 70.

In another embodiment, a recombinant DNA construct as described herein, wherein the at least one heterologous polynucleotide encodes a Lec1 polypeptide, wherein the Lec1 polypeptide comprises an amino acid sequence with at least 80%, 85%, 90%, 95% or 100% identity to SEQ ID NO: 17, 20, 25 or 65.

In another embodiment, a recombinant DNA construct as described herein, wherein the at least one heterologous polynucleotide encodes a FUSCA3 polypeptide comprises an amino acid sequence with at least 80%, 85%, 90%, 95% or 100% identity to SEQ ID NO: 32, 38, 45 or 49.

In another embodiment, a plant or a seed comprising any of the recombinant DNA constructs described above. The plant and the seed may be an oilseed plant and seed. The plant or seed may be a soybean plant or seed.

In another embodiment, a recombinant DNA construct as described herein, wherein the recombinant DNA construct further comprises a seed-specific promoter operably linked to a second heterologous polynucleotide encoding a DGAT polypeptide. The second heterologous polynucleotide may encode a DGAT1 polypeptide. The DGAT1 polypeptide may comprise an amino acid sequence with at least 80%, 85%, 90%, 95% or 100% sequence identity to SEQ ID NO: 55. The second heterologous polynucleotide may encode a DGAT2 polypeptide. The DGAT2 polypeptide may comprise an amino acid sequence with at least 80%, 85%, 90%, 95% or 100% sequence identity to SEQ ID NO: 60.

In another embodiment, a plant or a seed comprising the recombinant DNA constructs described above, wherein co-expression of said polypeptide and said DGAT polypeptide in a transgenic soybean seed comprising the recombinant DNA construct results in an increased oil content in the transgenic seed, when compared to a control seed that expresses said DGAT polypeptide from said seed-specific promoter by does not express said polypeptide selected from the group consisting of an ODP1 polypeptide, a Lec1 polypeptide and a FUSCA3 polypeptide. The plant and the seed may be an oilseed plant and seed. The plant or seed may be a soybean plant or seed.

In another embodiment, a plant comprising a first recombinant DNA construct comprising a soybean or a *Medicago truncatula* sucrose synthase promoter operably linked to a first heterologous polynucleotide encoding a first polypeptide selected from the group consisting of an ODP1 polypeptide, a Lec1 polypeptide and a FUSCA3 polypeptide and a second recombinant DNA construct comprising a seed-specific promoter operably linked to a second heterologous polynucleotide encoding a DGAT polypeptide, wherein co-expression of said first polypeptide and said second polypeptide in a transgenic soybean seed comprising said first and said second recombinant DNA constructs results in an increased oil content in the transgenic seed, when compared to a control seed comprising only one, but not both, of the first and the second recombinant DNA constructs. The plant and the seed may be an oilseed plant and seed. The plant and the seed may be a soybean plant and seed.

In another embodiment, a method of increasing oil content of a soybean seed, the method comprising the steps of: (a) introducing into a regenerable soybean cell any one of the recombinant DNA constructs described herein; (b) regenerating a transgenic plant from the regenerable soybean cell of (a) wherein the transgenic plant comprises the recombinant DNA construct; and (c) selecting a transgenic plant of step (b), or a transgenic progeny plant from the transgenic plant of step (b), wherein seed of the transgenic plant or the transgenic progeny plant comprises the recombinant construct and exhibits increased seed oil content while maintaining normal germination, when compared to a control soybean seed not comprising the DNA recombinant construct. The percent oil content of the transgenic soybean seed may be at least 3%, 4%, 5%, 6%, 7%, 8%, 9%, 10%, 11%, 12%, 13%, 14% or 15%.

In another embodiment, a method of increasing oil content of a soybean seed, the method comprising the steps of: (a) introducing into a regenerable soybean cell a first recombinant DNA construct comprising a soybean or a *Medicago truncatula* sucrose synthase promoter operably linked to a first heterologous polynucleotide encoding a first polypeptide selected from the group consisting of an ODP1 polypeptide, a Lec1 polypeptide and a FUSCA3 polypeptide and a second recombinant DNA construct comprising a seed-specific promoter operably linked to a second heterologous polynucleotide encoding a DGAT polypeptide; (b) regenerating a transgenic plant from the regenerable soybean cell of (a) wherein the transgenic plant comprises the first and the second recombinant DNA constructs; and (c) selecting a transgenic plant of step (b), or a transgenic progeny plant from the transgenic plant of step (b), wherein seed of the transgenic plant or the transgenic progeny plant comprises the first and the second recombinant DNA constructs and wherein co-expression of said first polypeptide and said second polypeptide in a transgenic soybean seed comprising said first and said second recombinant DNA constructs results in an increased oil content in the transgenic soybean seed, when compared to a control soybean seed comprising only one, but not both, of the first and the second recombinant DNA constructs. The percent oil content of the transgenic soybean seed may be at least 3%, 4%, 5%, 6%, 7%, 8%, 9%, 10%, 11%, 12%, 13%, 14% or 15%.

In another embodiment, a transgenic plant obtained by any of the methods described herein, and transgenic seed of said transgenic plant.

In another embodiment, a vector, cell, plant, plant tissue or seed comprising any of the recombinant DNA constructs described herein.

BRIEF DESCRIPTION OF THE DRAWINGS AND SEQUENCE LISTING

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

FIG. 1 is a schematic diagram showing the promoter region and the 5' splice variants of GmSuS or Glyma13g17420. The identified GmSus promoter region encodes the 5' UTR from the cDNA transcript as well as an intron which splits the 5' UTR. The positions of AW boxes AW1 and AW2 are also shown.

FIG. 2 shows an alignment comparing the amino acid sequences of Glyma17g00950 (SEQ ID NO: 17), Glyma07g39820 (SEQ ID NO: 20) and GmLec1 (SEQ ID NO: 25). A majority consensus sequence (SEQ ID NO:108) is shown above the alignment.

FIG. 3A-FIG. 3B show an alignment comparing the amino acid sequences for Glyma16g05480 (SEQ ID NO: 32) and Glyma19g27340 (SEQ ID NO: 38), as predicted in the Glyma database, along with the predicted spliced sequence for GmFusca3-2 (SEQ ID NO: 45) and for GmFusca3-1 (SEQ ID NO: 49). A majority consensus sequence (SEQ ID NO:103) is shown above the alignment.

FIG. 4 shows the sequence diversity within different soybean lines of the genomic DNA region comprising the promoter, 5'-UTR and first intron of the Glyma13g17420 gene.

Figure 1:
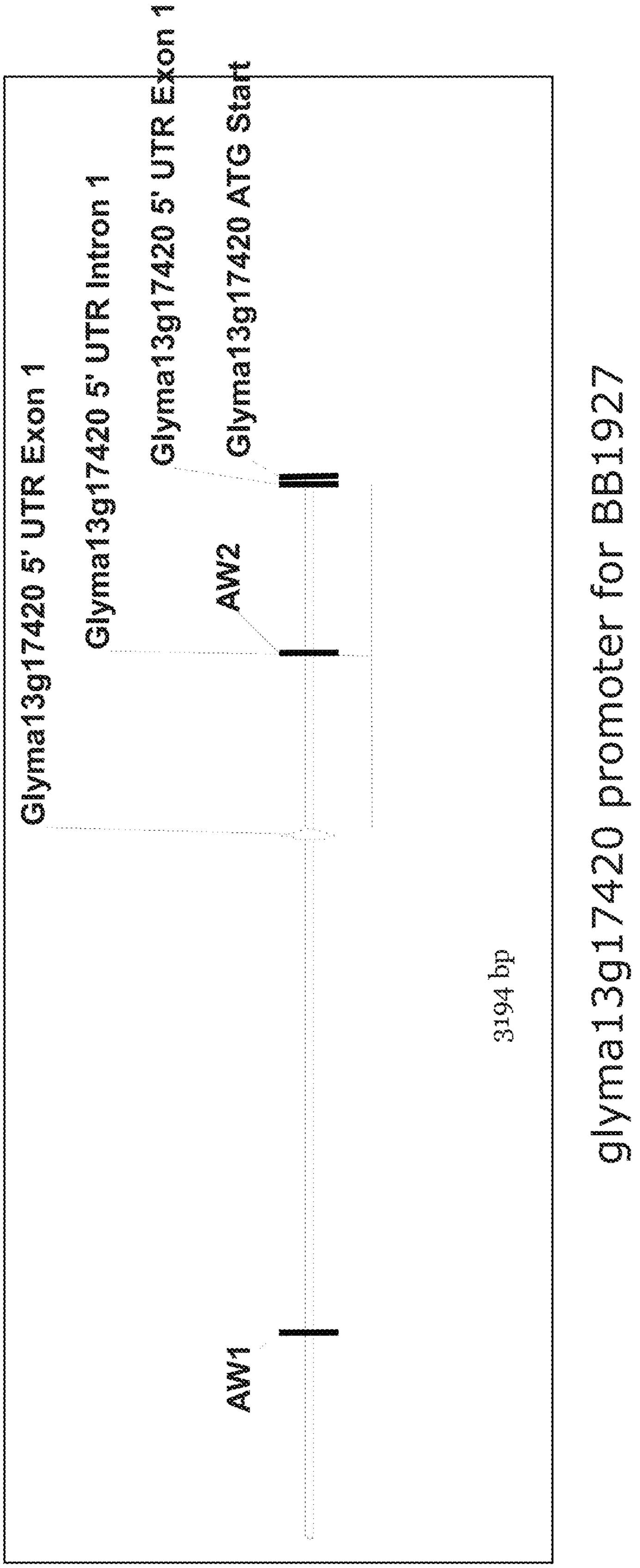

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

SEQ ID NO: 1 is the nucleotide sequence of the *Arabidopsis* Sucrose Synthase 2 gene (AT5G49190), corresponding to the locus described previously in PCT Publication No. WO 2010/114989, and corresponding to GI NO. 30695613.

SEQ ID NO: 2 is the amino acid sequence encoded by the sequence set forth in SEQ ID NO: 1, and corresponds to GI NO. 332008397.

SEQ ID NO: 3 is the genomic sequence of the soybean Sucrose Synthase gene corresponding to the locus Glyma13g17420.

SEQ ID NO: 4 is the cDNA sequence of the soybean Sucrose Synthase gene corresponding to the locus Glyma13g17420.

SEQ ID NO: 5 is the CDS (coding sequence) of the soybean Sucrose Synthase gene corresponding to the locus Glyma13g17420. The soybean homolog to the *Arabidopsis* sucrose synthase 2 gene set forth in SEQ ID NO: 5 is called GmSuS.

SEQ ID NO: 6 is the amino acid sequence encoded by SEQ ID NO: 5, and is the sequence of soybean Sucrose Synthase polypeptide.

SEQ ID NO: 7 is the sequence for the 5' end of EST sdp3c.pk014.n18.

SEQ ID NO: 8 is the sequence of the genomic DNA upstream of the start codon of GmSuS (SEQ ID NO: 5), corresponding to the promoter for GmSuS.

SEQ ID NOS: 9 and 10 are the sequences of the oligonucleotides GmSuSyProm-5 and GmSuSyProm-3 respectively.

SEQ ID NO: 11 is the sequence of pLF284 construct.

SEQ ID NO: 12 is the sequence of the plasmid pKR1963.

SEQ ID NO: 13 is the sequence of the construct pKR1964.

SEQ ID NO: 14 is the sequence of the construct pKR1965.

SEQ ID NO: 15 is the sequence of the cDNA done se2.11d12.

SEQ ID NO: 16 is the sequence of the soybean clone se2.11d12 from 38-718 bp, and is the coding sequence of Lec1b (GI: 158525282) and corresponds to Glyma17g00950.

SEQ ID NO: 17 is the amino acid sequence encoded by the nucleotide sequence given in SEQ ID NO: 16.

SEQ ID NO: 18 is the full insert sequence of the cDNA clone se1.pk0042.d8.

SEQ ID NO: 19 is the sequence from soybean cDNA clone se1.pk0042.d8 with a corrected start site, corresponding to Glyma07g39820.

SEQ ID NO: 20 is the amino acid sequence encoded by the sequence given in SEQ ID NO: 19.

SEQ ID NOS: 21 and 22 are the sequences of the oligonucleotides SA275 and SA276 respectively.

SEQ ID NO: 23 is the sequence of the construct Glyma17g00950/pCR8/GW/TOPO.

SEQ ID NO: 24 is the nucleotide sequence of GmLec1.

SEQ ID NO: 25 is the amino acid sequence encoded by the nucleotide sequence given in SEQ ID NO: 24.

SEQ ID NOS: 26 and 27 are the sequences of the oligonucleotides GmLec-5 and Gmlec-3 respectively.

SEQ ID NO: 28 is the sequence of pLF275 construct, containing GmLec1.

SEQ ID NO: 29 is the CDS of GmODP1.

SEQ ID NO: 30 is the amino acid sequence of GmODP1.

SEQ ID NO: 31 is the predicted CDS for Glyma16g05480.

SEQ ID NO: 32 is the amino acid sequence for Glyma16g05480.

SEQ ID NOS: 33 and 34 are the sequences of the oligonucleotides SA278 and SA279 respectively.

SEQ ID NO: 35 is the sequence of the plasmid Glyma16g05480/pCR8/GW/TOPO.

SEQ ID NO: 36 is the sequence of the cDNA insert in the plasmid Glyma16g05480/pCR8/GW/TOPO (SEQ ID NO: 35), determined by sequencing of the insert.

SEQ ID NO: 37 is the sequence of the predicted CDS of Glyma19g27340 from the Glyma database.

SEQ ID NO: 38 is the sequence of the predicted amino acid sequence of Glyma19g27340 from the Glyma database.

SEQ ID NO: 39 is the genomic sequence from the soybean genome database, upstream of and including Glyma19g27340.

SEQ ID NOS: 40 and 41 are the sequences of the oligonucleotides GmFusca3-1-5 and GmFusca3-3 respectively.

SEQ ID NO: 42 is the sequence of the construct pLF283.

SEQ ID NO: 43 is the sequence of the full length cDNA of the resulting PCR product for GmFusca3-2, amplified using the primers of SEQ ID NO: 40 and SEQ ID NO: 41.

SEQ ID NO: 44 is the sequence of the putative spliced CDS for GmFusca3-2.

SEQ ID NO: 45 is the sequence of the amino acid sequence for GmFusca3-2 encoded by SEQ ID NO: 44.

SEQ ID NO: 46 is the sequence of the oligonucleotide GmFusca3-2-5 used for amplifying GmFusca3-1.

SEQ ID NO: 47 is the sequence of the construct pFL282.

SEQ ID NO: 48 is the full nucleotide sequence of GmFusca3-1.

SEQ ID NO: 49 is the amino acid sequence of GmFusca3-1.

SEQ ID NO: 50 is the sequence of the construct pKR1968.

SEQ ID NO: 51 is the sequence of the construct pKR1971.

SEQ ID NO: 52 is the sequence of the construct pKR1969.

SEQ ID NO: 53 is the sequence of the construct pKR1970.

SEQ ID NO: 54 is the CDS of GmDGAT1cAII.

SEQ ID NO: 55 is the amino acid sequence of GmDGAT1cAII.

SEQ ID NO: 56 is the sequence of the construct pKR2098.

SEQ ID NO: 57 is the sequence of the construct pKR2100.

SEQ ID NO: 58 is the sequence of the construct pKR2099.

SEQ ID NO: 59 is the CDS of YLDGAT2.

SEQ ID NO: 60 is the amino acid sequence of YLDGAT2.

SEQ ID NO: 61 is the sequence of the construct pKR2082.

SEQ ID NO: 62 is the sequence of the construct pKR2084.

SEQ ID NO: 63 is the sequence of the construct pKR2083.

SEQ ID NO: 64 is the CDS of ZmLec1.

SEQ ID NO: 65 is the amino acid sequence of ZmLec1.

SEQ ID NOS: 66 and 67 are the sequences of the oligonucleotides oZLEC-1 and oZLEC-2 respectively.

SEQ ID NO: 68 is the sequence of the construct pKR2115.

SEQ ID NO: 69 is the CDS of ZmODP1.

SEQ ID NO: 70 is the amino acid sequence of ZmODP1.

SEQ ID NO: 71 is the sequence of the construct pKR2121.

SEQ ID NO: 72 is the sequence of the construct pKR2114.

SEQ ID NO: 73 is the sequence of the construct pKR2123.

SEQ ID NO: 74 is the sequence of the construct pKR2122.

SEQ ID NO: 75 is the sequence of the construct pKR2146.

SEQ ID NO: 76 is the sequence of the construct pKR2145.

SEQ ID NO: 77 is a conserved Lec1 sequence motif.

SEQ ID NO: 78 is the nucleotide sequence of the AW box.

SEQ ID NO: 79 is the nucleotide sequence of the predicted CDS for Medtr4g124660.2.

SEQ ID NO: 80 is the amino acid sequence encoded by SEQ ID NO: 79.

SEQ ID NO: 81 is the predicted nucleotide sequence of the Medtr4g124660.2 promoter region.

SEQ ID NO: 82 is the nucleotide sequence of the oMDSP-1F forward primer.

SEQ ID NO: 83 is the nucleotide sequence of the oMDSP-1R reverse primer.

SEQ ID NO: 84 is the nucleotide sequence of construct pKR2434.

SEQ ID NO: 85 is the actual nucleotide sequence of the Medtr4g124660.2 promoter region used in this study.

SEQ ID NO: 86 is the nucleotide sequence of construct pKR2446.

SEQ ID NO: 87 is the nucleotide sequence of construct pKR2457.

SEQ ID NO: 88 is the nucleotide sequence of construct pKR2461.

SEQ ID NO: 89 is the nucleotide sequence of construct pKR2465.

SEQ ID NO: 90 is the nucleotide sequence of amiRNA GM-MFAD2-1B.

SEQ ID NO: 91 is the nucleotide sequence of amiRNA Star Sequence 396b-GM-MFAD2-1B.

SEQ ID NO: 92 is the nucleotide sequence of amiRNA GM-MFAD2-2.

SEQ ID NO: 93 is the nucleotide sequence of amiRNA Star Sequence 159-GM-MFAD2-2.

SEQ ID NO: 94 is the nucleotide sequence of the soy genomic miRNA precursor 159.

SEQ ID NO: 95 is the nucleotide sequence of the soy genomic miRNA precursor 396b.

SEQ ID NO: 96 is the nucleotide sequence of the amiRNA precursor 396b-fad2-1b/159-fad2-2.

SEQ ID NO: 97 is the nucleotide sequence of construct pKR2109.

SEQ ID NO: 98 is the nucleotide sequence of construct pKR2118.

SEQ ID NO: 99 is the nucleotide sequence of construct pKR2120.

SEQ ID NO: 100 is the nucleotide sequence of construct pKR2119.

SEQ ID NO: 101 is the nucleotide sequence of nt 1857-1880 of SEQ ID NO: 81, which are deleted in SEQ ID NO: 85.

SEQ ID NO: 102 is the nucleotide sequence of a 25 bp insertion between nt 2224 and 2225 of SEQ ID NO: 81, which is present in SEQ ID NO: 85.

SEQ ID NO: 103 is the amino acid sequence of the majority consensus sequence presented in FIG. 3A-FIG. 3B.

SEQ ID NO: 104 is the nucleotide sequence of the alternative allele at chromosome GM13, position 21219096, presented in FIG. 4.

SEQ ID NO: 105 is the nucleotide sequence of the alternative allele at chromosome GM13, position 21219095, presented in FIG. 4.

SEQ ID NO: 106 is the nucleotide sequence of the alternative allele at chromosome GM13, position 21219097, presented in FIG. 4.

SEQ ID NO: 107 is the nucleotide sequence of the alternative allele at chromosome GM13, position 21216269, presented in FIG. 4.

SEQ ID NO: 108 is the amino acid sequence of the majority consensus sequence presented in FIG. 2.

DETAILED DESCRIPTION

The disclosure of each reference set forth herein is hereby incorporated by reference in its entirety.

As used herein and in the appended claims, the singular forms “a”, “an”, and “the” include plural reference unless the context clearly dictates otherwise. Thus, for example, reference to “a plant” includes a plurality of such plants; reference to “a cell” includes one or more cells and equivalents thereof known to those skilled in the art, and so forth.

In the context of this disclosure, a number of terms and abbreviations are used. The following definitions are provided.

The terms “monocot” and “monocotyledonous plant” are used interchangeably herein. A monocot of the current invention includes the Gramineae.

The terms “dicot” and “dicotyledonous plant” are used interchangeably herein. A dicot of the current invention includes the following families: Brassicaceae, Leguminosae, and Solanaceae.

The terms “full complement” and “full-length complement” are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Propagule" includes all products of meiosis and mitosis able to propagate a new plant, including but not limited to, seeds, spores and parts of a plant that serve as a means of vegetative reproduction, such as corms, tubers, offsets, or runners. Propagule also includes grafts where one portion of a plant is grafted to another portion of a different plant (even one of a different species) to create a living organism. Propagule also includes all plants and seeds produced by cloning or by bringing together meiotic products, or allowing meiotic products to come together to form an embryo or fertilized egg (naturally or with human intervention).

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes.

"Transgenic plant" also includes reference to plants which comprise more than one heterologous polynucleotide within their genome. Each heterologous polynucleotide may confer a different trait to the transgenic plant.

"Heterologous" with respect to sequence means a sequence that originates from a foreign species, or, if from the same species, is substantially modified from its native form in composition and/or genomic locus by deliberate human intervention.

"Progeny" comprises any subsequent generation of a plant.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "full complement" and "full-length complement" are used interchangeably herein, and refer to a complement of a given nucleotide sequence, wherein the complement and the nucleotide sequence consist of the same number of nucleotides and are 100% complementary.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector.

This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) Nature Biotechnol. 17:287-91).

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Inducible promoters selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include, but are not limited to, promoters regulated by light, heat, stress, flooding or drought, pathogens, phytohormones, wounding, or chemicals such as ethanol, jasmonate, salicylic acid, or safeners.

A minimal or basal promoter is a polynucleotide molecule that is capable of recruiting and binding the basal transcription machinery. One example of basal transcription machinery in eukaryotic cells is the RNA polymerase II complex and its accessory proteins.

Plant RNA polymerase II promoters, like those of other higher eukaryotes, are comprised of several distinct "cis-acting transcriptional regulatory elements," or simply "cis-elements," each of which appears to confer a different aspect of the overall control of gene expression. Examples of such cis-acting elements include, but are not limited to, such as TATA box and CCAAT or AGGA box. The promoter can roughly be divided in two parts: a proximal part, referred to as the core, and a distal part. The proximal part is believed to be responsible for correctly assembling the RNA polymerase II complex at the right position and for directing a basal level of transcription, and is also referred to as "minimal promoter" or "basal promoter". The distal part of the promoter is believed to contain those elements that regulate the spatio-temporal expression. In addition to the proximal and distal parts, other regulatory regions have also been described, that contain enhancer and/or repressors elements The latter elements can be found from a few kilobase pairs upstream from the transcription start site, in the introns, or even at the 3' side of the genes they regulate (Rombauts, S. et al. (2003) *Plant Physiology* 132:1162-1176, Nikolov and Burley, (1997) *Proc Natl Acad Sci USA* 94: 15-22), Tjian and Maniatis (1994) *Cell* 77: 5-8; Fessele et al., 2002 *Trends Genet* 18: 60-63, Messing et al., (1983)

*Genetic Engineering of Plants: an Agricultural Perspective*, Plenum Press, NY, pp 211-227).

When operably linked to a heterologous polynucleotide sequence, a promoter controls the transcription of the linked polynucleotide sequence.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395-4405 (1988); Callis et al., *Genes Dev.* 1:1183-1200 (1987).

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on over-expression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

RNA interference refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

Transcription factors are proteins that generally bind DNA in a sequence-specific manner and either activate or repress transcription initiation. At least three types of separate domains have been identified within transcription factors. One is necessary for sequence-specific DNA recognition, one for the activation/repression of transcriptional initiation, and one for the formation of protein-protein interactions (such as dimerization). Studies indicate that many plant transcription factors can be grouped into distinct classes based on their conserved DNA binding domains (Katagiri F and Chua N H, 1992. *Trends Genet.* 8:22-27; Menkens A E, Schindler U and Cashmore A R, 1995, *Trends in Biochem Sci.* 13:506-510; Martin C and Paz-Ares J, 1997, *Trends Genet.* 13:67-73). Each member of these families interacts and binds with distinct DNA sequence motifs that are often found in multiple gene promoters controlled by different regulatory signals.

Ovule Development Proteins (ODP) are transcription factors containing two AP2 domains. AP2 transcription factors (herein referred to interchangeably as "AP2 domain transcription factors", "AP2 proteins", "AP2/EREBP transcription factors", or "AP2 transcription factor proteins") such as ODP activate several genes in the oil or TAG biosynthetic pathway in the plant cell.

The term "ODP1" refers to an ovule development protein 1 that is involved with increasing oil content. ODP1 is a member of the APETALA2 (AP2) family of proteins that play a role in a variety of biological events including, but not limited to, oil content.

U.S. Patent Application No. 61/165,548 describes the use of an ODP1 gene for alteration of oil traits in plants. U.S. Pat. No. 7,579,529 describes an AP2 domain transcription factor and methods of its use. U.S. Pat. No. 7,157,621 discloses the use of ODP1 transcription factor for increasing oil content in plants. DuPont patent application WO 2010/114989 describes the use of an *Arabidopsis* Sus2 promoter to drive ODP1 (WRI1) expression in *Arabidopsis*.

The putative AP2/EREBP transcription factor WRINKLED1 (WRI1) is involved in the regulation of seed storage metabolism in *Arabidopsis* (Cemac and Benning (2004) *Plant J.* 40:575-585). Expression of the WRI1 cDNA under the control of the CaMV 35S promoter led to increased seed oil content. Oil-accumulating seedlings, however, showed aberrant development consistent with a prolonged embryonic state. Nucleic acid molecules encoding WRINKLED1-LIKE polypeptides and methods of use are also described in International Publication No. WO 2006/00732 A2.

The AP2/EREBP family of proteins is a plant-specific class of putative transcription factors that have been shown to regulate a wide-variety of developmental processes and are characterized by the presence of an AP2/ERF DNA binding domain. Specifically, AP2 (APETALA2) and EREBPs (ethylene-responsive element binding proteins) are the prototypic members of a family of transcription factors unique to plants, whose distinguishing characteristic is that they contain the so-called AP2 DNA-binding domain. DNA sequence analysis suggests that AP2 encodes a theoretical polypeptide of 432 aa, with a distinct 68 aa repeated motif termed the AP2 domain. This domain has been shown to be essential for AP2 functions and contains within the 68 aa motif an eighteen amino acid core region that is predicted to form an amphipathic $\alpha$-helix (Jofuku et al., Plant Cell 6:1211-1225, 1994). AP2-like domain-containing transcription factors have been also been identified in both *Arabidopsis thaliana* (Okamuro et al., (1997) *Proc. Natl. Acad. Sci. USA* 94:7076-7081) and in tobacco with the identification of the ethylene responsive element binding proteins (EREBPs) (Ohme-Takagi and Shinshi, (1995) *Plant Cell* 7:2:173-182,).

HAP proteins constitute a large family of transcription factors first identified in yeast. They combine to form a heteromeric protein complex that activates transcription by binding to CCAAT boxes in eukaryotic promoters. The orthologous Hap proteins display a high degree of evolutionary conservation in their functional domains in all species studied to date (Li et al. (1992) *Nucleic Acids Res* 20:1087-1091).

Leafy cotyledon1 (Lec1 or Lec1/Hap3) is a transcription factor that is a key regulator of seed development in plants. Lec1 is a CCAAT-binding factor (CBF)—type transcription factor. The terms "leafy cotyledon 1", "Lec1", and "Hap3/Lec1" are used interchangeably herein. LEC1 polypeptide is homologous to the HAP3 subunit of the CBF class of eukaryotic transcriptional activators that includes NF-Y, CP1, and HAP2/3/4/5 (Lotan et al. (1998) *Cell*, Vol. 93, 1195-1205, June 26).

The leafy cotyledon1 (LEC1) gene controls many distinct aspects of embryogenesis. The lec1 mutation is pleiotropic, which suggest that LEC1 has several roles in late embryo development. For example, LEC1 is required for specific aspects of seed maturation, inhibiting premature germination and plays a role in the specification of embryonic organ identity. Finally, LEC1 appears to act only during embryo development.

U.S. Pat. No. 6,235,975 describes leafy cotyledon1 genes and their uses. A pending US patent application (U.S. application Ser. No. 11/899,370) relates to isolated nucleic acid fragments encoding Lec1 related transcription factors. U.S. Pat. No. 7,294,759, U.S. Pat. No. 7,157,621, U.S. Pat. No. 7,888,560, U.S. Pat. No. 6,825,397 describe the use of Lec1 genes for altering oil content in plants.

In *Arabidopsis*, Lec1 has been shown to regulate the expression of fatty acid biosynthetic genes and Lec1 has also been shown to be involved in embryo development (Mu et al., *Plant Physiology* (2008) 148: 1042-1054; Lotan et al. (1998) *Cell*, Vol. 93, 1195-1205, June 26; PCT publication number WO/1998037184 & U.S. Pat. Nos. 6,235,975, 6,320,102, 6,545,201; PCT publication no. WO/2001064022 & U.S. Pat. No. 6,781,035, Braybrook, S. A. and Harada, J. J. (2008) *Trends Plant Sci* 13(12): 1360-1385).

WO 99/67405 describes leafy cotyledon1 genes and their uses. A maize Lec1 homologue of the *Arabidopsis* embryogenesis controlling gene AtLEC1 has been shown to increase oil content and transformation efficiencies in plants. See, for example, WO 03001902 and U.S. Pat. No. 6,512,165.

Other polypeptides that influence ovule and embryo development and stimulate cell growth, such as, Lec1, Kni, WUSCHEL, Zwille and Aintegumeta (ANT) allow for increased transformation efficiencies when expressed in plants. See, for example, U.S. Application No. 2003/0135889, herein incorporated by reference. In fact, a maize Lec1 homologue of the *Arabidopsis* embryogenesis controlling gene AtLEC1, has been shown to increase oil content and transformation efficiencies in plants. See, for example, WO 03001902 and U.S. Pat. No. 6,512,165.

Lec1 homologs may be further identified by using conserved sequence motifs, such as the following amino acid sequence (given in single letter code, with "x" representing any amino acid) (U.S. application No. 60/301,913). Underlined amino acids in the following sequence are those that are conserved in Lec1 but not found in Lec1-related proteins:

REQDxxMPxANVxRIMRxxLPxxAKISDDAKEx IQECVSExlSFxTxEANxRCxxxx RKTxxxE (SEQ ID NO:77)

The terms "FUS3", "FUSCA3" are used interchangeably herein. FUSCA3 is a transcription factor with a conserved VP1/ABI3-like B3 domain which is of functional importance for the regulation of seed maturation in *Arabidopsis thaliana*. It controls developmental timing in *Arabidopsis* through the hormones gibberellin and abscisic acid and is itself regulated by the Lec1 transcription factor (Luerssen et al. (1998) *Plant J* (1998) 15 (6): 755-7; Stone et al. (2001) *Proc Natl Acad Sci* 98 (20): 11806-11811; Lee et al. (2003) *Proc Natl Acad Sci* 100 (4): 2152-2156, U.S. Pat. No. 7,511,190 and U.S. Pat. No. 7,446,241, PCT Publication No. WO1998021336, PCT Publication No. WO2008157226, Braybrook, S. A. and Harada, J. J. (2008) *Trends Plant Sci* 13(12): 1360-1385). U.S. Pat. No. 7,612,253 describes methods of modulating cytokinin related processes in a plant using B3 domain proteins with a number of fusca3 homologs.

"Diacylglycerol acyltransferase" or "DGAT" (also known as "acyl-CoA-diacylglycerol acyltransferase" or "diacylglycerol O-acyltransferase") (EC 2.3.1.20) is an integral membrane protein that catalyzes the final enzymatic step in the production of triacylglycerols in plants, fungi and mammals. This enzyme is responsible for transferring an acyl group from acyl-coenzyme-A to the sn-3 position of 1,2-diacylglycerol ("DAG") to form triacylglycerol ("TAG"). DGAT is associated with membrane and lipid body fractions in plants and fungi, particularly, in oilseeds where it contributes to the storage of carbon used as energy reserves. DGAT is known to regulate TAG structure and direct TAG synthesis. Furthermore, it is known that the DGAT reaction is specific for oil synthesis (Lardizabal et al., *J. Biol. Chem.* 276(42):38862-28869 (2001)).

Two different families of DGAT proteins have been identified. The first family of DGAT proteins ("DGAT1") is related to the acyl-coenzyme A: cholesterol acyltransferase ("ACAT") and has been described in U.S. Pat. Nos. 6,100,077 and 6,344,548. A second family of DGAT proteins ("DGAT2") is unrelated to the DGAT1 family and is described in PCT Patent Publication WO 2004/011671 published Feb. 5, 2004. Other references to DGAT genes and their use in plants include PCT Publication No. WO1998/055,631 and U.S. Pat. No. 6,822,141.

"DGAT" and "diacylglycerol acyltransferase" are used interchangeably herein and refer to any member, or combination, of the DGAT1 or DGAT2 family of proteins.

Plant and fungal DGAT genes have been described previously (U.S. Pat. Nos. 7,198,937 and 7,465,565, US Publication No. 20080295204, U.S. application Ser. Nos. 12/470,569 and 12/470,517).

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"Lipid bodies" refer to lipid droplets that usually are bounded by specific proteins and a monolayer of phospholipid. These organelles are sites where most organisms transport/store neutral lipids. Lipid bodies are thought to arise from microdomains of the endoplasmic reticulum that contain TAG-biosynthesis enzymes; and, their synthesis and size appear to be controlled by specific protein components.

"Neutral lipids" refer to those lipids commonly found in cells in lipid bodies as storage fats and oils and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or TAG, respectively (or collectively, acylglycerols). A hydrolysis reaction must occur to release free fatty acids from acylglycerols.

The term "oil" refers to a lipid substance that is liquid at 25° C. and usually polyunsaturated. In contrast, the term "fat" refers to a lipid substance that is solid at 25° C. and usually saturated.

The terms "triacylglycerol", "oil" and "TAGs" are used interchangeably herein, and refer to neutral lipids composed of three fatty acyl residues esterified to a glycerol molecule (and such terms will be used interchangeably throughout the present disclosure herein). Such oils can contain long chain PUFAs (polyunsaturated fatty acids), as well as shorter saturated and unsaturated fatty acids and longer chain saturated fatty acids. Thus, "oil biosynthesis" generically refers to the synthesis of TAGs in the cell (PCT Publication Nos. WO2005063988, WO2007087492, WO2007101273 and WO2007103738, U.S. Pat. No. 7,812,216).

Oil and protein content in seeds can be determined using Near Infrared Spectroscopy by methods familiar to one skilled in the art (Agelet, et al. (2012) Journal of Agricultural and Food Chemistry, 60(34): 8314-8322). An apparatus and methods for NIR analysis of single seeds and multiple seeds has been described in U.S. Pat. No. 7,508,517, herein incorporated by reference. Additional methods for the analysis of seed composition are provided in U.S. Pat. No. 8,143,473, herein incorporated by reference.

*Medicago truncatula* is a small legume native to the Mediterranean region that is used in genomic research. This species has been used as a model organism for legume biology because it has a small diploid genome, is self-fertile, has a rapid generation time and prolific seed production, and is amenable to genetic transformation.

The term "sucrose synthase" (SUS) refers to an enzyme used in carbohydrate metabolism that catalyzes the reversible conversion of sucrose and uridine diphosphate (UDP) to UDP-glucose and fructose in vitro. The terms "Soybean sucrose synthase 2" and "GmSuS" are used interchangeably herein. The Soybean sucrose synthase gene is from genomic locus Glyma13g17420.

The term "germination" refers to the process by which a dormant seed begins to sprout and grow into a seedling.

"Normal germination", as used herein, refers to a germination rate for seed of a transgenic plant comprising the recombinant DNA construct that is within at least 85%, 86%, 87%, 88%, 89%, 90%, 91%, 92%, 93%, 94%, 95%, 96%, 97%, 98%, 99% or 100% of the observed germination rate, under the same conditions, for seed of a corresponding control plant that does not comprise the recombinant DNA construct.

In an embodiment of the present invention, the "cis-acting transcriptional regulatory elements" from the promoter sequence disclosed herein can be operably linked to "cis-acting transcriptional regulatory elements" from any heterologous promoter. Such a chimeric promoter molecule can be engineered to have desired regulatory properties. In an embodiment of this invention a fragment of the disclosed promoter sequence that can act either as a cis-regulatory sequence or a distal-regulatory sequence or as an enhancer sequence or a repressor sequence, may be combined with either a cis-regulatory or a distal regulatory or an enhancer sequence or a repressor sequence or any combination of any of these from a heterologous promoter sequence.

In a related embodiment, a cis-element of the disclosed promoter may confer a particular specificity such as conferring enhanced expression of operably linked polynucleotide molecules in certain tissues and therefore is also capable of regulating transcription of operably linked polynucleotide molecules. Consequently, any fragments, portions, or regions of the promoter comprising the polynucleotide sequence shown in SEQ ID NO: 3 can be used as regulatory polynucleotide molecules.

Promoter fragments that comprise regulatory elements can be added, for example, fused to the 5' end of, or inserted within, another promoter having its own partial or complete regulatory sequences (Fluhr et al., Science 232:1106-1112, 1986; Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant Mol. Biol. 15:373-381, 1991; 1987; Aryan et al., Mol. Gen. Genet. 225:65-71, 1991).

Cis elements can be identified by a number of techniques, including deletion analysis, i.e., deleting one or more nucleotides from the 5' end or internal to a promoter; DNA binding protein analysis using DNase I footprinting; methylation interference; electrophoresis mobility-shift assays, in vivo genomic footprinting by ligation-mediated PCR; and other conventional assays; or by sequence similarity with known cis element motifs by conventional sequence comparison methods. The fine structure of a cis element can be further studied by mutagenesis (or substitution) of one or more nucleotides or by other conventional methods (see for example, *Methods in Plant Biochemistry and Molecular Biology*, Dashek, ed., CRC Press, 1997, pp. 397-422; and *Methods in Plant Molecular Biology*, Maliga et al., eds., Cold Spring Harbor Press, 1995, pp. 233-300).

Cis elements can be obtained by chemical synthesis or by cloning from promoters that include such elements, and they can be synthesized with additional flanking sequences that contain useful restriction enzyme sites to facilitate subsequent manipulation. Promoter fragments may also comprise other regulatory elements such as enhancer domains, which may further be useful for constructing chimeric molecules.

Methods for construction of chimeric and variant promoters of the present invention include, but are not limited to, combining control elements of different promoters or duplicating portions or regions of a promoter (see for example, U.S. Pat. No. 4,990,607; U.S. Pat. No. 5,110,732; and U.S. Pat. No. 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In an embodiment of the present invention, the soy sucrose synthase promoter disclosed herein can be modified. Those skilled in the art can create promoters that have variations in the polynucleotide sequence. The polynucleotide sequence of the promoter of the present invention as shown in SEQ ID NO: 8 may be modified or altered to enhance their control characteristics. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

The present invention encompasses functional fragments and variants of the promoter sequence disclosed herein.

A "functional fragment" herein is defined as any subset of contiguous nucleotides of the promoter sequence disclosed herein, that can perform the same, or substantially similar function as the full length promoter sequence disclosed herein. A "functional fragment" with substantially similar function to the full length promoter disclosed herein refers to a functional fragment that retains largely the same level of activity as the full length promoter sequence and exhibits the same pattern of expression as the full length promoter sequence. A "functional fragment" of the promoter sequence disclosed herein exhibits constitutive expression.

An embodiment of this invention is a functional fragment of SEQ ID NO: 8, that comprises at least 50, 100, 200, 300, 400, 500, 1000, 1500, 2000, 2500 or 3000 contiguous nucleotides from the 3' end of the polynucleotide sequence of SEQ ID NO: 8, SEQ ID NO: 81 or SEQ ID NO: 85.

A "variant", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof. Variant polynucleotides also encompass sequences derived from a mutagenic and recombinogenic procedure such as DNA shuffling. With such a procedure, one or more cis-elements for the promoter can be manipulated to create a new enhancer domain. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Substitutions, deletions, insertions or any combination thereof can be combined to produce a final construct.

For polynucleotides, naturally occurring variants can be identified with the use of well-known molecular biology techniques, such as, for example, with polymerase chain reaction (PCR) and hybridization techniques as outlined herein. Generally, variants of a particular polynucleotide of the invention will have at least about 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein. A biologically active variant of a polynucleotide of the invention may differ from that sequence by as few as 1-15 nucleic acid residues, as few as 1-10, such as 6-10, as few as 10, 9, 8, 7, 6, 5, 4, 3, 2, or even 1 nucleic acid residue.

The promoter of the present invention may also be a promoter which comprises a nucleotide sequence hybridizable under stringent conditions with the complementary strand of the nucleotide sequence of SEQ ID NO: 8, SEQ ID NO: 81 or SEQ ID NO: 85.

Hybridization of such sequences may be carried out under stringent conditions. The terms "stringent conditions" and "stringent hybridization conditions" as used herein refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing).

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

Stringent conditions may also be achieved with the addition of destabilizing agents such as formamide.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ (thermal melting point) can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See also Sambrook.

In an embodiment of the current invention, isolated sequences that have seed-specific promoter activity and which hybridize under stringent conditions to the soybean sucrose synthase promoter sequence disclosed herein, or to fragments thereof, are encompassed by the present invention. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein.

It is well understood by those skilled in the art that different terminator sequences may be used for the constructs described in the current invention. Terminators include, but are not limited to, bean phaseolin 3' terminator (WO 2004/071467), *Glycine max* Myb2 3' (U.S. application Ser. No. 12/486,793), *Glycine max* kunitz trypsin inhibitor 3' (WO 2004/071467), *Glycine max* BD30 (also called P34) 3' (WO 2004/071467), *Pisum sativum* legumin A2 3' (WO 2004/071467), and *Glycine max* albumin 2S 3' (WO 2004/071467).

In addition, WO 2004/071467 and U.S. Pat. No. 7,129,089 describe the further linking together of individual promoter/gene/transcription terminator cassettes in unique combinations and orientations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination or orientations. In so doing, any combination and orientation of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, *CABIOS.* 5:151-153 (1989); Higgins, D. G. et al., *Comput. Appl. Biosci.* 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Compositions:

A composition of the present invention is a plant comprising in its genome any of the recombinant DNA constructs (including any of the suppression DNA constructs) of the present invention (such as any of the constructs discussed above). Compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit altered oil content or used in a breeding program to produce hybrid seed, which can be grown to produce plants that would exhibit such altered oil content.

The modified seed and grain of the invention can also be obtained by breeding with transgenic plants, by breeding between independent transgenic events, by breeding of plants with one or more alleles (including mutant alleles) of genes encoding the proteins of the invention. Breeding, including introgression of transgenic and mutant loci into elite breeding germplasm and adaptation (improvement) of breeding germplasm to the expression of transgenes and mutant alleles, can be facilitated by methods such as by marker assisted selected breeding.

Embodiments of the current invention include:

In one embodiment, a recombinant DNA construct comprising at least one heterologous polynucleotide encoding a polypeptide selected from the group consisting of an ODP1 polypeptide, a Lec1 polypeptide and a FUSCA3 polypeptide, wherein the at least one polynucleotide is operably linked to a soybean or a *Medicago truncatula* sucrose synthase promoter, wherein expression of said polypeptide in a transgenic soybean seed comprising said recombinant DNA construct results in an increased oil content in the transgenic soybean seed, when compared to a control soybean seed not comprising the recombinant DNA construct.

In another embodiment, a recombinant DNA construct comprising at least one heterologous polynucleotide encoding a polypeptide selected from the group consisting of an ODP1 polypeptide, a Lec1 polypeptide and a FUSCA3 polypeptide, wherein the at least one polynucleotide is operably linked to a seed-specific sucrose synthase promoter from a plant, wherein expression of said polypeptide in a transgenic soybean seed comprising said recombinant DNA construct is expressed in developing seeds in synchrony with oil and protein accumulation, and results in an increased oil content in the transgenic soybean seed, when compared to a control soybean seed not comprising the recombinant DNA construct. The seed-specific sucrose synthase promoter may be from an oilseed plant. The seed-specific sucrose synthase promoter may be from a legume plant.

In another embodiment, said transgenic soybean seed comprising said recombinant DNA construct has normal germination, when compared to a control soybean seed not comprising the recombinant DNA construct.

In another embodiment, said transgenic soybean seed comprising said recombinant DNA construct has a germination rate that is at least 85%, 86%, 87%, 88%, 89%, 90%, 91%, 92%, 93%, 94%, 95%, 96%, 97%, 98%, 99% or 100% of the observed germination rate, under the same conditions, when compared to a control soybean seed not comprising the recombinant DNA construct.

In another embodiment, the soybean sucrose synthase promoter comprises a nucleic acid sequence selected from the group consisting of: (a) the nucleic acid sequence of SEQ ID NO: 8, (b) a nucleic acid sequence with at least 95% sequence identity to the nucleic acid sequence of SEQ ID NO: 8, (c) a nucleic acid sequence that hybridizes to SEQ ID NO: 8 under stringent conditions; and (d) a nucleic acid sequence comprising a functional fragment of (a), (b) or (c).

In another embodiment, the soybean sucrose synthase promoter is an allele of SEQ ID NO: 8.

In another embodiment, the soybean sucrose synthase promoter differs from SEQ ID NO: 8 in at least one way as described in FIG. 4.

In another embodiment, the *Medicago truncatula* sucrose synthase promoter comprises a nucleic acid sequence selected from the group consisting of: (a) the nucleic acid sequence of SEQ ID NO: 81 or SEQ ID NO: 85, (b) a nucleic acid sequence with at least 95% sequence identity to the nucleic acid sequence of SEQ ID NO: 81 or SEQ ID NO:85, (c) a nucleic acid sequence that hybridizes to SEQ ID NO: 81 or SEQ ID NO:85 under stringent conditions; and (d) a nucleic acid sequence comprising a functional fragment of (a), (b) or (c).

In another embodiment, the *Medicago truncatula* sucrose synthase promoter is an allele of SEQ ID NO: 81 or SEQ ID NO: 85.

In another embodiment, the *Medicago truncatula* sucrose synthase promoter differs from SEQ ID NO:81 in at least one of the following ways: nt 67 is a T, nt 489 is a C, nts 553-555 (TTG) are deleted, nt 629 is an A, nt 649 is a C, nt 715 is an A, nt 784 is a C, nt 800 is a G, nt 893 is a G, nt 1166 is an A, nt 1535 is deleted (T), nt 1700 is a G, nt 1718 is a C, nt 1857-1880 are deleted (ATTTTAGAATATG-CAATAAAATTG; SEQ ID NO: 101), nt 1953 is a G, nt 2038 is deleted (A), there is a 25 bp insertion between nt 2224 and 2225 (AGGCTTGAGGAATAAGATAAGACT-TGT; SEQ ID NO: 102), an A is inserted between nt 2225 and 2226, nt 2421 is a G, a C is inserted between nt 2734 and 2735 and nt 2881 is a T.

In another embodiment, the ODP1 polypeptide comprises an amino acid sequence with at least 80%, 85%, 90%, 95% or 100% identity to SEQ ID NO: 30 or SEQ ID NO: 70.

In another embodiment, the ODP1 polypeptide is an allele of SEQ ID NO: 30 or SEQ ID NO: 70.

In another embodiment, the ODP1 polypeptide comprises two APETALA2 (AP2) domains.

ODP1 sequences have also been disclosed in PCT Publication Number WO2010114989, US patent number U.S. Pat. No. 7,157,621, and US20100242138, each of which are incorporated herein by reference.

In one embodiment, the Lec1 polypeptide comprises an amino acid sequence with at least 80%, 85%, 90%, 95% or 100% identity to SEQ ID NO: 17, 20, 25 or 65.

In another embodiment, the Lec1 polypeptide is an allele of SEQ ID NO: 17, 20, 25 or 65.

In another embodiment, the Lec1 polypeptide comprises the amino acid sequence of SEQ ID NO:77.

Lec1 sequences have also been disclosed in the following: U.S. Pat. No. 7,294,754; U.S. Pat. No. 6,825,397; U.S. Pat. No. 7,812,216; US Publication Numbers US20100319086, US20110162101, US20110099665 and US20080313770; and U.S. Pat. No. 7,317,146; each of which is incorporated herein by reference.

In one embodiment, the FUSCA3 polypeptide comprises an amino acid sequence with at least 80%, 85%, 90%, 95% or 100% identity to SEQ ID NO: 32, 38, 45 or 49.

In another embodiment, the FUSCA3 polypeptide is an allele of SEQ ID NO: 32, 38, 45 or 49.

In another embodiment, the recombinant construct further comprises a second heterologous polynucleotide encoding a DGAT polypeptide operably linked to a seed-specific promoter. In one embodiment, the second polynucleotide is a DGAT1 polypeptide. In one embodiment, the DGAT1 polypeptide comprises an amino acid sequence with at least 80%, 85%, 90%, 95% or 100% sequence identity to SEQ ID NO: 55.

In another embodiment, the DGAT1 polypeptide is an allele of SEQ ID NO: 55.

In one embodiment, the second polynucleotide is a DGAT2 polypeptide. In one embodiment, the DGAT2 polypeptide comprises an amino acid sequence with at least 80%, 85%, 90%, 95% or 100% sequence identity to SEQ ID NO: 60.

In another embodiment, the DGAT2 polypeptide is an allele of SEQ ID NO: 60.

DGAT sequences have also been described in the following: US Publication Numbers US20080295204, US20090293152, US20090293151, US20090158460, US20090293150 and US20090291479; U.S. Pat. No. 7,273,746 and U.S. Pat. No. 7,267,976; and PCT Publication No. WO2011062748; each of which is incorporated herein by reference.

In one embodiment, a plant comprising a first recombinant DNA construct comprising a soybean or a *Medicago truncatula* sucrose synthase promoter operably linked to a first heterologous polynucleotide encoding a first polypeptide selected from the group consisting of an ODP1 polypeptide, a Lec1 polypeptide and a FUSCA3 polypeptide and a second recombinant DNA construct comprising a seed-specific promoter operably linked to a second heterologous polynucleotide encoding a DGAT polypeptide, wherein co-expression of said first polypeptide and said second polypeptide in a transgenic soybean seed comprising said first and said second recombinant DNA constructs results in an increased oil content in the transgenic seed, when compared to a control seed comprising only one, but not both, of the first and the second recombinant DNA constructs. The plant and the seed may be an oilseed plant and seed. The plant and the seed may be a soybean plant and seed.

One embodiment of the invention is a method of increasing oil content of a soybean seed, the method comprising the steps of: (a) introducing into a regenerable soybean cell one or more recombinant DNA constructs as described herein; (b) regenerating a transgenic plant from the regenerable soybean cell of (a) wherein the transgenic plant comprises the recombinant DNA construct; and (c) selecting a transgenic plant of step (b), or a transgenic progeny plant from the transgenic plant of step (b), wherein seed of the transgenic plant or the transgenic progeny plant comprises the recombinant DNA construct and wherein expression of said one or more polypeptides in the transgenic soybean seed comprising said recombinant DNA construct results in an increased oil content in the transgenic soybean seed, when compared to a control soybean seed not comprising said one or more recombinant DNA constructs. The percent oil content of the transgenic soybean seed may be at least 3%, 4%, 5%, 6%, 7%, 8%, 9%, 10%, 11%, 12%, 13%, 14% or 15%.

One embodiment of the invention is a method of increasing oil content of a soybean seed, the method comprising the steps of: (a) introducing into a regenerable soybean cell a first recombinant DNA construct comprising a soybean or a *Medicago truncatula* sucrose synthase promoter operably linked to a first heterologous polynucleotide encoding a first polypeptide selected from the group consisting of an ODP1 polypeptide, a Lec1 polypeptide and a FUSCA3 polypeptide and a second recombinant DNA construct comprising a seed-specific promoter operably linked to a second heterologous polynucleotide encoding a DGAT polypeptide; (b) regenerating a transgenic plant from the regenerable soybean cell of (a) wherein the transgenic plant comprises the first and the second recombinant DNA constructs; and (c) selecting a transgenic plant of step (b), or a transgenic progeny plant from the transgenic plant of step (b), wherein seed of the transgenic plant or the transgenic progeny plant comprises the first and the second recombinant DNA constructs and wherein co-expression of said first polypeptide and said second polypeptide in a transgenic soybean seed comprising said first and said second recombinant DNA constructs results in an increased oil content in the transgenic soybean seed, when compared to a control soybean seed comprising only one, but not both, of the first and the second recombinant DNA constructs. The percent oil content of the transgenic soybean seed may be at least 3%, 4%, 5%, 6%, 7%, 8%, 9%, 10%, 11%, 12%, 13%, 14% or 15%.

One embodiment of the invention is a method of increasing oil content of a soybean seed, the method comprising the steps of: (a) introducing into a first regenerable soybean cell a first recombinant DNA construct comprising a soybean or a *Medicago truncatula* sucrose synthase promoter operably linked to a first heterologous polynucleotide encoding a first polypeptide selected from the group consisting of an ODP1 polypeptide, a Lec1 polypeptide and a FUSCA3 polypeptide; (b) regenerating a first transgenic plant from the first regenerable soybean cell of (a) wherein the transgenic plant comprises the first recombinant DNA construct; (c) introducing into a second regenerable soybean cell a second recombinant DNA construct comprising a seed-specific promoter operably linked to a second heterologous polynucleotide encoding a DGAT polypeptide; (d) regenerating a second transgenic plant from the second regenerable soybean cell of (c) wherein the transgenic plant comprises the second recombinant DNA construct; (e) crossing the first transgenic plant with the second transgenic plant; and (f) selecting a third transgenic plant from the cross of step (e), wherein seed of the third transgenic plant comprises the first and the second recombinant DNA constructs and wherein co-expression of said first polypeptide and said second polypeptide in said transgenic soybean seed results in an increased oil content in the transgenic soybean seed, when compared to a control soybean seed comprising only one, but not both, of the first and the second recombinant DNA constructs. The percent oil content of the transgenic soybean seed may be at least 3%, 4%, 5%, 6%, 7%, 8%, 9%, 10%, 11%, 12%, 13%, 14% or 15%.

One embodiment of the invention is a method of increasing oil content of a soybean seed, the method comprising the steps of:

(a) crossing the following:

(i) a first transgenic soybean plant comprising a first recombinant DNA construct comprising a soybean or a *Medicago truncatula* sucrose synthase promoter operably linked to a first heterologous polynucleotide encoding a first polypeptide selected from the group consisting of an ODP1 polypeptide, a Lec1 polypeptide and a FUSCA3 polypeptide; with (ii) a second transgenic soybean plant comprising a second recombinant DNA construct comprising a seed-specific promoter operably linked to a second heterologous polynucleotide encoding a DGAT polypeptide; and (b) selecting a third transgenic plant from the cross of step (a), wherein seed of the third transgenic plant comprises the first and the second recombinant DNA constructs and wherein co-expression of said first polypeptide and said second polypeptide in said transgenic soybean seed results in an increased oil content in the transgenic soybean seed, when compared to a control soybean seed comprising only one, but not both, of the first and the second recombinant DNA constructs. The percent oil content of the transgenic soybean seed may be at least 3%, 4%, 5%, 6%, 7%, 8%, 9%, 10%, 11%, 12%, 13%, 14% or 15%.

In one embodiment, a transgenic soybean seed comprising a recombinant DNA construct comprising a soybean or a *Medicago truncatula* sucrose synthase promoter operably linked to a heterologous polynucleotide encoding a polypeptide selected from the group consisting of an ODP1 polypeptide, a Lec1 polypeptide and a FUSCA3 polypeptide, wherein expression of said polypeptide in said transgenic soybean seed comprising said recombinant DNA construct results in an increased oil content in the transgenic seed, when compared to a control soybean seed not comprising the recombinant DNA construct.

In one embodiment, the percent increase in oil content is at least 10%. In additional embodiments, the percent increase is at least 20%, 30%, 40%, 50%, 60%, 70% or 80%.

In one embodiment, a transgenic soybean seed comprising a first recombinant DNA construct comprising a soybean or a *Medicago truncatula* sucrose synthase promoter operably linked to a first heterologous polynucleotide encoding a first polypeptide selected from the group consisting of an ODP1 polypeptide, a Lec1 polypeptide and a FUSCA3 polypeptide and a second recombinant DNA construct comprising a seed-specific promoter operably linked to a second heterologous polynucleotide encoding a DGAT polypeptide, wherein co-expression of said first polypeptide and said second polypeptide in a transgenic soybean seed comprising said first and said second recombinant DNA constructs results in an increased oil content in the transgenic seed, when compared to a control soybean seed comprising only one, but not both, of the first and the second recombinant DNA constructs.

In one embodiment, the percent increase in oil content is at least 10%. In additional embodiments, the percent increase is at least 20%, 30%, 40%, 50%, 60%, 70% or 80%.

In the above embodiments, the control seed comprising only one, but not both, of the first and the second recombinant DNA constructs may be either: (a) a control seed comprising the first recombinant DNA construct but not comprising the second recombinant DNA construct, or (b) a control seed comprising the second recombinant DNA construct but not comprising the first recombinant DNA construct.

Additional embodiments include a vector, cell, plant, or seed comprising one or more of the recombinant DNA constructs described in the present invention.

The invention also encompasses regenerated, mature and fertile transgenic plants comprising one or more of the recombinant DNA constructs described above, transgenic seeds produced therefrom, T1 and subsequent generations. The transgenic plant cells, tissues, plants, and seeds may comprise at least one recombinant DNA construct of interest.

In another embodiment, the plant or seed comprising the recombinant DNA construct described herein may be at least one selected from the group consisting of: a dicotyledonous plant or seed; a legume plant or seed; an oilseed plant or seed; and a soybean plant or seed.

In another embodiment, the transgenic soybean seeds of the invention may be processed to yield soy oil, soy products and/or soy by-products. Soy products and by-products are described in U.S. Pat. No. 8,143,473, herein incorporated by reference.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Identification and Cloning of the Soy Sucrose Synthase Promoter

The *Arabidopsis* Sucrose Synthase 2 gene has been described previously (PCT Publication No. WO 2010/114989) and the nucleotide and amino acid sequences are set forth in SEQ ID NO: 1 and SEQ ID NO: 2, respectively. A soybean homolog of the *Arabidopsis* Sucrose Synthase 2 gene was identified by conducting BLAST (Basic Local Alignment Search Tool; Altschul et al., *J. Mol. Biol.* 215: 403-410 (1993)) searches for similarity to sequences contained in the Soybean Genome Project, DoE Joint Genome Institute "Glyma1.01" gene set. Specifically, the *Arabidopsis* Sucrose Synthase 2 amino acid sequence (SEQ ID NO: 2) was used with the TBLASTN algorithm provided by National Center for Biotechnology Information (NCBI) with default parameters except the Filter Option was set to OFF.

The soybean homolog to the *Arabidopsis* Sucrose Synthase 2 gene identified corresponded to Glyma13g17420 and the predicted genomic, cDNA, CDS and corresponding amino acid sequences from Glyma are set forth in SEQ IDs NO: 3-6, respectively.

Soybean cDNA libraries from developing soybean (e.g. cDNA library sdp3c) were prepared, clones sequenced and sequence was analyzed as described in U.S. Pat. No. 7,157,621 (the contents of which are herein incorporated by reference). A similar TBLASTN search against sequences from these soybean cDNA libraries identified a cDNA (EST sdp3c.pk014.n18) with a 5' end that differed from that predicted in the Glyma13g17420 cDNA sequence (SEQ ID NO: 4) in that the intron was splice differently. The sequence for the 5' end of EST sdp3c.pk014.n18 that was sequenced is set forth in SEQ ID NO: 7. The CDS from sdp3c.pk014.n18 appears to be the same as that for Glyma13g17420 (SEQ ID NO: 5). The soybean homolog to the *Arabidopsis* sucrose synthase 2 gene set forth in SEQ ID NO: 5 was named GmSus.

A region of genomic DNA upstream of the start codon of GmSus (SEQ ID NO: 5) was identified from the Glyma database by conducting BLAST searches as a promoter region and the sequence is set forth in SEQ ID NO: 8. FIG. 1 shows a schematic of the GmSus promoter region.

The identified GmSus promoter region encodes the 5' UTR from the cDNA transcript (bp 2101 to 3191 from SEQ ID NO: 8) as well as an intron (bp 2134 to 3168 from SEQ ID NO: 8). The 5' UTR region and intron was included as part of the promoter region as it contained an AW box (AW2 in FIG. 1) from bp 2662 to 2675 of SEQ ID NO: 8 within the intron. Another AW box (AW1 in FIG. 1) occurs from bp 616 to bp 629 of SEQ ID NO: 8. AW boxes consist of the nucleotide sequence [CnTnG](n)7[CG](SEQ ID NO:78), where n is any nucleotide, and AW boxes are important binding sites for transcription factors such as wri1 in *Arabidopsis* (Maeo, K et al. (2009) *Plant Journal* 60(3): 476-487).

Genomic DNA was isolated from leaves of approximately 4 week old soy 93B86 plants using the DNEASY® Plant Mini Kit (Qiagen, Valencia, Calif.) and following the manufacture's protocol. The GmSus promoter region (SEQ ID NO:8) was PCR-amplified from 93B86 genomic DNA using oligonucleotides GmSuSyProm-5 (SEQ ID NO:9) and GmSuSyProm-5 (SEQ ID NO:10) with the PHUSION™ High-Fidelity DNA Polymerase (Cat. No. F553S, Finnzymes Oy, Finland), following the manufacturer's protocol. The resulting DNA fragment was cloned into the pCR®-BLUNT® cloning vector using the ZERO BLUNT® PCR Cloning Kit (Invitrogen Corporation), following the manufacturer's protocol, to produce pLF284 (SEQ ID NO:11).

The EcoRI fragment of pLF284 (SEQ ID NO: 11), containing the GmSus promoter region (called GmSusPro), was cloned into the EcoRI site of pNEB193 (New England BioLabs, Beverly, Mass.) to produce pKR1963 (SEQ ID NO: 12).

Plasmid pKR1543, which was previously described in PCT Publication No. WO 2011/079005 (published on Jun. 30, 2011, the contents of which are herein incorporated by reference), was digested with NotI/XbaI and the fragment containing the Leg terminator, previously described in PCT Publication No. WO 2004/071467 (published on Aug. 26, 2004, the contents of which are herein incorporated by reference) was cloned into the NotI/XbaI fragment of pKR1963 (SEQ ID NO: 12), containing the GmSusPro, to produce pKR1964 (SEQ ID NO: 13).

The BsiWI fragment of pKR1964 (SEQ ID NO: 13), containing the GmSusPro, was cloned into the BsiWI site of pKR325, previously described in PCT Publication No. WO 2004/071467, to produce pKR1965 (SEQ ID NO: 14). Plasmid pKR1965 contains a NotI site flanked by the GmSusPro and the Leg terminator as well as the hygromycin B phosphotransferase gene [Gritz, L. and Davies, J. (1983) *Gene* 25:179-188], flanked by the T7 promoter and transcription terminator, a bacterial origin of replication (ori) for selection and replication in *E. coli* and the hygromycin B phosphotransferase gene, flanked by the 35S promoter [Odell et al., (1985) *Nature* 313:810-812] and NOS 3' transcription terminator [Depicker et al., (1982) *J. Mol. Appl. Genet.* 1:561:570](35S/hpt/NOS3' cassette) for selection in soybean. In this way, polynucleotides (e.g., protein-coding regions) flanked by NotI sites can be cloned into the NotI site of pKR1965 (SEQ ID NO: 14) and expressed in soy.

Example 2

Cloning Lec1, Fusca3 and ODP1 Homologs from Soybean

GmLec1 from cDNA:

Soybean cDNA library se2, derived from developing soybean seeds (*Glycine max* L.) harvested at 13 days after flowering (DAF) was prepared, cDNA clones were sequenced and the sequence was analyzed as described in U.S. Pat. No. 7,157,621.

A cDNA clone (se2.11d12) was identified from cDNA library se2 with homology to transcription factor LEAFY COTYLEDON1 (Lec1) (Lotan, T. et al. (1998) *Cell* 93(7): 1195-1205).

The cDNA clone was fully sequenced by methods described in U.S. Pat. No. 7,157,621 and its sequence is set forth in SEQ ID NO: 15. This clone appears to have 2 separate cDNA clones inserted into it but the sequence from 38-718 bp is 100% identical to the coding sequence of lec1b (NCBI Accession #EU088289.1 GI:158525282) and to the CDS of Glyma17g00950 based on a blast comparison. The coding sequence from clone se2.11d12, which corresponds to that of Glyma17g00950, is shown in SEQ ID NO:16 and the encoded amino acid sequence is shown in SEQ ID NO:17.

A separate cDNA clone (se1.pk0042.d8) identified from cDNA library se1, derived from developing soybean seeds (*Glycine max* L.) harvested at 6-10 DAF and described in U.S. Pat. No. 7,157,621, also contained a lec1 homolog as determined by blast analysis. The full insert sequence of se1.pk0042.d8 is shown in SEQ ID NO:18. The sequence from cDNA clone se1.pk0042.d8 is 99% identical to the coding sequence of lec1a (NCBI Accession #EU088288.1 GI:158525280) and 100% identical to the CDS of Glyma07g39820 based on a blast comparison. The coding sequence from clone se1.pk0042.d8 appears to be 2 nt short of the ATG but is shown in SEQ ID NO: 19 with the correct start as compared to Glyma07g39820. The corresponding encoded amino acid sequence is shown in SEQ ID NO: 20.

DNA was also prepared from an aliquot of cDNA library se2 using the QIAprep® Spin Miniprep Kit (Qiagen Inc., Valencia, Calif.) following the manufacturer's protocol. The DNA from the cDNA library was used as template in a PCR reaction using oligonucleotides SA275 (SEQ ID NO: 21) and SA276 (SEQ ID NO: 22), using the "Platinum"-brand Taq DNA polymerase (Life Technologies), following the manufacturer's protocol. The PCR fragment was cloned using the pCR®8GW/TOPO® TA Cloning Kit (Invitrogen Corporation) to produce plasmid Glyma17g00950/pCR8/GW/TOPO (SEQ ID NO: 23). The CDS from the PCR product contained in Glyma17g00950/pCR8/GW/TOPO (SEQ ID NO: 23), named GmLec1, is set forth in SEQ ID NO: 24 and the corresponding amino acid sequence of GmLec1 is set forth in SEQ ID NO: 25. It should be noted that both the CDS and amino acid sequence of GmLec1 are different than those corresponding to either Glyma17g00950 or Glyma07g39820. An alignment comparing the amino acid sequences of Glyma17g00950 (SEQ ID NO: 17), Glyma07g39820 (SEQ ID NO: 20) and GmLec1 (SEQ ID NO: 25) is shown in FIG. 2.

GmLec1 gene was PCR-amplified from Glyma17g00950/pCR8/GW/TOPO (SEQ ID NO: 23) using oligonucleotides Gmlec-5 (SEQ ID NO:26) and Gmlec-3 (SEQ ID NO:27) with the PHUSION™ High-Fidelity DNA Polymerase (Cat. No. F553S, Finnzymes Oy, Finland), following the manufacturer's protocol. The PCR fragment was cloned into the pCR®-BLUNT® cloning vector using the ZERO BLUNT® PCR Cloning Kit (Invitrogen Corporation), following the manufacturer's protocol, to produce pLF275 (SEQ ID NO: 28).

NotI Fragment Containing GmODP1:

The soybean ODP (GmODP1) is described in U.S. Pat. No. 7,157,621. The cloning of GmODP1 with flanking NotI sites into plasmid KS334 was previously described in PCT Publication No. WO 2010/114989 (published on Oct. 7, 2010, the contents of which are herein incorporated by reference). It should be noted that there is a typo in the map of KS334 (SEQ ID NO: 14 in WO2010/114989) and that there should be an additional 3 nucleotides (TGA) at position 1237 to form a stop codon and end the CDS in KS334. The CDS and amino acid sequence of GmODP1 from WO2010/114989 are set forth here in SEQ ID NO: 29 and SEQ ID NO: 30, respectively.

PCR GmFusca3-1 & GmFusca3-2 from cDNA:

Based on BLAST analysis of the soy genome sequence database, Glyma16g05480 was identified with homology to the Fusca3 transcription factor (Luerssen, H. et al. (1998) *Plant Journal,* 15(6): 755-764). The predicted CDS and amino acid sequence for Glyma16g05480 as predicted in the Glyma database are shown in SEQ ID NO: 31 and SEQ ID NO: 32, respectively.

DNA prepared from an aliquot of cDNA library se2 (described above) was used as template in a PCR reaction using oligonucleotides SA278 (SEQ ID NO: 33) and SA279 (SEQ ID NO: 34), using the "Platinum"-brand Taq DNA polymerase (Life Technologies), following the manufacturer's protocol. The PCR fragment was cloned using the pCR®8GW/TOPO® TA Cloning Kit (Invitrogen Corporation) to produce plasmid Glyma16g05480/pCR8/GW/TOPO (SEQ ID NO: 35). The cDNA insert in Glyma16g05480/pCR8/GW/TOPO (SEQ ID NO: 35) was sequenced and the sequence is set forth in SEQ ID NO: 36.

The cDNA insert (SEQ ID NO: 36) was analyzed by BLAST and was found to be different than what was predicted for Glyma16g05480 (SEQ ID NO: 31). The sequence also did not code for a perfect CDS as early stop codons within were found. Comparison of the cDNA insert sequence to the genome sequence in Glyma revealed the 3' end of cDNA insert to be 100% identical to the predicted coding sequence of Glyma19g27340. The predicted CDS and corresponding amino acid sequence of Glyma19g27340 from the Glyma database are set forth in SEQ ID NO: 37 and SEQ ID NO: 38, respectively.

The cDNA insert is larger than the predicted CDS for Glyma 19g27340 (SEQ ID NO: 38) and has an additional 1193 bp at the 5' end. Further comparison of the cDNA insert to genomic sequence upstream of the CDS from Glyma19g27340 (SEQ ID NO: 37) reveals 100% identity, with the exception of a single nucleotide coming from oligo SA278 (SEQ ID NO: 33). The full genomic DNA sequence, from the soy genome database, upstream of and including Glyma19g27340 is set forth in SEQ ID NO: 39.

The cDNA insert (SEQ ID NO: 36) did not code for a complete CDS and it was determined that either an unspliced intron sequence was contained with the cDNA sequence or that an alternate start codon was present. The full length sequence from the cDNA insert (called GmFusca3-2), which may contain introns, was PCR-amplified using oligonucleotides GmFusca3-1-5 (SEQ ID NO: 40) and GmFusca3-3 (SEQ ID NO: 41) with the PHUSION™ High-Fidelity DNA Polymerase (Cat. No. F553S, Finnzymes Oy, Finland), following the manufacturer's protocol.

The PCR fragment was cloned into the pCR®-BLUNT® cloning vector using the ZERO BLUNT® PCR Cloning Kit (Invitrogen Corporation), following the manufacturer's protocol, to produce pLF283 (SEQ ID NO: 42).

The full length cDNA of the resulting PCR product for GmFusca3-2 is shown in SEQ ID NO: 43 and is identical to the original cDNA (SEQ ID NO: 36) except that nucleotide 17 has been changed from C to T to agree with that predicted in Glyma19g27340 genomic DNA sequence. A putative spliced CDS as well as the corresponding encoded amino acid sequence for GmFusca3-2 is shown in SEQ ID NO: 44 and SEQ ID NO: 45, respectively.

A second shorter ORF sequence contained within the cDNA insert (SEQ ID NO: 36), called GmFusca3-1, was PCR-amplified using oligonucleotides GmFusca3-2-5 (SEQ ID NO: 46) and GmFusca3-3 (SEQ ID NO: 41) with the PHUSION™ High-Fidelity DNA Polymerase (Cat. No. F553S, Finnzymes Oy, Finland), following the manufacturer's protocol.

The resulting PCR fragment containing Fusca3-1 was cloned into the pCR®-BLUNT® cloning vector using the ZERO BLUNT® PCR Cloning Kit (Invitrogen Corporation), following the manufacturer's protocol, to produce pLF282 (SEQ ID NO: 47).

The full sequence contains no unspliced introns and the coding sequence as well as the corresponding encoded amino acid sequence of GmFusca3-1 is shown in SEQ ID NO: 48 and 49, respectively.

An alignment comparing the amino acid sequences for Glyma16g05480 (SEQ ID NO: 32) and Glyma19g27340 (SEQ ID NO: 38), as predicted in the Glyma database, along with the predicted spliced sequence for GmFusca3-2 (SEQ ID NO: 45) and for GmFusca3-1 (SEQ ID NO: 49) is shown in FIG. 3.

Example 3

Expressing GmLec1, GmODP1, GmFusca-3-1 and GmFusca3-2 in Soybean Embryos Under Control of the GmSus Promoter The NotI fragment of pLF275 (SEQ ID NO: 28), containing GmLec1, the NotI fragment of KS334, containing GmODP1, the NotI fragment of pLF282 (SEQ ID NO: 47), containing GmFusca3-1, and the NotI fragment of pLF283 (SEQ ID NO: 42), containing GmFusca3-2 were cloned into the NotI site of pKR1965 (SEQ ID NO: 14) to produce pKR1968 (SEQ ID NO: 50), pKR1971 (SEQ ID NO: 51), pKR1969 (SEQ ID NO: 52) and pKR1970 (SEQ ID NO: 53), respectively. In this way, the respective transcription factors could be expressed behind the soy sucrose synthase promoter (GmSusPro). Plasmid pKR278, previously described in PCT Publication No. WO 2008/147935 (published on Oct. 13, 2009, the contents of which are incorporated by reference), and containing no transcription factor, but having the hygromycin selectable marker, was used as a negative control.

DNA from plasmids pKR1968 (SEQ ID NO: 50), pKR1971 (SEQ ID NO: 51), pKR1969 (SEQ ID NO: 52), pKR1970 (SEQ ID NO: 53) and pKR278 was prepared for particle bombardment into soybean embryogenic suspension culture and transformed exactly as described previously in PCT Publication No. WO 2008/147935. Soybean embryogenic suspension culture was initiated, grown, maintained and bombarded and events were selected and matured on SHaM media also exactly as described in PCT Publication No. WO 2008/147935. A summary of genes, plasmids and model system experiment ("MSE") numbers is shown in Table 1.

TABLE 1

Summary of Genes, Plasmids and Experiments

| Experiment | Plasmid | Gene | SEQ ID NO nt | SEQ ID NO aa |
|---|---|---|---|---|
| MSE 2863 | pKR1968 | GmLec1 | 24 | 25 |
| MSE 2864 | pKR1969 | GmFusca3-1 | 48 | 49 |
| MSE 2865 | pKR1970 | GmFusca3-2 | 44 | 45 |
| MSE 2866 | pKR1971 | GmODP1 | 29 | 30 |
| MSE 2867 | pKR278 | Empty Vector Control | — | — |

Approximately 10-20 matured embryos from each of approximately 30 events per bombardment experiment were lyophilized, ground, oil content was measured by NMR and fatty acid profile was evaluated by FAME-GC analysis exactly as described in PCT Publication No. WO 2008/147935. The results for oil content and fatty acid profile for each event as well as the average of all events (Avg.) and average for the top 5 events having highest oil content (Top5 Avg.) are shown in Table 2.

In Table 2, results are sorted based on oil content from highest to lowest. In Table 2, oil content is reported as a percent of total dry weight (% Oil) and fatty acid content for each fatty acid [palmitic acid (16:0), stearic acid (18:0), oleic acid (18:1), linoleic acid (18:2) & alpha-linolenic acid (18:3)] is reported as a weight % of total fatty acids.

TABLE 2

Summary of Oil Content and Fatty Acid Profiles for Events Expressing GmLec1, GmFusca3-1, GmFusca3-2, GmODP1 or Empty Vector Control

| | % oil | 16:0 | 18:0 | 18:%1 | 18:2 | 18:3 |
|---|---|---|---|---|---|---|
| 2863-3 | 9.9 | 15.6 | 7.0 | 17.9 | 48.3 | 11.2 |
| 2863-21 | 9.3 | 14.7 | 8.8 | 18.5 | 46.5 | 11.5 |
| 2863-24 | 8.6 | 15.5 | 7.9 | 17.1 | 46.1 | 13.4 |
| 2863-13 | 8.2 | 17.1 | 5.9 | 16.3 | 46.4 | 14.4 |
| 2863-6 | 7.7 | 15.3 | 8.6 | 18.9 | 44.0 | 13.3 |
| 2863-29 | 7.6 | 15.8 | 9.0 | 19.1 | 42.3 | 13.8 |
| 2863-11 | 7.4 | 15.8 | 8.1 | 18.4 | 44.2 | 13.5 |
| 2863-30 | 7.1 | 15.9 | 5.7 | 20.5 | 43.8 | 14.1 |
| 2863-23 | 7.1 | 16.5 | 6.3 | 21.0 | 42.1 | 14.1 |
| 2863-7 | 6.8 | 15.9 | 7.8 | 16.2 | 45.5 | 14.6 |
| 2863-22 | 6.6 | 15.7 | 7.7 | 18.4 | 43.9 | 14.3 |
| 2863-25 | 6.4 | 14.6 | 6.5 | 20.6 | 43.1 | 15.2 |
| 2863-5 | 6.4 | 16.7 | 6.2 | 19.0 | 43.2 | 15.0 |
| 2863-19 | 6.2 | 16.2 | 5.7 | 20.4 | 42.7 | 15.1 |
| 2863-8 | 6.1 | 15.9 | 9.7 | 18.7 | 41.6 | 14.2 |
| 2863-14 | 5.9 | 15.8 | 8.3 | 16.9 | 44.1 | 14.9 |
| 2863-10 | 5.8 | 17.2 | 7.1 | 17.4 | 43.9 | 14.5 |

TABLE 2-continued

Summary of Oil Content and Fatty Acid Profiles for Events Expressing GmLec1, GmFusca3-1, GmFusca3-2, GmODP1 or Empty Vector Control

| | % oil | 16:0 | 18:0 | 18:%1 | 18:2 | 18:3 |
|---|---|---|---|---|---|---|
| 2863-2 | 5.7 | 16.7 | 5.7 | 19.8 | 41.9 | 16.0 |
| 2863-1 | 5.6 | 17.0 | 6.1 | 20.1 | 41.9 | 14.9 |
| 2863-9 | 5.3 | 16.6 | 8.7 | 18.9 | 41.5 | 14.3 |
| 2863-26 | 5.3 | 15.2 | 8.3 | 16.4 | 43.9 | 16.2 |
| 2863-28 | 5.3 | 17.2 | 4.5 | 14.9 | 46.3 | 17.1 |
| 2863-27 | 5.0 | 17.5 | 5.6 | 12.9 | 48.1 | 16.0 |
| 2863-4 | 5.0 | 16.9 | 5.6 | 18.9 | 42.4 | 16.2 |
| 2863-20 | 4.9 | 16.3 | 6.0 | 20.1 | 42.4 | 15.2 |
| 2863-16 | 4.7 | 17.9 | 5.0 | 14.1 | 45.9 | 17.1 |
| 2863-17 | 4.2 | 18.1 | 4.1 | 12.7 | 46.1 | 19.1 |
| 2863-15 | 3.2 | 19.3 | 4.6 | 15.1 | 42.2 | 18.8 |
| 2863-12 | 3.2 | 17.6 | 5.1 | 15.3 | 43.5 | 18.5 |
| 2863-18 | 2.5 | 17.3 | 5.6 | 17.0 | 37.8 | 22.4 |
| Avg. | 6.1 | 16.5 | 6.7 | 17.7 | 43.9 | 15.3 |
| Top5 Avg. | 8.7 | 15.6 | 7.6 | 17.7 | 46.2 | 12.7 |
| 2864-10 | 7.6 | 14.9 | 6.2 | 16.4 | 46.5 | 15.9 |
| 2864-15 | 7.6 | 15.0 | 9.2 | 18.6 | 44.3 | 12.9 |
| 2864-25 | 7.5 | 15.9 | 5.5 | 20.3 | 44.1 | 14.2 |
| 2864-12 | 7.3 | 17.3 | 4.9 | 13.4 | 49.8 | 14.5 |
| 2864-18 | 7.2 | 15.2 | 8.6 | 18.1 | 44.5 | 13.6 |
| 2864-6 | 6.9 | 15.3 | 8.7 | 18.6 | 42.7 | 14.8 |
| 2864-26 | 6.8 | 16.2 | 7.3 | 16.9 | 45.1 | 14.5 |
| 2864-7 | 6.8 | 14.8 | 8.1 | 17.8 | 43.8 | 15.4 |
| 2864-28 | 6.2 | 17.6 | 4.5 | 11.2 | 50.4 | 16.4 |
| 2864-19 | 6.0 | 15.6 | 9.4 | 18.8 | 41.6 | 14.6 |
| 2864-1 | 5.9 | 17.1 | 6.8 | 14.7 | 46.3 | 15.2 |
| 2864-17 | 5.8 | 16.8 | 6.9 | 22.0 | 41.4 | 12.9 |
| 2864-2 | 5.8 | 16.6 | 5.0 | 20.7 | 43.4 | 14.5 |
| 2864-9 | 5.7 | 17.2 | 5.8 | 12.7 | 47.1 | 17.2 |
| 2864-22 | 5.6 | 16.6 | 6.3 | 13.8 | 47.3 | 16.0 |
| 2864-4 | 5.6 | 16.0 | 7.6 | 22.1 | 40.6 | 13.8 |
| 2864-27 | 5.0 | 15.8 | 10.0 | 20.8 | 39.2 | 14.3 |
| 2864-3 | 4.9 | 17.4 | 6.5 | 20.7 | 39.8 | 15.6 |
| 2864-11 | 4.6 | 15.4 | 5.3 | 17.4 | 44.2 | 17.8 |
| 2864-30 | 4.4 | 17.4 | 6.7 | 15.2 | 43.2 | 17.5 |
| 2864-29 | 4.1 | 17.2 | 6.8 | 15.5 | 42.0 | 18.5 |
| 2864-8 | 4.0 | 16.9 | 4.9 | 18.4 | 42.1 | 17.7 |
| 2864-31 | 3.8 | 18.1 | 4.9 | 13.5 | 44.4 | 19.1 |
| 2864-14 | 3.7 | 17.1 | 5.5 | 18.5 | 42.4 | 16.5 |
| 2864-24 | 3.6 | 17.4 | 5.8 | 18.8 | 39.7 | 18.4 |
| 2864-5 | 3.5 | 16.2 | 7.7 | 19.0 | 43.6 | 13.5 |
| 2864-21 | 3.3 | 16.4 | 4.6 | 14.4 | 44.2 | 20.4 |
| 2864-13 | 2.9 | 17.6 | 6.0 | 18.6 | 38.8 | 19.1 |
| 2864-23 | 2.6 | 18.4 | 5.1 | 13.3 | 41.7 | 21.5 |
| 2864-20 | 2.5 | 17.9 | 4.7 | 13.5 | 41.8 | 22.2 |
| 2864-16 | 2.1 | 16.0 | 6.2 | 13.2 | 43.9 | 20.6 |
| Avg. | 5.1 | 16.5 | 6.5 | 17.0 | 43.5 | 16.4 |
| Top5 Avg. | 7.5 | 15.7 | 6.9 | 17.3 | 45.9 | 14.2 |
| 2865-7 | 7.6 | 16.5 | 5.6 | 20.1 | 45.0 | 12.7 |
| 2865-24 | 5.9 | 17.6 | 4.1 | 13.9 | 50.5 | 13.9 |
| 2865-29 | 5.6 | 17.1 | 4.1 | 14.5 | 47.8 | 16.6 |
| 2865-14 | 5.1 | 16.1 | 6.2 | 19.6 | 42.5 | 15.6 |
| 2865-27 | 5.1 | 19.3 | 4.0 | 13.7 | 48.2 | 14.8 |
| 2865-23 | 5.0 | 18.9 | 4.1 | 15.8 | 45.9 | 15.3 |
| 2865-8 | 4.9 | 16.9 | 6.2 | 16.1 | 47.5 | 13.3 |
| 2865-25 | 4.8 | 18.3 | 4.1 | 15.2 | 46.6 | 15.8 |
| 2865-21 | 4.7 | 18.4 | 4.4 | 15.3 | 47.0 | 14.9 |
| 2865-1 | 4.5 | 18.9 | 4.2 | 14.4 | 46.8 | 15.8 |
| 2865-13 | 4.3 | 19.3 | 4.1 | 14.5 | 47.9 | 14.3 |
| 2865-12 | 4.3 | 17.1 | 4.8 | 15.8 | 43.0 | 19.3 |
| 2865-20 | 4.1 | 16.8 | 4.1 | 14.6 | 47.6 | 16.9 |
| 2865-28 | 3.6 | 18.4 | 5.6 | 20.2 | 42.1 | 13.7 |
| 2865-18 | 3.4 | 19.2 | 4.7 | 14.9 | 45.0 | 16.2 |
| 2865-11 | 3.3 | 16.8 | 5.5 | 18.2 | 45.1 | 14.5 |
| 2865-30 | 3.0 | 15.5 | 5.3 | 15.5 | 43.3 | 20.5 |
| 2865-6 | 2.9 | 17.2 | 5.5 | 18.1 | 41.2 | 18.1 |
| 2865-15 | 2.9 | 19.2 | 4.2 | 13.2 | 44.7 | 18.6 |
| 2865-5 | 2.8 | 18.6 | 4.6 | 12.2 | 44.1 | 20.5 |
| 2865-22 | 2.4 | 19.8 | 5.1 | 15.6 | 43.4 | 16.0 |
| 2865-10 | 2.3 | 18.0 | 5.4 | 19.2 | 42.8 | 14.6 |
| 2865-9 | 2.1 | 19.4 | 4.4 | 12.0 | 41.1 | 23.1 |
| 2865-2 | 2.0 | 18.7 | 4.4 | 13.3 | 43.8 | 19.8 |
| 2865-3 | 1.9 | 18.0 | 5.5 | 16.0 | 43.0 | 17.4 |
| 2865-19 | 1.6 | 17.9 | 5.3 | 14.0 | 42.7 | 20.1 |

TABLE 2-continued

Summary of Oil Content and Fatty Acid Profiles for Events Expressing GmLec1, GmFusca3-1, GmFusca3-2, GmODP1 or Empty Vector Control

| | % oil | 16:0 | 18:0 | 18:%1 | 18:2 | 18:3 |
|---|---|---|---|---|---|---|
| 2865-4 | 1.4 | 17.9 | 4.5 | 11.7 | 44.5 | 21.5 |
| 2865-16 | 1.3 | 18.2 | 5.5 | 12.9 | 41.0 | 22.3 |
| 2865-17 | 1.1 | 17.7 | 5.4 | 17.9 | 37.3 | 21.7 |
| Avg. | 3.6 | 18.0 | 4.9 | 15.5 | 44.5 | 17.2 |
| Top5 Avg. | 5.9 | 17.3 | 4.8 | 16.4 | 46.8 | 14.7 |
| 2866-10 | 9.8 | 19.0 | 6.3 | 19.8 | 44.6 | 10.3 |
| 2866-23 | 9.6 | 15.5 | 6.2 | 22.1 | 45.2 | 11.0 |
| 2866-12 | 8.4 | 13.5 | 7.0 | 23.3 | 45.1 | 11.1 |
| 2866-13 | 8.1 | 16.0 | 5.6 | 21.6 | 44.2 | 12.6 |
| 2866-5 | 8.1 | 16.7 | 5.7 | 24.3 | 42.5 | 10.8 |
| 2866-1 | 7.8 | 15.6 | 7.1 | 26.0 | 40.1 | 11.2 |
| 2866-9 | 6.6 | 15.5 | 8.5 | 29.6 | 36.0 | 10.4 |
| 2866-3 | 6.6 | 15.4 | 8.9 | 28.9 | 37.0 | 9.7 |
| 2866-7 | 6.6 | 15.7 | 8.9 | 20.0 | 42.2 | 13.1 |
| 2866-18 | 6.5 | 15.8 | 8.7 | 20.3 | 42.7 | 12.5 |
| 2866-6 | 6.3 | 16.0 | 7.7 | 18.7 | 43.2 | 14.4 |
| 2866-26 | 5.6 | 15.9 | 6.9 | 22.9 | 43.0 | 11.3 |
| 2866-29 | 5.6 | 16.4 | 6.3 | 22.9 | 40.7 | 13.7 |
| 2866-21 | 5.5 | 15.7 | 7.8 | 27.2 | 38.5 | 10.8 |
| 2866-20 | 5.4 | 16.4 | 7.3 | 25.0 | 38.6 | 12.7 |
| 2866-11 | 5.2 | 17.6 | 6.1 | 22.8 | 40.5 | 12.9 |
| 2866-4 | 4.7 | 16.6 | 6.5 | 22.7 | 40.0 | 14.2 |
| 2866-8 | 4.7 | 15.8 | 7.6 | 29.4 | 36.1 | 11.1 |
| 2866-16 | 4.6 | 14.5 | 9.2 | 30.6 | 35.2 | 10.5 |
| 2866-27 | 4.5 | 17.6 | 6.7 | 18.8 | 44.8 | 12.1 |
| 2866-15 | 4.5 | 17.0 | 6.2 | 24.2 | 37.8 | 14.8 |
| 2866-24 | 4.4 | 17.3 | 4.9 | 13.1 | 50.6 | 14.1 |
| 2866-30 | 3.7 | 16.7 | 5.8 | 18.5 | 46.1 | 12.9 |
| 2866-2 | 3.7 | 16.6 | 5.9 | 21.3 | 39.6 | 16.6 |
| 2866-31 | 3.6 | 18.1 | 4.8 | 14.6 | 48.6 | 14.0 |
| 2866-19 | 3.5 | 19.3 | 4.8 | 13.9 | 47.3 | 14.7 |
| 2866-28 | 3.5 | 17.1 | 6.7 | 19.9 | 42.8 | 13.5 |
| 2866-17 | 3.4 | 18.0 | 5.0 | 16.2 | 46.2 | 14.6 |
| 2866-14 | 3.3 | 18.7 | 5.3 | 15.0 | 45.1 | 15.8 |
| 2866-22 | 2.5 | 17.2 | 5.2 | 13.8 | 48.3 | 15.5 |
| 2866-25 | 2.0 | 17.8 | 5.3 | 17.1 | 43.8 | 16.1 |
| Avg. | 5.4 | 16.6 | 6.6 | 21.4 | 42.5 | 12.9 |
| Top5 Avg. | 8.8 | 16.2 | 6.2 | 22.2 | 44.3 | 11.2 |
| 2867-5 | 7.6 | 17.2 | 5.7 | 14.5 | 48.9 | 13.7 |
| 2867-24 | 6.2 | 17.9 | 5.1 | 13.1 | 48.6 | 15.3 |
| 2867-18 | 6.0 | 17.9 | 5.7 | 14.5 | 45.0 | 16.8 |
| 2867-19 | 5.7 | 16.1 | 7.1 | 18.1 | 43.2 | 15.5 |
| 2867-20 | 5.5 | 16.8 | 5.8 | 13.3 | 49.6 | 14.5 |
| 2867-29 | 5.4 | 16.2 | 6.4 | 22.4 | 40.3 | 14.7 |
| 2867-2 | 5.2 | 16.4 | 7.7 | 16.6 | 45.3 | 14.0 |
| 2867-15 | 5.1 | 16.8 | 5.8 | 20.0 | 43.1 | 14.4 |
| 2867-7 | 5.0 | 16.7 | 6.5 | 15.4 | 47.9 | 13.5 |
| 2867-28 | 4.9 | 16.9 | 6.6 | 14.2 | 46.7 | 15.6 |
| 2867-13 | 4.8 | 16.8 | 6.4 | 23.9 | 37.7 | 15.2 |
| 2867-26 | 4.8 | 16.2 | 7.4 | 17.8 | 46.2 | 12.5 |
| 2867-1 | 4.7 | 15.8 | 8.5 | 18.7 | 44.3 | 12.7 |

TABLE 2-continued

Summary of Oil Content and Fatty Acid Profiles for Events Expressing GmLec1, GmFusca3-1, GmFusca3-2, GmODP1 or Empty Vector Control

| | % oil | 16:0 | 18:0 | 18:%1 | 18:2 | 18:3 |
|---|---|---|---|---|---|---|
| 2867-16 | 4.7 | 16.1 | 7.7 | 18.2 | 43.4 | 14.7 |
| 2867-30 | 4.6 | 16.2 | 6.2 | 22.5 | 40.6 | 14.6 |
| 2867-11 | 4.6 | 17.5 | 6.4 | 21.6 | 40.4 | 14.1 |
| 2867-25 | 4.6 | 17.1 | 7.2 | 16.5 | 44.2 | 15.1 |
| 2867-23 | 4.4 | 16.5 | 7.0 | 15.5 | 46.7 | 14.4 |
| 2867-14 | 4.2 | 18.2 | 6.0 | 15.2 | 44.5 | 16.0 |
| 2867-6 | 4.2 | 16.1 | 6.5 | 25.8 | 37.5 | 14.2 |
| 2867-9 | 4.2 | 17.0 | 6.5 | 15.3 | 46.3 | 14.9 |
| 2867-8 | 4.1 | 16.2 | 5.2 | 18.7 | 42.1 | 17.9 |
| 2867-10 | 4.0 | 17.1 | 5.5 | 19.4 | 42.6 | 15.3 |
| 2867-27 | 4.0 | 17.1 | 6.6 | 26.4 | 35.6 | 14.4 |
| 2867-21 | 3.8 | 16.3 | 6.1 | 21.2 | 43.5 | 12.9 |
| 2867-17 | 3.4 | 17.7 | 6.6 | 15.9 | 43.8 | 16.0 |
| 2867-12 | 3.4 | 17.3 | 7.0 | 20.9 | 39.3 | 15.5 |
| 2867-31 | 3.4 | 16.5 | 7.4 | 17.9 | 43.5 | 14.7 |
| 2867-4 | 3.2 | 18.2 | 4.8 | 11.0 | 47.6 | 18.4 |
| 2867-22 | 3.0 | 16.9 | 6.3 | 22.0 | 39.2 | 15.6 |
| 2867-3 | 2.3 | 17.9 | 5.8 | 13.6 | 46.0 | 16.6 |
| Avg. | 4.5 | 16.9 | 6.4 | 18.1 | 43.7 | 14.9 |
| Top5 Avg. | 6.2 | 17.2 | 5.9 | 14.7 | 47.1 | 15.2 |

A summary comparing the average oil content and average fatty acid profile for all events in each experiment is shown in Table 3. In Table 3, average oil content is reported as a percent of total dry weight (Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 3 also shows the change in oil content (Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 3

Summary of Average Oil Content and Fatty Acid Profiles for All Events Expressing GmLec1, GmFusca3-1, GmFusca3-2, GmODP1 or Empty Vector Control

| MSE | Vector (Gene) | Avg. Oil | Avg. % Inc | 16:0 | 18:0 | 18:1 | 18:2 | 18:3 |
|---|---|---|---|---|---|---|---|---|
| 2863 | pKR1968 (GmLec1) | 6.1 | 34% | 16.5 | 6.7 | 17.7 | 43.9 | 15.3 |
| 2864 | pKR1969 (GmFusca3-1) | 5.1 | 13% | 16.5 | 6.5 | 17.0 | 43.5 | 16.4 |
| 2865 | pKR1970 (GmFusca3-2) | 3.6 | −21% | 18.0 | 4.9 | 15.5 | 44.5 | 17.2 |
| 2866 | pKR1971 (GmODP1) | 5.4 | 19% | 16.6 | 6.6 | 21.4 | 42.5 | 12.9 |
| 2867 | pKR278 (Control) | 4.5 | 0% | 16.9 | 6.4 | 18.1 | 43.7 | 14.9 |

A summary comparing the average oil content and average fatty acid profile of the top 5 events having the highest oil content for each experiment is shown in Table 4. In Table 4, average oil for the 5 events having highest oil content is reported as a percent of total dry weight (Top5 Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 4 also shows the change in oil content (Top5 Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 4

Summary of Average Oil Content and Fatty Acid Profiles for the Top5 Events Having Highest Oil Contents and Expressing GmLec1, GmFusca3-1, GmFusca3-2, GmODP1 or Empty Vector Control

| MSE | Gene (Vector) | Avg. Oil | Avg. % Inc | 16:0 | 18:0 | 18:1 | 18:2 | 18:3 |
|---|---|---|---|---|---|---|---|---|
| 2863 | GmLec1 (pKR1968) | 8.7 | 41% | 15.6 | 7.6 | 17.7 | 46.2 | 12.7 |
| 2864 | GmFusca3-1 (pKR1969) | 7.5 | 21% | 15.7 | 6.9 | 17.3 | 45.9 | 14.2 |
| 2865 | GmFusca3-2 (pKR1970) | 5.9 | −5% | 17.3 | 4.8 | 16.4 | 46.8 | 14.7 |
| 2866 | GmODP1 (pKR1971) | 8.8 | 43% | 16.2 | 6.2 | 22.2 | 44.3 | 11.2 |
| 2867 | Control (pKR278) | 6.2 | 0% | 17.2 | 5.9 | 14.7 | 47.1 | 15.2 |

Both Tables 3 and 4 demonstrate that expression of GmLec1, GmFusca3-1 and GmODP1 lead to an increase in oil content in soy.

Example 4

Co-Expressing GmLec1, GmODP1, GmFusca-3-1 and GmFusca3-2 with GmDGAT1cAII in Soybean Embryos Plasmid pKR1520 was previously described in PCT Publication No. WO 2009/143397 (published on Nov. 26, 2009, the contents of which are incorporated by reference) and contains a modified soy DGAT1 (called GmDGAT1cAII here and called GM-DGAT1c9c10c11 in WO 2009/143397) under control of the seed-specific, soy beta-conglycinin promoter. The CDS and amino acid sequence of GmDGAT1cAII from PCT Publication No. WO 2009/143397 is set forth in SEQ ID NO: 54 and SEQ ID NO: 55, respectively.

The SbfI fragment of pKR1968 (SEQ ID NO: 50), containing GmLec1, the SbfI fragment of pKR1971 (SEQ ID NO: 51), containing GmODP1 and the SbfI fragment of pKR1969 (SEQ ID NO: 52), containing GmFusca3-1, were cloned into the SbfI site of pKR1520 to produce pKR2098 (SEQ ID NO: 56), pKR2100 (SEQ ID NO: 57) and pKR2099 (SEQ ID NO: 58), respectively. In this way, the respective transcription factors could be expressed behind the soy sucrose synthase promoter (GmSusPro) and co-expressed with GmDGAT1cAII (SEQ ID NO: 54).

DNA from plasmids pKR2098 (SEQ ID NO: 56), pKR2100 (SEQ ID NO: 57) and pKR2099 (SEQ ID NO: 58) and pKR1520 was prepared for particle bombardment into soybean embryogenic suspension culture and transformed exactly as described previously in PCT Publication No. WO 2008/147935. Soybean embryogenic suspension culture was initiated, grown, maintained and bombarded and events were selected and matured on SHaM media also exactly as described in PCT Publication No. WO 2008/147935. A summary of genes, plasmids and model system experiment numbers is shown in Table 5.

TABLE 5

Summary of Genes, Plasmids and Experiments

| Experiment | Plasmid | Gene1[1,2] | Gene2 | Gene2 SEQ ID NO nt | Gene2 SEQ ID NO aa |
|---|---|---|---|---|---|
| MSE 2984 | pKR1520 | GmDGAT1cAII | — | — | — |
| MSE 2985 | pKR2098 | GmDGAT1cAII | GmLec1 | 24 | 25 |
| MSE 2986 | pKR2099 | GmDGAT1cAII | GmFusca3-1 | 48 | 49 |
| MSE 2987 | pKR2100 | GmDGAT1cAII | GmODP1 | 29 | 30 |

[1]Gene1 nucleotide sequence of SEQ ID NO: 54
[2]Gene1 amino acid sequence of SEQ ID NO: 55

Approximately 10-20 matured embryos from each of approximately 30 events per bombardment experiment were lyophilized, ground, oil content was measured by NMR and fatty acid profile was evaluated by FAME-GC analysis exactly as described in PCT Publication No. WO 2008/147935. The results for oil content and fatty acid profile for each event as well as the average of all events (Avg.) and average for the top 5 events having highest oil content (Top5 Avg.) are shown in Table 6.

In Table 6, results are sorted based on oil content from highest to lowest. In Table 6, oil content is reported as a percent of total dry weight (% Oil) and fatty acid content for each fatty acid [palmitic acid (16:0), stearic acid (18:0), oleic acid (18:1), linoleic acid (18:2) & alpha-linolenic acid (18:3)] is reported as a weight % of total fatty acids.

TABLE 6

Summary of Oil Content and Fatty Acid Profiles for Events Expressing GmDGAT1cAll with GmLec1, GmFusca3-1 or GmODP1

| | % oil | 16:0 | 18:0 | 18:1 | 18:2 | 18:3 |
|---|---|---|---|---|---|---|
| 2984-2 | 9.32 | 14.46 | 7.12 | 32.85 | 36.23 | 9.34 |
| 2984-29 | 8.43 | 14.33 | 8.26 | 31.62 | 36.64 | 9.15 |
| 2984-4 | 7.83 | 14.70 | 7.20 | 28.72 | 37.99 | 11.39 |
| 2984-24 | 6.86 | 15.52 | 6.84 | 26.74 | 41.07 | 9.83 |
| 2984-6 | 6.60 | 16.94 | 5.65 | 20.30 | 36.75 | 20.36 |
| 2984-8 | 6.46 | 14.45 | 7.54 | 32.53 | 36.10 | 9.38 |
| 2984-25 | 6.41 | 14.93 | 7.19 | 29.25 | 37.09 | 11.54 |
| 2984-11 | 5.86 | 15.32 | 6.32 | 26.67 | 37.50 | 14.20 |
| 2984-30 | 5.56 | 16.39 | 6.21 | 23.04 | 40.99 | 13.37 |
| 2984-12 | 5.34 | 15.83 | 6.18 | 24.45 | 38.38 | 15.16 |
| 2984-18 | 4.81 | 16.78 | 5.59 | 18.05 | 44.53 | 15.06 |
| 2984-19 | 4.56 | 15.38 | 6.88 | 29.28 | 35.27 | 13.19 |
| 2984-7 | 4.27 | 15.56 | 5.73 | 29.14 | 35.31 | 14.26 |
| 2984-16 | 4.25 | 16.44 | 5.84 | 21.69 | 40.16 | 15.87 |
| 2984-31 | 4.20 | 15.22 | 6.04 | 22.50 | 39.87 | 16.37 |
| 2984-28 | 4.19 | 15.76 | 6.15 | 26.96 | 36.72 | 14.41 |
| 2984-1 | 3.87 | 15.78 | 6.82 | 29.12 | 35.13 | 13.15 |
| 2984-27 | 3.75 | 16.05 | 6.67 | 25.82 | 36.68 | 14.78 |
| 2984-21 | 3.36 | 15.93 | 6.97 | 25.76 | 37.04 | 14.31 |
| 2984-5 | 3.25 | 16.04 | 5.34 | 21.85 | 38.82 | 17.95 |
| 2984-13 | 3.21 | 16.28 | 7.58 | 22.99 | 38.11 | 15.03 |
| 2984-3 | 3.20 | 16.80 | 5.81 | 23.71 | 36.80 | 16.88 |
| 2984-14 | 3.04 | 16.70 | 6.74 | 23.50 | 38.30 | 14.76 |
| 2984-20 | 3.00 | 16.68 | 6.75 | 21.83 | 38.83 | 15.92 |
| 2984-23 | 2.94 | 16.67 | 7.14 | 26.96 | 34.93 | 14.31 |
| 2984-15 | 2.71 | 16.89 | 5.36 | 17.26 | 40.57 | 19.92 |
| 2984-26 | 2.65 | 17.07 | 5.53 | 23.87 | 35.64 | 17.88 |
| 2984-10 | 2.58 | 17.16 | 5.07 | 19.58 | 39.15 | 19.05 |
| 2984-9 | 2.53 | 18.99 | 4.57 | 20.90 | 37.35 | 18.19 |

TABLE 6-continued

Summary of Oil Content and Fatty Acid Profiles for Events Expressing GmDGAT1cAll with GmLec1, GmFusca3-1 or GmODP1

| | % oil | 16:0 | 18:0 | 18:1 | 18:2 | 18:3 |
|---|---|---|---|---|---|---|
| 2984-22 | 2.52 | 17.24 | 5.35 | 18.79 | 40.42 | 18.21 |
| 2984-17 | 2.45 | 17.21 | 5.61 | 21.36 | 38.97 | 16.85 |
| Avg. | 4.50 | 16.11 | 6.32 | 24.74 | 37.98 | 14.84 |
| Top5 Avg. | 7.77 | 15.19 | 7.02 | 28.04 | 37.73 | 12.01 |
| '2985-1 | 11.32 | 14.05 | 6.20 | 33.72 | 38.52 | 7.52 |
| 2985-9 | 10.54 | 13.39 | 8.11 | 35.06 | 35.71 | 7.73 |
| 2985-23 | 10.18 | 14.30 | 6.93 | 32.93 | 37.45 | 8.38 |
| 2985-28 | 9.87 | 13.71 | 8.71 | 37.57 | 34.84 | 7.18 |
| 2985-19 | 9.39 | 14.42 | 8.81 | 31.25 | 38.24 | 9.29 |
| 2985-17 | 9.11 | 14.57 | 6.32 | 28.39 | 40.70 | 10.01 |
| 2985-24 | 8.94 | 14.19 | 7.08 | 34.90 | 35.81 | 8.21 |
| 2985-11 | 8.04 | 14.90 | 7.13 | 31.07 | 37.27 | 9.83 |
| 2985-18 | 7.57 | 16.08 | 5.19 | 18.95 | 46.29 | 13.50 |
| 2985-29 | 7.29 | 15.24 | 7.14 | 28.32 | 38.60 | 10.70 |
| 2985-25 | 7.25 | 13.74 | 7.43 | 37.53 | 34.10 | 7.20 |
| 2985-14 | 6.88 | 15.20 | 6.96 | 31.79 | 36.42 | 9.62 |
| 2985-6 | 6.67 | 14.97 | 6.56 | 28.93 | 38.71 | 10.84 |
| 2985-30 | 6.46 | 15.96 | 6.53 | 16.84 | 45.97 | 14.70 |
| 2985-27 | 6.36 | 15.33 | 6.64 | 26.34 | 40.21 | 11.48 |
| 2985-5 | 6.25 | 15.60 | 5.96 | 24.88 | 40.29 | 13.26 |
| 2985-15 | 6.17 | 16.85 | 5.42 | 25.02 | 40.57 | 12.15 |
| 2985-26 | 5.94 | 15.84 | 6.33 | 27.64 | 38.09 | 12.10 |
| 2985-3 | 5.86 | 15.48 | 6.40 | 24.48 | 39.93 | 13.71 |
| 2985-2 | 5.12 | 16.34 | 5.90 | 22.18 | 40.69 | 14.90 |
| 2985-12 | 5.10 | 16.51 | 6.55 | 23.07 | 38.63 | 15.25 |
| 2985-13 | 5.05 | 16.32 | 6.07 | 18.51 | 45.20 | 13.89 |
| 2985-31 | 4.75 | 17.38 | 6.33 | 21.32 | 40.38 | 14.60 |
| 2985-4 | 4.41 | 17.06 | 5.10 | 18.20 | 42.54 | 17.10 |
| 2985-21 | 4.38 | 15.99 | 6.41 | 19.61 | 42.79 | 15.19 |
| 2985-22 | 4.28 | 17.00 | 6.07 | 23.15 | 40.43 | 13.36 |
| 2985-10 | 3.71 | 16.56 | 5.93 | 24.73 | 39.45 | 13.32 |
| 2985-16 | 3.29 | 16.62 | 5.38 | 20.23 | 38.80 | 18.97 |
| 2985-7 | 3.26 | 16.95 | 6.46 | 21.87 | 40.53 | 14.19 |
| 2985-8 | 2.84 | 16.88 | 5.26 | 19.34 | 39.99 | 18.54 |
| 2985-20 | 2.46 | 20.08 | 5.07 | 16.79 | 39.65 | 18.41 |
| Avg. | 6.41 | 15.73 | 6.33 | 25.95 | 39.57 | 12.42 |
| Top5 Avg. | 10.26 | 13.97 | 6.95 | 34.10 | 36.95 | 8.02 |
| 2986-13 | 12.08 | 14.11 | 7.29 | 29.76 | 40.57 | 8.26 |
| 2986-14 | 9.48 | 15.35 | 7.22 | 27.69 | 39.56 | 10.19 |
| 2986-21 | 8.96 | 14.52 | 6.68 | 31.53 | 38.85 | 8.42 |
| 2986-2 | 8.49 | 15.69 | 7.16 | 27.15 | 39.78 | 10.22 |
| 2986-7 | 8.22 | 14.73 | 6.70 | 37.98 | 32.64 | 7.96 |
| 2986-17 | 8.13 | 15.65 | 6.55 | 22.13 | 44.57 | 11.09 |
| 2986-12 | 7.93 | 16.01 | 5.59 | 25.79 | 41.51 | 11.10 |
| 2986-1 | 7.87 | 14.34 | 7.24 | 32.35 | 37.08 | 8.99 |
| 2986-5 | 7.56 | 15.06 | 6.12 | 33.97 | 36.01 | 8.85 |
| 2986-16 | 7.53 | 15.36 | 6.91 | 32.19 | 36.34 | 9.21 |
| 2986-3 | 7.43 | 15.21 | 5.16 | 17.26 | 46.98 | 15.39 |
| 2986-24 | 7.13 | 15.93 | 6.26 | 20.01 | 45.26 | 12.54 |
| 2986-18 | 6.79 | 15.97 | 6.13 | 20.41 | 44.98 | 12.50 |
| 2986-19 | 6.73 | 15.83 | 6.33 | 21.92 | 42.56 | 13.35 |
| 2986-6 | 6.48 | 13.40 | 8.25 | 44.98 | 27.01 | 6.36 |
| 2986-23 | 6.25 | 15.99 | 6.28 | 22.04 | 42.68 | 13.01 |
| 2986-15 | 6.04 | 16.04 | 6.23 | 23.80 | 41.36 | 12.57 |
| 2986-20 | 5.98 | 17.17 | 5.96 | 23.94 | 41.44 | 11.49 |
| 2986-25 | 5.94 | 16.05 | 6.56 | 19.97 | 43.82 | 13.61 |
| 2986-27 | 5.80 | 14.18 | 6.40 | 27.22 | 39.60 | 12.60 |
| 2986-29 | 5.51 | 16.00 | 5.04 | 21.20 | 43.39 | 14.37 |
| 2986-9 | 5.48 | 15.77 | 6.72 | 19.81 | 42.90 | 14.79 |
| 2986-4 | 5.42 | 16.95 | 5.97 | 19.96 | 44.57 | 12.56 |
| 2986-10 | 4.95 | 16.33 | 6.66 | 23.74 | 39.55 | 13.72 |
| 2986-30 | 4.65 | 16.25 | 6.37 | 21.89 | 42.77 | 12.73 |
| 2986-11 | 4.51 | 15.98 | 6.52 | 27.94 | 37.95 | 11.61 |
| 2986-8 | 4.36 | 17.29 | 5.63 | 20.77 | 40.92 | 15.40 |
| 2986-26 | 4.06 | 17.21 | 5.52 | 20.73 | 43.19 | 13.36 |
| 2986-22 | 3.96 | 16.46 | 6.26 | 28.71 | 37.50 | 11.08 |
| 2986-28 | 3.28 | 17.67 | 5.64 | 20.27 | 41.54 | 14.88 |
| Avg. | 6.57 | 15.75 | 6.38 | 25.57 | 40.56 | 11.74 |
| Top5 Avg. | 9.45 | 14.88 | 7.01 | 30.82 | 38.28 | 9.01 |
| 2987-20 | 12.17 | 14.93 | 6.81 | 34.83 | 36.56 | 6.87 |
| 2987-5 | 11.26 | 13.58 | 7.25 | 31.24 | 39.66 | 8.27 |
| 2987-29 | 10.88 | 15.09 | 7.40 | 36.20 | 34.60 | 6.71 |
| 2987-16 | 10.57 | 14.09 | 7.46 | 33.87 | 36.42 | 8.16 |
| 2987-23 | 8.79 | 15.14 | 7.81 | 35.32 | 33.79 | 7.94 |
| 2987-13 | 8.68 | 16.00 | 5.65 | 23.11 | 43.90 | 11.35 |

TABLE 6-continued

Summary of Oil Content and Fatty Acid Profiles for Events Expressing GmDGAT1cAll with GmLec1, GmFusca3-1 or GmODP1

| | % oil | 16:0 | 18:0 | 18:1 | 18:2 | 18:3 |
|---|---|---|---|---|---|---|
| 2987-2 | 8.53 | 15.23 | 7.36 | 33.83 | 34.58 | 9.01 |
| 2987-28 | 7.93 | 13.55 | 9.78 | 40.08 | 29.47 | 7.12 |
| 2987-19 | 7.92 | 15.16 | 6.44 | 19.87 | 46.41 | 12.13 |
| 2987-4 | 7.37 | 14.91 | 6.56 | 26.12 | 41.57 | 10.84 |
| 2987-27 | 6.45 | 15.89 | 7.07 | 25.71 | 39.42 | 11.91 |
| 2987-17 | 6.31 | 16.71 | 6.26 | 22.14 | 42.71 | 12.17 |
| 2987-22 | 6.29 | 15.56 | 6.52 | 23.53 | 42.86 | 11.53 |
| 2987-15 | 5.95 | 15.59 | 6.35 | 21.63 | 43.38 | 13.05 |
| 2987-9 | 5.93 | 15.88 | 5.83 | 22.21 | 41.06 | 15.02 |
| 2987-14 | 5.81 | 17.54 | 6.82 | 32.38 | 32.46 | 10.79 |
| 2987-1 | 5.67 | 16.70 | 5.59 | 20.52 | 44.56 | 12.64 |
| 2987-26 | 5.61 | 15.98 | 6.41 | 24.77 | 39.04 | 13.80 |
| 2987-30 | 5.53 | 15.96 | 6.26 | 23.42 | 40.36 | 13.99 |
| 2987-3 | 5.30 | 16.46 | 6.34 | 24.45 | 40.62 | 12.12 |
| 2987-10 | 4.79 | 15.82 | 7.19 | 26.35 | 39.72 | 10.92 |
| 2987-25 | 4.67 | 15.89 | 7.76 | 29.34 | 36.64 | 10.37 |
| 2987-6 | 4.66 | 15.68 | 6.62 | 27.99 | 36.93 | 12.80 |
| 2987-8 | 4.54 | 16.20 | 6.11 | 26.29 | 38.62 | 12.78 |
| 2987-21 | 4.52 | 14.91 | 8.32 | 35.11 | 32.32 | 9.34 |
| 2987-18 | 4.18 | 15.80 | 7.21 | 29.57 | 35.85 | 11.57 |
| 2987-24 | 3.73 | 15.11 | 6.88 | 24.86 | 40.85 | 12.30 |
| 2987-11 | 3.61 | 17.46 | 5.35 | 20.08 | 40.96 | 16.15 |
| 2987-7 | 3.51 | 15.53 | 6.22 | 30.82 | 34.50 | 12.93 |
| 2987-12 | 3.21 | 16.81 | 6.73 | 22.57 | 38.75 | 15.15 |
| Avg. | 6.48 | 15.64 | 6.81 | 27.61 | 38.62 | 11.32 |
| Top5 Avg. | 10.73 | 14.56 | 7.35 | 34.29 | 36.20 | 7.59 |

A summary comparing the average oil content and average fatty acid profile for all events in each experiment is shown in Table 7. In Table 7, average oil content is reported as a percent of total dry weight (Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 3 also shows the change in oil content (Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 7

Summary of Average Oil Content and Fatty Acid Profiles for All Events Expressing GmDGAT1cAll with GmLec1, GmFusca3-1 or GmODP1

| MSE | Vector (Gene) | Avg. Oil | Avg. % Inc | 16:0 | 18:0 | 18:1 | 18:2 | 18:3 |
|---|---|---|---|---|---|---|---|---|
| 2984 | pKR1520 (n/a) | 4.5 | 0% | 16.1 | 6.3 | 24.7 | 38.0 | 14.8 |
| 2985 | pKR2098 (GmLec1) | 6.4 | 42% | 15.7 | 6.3 | 26.0 | 39.6 | 12.4 |
| 2986 | pKR2099 (GmFusca3-1) | 6.6 | 46% | 15.7 | 6.4 | 25.6 | 40.6 | 11.7 |
| 2987 | pKR2100 (GmODP1) | 6.5 | 44% | 15.6 | 6.8 | 27.6 | 38.6 | 11.3 |

A summary comparing the average oil content and average fatty acid profile of the top 5 events having the highest oil content for each experiment is shown in Table 8. In Table 8, average oil for the 5 events having highest oil content is reported as a percent of total dry weight (Top5 Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 4 also shows the change in oil content (Top5 Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 8

Summary of Average Oil Content and Fatty Acid Profiles for the Top5 Events Having Highest Oil Contents and Expressing GmDGAT1cAII with GmLec1, GmFusca3-1 or GmODP1

| MSE | Vector (Gene) | Avg Oil | Avg % Inc | 16:0 | 18:0 | 18:1 | 18:2 | 18:3 |
|---|---|---|---|---|---|---|---|---|
| 2984 | pKR1520 (n/a) | 7.8 | 0% | 15.2 | 7.0 | 28.0 | 37.7 | 12.0 |
| 2985 | pKR2098 (GmLec1) | 10.3 | 32% | 14.0 | 7.0 | 34.1 | 37.0 | 8.0 |
| 2986 | pKR2099 (GmFusca3-1) | 9.4 | 22% | 14.9 | 7.0 | 30.8 | 38.3 | 9.0 |
| 2987 | pKR2100 (GmODP1) | 10.7 | 38% | 14.6 | 7.3 | 34.3 | 36.2 | 7.6 |

Both Tables 7 and 8 demonstrate that expression of GmLec1, GmFusca3-1 and GmODP1 with GmDGAT1cAII lead to an increase in oil content in soy above that for GmDGAT1cAII alone.

Example 5

Co-Expressing GmLec1, GmODP1, GmFusca-3-1 and GmFusca3-2 With YLDGAT2 in Soybean Embryos Plasmid pKR1256 was previously described in PCT Publication No. WO 2008/147935 and contains a *Yarrowia lipolytica* DGAT2 (called YLDGAT2 in WO 2008/147935) under control of the seed-specific, soy beta-conglycinin promoter. The CDS and aa sequence of YLDGAT2 from PCT Publication No. WO 2008/147935 is set forth in SEQ ID NO: 59 and SEQ ID NO: 60, respectively.

The SbfI fragment of pKR1968 (SEQ ID NO: 50), containing GmLec1, the SbfI fragment of pKR1971 (SEQ ID NO: 51), containing GmODP1 and the SbfI fragment of pKR1969 (SEQ ID NO: 52), containing GmFusca3-1, were cloned into the SbfI site of pKR1256 to produce pKR2082 (SEQ ID NO: 61), pKR2084 (SEQ ID NO: 62) and pKR2083 (SEQ ID NO: 63), respectively. In this way, the respective transcription factors could be expressed behind the soy sucrose synthase promoter (GmSusPro) and co-expressed with YLDGAT2 (SEQ ID NO: 59).

DNA from plasmids pKR2082 (SEQ ID NO: 61), pKR2084 (SEQ ID NO: 62) and pKR2083 (SEQ ID NO: 63) and pKR1256 was prepared for particle bombardment into soybean embryogenic suspension culture and transformed exactly as described previously in PCT Publication No. WO 2008/147935. Soybean embryogenic suspension culture was initiated, grown, maintained and bombarded and events were selected and matured on SHaM media also exactly as described in PCT Publication No. WO 2008/147935. A summary of genes, plasmids and model system experiment numbers is shown in Table 9.

TABLE 9

Summary of Genes, Plasmids and Experiments

| Experiment | Plasmid | Gene1[1,2] | Gene2 | Gene2 SEQ ID NO nt | Gene2 SEQ ID NO aa |
|---|---|---|---|---|---|
| 3017 | pKR1256 | YLDGAT2 | — | — | — |
| 3018 | pKR2082 | YLDGAT2 | GmLec1 | 24 | 25 |
| 3019 | pKR2083 | YLDGAT2 | GmFusca3-1 | 48 | 49 |
| 3020 | pKR2084 | YLDGAT2 | GmODP | 29 | 30 |

[1]Gene1 nucleotide sequence of SEQ ID NO: 59

[2]Gene1 amino acid sequence of SEQ ID NO: 60

Approximately 10-20 matured embryos from each of approximately 30 events per bombardment experiment were lyophilized, ground, oil content was measured by NMR and fatty acid profile was evaluated by FAME-GC analysis exactly as described in PCT Publication No. WO 2008/147935. The results for oil content and fatty acid profile for each event as well as the average of all events (Avg.) and average for the top 5 events having highest oil content (Top5 Avg.) are shown in Table 10.

In Table 10, results are sorted based on oil content from highest to lowest. In Table 10, oil content is reported as a percent of total dry weight (% Oil) and fatty acid content for each fatty acid [palmitic acid (16:0), stearic acid (18:0), oleic acid (18:1), linoleic acid (18:2) & alpha-linolenic acid (18:3)] is reported as a weight % of total fatty acids.

TABLE 10

Summary of Oil Content and Fatty Acid Profiles for Events Expressing YLDGAT2 with GmLec1, GmFusca3-1 or GmODP1

| | % oil | 16:0 | 18:0 | 18:1 | 18:2 | 18:3 |
|---|---|---|---|---|---|---|
| 3017-13 | 13.72 | 12.08 | 6.15 | 29.99 | 44.30 | 7.48 |
| 3017-18 | 13.14 | 12.08 | 5.73 | 33.42 | 40.61 | 8.16 |
| 3017-25 | 12.64 | 14.47 | 5.31 | 17.82 | 51.29 | 11.11 |
| 3017-22 | 12.36 | 13.29 | 6.21 | 27.79 | 42.62 | 10.09 |
| 3017-32 | 11.14 | 13.46 | 6.07 | 27.14 | 44.74 | 8.59 |
| 3017-4 | 10.76 | 14.14 | 5.79 | 28.40 | 41.94 | 9.73 |
| 3017-9 | 10.70 | 14.87 | 5.23 | 22.81 | 46.72 | 10.38 |
| 3017-16 | 10.57 | 14.79 | 5.38 | 21.80 | 47.42 | 10.60 |
| 3017-8 | 10.57 | 14.81 | 6.29 | 25.54 | 43.89 | 9.48 |
| 3017-17 | 9.48 | 12.33 | 5.89 | 32.24 | 42.96 | 6.58 |
| 3017-19 | 9.41 | 14.20 | 5.91 | 23.85 | 44.80 | 11.25 |
| 3017-2 | 9.39 | 15.20 | 5.37 | 22.87 | 44.49 | 12.07 |
| 3017-23 | 9.03 | 12.09 | 8.97 | 39.60 | 32.75 | 6.59 |
| 3017-14 | 9.02 | 15.29 | 6.03 | 23.78 | 43.09 | 11.81 |
| 3017-5 | 8.89 | 14.78 | 7.68 | 24.09 | 41.71 | 11.74 |
| 3017-3 | 8.41 | 15.15 | 6.32 | 28.80 | 40.19 | 9.54 |
| 3017-1 | 8.40 | 15.50 | 6.15 | 21.90 | 42.45 | 14.00 |
| 3017-29 | 8.14 | 14.99 | 6.72 | 28.17 | 39.30 | 10.83 |
| 3017-15 | 8.01 | 14.83 | 6.92 | 25.24 | 41.34 | 11.66 |
| 3017-34 | 7.99 | 14.61 | 6.89 | 25.68 | 43.83 | 8.99 |
| 3017-10 | 7.93 | 14.62 | 7.49 | 27.24 | 40.62 | 10.03 |
| 3017-7 | 7.52 | 14.57 | 6.61 | 29.19 | 39.82 | 9.81 |
| 3017-30 | 7.50 | 14.61 | 7.04 | 26.97 | 42.70 | 8.68 |
| 3017-27 | 7.36 | 14.34 | 8.91 | 30.81 | 37.02 | 8.92 |
| 3017-21 | 7.25 | 14.12 | 8.58 | 30.87 | 37.73 | 8.69 |
| 3017-28 | 6.63 | 14.82 | 6.95 | 29.47 | 38.94 | 9.82 |
| 3017-24 | 5.99 | 14.96 | 9.85 | 31.34 | 35.56 | 8.29 |
| 3017-6 | 5.98 | 15.91 | 6.64 | 25.13 | 40.68 | 11.64 |
| 3017-20 | 5.86 | 14.84 | 6.67 | 26.23 | 42.46 | 9.80 |
| 3017-26 | 5.72 | 13.98 | 10.16 | 35.42 | 32.62 | 7.83 |

TABLE 10-continued

Summary of Oil Content and Fatty Acid Profiles for Events Expressing YLDGAT2 with GmLec1, GmFusca3-1 or GmODP1

| | % oil | 16:0 | 18:0 | 18:1 | 18:2 | 18:3 |
|---|---|---|---|---|---|---|
| 3017-11 | 5.58 | 13.20 | 7.63 | 37.58 | 34.02 | 7.57 |
| 3017-31 | 5.33 | 14.05 | 8.45 | 32.66 | 35.81 | 9.03 |
| 3017-33 | 4.70 | 14.90 | 8.12 | 32.46 | 34.61 | 9.91 |
| 3017-12 | 4.49 | 14.94 | 6.07 | 26.27 | 40.63 | 12.09 |
| Avg. | 8.52 | 14.32 | 6.89 | 28.02 | 40.99 | 9.79 |
| Top5 Avg. | 12.60 | 13.08 | 5.90 | 27.23 | 44.71 | 9.09 |
| 3018-29 | 16.95 | 11.61 | 5.42 | 32.58 | 43.67 | 6.72 |
| 3018-17 | 15.19 | 10.65 | 6.96 | 38.09 | 38.24 | 6.06 |
| 3018-22 | 14.87 | 9.66 | 7.05 | 48.08 | 30.24 | 4.98 |
| 3018-16 | 14.51 | 11.46 | 6.52 | 38.75 | 37.38 | 5.88 |
| 3018-27 | 14.00 | 11.39 | 6.00 | 39.98 | 36.40 | 6.23 |
| 3018-4 | 12.90 | 11.32 | 6.54 | 34.78 | 40.20 | 7.16 |
| 3018-19 | 12.26 | 13.06 | 5.28 | 31.71 | 42.04 | 7.90 |
| 3018-2 | 11.72 | 11.57 | 4.94 | 32.05 | 42.96 | 8.48 |
| 3018-20 | 11.65 | 10.89 | 5.08 | 38.25 | 37.85 | 7.93 |
| 3018-11 | 11.47 | 12.37 | 6.68 | 38.24 | 35.18 | 7.54 |
| 3018-13 | 10.84 | 11.85 | 7.36 | 41.64 | 33.08 | 6.06 |
| 3018-30 | 10.41 | 14.51 | 5.98 | 25.16 | 44.25 | 10.11 |
| 3018-7 | 10.03 | 10.84 | 7.56 | 46.85 | 29.72 | 5.03 |
| 3018-8 | 10.00 | 15.36 | 5.09 | 20.72 | 48.63 | 10.22 |
| 3018-15 | 9.81 | 12.34 | 8.07 | 39.27 | 32.70 | 7.63 |
| 3018-25 | 9.80 | 12.45 | 5.76 | 33.67 | 41.00 | 7.11 |
| 3018-9 | 9.32 | 14.09 | 5.71 | 22.46 | 49.20 | 8.54 |
| 3018-28 | 9.21 | 12.94 | 8.87 | 34.67 | 34.39 | 7.72 |
| 3018-12 | 9.21 | 15.40 | 5.47 | 24.61 | 43.40 | 11.11 |
| 3018-23 | 9.19 | 15.47 | 8.14 | 27.57 | 38.98 | 9.83 |
| 3018-24 | 9.06 | 14.64 | 7.51 | 27.12 | 41.56 | 9.17 |
| 3018-5 | 8.97 | 14.06 | 5.23 | 26.34 | 45.06 | 9.31 |
| 3018-18 | 8.95 | 12.56 | 6.73 | 37.59 | 34.39 | 8.73 |
| 3018-3 | 8.27 | 12.99 | 6.84 | 34.06 | 38.34 | 7.77 |
| 3018-26 | 8.00 | 15.82 | 5.74 | 22.39 | 45.62 | 10.43 |
| 3018-21 | 5.99 | 13.63 | 8.88 | 34.58 | 34.47 | 8.44 |
| 3018-1 | 5.98 | 15.00 | 8.98 | 30.75 | 35.25 | 10.01 |
| 3018-10 | 5.72 | 14.11 | 7.29 | 36.00 | 35.14 | 7.46 |
| 3018-6 | 5.49 | 14.13 | 6.87 | 27.10 | 41.60 | 10.29 |
| 3018-14 | 4.49 | 14.47 | 6.75 | 36.34 | 34.50 | 7.93 |
| Avg. | 10.14 | 13.02 | 6.64 | 33.38 | 38.85 | 8.06 |
| Top5 Avg. | 15.10 | 10.95 | 6.39 | 39.49 | 37.19 | 5.98 |
| 3019-27 | 11.11 | 15.22 | 4.66 | 23.96 | 46.19 | 9.97 |
| 3019-23 | 10.06 | 12.24 | 5.28 | 27.99 | 43.63 | 10.86 |
| 3019-4 | 9.83 | 11.43 | 6.94 | 43.16 | 32.24 | 6.23 |
| 3019-7 | 9.77 | 11.22 | 6.15 | 37.45 | 37.56 | 7.62 |
| 3019-15 | 9.16 | 12.50 | 6.60 | 39.08 | 34.52 | 7.30 |
| 3019-20 | 8.67 | 16.44 | 5.12 | 19.31 | 46.64 | 12.49 |
| 3019-12 | 8.22 | 12.27 | 7.06 | 38.86 | 33.71 | 8.10 |
| 3019-17 | 8.07 | 16.60 | 5.47 | 26.70 | 40.57 | 10.66 |
| 3019-11 | 7.78 | 13.40 | 6.26 | 31.75 | 38.36 | 10.22 |
| 3019-24 | 7.76 | 13.56 | 5.79 | 34.04 | 37.79 | 8.82 |
| 3019-19 | 7.21 | 15.81 | 5.83 | 21.60 | 43.54 | 13.23 |
| 3019-6 | 7.07 | 12.94 | 6.45 | 33.73 | 37.02 | 9.86 |
| 3019-13 | 7.07 | 14.26 | 5.42 | 35.78 | 36.24 | 8.30 |
| 3019-3 | 6.94 | 13.72 | 5.57 | 39.86 | 33.47 | 7.39 |
| 3019-2 | 6.84 | 13.36 | 6.58 | 30.96 | 38.13 | 10.97 |
| 3019-10 | 6.80 | 14.81 | 6.49 | 26.45 | 41.18 | 11.07 |
| 3019-5 | 6.73 | 14.48 | 4.78 | 28.73 | 40.26 | 11.76 |
| 3019-30 | 6.52 | 13.40 | 6.23 | 36.19 | 35.51 | 8.67 |
| 3019-21 | 6.47 | 15.74 | 7.75 | 24.42 | 40.60 | 11.49 |
| 3019-14 | 6.27 | 15.39 | 7.18 | 23.21 | 41.62 | 12.59 |
| 3019-1 | 5.93 | 15.61 | 7.27 | 23.55 | 41.13 | 12.44 |
| 3019-29 | 5.69 | 14.67 | 5.72 | 22.51 | 41.63 | 15.48 |
| 3019-18 | 5.54 | 14.58 | 4.85 | 36.76 | 35.78 | 8.04 |
| 3019-16 | 5.48 | 16.00 | 5.62 | 25.73 | 40.35 | 12.29 |
| 3019-22 | 4.63 | 16.81 | 6.03 | 20.42 | 43.23 | 13.51 |
| 3019-9 | 4.21 | 16.90 | 4.07 | 24.22 | 41.43 | 13.38 |
| 3019-8 | 3.87 | 16.96 | 5.46 | 20.23 | 40.10 | 17.23 |
| 3019-26 | 3.83 | 16.75 | 6.65 | 24.01 | 38.72 | 13.86 |
| 3019-28 | 3.44 | 16.98 | 5.19 | 21.93 | 42.09 | 13.81 |
| 3019-25 | 3.05 | 17.10 | 5.38 | 19.21 | 39.89 | 18.42 |
| Avg. | 6.80 | 14.71 | 5.93 | 28.73 | 39.44 | 11.20 |
| Top5 Avg. | 9.99 | 12.52 | 5.93 | 34.33 | 38.83 | 8.40 |
| 3020-4 | 18.24 | 11.66 | 5.14 | 42.44 | 35.63 | 5.13 |
| 3020-2 | 17.99 | 14.04 | 5.23 | 40.23 | 35.32 | 5.18 |
| 3020-16 | 15.32 | 14.60 | 4.66 | 32.03 | 41.59 | 7.12 |
| 3020-10 | 14.86 | 10.19 | 6.05 | 44.43 | 33.95 | 5.39 |
| 3020-28 | 14.26 | 10.64 | 6.90 | 41.20 | 36.44 | 4.81 |
| 3020-21 | 13.75 | 14.84 | 4.76 | 25.37 | 45.76 | 9.26 |
| 3020-11 | 13.00 | 11.26 | 6.37 | 35.10 | 39.89 | 7.39 |
| 3020-20 | 12.26 | 14.91 | 4.81 | 33.19 | 38.68 | 8.40 |
| 3020-24 | 12.06 | 13.49 | 4.95 | 39.62 | 34.81 | 7.13 |
| 3020-27 | 12.02 | 13.37 | 7.85 | 37.87 | 34.44 | 6.48 |
| 3020-14 | 11.70 | 13.88 | 5.89 | 42.81 | 31.65 | 5.78 |
| 3020-22 | 11.32 | 15.05 | 4.24 | 22.49 | 47.99 | 10.22 |
| 3020-30 | 11.08 | 14.99 | 5.43 | 26.34 | 43.96 | 9.28 |
| 3020-18 | 10.19 | 15.53 | 5.47 | 35.57 | 35.97 | 7.47 |
| 3020-23 | 9.71 | 12.39 | 6.38 | 45.44 | 29.30 | 6.49 |
| 3020-25 | 9.68 | 12.55 | 6.81 | 44.02 | 30.15 | 6.47 |
| 3020-1 | 9.37 | 12.21 | 6.23 | 39.89 | 34.65 | 7.02 |
| 3020-26 | 8.60 | 12.44 | 6.36 | 38.32 | 34.56 | 8.31 |
| 3020-12 | 8.48 | 14.01 | 6.49 | 37.51 | 34.00 | 8.00 |
| 3020-3 | 8.29 | 12.29 | 6.92 | 33.60 | 38.01 | 9.18 |
| 3020-17 | 8.17 | 14.81 | 5.14 | 23.98 | 44.24 | 11.83 |
| 3020-6 | 7.46 | 12.93 | 7.35 | 40.18 | 31.90 | 7.64 |
| 3020-13 | 7.39 | 15.19 | 6.69 | 24.53 | 41.62 | 11.98 |
| 3020-19 | 7.34 | 15.34 | 6.88 | 24.47 | 40.59 | 12.72 |
| 3020-8 | 6.50 | 15.65 | 7.96 | 25.19 | 39.40 | 11.79 |
| 3020-7 | 6.15 | 17.20 | 6.39 | 29.08 | 37.37 | 9.96 |
| 3020-15 | 5.63 | 15.85 | 7.51 | 27.81 | 36.66 | 12.17 |
| 3020-9 | 5.34 | 14.05 | 6.54 | 43.17 | 27.99 | 8.25 |
| 3020-29 | 4.63 | 18.01 | 6.17 | 32.09 | 33.33 | 10.39 |
| 3020-5 | 3.67 | 15.71 | 7.21 | 28.74 | 34.84 | 13.49 |
| Avg. | 10.15 | 13.97 | 6.16 | 34.56 | 36.82 | 8.49 |
| Top5 Avg. | 16.13 | 12.23 | 5.60 | 40.07 | 36.59 | 5.53 |

A summary comparing the average oil content and average fatty acid profile for all events in each experiment is shown in Table 11. In Table 11, average oil content is reported as a percent of total dry weight (Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 11 also shows the change in oil content (Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 11

Summary of Average Oil Content and Fatty Acid Profiles for All Events Expressing YLDGAT2 with GmLec1, GmFusca3-1 or GmODP1

| MSE | Vector (Gene) | Avg Oil | % Inc | 16:0 | 18:0 | 18:1 | 18:2 | 18:3 |
|---|---|---|---|---|---|---|---|---|
| 3017 | pKR1256 (n/a) | 8.5 | 0% | 14.3 | 6.9 | 28.0 | 41.0 | 9.8 |
| 3018 | pKR2082 (GmLec1) | 10.1 | 19% | 13.0 | 6.6 | 33.4 | 38.8 | 8.1 |
| 3019 | pKR2083 (GmFusca3-1) | 6.8 | −20% | 14.7 | 5.9 | 28.7 | 39.4 | 11.2 |
| 3020 | pKR2084 (GmODP1) | 10.1 | 19% | 14.0 | 6.2 | 34.6 | 36.8 | 8.5 |

A summary comparing the average oil content and average fatty acid profile of the top 5 events having the highest oil content for each experiment is shown in Table 12. In Table 12, average oil for the 5 events having highest oil content is reported as a percent of total dry weight (Top5 Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 12 also shows the change in oil content (Top5 Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 12

Summary of Average Oil Content and Fatty Acid Profiles for the Top5 Events Having Highest Oil Contents and Expressing YLDGAT2 with GmLec1, GmFusca3-1 or GmODP1

| MSE | Vector (Gene) | Avg. Oil | Avg. % Inc | 16:0 | 18:0 | 18:1 | 18:2 | 18:3 |
|---|---|---|---|---|---|---|---|---|
| 3017 | pKR1256 (n/a) | 12.8 | 0% | 13.1 | 5.9 | 27.2 | 44.7 | 9.1 |
| 3018 | pKR2082 (GmLec1) | 15.1 | 20% | 11.0 | 6.4 | 39.5 | 37.2 | 6.0 |
| 3019 | pKR2083 (GmFusca3-1) | 10.0 | −21% | 12.5 | 5.9 | 34.3 | 38.8 | 8.4 |
| 3020 | pKR2084 (GmODP) | 16.1 | 28% | 12.2 | 5.6 | 40.1 | 36.6 | 5.5 |

Both Tables 11 and 12 demonstrate that expression of GmLec1 and GmODP1 with YLDGAT2 lead to an increase in oil content in soy above that for YLDGAT2 alone.

Example 6

Cloning Lec1 and ODP1 Homologs from Maize

ZmLec1 with Flanking NotI Sites:

The maize Lec1 (ZmLec1) is described in U.S. Pat. No. 6,825,397. The CDS and aa sequences for ZmLec1 are set forth in SEQ ID NO: 64 and SEQ ID NO: 65, respectively.

ZmLec1 was PCR-amplified from a cDNA clone using oligonucleotides oZLEC-1 (SEQ ID NO: 66) and oZLEC-2 (SEQ ID NO: 67) with the PHUSION™ High-Fidelity DNA Polymerase (Cat. No. F553S, Finnzymes Oy, Finland), following the manufacturer's protocol. The PCR fragment was cloned into the pCR®-BLUNT® cloning vector using the ZERO BLUNT® PCR Cloning Kit (Invitrogen Corporation), following the manufacturer's protocol, to produce pKR2115 (SEQ ID NO: 68).

ZmODP1 with Flanking NotI Sites:

The maize ODP1 (ZmODP1) is described in U.S. Pat. No. 7,157,621. The cloning of ZmODP1 with flanking NotI sites into plasmid KS336 was previously described in PCT Publication No. WO 2010/114989 (published on Oct. 7, 2010, the contents of which are herein incorporated by reference). It should be noted that there is a typo in the map of KS336 (SEQ ID NO: 6 in WO2010/114989) and that there should be an additional 3 nucleotides (TGA) at position 1192 to form a stop codon and end the CDS in KS336. The CDS and amino acid sequence of ZmODP1 in KS336 from WO2010/114989 are set forth here in SEQ ID NO: 69 and SEQ ID NO: 70, respectively.

Example 7

Expressing ZmLec1 and ZmODP1 in Soybean Embryos Under Control of the GmSus Promoter The NotI fragment of pKR2115 (SEQ ID NO: 68), containing ZmLec1 and the NotI fragment of KS336, containing ZmODP1 were cloned into the NotI site of pKR1965 (SEQ ID NO: 14) to produce pKR2121 (SEQ ID NO: 71) and pKR2114 (SEQ ID NO: 72), respectively. In this way, the respective transcription factors could be expressed behind the soy sucrose synthase promoter (GmSusPro). Plasmid pKR278, containing no transcription factor, but having the hygromycin selectable marker, was used as a negative control.

DNA from plasmids pKR2121 (SEQ ID NO: 71), pKR2114 (SEQ ID NO: 72) and pKR278 was prepared for particle bombardment into soybean embryogenic suspension culture and transformed exactly as described previously in PCT Publication No. WO 2008/147935. Soybean embryogenic suspension culture was initiated, grown, maintained and bombarded and events were selected and matured on SHaM media also exactly as described in PCT Publication No. WO 2008/147935. A summary of genes, plasmids and model system experiment numbers is shown in Table 13.

TABLE 13

Summary of Genes, Plasmids and Experiments

| Experiment | Plasmid | Gene | SEQ ID NO nt | SEQ ID NO aa |
|---|---|---|---|---|
| MSE 3053 | pKR2114 | ZmODP1 | 69 | 70 |
| MSE 3054 | pKR2121 | ZmLec1 | 64 | 65 |
| MSE 3055 | pKR278 | Empty Vector Control | — | — |

Approximately 10-20 matured embryos from each of approximately 30 events per bombardment experiment were lyophilized, ground, oil content was measured by NMR and fatty acid profile was evaluated by FAME-GC analysis exactly as described in PCT Publication No. WO 2008/147935. The results for oil content and fatty acid profile for each event as well as the average of all events (Avg.) and average for the top 5 events having highest oil content (Top5 Avg.) are shown in Table 14.

In Table 14, results are sorted based on oil content from highest to lowest. In Table 14, oil content is reported as a percent of total dry weight (% Oil) and fatty acid content for each fatty acid [palmitic acid (16:0), stearic acid (18:0), oleic acid (18:1), linoleic acid (18:2) & alpha-linolenic acid (18:3)] is reported as a weight % of total fatty acids.

TABLE 14

Summary of Oil Content and Fatty Acid Profiles for the Events Expressing ZmLec1, ZmODP1 Empty Vector Control

| | % oil | 16:0 | 18:0 | 18:1 | 18:2 | 18:3 |
|---|---|---|---|---|---|---|
| 3053-21 | 10.6 | 16.6 | 4.4 | 17.1 | 50.6 | 11.3 |
| 3053-1 | 9.8 | 17.0 | 4.8 | 18.0 | 48.8 | 11.4 |
| 3053-31 | 9.4 | 15.6 | 4.8 | 17.5 | 50.2 | 11.9 |
| 3053-25 | 9.2 | 16.1 | 4.8 | 20.6 | 47.3 | 11.3 |
| 3053-20 | 8.9 | 16.9 | 4.6 | 19.9 | 47.5 | 11.1 |
| 3053-7 | 8.6 | 16.4 | 4.4 | 19.6 | 45.9 | 13.6 |
| 3053-27 | 8.5 | 17.1 | 3.4 | 15.4 | 50.8 | 13.2 |
| 3053-18 | 8.3 | 15.6 | 5.6 | 17.1 | 49.2 | 12.5 |
| 3053-23 | 8.2 | 15.9 | 4.9 | 17.1 | 49.3 | 12.8 |
| 3053-11 | 8.1 | 16.8 | 5.1 | 21.1 | 44.9 | 12.1 |
| 3053-29 | 8.1 | 17.0 | 5.2 | 19.0 | 47.2 | 11.6 |
| 3053-12 | 8.0 | 16.6 | 6.1 | 21.5 | 43.2 | 12.5 |
| 3053-5 | 7.9 | 17.1 | 5.1 | 20.5 | 43.9 | 13.4 |
| 3053-2 | 7.8 | 15.8 | 3.8 | 16.9 | 49.8 | 13.7 |
| 3053-10 | 7.7 | 17.0 | 5.6 | 21.4 | 44.8 | 11.2 |
| 3053-13 | 7.6 | 17.4 | 4.8 | 19.2 | 45.3 | 13.3 |
| 3053-3 | 7.4 | 15.7 | 6.1 | 19.5 | 46.6 | 12.2 |
| 3053-15 | 7.3 | 15.5 | 5.5 | 19.1 | 46.6 | 13.2 |
| 3053-6 | 6.8 | 16.5 | 5.2 | 20.5 | 44.0 | 13.7 |
| 3053-17 | 6.8 | 16.7 | 5.8 | 24.7 | 41.9 | 10.9 |
| 3053-4 | 6.7 | 17.7 | 4.7 | 16.1 | 47.7 | 13.7 |
| 3053-24 | 6.7 | 16.3 | 7.1 | 24.6 | 39.8 | 12.2 |
| 3053-26 | 6.7 | 16.4 | 5.9 | 16.6 | 45.9 | 15.2 |
| 3053-16 | 6.5 | 17.3 | 5.3 | 19.5 | 44.8 | 13.1 |
| 3053-19 | 6.5 | 17.8 | 5.2 | 20.9 | 43.3 | 12.8 |
| 3053-9 | 6.3 | 18.2 | 5.1 | 20.8 | 43.4 | 12.5 |
| 3053-28 | 6.2 | 16.6 | 5.8 | 17.9 | 45.2 | 14.5 |
| 3053-14 | 6.0 | 16.8 | 6.4 | 25.0 | 39.9 | 11.8 |
| 3053-8 | 6.0 | 17.4 | 5.6 | 18.7 | 44.9 | 13.5 |
| 3053-30 | 5.7 | 17.2 | 6.7 | 26.7 | 38.3 | 11.1 |
| 3053-22 | 3.7 | 17.0 | 5.4 | 19.2 | 44.0 | 14.5 |
| Avg. | 7.5 | 16.7 | 5.3 | 19.7 | 45.6 | 12.6 |
| Top5 Avg. | 9.6 | 16.4 | 4.7 | 18.6 | 48.9 | 11.4 |

TABLE 14-continued

Summary of Oil Content and Fatty Acid Profiles for the Events Expressing ZmLec1, ZmODP1 Empty Vector Control

| | % oil | 16:0 | 18:0 | 18:1 | 18:2 | 18:3 |
|---|---|---|---|---|---|---|
| 3054-11 | 9.1 | 15.9 | 5.4 | 21.9 | 45.3 | 11.5 |
| 3054-6 | 8.6 | 16.7 | 5.1 | 19.0 | 47.5 | 11.8 |
| 3054-25 | 8.3 | 16.2 | 5.7 | 21.0 | 44.4 | 12.7 |
| 3054-26 | 8.2 | 17.0 | 5.1 | 22.1 | 43.5 | 12.3 |
| 3054-7 | 7.8 | 15.6 | 6.8 | 17.6 | 48.0 | 12.0 |
| 3054-27 | 7.8 | 16.5 | 5.0 | 21.1 | 44.3 | 13.1 |
| 3054-10 | 7.4 | 15.9 | 3.4 | 15.5 | 50.0 | 15.3 |
| 3054-16 | 7.2 | 15.3 | 5.9 | 19.1 | 47.4 | 12.3 |
| 3054-17 | 7.1 | 16.3 | 4.9 | 21.8 | 42.5 | 14.4 |
| 3054-21 | 7.0 | 16.1 | 6.2 | 19.9 | 45.0 | 12.7 |
| 3054-4 | 6.9 | 15.8 | 5.3 | 18.6 | 46.9 | 13.4 |
| 3054-28 | 6.4 | 15.8 | 5.4 | 20.2 | 44.7 | 13.8 |
| 3054-19 | 6.4 | 16.1 | 5.8 | 18.1 | 45.9 | 14.1 |
| 3054-13 | 5.9 | 16.4 | 6.0 | 22.9 | 41.9 | 12.9 |
| 3054-9 | 5.7 | 16.2 | 5.1 | 18.3 | 46.4 | 14.0 |
| 3054-1 | 5.3 | 17.7 | 5.2 | 22.0 | 41.6 | 13.5 |
| 3054-24 | 5.1 | 16.2 | 5.7 | 21.6 | 42.7 | 13.8 |
| 3054-5 | 4.9 | 15.7 | 5.0 | 18.3 | 44.5 | 16.5 |
| 3054-14 | 4.9 | 15.5 | 5.2 | 25.7 | 39.2 | 14.4 |
| 3054-12 | 4.9 | 16.9 | 5.4 | 22.7 | 41.1 | 13.9 |
| 3054-22 | 4.5 | 16.6 | 6.5 | 32.2 | 33.4 | 11.3 |
| 3054-8 | 4.2 | 17.0 | 4.7 | 17.0 | 42.4 | 19.0 |
| 3054-23 | 4.2 | 18.3 | 5.3 | 21.8 | 40.4 | 14.1 |
| 3054-20 | 4.2 | 19.1 | 5.2 | 20.0 | 38.4 | 17.3 |
| 3054-18 | 4.1 | 15.8 | 7.7 | 26.9 | 38.9 | 10.7 |
| 3054-15 | 2.7 | 17.0 | 6.9 | 25.3 | 38.1 | 12.7 |
| 3054-2 | 2.6 | 17.7 | 6.5 | 26.6 | 36.5 | 12.8 |
| 3054-3 | 2.5 | 16.5 | 5.7 | 21.5 | 39.4 | 16.9 |
| Avg. | 5.9 | 16.5 | 5.6 | 21.4 | 42.9 | 13.7 |
| Top5 Avg. | 8.4 | 16.3 | 5.6 | 20.3 | 45.7 | 12.1 |
| 3055-29 | 6.4 | 16.3 | 6.9 | 17.3 | 46.2 | 13.3 |
| 3055-30 | 5.8 | 16.5 | 6.8 | 18.5 | 45.1 | 13.2 |
| 3055-3 | 5.7 | 16.2 | 7.6 | 17.8 | 44.5 | 13.8 |
| 3055-28 | 5.7 | 16.3 | 7.1 | 26.5 | 38.7 | 11.5 |
| 3055-12 | 5.5 | 17.0 | 5.9 | 17.1 | 45.3 | 14.7 |
| 3055-19 | 5.5 | 15.1 | 6.1 | 17.5 | 46.3 | 15.0 |
| 3055-15 | 5.3 | 17.2 | 7.1 | 18.0 | 43.4 | 14.3 |
| 3055-25 | 5.2 | 16.2 | 8.0 | 17.3 | 44.7 | 13.7 |
| 3055-13 | 5.2 | 16.5 | 7.3 | 16.7 | 45.1 | 14.5 |
| 3055-4 | 5.2 | 17.6 | 6.3 | 23.3 | 39.3 | 13.4 |
| 3055-20 | 4.7 | 16.9 | 6.0 | 16.8 | 44.5 | 15.8 |
| 3055-24 | 4.4 | 18.0 | 5.2 | 21.0 | 41.3 | 14.5 |
| 3055-11 | 4.2 | 18.5 | 5.4 | 20.8 | 39.9 | 15.4 |
| 3055-17 | 4.1 | 17.8 | 5.7 | 23.8 | 37.5 | 15.2 |
| 3055-7 | 4.1 | 17.8 | 5.0 | 18.8 | 42.9 | 15.4 |
| 3055-16 | 3.9 | 18.1 | 6.7 | 21.4 | 39.1 | 14.7 |
| 3055-27 | 3.8 | 17.3 | 6.7 | 17.7 | 42.6 | 15.7 |
| 3055-21 | 3.7 | 19.1 | 4.7 | 19.4 | 39.7 | 17.1 |
| 3055-22 | 3.6 | 18.0 | 5.0 | 19.6 | 41.6 | 15.8 |
| 3055-23 | 3.6 | 18.6 | 4.5 | 17.7 | 39.5 | 19.6 |
| 3055-1 | 3.6 | 17.9 | 5.8 | 16.0 | 42.6 | 17.8 |
| 3055-8 | 3.5 | 17.6 | 5.4 | 19.3 | 40.8 | 16.9 |
| 3055-5 | 3.4 | 18.9 | 5.7 | 24.8 | 36.9 | 13.6 |
| 3055-2 | 3.3 | 17.9 | 3.5 | 16.4 | 43.1 | 19.0 |
| 3055-6 | 3.3 | 18.6 | 5.5 | 21.5 | 38.9 | 15.5 |
| 3055-9 | 3.0 | 19.1 | 4.3 | 16.4 | 40.4 | 19.9 |
| 3055-14 | 2.5 | 18.1 | 4.8 | 20.9 | 37.3 | 18.8 |
| 3055-18 | 2.4 | 18.2 | 4.3 | 16.0 | 39.9 | 21.6 |
| 3055-10 | 2.2 | 19.1 | 4.6 | 18.3 | 37.1 | 21.0 |
| 3055-26 | 2.1 | 18.7 | 5.0 | 21.2 | 38.3 | 16.8 |
| Avg. | 4.2 | 17.6 | 5.8 | 19.3 | 41.4 | 15.9 |
| Top5 Avg. | 5.8 | 16.5 | 6.9 | 19.4 | 43.9 | 13.3 |

A summary comparing the average oil content and average fatty acid profile for all events in each experiment is shown in Table 15. In Table 15, average oil content is reported as a percent of total dry weight (Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 15 also shows the change in oil content (Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 15

Summary of Average Oil Content and Fatty Acid Profiles for All Events Expressing ZmLec1, ZmODP1 or Empty Vector Control

| MSE | Vector (Gene) | Avg. Oil | Avg. % Inc | 16:0 | 18:0 | 18:1 | 18:2 | 18:3 |
|---|---|---|---|---|---|---|---|---|
| 3053 | pKR2114 (ZmODP1) | 7.5 | 80% | 16.7 | 5.3 | 19.7 | 45.6 | 12.6 |
| 3054 | pKR2121 (ZmLec1) | 5.9 | 41% | 18.5 | 5.6 | 21.4 | 42.9 | 13.7 |
| 3055 | pKR278 (Control) | 4.2 | 0% | 17.6 | 5.8 | 19.3 | 41.4 | 15.9 |

A summary comparing the average oil content and average fatty acid profile of the top 5 events having the highest oil content for each experiment is shown in Table 16. In Table 16, average oil for the 5 events having highest oil content is reported as a percent of total dry weight (Top5 Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 16 also shows the change in oil content (Top5 Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 16

Summary of Average Oil Content and Fatty Acid Profiles for the Top5 Events Having Highest Oil Contents and Expressing ZmLec1, ZmODP1 or Empty Vector Control

| MSE | Vector (Gene) | Avg. Oil | Avg. % Inc | 16:0 | 18:0 | 18:1 | 18:2 | 18:3 |
|---|---|---|---|---|---|---|---|---|
| 3053 | pKR2114 (ZmODP1) | 9.6 | 65% | 16.4 | 4.7 | 18.6 | 48.9 | 11.4 |
| 3054 | pKR2121 (ZmLec1) | 8.4 | 44% | 16.3 | 5.6 | 20.3 | 45.7 | 12.1 |
| 3055 | pKR278 (Control) | 5.8 | 0% | 16.5 | 6.9 | 19.4 | 43.9 | 13.3 |

Both Tables 15 and 16 demonstrate that expression of ZmLec1 and ZmODP1 lead to an increase in oil content in soy.

Example 8

Co-Expressing ZmLec1 and ZmODP1 with GmDGAT1cAII in Soy Embryos

The SbfI fragment of pKR2121 (SEQ ID NO: 71), containing ZmLec1, and the SbfI fragment of pKR2114 (SEQ ID NO: 72), containing ZmODP1, were cloned into the SbfI site of pKR1520 to produce pKR2123 (SEQ ID NO: 73) and pKR2122 (SEQ ID NO: 74), respectively. In this way, the respective transcription factors could be expressed behind the soy sucrose synthase promoter (GmSusPro) and co-expressed with GmDGAT1cAII (SEQ ID NO: 54).

DNA from plasmids pKR2123 (SEQ ID NO: 73), pKR2122 (SEQ ID NO: 74) and pKR1520 was prepared for particle bombardment into soybean embryogenic suspension culture and transformed exactly as described previously in PCT Publication No. WO 2008/147935. Soybean embryogenic suspension culture was initiated, grown, maintained and bombarded and events were selected and matured on SHaM media also exactly as described in PCT Publication No. WO 2008/147935. A summary of genes, plasmids and model system experiment numbers is shown in Table 17.

TABLE 17

Summary of Genes, Plasmids and Experiments

| Experiment | Plasmid | Gene1[1,2] | Gene2 | SEQ ID NO nt | SEQ ID NO aa |
|---|---|---|---|---|---|
| MSE 3006 | pKR1520 | GmDGAT1cAll | — | — | — |
| MSE 3009 | pKR2122 | GmDGAT1cAll | ZmODP1 | 69 | 70 |
| MSE 3010 | pKR2123 | GmDGAT1cAll | ZmLec1 | 64 | 65 |

[1]Gene1 nucleotide sequence of SEQ ID NO: 54
[2]Gene1 amino acid sequence of SEQ ID NO: 55

Approximately 10-20 matured embryos from each of approximately 30 events per bombardment experiment were lyophilized, ground, oil content was measured by NMR and fatty acid profile was evaluated by FAME-GC analysis exactly as described in PCT Publication No. WO 2008/147935. The results for oil content and fatty acid profile for each event as well as the average of all events (Avg.) and average for the top 5 events having highest oil content (Top5 Avg.) are shown in Table 18.

In Table 18, results are sorted based on oil content from highest to lowest. In Table 18, oil content is reported as a percent of total dry weight (% Oil) and fatty acid content for each fatty acid [palmitic acid (16:0), stearic acid (18:0), oleic acid (18:1), linoleic acid (18:2) & alpha-linolenic acid (18:3)] is reported as a weight % of total fatty acids.

TABLE 18

Summary of Oil Content and Fatty Acid Profiles for Events Expressing GmDGAT1cAll with ZmLec1 or ZmODP1

| | % oil | 16:0 | 18:0 | 18:1 | 18:2 | 18:3 |
|---|---|---|---|---|---|---|
| 3006-28 | 15.46 | 12.83 | 5.81 | 34.01 | 40.95 | 6.41 |
| 3006-10 | 13.29 | 13.49 | 5.69 | 33.99 | 39.36 | 7.48 |
| 3006-19 | 13.12 | 13.84 | 4.51 | 27.42 | 44.84 | 9.38 |
| 3006-2 | 12.10 | 14.43 | 5.55 | 26.44 | 45.18 | 8.41 |
| 3006-3 | 11.99 | 13.03 | 5.65 | 32.35 | 40.09 | 8.88 |
| 3006-23 | 11.96 | 14.84 | 4.66 | 27.88 | 44.12 | 8.50 |
| 3006-24 | 11.49 | 13.02 | 7.30 | 33.49 | 38.56 | 7.64 |
| 3006-27 | 10.87 | 14.01 | 6.32 | 32.49 | 39.31 | 7.87 |
| 3006-1 | 10.85 | 13.82 | 6.53 | 31.04 | 40.49 | 8.12 |
| 3006-26 | 10.22 | 15.49 | 5.13 | 22.72 | 46.85 | 9.81 |
| 3006-20 | 10.19 | 15.49 | 4.65 | 21.58 | 47.28 | 11.01 |
| 3006-4 | 10.05 | 15.67 | 3.93 | 18.28 | 50.17 | 11.96 |
| 3006-25 | 10.04 | 14.35 | 7.08 | 27.96 | 41.52 | 9.09 |
| 3006-8 | 9.93 | 15.02 | 6.90 | 27.71 | 40.94 | 9.43 |
| 3006-6 | 9.51 | 17.52 | 4.38 | 17.94 | 48.66 | 11.51 |
| 3006-31 | 9.37 | 15.55 | 3.98 | 17.39 | 49.82 | 13.27 |
| 3006-7 | 9.27 | 16.20 | 5.90 | 23.30 | 43.50 | 11.10 |
| 3006-14 | 9.15 | 15.87 | 5.43 | 22.58 | 45.39 | 10.72 |
| 3006-21 | 8.75 | 15.23 | 5.32 | 20.46 | 47.62 | 11.38 |
| 3006-11 | 8.72 | 17.05 | 3.64 | 17.79 | 48.24 | 13.28 |
| 3006-15 | 8.65 | 13.41 | 8.25 | 39.07 | 32.68 | 6.60 |
| 3006-16 | 8.49 | 15.51 | 5.18 | 21.14 | 47.31 | 10.87 |
| 3006-30 | 8.48 | 14.77 | 6.08 | 23.92 | 44.56 | 10.66 |
| 3006-29 | 7.97 | 16.89 | 5.40 | 23.91 | 42.01 | 11.78 |
| 3006-18 | 7.43 | 15.84 | 5.42 | 21.80 | 45.40 | 11.55 |
| 3006-5 | 7.32 | 15.87 | 6.10 | 24.44 | 43.06 | 10.53 |
| 3006-12 | 6.59 | 17.85 | 6.26 | 27.20 | 38.06 | 10.62 |
| 3006-9 | 6.18 | 15.71 | 5.60 | 23.23 | 43.00 | 12.46 |
| 3006-17 | 6.14 | 15.66 | 6.81 | 24.98 | 41.52 | 11.03 |
| 3006-13 | 5.87 | 14.57 | 7.04 | 26.12 | 42.22 | 10.05 |
| 3006-22 | 3.13 | 15.44 | 7.76 | 28.15 | 37.39 | 11.26 |

TABLE 18-continued

Summary of Oil Content and Fatty Acid Profiles for Events Expressing GmDGAT1cAll with ZmLec1 or ZmODP1

| | % oil | 16:0 | 18:0 | 18:1 | 18:2 | 18:3 |
|---|---|---|---|---|---|---|
| Avg. | 9.44 | 15.11 | 5.75 | 25.83 | 43.23 | 10.08 |
| Top5 Avg. | 13.19 | 13.52 | 5.44 | 30.84 | 42.08 | 8.11 |
| 3009-9 | 20.60 | 13.13 | 4.48 | 34.94 | 41.26 | 6.19 |
| 3009-8 | 17.21 | 13.31 | 6.15 | 30.24 | 43.29 | 7.01 |
| 3009-16 | 14.42 | 14.15 | 6.13 | 37.01 | 35.96 | 6.75 |
| 3009-6 | 14.40 | 11.74 | 5.79 | 33.69 | 42.37 | 6.41 |
| 3009-21 | 13.69 | 12.95 | 6.41 | 33.22 | 40.13 | 7.30 |
| 3009-3 | 12.99 | 13.56 | 7.47 | 30.41 | 40.69 | 7.88 |
| 3009-17 | 12.27 | 14.37 | 6.80 | 37.81 | 34.41 | 6.60 |
| 3009-13 | 11.12 | 13.78 | 8.03 | 37.56 | 33.72 | 6.91 |
| 3009-10 | 10.93 | 15.78 | 4.90 | 19.06 | 48.61 | 11.64 |
| 3009-28 | 10.85 | 14.55 | 4.65 | 19.63 | 49.88 | 11.29 |
| 3009-23 | 10.26 | 13.71 | 7.05 | 43.30 | 29.99 | 5.96 |
| 3009-26 | 9.92 | 15.60 | 5.79 | 27.33 | 41.87 | 9.40 |
| 3009-4 | 9.70 | 15.82 | 5.24 | 30.04 | 40.64 | 8.26 |
| 3009-29 | 9.49 | 14.37 | 6.20 | 25.89 | 43.74 | 9.79 |
| 3009-22 | 9.45 | 14.05 | 7.25 | 33.34 | 37.01 | 8.35 |
| 3009-18 | 9.39 | 14.78 | 5.41 | 22.88 | 46.23 | 10.70 |
| 3009-24 | 9.25 | 15.44 | 6.43 | 24.34 | 43.37 | 10.42 |
| 3009-5 | 9.18 | 14.95 | 4.74 | 20.21 | 48.01 | 12.10 |
| 3009-25 | 8.97 | 16.10 | 5.17 | 19.54 | 47.70 | 11.50 |
| 3009-7 | 8.86 | 15.62 | 5.05 | 18.50 | 49.05 | 11.77 |
| 3009-20 | 8.85 | 13.87 | 7.36 | 33.99 | 36.25 | 8.52 |
| 3009-1 | 8.19 | 15.06 | 5.35 | 21.07 | 45.91 | 12.61 |
| 3009-19 | 8.17 | 15.69 | 5.67 | 25.02 | 42.23 | 11.40 |
| 3009-2 | 8.02 | 15.11 | 4.98 | 20.67 | 46.58 | 12.66 |
| 3009-14 | 7.85 | 16.77 | 5.76 | 22.50 | 43.11 | 11.87 |
| 3009-31 | 7.61 | 14.88 | 6.38 | 26.16 | 42.38 | 10.21 |
| 3009-27 | 7.21 | 14.74 | 7.83 | 19.47 | 46.43 | 11.52 |
| 3009-30 | 7.14 | 15.23 | 6.04 | 23.66 | 44.16 | 10.90 |
| 3009-15 | 6.68 | 15.08 | 6.35 | 25.94 | 42.57 | 10.05 |
| 3009-11 | 6.55 | 16.25 | 5.89 | 25.36 | 40.89 | 11.61 |
| 3009-12 | 5.05 | 16.55 | 4.32 | 16.91 | 46.12 | 16.09 |
| Avg. | 10.14 | 14.74 | 5.97 | 27.09 | 42.41 | 9.80 |
| Top5 Avg. | 16.06 | 13.06 | 5.79 | 33.82 | 40.60 | 6.73 |
| 3010-18 | 16.30 | 12.38 | 4.54 | 30.86 | 44.74 | 7.48 |
| 3010-19 | 15.93 | 11.72 | 4.75 | 34.72 | 40.70 | 8.10 |
| 3010-2 | 15.70 | 12.48 | 4.09 | 32.28 | 42.54 | 8.61 |
| 3010-5 | 15.57 | 12.17 | 5.61 | 36.18 | 37.99 | 8.04 |
| 3010-30 | 15.40 | 12.66 | 4.52 | 33.89 | 41.29 | 7.64 |
| 3010-25 | 14.61 | 13.34 | 3.96 | 28.41 | 45.46 | 8.83 |
| 3010-3 | 13.94 | 12.74 | 5.10 | 31.91 | 40.89 | 9.36 |
| 3010-1 | 13.90 | 14.34 | 4.49 | 27.04 | 45.95 | 8.17 |
| 3010-17 | 13.68 | 13.09 | 5.03 | 29.39 | 42.66 | 9.83 |
| 3010-8 | 13.63 | 11.75 | 4.35 | 34.60 | 40.51 | 8.79 |
| 3010-26 | 13.55 | 13.37 | 4.79 | 34.23 | 38.78 | 8.83 |
| 3010-22 | 13.34 | 13.06 | 4.26 | 30.03 | 43.97 | 8.68 |
| 3010-14 | 13.34 | 12.48 | 4.51 | 34.89 | 39.12 | 9.00 |
| 3010-29 | 13.07 | 12.82 | 5.22 | 37.70 | 35.65 | 8.61 |
| 3010-13 | 12.65 | 12.55 | 4.52 | 31.75 | 41.68 | 9.50 |
| 3010-15 | 12.56 | 13.30 | 4.27 | 30.08 | 43.03 | 9.32 |
| 3010-16 | 11.56 | 12.03 | 4.99 | 35.16 | 38.47 | 9.35 |
| 3010-27 | 11.52 | 11.81 | 5.35 | 34.44 | 38.57 | 9.83 |
| 3010-9 | 11.26 | 13.73 | 3.97 | 23.11 | 48.56 | 10.63 |
| 3010-6 | 10.10 | 14.78 | 4.56 | 18.36 | 50.94 | 11.36 |
| 3010-4 | 9.97 | 15.52 | 4.40 | 20.60 | 47.99 | 11.49 |
| 3010-23 | 9.77 | 12.37 | 5.58 | 34.07 | 38.25 | 9.73 |
| 3010-24 | 9.49 | 14.30 | 3.96 | 17.14 | 51.54 | 13.07 |
| 3010-31 | 9.02 | 16.48 | 4.12 | 20.22 | 46.66 | 12.52 |
| 3010-21 | 8.57 | 15.25 | 4.48 | 25.46 | 43.10 | 11.71 |
| 3010-7 | 8.39 | 15.82 | 3.19 | 15.07 | 51.22 | 14.70 |
| 3010-28 | 8.01 | 16.07 | 3.92 | 17.45 | 49.89 | 12.67 |
| 3010-10 | 7.89 | 13.83 | 4.40 | 18.47 | 48.61 | 14.68 |
| -11 | 7.60 | 18.93 | 3.83 | 18.45 | 44.69 | 14.10 |
| 3010-12 | 7.58 | 16.09 | 5.28 | 21.85 | 44.01 | 12.77 |
| 3010-20 | 6.35 | 13.92 | 5.13 | 17.60 | 49.14 | 14.20 |
| Avg. | 11.75 | 13.72 | 4.55 | 27.59 | 43.76 | 10.37 |
| Top5 Avg. | 15.78 | 12.28 | 4.70 | 33.59 | 41.45 | 7.98 |

A summary comparing the average oil content and average fatty acid profile for all events in each experiment is shown in Table 19. In Table 19, average oil content is reported as a percent of total dry weight (Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 3 also shows the change in oil content (Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 19

Summary of Average Oil Content and Fatty Acid Profiles for All Events Expressing GmDGAT1cAll with ZmLec1 or ZmODP1

| MSE | Vector (Gene2) | Avg. Oil | Avg. % Inc | 16:0 | 18:0 | 18:1 | 18:2 | 18:3 |
|---|---|---|---|---|---|---|---|---|
| 3006 | pKR1520 (n/a) | 9.4 | 0% | 15.1 | 5.8 | 25.8 | 43.2 | 10.1 |
| 3009 | pKR2122 (ZmODP1) | 10.1 | 7% | 14.7 | 6.0 | 27.1 | 42.4 | 9.8 |
| 3010 | pKR2123 (ZmLec1) | 11.8 | 25% | 13.7 | 4.6 | 27.6 | 43.8 | 10.4 |

A summary comparing the average oil content and average fatty acid profile of the top 5 events having the highest oil content for each experiment is shown in Table 20. In Table 20, average oil for the 5 events having highest oil content is reported as a percent of total dry weight (Top5 Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 4 also shows the change in oil content (Top5 Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 20

Summary of Average Oil Content and Fatty Acid Profiles for the Top5 Events Having Highest Oil Contents and Expressing GmDGAT1cAll with ZmLec1 or ZmODP1

| MSE | Vector (Gene) | Avg. Oil | Avg. % Inc | 16:0 | 18:0 | 18:1 | 18:2 | 18:3 |
|---|---|---|---|---|---|---|---|---|
| 3006 | pKR1520 (n/a) | 13.2 | 0% | 13.5 | 5.4 | 30.8 | 42.1 | 8.1 |
| 3009 | pKR2122 (ZmODP) | 16.1 | 22% | 13.1 | 5.8 | 33.8 | 40.6 | 6.7 |
| 3010 | pKR2123 (ZmLec1) | 15.8 | 20% | 12.3 | 4.7 | 33.6 | 41.5 | 8.0 |

Both Tables 19 and 20 demonstrate that expression of ZmLec1 and ZmODP1 with GmDGAT1cAII lead to an increase in oil content in soy above that for GmDGAT1cAII alone.

Example 9

Co-Expressing ZmLec1 and ZmODP1 with YLDGAT2 in Soy Embryos

The SbfI fragment of pKR2121 (SEQ ID NO: 71), containing ZmLec1, and the SbfI fragment of pKR2114 (SEQ ID NO: 72), containing ZmODP1, were cloned into the SbfI site of pKR1256 to produce pKR2146 (SEQ ID NO: 75) and pKR2145 (SEQ ID NO: 76), respectively. In this way, the respective transcription factors could be expressed behind the soy sucrose synthase promoter (GmSusPro) and co-expressed with YLDGAT2 (SEQ ID NO: 59).

DNA from plasmids pKR2146 (SEQ ID NO: 75), pKR2145 (SEQ ID NO: 76) and pKR1256 was prepared for particle bombardment into soybean embryogenic suspension culture and transformed exactly as described previously in PCT Publication No. WO 2008/147935. Soybean embryogenic suspension culture was initiated, grown, maintained and bombarded and events were selected and matured on SHaM media also exactly as described in PCT Publication No. WO 2008/147935. A summary of genes, plasmids and model system experiment numbers is shown in Table 21.

TABLE 21

Summary of Genes, Plasmids and Experiments

| Experiment | Plasmid | Gene1[1,2] | Gene2 | Gene2 - SEQ ID NO nt | aa |
|---|---|---|---|---|---|
| 3073 | pKR1256 | YLDGAT2 | — | — | — |
| 3076 | pKR2145 | YLDGAT2 | ZmODP1 | 69 | 70 |
| 3077 | pKR2146 | YLDGAT2 | ZmLec1 | 64 | 65 |

[1]Gene1 nucleotide sequence of SEQ ID NO: 59
[2]Gene1 amino acid sequence of SEQ ID NO: 60

Approximately 10-20 matured embryos from each of approximately 30 events per bombardment experiment were lyophilized, ground, oil content was measured by NMR and fatty acid profile was evaluated by FAME-GC analysis exactly as described in PCT Publication No. WO 2008/147935. The results for oil content and fatty acid profile for each event as well as the average of all events (Avg.) and average for the top 5 events having highest oil content (Top5 Avg.) are shown in Table 22.

In Table 22, results are sorted based on oil content from highest to lowest. In Table 22, oil content is reported as a percent of total dry weight (% Oil) and fatty acid content for each fatty acid [palmitic acid (16:0), stearic acid (18:0), oleic acid (18:1), linoleic acid (18:2) & alpha-linolenic acid (18:3)] is reported as a weight % of total fatty acids.

TABLE 22

Summary of Oil Content and Fatty Acid Profiles for Events Expressing YLDGAT2 with ZmLec1 or ZmODP1

| Event | % oil | 16:0 | 18:0 | 18:1 | 18:2 | 18:3 |
|---|---|---|---|---|---|---|
| 3073-30 | 9.2 | 13.5 | 5.6 | 30.6 | 40.0 | 10.3 |
| 3073-28 | 7.8 | 17.0 | 3.7 | 18.8 | 45.8 | 14.8 |
| 3073-14 | 7.6 | 13.4 | 6.1 | 33.1 | 36.5 | 11.0 |
| 3073-15 | 6.9 | 16.0 | 5.7 | 22.3 | 42.1 | 13.9 |
| 3073-20 | 6.7 | 16.0 | 6.0 | 24.0 | 40.8 | 13.2 |
| 3073-1 | 6.6 | 14.2 | 6.5 | 32.6 | 36.1 | 10.6 |
| 3073-11 | 6.5 | 17.5 | 4.7 | 17.9 | 44.3 | 15.6 |
| 3073-10 | 6.4 | 14.1 | 6.6 | 27.9 | 38.3 | 13.1 |
| 3073-7 | 6.3 | 17.0 | 4.5 | 20.9 | 41.5 | 16.1 |
| 3073-24 | 6.2 | 14.7 | 6.1 | 28.7 | 38.0 | 12.5 |
| 3073-18 | 6.2 | 17.1 | 5.4 | 20.1 | 43.2 | 14.2 |
| 3073-29 | 6.1 | 17.3 | 5.3 | 20.4 | 41.0 | 16.0 |
| 3073-22 | 6.0 | 14.5 | 5.4 | 27.1 | 39.4 | 13.5 |
| 3073-5 | 6.0 | 14.1 | 5.2 | 18.1 | 45.0 | 17.6 |
| 3073-3 | 5.7 | 18.6 | 5.3 | 24.1 | 38.6 | 13.4 |
| 3073-2 | 5.7 | 16.5 | 5.5 | 21.5 | 41.3 | 15.1 |
| 3073-23 | 5.5 | 16.3 | 4.7 | 19.7 | 43.6 | 15.8 |
| 3073-6 | 5.5 | 17.1 | 6.0 | 24.7 | 38.9 | 13.4 |
| 3073-8 | 5.4 | 17.3 | 5.0 | 20.1 | 41.7 | 15.9 |
| 3073-17 | 5.3 | 15.4 | 5.2 | 22.3 | 43.6 | 13.4 |
| 3073-13 | 5.1 | 14.9 | 7.0 | 29.9 | 36.7 | 11.5 |
| 3073-16 | 4.6 | 16.8 | 6.4 | 24.7 | 38.1 | 14.0 |
| 3073-25 | 4.5 | 16.4 | 5.7 | 22.9 | 39.6 | 15.5 |
| 3073-4 | 4.4 | 15.7 | 5.1 | 29.8 | 35.6 | 13.8 |
| 3073-27 | 4.3 | 15.3 | 5.9 | 22.0 | 38.2 | 18.6 |
| 3073-19 | 4.3 | 16.6 | 6.5 | 23.5 | 38.9 | 14.5 |
| 3073-21 | 3.9 | 16.9 | 5.1 | 21.2 | 39.4 | 17.4 |
| 3073-26 | 3.8 | 17.1 | 4.7 | 18.8 | 39.5 | 19.8 |
| 3073-12 | 3.6 | 16.2 | 4.5 | 18.3 | 42.6 | 18.4 |
| 3073-9 | 3.0 | 17.5 | 4.9 | 21.4 | 38.6 | 17.6 |
| Avg. | 5.6 | 16.0 | 5.5 | 23.6 | 40.2 | 14.7 |
| Top5 Avg. | 7.6 | 15.2 | 5.4 | 25.7 | 41.0 | 12.6 |
| 3076-4 | 18.8 | 11.3 | 4.4 | 34.3 | 43.9 | 6.1 |
| 3076-2 | 15.4 | 12.3 | 6.7 | 34.0 | 40.5 | 6.5 |
| 3076-15 | 13.2 | 11.1 | 6.3 | 38.9 | 37.5 | 6.2 |
| 3076-12 | 12.1 | 11.2 | 7.6 | 32.5 | 41.3 | 7.4 |
| 3076-28 | 11.7 | 12.2 | 7.0 | 29.9 | 42.3 | 8.6 |
| 3076-5 | 11.4 | 13.4 | 6.9 | 29.0 | 41.6 | 9.0 |
| 3076-3 | 11.2 | 11.2 | 9.2 | 30.4 | 41.5 | 7.7 |
| 3076-13 | 11.0 | 11.7 | 5.3 | 33.7 | 41.4 | 7.9 |
| 3076-9 | 11.0 | 12.4 | 7.9 | 26.5 | 44.0 | 9.2 |
| 3076-26 | 10.5 | 13.9 | 5.3 | 38.1 | 36.0 | 6.8 |
| 3076-29 | 10.5 | 13.7 | 7.6 | 30.7 | 39.6 | 8.3 |
| 3076-10 | 10.2 | 14.1 | 6.0 | 29.8 | 41.2 | 9.0 |
| 3076-25 | 10.1 | 12.1 | 7.2 | 34.6 | 37.5 | 8.5 |
| 3076-27 | 9.2 | 13.7 | 6.1 | 34.0 | 39.3 | 7.0 |
| 3076-18 | 8.9 | 14.4 | 7.2 | 22.4 | 44.4 | 11.7 |
| 3076-24 | 8.9 | 13.7 | 7.8 | 26.8 | 42.1 | 9.7 |
| 3076-22 | 8.8 | 12.7 | 7.2 | 27.3 | 42.3 | 10.5 |
| 3076-8 | 8.8 | 14.1 | 7.0 | 26.1 | 41.6 | 11.1 |
| 3076-23 | 8.7 | 14.0 | 4.5 | 31.4 | 40.1 | 10.0 |
| 3076-11 | 8.3 | 15.1 | 6.6 | 17.9 | 47.5 | 13.0 |
| 3076-31 | 8.3 | 15.1 | 6.6 | 21.3 | 44.2 | 12.8 |
| 3076-21 | 8.1 | 13.4 | 6.6 | 32.2 | 39.9 | 7.9 |
| 3076-1 | 7.8 | 13.5 | 7.6 | 30.2 | 39.2 | 9.5 |
| 3076-17 | 7.7 | 15.5 | 4.8 | 17.9 | 47.4 | 14.4 |
| 3076-20 | 7.1 | 15.8 | 5.5 | 16.3 | 47.0 | 15.4 |
| 3076-16 | 6.8 | 14.9 | 5.6 | 23.8 | 43.2 | 12.4 |
| 3076-7 | 6.7 | 14.6 | 7.2 | 24.9 | 41.5 | 11.8 |
| 3076-14 | 6.2 | 15.8 | 5.4 | 19.1 | 45.3 | 14.5 |
| 3076-6 | 6.1 | 15.8 | 7.3 | 20.6 | 43.6 | 12.7 |
| 3076-19 | 4.6 | 15.9 | 6.0 | 20.4 | 44.1 | 13.5 |
| 3076-30 | 3.5 | 16.0 | 6.2 | 21.1 | 43.7 | 13.1 |
| Avg. | 9.4 | 13.7 | 6.5 | 27.6 | 42.1 | 10.1 |
| Top5 Avg. | 14.2 | 11.6 | 6.4 | 33.9 | 41.1 | 7.0 |
| 3076-16 | 15.5 | 11.5 | 6.7 | 35.0 | 39.4 | 7.3 |
| 3076-10 | 13.9 | 11.9 | 6.6 | 33.8 | 40.4 | 7.2 |
| 3076-21 | 12.6 | 10.2 | 8.2 | 41.9 | 33.0 | 6.7 |
| 3076-3 | 12.0 | 10.2 | 7.0 | 42.9 | 33.1 | 6.7 |
| 3076-23 | 11.5 | 11.7 | 8.0 | 37.1 | 36.9 | 6.2 |
| 3076-12 | 11.4 | 12.3 | 6.5 | 32.8 | 39.3 | 9.0 |
| 3076-26 | 10.9 | 12.2 | 5.6 | 30.5 | 42.0 | 9.7 |
| 3076-27 | 10.9 | 13.6 | 6.0 | 28.9 | 41.5 | 9.9 |
| 3076-22 | 10.7 | 11.8 | 6.4 | 38.3 | 35.3 | 8.2 |
| 3076-24 | 10.7 | 12.8 | 6.6 | 31.8 | 39.1 | 9.7 |
| 3076-5 | 10.4 | 11.0 | 4.1 | 37.1 | 40.6 | 7.2 |
| 3076-9 | 10.3 | 15.2 | 5.7 | 21.6 | 46.5 | 10.9 |
| 3076-17 | 10.0 | 13.3 | 6.8 | 34.7 | 36.8 | 8.5 |
| 3076-6 | 9.7 | 10.9 | 7.6 | 44.8 | 30.5 | 6.2 |
| 3076-13 | 9.6 | 15.1 | 5.8 | 20.8 | 47.5 | 10.8 |
| 3076-4 | 9.2 | 14.6 | 8.0 | 26.1 | 42.0 | 9.3 |
| 3076-15 | 8.9 | 13.7 | 4.6 | 33.1 | 36.7 | 12.0 |
| 3076-20 | 8.1 | 14.8 | 6.0 | 27.2 | 39.7 | 12.3 |
| 3076-11 | 7.5 | 12.7 | 6.3 | 36.7 | 35.1 | 9.2 |
| 3077-1 | 6.8 | 15.3 | 6.0 | 28.5 | 38.6 | 11.5 |
| 3076-25 | 6.7 | 15.8 | 5.2 | 22.8 | 43.0 | 13.3 |
| 3076-8 | 6.5 | 15.9 | 6.1 | 21.6 | 45.0 | 11.4 |
| 3076-7 | 5.3 | 17.1 | 7.4 | 28.9 | 36.6 | 10.1 |
| 3076-19 | 4.4 | 15.0 | 4.0 | 17.9 | 48.6 | 14.5 |
| 3076-28 | 4.3 | 14.0 | 3.6 | 26.7 | 42.2 | 13.4 |
| 3076-2 | 3.5 | 16.7 | 3.4 | 17.0 | 44.3 | 18.6 |
| 3076-18 | 3.1 | 15.4 | 3.6 | 21.7 | 41.2 | 18.0 |
| 3076-14 | 2.6 | 16.2 | 6.1 | 25.3 | 39.2 | 13.2 |
| Avg. | 8.8 | 13.6 | 6.0 | 30.2 | 39.8 | 10.4 |
| Top5 Avg. | 13.1 | 11.1 | 7.3 | 38.2 | 36.6 | 6.8 |

A summary comparing the average oil content and average fatty acid profile for all events in each experiment is shown in Table 23. In Table 23, average oil content is reported as a percent of total dry weight (Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 3 also shows the change in oil content (Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 23

Summary of Average Oil Content and Fatty Acid Profiles for All Events Expressing YLDGAT2 with ZmLec1 or ZmODP1

| MSE | Vector (Gene2) | Avg. Oil | Avg. % Inc | 16:0 | 18:0 | 18:1 | 18:2 | 18:3 |
|---|---|---|---|---|---|---|---|---|
| 3073 | pKR1256 (n/a) | 5.6 | 0% | 16.0 | 5.5 | 23.6 | 40.2 | 14.7 |
| 3076 | pKR2145 (ZmODP1) | 9.4 | 67% | 13.7 | 6.5 | 27.6 | 42.1 | 10.1 |
| 3077 | pKR2146 (ZmLec1) | 8.8 | 57% | 13.6 | 6.0 | 30.2 | 39.8 | 10.4 |

A summary comparing the average oil content and average fatty acid profile of the top 5 events having the highest oil content for each experiment is shown in Table 24. In Table 24, average oil for the 5 events having highest oil content is reported as a percent of total dry weight (Top5 Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 4 also shows the change in oil content (Top5 Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 24

Summary of Average Oil Content and Fatty Acid Profiles for the Top5 Events Having Highest Oil Contents and Expressing YLDGAT2 with ZmLec1 or ZmODP1

| MSE | Vector (Gene2) | Avg. Oil | Avg. % Inc | 16:0 | 18:0 | 18:1 | 18:2 | 18:3 |
|---|---|---|---|---|---|---|---|---|
| 3073 | pKR1256 (n/a) | 7.6 | 0% | 15.2 | 5.4 | 25.7 | 41.0 | 12.6 |
| 3076 | pKR2145 (ZmODP1) | 14.2 | 86% | 11.6 | 6.4 | 33.9 | 41.1 | 7.0 |
| 3077 | pKR2146 (ZmLec1) | 13.1 | 72% | 11.1 | 7.3 | 38.2 | 36.6 | 6.8 |

Both Tables 23 and 24 demonstrate that expression of ZmLec1 and ZmODP1 with YLDGAT2 lead to an increase in oil content in soy above that for YLDGAT2 alone.

Example 10

Identification and Cloning of the *Medicago truncatula* Sucrose Synthase Promoter The amino acid sequence of the soybean homolog (Glyma13g17420) to the *Arabidopsis* Sucrose Synthase 2 gene was identified (SEQ ID NO: 6).

A *Medicago truncatula* homolog of Glyma13g17420 (SEQ ID NO: 6) was identified by conducting BLAST (Basic Local Alignment Search Tool; Altschul et al., *J. Mol. Biol.* 215:403-410 (1993)) searches for similarity to sequences contained in the *Medicago truncatula* Genome Project "Mt3.5.1 Release" gene set. Sequence information from the *Medicago truncatula* Genome Project is available at the J. Craig Venter Institute. Specifically, the Glyma13g917420 amino acid sequence (SEQ ID NO: 6) was used with the TBLASTN algorithm provided by National Center for Biotechnology Information (NCBI) with default parameters except the Filter Option was set to OFF.

The *Medicago truncatula* homolog identified corresponded to Medtr4g124660.2 and the predicted CDS and corresponding amino acid sequences for Medtr4g124660.2 are set forth in SEQ ID NO: 79 and SEQ ID NO: 80, respectively. The predicted amino acid sequence of Medtr4g124660 shares 93.3% sequence identity to the predicted amino acid sequence of Glyma13g17420 in a CLUSTAL W alignment. *Medicago truncatula* gene expression data is available at the Bio-Array Resource for Plant Biology at the University of Toronto (Winter, D; et al. PLoS One (2007), 2(8):e718). Analysis of the *Medicago truncatula* gene expression data revealed that Medtr4g124660 is expressed in developing seeds in synchrony with oil and protein accumulation.

A 3.3 kb promoter region of genomic DNA upstream of the start codon of Medtr4g124660.2 was identified from the Medicago "Mt3.5.1 Release" and the sequence is set forth in SEQ ID NO: 81.

*Medicago truncatula* seeds were sterilized and germinated on plates using methods familiar to one skilled in the art. Genomic DNA was isolated from leaves of approximately 3 week old *Medicago truncatula* seedlings using the DNEASY® Plant Mini Kit (Qiagen, Valencia, Calif.) and following the manufacture's protocol. The Medtr4g124660.2 promoter region (SEQ ID NO: 81) was PCR-amplified from the genomic DNA using forward primer oMDSP-1F (SEQ ID NO: 82) and reverse primer oMDSP-1R (SEQ ID NO: 83) with the PHUSION™ High-Fidelity DNA Polymerase (Cat. No. F553S, Finnzymes Oy, Finland), following the manufacturer's protocol. The resulting DNA fragment was cloned into the pCR®-BLUNT® cloning vector using the ZERO BLUNT® PCR Cloning Kit (Invitrogen Corporation), following the manufacturer's protocol, to produce pKR2434 (SEQ ID NO: 84).

The sequence of the promoter region sequence for multiple individual PCR products was determined from a number of clones and the actual sequence is set forth is SEQ ID NO: 85. The actual promoter sequence differs from SEQ ID NO: 81 in that nt 67 is a T, nt 489 is a C, nts 553-555 (TTG) are deleted, nt 629 is an A, nt 649 is a C, nt 715 is an A, nt 784 is a C, nt 800 is a G, nt 893 is a G, nt 1166 is an A, nt 1535 is deleted (T), nt 1700 is a G, nt 1718 is a C, nt 1857-1880 are deleted (ATTTTAGAATATG-CAATAAAATTG; SEQ ID NO: 101), nt 1953 is a G, nt 2038 is deleted (A), there is a 25 bp insertion between nt 2224 and 2225 (AGGCTTGAGGAATAAGATAAGACT-TGT; SEQ ID NO: 102), an A is inserted between nt 2225 and 2226, nt 2421 is a G, a C is inserted between nt 2734 and 2735 and nt 2881 is a T. These differences are likely due to a different cultivar of *Medicago truncatula* being used than that of used to determine the genome sequence.

The actual Medtr4g124660.2 promoter region (called MTSusPro; SEQ ID NO: 85) encodes the 5' UTR from nt 2495-3285 including an intron from nt 2524-3272.

Plasmid pKR1964 (SEQ ID NO: 13) was digested with NotI/SalI and the fragment containing the Leg terminator was cloned into the NotI/XhoI fragment of pKR2434 (SEQ ID NO: 84), containing the MTSusPro, to produce pKR2446 (SEQ ID NO: 86).

The BsiWI fragment of pKR2446 (SEQ ID NO: 86), containing the MTSusPro, was cloned into the BsiWI site of pKR325 to produce pKR2457 (SEQ ID NO: 87). Plasmid pKR2457 contains a NotI site flanked by the MTSusPro and the Leg terminator as well as the hygromycin B phosphotransferase gene [Gritz, L. and Davies, J. (1983) *Gene* 25:179-188], flanked by the T7 promoter and transcription terminator, a bacterial origin of replication (ori) for selection and replication in *E. coli* and the hygromycin B phosphotransferase gene, flanked by the 35S promoter [Odell et al., (1985) *Nature* 313:810-812] and NOS 3' transcription terminator [Depicker et al., (1982) *J. Mol. Appl. Genet.* 1:561: 570](35S/hpt/NOS3' cassette) for selection in soybean. In this way, polynucleotides (e.g., protein-coding regions) flanked by NotI sites can be cloned into the NotI site of pKR2457 (SEQ ID NO: 87) and subsequently expressed in soybean.

Example 11

Expressing GmODP1 in Soybean Embryos Under Control of the *Medicago truncatula* Sucrose Synthase Promoter MTSusPro The NotI fragment of KS334, containing GmODP1 was cloned into the NotI site of pKR2457 (SEQ ID NO: 87) to produce pKR2461 (SEQ ID NO: 88). In this way, the GmODP1 could be expressed behind the *Medicago truncatula* sucrose synthase promoter (MTSusPro).

Plasmid pKR278, previously described in PCT Publication No. WO 2008/147935, and containing no transcription factor, was used as a negative control.

DNA from plasmids pKR2461 (SEQ ID NO: 88) and pKR278 was prepared for particle bombardment into soybean embryogenic suspension culture and transformed exactly as described previously in PCT Publication No. WO 2008/147935. Soybean embryogenic suspension culture was initiated, grown, maintained and bombarded and events were selected and matured on SHaM media also exactly as described in PCT Publication No. WO 2008/147935. A summary of genes, plasmids and model system experiment ("MSE") numbers is shown in Table 25.

TABLE 25

Summary of Genes, Plasmids and Experiments

| Experiment | Plasmid | Gene | SEQ ID NO nt | SEQ ID NO aa |
|---|---|---|---|---|
| MSE 3405 | pKR2461 | GmODP1 | 29 | 30 |
| MSE 3408 | pKR278 | Empty Vector Control | — | — |

Approximately 10-20 matured embryos from each of approximately 30 events per bombardment experiment were lyophilized, ground, oil content was measured by NMR and fatty acid profile was evaluated by FAME-GC analysis exactly as described in PCT Publication No. WO 2008/147935. The results for oil content and fatty acid profile for each event as well as the average of all events (Avg.) and average for the top 5 events having highest oil content (Top5 Avg.) are shown in Table 26.

In Table 26, results are sorted based on oil content from highest to lowest. In Table 26, oil content is reported as a percent of total dry weight (% Oil) and fatty acid content for each fatty acid [palmitic acid (16:0), stearic acid (18:0), oleic acid (18:1), linoleic acid (18:2) & alpha-linolenic acid (18:3)] is reported as a weight % of total fatty acids.

TABLE 26

Summary of Oil Content and Fatty Acid Profiles for Events Expressing GmODP1 or Empty Vector Control

| | % oil | 16:0 | 18:0 | 18:1 | 18:2 | 18:3 |
|---|---|---|---|---|---|---|
| 3405-6 | 8.75 | 16.15 | 4.56 | 19.73 | 47.20 | 12.35 |
| 3405-8 | 8.42 | 16.90 | 4.13 | 17.50 | 47.66 | 13.81 |
| 3405-28 | 7.82 | 14.81 | 4.74 | 17.99 | 48.88 | 13.57 |
| 3405-22 | 7.51 | 18.94 | 4.47 | 15.69 | 48.33 | 12.57 |
| 3405-10 | 7.45 | 15.90 | 6.32 | 23.41 | 42.44 | 11.94 |
| 3405-26 | 7.21 | 15.84 | 4.56 | 22.97 | 43.57 | 13.06 |
| 3405-18 | 7.20 | 14.51 | 6.66 | 21.47 | 44.01 | 13.35 |
| 3405-16 | 7.13 | 15.65 | 6.57 | 26.47 | 38.88 | 12.44 |
| 3405-17 | 7.03 | 13.38 | 5.55 | 27.10 | 42.71 | 11.25 |
| 3405-30 | 7.03 | 14.99 | 5.89 | 23.63 | 42.16 | 13.33 |
| 3405-23 | 7.00 | 16.99 | 6.17 | 25.64 | 39.15 | 12.05 |
| 3405-25 | 6.98 | 15.91 | 6.33 | 23.96 | 40.73 | 13.06 |
| 3405-15 | 6.71 | 16.58 | 4.53 | 19.49 | 44.44 | 14.96 |
| 3405-9 | 6.46 | 15.62 | 6.43 | 25.38 | 39.38 | 13.19 |
| 3405-5 | 6.33 | 15.53 | 6.65 | 26.24 | 37.94 | 13.64 |
| 3405-3 | 6.11 | 15.99 | 6.55 | 24.56 | 40.56 | 12.35 |
| 3405-12 | 6.03 | 16.60 | 6.28 | 21.03 | 42.76 | 13.32 |
| 3405-4 | 5.96 | 16.88 | 5.00 | 20.83 | 45.03 | 12.27 |
| 3405-14 | 5.39 | 17.58 | 5.60 | 23.24 | 38.95 | 14.64 |
| 3405-1 | 5.27 | 15.57 | 5.81 | 24.92 | 42.12 | 11.58 |
| 3405-29 | 5.13 | 15.38 | 6.49 | 29.95 | 36.53 | 11.65 |
| 3405-11 | 4.82 | 15.71 | 6.72 | 26.72 | 37.89 | 12.96 |
| 3405-13 | 4.46 | 16.99 | 4.21 | 14.27 | 46.23 | 18.30 |
| 3405-27 | 4.39 | 17.63 | 4.01 | 16.00 | 44.45 | 17.91 |
| 3405-2 | 4.26 | 17.24 | 5.13 | 18.15 | 43.89 | 15.59 |
| 3405-19 | 4.02 | 16.78 | 4.03 | 17.55 | 41.47 | 20.17 |
| 3405-7 | 3.80 | 17.47 | 5.41 | 19.24 | 39.73 | 18.15 |
| 3405-20 | 3.40 | 16.52 | 5.91 | 23.70 | 37.76 | 16.12 |
| 3405-21 | 3.17 | 15.01 | 5.54 | 19.70 | 42.96 | 16.79 |
| 3405-24 | 3.05 | 16.87 | 5.46 | 21.12 | 40.50 | 16.05 |
| Avg. | 5.94 | 16.20 | 5.52 | 21.92 | 42.28 | 14.08 |
| Top5 | 7.99 | 16.54 | 4.85 | 18.87 | 46.90 | 12.85 |
| 3408-3 | 8.19 | 15.10 | 6.50 | 25.26 | 40.59 | 12.56 |
| 3408-6 | 6.36 | 15.50 | 5.91 | 22.56 | 43.40 | 12.62 |
| 3408-4 | 4.84 | 16.08 | 8.02 | 33.94 | 30.43 | 11.53 |
| 3408-2 | 4.61 | 16.26 | 5.09 | 15.84 | 44.05 | 18.76 |
| 3408-9 | 4.39 | 18.15 | 4.52 | 21.48 | 38.24 | 17.63 |
| 3408-7 | 4.23 | 16.44 | 6.11 | 26.28 | 34.96 | 16.22 |
| 3408-1 | 3.99 | 16.20 | 6.51 | 17.74 | 40.81 | 18.75 |
| 3408-10 | 3.62 | 17.37 | 6.26 | 23.12 | 35.29 | 17.96 |
| Avg. | 5.03 | 16.39 | 6.11 | 23.28 | 38.47 | 15.75 |
| Top5 | 5.68 | 16.22 | 6.01 | 23.81 | 39.34 | 14.62 |

A summary comparing the average oil content and average fatty acid profile for all events in each experiment is shown in Table 27. In Table 27, average oil content is reported as a percent of total dry weight (Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 27 also shows the change in oil content (Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 27

Summary of Average Oil Content and Fatty Acid Profiles for All Events Expressing GmODP1 or Empty Vector Control

| MSE | Vector (Gene) | Avg. Oil | Avg. % Inc | 16:0 | 18:0 | 18:1 | 18:2 | 18:3 |
|---|---|---|---|---|---|---|---|---|
| 3405 | pKR2461 (GmODP1) | 5.94 | 18% | 16.20 | 5.52 | 21.92 | 42.28 | 14.08 |
| 3408 | pKR278 (Control) | 5.03 | 0% | 16.22 | 6.01 | 23.81 | 39.34 | 14.62 |

A summary comparing the average oil content and average fatty acid profile of the top 5 events having the highest oil content for each experiment is shown in Table 28. In Table 28, average oil for the 5 events having highest oil content is reported as a percent of total dry weight (Top5 Avg.Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 28 also shows the change in oil content (Top5 Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 28

Summary of Average Oil Content and Fatty Acid Profiles for the Top5 Events Having Highest Oil Contents and Expressing GmODP1 or Empty Vector Control

| MSE | Gene (Vector) | Avg. Oil | Avg. % Inc | 16:0 | 18:0 | 18:1 | 18:2 | 18:3 |
|---|---|---|---|---|---|---|---|---|
| 3405 | GmODP1 (pKR2461) | 7.99 | 41% | 4.85 | 18.87 | 46.90 | 12.85 | 4.85 |
| 3408 | Control (pKR278) | 5.68 | 0% | 16.22 | 8.01 | 23.81 | 39.34 | 14.62 |

Both Tables 27 and 28 demonstrate that expression of GmODP1, under control of the MTSusPro, leads to an increase in oil content in soy.

Example 12

Co-Expressing GmODP1 Under Control of the MTSusPro with YLDGAT2 in Soybean Embryos The SbfI fragment of pKR2461 (SEQ ID NO: 88), containing GmODP1 was cloned into the SbfI site of pKR1256 to produce pKR2465 (SEQ ID NO: 89). In this way, the GmODP1 could be expressed behind the *Medicago truncatula* sucrose synthase promoter (MtSusPro) and co-expressed with YLDGAT2 (SEQ ID NO: 59).

DNA from plasmid pKR2465 (SEQ ID NO: 89) was prepared for particle bombardment into soybean embryogenic suspension culture and transformed exactly as described previously in PCT Publication No. WO 2008/147935. Soybean embryogenic suspension culture was initiated, grown, maintained and bombarded and events were selected and matured on SHaM media also exactly as described in PCT Publication No. WO 2008/147935. A summary of genes, plasmids and model system experiment numbers is shown in Table 29.

TABLE 29

Summary of Genes, Plasmids and Experiments

| Experiment | Plasmid | Gene1[1,2] | Gene2 | Gene2 SEQ ID NO nt | Gene2 SEQ ID NO aa |
|---|---|---|---|---|---|
| 3013 | pKR1256 | YLDGAT2 | — | — | — |
| 3410 | pKR2465 | YLDGAT2 | GmODP | 29 | 30 |

[1]Gene1 nucleotide sequence of SEQ ID NO: 59

[2]Gene1 amino acid sequence of SEQ ID NO: 60

Approximately 10-20 matured embryos from each of approximately 30 events per bombardment experiment were lyophilized, ground, oil content was measured by NMR and fatty acid profile was evaluated by FAME-GC analysis exactly as described in PCT Publication No. WO 2008/147935. The results for oil content and fatty acid profile for each event as well as the average of all events (Avg.) and average for the top 5 events having highest oil content (Top5 Avg.) are shown in Table 30.

In Table 30, results are sorted based on oil content from highest to lowest. In Table 30, oil content is reported as a percent of total dry weight (% Oil) and fatty acid content for each fatty acid [palmitic acid (16:0), stearic acid (18:0), oleic acid (18:1), linoleic acid (18:2) & alpha-linolenic acid (18:3)] is reported as a weight % of total fatty acids.

TABLE 30

Summary of Oil Content and Fatty Acid Profiles for Events Expressing YLDGAT2 with GmODP1

| | % oil | 16:0 | 18:0 | 18:1 | 18:2 | 18:3 |
|---|---|---|---|---|---|---|
| 3410-13 | 12.84 | 14.00 | 7.52 | 38.62 | 33.00 | 6.86 |
| 3410-14 | 12.65 | 13.74 | 7.78 | 39.15 | 32.53 | 6.79 |
| 3410-10 | 10.91 | 12.35 | 7.43 | 39.29 | 33.65 | 7.28 |
| 3410-7 | 9.54 | 12.20 | 6.76 | 43.82 | 30.17 | 7.05 |
| 3410-12 | 9.24 | 13.10 | 6.50 | 31.48 | 38.65 | 10.27 |
| 3410-2 | 8.13 | 15.47 | 7.18 | 25.92 | 40.37 | 11.06 |
| 3410-1 | 7.71 | 15.31 | 7.93 | 26.95 | 38.07 | 11.74 |
| 3410-18 | 7.33 | 15.77 | 7.72 | 24.84 | 38.95 | 12.72 |
| 3410-20 | 7.21 | 15.86 | 6.26 | 24.01 | 40.70 | 13.17 |
| 3410-11 | 6.69 | 15.83 | 6.90 | 24.91 | 39.65 | 12.71 |
| 3410-22 | 6.00 | 19.18 | 7.02 | 21.20 | 38.22 | 14.38 |
| 3410-9 | 5.81 | 17.73 | 4.70 | 16.30 | 42.22 | 19.05 |
| 3410-3 | 5.60 | 16.69 | 6.26 | 22.27 | 38.26 | 16.51 |
| 3410-24 | 5.33 | 16.38 | 5.35 | 25.80 | 38.16 | 14.30 |
| 3410-6 | 5.21 | 12.97 | 6.87 | 31.30 | 37.10 | 11.77 |
| 3410-21 | 5.12 | 16.93 | 7.01 | 21.80 | 35.00 | 19.27 |
| 3410-8 | 5.04 | 15.87 | 6.20 | 24.22 | 39.68 | 14.03 |
| 3410-17 | 5.03 | 18.12 | 5.35 | 21.09 | 40.85 | 14.59 |
| 3410-16 | 4.96 | 15.07 | 6.42 | 23.73 | 38.66 | 16.12 |
| 3410-23 | 4.43 | 17.11 | 5.88 | 21.63 | 38.75 | 16.63 |
| 3410-4 | 3.46 | 17.68 | 5.71 | 17.57 | 42.30 | 16.72 |
| 3410-19 | 3.42 | 17.88 | 5.24 | 19.63 | 40.96 | 16.29 |
| 3410-15 | 3.39 | 15.10 | 4.93 | 18.06 | 40.91 | 21.00 |
| 3410-5 | 2.70 | 16.45 | 5.58 | 19.40 | 37.47 | 21.10 |
| Avg. | 6.57 | 15.70 | 6.44 | 25.96 | 38.10 | 13.81 |
| Top5 Avg. | 11.04 | 13.08 | 7.20 | 38.47 | 33.60 | 7.65 |
| 3413-17 | 9.79 | 12.44 | 4.66 | 37.55 | 35.95 | 9.40 |
| 3413-28 | 9.55 | 14.97 | 5.89 | 21.69 | 46.18 | 11.27 |
| 3413-29 | 9.00 | 13.79 | 5.32 | 33.06 | 37.80 | 10.03 |
| 3413-6 | 8.59 | 13.37 | 4.79 | 31.02 | 38.32 | 12.51 |
| 3413-27 | 7.50 | 14.37 | 7.30 | 30.67 | 36.18 | 11.47 |
| 3413-12 | 7.46 | 12.90 | 6.09 | 34.45 | 35.44 | 11.12 |
| 3413-13 | 7.03 | 13.39 | 6.70 | 29.70 | 36.93 | 13.28 |
| 3413-25 | 6.77 | 17.27 | 6.84 | 23.25 | 40.01 | 12.62 |
| 3413-26 | 6.76 | 16.17 | 4.52 | 23.89 | 39.80 | 15.62 |
| 3413-24 | 6.70 | 16.57 | 4.20 | 22.35 | 42.27 | 14.61 |
| 3413-19 | 6.33 | 15.79 | 6.91 | 26.12 | 38.09 | 13.09 |
| 3413-21 | 5.99 | 18.60 | 5.10 | 20.36 | 40.78 | 15.15 |
| 3413-9 | 5.71 | 14.86 | 3.99 | 24.64 | 39.24 | 17.28 |
| 3413-23 | 5.54 | 16.32 | 4.11 | 20.13 | 41.63 | 17.81 |

TABLE 30-continued

Summary of Oil Content and Fatty Acid Profiles for Events Expressing YLDGAT2 with GmODP1

| | % oil | 16:0 | 18:0 | 18:1 | 18:2 | 18:3 |
|---|---|---|---|---|---|---|
| 3413-2 | 5.39 | 15.11 | 4.09 | 24.74 | 39.50 | 16.56 |
| 3413-20 | 5.26 | 16.83 | 4.30 | 21.17 | 40.63 | 17.06 |
| 3413-11 | 5.23 | 15.29 | 5.65 | 26.43 | 37.27 | 15.35 |
| 3413-14 | 5.11 | 16.70 | 4.60 | 22.63 | 38.10 | 17.97 |
| 3413-18 | 4.61 | 16.73 | 3.82 | 18.75 | 41.48 | 19.21 |
| 3413-16 | 4.18 | 16.62 | 3.71 | 20.39 | 37.95 | 21.32 |
| 3413-15 | 4.12 | 16.87 | 4.46 | 19.87 | 41.60 | 17.20 |
| 3413-22 | 3.57 | 17.47 | 3.58 | 15.47 | 41.65 | 21.83 |
| 3413-5 | 3.56 | 16.90 | 3.88 | 17.62 | 39.90 | 21.71 |
| 3413-3 | 3.24 | 16.90 | 4.34 | 17.33 | 41.69 | 19.73 |
| 3413-7 | 2.97 | 16.31 | 5.25 | 18.53 | 37.52 | 22.39 |
| 3413-10 | 2.96 | 17.36 | 3.86 | 14.13 | 41.16 | 23.49 |
| 3413-8 | 2.93 | 16.62 | 5.51 | 23.68 | 39.11 | 15.09 |
| 3413-4 | 2.88 | 18.11 | 3.68 | 14.51 | 41.08 | 22.62 |
| 3413-1 | 2.28 | 16.97 | 5.10 | 20.71 | 38.28 | 18.94 |
| Avg. | 5.55 | 15.92 | 4.91 | 23.27 | 39.50 | 16.41 |
| Top5 Avg. | 8.89 | 13.79 | 5.59 | 30.80 | 38.89 | 10.93 |

A summary comparing the average oil content and average fatty acid profile for all events in each experiment is shown in Table 31. In Table 31, average oil content is reported as a percent of total dry weight (Avg.Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 31 also shows the change in oil content (Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 31

Summary of Average Oil Content and Fatty Acid Profiles for All Events Expressing YLDGAT2 with GmODP1

| MSE | Vector (Gene) | Avg. Oil | Avg. % Inc | 16:0 | 18:0 | 18:1 | 18:2 | 18:3 |
|---|---|---|---|---|---|---|---|---|
| 3413 | pKR1256 (n/a) | 5.55 | 0% | 15.70 | 6.44 | 25.96 | 38.10 | 13.81 |
| 3410 | pKR2465 (GmODP1) | 6.57 | 18% | 14.0 | 6.2 | 34.6 | 36.8 | 8.5 |

A summary comparing the average oil content and average fatty acid profile of the top 5 events having the highest oil content for each experiment is shown in Table 32. In Table 32, average oil for the 5 events having highest oil content is reported as a percent of total dry weight (Top5 Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 12 also shows the change in oil content (Top5 Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 32

Summary of Average Oil Content and Fatty Acid Profiles for the Top5 Events Having Highest Oil Contents and Expressing YLDGAT2 with GmODP1

| MSE | Vector (Gene) | Avg. Oil | Avg. % Inc | 16:0 | 18:0 | 18:1 | 18:2 | 18:3 |
|---|---|---|---|---|---|---|---|---|
| 3413 | pKR1256 (n/a) | 8.89 | 0% | 13.1 | 5.9 | 27.2 | 44.7 | 9.1 |
| 3410 | pKR2465 (GmODP1) | 11.04 | 24% | 13.79 | 5.59 | 30.80 | 38.89 | 10.93 |

Both Tables 31 and 32 demonstrate that expression of GmODP1, under control of the MtSusPro, with YLDGAT2 lead to an increase in oil content in soy above that for YLDGAT2 alone.

Example 13

Expressing GmLec1, GmODP1 and GmFusca-3-1 in Soybean Seed Under Control of the GmSus Promoter Artificial microRNAs Silencing Fad2 Genes as Reporter for Transgenic Events:

The fatty acid desaturase 2-1 (Fad2-1) or 2-2 (fad2-2) gene families (Heppard, E P, et al. (1996) Plant Physiology, 110(1): 311-319), also known as delta-12 desaturase or omega-6 desaturase (U.S. Pat. No. 6,872,872B1, U.S. Pat. No. 6,919,466B2 and U.S. Pat. No. 7,105,721B2), convert oleic acid into linoleic acid. Effective silencing of the fad2-1 and fad2-2 gene families seed-specifically in soy results in seed oil having an increased oleic acid content which can be detected using methods known to one skilled in the art such as those described herein. This increased oleic acid content can be used as a reporter to identify transgenic seed in segregating seed populations from null seed.

The design and synthesis of artificial microRNAs (amiRNAs), and the respective STAR sequences that pair with amiRNAs, for silencing the soy fad2-1 and fad2-2 genes was previously described in US20090155910A1 (WO 2009/079532) (the contents of which are incorporated by reference) and the sequences are described in Table 33.

TABLE 33 amiRNA and Star Sequences For Soy fad2-1 and fad2-2

| Gene Family | amiRNA | SEQ ID NO | STAR Sequence | SEQ ID NO |
|---|---|---|---|---|
| GmFad2-1 | GM-MFAD2-1B | 90 | 396b-GM-MFAD2-1B | 91 |
| GmFad2-2 | GM-MFAD2-2 | 92 | 159-GM-MFAD2-2 | 93 |

The identification of the genomic miRNA precursor sequences 159 and 396b was described previously in US20090155910A1 (WO 2009/079532) and their sequences are set forth in SEQ ID NO: 94 and SEQ ID NO: 95, respectively.

Genomic miRNA precursor sequences 159 (SEQ ID NO: 94) and 396b (SEQ ID NO: 95) were converted to amiRNA precursors 396b-fad2-1b and 159-fad2-2 using overlapping PCR as previously described in US20090155910A1 (WO 2009/079532).

amiRNA precursor 159-fad2-2 was cloned downstream of 396b-fad2-1 b to produce the amiRNA precursor 396b-fad2-1 b/159-fad2-2 (SEQ ID NO: 96).

The amiRNA precursor 396b-fad2-1b/159-fad2-2 (SEQ ID NO: 96) is 1577 nt in length and is substantially similar to the deoxyribonucleotide sequence set forth in SEQ ID NO: 95 (from nt 1 to 574 of 396b-fad2-1 b/159-fad2-2) wherein nucleotides 196 to 216 of SEQ ID NO: 95 are replaced by GM-MFAD2-1B amiRNA (SEQ ID NO: 90) and wherein nucleotides 262 to 282 of SEQ ID NO: 95 are replaced by 396b-GM-MFAD2-1B Star Sequence (SEQ ID NO: 91). The amiRNA precursor 396b-fad2-1 b/159-fad2-2 (SEQ ID NO: 96) is also, substantially similar to the deoxyribonucleotide sequence set forth in SEQ ID NO: 94 (from nt 620 to 1577 of 396b-fad2-1 b/159-fad2-2) wherein nucleotides 276 to 296 of SEQ ID NO: 94 are replaced by GM-MFAD2-2 amiRNA (SEQ ID NO: 92) and wherein nucleotides 121 to 141 of SEQ ID NO: 94 are replaced by 159-GM-MFAD2-2 Star Sequence (SEQ ID NO: 93). In amiRNA precursor 396b-fad2-1b/159-fad2-2, nt 575 to 610 are derived from cloning.

Construction of Soybean Expression Vector pKR2109:

Using standard PCR and cloning methods by one skilled in the art, the following DNA elements were assembled to produce the 8095 bp soybean expression vector pKR2109 (SEQ ID NO: 97) and having unique SbfI (nt 8093) and BsiWI (nt 1) restriction sites for cloning expression cassettes.

In pKR2109 (SEQ ID NO: 97), sequence 21-36 is a sequence of DNA comprising ORF stop codons in all 6 frames (ORFSTOP-A). Sequence 65-2578 is vector backbone containing the T7 promoter (sequence 1297-1394), the hygromycin phosphotransferase (hpt) gene coding region (sequence 1395-2435) and the T7 terminator (sequence 2436-2582). Sequence 2616-2632 is a sequence of DNA comprising ORF stop codons in all 6 frames (ORFSTOP-B). Sequence 2698-4006 is the constitutive soy SAMS promoter (U.S. Pat. No. 7,217,858). Sequence 4011-4058 is a FLP recombinase recognition site FRT1 (U.S. Pat. No. 8,293,533). Sequence 4068-5093 is the hygromycin phosphotransferase (hpt) gene coding region for selection in soy. Sequence 5102-5382 is the NOS 3' transcription terminator (Depicker et al., *J. Mol. Appl. Genet.* 1:561-570 (1982)). Sequence 5400-6170 is the 776 bp fragment of the soy annexin promoter (described in Applicants' Assignee's U.S. Pat. No. 7,129,089). Sequence 6179-7756 is the amiRNA precursor 396b-fad2-1 b/159-fad2-2 (SEQ ID NO: 96). Sequence 7773-7988 is the soy BD30 transcription terminator (described in Applicants' Assignee's U.S. Pat. No. 8,084,074). Sequence 8021-8068 is a FLP recombinase recognition site FRT87 (U.S. Pat. No. 8,293,533).

Expressing GmLec1, GmODP1 and GmFusca3-1 in Soybean Under Control of the GmSus Promoter:

The SbfI fragments of pKR1968 (SEQ ID NO: 50), containing GmLec1, pKR1971 (SEQ ID NO: 51), containing GmODP1 and pKR1969 (SEQ ID NO: 52), containing GmFusca3-1 were cloned into the SbfI site of pKR2109 (SEQ ID NO: 97) to produce pKR2118 (SEQ ID NO: 98), pKR2120 (SEQ ID NO: 99) and pKR2119 (SEQ ID NO: 100), respectively.

Each experiment was given a name and a summary of the experiment name, construct used and genes expressed is shown in Table 34.

TABLE 34

Summary of Genes, Plasmids and Experiments

| Experiment | Plasmid | Gene | Gene SEQ ID NO nt | Gene SEQ ID NO aa |
|---|---|---|---|---|
| Oil108 | pKR2119 | GmFusca3-1 | 48 | 49 |
| Oil109 | pKR2120 | GmODP1 | 29 | 30 |
| Oil110 | pKR2118 | GmLec1 | 24 | 25 |

DNA from these plasmids was prepared for particle bombardment into soybean embryogenic suspension culture and transformed exactly as described previously in PCT Publication No. WO 2008/147935. Soybean embryogenic suspension culture was initiated, grown and maintained and events were selected and matured exactly as described in PCT Publication No. WO 2008/147935. In this case, hygromycin was used for selection. Events from each of the 3 experiments were screened at the embryo stage for fatty acid profile by methods described herein and those displaying an increased oleic acid phenotype were advanced.

Embryos from selected events were dried and germinated and T0 plants were grown and maintained exactly as described in PCT Publication No. WO 2008/147935.

Approximately 36 T1 seeds from T0 plants for each event were harvested and individual T1 seed were analyzed for oil and protein content using Near Infrared Spectroscopy by methods familiar to one skilled in the art [Agelet, et al. (2012) Journal of Agricultural and Food Chemistry, 60(34): 8314-8322].

Seeds were also analyzed for fatty acid profile in order to identify transgenic and null seed. Those seed having oleic acid contents higher than approximately 30%, resulting from expression of the amiRNA precursor 396b-fad2-1 b/159-fad2-2, were considered transgenic. Those with approximately less than 30% oleic acid content were considered null seed.

For each event, the average oil content of all transgenic seed and all null seed was determined. The average oil content of null seed was then subtracted from the average oil content of the transgenic seed and the difference is reported in Table 35 (Avg. Oil Delta %). The difference in average protein content between transgenic and null seed was similarly determined and is shown in Table 35 (Avg. Pro Delta %). The sum of the Avg. Oil Delta % and Avg. Pro Delta % (Avg. Proil Delta %) is also shown in Table 35. For a representative number of events of each construct at least 24 seeds were germinated in soil and germination rate was determined 10 days after planting.

In Table 35, the experiment name (Exp.), the gene being expressed (Gene) and the event name (Event) are also shown.

TABLE 35

Summary of Difference In Average Oil and Protein Contents Between Transgenic and Null T1 Seed for Soybean Events Expressing GmLec1, GmFusca3-1 or GmODP1

| Exp. | Gene | Event | Avg. Oil Delta % | Avg. Pro Delta % | Avg. Proil Delta % | Germination % |
|---|---|---|---|---|---|---|
| Oil 108 | GmFusca3-1 | 8798.10.3 | 1.3 | 2 | 3.3 | 78 |
| Oil 108 | GmFusca3-1 | 8798.4.1 | 1.2 | 1.5 | 2.7 | 71 |
| Oil 108 | GmFusca3-1 | 8798.1.2 | 1 | 1.6 | 2.6 | 49 |

TABLE 35-continued

Summary of Difference In Average Oil and Protein Contents Between Transgenic and Null T1 Seed for Soybean Events Expressing GmLec1, GmFusca3-1 or GmODP1

| Exp. | Gene | Event | Avg. Oil Delta % | Avg. Pro Delta % | Avg. Proil Delta % | Germination % |
|---|---|---|---|---|---|---|
| Oil 108 | GmFusca3-1 | 8798.6.3 | 1 | 1.5 | 2.5 | 20 |
| Oil 108 | GmFusca3-1 | 8798.3.2 | 0.7 | 1.7 | 2.5 | |
| Oil 108 | GmFusca3-1 | 8798.4.3 | 1 | 1.3 | 2.3 | 57 |
| Oil 108 | GmFusca3-1 | 8798.8.1 | −0.5 | 2.7 | 2.2 | |
| Oil 108 | GmFusca3-1 | 8798.1.2 | 0.5 | 1.5 | 2 | 49 |
| Oil 108 | GmFusca3-1 | 8798.9.4 | 0.3 | 0.2 | 0.5 | |
| Oil 109 | GmODP1 | 8810.5.1 | 1.9 | 2.4 | 4.3 | 99 |
| Oil 109 | GmODP1 | 8787.3.3 | 1.2 | 1.9 | 3.1 | 95 |
| Oil 109 | GmODP1 | 8787.12.2 | 0.4 | 2.4 | 2.8 | 90 |
| Oil 109 | GmODP1 | 878710.1 | 1.4 | 0.9 | 2.2 | 87 |
| Oil 109 | GmODP1 | 8787.4.1 | 0.7 | 1.4 | 2 | |
| Oil 109 | GmODP1 | 8787.8.4 | 1.1 | 0.8 | 1.9 | |
| Oil 109 | GmODP1 | 8787.10.5 | −0.2 | 1.8 | 1.7 | |
| Oil 109 | GmODP1 | 8787.7.3 | 1.3 | 0.4 | 1.7 | 79 |
| Oil 109 | GmODP1 | 8787.3.2 | 0.3 | 0.8 | 1.1 | |
| Oil 109 | GmODP1 | 8787.1.1 | −0.2 | 1 | 0.8 | 85 |
| Oil 109 | GmODP1 | 8787.6.4 | 0.2 | 0.4 | 0.7 | |
| Oil 109 | GmODP1 | 8787.12.3 | 1.7 | −1 | 0.6 | 95 |
| Oil 109 | GmODP1 | 8787.11.4 | 0 | 0.5 | 0.5 | 94 |
| Oil 109 | GmODP1 | 8787.6.3 | −1.5 | 0.5 | −1 | 83 |
| Oil 110 | GmLec1 | 8781.6.1 | 1 | 2 | 2.9 | 33 |
| Oil 110 | GmLec1 | 8781.2.2 | 0.9 | 1.8 | 2.8 | 91 |
| Oil 110 | GmLec1 | 8781.2.3 | 1.2 | 1.5 | 2.8 | 81 |
| Oil 110 | GmLec1 | 8781.10.5 | 0.9 | 1.9 | 2.8 | 81 |
| Oil 110 | GmLec1 | 8781.3.6 | 0.8 | 1.5 | 2.3 | 32 |
| Oil 110 | GmLec1 | 8781.11.2 | 0.7 | 1.3 | 2 | 69 |
| Oil 110 | GmLec1 | 8781.11.1 | 0.3 | 0.5 | 0.7 | |

Table 35 shows that average oil and protein content is increased when GmFusca3-1, GmODP1 or GmLec1 is over-expressed in soybean under control of the GmSus promoter when compared to the average of null seed. Oil and protein are increased by as high as 2.9 to 4.3 points in these events. Table 35 also shows that T1 seed germination frequency of events with significant oil and protein increase due to expression of ODP1, LEC1 and Fusca3 transcription factors can be as high as 99%, 91% and 78%, respectively.

T1 seed from events segregating as single copy (HiOleic Phenotype:Null=3:1) were planted, plants were grown exactly as for T0 plants and T2 seed were obtained. T2 seed from these events were analyzed for oleic acid, oil and protein content exactly as described herein and results are shown for Oil109 in Table 36.

For each event, the average oil content of all transgenic homozygous T2 seed and all null seed was determined. The average oil content of null seed was then subtracted from the average oil content of the homozygous T2 transgenic seed and the difference is reported in Table 36 (Avg. Oil Delta %). The difference in average protein content between T2 homozygous transgenic and null seed was similarly determined and is shown in Table 36 (Avg. Pro Delta %). The sum of the Avg. Oil Delta % and Avg. Pro Delta % (Avg. Proil Delta %) is also shown in Table 36.

TABLE 36

Summary of Difference In Average Oil and Protein Contents Between Homozygous Transgenic and Null T2 Seed for Soybean Events Expressing GmODP1

| Exp. | Gene | Event | Avg. Oil Delta % | Avg. Pro Delta % | Avg. Proil Delta % |
|---|---|---|---|---|---|
| Oil 109 | GmODP1 | 8787.10.1 | 1.8 | 2.8 | 4.7 |
| Oil 109 | GmODP1 | 8787.7.3 | 1.3 | 2.9 | 4.2 |
| Oil 109 | GmODP1 | 8810.5.1 | 1.5 | 1.5 | 3.0 |

Table 36 shows that average oil and protein content is increased when GmODP1 is over-expressed in soybean under control of the GmSus promoter when compared to the average of null seed. Oil and protein are increased by as high as 3.0 to 4.7 points in these single copy events.

Example 14

Identification of Seed Specific Promoters to Drive Expression of Transcription Factors in Leguminous Oilseed Plants The *Arabidopsis* sucrose synthase gene family and the role of specific gene family members during seed development, specifically the mobilization of sucrose for seed storage compound biosynthesis, has been described (Ruuska S A, et al. (2002) Plant Cell 14: 1191-1206; Baud S, et al. (2004) J Exp Bot 55: 397-409; Baud S and Graham I A (2006) Plant J 46: 155-169; Angeles-Nunez, J G and Tiessen, A. (2010) Planta 232(3): 701-718; Angeles-Nunez, J G and Tiessen, A (2012) Plant Mol Biol 78(4-5): 377-392). The current invention describes the utility of a promoter sequence of a specific soybean sucrose synthase gene family member, Glyma13g17420, that is highly similar in deduced amino acid sequence to the At5g49190 gene product (PCT Publication No. WO 2010114989 A1), to direct expression of native or heterologous transcription factor genes such as LEC1, FUSCA3 and ODP1 in a manner that allows for increased accumulation of protein and oil during seed development of leguminous oil seeds. Glyma13g17420 is expressed during soybean embryo maturation in synchrony with accumulation of oil and protein (Severin A J, et al. (2010) BMC Plant Biology 10:160). Genes homologous to Glyma13g17420 can be identified in other leguminous plant species based on amino acid sequence similarity to the Glyma13g17420 gene product and expression pattern of the homolog during seed development. One skilled in the art will recognize that promoter sequences of these genes will have utility for expression of transcription factor genes for increased protein and oil accumulation in leguminous oil seeds.

Example 15

Identification of Sequence Variability in the Glyma13g17420 Promoter and 5'-UTR in *Glycine max* Breeding Lines Genomic DNA sequencing of a number of soybean lines was performed by next generation high throughput sequencing methods according to manufacturer instructions (Illumina, San Diego, USA). Genomic sequence corresponding to the promoter, 5'-UTR and first exon of the Glyma13g17420 gene (SEQ ID NO: 8) was assembled for each soybean line from the genomic sequencing reads. This region corresponds to the sequence Gm13:21,216,136-21,219,309 in the Soybean Genomic Assembly Glyma1.01 (JGI). Short read sequencing data were extracted for this region from the soybean lines. Polymorphic variants and insertion/deletion variants were detected from the sequencing data and the alignments were visually inspected to ascertain whether the identified variants may have been caused by sequencing error.

The sequencing results are summarized in FIG. 4 (lines w/o variants were not reported). The results indicate that significant diversity in the genomic DNA sequence that comprises the promoter, 5'-UTR and first intron of the Glyma13g17420 gene exists within different soybean lines. One skilled in the art will recognize that regulatory sequences of the Glyma13g17420 gene including promoter, 5'-UTR and first intron derived from divergent soybean (*Glycine max*) accessions will have utility for expression of transcription factor genes for increased protein and oil accumulation in leguminous oil seeds.

We claim:

1. A soybean plant or soybean seed comprising a recombinant DNA construct, the recombinant construct comprising:

(a) at least one polynucleotide encoding an ovule development protein 1 (ODP1) polypeptide having at least 95% sequence identity to SEQ ID NO: 70, wherein the at least one polynucleotide is operably linked to a promoter comprising a nucleic acid sequence having at least 95% sequence identity to SEQ ID NO: 8; and (b) a nucleic acid sequence encoding a diglyceride acyltransferase (DGAT) polypeptide having at least 95% sequence identity to SEQ ID NO: 55;

wherein expression of said polypeptides in the soybean seed or a seed produced by the soybean plant results in an increased oil content in the soybean seed and the seed produced by the soybean plant, when compared to a control soybean seed not comprising the recombinant DNA construct.

2. The soybean plant or soybean seed of claim 1, wherein the transgenic soybean seed or a seed produced by the soybean plant comprising the recombinant DNA construct has normal germination, when compared to a control soybean seed not comprising the recombinant DNA construct.

3. The soybean plant or soybean seed of claim 1, wherein the promoter comprises SEQ ID NO: 8.

4. The soybean plant or soybean seed of claim 1, wherein the ODP1 polypeptide comprises an amino acid sequence with at least 98% sequence identity to SEQ ID NO: 70.

5. The soybean plant or soybean seed of claim 1, wherein the ODP1 polypeptide comprises SEQ ID NO: 70.

6. The soybean plant or soybean seed of claim 1, wherein the recombinant DNA construct further comprises a seed-specific promoter operably linked to the nucleotide sequence of (b).

7. The soybean plant or soybean seed of claim 6 wherein the nucleotide sequence of (b) encodes a polypeptide comprising an amino acid sequence with at least 98% sequence identity to SEQ ID NO: 55.

8. The plant or a seed of claim 1, wherein the plant or seed is a seed.

9. The plant or seed of claim 8, wherein co-expression of said ODP1 polypeptide and said DGAT polypeptide in the seed results in an increased oil content in the seed, when compared to a control seed that expresses said DGAT polypeptide from said seed-specific promoter but does not express said ODP1 polypeptide.

10. The plant or a seed of claim 1, wherein the nucleic acid sequence encoding a polypeptide having at least 95% sequence identity to SEQ ID NO: 55 is operably linked to a seed-specific promoter, and wherein co-expression of said ODP1 polypeptide having at least 95% sequence identity to SEQ ID NO: 70 and said DGAT polypeptide having at least 95% sequence identity to SEQ ID NO: 55 results in an increased oil content in the seed or a seed produced by the soybean plant, when compared to a control seed comprising only one, but not both, of the polynucleotide operably linked to the promoter and the nucleic acid sequence operably linked to the seed-specific promoter.

11. The plant or seed of claim 10, wherein said plant or seed is a seed.

12. A method of increasing oil content of a soybean seed, the method comprising the steps of:

a) introducing into a regenerable soybean cell a recombinant DNA construct comprising (i) a polynucleotide encoding a polypeptide having at least 95% sequence identity to SEQ ID NO: 70, the polynucleotide operably linked to a promoter comprising a nucleic acid sequence having at least 95% sequence identity to SEQ ID NO: 8 and (ii) a nucleic acid sequence encoding a polypeptide having at least 95% sequence identity to SEQ ID NO: 55;

b) regenerating a transgenic plant from the regenerable soybean cell of (a) wherein the transgenic plant comprises the recombinant DNA construct; and c) selecting a transgenic plant of step (b), or a transgenic progeny plant from the transgenic plant of step (b), wherein seed of the transgenic plant or the transgenic progeny plant comprises the recombinant construct and exhibits increased seed oil content while maintaining normal germination, when compared to a control soybean seed not comprising the DNA recombinant construct.

13. A method of increasing oil content of a soybean seed, the method comprising the steps of: a) introducing into a regenerable soybean cell a first recombinant DNA construct comprising (i) a polynucleotide encoding a polypeptide having at least 95% sequence identity to SEQ ID NO: 70, the polynucleotide operably linked to a soybean sucrose synthase promoter comprising a nucleic acid sequence having at least 95% sequence identity to SEQ ID NO: 8 and a second recombinant DNA construct comprising a seed-specific promoter operably linked to a second heterologous polynucleotide encoding a DGAT polypeptide having at least 95% sequence identity to SEQ ID NO: 55;

b) regenerating a transgenic plant from the regenerable soybean cell of (a) wherein the transgenic plant comprises the recombinant DNA construct and the second recombinant DNA construct; and c) selecting a transgenic plant of step (b), or a transgenic progeny plant from the transgenic plant of step (b), wherein seed of the transgenic plant or the transgenic progeny plant comprises the recombinant DNA construct and the second recombinant DNA construct, and wherein co-expression of said polypeptide and said DGAT polypeptide in a transgenic soybean seed results in an increased oil content in the transgenic soybean seed, when compared to a control soybean seed comprising only one, but not both, of the recombinant DNA construct and the second recombinant DNA constructs.

* * * * *

SEQUENCE LISTING

```
<160> NUMBER OF SEQ ID NOS: 108

<210> SEQ ID NO 1
<211> LENGTH: 2511
<212> TYPE: DNA
<213> ORGANISM: Arabidopsis Thaliana

<400> SEQUENCE: 1

atgccgactg gtaggttcga gactatgcgt gaatgggttt atgacgctat ctctgctcaa      60

cgcaatgagc tcctctctct tttctccaga tatgtagccc agggaaaggg gatattgcag     120

tcccaccagc tgattgatga gttccttaag actgtgaaag ttgatggaac attagaagat     180

cttaacaaaa gtccattcat gaaagttctg cagtctgcag aggaagccat agttttgcct     240

ccatttgttg ctttggctat acgtcccaga cctggtgtta gggaatatgt ccgtgtgaat     300

gtgtatgagc tgagcgtaga tcatttaact gtttctgaat atcttcggtt taaggaagag     360

ctcgttaatg gccatgccaa tggagattat ctccttgaac ttgattttga acctttcaat     420

gcaacattgc ctcgcccaac tcgttcatca tccattggga atggggttca gttcctcaat     480

cgtcacctct cttcaattat gttccgtaac aaagaaagca tggagccttt gcttgagttt     540

ctccgcactc acaaacatga tggccgtcct atgatgctga atgatcgaat acagaatatc     600

cccatacttc agggagcttt ggcaagagca gaggagttcc tttctaaact tcctctggca     660

acaccatact ctgaattcga atttgaacta caagggatgg gatttgaaag gggatggggt     720

gacacagcac agaaggtttc agaaatggtg catcttcttc tggacatact ccaggcacct     780

gatccttctg tcttggagac gtttctagga aggattccta tggtgttcaa tgttgtgatt     840

ttgtctccgc atggttactt tggccaagcc aatgtcttgg gtctgcctga tactggtgga     900

caggttgtct acattcttga tcaagtacgt gcattggaaa atgagatgct ccttaggata     960

cagaagcaag gactggaagt tattccaaag attctcattg taacaagact gctacccgaa    1020

gcaaagggaa caacgtgcaa ccagaggtta gaaagagtta gtggtacaga acacgcacac    1080

attctgcgaa taccatttag gactgaaaag ggaattcttc gcaagtggat ctcaaggttt    1140

gatgtctggc catacctgga gacttttgca gaggatgcat caaatgaaat ttctgcggag    1200

ttgcagggtg taccaaatct catcattggc aactacagtg atggaaatct cgttgcttct    1260

ttgttagcta gtaagctagg tgtgatacag tgtaatattg ctcatgcttt agagaaaacc    1320

aagtaccccg agtctgacat ttactggaga aaccatgaag ataagtatca cttttcaagt    1380

cagttcactg cagatctaat tgccatgaat aatgccgatt tcatcatcac cagcacatac    1440

caagagattg cgggaagcaa gaacaatgtt gggcaatacg agagccacac agctttcact    1500

atgcctggtc tttaccgagt tgttcatgga attgatgtct ttgatcctaa gtttaatata    1560

gtctctccag gagctgatat gaccatatac tttccatatt ctgacaagga aagaagactc    1620
```

-continued

```
actgcccttc atgagtcaat tgaagaactc ctctttagtg ccgaacagaa tgatgagcat   1680

gttggtttac tgagcgacca atcgaagcca atcatcttct ctatggcaag acttgacagg   1740

gtgaaaaact tgactgggct agttgaatgc tatgccaaga atagcaagct tagagagctt   1800

gcaaatcttg ttatagtcgg tggctacatc gatgagaatc agtccaggga tagagaggaa   1860

atggctgaga tacaaaagat gcacagcctg attgagcagt atgatttaca cggtgagttt   1920

aggtggatag ctgctcaaat gaaccgtgct cgaaatggtg agctttaccg ttatatcgca   1980

gacacaaaag gtgtttttgt tcagcctgct ttctatgaag catttgggct tacggttgtg   2040

gaatcaatga cttgtgcact cccaacgttt gctacctgtc atggtggacc cgcagagatt   2100

atcgaaaacg gagtttctgg gttccacatt gacccatatc atccagacca ggttgcagct   2160

accttggtca gcttctttga gacctgtaac accaatccaa atcattgggt taaaatctct   2220

gaaggagggc tcaagcgaat ctatgaaagg tacacatgga agaagtactc agagagactg   2280

cttaccctgg ctggagtcta tgcattctgg aaacatgtgt ctaagctcga aaggagagaa   2340

acacgacgtt acctagagat gttttactca ttgaaatttc gtgatttggc caattcaatc   2400

ccgctggcaa cagatgagaa ctgatcatga cagggtagga ttttatttcc tgcactttct   2460

ttagatcttt tgtttgtgtt atcttgaata aaaattgttg ggttttgttt c            2511


<210> SEQ ID NO 2
<211> LENGTH: 807
<212> TYPE: PRT
<213> ORGANISM: Arabidopsis thaliana

<400> SEQUENCE: 2

Met Pro Thr Gly Arg Phe Glu Thr Met Arg Glu Trp Val Tyr Asp Ala
1               5                   10                  15

Ile Ser Ala Gln Arg Asn Glu Leu Leu Ser Leu Phe Ser Arg Tyr Val
            20                  25                  30

Ala Gln Gly Lys Gly Ile Leu Gln Ser His Gln Leu Ile Asp Glu Phe
        35                  40                  45

Leu Lys Thr Val Lys Val Asp Gly Thr Leu Glu Asp Leu Asn Lys Ser
    50                  55                  60

Pro Phe Met Lys Val Leu Gln Ser Ala Glu Glu Ala Ile Val Leu Pro
65                  70                  75                  80

Pro Phe Val Ala Leu Ala Ile Arg Pro Arg Pro Gly Val Arg Glu Tyr
                85                  90                  95

Val Arg Val Asn Val Tyr Glu Leu Ser Val Asp His Leu Thr Val Ser
            100                 105                 110

Glu Tyr Leu Arg Phe Lys Glu Glu Leu Val Asn Gly His Ala Asn Gly
        115                 120                 125

Asp Tyr Leu Leu Glu Leu Asp Phe Glu Pro Phe Asn Ala Thr Leu Pro
    130                 135                 140

Arg Pro Thr Arg Ser Ser Ser Ile Gly Asn Gly Val Gln Phe Leu Asn
145                 150                 155                 160

Arg His Leu Ser Ser Ile Met Phe Arg Asn Lys Glu Ser Met Glu Pro
                165                 170                 175

Leu Leu Glu Phe Leu Arg Thr His Lys His Asp Gly Arg Pro Met Met
            180                 185                 190

Leu Asn Asp Arg Ile Gln Asn Ile Pro Ile Leu Gln Gly Ala Leu Ala
        195                 200                 205

Arg Ala Glu Glu Phe Leu Ser Lys Leu Pro Leu Ala Thr Pro Tyr Ser
    210                 215                 220
```

```
Glu Phe Glu Phe Glu Leu Gln Gly Met Gly Phe Glu Arg Gly Trp Gly
225                 230                 235                 240

Asp Thr Ala Gln Lys Val Ser Glu Met Val His Leu Leu Leu Asp Ile
                245                 250                 255

Leu Gln Ala Pro Asp Pro Ser Val Leu Glu Thr Phe Leu Gly Arg Ile
            260                 265                 270

Pro Met Val Phe Asn Val Val Ile Leu Ser Pro His Gly Tyr Phe Gly
        275                 280                 285

Gln Ala Asn Val Leu Gly Leu Pro Asp Thr Gly Gly Gln Val Val Tyr
    290                 295                 300

Ile Leu Asp Gln Val Arg Ala Leu Glu Asn Glu Met Leu Leu Arg Ile
305                 310                 315                 320

Gln Lys Gln Gly Leu Glu Val Ile Pro Lys Ile Leu Ile Val Thr Arg
                325                 330                 335

Leu Leu Pro Glu Ala Lys Gly Thr Thr Cys Asn Gln Arg Leu Glu Arg
            340                 345                 350

Val Ser Gly Thr Glu His Ala His Ile Leu Arg Ile Pro Phe Arg Thr
        355                 360                 365

Glu Lys Gly Ile Leu Arg Lys Trp Ile Ser Arg Phe Asp Val Trp Pro
    370                 375                 380

Tyr Leu Glu Thr Phe Ala Glu Asp Ala Ser Asn Glu Ile Ser Ala Glu
385                 390                 395                 400

Leu Gln Gly Val Pro Asn Leu Ile Ile Gly Asn Tyr Ser Asp Gly Asn
                405                 410                 415

Leu Val Ala Ser Leu Leu Ala Ser Lys Leu Gly Val Ile Gln Cys Asn
            420                 425                 430

Ile Ala His Ala Leu Glu Lys Thr Lys Tyr Pro Glu Ser Asp Ile Tyr
        435                 440                 445

Trp Arg Asn His Glu Asp Lys Tyr His Phe Ser Ser Gln Phe Thr Ala
    450                 455                 460

Asp Leu Ile Ala Met Asn Asn Ala Asp Phe Ile Ile Thr Ser Thr Tyr
465                 470                 475                 480

Gln Glu Ile Ala Gly Ser Lys Asn Asn Val Gly Gln Tyr Glu Ser His
                485                 490                 495

Thr Ala Phe Thr Met Pro Gly Leu Tyr Arg Val Val His Gly Ile Asp
            500                 505                 510

Val Phe Asp Pro Lys Phe Asn Ile Val Ser Pro Gly Ala Asp Met Thr
        515                 520                 525

Ile Tyr Phe Pro Tyr Ser Asp Lys Glu Arg Arg Leu Thr Ala Leu His
    530                 535                 540

Glu Ser Ile Glu Glu Leu Leu Phe Ser Ala Glu Gln Asn Asp Glu His
545                 550                 555                 560

Val Gly Leu Leu Ser Asp Gln Ser Lys Pro Ile Ile Phe Ser Met Ala
                565                 570                 575

Arg Leu Asp Arg Val Lys Asn Leu Thr Gly Leu Val Glu Cys Tyr Ala
            580                 585                 590

Lys Asn Ser Lys Leu Arg Glu Leu Ala Asn Leu Val Ile Val Gly Gly
        595                 600                 605

Tyr Ile Asp Glu Asn Gln Ser Arg Asp Arg Glu Glu Met Ala Glu Ile
    610                 615                 620

Gln Lys Met His Ser Leu Ile Glu Gln Tyr Asp Leu His Gly Glu Phe
625                 630                 635                 640
```

-continued

```
Arg Trp Ile Ala Ala Gln Met Asn Arg Ala Arg Asn Gly Glu Leu Tyr
            645                 650                 655

Arg Tyr Ile Ala Asp Thr Lys Gly Val Phe Val Gln Pro Ala Phe Tyr
        660                 665                 670

Glu Ala Phe Gly Leu Thr Val Val Glu Ser Met Thr Cys Ala Leu Pro
    675                 680                 685

Thr Phe Ala Thr Cys His Gly Gly Pro Ala Glu Ile Ile Glu Asn Gly
    690                 695                 700

Val Ser Gly Phe His Ile Asp Pro Tyr His Pro Asp Gln Val Ala Ala
705                 710                 715                 720

Thr Leu Val Ser Phe Phe Glu Thr Cys Asn Thr Asn Pro Asn His Trp
            725                 730                 735

Val Lys Ile Ser Glu Gly Gly Leu Lys Arg Ile Tyr Glu Arg Tyr Thr
        740                 745                 750

Trp Lys Lys Tyr Ser Glu Arg Leu Leu Thr Leu Ala Gly Val Tyr Ala
    755                 760                 765

Phe Trp Lys His Val Ser Lys Leu Glu Arg Arg Glu Thr Arg Arg Tyr
    770                 775                 780

Leu Glu Met Phe Tyr Ser Leu Lys Phe Arg Asp Leu Ala Asn Ser Ile
785                 790                 795                 800

Pro Leu Ala Thr Asp Glu Asn
            805
```

<210> SEQ ID NO 3
<211> LENGTH: 5241
<212> TYPE: DNA
<213> ORGANISM: Glycine max

<400> SEQUENCE: 3

```
ccttatcgtt gttctgcctc tcctctgttt cggtgctctg ttcaccactt ccacgtgaga      60

atgatcttcc ttctttgcat gttcattctc tcgtgaccac tggatcagac tccatgttct     120

gatccagggt ctctctctaa cgcctgtact ttcatccatg accaccttaa aaacaacatg     180

ggggtggtgc tgttacacta actctgtttc tggggtgctg tctttgttca attttactca     240

gaaaatatct tttcttggat tctattcggt gtgtgggaac atgatcctgt cggtcggttg     300

tttttaggtt aatccttaac tggttacaag gatctaacgc ttgaatgcat gtcctgagtt     360

aaagaaacaa aagaagaaca cacctagtac agcctggcct cgaaccaaga acttctttgt     420

tggtttctca ttattactaa aataaaataa agtatacgtt ttcttttttc tttgggatga     480

acggttcaga cttatgagaa gtttaagcta atcctgtagt ggagtgttca atttatttta     540

aactttaaag caatagctca agcactaaac ttctttttca agttcaacca ctttggtagc     600

ttgctaattg ctgctattgt tctaattaat taatgtaatt attgtttaaa aaagaaaagt     660

tggtgacact ggaataaaaa agtgtactat ctggcaatta ttcttctgca gcaatgtttg     720

aggttgaaat cttagtagaa caaagtagaa gatctggtat ttatattttt tgtagacaga     780

tggtgggggt gggtggtagg ccttgaaatc caatatagtt ttgtagaata attttattat     840

ttttttttt tgctcacttg tttgtggtat tgattttgtg atgactcaag attaatgatt     900

taccttcatt tttttcatgg tgacatatta tgtatattct tgatctgttt cttacacttc     960

tttttcgttg ttgtagctgt tgaagtcttt ccctagccaa tggccaccga tcgtttgacc    1020

cgggttcaca gtctccgtga gaggcttgat gaaaccctca ctgccaacag gaatgaaatt    1080

ttggcccttc tgtcaaggta actcatcatt cttgtttttg gtttagaaga ttttttttaaa   1140
```

-continued

```
agtcaaagtg ttttctctct ttaatggtag tgaagttcta ctaactatgt ttagacagtg   1200
agtttgttta aggaaactca atttgtgttt gtgtgtgttc tgtctttaaa ggtggtgaaa   1260
gttctactat gtatgtgttg tggaagcagt agtgtaacac taagaatgtt atgaaatttt   1320
gataggatcg aagccaaggg caagggcatc ctgcaacacc accaggtcat tgctgagttt   1380
gaggaaatcc ctgaggagaa cagacagaag ctcactgatg gtgcctttgg agaagtcttg   1440
agatctacac aggtaactaa catttgagct ttaaaaatag gagaggtttt agctatgatc   1500
cttggtgttt tttttgtttt gttgattttc ttatttctat gttgtaggaa gccatagttt   1560
tgccaccatg ggttgctctg gctgttcgtc caagacctgg tgtgtgggag tacctgagag   1620
tgaatgtgca cgctcttgtt gttgaggagt tgcaacctgc tgagtacctg cacttcaagg   1680
aagaacttgt tgacggaagg tgaagaaaaa aaggctttga atttgtgtta aagcggtgta   1740
cttgttttgt tatgttactt gcacaaatta taaacatttc tctcactttc attgcagttc   1800
taatggcaac tttgtgcttg agttggactt tgaaccattc aatgcagcct tcccccgccc   1860
aactcttaac aagtcaattg gaaatggtgt gcaattcctc aaccgtcacc tttctgccaa   1920
actcttccac gacaaggaga gcttgcaccc acttttggag ttcctcaggc ttcacagcgt   1980
caagggaaag gtaggtgtct atttctactc tttaaactag agtaaagcaa ggtagtgagg   2040
agtttatgca tgtgtaagac acattcttca gtagttcaat ggcttgaata tctacatcca   2100
tgtttggacc atgtctagta accagatcta gagtacaaat ctaatgtgtg tagcatatag   2160
tatctctagc atgttgaact taaggcatga agttagtttt aataggttaa ttttgttgtg   2220
tattttactg atgaagattt ttattttttg gaatatgcag actttgatgt tgaatgacag   2280
aattcaaaac ccagatgcac tccaacatgt tctgaggaaa gctgaggagt atctgggcac   2340
agtgcctcct gaaactccct actcagaatt tgagcacaag ttccaggaga ttggtttgga   2400
gagagggtgg ggtgacaacg cggagcgtgt ccttgagtca attcaacttc tcttggatct   2460
tcttgaggcc cctgacccgt gcacccttga gactttcctt ggaagaatcc ctatggtgtt   2520
caatgttgtt attctttctc cccatggtta ctttgcccaa gataatgtct tgggataccc   2580
tgacactggt ggccaggttg tttacatctt ggatcaagtt cgtgctttgg agaatgagat   2640
gctccatcgc attaagcaac aaggattgga cattgttcct cgtattctca ttgtatgtcc   2700
tagtacatag ttgtgaagtg tttcagcaag ctaaattaag cttacttgtg tatagtgtgt   2760
gtaatgtgga tatgttattc taattggtgc ttgtgaatgt tgttaaaatg cagatcaccc   2820
gtcttctccc cgatgcagta ggaactactt gtggccaacg tcttgagaag gtgttcggaa   2880
ctgagcactc ccacattctt cgagttccct ttagaactga gaagggaatt gttcgcaagt   2940
ggatctcaag attcgaagtc tggccctact tggaaactta cactgaggta aatttttgac   3000
cccatcataa tattgacacc gtttaagaat ttttgatgtg ttttaactta tccaatccaa   3060
attgtgtctt gttaacagga tgttgcccac gagcttgcca aagagttgca aggcaagcca   3120
gatctgattg ttggaaacta cagtgatgga aacattgtcg cttctttgtt ggcacataaa   3180
ttaggtgtca ctcaggttgg tctacataac atgtctagtt aaagttgtta ggaccttata   3240
ctttggaatt caggggccta agttttttct ctttgtcaac tgtagtgtac cattgctcac   3300
gcacttgaga agaccaaata ccccgaatcc gacatttact ggaaaaaatt ggaagagaga   3360
taccacttct cttgccaatt cacagctgat ctatttgcca tgaaccacac agatttcatt   3420
atcaccagta ccttccagga gattgctgga aggtgagcta acccttttac atttttgttc   3480
ttttgcctat tttttcattt attttattga ttagcttact aaaattcttg tatcattgtt   3540
```

caaatacttt tacagcaagg acactgttgg acagtacgaa tctcacacag ccttcaccct 3600
tcctggactc taccgcgttg tgcatggtat tgatgtcttt gatccaaaat tcaacattgt 3660
ctcccctgga gctgatcaaa ccatttactt cccccacact gaaaccagcc gtaggttgac 3720
atccttccac cctgaaatcg aagaactcct ttacagctca gtggagaatg aagaacacat 3780
gttagtttct cctctcattt ccttgatgtt atctaatcat agtatcatga atggtcacaa 3840
tttcatcaaa atgtttgata ttgtgagaaa ttgcagacag acacagctgg gttagaccac 3900
aaagaaccgt tttttttttt ttttaaaaaa agaagaaaac cttggatatc atcatgcata 3960
gaagaacatt tgtctaatgc aaattcatgt atgacagatg tgtgctgaag gaccgcagca 4020
agccaattat cttcaccatg gcaaggttgg atcgagtgaa gaacatcaca ggacttgtgg 4080
agtggtacgg taagaacgcg aagctgaggg agctggtgaa ccttgtggtt gttgctggag 4140
acaggaggaa ggagtcaaag gacttggaag aaaaggccga gatgaagaag atgtacggcc 4200
tgatcgagac ctacaagttg aacggccaat tcagatggat ttcatcgcag atgaaccgtg 4260
tgaggaatgg agagctctac cgcgtgatct gcgacaccag gggtgctttc gtgcagcctg 4320
ctgtatacga ggcttttggt ttgacagtgg ttgaggccat gacttgcggc ttgccaacat 4380
tcgccacatg caatggtggt cctgctgaga tcattgtgca cggcaagtct ggcttccaca 4440
ttgaccctta ccatggtgac cgtgctgctg atctccttgt tgacttcttt gagaagtgca 4500
agcttgaccc aactcactgg gacaagatct caaaggctgg tctccagcgt attgaagaga 4560
agtaagcata ttaattctga atcaatgtgt ttctgttctg tctgttgtgg taattaatca 4620
ttttctttct tcttccacag gtacacatgg caaatttact ctcagaggct tctcactctc 4680
accggtgtct atggcttctg gaagcatgtg tctaaccttg accgccgtga gagccgccgc 4740
tatctcgaga tgttctatgc tctcaagtac cgcaaattgg tatgtatagt atagtactcc 4800
ctctgctcat ttttattcag tgaattttac actataattt ttttcttatt aaaagggcta 4860
ttttctcttc atatttttac cttgaaatat gttgtcattg aacttgctaa tgtatcttgt 4920
tattgttttt acctttaggc tgagtctgtg ccccttgctg ctgagtaaac tgaggataaa 4980
gagttggata aagaaatgga ggaaccggct ttttctttct catttggagt ttgtcgcact 5040
tgagttttat aaataatgtc cgtgatttta gttttgtgat taagctttcg ataagaggag 5100
agaaagagaa ggaaaaaaaa agttgctttt ttttttgttg ttgcatgatt tggatcttga 5160
ttggaaaagc ttcgaattgg ggtagtttta cccatcaatt caattttaag ccgtgccttc 5220
ttcactttgc cgtgtctaat a 5241

<210> SEQ ID NO 4
<211> LENGTH: 3132
<212> TYPE: DNA
<213> ORGANISM: Glycine max

<400> SEQUENCE: 4
ccttatcgtt gttctgcctc tcctctgttt cggtgctctg ttcaccactt ccacgtgaga 60
atgatcttcc ttctttgcat gttcattctc tcgtgaccac tggatcagac tccatgttct 120
gatccagggt ctctctctaa cgcctgtact ttcatccatg accaccttaa aaacaacatg 180
ggggtggtgc tgttacacta actctgtttc tggggtgctg tctttgttca attttactca 240
gaaaatatct tttcttggat tctattcggt gtgtgggaac atgatcctgt cggtcggttg 300
tttttaggtt aatccttaac tggttacaag gatctaacgc ttgaatgcat gtcctgagtt 360

-continued

```
aaagaaacaa aagaagaaca cacctagtac agcctggcct cgaaccaaga acttctttct    420
gttgaagtct ttccctagcc aatggccacc gatcgtttga cccgggttca cagtctccgt    480
gagaggcttg atgaaaccct cactgccaac aggaatgaaa ttttggccct tctgtcaagg    540
atcgaagcca agggcaaggg catcctgcaa caccaccagg tcattgctga gtttgaggaa    600
atccctgagg agaacagaca gaagctcact gatggtgcct ttggagaagt cttgagatct    660
acacaggaag ccatagtttt gccaccatgg gttgctctgg ctgttcgtcc aagacctggt    720
gtgtgggagt acctgagagt gaatgtgcac gctcttgttg ttgaggagtt gcaacctgct    780
gagtacctgc acttcaagga agaacttgtt gacggaagtt ctaatggcaa ctttgtgctt    840
gagttggact ttgaaccatt caatgcagcc ttcccccgcc caactcttaa caagtcaatt    900
ggaaatggtg tgcaattcct caaccgtcac ctttctgcca aactcttcca cgacaaggag    960
agcttgcacc cacttttgga gttcctcagg cttcacagcg tcaagggaaa gactttgatg   1020
ttgaatgaca gaattcaaaa cccagatgca ctccaacatg ttctgaggaa agctgaggag   1080
tatctgggca cagtgcctcc tgaaactccc tactcagaat ttgagcacaa gttccaggag   1140
attggtttgg agagagggtg ggtgacaac gcggagcgtg tccttgagtc aattcaactt   1200
ctcttggatc ttcttgaggc ccctgacccg tgcacccttg agactttcct tggaagaatc   1260
cctatggtgt tcaatgttgt tattctttct ccccatggtt actttgccca agataatgtc   1320
ttgggatacc ctgacactgg tggccaggtt gtttacatct tggatcaagt tcgtgctttg   1380
gagaatgaga tgctccatcg cattaagcaa caaggattgg acattgttcc tcgtattctc   1440
attatcaccc gtcttctccc cgatgcagta ggaactactt gtggccaacg tcttgagaag   1500
gtgttcggaa ctgagcactc ccacattctt cgagttccct ttagaactga gaagggaatt   1560
gttcgcaagt ggatctcaag attcgaagtc tggccctact tggaaactta cactgaggat   1620
gttgcccacg agcttgccaa agagttgcaa ggcaagccag atctgattgt tggaaactac   1680
agtgatggaa acattgtcgc ttctttgttg gcacataaat taggtgtcac tcagtgtacc   1740
attgctcacg cacttgagaa gaccaaatac cccgaatccg acatttactg gaaaaaattg   1800
gaagagagat accacttctc ttgccaattc acagctgatc tatttgccat gaaccacaca   1860
gatttcatta tcaccagtac cttccaggag attgctggaa gcaaggacac tgttggacag   1920
tacgaatctc acacagcctt caccccttcct ggactctacc gcgttgtgca tggtattgat   1980
gtctttgatc caaaattcaa cattgtctcc cctggagctg atcaaaccat ttacttcccc   2040
cacactgaaa ccagccgtag gttgacatcc ttccaccctg aaatcgaaga actcctttac   2100
agctcagtgg agaatgaaga acacatatgt gtgctgaagg accgcagcaa gccaattatc   2160
ttcaccatgg caaggttgga tcgagtgaag aacatcacag gacttgtgga gtggtacggt   2220
aagaacgcga agctgaggga gctggtgaac cttgtggttg ttgctggaga caggaggaag   2280
gagtcaaagg acttggaaga aaaggccgag atgaagaaga tgtacggcct gatcgagacc   2340
tacaagttga acggccaatt cagatggatt tcatcgcaga tgaaccgtgt gaggaatgga   2400
gagctctacc gcgtgatctg cgacaccagg ggtgctttcg tgcagcctgc tgtatacgag   2460
gcttttggtt tgacagtggt tgaggccatg acttgcggct tgccaacatt cgccacatgc   2520
aatggtggtc ctgctgagat cattgtgcac ggcaagtctg gcttccacat tgacccttac   2580
catggtgacc gtgctgctga tctccttgtt gacttctttg agaagtgcaa gcttgaccca   2640
actcactggg acaagatctc aaaggctggt ctccagcgta ttgaagagaa gtacacatgg   2700
caaatttact ctcagaggct tctcactctc accggtgtct atggcttctg gaagcatgtg   2760
```

```
tctaaccttg accgccgtga gagccgccgc tatctcgaga tgttctatgc tctcaagtac   2820
cgcaaattgg ctgagtctgt gccccttgct gctgagtaaa ctgaggataa agagttggat   2880
aaagaaatgg aggaaccggc tttttctttc tcatttggag tttgtcgcac ttgagtttta   2940
taaataatgt ccgtgatttt agttttgtga ttaagctttc gataagagga gagaaagaga   3000
aggaaaaaaa aagttgcttt ttttttgtt gttgcatgat ttggatcttg attggaaaag   3060
cttcgaattg gggtagtttt acccatcaat tcaattttaa gccgtgcctt cttcactttg   3120
ccgtgtctaa ta                                                       3132
```

<210> SEQ ID NO 5
<211> LENGTH: 2418
<212> TYPE: DNA
<213> ORGANISM: Glycine max

<400> SEQUENCE: 5

```
atggccaccg atcgtttgac ccgggttcac agtctccgtg agaggcttga tgaaaccctc     60
actgccaaca ggaatgaaat tttggccctt ctgtcaagga tcgaagccaa gggcaagggc    120
atcctgcaac accaccaggt cattgctgag tttgaggaaa tccctgagga gaacagacag    180
aagctcactg atggtgcctt tggagaagtc ttgagatcta cacaggaagc catagttttg    240
ccaccatggg ttgctctggc tgttcgtcca agacctggtg tgtgggagta cctgagagtg    300
aatgtgcacg ctcttgttgt tgaggagttg caacctgctg agtacctgca cttcaaggaa    360
gaacttgttg acggaagttc taatggcaac tttgtgcttg agttggactt tgaaccattc    420
aatgcagcct tcccccgccc aactcttaac aagtcaattg gaaatggtgt gcaattcctc    480
aaccgtcacc tttctgccaa actcttccac gacaaggaga gcttgcaccc acttttggag    540
ttcctcaggc ttcacagcgt caagggaaag actttgatgt tgaatgacag aattcaaaac    600
ccagatgcac tccaacatgt tctgaggaaa gctgaggagt atctgggcac agtgcctcct    660
gaaactccct actcagaatt tgagcacaag ttccaggaga ttggtttgga gagagggtgg    720
ggtgacaacg cggagcgtgt ccttgagtca attcaacttc tcttggatct tcttgaggcc    780
cctgacccgt gcacccttga gactttcctt ggaagaatcc ctatggtgtt caatgttgtt    840
attctttctc cccatggtta ctttgcccaa gataatgtct tgggataccc tgacactggt    900
ggccaggttg tttacatctt ggatcaagtt cgtgctttgg agaatgagat gctccatcgc    960
attaagcaac aaggattgga cattgttcct cgtattctca ttatcacccg tcttctcccc   1020
gatgcagtag gaactacttg tggccaacgt cttgagaagg tgttcggaac tgagcactcc   1080
cacattcttc gagttccctt tagaactgag aagggaattg ttcgcaagtg gatctcaaga   1140
ttcgaagtct ggccctactt ggaaacttac actgaggatg ttgcccacga gcttgccaaa   1200
gagttgcaag gcaagccaga tctgattgtt ggaaactaca gtgatggaaa cattgtcgct   1260
tctttgttgg cacataaatt aggtgtcact cagtgtacca ttgctcacgc acttgagaag   1320
accaaatacc ccgaatccga catttactgg aaaaaattgg aagagagata ccacttctct   1380
tgccaattca cagctgatct atttgccatg aaccacacag atttcattat caccagtacc   1440
ttccaggaga ttgctggaag caaggacact gttggacagt acgaatctca cacagccttc   1500
acccttcctg gactctaccg cgttgtgcat ggtattgatg tctttgatcc aaaattcaac   1560
attgtctccc ctggagctga tcaaaccatt tacttccccc acactgaaac cagccgtagg   1620
ttgacatcct tccaccctga aatcgaagaa ctcctttaca gctcagtgga gaatgaagaa   1680
```

-continued

```
cacatatgtg tgctgaagga ccgcagcaag ccaattatct tcaccatggc aaggttggat   1740

cgagtgaaga acatcacagg acttgtggag tggtacggta agaacgcgaa gctgagggag   1800

ctggtgaacc ttgtggttgt tgctggagac aggaggaagg agtcaaagga cttggaagaa   1860

aaggccgaga tgaagaagat gtacggcctg atcgagacct acaagttgaa cggccaattc   1920

agatggattt catcgcagat gaaccgtgtg aggaatggag agctctaccg cgtgatctgc   1980

gacaccaggg gtgctttcgt gcagcctgct gtatacgagg cttttggttt gacagtggtt   2040

gaggccatga cttgcggctt gccaacattc gccacatgca atggtggtcc tgctgagatc   2100

attgtgcacg gcaagtctgg cttccacatt gacccttacc atggtgaccg tgctgctgat   2160

ctccttgttg acttctttga gaagtgcaag cttgacccaa ctcactggga caagatctca   2220

aaggctggtc tccagcgtat tgaagagaag tacacatggc aaatttactc tcagaggctt   2280

ctcactctca ccggtgtcta tggcttctgg aagcatgtgt ctaaccttga ccgccgtgag   2340

agccgccgct atctcgagat gttctatgct ctcaagtacc gcaaattggc tgagtctgtg   2400

ccccttgctg ctgagtaa                                                 2418


<210> SEQ ID NO 6
<211> LENGTH: 805
<212> TYPE: PRT
<213> ORGANISM: Glycine max

<400> SEQUENCE: 6

Met Ala Thr Asp Arg Leu Thr Arg Val His Ser Leu Arg Glu Arg Leu
1               5                   10                  15

Asp Glu Thr Leu Thr Ala Asn Arg Asn Glu Ile Leu Ala Leu Leu Ser
            20                  25                  30

Arg Ile Glu Ala Lys Gly Lys Gly Ile Leu Gln His His Gln Val Ile
        35                  40                  45

Ala Glu Phe Glu Glu Ile Pro Glu Glu Asn Arg Gln Lys Leu Thr Asp
    50                  55                  60

Gly Ala Phe Gly Glu Val Leu Arg Ser Thr Gln Glu Ala Ile Val Leu
65                  70                  75                  80

Pro Pro Trp Val Ala Leu Ala Val Arg Pro Arg Pro Gly Val Trp Glu
                85                  90                  95

Tyr Leu Arg Val Asn Val His Ala Leu Val Val Glu Glu Leu Gln Pro
            100                 105                 110

Ala Glu Tyr Leu His Phe Lys Glu Glu Leu Val Asp Gly Ser Ser Asn
        115                 120                 125

Gly Asn Phe Val Leu Glu Leu Asp Phe Glu Pro Phe Asn Ala Ala Phe
    130                 135                 140

Pro Arg Pro Thr Leu Asn Lys Ser Ile Gly Asn Gly Val Gln Phe Leu
145                 150                 155                 160

Asn Arg His Leu Ser Ala Lys Leu Phe His Asp Lys Glu Ser Leu His
                165                 170                 175

Pro Leu Leu Glu Phe Leu Arg Leu His Ser Val Lys Gly Lys Thr Leu
            180                 185                 190

Met Leu Asn Asp Arg Ile Gln Asn Pro Asp Ala Leu Gln His Val Leu
        195                 200                 205

Arg Lys Ala Glu Glu Tyr Leu Gly Thr Val Pro Pro Glu Thr Pro Tyr
    210                 215                 220

Ser Glu Phe Glu His Lys Phe Gln Glu Ile Gly Leu Glu Arg Gly Trp
225                 230                 235                 240
```

-continued

```
Gly Asp Asn Ala Glu Arg Val Leu Glu Ser Ile Gln Leu Leu Leu Asp
                245                 250                 255

Leu Leu Glu Ala Pro Asp Pro Cys Thr Leu Glu Thr Phe Leu Gly Arg
            260                 265                 270

Ile Pro Met Val Phe Asn Val Val Ile Leu Ser Pro His Gly Tyr Phe
        275                 280                 285

Ala Gln Asp Asn Val Leu Gly Tyr Pro Asp Thr Gly Gly Gln Val Val
    290                 295                 300

Tyr Ile Leu Asp Gln Val Arg Ala Leu Glu Asn Glu Met Leu His Arg
305                 310                 315                 320

Ile Lys Gln Gln Gly Leu Asp Ile Val Pro Arg Ile Leu Ile Ile Thr
                325                 330                 335

Arg Leu Leu Pro Asp Ala Val Gly Thr Thr Cys Gly Gln Arg Leu Glu
            340                 345                 350

Lys Val Phe Gly Thr Glu His Ser His Ile Leu Arg Val Pro Phe Arg
        355                 360                 365

Thr Glu Lys Gly Ile Val Arg Lys Trp Ile Ser Arg Phe Glu Val Trp
    370                 375                 380

Pro Tyr Leu Glu Thr Tyr Thr Glu Asp Val Ala His Glu Leu Ala Lys
385                 390                 395                 400

Glu Leu Gln Gly Lys Pro Asp Leu Ile Val Gly Asn Tyr Ser Asp Gly
                405                 410                 415

Asn Ile Val Ala Ser Leu Leu Ala His Lys Leu Gly Val Thr Gln Cys
            420                 425                 430

Thr Ile Ala His Ala Leu Glu Lys Thr Lys Tyr Pro Glu Ser Asp Ile
        435                 440                 445

Tyr Trp Lys Lys Leu Glu Glu Arg Tyr His Phe Ser Cys Gln Phe Thr
    450                 455                 460

Ala Asp Leu Phe Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Thr Ala Phe Thr Leu Pro Gly Leu Tyr Arg Val Val His Gly Ile
            500                 505                 510

Asp Val Phe Asp Pro Lys Phe Asn Ile Val Ser Pro Gly Ala Asp Gln
        515                 520                 525

Thr Ile Tyr Phe Pro His Thr Glu Thr Ser Arg Arg Leu Thr Ser Phe
    530                 535                 540

His Pro Glu Ile Glu Glu Leu Leu Tyr Ser Ser Val Glu Asn Glu Glu
545                 550                 555                 560

His Ile Cys Val Leu Lys Asp Arg Ser Lys Pro Ile Ile Phe Thr Met
                565                 570                 575

Ala Arg Leu Asp Arg Val Lys Asn Ile Thr Gly Leu Val Glu Trp Tyr
            580                 585                 590

Gly Lys Asn Ala Lys Leu Arg Glu Leu Val Asn Leu Val Val Val Ala
        595                 600                 605

Gly Asp Arg Arg Lys Glu Ser Lys Asp Leu Glu Glu Lys Ala Glu Met
    610                 615                 620

Lys Lys Met Tyr Gly Leu Ile Glu Thr Tyr Lys Leu Asn Gly Gln Phe
625                 630                 635                 640

Arg Trp Ile Ser Ser Gln Met Asn Arg Val Arg Asn Gly Glu Leu Tyr
                645                 650                 655

Arg Val Ile Cys Asp Thr Arg Gly Ala Phe Val Gln Pro Ala Val Tyr
```

```
            660                 665                 670

Glu Ala Phe Gly Leu Thr Val Val Glu Ala Met Thr Cys Gly Leu Pro
        675                 680                 685

Thr Phe Ala Thr Cys Asn Gly Gly Pro Ala Glu Ile Ile Val His Gly
    690                 695                 700

Lys Ser Gly Phe His Ile Asp Pro Tyr His Gly Asp Arg Ala Ala Asp
705                 710                 715                 720

Leu Leu Val Asp Phe Phe Glu Lys Cys Lys Leu Asp Pro Thr His Trp
                725                 730                 735

Asp Lys Ile Ser Lys Ala Gly Leu Gln Arg Ile Glu Glu Lys Tyr Thr
            740                 745                 750

Trp Gln Ile Tyr Ser Gln Arg Leu Leu Thr Leu Thr Gly Val Tyr Gly
        755                 760                 765

Phe Trp Lys His Val Ser Asn Leu Asp Arg Arg Glu Ser Arg Arg Tyr
    770                 775                 780

Leu Glu Met Phe Tyr Ala Leu Lys Tyr Arg Lys Leu Ala Glu Ser Val
785                 790                 795                 800

Pro Leu Ala Ala Glu
                805


<210> SEQ ID NO 7
<211> LENGTH: 313
<212> TYPE: DNA
<213> ORGANISM: Glycine max

<400> SEQUENCE: 7

ccccctctc tttttgcgt tcattctgtt ttcctgttga agtctttccc tagccaatgg      60

ccaccgatcg tttgacccgg gttcacagtc tccgtgagag gcttgatgaa accctcactg    120

ccaacaggaa tgaaattttg gcccttctgt caaggatcga agccaagggc aagggcatcc    180

tgcaacacca ccaggtcatt gctgagtttg aggaaatccc tgaggagaac agacagaagc    240

tcactgatgg tgcctttgga gaagtcttga gatctacaca ggaagccata gttttgccac    300

catgggttgc tct                                                       313


<210> SEQ ID NO 8
<211> LENGTH: 3191
<212> TYPE: DNA
<213> ORGANISM: Glycine max

<400> SEQUENCE: 8

aggtaaattg cagctgaagg acagtgaagg gtgaatttat ccatttaaac cattttcttt     60

ttaacacatt tcttatggta atctcttctc actacactat aaaaatggct tctcaatccc    120

atttctaca tcatcccatt ctattgagtt ttgtttattt gctttcactt ttttttttat    180

ctgcctcttc ccttaatttg cttgacttct tcttcacatt ttgctttgtt ttctcctccg    240

gcttccggta tttcaaattc aagatgagca agttgaaatt tataaataga aatacagata    300

ttatttacaa cgtcaaatct ttggtatttt caatatttga atggggtaaa tttgtcatat    360

agtcatcatc actgactact tatctaacct atttaatttg gagcatattc tttataaggt    420

ccctctcacg gccaatgtct aattattgat atacagctct tgttttctag tgctgcttat    480

aatattatct acacatatat atggtactgc acactactac tatatagtag taagtaaact    540

agcaacagcc ggggccaaac tccaataact aggcattggg gtttagttgg taatataaat    600

ataacatcaa aaagtctttg cttgtgacga acatcacaat gcacccacca ttgatgccac    660
```

gacagacatt gttaattttt tttttaattt ttaaaaaaga agcaattcca atagttctat 720
attacaatct cacgtgatcc aagcacaacg tttcattttt tgtacatgct cgatatataa 780
ataatatttc attttatagt aaaatataat gacattttcg aatataattt ttgaaatttc 840
attttccaaa tgaaatacta atattaatat taatgagatt accacaaatc atgttatgaa 900
tgaaataaag agttttggca ttctaacttt ctttgaatag aacaaaatgt atacaacact 960
ctccatatat acacgattta ttcagggatc atatacattc tctcatgatt aacatagtct 1020
gctttcttca cgtctaagca gataattttt ggtccacaag ataaaattat cattagtcgt 1080
tttaattaat tccttgagca tcaagcacta aaataattaa acttctccat taccaaaaaa 1140
aaaagatagg tgattcagta acatgtagta ctagtactac tgattttttt tttcttttga 1200
ttttaatgaa tggttcgtat cgagcatcga gaaatccatt tattaggtgt gtaatgtaat 1260
agtagtattt ccttgatttt cagtaataag atggattctt acatttatat ctgtttgaca 1320
gaaaatgttg tcaatgcatt tcttgggcac aaagtttttt gaaacatgaa ttaatttttt 1380
caaaatattt atgacatcaa attgacccta aaataagtga taaagcttta acgtggaatg 1440
acattaattt ttccatgata aataaaacac ttaaaacatt ttaatattaa tattataatc 1500
agttacaact atgttcaatt aatgcaataa cttttaaata aatattaaaa tatttttttt 1560
ctgttctcca ataaagagat cttgttgcac ggaaaaagtc acattcttat ttagtaaaaa 1620
attataatta ttgtttgaaa aatatcattt tcactgcaga aaatttgatc cagctctaca 1680
gatcatactt ttattgtaca ataatacaat aaaaatattc atctgcagga aatatcattt 1740
tcattgtaca ataatataaa gataaatata taccagaaaa gaaaaagaaa ctgatgtggc 1800
acaatgtatt cactgaaaga atgcatattg tatttcacct ttcaagcagc actaagaata 1860
tacttctttt attatacttg tgcatttact caaccaccct cggtggagta agaaagaaga 1920
tagataaaag ttttttttga catttggtga atctcttaat taaaaaaata aaataatcca 1980
tttcctttat ttaatttctt ttttcccatc tgtgaaattc caattctgct tcgcgctcct 2040
gtctataaat tgacttagcc accacctcag tttccattca ttcacttctt ctctttatac 2100 ccccccctctc ttttttgcgt tcattctgtt ttcgtaagta ctgttgtttt tctcttctat 2160
ttcttttttt gtttgtgttg tttttttttc ttccttatcg ttgttctgcc tctcctctgt 2220
ttcggtgctc tgttcaccac ttccacgtga gaatgatctt ccttctttgc atgttcattc 2280
tctcgtgacc actggatcag actccatgtt ctgatccagg gtctctctct aacgcctgta 2340
ctttcatcca tgaccacctt aaaaacaaca tgggggtggt gctgttacac taactctgtt 2400
tctggggtgc tgtctttgtt caattttact cagaaaatat cttttcttgg attctattcg 2460
gtgtgtggga acatgatcct gtcggtcggt tgtttttagg ttaatcctta actggttaca 2520
aggatctaac gcttgaatgc atgtcctgag ttaaagaaac aaaagaagaa cacacctagt 2580
acagcctggc ctcgaaccaa gaacttcttt gttggtttct cattattact aaaataaaat 2640
aaagtatacg ttttcttttt tctttgggat gaacggttca gacttatgag aagtttaagc 2700
taatcctgta gtggagtgtt caatttattt taaactttaa agcaatagct caagcactaa 2760
acttcttttt caagttcaac cactttggta gcttgctaat tgctgctatt gttctaatta 2820
attaatgtaa ttattgttta aaaaagaaaa gttggtgaca ctggaataaa aaagtgtact 2880
atctggcaat tattcttctg cagcaatgtt tgaggttgaa atcttagtag aacaaagtag 2940
aagatctggt atttatattt tttgtagaca gatggtgggg gtgggtggta ggccttgaaa 3000
tccaatatag ttttgtagaa taattttatt attttttttt tttgctcact tgtttgtggt 3060
attgattttg tgatgactca agattaatga tttaccttca ttttttttcat ggtgacatat 3120 tatgtatatt cttgatctgt ttcttacact tctttttcgt tgttgtagct gttgaagtct 3180
ttccctagcc a 3191

<210> SEQ ID NO 9
<211> LENGTH: 43
<212> TYPE: DNA
<213> ORGANISM: artificial sequence
<220> FEATURE:
<223> OTHER INFORMATION: primer

<400> SEQUENCE: 9
acgtacgtcc tgcaggtaaa ttgcagctga aggacagtga agg 43

<210> SEQ ID NO 10
<211> LENGTH: 38
<212> TYPE: DNA
<213> ORGANISM: artificial sequence
<220> FEATURE:
<223> OTHER INFORMATION: primer

<400> SEQUENCE: 10
ccatggtgcg gccgcagact tcaacagcta caacaacg 38

<210> SEQ ID NO 11
<211> LENGTH: 6720
<212> TYPE: DNA
<213> ORGANISM: artificial sequence
<220> FEATURE:
<223> OTHER INFORMATION: plasmid sequence

<400> SEQUENCE: 11
cctgaattcc agcacactgg cggccgttac tagtggatcc gagctcggta ccaagcttga 60
tgcatagctt gagtattcta acgcgtcacc taaatagctt ggcgtaatca tggtcatagc 120
tgtttcctgt gtgaaattgt tatccgctca caattccaca caacatacga gccggaagca 180
taaagtgtaa agcctggggt gcctaatgag tgagctaact cacattaatt gcgttgcgct 240
cactgcccgc tttccagtcg ggaaacctgt cgtgccagct gcattaatga atcggccaac 300
gcgcggggag aggcggtttg cgtattgggc gctcttccgc ttcctcgctc actgactcgc 360
tgcgctcggt cgttcggctg cggcgagcgg tatcagctca ctcaaaggcg gtaatacggt 420
tatccacaga atcaggggat aacgcaggaa agaacatgtg agcaaaaggc cagcaaaagg 480
ccaggaaccg taaaaaggcc gcgttgctgg cgtttttcca taggctccgc ccccctgacg 540
agcatcacaa aaatcgacgc tcaagtcaga ggtggcgaaa cccgacagga ctataaagat 600
accaggcgtt tccccctgga agctccctcg tgcgctctcc tgttccgacc ctgccgctta 660
ccggatacct gtccgccttt ctcccttcgg gaagcgtggc gctttctcat agctcacgct 720
gtaggtatct cagttcggtg taggtcgttc gctccaagct gggctgtgtg cacgaacccc 780
ccgttcagcc cgaccgctgc gccttatccg gtaactatcg tcttgagtcc aacccggtaa 840
gacacgactt atcgccactg gcagcagcca ctggtaacag gattagcaga gcgaggtatg 900
taggcggtgc tacagagttc ttgaagtggt ggcctaacta cggctacact agaagaacag 960
tatttggtat ctgcgctctg ctgaagccag ttaccttcgg aaaaagagtt ggtagctctt 1020
gatccggcaa acaaaccacc gctggtagcg gtggtttttt tgtttgcaag cagcagatta 1080
cgcgcagaaa aaaaggatct caagaagatc ctttgatctt ttctacgggg tctgacgctc 1140

-continued

```
agtggaacga aaactcacgt taagggattt tggtcatgag attatcaaaa aggatcttca   1200
cctagatcct tttaaattaa aaatgaagtt ttagcacgtg tcagtcctgc tcctcggcca   1260
cgaagtgcac gcagttgccg gccgggtcgc gcagggcgaa ctcccgcccc cacggctgct   1320
cgccgatctc ggtcatggcc ggcccggagg cgtcccggaa gttcgtggac acgacctccg   1380
accactcggc gtacagctcg tccaggccgc gcacccacac ccaggccagg gtgttgtccg   1440
gcaccacctg gtcctggacc gcgctgatga acagggtcac gtcgtcccgg accacaccgg   1500
cgaagtcgtc ctccacgaag tcccgggaga acccgagccg gtcggtccag aactcgaccg   1560
ctccggcgac gtcgcgcgcg gtgagcaccg gaacggcact ggtcaacttg gccatggtgg   1620
ccctcctcac gtgctattat tgaagcattt atcagggtta ttgtctcatg agcggataca   1680
tatttgaatg tatttagaaa aataaacaaa taggggttcc gcgcacattt ccccgaaaag   1740
tgccacctga tgcggtgtga aataccgcac agatgcgtaa ggagaaaata ccgcatcagg   1800
aaattgtaag cgttaataat tcagaagaac tcgtcaagaa ggcgatagaa ggcgatgcgc   1860
tgcgaatcgg gagcggcgat accgtaaagc acgaggaagc ggtcagccca ttcgccgcca   1920
agctcttcag caatatcacg ggtagccaac gctatgtcct gatagcggtc cgccacaccc   1980
agccggccac agtcgatgaa tccagaaaag cggccatttt ccaccatgat attcggcaag   2040
caggcatcgc catgggtcac gacgagatcc tcgccgtcgg gcatgctcgc cttgagcctg   2100
gcgaacagtt cggctggcgc gagcccctga tgctcttcgt ccagatcatc ctgatcgaca   2160
agaccggctt ccatccgagt acgtgctcgc tcgatgcgat gtttcgcttg gtggtcgaat   2220
gggcaggtag ccggatcaag cgtatgcagc cgccgcattg catcagccat gatggatact   2280
ttctcggcag gagcaaggtg agatgacagg agatcctgcc ccggcacttc gcccaatagc   2340
agccagtccc ttcccgcttc agtgacaacg tcgagcacag ctgcgcaagg aacgcccgtc   2400
gtggccagcc acgatagccg cgctgcctcg tcttgcagtt cattcagggc accggacagg   2460
tcggtcttga caaaaagaac cgggcgcccc tgcgctgaca gccggaacac ggcggcatca   2520
gagcagccga ttgtctgttg tgcccagtca tagccgaata gcctctccac ccaagcggcc   2580
ggagaacctg cgtgcaatcc atcttgttca atcatgcgaa acgatcctca tcctgtctct   2640
tgatcagagc ttgatcccct gcgccatcag atccttggcg gcaagaaagc catccagttt   2700
actttgcagg gcttcccaac cttaccagag ggcgccccag ctggcaattc cggttcgctt   2760
gctgtccata aaaccgccca gtctagctat cgccatgtaa gcccactgca agctacctgc   2820
tttctctttg cgcttgcgtt ttcccttgtc cagatagccc agtagctgac attcatccgg   2880
ggtcagcacc gtttctgcgg actggctttc tacgtgaaaa ggatctaggt gaagatcctt   2940
tttgataatc tcatgcctga catttatatt ccccagaaca tcaggttaat ggcgtttttg   3000
atgtcatttt cgcggtggct gagatcagcc acttcttccc cgataacgga gaccggcaca   3060
ctggccatat cggtggtcat catgcgccag ctttcatccc cgatatgcac caccgggtaa   3120
agttcacggg agactttatc tgacagcaga cgtgcactgg ccagggggat caccatccgt   3180
cgccccggcg tgtcaataat atcactctgt acatccacaa acagacgata acggctctct   3240
cttttatagg tgtaaacctt aaactgccgt acgtataggc tgcgcaactg ttgggaaggg   3300
cgatcggtgc gggcctcttc gctattacgc cagctggcga aagggggatg tgctgcaagg   3360
cgattaagtt gggtaacgcc agggttttcc cagtcacgac gttgtaaaac gacggccagt   3420
gaattgtaat acgactcact atagggcgaa ttgggccctc tagatgcatg ctcgagcggc   3480
cgccagtgtg atggatatct gcagaattca ggacgtacgt cctgcaggta aattgcagct   3540
```

gaaggacagt gaagggtgaa tttatccatt taaaccattt tctttttaac acatttctta 3600
tggtaatctc ttctcactac actataaaaa tggcttctca atcccatttt ctacatcatc 3660
ccattctatt gagttttgtt tatttgcttt cacttttttt tttatctgcc tcttccctta 3720
atttgcttga cttcttcttc acattttgct ttgttttctc ctccggcttc cggtatttca 3780
aattcaagat gagcaagttg aaatttataa atagaaatac agatattatt tacaacgtca 3840
aatctttggt attttcaata tttgaatggg gtaaatttgt catatagtca tcatcactga 3900
ctacttatct aacctattta atttggagca tattctttat aaggtccctc tcacggccaa 3960
tgtctaatta ttgatataca gctcttgttt tctagtgctg cttataatat tatctacaca 4020
tatatatggt actgcacact actactatat agtagtaagt aaactagcaa cagccggggc 4080
caaactccaa taactaggca ttggggttta gttggtaata taaatataac atcaaaaagt 4140
ctttgcttgt gacgaacatc acaatgcacc caccattgat gccacgacag acattgttaa 4200
tttttttttt aatttttaaa aaagaagcaa ttccaatagt tctatattac aatctcacgt 4260
gatccaagca caacgtttca ttttttgtac atgctcgata tataaataat atttcatttt 4320
atagtaaaat ataatgacat tttcgaatat aatttttgaa atttcatttt ccaaatgaaa 4380
tactaatatt aatattaatg agattaccac aaatcatgtt atgaatgaaa taaagagttt 4440
tggcattcta actttctttg aatagaacaa aatgtataca acactctcca tatatacacg 4500
atttattcag ggatcatata cattctctca tgattaacat agtctgcttt cttcacgtct 4560
aagcagataa tttttggtcc acaagataaa attatcatta gtcgttttaa ttaattcctt 4620
gagcatcaag cactaaaata attaaacttc tccattacca aaaaaaaaag ataggtgatt 4680
cagtaacatg tagtactagt actactgatt tttttttct tttgatttta atgaatggtt 4740
cgtatcgagc atcgagaaat ccatttatta ggtgtgtaat gtaatagtag tatttccttg 4800
attttcagta ataagatgga ttcttacatt tatatctgtt tgacagaaaa tgttgtcaat 4860
gcatttcttg ggcacaaagt tttttgaaac atgaattaat tttttcaaaa tatttatgac 4920
atcaaattga ccctaaaata agtgataaag ctttaacgtg gaatgacatt aatttttcca 4980
tgataaataa aacacttaaa acattttaat attaatatta taatcagtta caactatgtt 5040
caattaatgc aataactttt aaataaatat taaaatattt tttttctgtt ctccaataaa 5100
gagatcttgt tgcacggaaa aagtcacatt cttatttagt aaaaaattat aattattgtt 5160
tgaaaaatat cattttcact gcagaaaatt tgatccagct ctacagatca tacttttatt 5220
gtacaataat acaataaaaa tattcatctg caggaaatat cattttcatt gtacaataat 5280
ataaagataa atatatacca gaaaagaaaa agaaactgat gtggcacaat gtattcactg 5340
aaagaatgca tattgtattt cacctttcaa gcagcactaa gaatatactt cttttattat 5400
acttgtgcat ttactcaacc accctcggtg gagtaagaaa gaagatagat aaaagttttt 5460
tttgacattt ggtgaatctc ttaattaaaa aaataaaata atccatttcc tttatttaat 5520 ttctttttc ccatctgtga aattccaatt ctgcttcgcg ctcctgtcta taaattgact 5580
tagccaccac ctcagtttcc attcattcac ttcttctctt tataccccc ctctcttttt 5640 tgcgttcatt ctgttttcgt aagtactgtt gtttttctct tctatttctt tttttgtttg 5700
tgttgttttt ttttcttcct tatcgttgtt ctgcctctcc tctgtttcgg tgctctgttc 5760
accacttcca cgtgagaatg atcttccttc tttgcatgtt cattctctcg tgaccactgg 5820
atcagactcc atgttctgat ccagggtctc tctctaacgc ctgtactttc atccatgacc 5880

-continued

```
accttaaaaa caacatgggg gtggtgctgt tacactaact ctgtttctgg ggtgctgtct   5940

ttgttcaatt ttactcagaa aatatctttt cttggattct attcggtgtg tgggaacatg   6000

atcctgtcgg tcggttgttt ttaggttaat ccttaactgg ttacaaggat ctaacgcttg   6060

aatgcatgtc ctgagttaaa gaaacaaaag aagaacacac ctagtacagc ctggcctcga   6120

accaagaact tctttgttgg tttctcatta ttactaaaat aaaataaagt atacgttttc   6180

ttttttcttt gggatgaacg gttcagactt atgagaagtt taagctaatc ctgtagtgga   6240

gtgttcaatt tattttaaac tttaaagcaa tagctcaagc actaaacttc tttttcaagt   6300

tcaaccactt tggtagcttg ctaattgctg ctattgttct aattaattaa tgtaattatt   6360

gtttaaaaaa gaaaagttgg tgacactgga ataaaaaagt gtactatctg gcaattattc   6420

ttctgcagca atgtttgagg ttgaaatctt agtagaacaa agtagaagat ctggtattta   6480

tatttttgt agacagatgg tgggggtggg tggtaggcct tgaaatccaa tatagttttg   6540

tagaataatt ttattatttt tttttttgc tcacttgttt gtggtattga ttttgtgatg   6600

actcaagatt aatgatttac cttcattttt ttcatggtga catattatgt atattcttga   6660

tctgtttctt acacttcttt ttcgttgttg tagctgttga agtctgcggc cgcaccatgg   6720
```

<210> SEQ ID NO 12
<211> LENGTH: 5933
<212> TYPE: DNA
<213> ORGANISM: artificial sequence
<220> FEATURE:
<223> OTHER INFORMATION: plasmid sequence

<400> SEQUENCE: 12

```
aattcgagct cggtacccgg gggcgcgccg gatccttaat taagtctaga gtcgactgtt     60

taaacctgca ggcatgcaag cttggcgtaa tcatggtcat agctgtttcc tgtgtgaaat    120

tgttatccgc tcacaattcc acacaacata cgagccggaa gcataaagtg taaagcctgg    180

ggtgcctaat gagtgagcta actcacatta attgcgttgc gctcactgcc cgctttccag    240

tcgggaaacc tgtcgtgcca gctgcattaa tgaatcggcc aacgcgcggg gagaggcggt    300

ttgcgtattg ggcgctcttc cgcttcctcg ctcactgact cgctgcgctc ggtcgttcgg    360

ctgcggcgag cggtatcagc tcactcaaag gcggtaatac ggttatccac agaatcaggg    420

gataacgcag gaaagaacat gtgagcaaaa ggccagcaaa aggccaggaa ccgtaaaaag    480

gccgcgttgc tggcgttttt ccataggctc cgcccccctg acgagcatca caaaaatcga    540

cgctcaagtc agaggtggcg aaacccgaca ggactataaa gataccaggc gtttccccct    600

ggaagctccc tcgtgcgctc tcctgttccg accctgccgc ttaccggata cctgtccgcc    660

tttctccctt cgggaagcgt ggcgctttct catagctcac gctgtaggta tctcagttcg    720

gtgtaggtcg ttcgctccaa gctgggctgt gtgcacgaac cccccgttca gcccgaccgc    780

tgcgccttat ccggtaacta tcgtcttgag tccaacccgg taagacacga cttatcgcca    840

ctggcagcag ccactggtaa caggattagc agagcgaggt atgtaggcgg tgctacagag    900

ttcttgaagt ggtggcctaa ctacggctac actagaagga cagtatttgg tatctgcgct    960

ctgctgaagc cagttacctt cggaaaaaga gttggtagct cttgatccgg caaacaaacc   1020

accgctggta gcggtggttt ttttgtttgc aagcagcaga ttacgcgcag aaaaaaagga   1080

tctcaagaag atcctttgat cttttctacg gggtctgacg ctcagtggaa cgaaaactca   1140

cgttaaggga ttttggtcat gagattatca aaaaggatct tcacctagat ccttttaaat   1200

taaaaatgaa gttttaaatc aatctaaagt atatatgagt aaacttggtc tgacagttac   1260
```

```
caatgcttaa tcagtgaggc acctatctca gcgatctgtc tatttcgttc atccatagtt   1320
gcctgactcc ccgtcgtgta gataactacg atacgggagg gcttaccatc tggccccagt   1380
gctgcaatga taccgcgaga cccacgctca ccggctccag atttatcagc aataaaccag   1440
ccagccggaa gggccgagcg cagaagtggt cctgcaactt tatccgcctc catccagtct   1500
attaattgtt gccgggaagc tagagtaagt agttcgccag ttaatagttt gcgcaacgtt   1560
gttgccattg ctacaggcat cgtggtgtca cgctcgtcgt ttggtatggc ttcattcagc   1620
tccggttccc aacgatcaag gcgagttaca tgatccccca tgttgtgcaa aaaagcggtt   1680
agctccttcg gtcctccgat cgttgtcaga agtaagttgg ccgcagtgtt atcactcatg   1740
gttatggcag cactgcataa ttctcttact gtcatgccat ccgtaagatg cttttctgtg   1800
actggtgagt actcaaccaa gtcattctga gaatagtgta tgcggcgacc gagttgctct   1860
tgcccggcgt caatacggga taataccgcg ccacatagca gaactttaaa agtgctcatc   1920
attggaaaac gttcttcggg gcgaaaactc tcaaggatct taccgctgtt gagatccagt   1980
tcgatgtaac ccactcgtgc acccaactga tcttcagcat cttttacttt caccagcgtt   2040
tctgggtgag caaaaacagg aaggcaaaat gccgcaaaaa agggaataag ggcgacacgg   2100
aaatgttgaa tactcatact cttccttttt caatattatt gaagcattta tcagggttat   2160
tgtctcatga gcggatacat atttgaatgt atttagaaaa ataaacaaat aggggttccg   2220
cgcacatttc cccgaaaagt gccacctgac gtctaagaaa ccattattat catgacatta   2280
acctataaaa ataggcgtat cacgaggccc tttcgtctcg cgcgtttcgg tgatgacggt   2340
gaaaacctct gacacatgca gctcccggag acggtcacag cttgtctgta agcggatgcc   2400
gggagcagac aagcccgtca gggcgcgtca gcgggtgttg gcgggtgtcg gggctggctt   2460
aactatgcgg catcagagca gattgtactg agagtgcacc atatgcggtg tgaaataccg   2520
cacagatgcg taaggagaaa ataccgcatc aggcgccatt cgccattcag gctgcgcaac   2580
tgttgggaag ggcgatcggt gcgggcctct tcgctattac gccagctggc gaaaggggga   2640
tgtgctgcaa ggcgattaag ttgggtaacg ccagggtttt cccagtcacg acgttgtaaa   2700
acgacggcca gtgaattcag gacgtacgtc ctgcaggtaa attgcagctg aaggacagtg   2760
aagggtgaat ttatccattt aaaccatttt ctttttaaca catttcttat ggtaatctct   2820
tctcactaca ctataaaaat ggcttctcaa tcccattttc tacatcatcc cattctattg   2880
agttttgttt atttgctttc actttttttt ttatctgcct cttcccttaa tttgcttgac   2940
ttcttcttca cattttgctt tgttttctcc tccggcttcc ggtatttcaa attcaagatg   3000
agcaagttga aatttataaa tagaaataca gatattattt acaacgtcaa atctttggta   3060
ttttcaatat ttgaatgggg taaatttgtc atatagtcat catcactgac tacttatcta   3120
acctatttaa tttggagcat attctttata aggtccctct cacggccaat gtctaattat   3180
tgatatacag ctcttgtttt ctagtgctgc ttataatatt atctacacat atatatggta   3240
ctgcacacta ctactatata gtagtaagta aactagcaac agccggggcc aaactccaat   3300
aactaggcat tggggtttag ttggtaatat aaatataaca tcaaaaagtc tttgcttgtg   3360
acgaacatca caatgcaccc accattgatg ccacgacaga cattgttaat ttttttttta   3420
atttttaaaa aagaagcaat tccaatagtt ctatattaca atctcacgtg atccaagcac   3480
aacgtttcat tttttgtaca tgctcgatat ataaataata tttcatttta tagtaaaata   3540
taatgacatt ttcgaatata atttttgaaa tttcattttc caaatgaaat actaatatta   3600
```

-continued atattaatga gattaccaca aatcatgtta tgaatgaaat aaagagtttt ggcattctaa 3660
ctttctttga atagaacaaa atgtatacaa cactctccat atatacacga tttattcagg 3720
gatcatatac attctctcat gattaacata gtctgctttc ttcacgtcta agcagataat 3780
ttttggtcca caagataaaa ttatcattag tcgttttaat taattccttg agcatcaagc 3840
actaaaataa ttaaacttct ccattaccaa aaaaaaaaga taggtgattc agtaacatgt 3900
agtactagta ctactgattt tttttttctt ttgattttaa tgaatggttc gtatcgagca 3960
tcgagaaatc catttattag gtgtgtaatg taatagtagt atttccttga ttttcagtaa 4020
taagatggat tcttacattt atatctgttt gacagaaaat gttgtcaatg catttcttgg 4080
gcacaaagtt ttttgaaaca tgaattaatt ttttcaaaat atttatgaca tcaaattgac 4140
cctaaaataa gtgataaagc tttaacgtgg aatgacatta atttttccat gataaataaa 4200
acacttaaaa cattttaata ttaatattat aatcagttac aactatgttc aattaatgca 4260
ataactttta aataaatatt aaaatatttt ttttctgttc tccaataaag agatcttgtt 4320
gcacggaaaa agtcacattc ttatttagta aaaaattata attattgttt gaaaaatatc 4380
attttcactg cagaaaattt gatccagctc tacagatcat acttttattg tacaataata 4440
caataaaaat attcatctgc aggaaatatc attttcattg tacaataata taaagataaa 4500
tatataccag aaaagaaaaa gaaactgatg tggcacaatg tattcactga aagaatgcat 4560
attgtatttc acctttcaag cagcactaag aatatacttc ttttattata cttgtgcatt 4620
tactcaacca ccctcggtgg agtaagaaag aagatagata aaagtttttt ttgacatttg 4680
gtgaatctct taattaaaaa aataaaataa tccatttcct ttatttaatt tctttttttcc 4740
catctgtgaa attccaattc tgcttcgcgc tcctgtctat aaattgactt agccaccacc 4800
tcagtttcca ttcattcact tcttctcttt atacccccc tctctttttt gcgttcattc 4860
tgttttcgta agtactgttg tttttctctt ctatttcttt ttttgtttgt gttgtttttt 4920
tttcttcctt atcgttgttc tgcctctcct ctgtttcggt gctctgttca ccacttccac 4980
gtgagaatga tcttccttct ttgcatgttc attctctcgt gaccactgga tcagactcca 5040
tgttctgatc cagggtctct ctctaacgcc tgtactttca tccatgacca ccttaaaaac 5100
aacatggggg tggtgctgtt acactaactc tgtttctggg gtgctgtctt tgttcaattt 5160
tactcagaaa atatcttttc ttggattcta ttcggtgtgt gggaacatga tcctgtcggt 5220
cggttgtttt taggttaatc cttaactggt tacaaggatc taacgcttga atgcatgtcc 5280
tgagttaaag aaacaaaaga agaacacacc tagtacagcc tggcctcgaa ccaagaactt 5340
ctttgttggt ttctcattat tactaaaata aaataaagta tacgttttct tttttctttg 5400
ggatgaacgg ttcagactta tgagaagttt aagctaatcc tgtagtggag tgttcaattt 5460
attttaaact ttaaagcaat agctcaagca ctaaacttct ttttcaagtt caaccacttt 5520
ggtagcttgc taattgctgc tattgttcta attaattaat gtaattattg tttaaaaaag 5580
aaaagttggt gacactggaa taaaaaagtg tactatctgg caattattct tctgcagcaa 5640
tgtttgaggt tgaaatctta gtagaacaaa gtagaagatc tggtatttat attttttgta 5700
gacagatggt gggggtgggt ggtaggcctt gaaatccaat atagttttgt agaataattt 5760
tattattttt tttttttgct cacttgtttg tggtattgat tttgtgatga ctcaagatta 5820
atgatttacc ttcatttttt tcatggtgac atattatgta tattcttgat ctgtttctta 5880
cacttctttt tcgttgttgt agctgttgaa gtctgcggcc gcaccatggc ctg 5933

<210> SEQ ID NO 13
<211> LENGTH: 6647
<212> TYPE: DNA
<213> ORGANISM: artificial sequence
<220> FEATURE:
<223> OTHER INFORMATION: plasmid sequence

<400> SEQUENCE: 13
ctagagtcga ctgtttaaac ctgcaggcat gcaagcttgg cgtaatcatg gtcatagctg 60
tttcctgtgt gaaattgtta tccgctcaca attccacaca acatacgagc cggaagcata 120
aagtgtaaag cctggggtgc ctaatgagtg agctaactca cattaattgc gttgcgctca 180
ctgcccgctt tccagtcggg aaacctgtcg tgccagctgc attaatgaat cggccaacgc 240
gcggggagag gcggtttgcg tattgggcgc tcttccgctt cctcgctcac tgactcgctg 300
cgctcggtcg ttcggctgcg gcgagcggta tcagctcact caaaggcggt aatacggtta 360
tccacagaat caggggataa cgcaggaaag aacatgtgag caaaaggcca gcaaaaggcc 420
aggaaccgta aaaaggccgc gttgctggcg tttttccata ggctccgccc ccctgacgag 480
catcacaaaa atcgacgctc aagtcagagg tggcgaaacc cgacaggact ataaagatac 540
caggcgtttc cccctggaag ctccctcgtg cgctctcctg ttccgaccct gccgcttacc 600
ggatacctgt ccgcctttct cccttcggga agcgtggcgc tttctcatag ctcacgctgt 660
aggtatctca gttcggtgta ggtcgttcgc tccaagctgg gctgtgtgca cgaacccccc 720
gttcagcccg accgctgcgc cttatccggt aactatcgtc ttgagtccaa cccggtaaga 780
cacgacttat cgccactggc agcagccact ggtaacagga ttagcagagc gaggtatgta 840
ggcggtgcta cagagttctt gaagtggtgg cctaactacg gctacactag aaggacagta 900
tttggtatct gcgctctgct gaagccagtt accttcggaa aaagagttgg tagctcttga 960
tccggcaaac aaaccaccgc tggtagcggt ggtttttttg tttgcaagca gcagattacg 1020
cgcagaaaaa aaggatctca agaagatcct ttgatctttt ctacggggtc tgacgctcag 1080
tggaacgaaa actcacgtta agggattttg gtcatgagat tatcaaaaag gatcttcacc 1140
tagatccttt taaattaaaa atgaagtttt aaatcaatct aaagtatata tgagtaaact 1200
tggtctgaca gttaccaatg cttaatcagt gaggcaccta tctcagcgat ctgtctattt 1260
cgttcatcca tagttgcctg actccccgtc gtgtagataa ctacgatacg ggagggctta 1320
ccatctggcc ccagtgctgc aatgataccg cgagacccac gctcaccggc tccagattta 1380
tcagcaataa accagccagc cggaagggcc gagcgcagaa gtggtcctgc aactttatcc 1440
gcctccatcc agtctattaa ttgttgccgg gaagctagag taagtagttc gccagttaat 1500
agtttgcgca acgttgttgc cattgctaca ggcatcgtgg tgtcacgctc gtcgtttggt 1560
atggcttcat tcagctccgg ttcccaacga tcaaggcgag ttacatgatc ccccatgttg 1620
tgcaaaaaag cggttagctc cttcggtcct ccgatcgttg tcagaagtaa gttggccgca 1680
gtgttatcac tcatggttat ggcagcactg cataattctc ttactgtcat gccatccgta 1740
agatgctttt ctgtgactgg tgagtactca accaagtcat tctgagaata gtgtatgcgg 1800
cgaccgagtt gctcttgccc ggcgtcaata cgggataata ccgcgccaca tagcagaact 1860
ttaaaagtgc tcatcattgg aaaacgttct tcggggcgaa aactctcaag gatcttaccg 1920
ctgttgagat ccagttcgat gtaacccact cgtgcaccca actgatcttc agcatctttt 1980
actttcacca gcgtttctgg gtgagcaaaa acaggaaggc aaaatgccgc aaaaaaggga 2040
ataagggcga cacggaaatg ttgaatactc atactcttcc tttttcaata ttattgaagc 2100

-continued atttatcagg gttattgtct catgagcgga tacatatttg aatgtattta gaaaaataaa 2160
caaatagggg ttccgcgcac atttccccga aaagtgccac ctgacgtcta agaaaccatt 2220
attatcatga cattaaccta taaaaatagg cgtatcacga ggccctttcg tctcgcgcgt 2280
ttcggtgatg acggtgaaaa cctctgacac atgcagctcc cggagacggt cacagcttgt 2340
ctgtaagcgg atgccgggag cagacaagcc cgtcagggcg cgtcagcggg tgttggcggg 2400
tgtcggggct ggcttaacta tgcggcatca gagcagattg tactgagagt gcaccatatg 2460
cggtgtgaaa taccgcacag atgcgtaagg agaaaatacc gcatcaggcg ccattcgcca 2520
ttcaggctgc gcaactgttg ggaagggcga tcggtgcggg cctcttcgct attacgccag 2580
ctggcgaaag ggggatgtgc tgcaaggcga ttaagttggg taacgccagg gttttcccag 2640
tcacgacgtt gtaaaacgac ggccagtgaa ttcaggacgt acgtcctgca ggtaaattgc 2700
agctgaagga cagtgaaggg tgaatttatc catttaaacc attttctttt taacacattt 2760
cttatggtaa tctcttctca ctacactata aaaatggctt ctcaatccca ttttctacat 2820
catcccattc tattgagttt tgtttatttg ctttcacttt tttttttatc tgcctcttcc 2880
cttaatttgc ttgacttctt cttcacattt tgctttgttt tctcctccgg cttccggtat 2940
ttcaaattca agatgagcaa gttgaaattt ataaatagaa atacagatat tatttacaac 3000
gtcaaatctt tggtattttc aatatttgaa tggggtaaat ttgtcatata gtcatcatca 3060
ctgactactt atctaaccta tttaatttgg agcatattct ttataaggtc cctctcacgg 3120
ccaatgtcta attattgata tacagctctt gttttctagt gctgcttata atattatcta 3180
cacatatata tggtactgca cactactact atatagtagt aagtaaacta gcaacagccg 3240
gggccaaact ccaataacta ggcattgggg tttagttggt aatataaata taacatcaaa 3300
aagtctttgc ttgtgacgaa catcacaatg cacccaccat tgatgccacg acagacattg 3360
ttaatttttt ttttaatttt taaaaaagaa gcaattccaa tagttctata ttacaatctc 3420
acgtgatcca agcacaacgt ttcatttttt gtacatgctc gatatataaa taatatttca 3480
ttttatagta aaatataatg acattttcga atataatttt tgaaatttca ttttccaaat 3540
gaaatactaa tattaatatt aatgagatta ccacaaatca tgttatgaat gaaataaaga 3600
gttttggcat tctaactttc tttgaataga acaaaatgta tacaacactc tccatatata 3660
cacgatttat tcagggatca tatacattct ctcatgatta acatagtctg ctttcttcac 3720
gtctaagcag ataattttg gtccacaaga taaaattatc attagtcgtt ttaattaatt 3780
ccttgagcat caagcactaa aataattaaa cttctccatt accaaaaaaa aaagataggt 3840
gattcagtaa catgtagtac tagtactact gatttttttt ttcttttgat tttaatgaat 3900
ggttcgtatc gagcatcgag aaatccattt attaggtgtg taatgtaata gtagtatttc 3960
cttgattttc agtaataaga tggattctta catttatatc tgtttgacag aaaatgttgt 4020
caatgcattt cttgggcaca aagtttttg aaacatgaat taattttttc aaaatattta 4080
tgacatcaaa ttgaccctaa aataagtgat aaagctttaa cgtggaatga cattaatttt 4140
tccatgataa ataaaacact taaaacattt taatattaat attataatca gttacaacta 4200
tgttcaatta atgcaataac ttttaaataa atattaaaat atttttttc tgttctccaa 4260
taaagagatc ttgttgcacg gaaaaagtca cattcttatt tagtaaaaaa ttataattat 4320
tgtttgaaaa atatcatttt cactgcagaa aatttgatcc agctctacag atcatacttt 4380
tattgtacaa taatacaata aaaatattca tctgcaggaa atatcatttt cattgtacaa 4440
taatataaag ataaatatat accagaaaag aaaaagaaac tgatgtggca caatgtattc 4500

```
actgaaagaa tgcatattgt atttcacctt tcaagcagca ctaagaatat acttctttta   4560
ttatacttgt gcatttactc aaccaccctc ggtggagtaa gaaagaagat agataaaagt   4620
tttttttgac atttggtgaa tctcttaatt aaaaaaataa aataatccat ttcctttatt   4680
taatttcttt tttcccatct gtgaaattcc aattctgctt cgcgctcctg tctataaatt   4740
gacttagcca ccacctcagt ttccattcat tcacttcttc tctttatacc ccccctctct   4800
tttttgcgtt cattctgttt tcgtaagtac tgttgttttt ctcttctatt tcttttttttg   4860
tttgtgttgt tttttttttct tccttatcgt tgttctgcct ctcctctgtt tcggtgctct   4920
gttcaccact tccacgtgag aatgatcttc cttctttgca tgttcattct ctcgtgacca   4980
ctggatcaga ctccatgttc tgatccaggg tctctctcta acgcctgtac tttcatccat   5040
gaccacctta aaaacaacat gggggtggtg ctgttacact aactctgttt ctggggtgct   5100
gtctttgttc aattttactc agaaaatatc ttttcttgga ttctattcgg tgtgtgggaa   5160
catgatcctg tcggtcggtt gtttttaggt taatccttaa ctggttacaa ggatctaacg   5220
cttgaatgca tgtcctgagt taaagaaaca aaagaagaac acacctagta cagcctggcc   5280
tcgaaccaag aacttctttg ttggtttctc attattacta aaataaaata aagtatacgt   5340
tttctttttt ctttgggatg aacggttcag acttatgaga agtttaagct aatcctgtag   5400
tggagtgttc aatttatttt aaactttaaa gcaatagctc aagcactaaa cttctttttc   5460
aagttcaacc actttggtag cttgctaatt gctgctattg ttctaattaa ttaatgtaat   5520
tattgtttaa aaaagaaaag ttggtgacac tggaataaaa aagtgtacta tctggcaatt   5580
attcttctgc agcaatgttt gaggttgaaa tcttagtaga acaaagtaga agatctggta   5640
tttatatttt ttgtagacag atggtggggg tgggtggtag gccttgaaat ccaatatagt   5700
tttgtagaat aattttatta tttttttttt ttgctcactt gtttgtggta ttgattttgt   5760
gatgactcaa gattaatgat ttaccttcat ttttttcatg gtgacatatt atgtatattc   5820
ttgatctgtt tcttacactt ctttttcgtt gttgtagctg ttgaagtctg cggccgcatt   5880
tcgcaccaaa tcaatgaaag taataatgaa aagtctgaat aagaatactt aggcttagat   5940
gcctttgtta cttgtgtaaa ataacttgag tcatgtacct ttggcggaaa cagaataaat   6000
aaaaggtgaa attccaatgc tctatgtata agttagtaat acttaatgtg ttctacggtt   6060
gtttcaatat catcaaactc taattgaaac tttagaacca caaatctcaa tcttttctta   6120
atgaaatgaa aaatcttaat tgtaccatgt ttatgttaaa caccttacaa ttaattggtt   6180
ggagaggagg accaaccgat gggacaacat tgggagaaag agattcaatg gagatttgga   6240
taggagaaca acattctttt tcacttcaat acaagatgag tgcaacacta aggatatgta   6300
tgagactttc agaagctacg acaacataga tgagtgaggt ggtgattcct agcaagaaag   6360
acattagagg aagccaaaat cgaacaagga agacatcaag ggcaagagac aggaccatcc   6420
atctcaggaa aaggagcttt gggatagtcc gagaagttgt acaagaaatt ttttggaggg   6480
tgagtgatgc attgctggtg actttaactc aatcaaaatt gagaaagaaa gaaaagggag   6540
ggggctcaca tgtgaataga agggaaacgg gagaatttta cagttttgat ctaatgggca   6600
tcccagctag tggtaacata ttcaccatgt ttaaccttca cgtacgt                 6647
```

<210> SEQ ID NO 14
<211> LENGTH: 9266
<212> TYPE: DNA
<213> ORGANISM: artificial sequence
<220> FEATURE:

<223> OTHER INFORMATION: plasmid sequence

<400> SEQUENCE: 14

```
gtacgtgaag gttaaacatg gtgaatatgt taccactagc tgggatgccc attagatcaa     60
aactgtaaaa ttctcccgtt tcccttctat tcacatgtga gccccctccc ttttctttct    120
ttctcaattt tgattgagtt aaagtcacca gcaatgcatc actcaccctc caaaaaattt    180
cttgtacaac ttctcggact atcccaaagc tccttttcct gagatggatg gtcctgtctc    240
ttgcccttga tgtcttcctt gttcgatttt ggcttcctct aatgtctttc ttgctaggaa    300
tcaccacctc actcatctat gttgtcgtag cttctgaaag tctcatacat atccttagtg    360
ttgcactcat cttgtattga agtgaaaaag aatgttgttc tcctatccaa atctccattg    420
aatctctttc tcccaatgtt gtcccatcgg ttggtcctcc tctccaacca attaattgta    480
aggtgtttaa cataaacatg gtacaattaa gatttttcat ttcattaaga aaagattgag    540
atttgtggtt ctaaagtttc aattagagtt tgatgatatt gaaacaaccg tagaacacat    600
taagtattac taacttatac atagagcatt ggaatttcac cttttattta ttctgtttcc    660
gccaaaggta catgactcaa gttattttac acaagtaaca aaggcatcta agcctaagta    720
ttcttattca gacttttcat tattactttc attgatttgg tgcgaaatgc ggccgcagac    780
ttcaacagct acaacaacga aaaagaagtg taagaaacag atcaagaata tacataatat    840
gtcaccatga aaaaaatgaa ggtaaatcat taatcttgag tcatcacaaa atcaatacca    900
caaacaagtg agcaaaaaaa aaaaataata aaattattct acaaaactat attggatttc    960
aaggcctacc acccaccccc accatctgtc tacaaaaaat ataaatacca gatcttctac   1020
tttgttctac taagatttca acctcaaaca ttgctgcaga agaataattg ccagatagta   1080
cactttttta ttccagtgtc accaactttt cttttttaaa caataattac attaattaat   1140
tagaacaata gcagcaatta gcaagctacc aaagtggttg aacttgaaaa agaagtttag   1200
tgcttgagct attgctttaa agtttaaaat aaattgaaca ctccactaca ggattagctt   1260
aaacttctca taagtctgaa ccgttcatcc caaagaaaaa agaaaacgta tactttattt   1320
tattttagta ataatgagaa accaacaaag aagttcttgg ttcgaggcca ggctgtacta   1380
ggtgtgttct tcttttgttt ctttaactca ggacatgcat tcaagcgtta gatccttgta   1440
accagttaag gattaaccta aaaacaaccg accgacagga tcatgttccc acacaccgaa   1500
tagaatccaa gaaaagatat tttctgagta aaattgaaca aagacagcac cccagaaaca   1560
gagttagtgt aacagcacca cccccatgtt gtttttaagg tggtcatgga tgaaagtaca   1620
ggcgttagag agagaccctg gatcagaaca tggagtctga tccagtggtc acgagagaat   1680
gaacatgcaa agaaggaaga tcattctcac gtggaagtgg tgaacagagc accgaaacag   1740
aggagaggca gaacaacgat aaggaagaaa aaaaaacaac acaaacaaaa aaagaaatag   1800
aagagaaaaa caacagtact tacgaaaaca gaatgaacgc aaaaaagaga ggggggggtat   1860
aaagagaaga agtgaatgaa tggaaactga ggtggtggct aagtcaattt atagacagga   1920
gcgcgaagca gaattggaat ttcacagatg ggaaaaaaga aattaaataa aggaaatgga   1980
ttattttatt tttttaatta agagattcac caaatgtcaa aaaaaacttt tatctatctt   2040
ctttcttact ccaccgaggg tggttgagta aatgcacaag tataataaaa gaagtatatt   2100
cttagtgctg cttgaaaggt gaaatacaat atgcattctt tcagtgaata cattgtgcca   2160
catcagtttc tttttctttt ctggtatata tttatcttta tattattgta caatgaaaat   2220
gatatttcct gcagatgaat atttttattg tattattgta caataaaagt atgatctgta   2280
```

-continued

```
gagctggatc aaattttctg cagtgaaaat gatatttttc aaacaataat tataattttt   2340
tactaaataa gaatgtgact ttttccgtgc aacaagatct ctttattgga gaacagaaaa   2400
aaaatatttt aatatttatt taaaagttat tgcattaatt gaacatagtt gtaactgatt   2460
ataatattaa tattaaaatg ttttaagtgt tttatttatc atggaaaaat taatgtcatt   2520
ccacgttaaa gctttatcac ttattttagg gtcaatttga tgtcataaat attttgaaaa   2580
aattaattca tgtttcaaaa aactttgtgc ccaagaaatg cattgacaac attttctgtc   2640
aaacagatat aaatgtaaga atccatctta ttactgaaaa tcaaggaaat actactatta   2700
cattacacac ctaataaatg gatttctcga tgctcgatac gaaccattca ttaaaatcaa   2760
aagaaaaaaa aaatcagtag tactagtact acatgttact gaatcaccta tcttttttttt   2820
ttggtaatgg agaagtttaa ttattttagt gcttgatgct caaggaatta attaaaacga   2880
ctaatgataa ttttatcttg tggaccaaaa attatctgct tagacgtgaa gaaagcagac   2940
tatgttaatc atgagagaat gtatatgatc cctgaataaa tcgtgtatat atggagagtg   3000
ttgtatacat tttgttctat tcaaagaaag ttagaatgcc aaaactcttt atttcattca   3060
taacatgatt tgtggtaatc tcattaatat taatattagt atttcatttg gaaaatgaaa   3120
tttcaaaaat tatattcgaa aatgtcatta tattttacta taaaatgaaa tattatttat   3180
atatcgagca tgtacaaaaa atgaaacgtt gtgcttggat cacgtgagat tgtaatatag   3240
aactattgga attgcttctt ttttaaaaat taaaaaaaaa attaacaatg tctgtcgtgg   3300
catcaatggt gggtgcattg tgatgttcgt cacaagcaaa gactttttga tgttatattt   3360
atattaccaa ctaaacccca atgcctagtt attggagttt ggccccggct gttgctagtt   3420
tacttactac tatatagtag tagtgtgcag taccatatat atgtgtagat aatattataa   3480
gcagcactag aaaacaagag ctgtatatca ataattagac attggccgtg agagggacct   3540
tataaagaat atgctccaaa ttaaataggt tagataagta gtcagtgatg atgactatat   3600
gacaaattta ccccattcaa atattgaaaa taccaaagat ttgacgttgt aaataatatc   3660
tgtatttcta tttataaatt tcaacttgct catcttgaat ttgaaatacc ggaagccgga   3720
ggagaaaaca aagcaaaatg tgaagaagaa gtcaagcaaa ttaagggaag aggcagataa   3780
aaaaaaaagt gaaagcaaat aaacaaaact caatagaatg ggatgatgta gaaaatggga   3840
ttgagaagcc atttttatag tgtagtgaga agagattacc ataagaaatg tgttaaaaag   3900
aaaatggttt aaatggataa attcaccctt cactgtcctt cagctgcaat ttacctgcag   3960
gacgtacgga tccgtcgacg gcgcgcccga tcatccggat atagttcctc ctttcagcaa   4020
aaaacccctc aagacccgtt tagaggcccc aaggggttat gctagttatt gctcagcggt   4080
ggcagcagcc aactcagctt cctttcgggc tttgttagca gccggatcga tccaagctgt   4140
acctcactat tcctttgccc tcggacgagt gctggggcgt cggtttccac tatcggcgag   4200
tacttctaca cagccatcgg tccagacggc cgcgcttctg cgggcgattt gtgtacgccc   4260
gacagtcccg gctccggatc ggacgattgc gtcgcatcga ccctgcgccc aagctgcatc   4320
atcgaaattg ccgtcaacca agctctgata gagttggtca agaccaatgc ggagcatata   4380
cgcccggagc cgcggcgatc ctgcaagctc cggatgcctc cgctcgaagt agcgcgtctg   4440
ctgctccata caagccaacc acggcctcca gaagaagatg ttggcgacct cgtattggga   4500
atccccgaac atcgcctcgc tccagtcaat gaccgctgtt atgcggccat tgtccgtcag   4560
gacattgttg gagccgaaat ccgcgtgcac gaggtgccgg acttcggggc agtcctcggc   4620
```

```
ccaaagcatc agctcatcga gagcctgcgc gacggacgca ctgacggtgt cgtccatcac   4680
agtttgccag tgatacacat ggggatcagc aatcgcgcat atgaaatcac gccatgtagt   4740
gtattgaccg attccttgcg gtccgaatgg gccgaacccg ctcgtctggc taagatcggc   4800
cgcagcgatc gcatccatag cctccgcgac cggctgcaga acagcgggca gttcggtttc   4860
aggcaggtct tgcaacgtga caccctgtgc acggcgggag atgcaatagg tcaggctctc   4920
gctgaattcc ccaatgtcaa gcacttccgg aatcgggagc gcggccgatg caaagtgccg   4980
ataaacataa cgatctttgt agaaaccatc ggcgcagcta tttacccgca ggacatatcc   5040
acgccctcct acatcgaagc tgaaagcacg agattcttcg ccctccgaga gctgcatcag   5100
gtcggagacg ctgtcgaact tttcgatcag aaacttctcg acagacgtcg cggtgagttc   5160
aggcttttcc atgggtatat ctccttctta aagttaaaca aaattatttc tagagggaaa   5220
ccgttgtggt ctccctatag tgagtcgtat taatttcgcg ggatcgagat cgatccaatt   5280
ccaatcccac aaaaatctga gcttaacagc acagttgctc ctctcagagc agaatcgggt   5340
attcaacacc ctcatatcaa ctactacgtt gtgtataacg gtccacatgc cggtatatac   5400
gatgactggg gttgtacaaa ggcggcaaca aacggcgttc ccggagttgc acacaagaaa   5460
tttgccacta ttacagaggc aagagcagca gctgacgcgt acacaacaag tcagcaaaca   5520
gacaggttga acttcatccc caaaggagaa gctcaactca agcccaagag ctttgctaag   5580
gccctaacaa gcccaccaaa gcaaaaagcc cactggctca cgctaggaac caaaaggccc   5640
agcagtgatc cagccccaaa agagatctcc tttgccccgg agattacaat ggacgatttc   5700
ctctatcttt acgatctagg aaggaagttc gaaggtgaag gtgacgacac tatgttcacc   5760
actgataatg agaaggttag cctcttcaat ttcagaaaga atgctgaccc acagatggtt   5820
agagaggcct acgcagcagg tctcatcaag acgatctacc cgagtaacaa tctccaggag   5880
atcaaatacc ttcccaagaa ggttaaagat gcagtcaaaa gattcaggac taattgcatc   5940
aagaacacag agaaagacat atttctcaag atcagaagta ctattccagt atggacgatt   6000
caaggcttgc ttcataaacc aaggcaagta atagagattg gagtctctaa aaaggtagtt   6060
cctactgaat ctaaggccat gcatggagtc taagattcaa atcgaggatc taacagaact   6120
cgccgtgaag actggcgaac agttcataca gagtctttta cgactcaatg acaagaagaa   6180
aatcttcgtc aacatggtgg agcacgacac tctggtctac tccaaaaatg tcaaagatac   6240
agtctcagaa gaccaaaggg ctattgagac ttttcaacaa aggataattt cgggaaacct   6300
cctcggattc cattgcccag ctatctgtca cttcatcgaa aggacagtag aaaaggaagg   6360
tggctcctac aaatgccatc attgcgataa aggaaaggct atcattcaag atgcctctgc   6420
cgacagtggt cccaaagatg gacccccacc cacgaggagc atcgtggaaa aagaagacgt   6480
tccaaccacg tcttcaaagc aagtggattg atgtgacatc tccactgacg taagggatga   6540
cgcacaatcc cactatcctt cgcaagaccc ttcctctata taaggaagtt catttcattt   6600
ggagaggaca cgctcgagct catttctcta ttacttcagc cataacaaaa gaactctttt   6660
ctcttcttat taaaccatga aaaagcctga actcaccgcg acgtctgtcg agaagtttct   6720
gatcgaaaag ttcgacagcg tctccgacct gatgcagctc tcggagggcg aagaatctcg   6780
tgctttcagc ttcgatgtag gagggcgtgg atatgtcctg cgggtaaata gctgcgccga   6840
tggtttctac aaagatcgtt atgtttatcg gcactttgca tcggccgcgc tcccgattcc   6900
ggaagtgctt gacattgggg aattcagcga gagcctgacc tattgcatct cccgccgtgc   6960
acagggtgtc acgttgcaag acctgcctga aaccgaactg cccgctgttc tgcagccggt   7020
```

```
cgcggaggcc atggatgcga tcgctgcggc cgatcttagc cagacgagcg ggttcggccc   7080
attcggaccg caaggaatcg gtcaatacac tacatggcgt gatttcatat gcgcgattgc   7140
tgatccccat gtgtatcact ggcaaactgt gatggacgac accgtcagtg cgtccgtcgc   7200
gcaggctctc gatgagctga tgctttgggc cgaggactgc cccgaagtcc ggcacctcgt   7260
gcacgcggat ttcggctcca acaatgtcct gacggacaat ggccgcataa cagcggtcat   7320
tgactggagc gaggcgatgt tcggggattc ccaatacgag gtcgccaaca tcttcttctg   7380
gaggccgtgg ttggcttgta tggagcagca gacgcgctac ttcgagcgga ggcatccgga   7440
gcttgcagga tcgccgcggc tccgggcgta tatgctccgc attggtcttg accaactcta   7500
tcagagcttg gttgacggca atttcgatga tgcagcttgg gcgcagggtc gatgcgacgc   7560
aatcgtccga tccggagccg ggactgtcgg gcgtacacaa atcgcccgca gaagcgcggc   7620
cgtctggacc gatggctgtg tagaagtact cgccgatagt ggaaaccgac gccccagcac   7680
tcgtccgagg gcaaaggaat agtgaggtac ctaaagaagg agtgcgtcga agcagatcgt   7740
tcaaacattt ggcaataaag tttcttaaga ttgaatcctg ttgccggtct tgcgatgatt   7800
atcatataat ttctgttgaa ttacgttaag catgtaataa ttaacatgta atgcatgacg   7860
ttatttatga gatgggtttt tatgattaga gtcccgcaat tatacattta atacgcgata   7920
gaaaacaaaa tatagcgcgc aaactaggat aaattatcgc gcgcggtgtc atctatgtta   7980
ctagatcgat gtcgaatcga tcaacctgca ttaatgaatc ggccaacgcg cggggagagg   8040
cggtttgcgt attgggcgct cttccgcttc ctcgctcact gactcgctgc gctcggtcgt   8100
tcggctgcgg cgagcggtat cagctcactc aaaggcggta atacggttat ccacagaatc   8160
aggggataac gcaggaaaga acatgtgagc aaaaggccag caaaaggcca ggaaccgtaa   8220
aaaggccgcg ttgctggcgt ttttccatag gctccgcccc cctgacgagc atcacaaaaa   8280
tcgacgctca agtcagaggt ggcgaaaccc gacaggacta taaagatacc aggcgtttcc   8340
ccctggaagc tccctcgtgc gctctcctgt tccgaccctg ccgcttaccg gatacctgtc   8400
cgcctttctc ccttcgggaa gcgtggcgct ttctcaatgc tcacgctgta ggtatctcag   8460
ttcggtgtag gtcgttcgct ccaagctggg ctgtgtgcac gaaccccccg ttcagcccga   8520
ccgctgcgcc ttatccggta actatcgtct tgagtccaac ccggtaagac acgacttatc   8580
gccactggca gcagccactg gtaacaggat tagcagagcg aggtatgtag gcggtgctac   8640
agagttcttg aagtggtggc ctaactacgg ctacactaga aggacagtat ttggtatctg   8700
cgctctgctg aagccagtta ccttcggaaa aagagttggt agctcttgat ccggcaaaca   8760
aaccaccgct ggtagcggtg gtttttttgt ttgcaagcag cagattacgc gcagaaaaaa   8820
aggatctcaa gaagatcctt tgatcttttc tacggggtct gacgctcagt ggaacgaaaa   8880
ctcacgttaa gggattttgg tcatgacatt aacctataaa aataggcgta tcacgaggcc   8940
ctttcgtctc gcgcgtttcg gtgatgacgg tgaaaacctc tgacacatgc agctcccgga   9000
gacggtcaca gcttgtctgt aagcggatgc cgggagcaga caagcccgtc agggcgcgtc   9060
agcgggtgtt ggcgggtgtc ggggctggct taactatgcg gcatcagagc agattgtact   9120
gagagtgcac catatggaca tattgtcgtt agaacgcggc tacaattaat acataacctt   9180
atgtatcata cacatacgat ttaggtgaca ctatagaacg gcgcgccaag cttggatctc   9240
ctgcaggatc tggccggccg gatctc                                        9266
```

<210> SEQ ID NO 15

<211> LENGTH: 1768
<212> TYPE: DNA
<213> ORGANISM: Glycine max

<400> SEQUENCE: 15

```
gcacgagctc tcttataatc acacacacac ctaccttaat agctatggaa actggaggct     60

ttcacggcta ccgcaagctc cccaacacca ccgctgggtt gaagctgtca gtgtcagaca    120

tgaacatgag gcagcaggta gcatcatcag atcacagtgc agccacagga gaggagaacg    180

aatgcacggt gagggagcaa gacaggttca tgccaatcgc caacgtgatt aggatcatgc    240

gcaagattct ccctccacac gcaaaaatct cggacgatgc aaaagaaaca atccaagagt    300

gcgtgtctga gtacatcagc ttcatcacag gtgaggcgaa cgagcgttgc cagagggagc    360

agcggaagac cataaccgca gaggacgtgc tttgggccat gagcaagctt ggattcgacg    420

actacatcga accgttgacc atgtaccttc accgctaccg tgaacttgag ggtgaccgca    480

cctctatgag gggtgaacca ctcgggaaga ggactgtgga atacgccacg cttggtgttg    540

ctactgcttt tgtccctcca ccctatcatc accacaatgg gtactttggt gctgccatgc    600

ccatggggac ttacgttagg gaagcgccac caaatacagc ctcctcccat caccaccacc    660

accaccacca ccaccatgct cgtggaatct ccaatgctca tgaaccaaat gctcgctcca    720

tataaaatta tataattatg actaggattc agaacaagac ttgatgatga ttagcttaac    780

tctcagtaat tggtgctaga gtactactgt tgttgaggat actttatttt ataattaagg    840

gctgggaagg gagttagtat attcctaatc ctaactatgt gcatctttaa tttatgaaat    900

cactttgttt taacctttga tgaaaaaaaa aaaaaaaaaa aactcgagac tagttctccg    960

tttctcgcca aacaaacaca aaatggctgc cttcagcggc gacgaaaccg cacctttctt   1020

tggcttcctc ggagccgccg ctgccctcgt tttttcctgt atgggagcgg cgtacggaac   1080

cgcgaagagc ggcgtcgggg ttgcgtcgat gggcgtgatg aggccggagc tggtgatgaa   1140

atcgatcgtg ccggttgtga tggctggtgt gttgggtatc tacggtttga tcattgcggt   1200

tatcataagt acgggcatta accctaaggc caaatcgtac tatctttttg acggctacgc   1260

ccacctctct tcaggtctcg cttgtggcct cgctggcctc tccgctggca tggccatcgg   1320

catcgttggc gatgccggtg ttagagcaaa tgctcagcag ccaaagcttt ttgttggaat   1380

gatactcatc ctcatttttg ctgaggcgtt ggcattatac ggtctcattg ttggcatcat   1440

cctctcttct cgtgctggcc aatccagggc tgactaataa attttcctgt tggatgccac   1500

agattgtgaa tgttactgtg aagtccgggt gggtaatgtt agtacacagc tgccgctttg   1560

gcttgctcaa gtgattctat ttatgtttac attataaaat tgaggctatc caggaagaaa   1620

gtcagtcgaa ctttccttag cccttcatta tttttagtta tatgctcaat ccagactaga   1680

atagagatct ccataataag acagatgtat gttttgattc catttacttt caatattgtt   1740

ttccactctt caaaaaaaaa aaaaaaaa                                       1768
```

<210> SEQ ID NO 16
<211> LENGTH: 681
<212> TYPE: PRT
<213> ORGANISM: Glycine max

<400> SEQUENCE: 16

```
Ala Thr Gly Gly Ala Ala Ala Cys Thr Gly Gly Ala Gly Gly Cys Thr
1               5                   10                  15

Thr Thr Cys Ala Cys Gly Gly Cys Thr Ala Cys Cys Gly Cys Ala Ala
            20                  25                  30
```

```
Gly Cys Thr Cys Cys Cys Cys Ala Ala Cys Ala Cys Cys Ala Cys Cys
        35                  40                  45

Gly Cys Thr Gly Gly Gly Thr Thr Gly Ala Ala Gly Cys Thr Gly Thr
    50                  55                  60

Cys Ala Gly Thr Gly Thr Cys Ala Gly Ala Cys Ala Thr Gly Ala Ala
65                  70                  75                  80

Cys Ala Thr Gly Ala Gly Gly Cys Ala Gly Cys Ala Gly Gly Thr Ala
                85                  90                  95

Gly Cys Ala Thr Cys Ala Thr Cys Ala Gly Ala Thr Cys Ala Cys Ala
            100                 105                 110

Gly Thr Gly Cys Ala Gly Cys Cys Ala Cys Ala Gly Gly Ala Gly Ala
        115                 120                 125

Gly Gly Ala Gly Ala Ala Cys Gly Ala Ala Thr Gly Cys Ala Cys Gly
    130                 135                 140

Gly Thr Gly Ala Gly Gly Gly Ala Gly Cys Ala Ala Gly Ala Cys Ala
145                 150                 155                 160

Gly Gly Thr Thr Cys Ala Thr Gly Cys Cys Ala Ala Thr Cys Gly Cys
                165                 170                 175

Cys Ala Ala Cys Gly Thr Gly Ala Thr Thr Ala Gly Gly Ala Thr Cys
            180                 185                 190

Ala Thr Gly Cys Gly Cys Ala Ala Gly Ala Thr Thr Cys Thr Cys Cys
        195                 200                 205

Cys Thr Cys Cys Ala Cys Ala Cys Gly Cys Ala Ala Ala Ala Ala Thr
    210                 215                 220

Cys Thr Cys Gly Gly Ala Cys Gly Ala Thr Gly Cys Ala Ala Ala Ala
225                 230                 235                 240

Gly Ala Ala Ala Cys Ala Ala Thr Cys Cys Ala Ala Gly Ala Gly Thr
                245                 250                 255

Gly Cys Gly Thr Gly Thr Cys Thr Gly Ala Gly Thr Ala Cys Ala Thr
            260                 265                 270

Cys Ala Gly Cys Thr Thr Cys Ala Thr Cys Ala Cys Ala Gly Gly Thr
        275                 280                 285

Gly Ala Gly Gly Cys Gly Ala Ala Cys Gly Ala Gly Cys Gly Thr Thr
    290                 295                 300

Gly Cys Cys Ala Gly Ala Gly Gly Gly Ala Gly Cys Ala Gly Cys Gly
305                 310                 315                 320

Gly Ala Ala Gly Ala Cys Cys Ala Thr Ala Ala Cys Cys Gly Cys Ala
                325                 330                 335

Gly Ala Gly Gly Ala Cys Gly Thr Gly Cys Thr Thr Thr Gly Gly Gly
            340                 345                 350

Cys Cys Ala Thr Gly Ala Gly Cys Ala Ala Gly Cys Thr Thr Gly Gly
        355                 360                 365

Ala Thr Thr Cys Gly Ala Cys Gly Ala Cys Thr Ala Cys Ala Thr Cys
    370                 375                 380

Gly Ala Ala Cys Cys Gly Thr Thr Gly Ala Cys Cys Ala Thr Gly Thr
385                 390                 395                 400

Ala Cys Cys Thr Thr Cys Ala Cys Cys Gly Cys Thr Ala Cys Cys Gly
                405                 410                 415

Thr Gly Ala Ala Cys Thr Thr Gly Ala Gly Gly Gly Thr Gly Ala Cys
            420                 425                 430

Cys Gly Cys Ala Cys Cys Thr Cys Thr Ala Thr Gly Ala Gly Gly Gly
        435                 440                 445
```

```
Gly Thr Gly Ala Ala Cys Cys Ala Cys Thr Cys Gly Gly Gly Ala Ala
    450                 455                 460

Gly Ala Gly Gly Ala Cys Thr Gly Thr Gly Gly Ala Ala Thr Ala Cys
465                 470                 475                 480

Gly Cys Cys Ala Cys Gly Cys Thr Thr Gly Gly Thr Gly Thr Thr Gly
                485                 490                 495

Cys Thr Ala Cys Thr Gly Cys Thr Thr Thr Thr Gly Thr Cys Cys Cys
            500                 505                 510

Thr Cys Cys Ala Cys Cys Cys Thr Ala Thr Cys Ala Thr Cys Ala Cys
        515                 520                 525

Cys Ala Cys Ala Ala Thr Gly Gly Gly Thr Ala Cys Thr Thr Thr Gly
    530                 535                 540

Gly Thr Gly Cys Thr Gly Cys Cys Ala Thr Gly Cys Cys Cys Ala Thr
545                 550                 555                 560

Gly Gly Gly Gly Ala Cys Thr Thr Ala Cys Gly Thr Thr Ala Gly Gly
                565                 570                 575

Gly Ala Ala Gly Cys Gly Cys Cys Ala Cys Cys Ala Ala Ala Thr Ala
            580                 585                 590

Cys Ala Gly Cys Cys Thr Cys Cys Thr Cys Cys Cys Ala Thr Cys Ala
        595                 600                 605

Cys Cys Ala Cys Cys Ala Cys Cys Ala Cys Cys Ala Cys Cys Ala Cys
    610                 615                 620

Cys Ala Cys Cys Ala Cys Cys Ala Thr Gly Cys Thr Cys Gly Thr Gly
625                 630                 635                 640

Gly Ala Ala Thr Cys Thr Cys Cys Ala Ala Thr Gly Cys Thr Cys Ala
                645                 650                 655

Thr Gly Ala Ala Cys Cys Ala Ala Ala Thr Gly Cys Thr Cys Gly Cys
            660                 665                 670

Thr Cys Cys Ala Thr Ala Thr Ala Ala
        675                 680
```

<210> SEQ ID NO 17
<211> LENGTH: 226
<212> TYPE: PRT
<213> ORGANISM: Glycine max

<400> SEQUENCE: 17

```
Met Glu Thr Gly Gly Phe His Gly Tyr Arg Lys Leu Pro Asn Thr Thr
1               5                   10                  15

Ala Gly Leu Lys Leu Ser Val Ser Asp Met Asn Met Arg Gln Gln Val
            20                  25                  30

Ala Ser Ser Asp His Ser Ala Ala Thr Gly Glu Glu Asn Glu Cys Thr
        35                  40                  45

Val Arg Glu Gln Asp Arg Phe Met Pro Ile Ala Asn Val Ile Arg Ile
    50                  55                  60

Met Arg Lys Ile Leu Pro Pro His Ala Lys Ile Ser Asp Asp Ala Lys
65                  70                  75                  80

Glu Thr Ile Gln Glu Cys Val Ser Glu Tyr Ile Ser Phe Ile Thr Gly
                85                  90                  95

Glu Ala Asn Glu Arg Cys Gln Arg Glu Gln Arg Lys Thr Ile Thr Ala
            100                 105                 110

Glu Asp Val Leu Trp Ala Met Ser Lys Leu Gly Phe Asp Asp Tyr Ile
        115                 120                 125

Glu Pro Leu Thr Met Tyr Leu His Arg Tyr Arg Glu Leu Glu Gly Asp
    130                 135                 140
```

-continued

Arg Thr Ser Met Arg Gly Glu Pro Leu Gly Lys Arg Thr Val Glu Tyr
145 150 155 160

Ala Thr Leu Gly Val Ala Thr Ala Phe Val Pro Pro Pro Tyr His His
165 170 175

His Asn Gly Tyr Phe Gly Ala Ala Met Pro Met Gly Thr Tyr Val Arg
180 185 190

Glu Ala Pro Pro Asn Thr Ala Ser Ser His His His His His His His
195 200 205

His His His Ala Arg Gly Ile Ser Asn Ala His Glu Pro Asn Ala Arg
210 215 220

Ser Ile
225

<210> SEQ ID NO 18
<211> LENGTH: 1115
<212> TYPE: PRT
<213> ORGANISM: Glycine max

<400> SEQUENCE: 18

Gly Gly Ala Ala Ala Cys Thr Gly Gly Ala Gly Gly Cys Thr Thr Thr
1 5 10 15

Cys Ala Thr Gly Gly Cys Thr Ala Cys Cys Gly Cys Ala Ala Gly Cys
20 25 30

Thr Cys Cys Cys Cys Ala Ala Cys Ala Cys Ala Ala Cys Cys Thr Cys
35 40 45

Thr Gly Gly Gly Thr Thr Gly Ala Ala Gly Cys Thr Gly Thr Cys Ala
50 55 60

Gly Thr Gly Thr Cys Ala Gly Ala Cys Ala Thr Gly Ala Ala Cys Ala
65 70 75 80

Thr Gly Ala Ala Cys Ala Thr Gly Ala Gly Gly Cys Ala Gly Cys Ala
85 90 95

Gly Cys Ala Gly Gly Thr Ala Gly Cys Ala Thr Cys Ala Thr Cys Ala
100 105 110

Gly Ala Thr Cys Ala Gly Ala Ala Cys Thr Gly Cys Ala Gly Cys Ala
115 120 125

Ala Cys Cys Ala Cys Ala Gly Thr Gly Cys Ala Gly Cys Ala Gly Gly
130 135 140

Ala Gly Ala Gly Gly Ala Gly Ala Ala Cys Gly Ala Ala Thr Gly Cys
145 150 155 160

Ala Cys Gly Gly Thr Gly Ala Gly Gly Gly Ala Gly Cys Ala Ala Gly
165 170 175

Ala Cys Ala Gly Gly Thr Thr Cys Ala Thr Gly Cys Cys Ala Ala Thr
180 185 190

Cys Gly Cys Thr Ala Ala Cys Gly Thr Gly Ala Thr Ala Cys Gly Gly
195 200 205

Ala Thr Cys Ala Thr Gly Cys Gly Cys Ala Ala Gly Ala Thr Thr Cys
210 215 220

Thr Cys Cys Cys Thr Cys Cys Ala Cys Ala Cys Gly Cys Ala Ala Ala
225 230 235 240

Ala Ala Thr Cys Thr Cys Cys Gly Ala Thr Gly Ala Thr Gly Cys Ala
245 250 255

Ala Ala Gly Gly Ala Gly Ala Cys Ala Ala Thr Cys Cys Ala Ala Gly
260 265 270

Ala Gly Thr Gly Cys Gly Thr Gly Thr Cys Gly Gly Ala Gly Thr Ala

-continued

```
        275                 280                 285

Cys Ala Thr Cys Ala Gly Cys Thr Thr Cys Ala Thr Cys Ala Cys Cys
    290                 295                 300

Gly Gly Gly Gly Ala Gly Gly Cys Cys Ala Ala Cys Gly Ala Gly Cys
305                 310                 315                 320

Gly Thr Thr Gly Cys Cys Ala Gly Ala Gly Gly Gly Ala Gly Cys Ala
                325                 330                 335

Gly Cys Gly Cys Ala Ala Gly Ala Cys Cys Ala Thr Ala Ala Cys Cys
            340                 345                 350

Gly Cys Ala Gly Ala Gly Gly Ala Cys Gly Thr Gly Cys Thr Thr Thr
        355                 360                 365

Gly Gly Gly Cys Ala Ala Thr Gly Ala Gly Thr Ala Ala Gly Cys Thr
    370                 375                 380

Thr Gly Gly Ala Thr Thr Cys Gly Ala Cys Gly Ala Cys Thr Ala Cys
385                 390                 395                 400

Ala Thr Cys Gly Ala Ala Cys Cys Gly Thr Thr Ala Ala Cys Cys Ala
                405                 410                 415

Thr Gly Thr Ala Cys Cys Thr Thr Cys Ala Cys Cys Gly Cys Thr Ala
            420                 425                 430

Cys Cys Gly Thr Gly Ala Gly Cys Thr Gly Gly Ala Gly Gly Gly Thr
        435                 440                 445

Gly Ala Cys Cys Gly Cys Ala Cys Cys Thr Cys Thr Ala Thr Gly Ala
    450                 455                 460

Gly Gly Gly Gly Thr Gly Ala Ala Cys Cys Gly Cys Thr Cys Gly Gly
465                 470                 475                 480

Gly Ala Ala Gly Ala Gly Gly Ala Cys Thr Gly Thr Gly Gly Ala Ala
                485                 490                 495

Thr Ala Thr Gly Cys Cys Ala Cys Gly Cys Thr Thr Gly Cys Thr Ala
            500                 505                 510

Cys Thr Gly Cys Thr Thr Thr Thr Gly Thr Gly Cys Cys Gly Cys Cys
        515                 520                 525

Ala Cys Cys Cys Thr Thr Thr Cys Ala Thr Cys Ala Cys Cys Ala Cys
    530                 535                 540

Ala Ala Thr Gly Gly Cys Thr Ala Cys Thr Thr Thr Gly Gly Thr Gly
545                 550                 555                 560

Cys Thr Gly Cys Cys Ala Thr Gly Cys Cys Ala Thr Gly Gly Gly
                565                 570                 575

Gly Ala Cys Thr Thr Ala Cys Gly Thr Thr Ala Gly Gly Gly Ala Ala
            580                 585                 590

Ala Cys Gly Cys Cys Ala Cys Cys Ala Ala Ala Thr Gly Cys Thr Gly
        595                 600                 605

Cys Gly Thr Cys Ala Thr Cys Thr Cys Ala Thr Cys Ala Cys Cys Ala
    610                 615                 620

Thr Cys Ala Thr Gly Gly Ala Ala Thr Cys Thr Cys Cys Ala Ala Thr
625                 630                 635                 640

Gly Cys Thr Cys Ala Thr Gly Ala Ala Cys Cys Ala Ala Ala Thr Gly
                645                 650                 655

Cys Thr Cys Gly Cys Thr Cys Cys Ala Thr Ala Thr Ala Ala Ala Ala
            660                 665                 670

Thr Thr Ala Ala Thr Gly Ala Ala Gly Ala Gly Thr Ala Cys Thr Gly
        675                 680                 685

Thr Thr Cys Ala Gly Thr Ala Gly Gly Ala Gly Ala Ala Cys Ala Ala
    690                 695                 700
```

Gly Ala Cys Thr Thr Cys Thr Thr Gly Gly Ala Cys Thr Thr Gly Ala
705 710 715 720

Thr Thr Ala Gly Cys Thr Thr Ala Ala Cys Thr Cys Thr Cys Ala Gly
725 730 735

Thr Gly Ala Thr Thr Gly Gly Thr Gly Thr Thr Ala Gly Ala Gly Thr
740 745 750

Ala Cys Thr Gly Thr Thr Gly Thr Thr Gly Ala Gly Gly Ala Thr Gly
755 760 765

Gly Thr Thr Ala Ala Thr Thr Thr Thr Ala Thr Ala Ala Thr Thr Ala
770 775 780

Ala Gly Gly Gly Cys Thr Gly Gly Gly Ala Ala Thr Thr Gly Gly Gly
785 790 795 800

Gly Ala Gly Thr Thr Ala Gly Thr Ala Thr Ala Thr Ala Thr Thr Cys
805 810 815

Cys Thr Ala Ala Thr Cys Cys Thr Ala Ala Thr Thr Ala Thr Gly Thr
820 825 830

Gly Cys Ala Thr Cys Thr Thr Thr Ala Ala Thr Thr Thr Ala Thr Gly
835 840 845

Gly Ala Ala Thr Ala Ala Cys Thr Thr Thr Gly Thr Thr Thr Thr Thr
850 855 860

Thr Gly Thr Thr Thr Thr Ala Ala Cys Thr Thr Cys Thr Gly Ala Thr
865 870 875 880

Ala Ala Thr Thr Thr Gly Gly Ala Thr Thr Thr Thr Cys Thr Gly Ala
885 890 895

Thr Gly Thr Thr Thr Ala Ala Thr Gly Thr Gly Gly Thr Thr Thr Thr
900 905 910

Gly Thr Cys Thr Ala Thr Cys Cys Cys Thr Thr Ala Thr Thr Ala Ala
915 920 925

Cys Ala Gly Thr Gly Cys Cys Ala Ala Gly Cys Thr Thr Ala Ala Gly
930 935 940

Gly Thr Thr Thr Thr Ala Gly Cys Cys Ala Thr Gly Cys Thr Cys Cys
945 950 955 960

Ala Ala Ala Ala Thr Gly Gly Ala Ala Thr Ala Cys Thr Thr Gly Thr
965 970 975

Ala Cys Thr Gly Thr Thr Ala Thr Gly Thr Thr Gly Thr Thr Cys Thr
980 985 990

Gly Gly Thr Ala Gly Thr Gly Ala Thr Gly Gly Thr Gly Ala Thr Gly
995 1000 1005

Ala Ala Ala Cys Cys Thr Gly Cys Ala Ala Gly Thr Thr Ala Thr
1010 1015 1020

Gly Thr Thr Thr Ala Thr Gly Thr Ala Thr Ala Ala Ala Gly Cys
1025 1030 1035

Cys Ala Cys Thr Ala Thr Thr Gly Ala Thr Cys Ala Ala Ala Ala
1040 1045 1050

Thr Thr Ala Gly Ala Gly Ala Ala Ala Thr Thr Ala Thr Cys Ala
1055 1060 1065

Thr Thr Thr Ala Ala Thr Ala Ala Gly Thr Ala Thr Cys Cys Thr
1070 1075 1080

Cys Cys Cys Ala Thr Gly Thr Thr Ala Ala Thr Thr Thr Thr Ala
1085 1090 1095

Ala Ala Ala Ala Ala Ala Ala Ala Ala Ala Ala Ala Ala Ala Ala
1100 1105 1110

Ala Ala
    1115

<210> SEQ ID NO 19
<211> LENGTH: 672
<212> TYPE: PRT
<213> ORGANISM: Glycine max

<400> SEQUENCE: 19

```
Ala Thr Gly Gly Ala Ala Ala Cys Thr Gly Gly Ala Gly Gly Cys Thr
1               5                   10                  15

Thr Thr Cys Ala Thr Gly Gly Cys Thr Ala Cys Cys Gly Cys Ala Ala
            20                  25                  30

Gly Cys Thr Cys Cys Cys Cys Ala Ala Cys Ala Cys Ala Ala Cys Cys
        35                  40                  45

Thr Cys Thr Gly Gly Gly Thr Thr Gly Ala Ala Gly Cys Thr Gly Thr
    50                  55                  60

Cys Ala Gly Thr Gly Thr Cys Ala Gly Ala Cys Ala Thr Gly Ala Ala
65                  70                  75                  80

Cys Ala Thr Gly Ala Ala Cys Ala Thr Gly Ala Gly Gly Cys Ala Gly
                85                  90                  95

Cys Ala Gly Cys Ala Gly Gly Thr Ala Gly Cys Ala Thr Cys Ala Thr
            100                 105                 110

Cys Ala Gly Ala Thr Cys Ala Gly Ala Ala Cys Thr Gly Cys Ala Gly
        115                 120                 125

Cys Ala Ala Cys Cys Ala Cys Ala Gly Thr Gly Cys Ala Gly Cys Ala
    130                 135                 140

Gly Gly Ala Gly Ala Gly Gly Ala Gly Ala Ala Cys Gly Ala Ala Thr
145                 150                 155                 160

Gly Cys Ala Cys Gly Gly Thr Gly Ala Gly Gly Gly Ala Gly Cys Ala
                165                 170                 175

Ala Gly Ala Cys Ala Gly Gly Thr Thr Cys Ala Thr Gly Cys Cys Ala
            180                 185                 190

Ala Thr Cys Gly Cys Thr Ala Ala Cys Gly Thr Gly Ala Thr Ala Cys
        195                 200                 205

Gly Gly Ala Thr Cys Ala Thr Gly Cys Gly Cys Ala Ala Gly Ala Thr
    210                 215                 220

Thr Cys Thr Cys Cys Cys Thr Cys Cys Ala Cys Ala Cys Gly Cys Ala
225                 230                 235                 240

Ala Ala Ala Ala Thr Cys Thr Cys Cys Gly Ala Thr Gly Ala Thr Gly
                245                 250                 255

Cys Ala Ala Ala Gly Gly Ala Gly Ala Cys Ala Ala Thr Cys Cys Ala
            260                 265                 270

Ala Gly Ala Gly Thr Gly Cys Gly Thr Gly Thr Cys Gly Gly Ala Gly
        275                 280                 285

Thr Ala Cys Ala Thr Cys Ala Gly Cys Thr Thr Cys Ala Thr Cys Ala
    290                 295                 300

Cys Cys Gly Gly Gly Gly Ala Gly Gly Cys Cys Ala Ala Cys Gly Ala
305                 310                 315                 320

Gly Cys Gly Thr Thr Gly Cys Cys Ala Gly Ala Gly Gly Gly Ala Gly
                325                 330                 335

Cys Ala Gly Cys Gly Cys Ala Ala Gly Ala Cys Cys Ala Thr Ala Ala
            340                 345                 350

Cys Cys Gly Cys Ala Gly Ala Gly Gly Ala Cys Gly Thr Gly Cys Thr
        355                 360                 365
```

```
Thr Thr Gly Gly Gly Cys Ala Ala Thr Gly Ala Gly Thr Ala Ala Gly
    370                 375                 380

Cys Thr Thr Gly Gly Ala Thr Thr Cys Gly Ala Cys Gly Ala Cys Thr
385                 390                 395                 400

Ala Cys Ala Thr Cys Gly Ala Ala Cys Cys Gly Thr Thr Ala Ala Cys
                405                 410                 415

Cys Ala Thr Gly Thr Ala Cys Cys Thr Thr Cys Ala Cys Cys Gly Cys
            420                 425                 430

Thr Ala Cys Cys Gly Thr Gly Ala Gly Cys Thr Gly Gly Ala Gly Gly
        435                 440                 445

Gly Thr Gly Ala Cys Cys Gly Cys Ala Cys Cys Thr Cys Thr Ala Thr
    450                 455                 460

Gly Ala Gly Gly Gly Gly Thr Gly Ala Ala Cys Cys Gly Cys Thr Cys
465                 470                 475                 480

Gly Gly Gly Ala Ala Gly Ala Gly Gly Ala Cys Thr Gly Thr Gly Gly
                485                 490                 495

Ala Ala Thr Ala Thr Gly Cys Cys Ala Cys Gly Cys Thr Thr Gly Cys
            500                 505                 510

Thr Ala Cys Thr Gly Cys Thr Thr Thr Thr Gly Thr Gly Cys Cys Gly
        515                 520                 525

Cys Cys Ala Cys Cys Cys Thr Thr Thr Cys Ala Thr Cys Ala Cys Cys
    530                 535                 540

Ala Cys Ala Ala Thr Gly Gly Cys Thr Ala Cys Thr Thr Thr Gly Gly
545                 550                 555                 560

Thr Gly Cys Thr Gly Cys Cys Ala Thr Gly Cys Cys Cys Ala Thr Gly
                565                 570                 575

Gly Gly Gly Ala Cys Thr Thr Ala Cys Gly Thr Thr Ala Gly Gly Gly
            580                 585                 590

Ala Ala Ala Cys Gly Cys Cys Ala Cys Cys Ala Ala Ala Thr Gly Cys
        595                 600                 605

Thr Gly Cys Gly Thr Cys Ala Thr Cys Thr Cys Ala Thr Cys Ala Cys
    610                 615                 620

Cys Ala Thr Cys Ala Thr Gly Gly Ala Ala Thr Cys Thr Cys Cys Ala
625                 630                 635                 640

Ala Thr Gly Cys Thr Cys Ala Thr Gly Ala Ala Cys Cys Ala Ala Ala
                645                 650                 655

Thr Gly Cys Thr Cys Gly Cys Thr Cys Cys Ala Thr Ala Thr Ala Ala
            660                 665                 670
```

<210> SEQ ID NO 20
<211> LENGTH: 223
<212> TYPE: PRT
<213> ORGANISM: Glycine max

<400> SEQUENCE: 20

```
Met Glu Thr Gly Gly Phe His Gly Tyr Arg Lys Leu Pro Asn Thr Thr
1               5                   10                  15

Ser Gly Leu Lys Leu Ser Val Ser Asp Met Asn Met Asn Met Arg Gln
            20                  25                  30

Gln Gln Val Ala Ser Ser Asp Gln Asn Cys Ser Asn His Ser Ala Ala
        35                  40                  45

Gly Glu Glu Asn Glu Cys Thr Val Arg Glu Gln Asp Arg Phe Met Pro
    50                  55                  60

Ile Ala Asn Val Ile Arg Ile Met Arg Lys Ile Leu Pro Pro His Ala
```

-continued

```
65                  70                  75                  80

Lys Ile Ser Asp Asp Ala Lys Glu Thr Ile Gln Glu Cys Val Ser Glu
                85                  90                  95

Tyr Ile Ser Phe Ile Thr Gly Glu Ala Asn Glu Arg Cys Gln Arg Glu
            100                 105                 110

Gln Arg Lys Thr Ile Thr Ala Glu Asp Val Leu Trp Ala Met Ser Lys
        115                 120                 125

Leu Gly Phe Asp Asp Tyr Ile Glu Pro Leu Thr Met Tyr Leu His Arg
    130                 135                 140

Tyr Arg Glu Leu Glu Gly Asp Arg Thr Ser Met Arg Gly Glu Pro Leu
145                 150                 155                 160

Gly Lys Arg Thr Val Glu Tyr Ala Thr Leu Ala Thr Ala Phe Val Pro
                165                 170                 175

Pro Pro Phe His His His Asn Gly Tyr Phe Gly Ala Ala Met Pro Met
            180                 185                 190

Gly Thr Tyr Val Arg Glu Thr Pro Pro Asn Ala Ala Ser Ser His His
        195                 200                 205

His His Gly Ile Ser Asn Ala His Glu Pro Asn Ala Arg Ser Ile
    210                 215                 220


<210> SEQ ID NO 21
<211> LENGTH: 24
<212> TYPE: DNA
<213> ORGANISM: artificial sequence
<220> FEATURE:
<223> OTHER INFORMATION: primer sequence

<400> SEQUENCE: 21

atggaaactg gaggctttca cggc                                            24


<210> SEQ ID NO 22
<211> LENGTH: 24
<212> TYPE: DNA
<213> ORGANISM: artificial sequence
<220> FEATURE:
<223> OTHER INFORMATION: primer sequence

<400> SEQUENCE: 22

ttatatggag cgagcatttg gttc                                            24


<210> SEQ ID NO 23
<211> LENGTH: 3519
<212> TYPE: DNA
<213> ORGANISM: artificial sequence
<220> FEATURE:
<223> OTHER INFORMATION: plasmid sequence

<400> SEQUENCE: 23

aagggcgaat tcgacccagc tttcttgtac aaagttggca ttataaaaaa taattgctca      60

tcaatttgtt gcaacgaaca ggtcactatc agtcaaaata aaatcattat ttgccatcca     120

gctgatatcc cctatagtga gtcgtattac atggtcatag ctgtttcctg gcagctctgg     180

cccgtgtctc aaaatctctg atgttacatt gcacaagata aaaatatatc atcatgcctc     240

ctctagacca gccaggacag aaatgcctcg acttcgctgc tgcccaaggt tgccgggtga     300

cgcacaccgt ggaaacggat gaaggcacga acccagtgga cataagcctg ttcggttcgt     360

aagctgtaat gcaagtagcg tatgcgctca cgcaactggt ccagaacctt gaccgaacgc     420

agcggtggta acggcgcagt ggcggttttc atggcttgtt atgactgttt ttttggggta     480
```

```
cagtctatgc ctcgggcatc caagcagcaa gcgcgttacg ccgtgggtcg atgtttgatg    540
ttatggagca gcaacgatgt tacgcagcag ggcagtcgcc ctaaaacaaa gttaaacatc    600
atgagggaag cggtgatcgc cgaagtatcg actcaactat cagaggtagt tggcgtcatc    660
gagcgccatc tcgaaccgac gttgctggcc gtacatttgt acggctccgc agtggatggc    720
ggcctgaagc cacacagtga tattgatttg ctggttacgg tgaccgtaag gcttgatgaa    780
acaacgcggc gagctttgat caacgacctt ttggaaactt cggcttcccc tggagagagc    840
gagattctcc gcgctgtaga agtcaccatt gttgtgcacg acgacatcat tccgtggcgt    900
tatccagcta agcgcgaact gcaatttgga gaatggcagc gcaatgacat tcttgcaggt    960
atcttcgagc cagccacgat cgacattgat ctggctatct tgctgacaaa agcaagagaa   1020
catagcgttg ccttggtagg tccagcggcg gaggaactct ttgatccggt tcctgaacag   1080
gatctatttg aggcgctaaa tgaaacctta acgctatgga actcgccgcc cgactgggct   1140
ggcgatgagc gaaatgtagt gcttacgttg tcccgcattt ggtacagcgc agtaaccggc   1200
aaaatcgcgc cgaaggatgt cgctgccgac tgggcaatgg agcgcctgcc ggcccagtat   1260
cagcccgtca tacttgaagc tagacaggct tatcttggac aagaagaaga tcgcttggcc   1320
tcgcgcgcag atcagttgga agaatttgtc cactacgtga aaggcgagat caccaaggta   1380
gtcggcaaat aaccctcgag ccacccatga ccaaaatccc ttaacgtgag ttacgcgtcg   1440
ttccactgag cgtcagaccc cgtagaaaag atcaaaggat cttcttgaga tccttttttt   1500
ctgcgcgtaa tctgctgctt gcaaacaaaa aaaccaccgc taccagcggt ggtttgtttg   1560
ccggatcaag agctaccaac tctttttccg aaggtaactg gcttcagcag agcgcagata   1620
ccaaatactg tccttctagt gtagccgtag ttaggccacc acttcaagaa ctctgtagca   1680
ccgcctacat acctcgctct gctaatcctg ttaccagtgg ctgctgccag tggcgataag   1740
tcgtgtctta ccgggttgga ctcaagacga tagttaccgg ataaggcgca gcggtcgggc   1800
tgaacggggg gttcgtgcac acagcccagc ttggagcgaa cgacctacac cgaactgaga   1860
tacctacagc gtgagcattg agaaagcgcc acgcttcccg aagggagaaa ggcggacagg   1920
tatccggtaa gcggcagggt cggaacagga gagcgcacga gggagcttcc agggggaaac   1980
gcctggtatc tttatagtcc tgtcgggttt cgccacctct gacttgagcg tcgatttttg   2040
tgatgctcgt caggggggcg gagcctatgg aaaaacgcca gcaacgcggc ctttttacgg   2100
ttcctggcct tttgctggcc ttttgctcac atgttctttc ctgcgttatc ccctgattct   2160
gtggataacc gtattaccgc ctttgagtga gctgataccg ctcgccgcag ccgaacgacc   2220
gagcgcagcg agtcagtgag cgaggaagcg gaagagcgcc caatacgcaa accgcctctc   2280
cccgcgcgtt ggccgattca ttaatgcagc tggcacgaca ggtttcccga ctggaaagcg   2340
ggcagtgagc gcaacgcaat taatacgcgt accgctagcc aggaagagtt tgtagaaacg   2400
caaaaaggcc atccgtcagg atggccttct gcttagtttg atgcctggca gtttatggcg   2460
ggcgtcctgc ccgccaccct ccgggccgtt gcttcacaac gttcaaatcc gctcccggcg   2520
gatttgtcct actcaggaga gcgttcaccg acaaacaaca gataaaacga aaggcccagt   2580
cttccgactg agcctttcgt tttatttgat gcctggcagt tccctactct cgcgttaacg   2640
ctagcatgga tgttttccca gtcacgacgt tgtaaaacga cggccagtct taagctcggg   2700
ccccaaataa tgattttatt ttgactgata gtgacctgtt cgttgcaaca aattgatgag   2760
caatgctttt ttataatgcc aactttgtac aaaaaagcag gctccgaatt cgcccttatg   2820
gaaactggag gctttcacgg ctaccgcaag ctccccaaca ccaccgctgg gttgaagctg   2880
```

-continued

```
tcagtgtcag acatgaacat gaacatgagg cagcagcagg tagcatcatc agatcagaac   2940

tgcagcaacc acagtgcagc aggagaggag aacgaatgca cggtgaggga gcaagacagg   3000

ttcatgccaa tcgctaacgt gatacggatc atgcgcaaga ttctccctcc acacgcaaaa   3060

atctccgatg atgcaaagga gacaatccaa gagtgcgtgt cggagtacat cagcttcatc   3120

accggggagg cgaacgagcg ttgccagagg gagcaacgga agaccataac cgcagaggac   3180

gtgctttggg ccatgagcaa gcttggattc gacgactaca tcgaaccgtt gaccatgtac   3240

cttcaccgct accgtgaact tgagggtgac cgcacctcta tgaggggtga accactcggg   3300

aagaggactg tggaatacgc cacgcttggt gttgctactg cttttgtccc tccaccctat   3360

catcaccaca atgggtactt tggtgctgcc atgcccatgg ggacttacgt tagggaagcg   3420

ccaccaaata cagcctcctc ccatcaccac caccaccacc accaccacca tgctcgtgga   3480

atctccaatg ctcatgaacc aaatgctcgc tccatataa                          3519
```

```
<210> SEQ ID NO 24
<211> LENGTH: 702
<212> TYPE: DNA
<213> ORGANISM: Glycine max

<400> SEQUENCE: 24

atggaaactg gaggctttca cggctaccgc aagctcccca acaccaccgc tgggttgaag     60

ctgtcagtgt cagacatgaa catgaacatg aggcagcagc aggtagcatc atcagatcag    120

aactgcagca accacagtgc agcaggagag gagaacgaat gcacggtgag ggagcaagac    180

aggttcatgc caatcgctaa cgtgatacgg atcatgcgca agattctccc tccacacgca    240

aaaatctccg atgatgcaaa ggagacaatc caagagtgcg tgtcggagta catcagcttc    300

atcaccgggg aggcgaacga gcgttgccag agggagcaac ggaagaccat aaccgcagag    360

gacgtgcttt gggccatgag caagcttgga ttcgacgact acatcgaacc gttgaccatg    420

taccttcacc gctaccgtga acttgagggt gaccgcacct ctatgagggg tgaaccactc    480

gggaagagga ctgtggaata cgccacgctt ggtgttgcta ctgcttttgt ccctccaccc    540

tatcatcacc acaatgggta ctttggtgct gccatgccca tggggactta cgttagggaa    600

gcgccaccaa atacagcctc ctcccatcac caccaccacc accaccacca ccatgctcgt    660

ggaatctcca atgctcatga accaaatgct cgctccatat aa                       702
```

```
<210> SEQ ID NO 25
<211> LENGTH: 233
<212> TYPE: PRT
<213> ORGANISM: Glycine max

<400> SEQUENCE: 25

Met Glu Thr Gly Gly Phe His Gly Tyr Arg Lys Leu Pro Asn Thr Thr
1               5                   10                  15

Ala Gly Leu Lys Leu Ser Val Ser Asp Met Asn Met Asn Met Arg Gln
            20                  25                  30

Gln Gln Val Ala Ser Ser Asp Gln Asn Cys Ser Asn His Ser Ala Ala
        35                  40                  45

Gly Glu Glu Asn Glu Cys Thr Val Arg Glu Gln Asp Arg Phe Met Pro
    50                  55                  60

Ile Ala Asn Val Ile Arg Ile Met Arg Lys Ile Leu Pro Pro His Ala
65                  70                  75                  80

Lys Ile Ser Asp Asp Ala Lys Glu Thr Ile Gln Glu Cys Val Ser Glu
```

-continued

```
                85                  90                  95

Tyr Ile Ser Phe Ile Thr Gly Glu Ala Asn Glu Arg Cys Gln Arg Glu
            100                 105                 110

Gln Arg Lys Thr Ile Thr Ala Glu Asp Val Leu Trp Ala Met Ser Lys
        115                 120                 125

Leu Gly Phe Asp Asp Tyr Ile Glu Pro Leu Thr Met Tyr Leu His Arg
    130                 135                 140

Tyr Arg Glu Leu Glu Gly Asp Arg Thr Ser Met Arg Gly Glu Pro Leu
145                 150                 155                 160

Gly Lys Arg Thr Val Glu Tyr Ala Thr Leu Gly Val Ala Thr Ala Phe
                165                 170                 175

Val Pro Pro Pro Tyr His His His Asn Gly Tyr Phe Gly Ala Ala Met
            180                 185                 190

Pro Met Gly Thr Tyr Val Arg Glu Ala Pro Pro Asn Thr Ala Ser Ser
        195                 200                 205

His His His His His His His His His His Ala Arg Gly Ile Ser Asn
    210                 215                 220

Ala His Glu Pro Asn Ala Arg Ser Ile
225                 230


<210> SEQ ID NO 26
<211> LENGTH: 40
<212> TYPE: DNA
<213> ORGANISM: artificial sequence
<220> FEATURE:
<223> OTHER INFORMATION: primer sequence

<400> SEQUENCE: 26

agcggccgca ccatggaaac tggaggcttt cacggctacc                              40


<210> SEQ ID NO 27
<211> LENGTH: 39
<212> TYPE: DNA
<213> ORGANISM: artificial sequence
<220> FEATURE:
<223> OTHER INFORMATION: primer sequence

<400> SEQUENCE: 27

tgcggccgct tatatggagc gagcatttgg ttcatgagc                               39


<210> SEQ ID NO 28
<211> LENGTH: 4235
<212> TYPE: DNA
<213> ORGANISM: artificial sequence
<220> FEATURE:
<223> OTHER INFORMATION: plasmid sequence

<400> SEQUENCE: 28

cctgaattcc agcacactgg cggccgttac tagtggatcc gagctcggta ccaagcttga      60

tgcatagctt gagtattcta acgcgtcacc taaatagctt ggcgtaatca tggtcatagc     120

tgtttcctgt gtgaaattgt tatccgctca caattccaca caacatacga gccggaagca     180

taaagtgtaa agcctggggt gcctaatgag tgagctaact cacattaatt gcgttgcgct     240

cactgcccgc tttccagtcg ggaaacctgt cgtgccagct gcattaatga atcggccaac     300

gcgcggggag aggcggtttg cgtattgggc gctcttccgc ttcctcgctc actgactcgc     360

tgcgctcggt cgttcggctg cggcgagcgg tatcagctca ctcaaaggcg gtaatacggt     420

tatccacaga atcaggggat aacgcaggaa agaacatgtg agcaaaaggc cagcaaaagg     480
```

-continued

```
ccaggaaccg taaaaaggcc gcgttgctgg cgtttttcca taggctccgc cccccctgacg    540
agcatcacaa aaatcgacgc tcaagtcaga ggtggcgaaa cccgacagga ctataaagat    600
accaggcgtt tccccctgga agctccctcg tgcgctctcc tgttccgacc ctgccgctta    660
ccggatacct gtccgccttt ctcccttcgg gaagcgtggc gctttctcat agctcacgct    720
gtaggtatct cagttcggtg taggtcgttc gctccaagct gggctgtgtg cacgaacccc    780
ccgttcagcc cgaccgctgc gccttatccg gtaactatcg tcttgagtcc aacccggtaa    840
gacacgactt atcgccactg gcagcagcca ctggtaacag gattagcaga gcgaggtatg    900
taggcggtgc tacagagttc ttgaagtggt ggcctaacta cggctacact agaagaacag    960
tatttggtat ctgcgctctg ctgaagccag ttaccttcgg aaaaagagtt ggtagctctt   1020
gatccggcaa acaaaccacc gctggtagcg gtggtttttt tgtttgcaag cagcagatta   1080
cgcgcagaaa aaaaggatct caagaagatc ctttgatctt ttctacgggg tctgacgctc   1140
agtggaacga aaactcacgt taagggattt tggtcatgag attatcaaaa aggatcttca   1200
cctagatcct tttaaattaa aaatgaagtt ttagcacgtg tcagtcctgc tcctcggcca   1260
cgaagtgcac gcagttgccg gccgggtcgc gcagggcgaa ctcccgcccc cacggctgct   1320
cgccgatctc ggtcatggcc ggcccggagg cgtcccggaa gttcgtggac acgacctccg   1380
accactcggc gtacagctcg tccaggccgc gcacccacac ccaggccagg gtgttgtccg   1440
gcaccacctg gtcctggacc gcgctgatga acagggtcac gtcgtcccgg accacaccgg   1500
cgaagtcgtc ctccacgaag tcccgggaga acccgagccg gtcggtccag aactcgaccg   1560
ctccggcgac gtcgcgcgcg gtgagcaccg gaacggcact ggtcaacttg gccatggtgg   1620
ccctcctcac gtgctattat tgaagcattt atcagggtta ttgtctcatg agcggataca   1680
tatttgaatg tatttagaaa aataaacaaa taggggttcc gcgcacattt ccccgaaaag   1740
tgccacctga tgcggtgtga aataccgcac agatgcgtaa ggagaaaata ccgcatcagg   1800
aaattgtaag cgttaataat tcagaagaac tcgtcaagaa ggcgatagaa ggcgatgcgc   1860
tgcgaatcgg gagcggcgat accgtaaagc acgaggaagc ggtcagccca ttcgccgcca   1920
agctcttcag caatatcacg ggtagccaac gctatgtcct gatagcggtc cgccacaccc   1980
agccggccac agtcgatgaa tccagaaaag cggccatttt ccaccatgat attcggcaag   2040
caggcatcgc catgggtcac gacgagatcc tcgccgtcgg gcatgctcgc cttgagcctg   2100
gcgaacagtt cggctggcgc gagcccctga tgctcttcgt ccagatcatc ctgatcgaca   2160
agaccggctt ccatccgagt acgtgctcgc tcgatgcgat gtttcgcttg gtggtcgaat   2220
gggcaggtag ccggatcaag cgtatgcagc cgccgcattg catcagccat gatggatact   2280
ttctcggcag gagcaaggtg agatgacagg agatcctgcc ccggcacttc gcccaatagc   2340
agccagtccc ttcccgcttc agtgacaacg tcgagcacag ctgcgcaagg aacgcccgtc   2400
gtggccagcc acgatagccg cgctgcctcg tcttgcagtt cattcagggc accggacagg   2460
tcggtcttga caaaaagaac cgggcgcccc tgcgctgaca gccggaacac ggcggcatca   2520
gagcagccga ttgtctgttg tgcccagtca tagccgaata gcctctccac ccaagcggcc   2580
ggagaacctg cgtgcaatcc atcttgttca atcatgcgaa acgatcctca tcctgtctct   2640
tgatcagagc ttgatcccct gcgccatcag atccttggcg gcaagaaagc catccagttt   2700
actttgcagg gcttcccaac cttaccagag ggcgccccag ctggcaattc cggttcgctt   2760
gctgtccata aaaccgccca gtctagctat cgccatgtaa gcccactgca agctacctgc   2820
tttctctttg cgcttgcgtt ttcccttgtc cagatagccc agtagctgac attcatccgg   2880
```

ggtcagcacc gtttctgcgg actggctttc tacgtgaaaa ggatctaggt gaagatcctt 2940
tttgataatc tcatgcctga catttatatt ccccagaaca tcaggttaat ggcgtttttg 3000
atgtcatttt cgcggtggct gagatcagcc acttcttccc cgataacgga gaccggcaca 3060
ctggccatat cggtggtcat catgcgccag ctttcatccc cgatatgcac caccgggtaa 3120
agttcacggg agactttatc tgacagcaga cgtgcactgg ccagggggat caccatccgt 3180
cgccccggcg tgtcaataat atcactctgt acatccacaa acagacgata acggctctct 3240
cttttatagg tgtaaacctt aaactgccgt acgtataggc tgcgcaactg ttgggaaggg 3300
cgatcggtgc gggcctcttc gctattacgc cagctggcga aagggggatg tgctgcaagg 3360
cgattaagtt gggtaacgcc agggttttcc cagtcacgac gttgtaaaac gacggccagt 3420
gaattgtaat acgactcact atagggcgaa ttgggccctc tagatgcatg ctcgagcggc 3480
cgccagtgtg atggatatct gcagaattca ggtgcggccg cttatatgga gcgagcattt 3540
ggttcatgag cattggagat tccacgagca tggtggtggt ggtggtggtg gtggtgatgg 3600
gaggaggctg tatttggtgg cgcttcccta acgtaagtcc ccatgggcat ggcagcacca 3660
aagtacccat tgtggtgatg atagggtgga gggacaaaag cagtagcaac accaagcgtg 3720
gcgtattcca cagtcctctt cccgagtggt tcacccctca tagaggtgcg gtcaccctca 3780
agttcacggt agcggtgaag gtacatggtc aacggttcga tgtagtcgtc gaatccaagc 3840
ttgctcatgg cccaaagcac gtcctctgcg gttatggtct tccgttgctc cctctggcaa 3900
cgctcgttcg cctccccggt gatgaagctg atgtactccg acacgcactc ttggattgtc 3960
tcctttgcat catcggagat ttttgcgtgt ggagggagaa tcttgcgcat gatccgtatc 4020
acgttagcga ttggcatgaa cctgtcttgc tccctcaccg tgcattcgtt ctcctctcct 4080
gctgcactgt ggttgctgca gttctgatct gatgatgcta cctgctgctg cctcatgttc 4140
atgttcatgt ctgacactga cagcttcaac ccagcggtgg tgttggggag cttgcggtag 4200
ccgtgaaagc ctccagtttc catggtgcgg ccgct 4235

<210> SEQ ID NO 29
<211> LENGTH: 1239
<212> TYPE: DNA
<213> ORGANISM: Glycine max

<400> SEQUENCE: 29
atgaagaggt ctccagcatc ttcttgttca tcatctactt cctctgttgg gtttgaagct 60
cccattgaaa aaagaaggcc taagcatcca aggaggaata atttgaagtc acaaaaatgc 120
aagcagaacc aaaccaccac tggtggcaga agaagctcta tctatagagg agttacaagg 180
cataggtgga cagggaggtt tgaagctcac ctatgggata agagctcttg gaacaacatt 240
cagagcaaga agggtcgaca agtttatttg gggggcatatg atactgaaga atctgcagcc 300
cgtacctatg accttgcagc ccttaaatac tggggaaaag atgcaaccct gaatttcccg 360
atagaaactt ataccaagga gctcgaggaa atggacaagg tttcaagaga agaatatttg 420
gcttctttgc ggcgccaaag cagtggcttt tctagaggcc tgtctaagta ccgtggggtt 480
gctaggcatc atcataatgg tcgctgggaa gcacgaattg gaagagtatg cggaaacaag 540
tacctctact tggggacata taaaactcaa gaggaggcag cagtggcata tgacatggca 600
gcaatagagt accgtggagt caatgcagtg accaattttg acataagcaa ctacatggac 660
aaaataaaga agaaaaatga ccaaacccaa caacaacaaa cagaagcaca aacggaaaca 720

-continued

```
gttcctaact cctctgactc tgaagaagta gaagtagaac aacagacaac aacaataacc    780

acaccacccc catctgaaaa tctgcacatg ccaccacagc agcaccaagt tcaatacacc    840

ccccatgtct ctccaaggga agaagaatca tcatcactga tcacaattat ggaccatgtg    900

cttgagcagg atctgccatg gagcttcatg tacactggct tgtctcagtt tcaagatcca    960

aacttggctt tctgcaaagg tgatgatgac ttggtgggca tgtttgatag tgcagggttt   1020

gaggaagaca ttgatttttct gttcagcact caacctggtg atgagactga gagtgatgtc   1080

aacaatatga gcgcagtttt ggatagtgtt gagtgtggag acacaaatgg ggctggtgga   1140

agcatgatgc atgtggataa caagcagaag atagtatcat ttgcttcttc accatcatct   1200

acaactacag tttcttgtga ctatgctcta gatctatga                          1239
```

<210> SEQ ID NO 30
<211> LENGTH: 412
<212> TYPE: PRT
<213> ORGANISM: Glycine max

<400> SEQUENCE: 30

```
Met Lys Arg Ser Pro Ala Ser Ser Cys Ser Ser Ser Thr Ser Ser Val
1               5                   10                  15

Gly Phe Glu Ala Pro Ile Glu Lys Arg Arg Pro Lys His Pro Arg Arg
            20                  25                  30

Asn Asn Leu Lys Ser Gln Lys Cys Lys Gln Asn Gln Thr Thr Thr Gly
        35                  40                  45

Gly Arg Arg Ser Ser Ile Tyr Arg Gly Val Thr Arg His Arg Trp Thr
    50                  55                  60

Gly Arg Phe Glu Ala His Leu Trp Asp Lys Ser Ser Trp Asn Asn Ile
65                  70                  75                  80

Gln Ser Lys Lys Gly Arg Gln Val Tyr Leu Gly Ala Tyr Asp Thr Glu
                85                  90                  95

Glu Ser Ala Ala Arg Thr Tyr Asp Leu Ala Ala Leu Lys Tyr Trp Gly
            100                 105                 110

Lys Asp Ala Thr Leu Asn Phe Pro Ile Glu Thr Tyr Thr Lys Glu Leu
        115                 120                 125

Glu Glu Met Asp Lys Val Ser Arg Glu Glu Tyr Leu Ala Ser Leu Arg
    130                 135                 140

Arg Gln Ser Ser Gly Phe Ser Arg Gly Leu Ser Lys Tyr Arg Gly Val
145                 150                 155                 160

Ala Arg His His His Asn Gly Arg Trp Glu Ala Arg Ile Gly Arg Val
                165                 170                 175

Cys Gly Asn Lys Tyr Leu Tyr Leu Gly Thr Tyr Lys Thr Gln Glu Glu
            180                 185                 190

Ala Ala Val Ala Tyr Asp Met Ala Ala Ile Glu Tyr Arg Gly Val Asn
        195                 200                 205

Ala Val Thr Asn Phe Asp Ile Ser Asn Tyr Met Asp Lys Ile Lys Lys
    210                 215                 220

Lys Asn Asp Gln Thr Gln Gln Gln Gln Thr Glu Ala Gln Thr Glu Thr
225                 230                 235                 240

Val Pro Asn Ser Ser Asp Ser Glu Glu Val Glu Val Glu Gln Gln Thr
                245                 250                 255

Thr Thr Ile Thr Thr Pro Pro Pro Ser Glu Asn Leu His Met Pro Pro
            260                 265                 270

Gln Gln His Gln Val Gln Tyr Thr Pro His Val Ser Pro Arg Glu Glu
        275                 280                 285
```

```
Glu Ser Ser Ser Leu Ile Thr Ile Met Asp His Val Leu Glu Gln Asp
    290                 295                 300

Leu Pro Trp Ser Phe Met Tyr Thr Gly Leu Ser Gln Phe Gln Asp Pro
305                 310                 315                 320

Asn Leu Ala Phe Cys Lys Gly Asp Asp Asp Leu Val Gly Met Phe Asp
                325                 330                 335

Ser Ala Gly Phe Glu Glu Asp Ile Asp Phe Leu Phe Ser Thr Gln Pro
            340                 345                 350

Gly Asp Glu Thr Glu Ser Asp Val Asn Asn Met Ser Ala Val Leu Asp
        355                 360                 365

Ser Val Glu Cys Gly Asp Thr Asn Gly Ala Gly Gly Ser Met Met His
    370                 375                 380

Val Asp Asn Lys Gln Lys Ile Val Ser Phe Ala Ser Ser Pro Ser Ser
385                 390                 395                 400

Thr Thr Thr Val Ser Cys Asp Tyr Ala Leu Asp Leu
                405                 410


<210> SEQ ID NO 31
<211> LENGTH: 1128
<212> TYPE: DNA
<213> ORGANISM: Glycine max

<400> SEQUENCE: 31

atgtttcctg tgtcttcacc atccatccgt cactcactgc ttggacaatc tctaaccacc      60

accaccacac catggcacca aaccctatgc cacaaactta accctgagaa agagaaccaa     120

ctactacagt cacagaaaac caaaaaaaca ctgtgtgtgt gtgtttgtgt gtcaaaaaaa     180

aaaaacccta agctaatgat gatggatccg cgacagcgag agaagctact tcacaaaacc     240

gaggcctgtg ctttcgtggc aggtgttgtt ccggagcttt cccttgtcac cgttccaggg     300

aacaacaaca acaccaacaa cgttaacaac aacaacaaca acgtttctca ttctcaatct     360

caccggaaga aaaggatggc cagacaaaga agatccacta accccacttt gttgatgaac     420

cctctcatca acaacaacaa caacaagtct ggttcttctc ttccttcgcc aagtactgct     480

tcctcctcgc acgtgccact ctcctcctca actctcccgc ccgcacgtga aatcgatcaa     540

agaaggttga gattcctttt ccagaaggag ttaaagaaca gtgatgttag ctcccttagg     600

agaatgatat tgccaaagaa agcagcagag gctttccttc cagctcttga atccaaagaa     660

ggaattgtaa tcagcatgga tgatatagat ggtcttcatg tatggagttt caagtacagg     720

ttttggccta acaataacag tcggatgtat gtacttgaaa atactggaga ctttgtcaac     780

acacatggcc ttcgctttgg agattccatt ttggtttacc aagatagtga aaacaacaat     840

tatgttattc aggcgaaaaa ggcttctgat caggatgaat ttatggaaga aactagtgat     900

accatcaatg atatcttcct taatgattat gaagtgaaca aacctggttg cttcaatgta     960

acctatcctg cagtgaatga tacaggcatg tcattcatat atgagactac cttctcaaat    1020

gactcccctc ttgatttttt gggtggatca atgaccaatt tttcaaggat tggaccagtt    1080

gaaacctttg gctctgttga gaatttgtca cttgatgact tctattaa                 1128


<210> SEQ ID NO 32
<211> LENGTH: 375
<212> TYPE: PRT
<213> ORGANISM: Glycine max

<400> SEQUENCE: 32
```

-continued

```
Met Phe Pro Val Ser Ser Pro Ser Ile Arg His Ser Leu Leu Gly Gln
1               5                   10                  15

Ser Leu Thr Thr Thr Thr Thr Pro Trp His Gln Thr Leu Cys His Lys
            20                  25                  30

Leu Asn Pro Glu Lys Glu Asn Gln Leu Leu Gln Ser Gln Lys Thr Lys
        35                  40                  45

Lys Thr Leu Cys Val Cys Val Cys Val Ser Lys Lys Lys Asn Pro Lys
    50                  55                  60

Leu Met Met Met Asp Pro Arg Gln Arg Glu Lys Leu Leu His Lys Thr
65                  70                  75                  80

Glu Ala Cys Ala Phe Val Ala Gly Val Val Pro Glu Leu Ser Leu Val
                85                  90                  95

Thr Val Pro Gly Asn Asn Asn Asn Thr Asn Asn Val Asn Asn Asn Asn
            100                 105                 110

Asn Asn Val Ser His Ser Gln Ser His Arg Lys Lys Arg Met Ala Arg
        115                 120                 125

Gln Arg Arg Ser Thr Asn Pro Thr Leu Leu Met Asn Pro Leu Ile Asn
    130                 135                 140

Asn Asn Asn Asn Lys Ser Gly Ser Ser Leu Pro Ser Pro Ser Thr Ala
145                 150                 155                 160

Ser Ser Ser His Val Pro Leu Ser Ser Ser Thr Leu Pro Pro Ala Arg
                165                 170                 175

Glu Ile Asp Gln Arg Arg Leu Arg Phe Leu Phe Gln Lys Glu Leu Lys
            180                 185                 190

Asn Ser Asp Val Ser Ser Leu Arg Arg Met Ile Leu Pro Lys Lys Ala
        195                 200                 205

Ala Glu Ala Phe Leu Pro Ala Leu Glu Ser Lys Glu Gly Ile Val Ile
    210                 215                 220

Ser Met Asp Asp Ile Asp Gly Leu His Val Trp Ser Phe Lys Tyr Arg
225                 230                 235                 240

Phe Trp Pro Asn Asn Asn Ser Arg Met Tyr Val Leu Glu Asn Thr Gly
                245                 250                 255

Asp Phe Val Asn Thr His Gly Leu Arg Phe Gly Asp Ser Ile Leu Val
            260                 265                 270

Tyr Gln Asp Ser Glu Asn Asn Asn Tyr Val Ile Gln Ala Lys Lys Ala
        275                 280                 285

Ser Asp Gln Asp Glu Phe Met Glu Glu Thr Ser Asp Thr Ile Asn Asp
    290                 295                 300

Ile Phe Leu Asn Asp Tyr Glu Val Asn Lys Pro Gly Cys Phe Asn Val
305                 310                 315                 320

Thr Tyr Pro Ala Val Asn Asp Thr Gly Met Ser Phe Ile Tyr Glu Thr
                325                 330                 335

Thr Phe Ser Asn Asp Ser Pro Leu Asp Phe Leu Gly Gly Ser Met Thr
            340                 345                 350

Asn Phe Ser Arg Ile Gly Pro Val Glu Thr Phe Gly Ser Val Glu Asn
        355                 360                 365

Leu Ser Leu Asp Asp Phe Tyr
    370                 375
```

<210> SEQ ID NO 33
<211> LENGTH: 27
<212> TYPE: DNA
<213> ORGANISM: artificial sequence
<220> FEATURE:
<223> OTHER INFORMATION: primer sequence

<400> SEQUENCE: 33
atgtttcctg tgtcttcacc atccatc 27

<210> SEQ ID NO 34
<211> LENGTH: 27
<212> TYPE: DNA
<213> ORGANISM: artificial sequence
<220> FEATURE:
<223> OTHER INFORMATION: primer sequence

<400> SEQUENCE: 34
taatagaagt catcaagtga caaattc 27

<210> SEQ ID NO 35
<211> LENGTH: 4535
<212> TYPE: DNA
<213> ORGANISM: artificial sequence
<220> FEATURE:
<223> OTHER INFORMATION: plasmid Glyma16g05480/pCR8/GW/TOPO

<400> SEQUENCE: 35
aagggcgaat tcgacccagc tttcttgtac aaagttggca ttataaaaaa taattgctca 60
tcaatttgtt gcaacgaaca ggtcactatc agtcaaaata aaatcattat ttgccatcca 120
gctgatatcc cctatagtga gtcgtattac atggtcatag ctgtttcctg gcagctctgg 180
cccgtgtctc aaaatctctg atgttacatt gcacaagata aaaatatatc atcatgcctc 240
ctctagacca gccaggacag aaatgcctcg acttcgctgc tgcccaaggt tgccgggtga 300
cgcacaccgt ggaaacggat gaaggcacga acccagtgga cataagcctg ttcggttcgt 360
aagctgtaat gcaagtagcg tatgcgctca cgcaactggt ccagaacctt gaccgaacgc 420
agcggtggta acggcgcagt ggcggttttc atggcttgtt atgactgttt ttttggggta 480
cagtctatgc ctcgggcatc caagcagcaa gcgcgttacg ccgtgggtcg atgtttgatg 540
ttatggagca gcaacgatgt tacgcagcag ggcagtcgcc ctaaaacaaa gttaaacatc 600
atgagggaag cggtgatcgc cgaagtatcg actcaactat cagaggtagt tggcgtcatc 660
gagcgccatc tcgaaccgac gttgctggcc gtacatttgt acggctccgc agtggatggc 720
ggcctgaagc cacacagtga tattgatttg ctggttacgg tgaccgtaag gcttgatgaa 780
acaacgcggc gagctttgat caacgacctt ttggaaactt cggcttcccc tggagagagc 840
gagattctcc gcgctgtaga agtcaccatt gttgtgcacg acgacatcat tccgtggcgt 900
tatccagcta agcgcgaact gcaatttgga gaatggcagc gcaatgacat tcttgcaggt 960
atcttcgagc cagccacgat cgacattgat ctggctatct tgctgacaaa agcaagagaa 1020
catagcgttg ccttggtagg tccagcggcg gaggaactct ttgatccggt tcctgaacag 1080
gatctatttg aggcgctaaa tgaaacctta acgctatgga actcgccgcc cgactgggct 1140
ggcgatgagc gaaatgtagt gcttacgttg tcccgcattt ggtacagcgc agtaaccggc 1200
aaaatcgcgc cgaaggatgt cgctgccgac tgggcaatgg agcgcctgcc ggcccagtat 1260
cagcccgtca tacttgaagc tagacaggct tatcttggac aagaagaaga tcgcttggcc 1320
tcgcgcgcag atcagttgga agaatttgtc cactacgtga aaggcgagat caccaaggta 1380
gtcggcaaat aaccctcgag ccacccatga ccaaaatccc ttaacgtgag ttacgcgtcg 1440
ttccactgag cgtcagaccc cgtagaaaag atcaaaggat cttcttgaga tcctttttt 1500 ctgcgcgtaa tctgctgctt gcaaacaaaa aaaccaccgc taccagcggt ggtttgtttg 1560

-continued

```
ccggatcaag agctaccaac tctttttccg aaggtaactg gcttcagcag agcgcagata   1620
ccaaatactg tccttctagt gtagccgtag ttaggccacc acttcaagaa ctctgtagca   1680
ccgcctacat acctcgctct gctaatcctg ttaccagtgg ctgctgccag tggcgataag   1740
tcgtgtctta ccgggttgga ctcaagacga tagttaccgg ataaggcgca gcggtcgggc   1800
tgaacggggg gttcgtgcac acagcccagc ttggagcgaa cgacctacac cgaactgaga   1860
tacctacagc gtgagcattg agaaagcgcc acgcttcccg aagggagaaa ggcggacagg   1920
tatccggtaa gcggcagggt cggaacagga gagcgcacga gggagcttcc agggggaaac   1980
gcctggtatc tttatagtcc tgtcgggttt cgccacctct gacttgagcg tcgatttttg   2040
tgatgctcgt caggggggcg gagcctatgg aaaaacgcca gcaacgcggc ctttttacgg   2100
ttcctggcct tttgctggcc ttttgctcac atgttctttc ctgcgttatc ccctgattct   2160
gtggataacc gtattaccgc ctttgagtga gctgataccg ctcgccgcag ccgaacgacc   2220
gagcgcagcg agtcagtgag cgaggaagcg gaagagcgcc caatacgcaa accgcctctc   2280
cccgcgcgtt ggccgattca ttaatgcagc tggcacgaca ggtttcccga ctggaaagcg   2340
ggcagtgagc gcaacgcaat taatacgcgt accgctagcc aggaagagtt tgtagaaacg   2400
caaaaaggcc atccgtcagg atggccttct gcttagtttg atgcctggca gtttatggcg   2460
ggcgtcctgc ccgccaccct ccgggccgtt gcttcacaac gttcaaatcc gctcccggcg   2520
gatttgtcct actcaggaga gcgttcaccg acaaacaaca gataaaacga aaggcccagt   2580
cttccgactg agcctttcgt tttatttgat gcctggcagt tccctactct cgcgttaacg   2640
ctagcatgga tgttttccca gtcacgacgt tgtaaaacga cggccagtct taagctcggg   2700
ccccaaataa tgattttatt ttgactgata gtgacctgtt cgttgcaaca aattgatgag   2760
caatgctttt ttataatgcc aactttgtac aaaaaagcag gctccgaatt cgcccttatg   2820
tttcctgtgt cttcaccatc catccgtcac tcactgcttg ggcaatctct aaccaccacc   2880
accaccccgc agcaccaaac cctatgccac aaacttaacc ctggtttgca ccacaccccc   2940
tattcacacg cagccacatt atcatcgatc atatcataat gtagccagca gaaagtgcca   3000
aatccaaaac caacccatga atccaatcct cacatttggt caccaaaact cattaaccca   3060
tatcatttag ataaagggag agagagagag agagagagag agaaagagag tgtgtgtgaa   3120
tgtgagtggg gggtggtgtt tcaattcatt tatgttatgg taaaagtaaa aggaagcaaa   3180
gggagaggat ggggagagga gtgaatgcag gatgcacaaa tgtcataaaa accagaccct   3240
tataatcaca aaaaaccttg ctaaaaatag aaaaaatcca aaaaaaaaag aagaagagag   3300
agagagagaa tttggattga gttgggttgg gggaagagaa gagtgaatga gagttccacc   3360
attgatctct taaacaccaa accccacacc catttcgtga gtgccgagcg tcgttctatc   3420
tatttttttct ctgcctacac acactgatac tgagagaaag agaaccaact actacagtca   3480
cagaaaacca aaaaaacact gtgttgtgtg tgtgtcaaaa aaaaaaccct aagctaatga   3540
tgatggatca gcgacagcga gagaagctgc ttcacaaaac cgaggcctgt gctttcgtgg   3600
caggtgttgt tccggagctt tcccttgtca ccgttccagg gaacaacacc aacaacgtta   3660
acaacaacaa caacgttgtt tctcattctc aatctaacgg gtcgggtcgg atccaggaaa   3720
acaaccacca ccttggactc gttgctgctg tcacctccgc cttcggtacc gttcaaagga   3780
agaaaaggat ggcgagacaa agaagatcca ctaaacccac ttcgttgatg aaccatctca   3840
acaaccataa gcacaacaag cctcgttctc ttccttctcc cagtgcatcc tcctcgtacg   3900
tgccactctc ctccgcaact ctccagcccg cacgtgaaat cgatcaaaga aggttgagat   3960
```

```
tccttttcca gaaggagtta aagaacagtg atgttagctc ccttaggaga atgatattgc   4020

caaagaaagc agcagaggct ttccttccag ctcttgaatc caaagaagga attgtaatca   4080

gcatggatga tatagatggt cttcatgtat ggagtttcaa gtacaggttt tggcctaaca   4140

acaacagtcg gatgtatgta cttgaaaata ctggagattt tgtcaacaca catggccttc   4200

gctttggaga ttccattatg gtttaccaag atagtgaaaa caacaattat gttattcagg   4260

ccaaaaaggc ttctgatcaa gatgaattta tggaagaaac tagtgatacc atcaatgata   4320

tcttccttaa tgattatgag gtgaacaaac ctggttgctt caatgtaact aatcctgcag   4380

tgaatgatac aggcatgtca ttcatatatg agactacctt ctcaaatgac tcccctcttg   4440

atttttgggg tggatcaatg accaattttt caaggattgg gccagttgaa acctttggct   4500

ctgttgagaa tttgtcactt gatgacttct attaa                              4535
```

```
<210> SEQ ID NO 36
<211> LENGTH: 1718
<212> TYPE: DNA
<213> ORGANISM: Glycine max

<400> SEQUENCE: 36

atgtttcctg tgtcttcacc atccatccgt cactcactgc ttgggcaatc tctaaccacc     60

accaccaccc cgcagcacca aaccctatgc cacaaactta accctggttt gcaccacacc    120

ccctattcac acgcagccac attatcatcg atcatatcat aatgtagcca gcagaaagtg    180

ccaaatccaa aaccaaccca tgaatccaat cctcacattt ggtcaccaaa actcattaac    240

ccatatcatt tagataaagg gagagagaga gagagagaga gagagaaaga gagtgtgtgt    300

gaatgtgagt ggggggtggt gtttcaattc atttatgtta tggtaaaagt aaaaggaagc    360

aaagggagag gatggggaga ggagtgaatg caggatgcac aaatgtcata aaaaccagac    420

ccttataatc acaaaaaacc ttgctaaaaa tagaaaaaat ccaaaaaaaa aagaagaaga    480

gagagagaga gaatttggat tgagttgggt tgggggaaga gaagagtgaa tgagagttcc    540

accattgatc tcttaaacac caaaccccac acccatttcg tgagtgccga gcgtcgttct    600

atctattttt tctctgccta cacacactga tactgagaga aagagaacca actactacag    660

tcacagaaaa ccaaaaaaac actgtgttgt gtgtgtgtca aaaaaaaaac cctaagctaa    720

tgatgatgga tcagcgacag cgagagaagc tgcttcacaa aaccgaggcc tgtgctttcg    780

tggcaggtgt tgttccggag ctttcccttg tcaccgttcc agggaacaac accaacaacg    840

ttaacaacaa caacaacgtt gtttctcatt ctcaatctaa cgggtcgggt cggatccagg    900

aaaacaacca ccaccttgga ctcgttgctg ctgtcacctc cgccttcggt accgttcaaa    960

ggaagaaaag gatggcgaga caaagaagat ccactaaacc cacttcgttg atgaaccatc   1020

tcaacaacca taagcacaac aagcctcgtt ctcttccttc tcccagtgca tcctcctcgt   1080

acgtgccact ctcctccgca actctccagc ccgcacgtga aatcgatcaa agaaggttga   1140

gattcctttt ccagaaggag ttaaagaaca gtgatgttag ctcccttagg agaatgatat   1200

tgccaaagaa agcagcagag gctttccttc cagctcttga atccaaagaa ggaattgtaa   1260

tcagcatgga tgatatagat ggtcttcatg tatggagttt caagtacagg ttttggccta   1320

acaacaacag tcggatgtat gtacttgaaa atactggaga ttttgtcaac acacatggcc   1380

ttcgctttgg agattccatt atggtttacc aagatagtga aaacaacaat tatgttattc   1440

aggccaaaaa ggcttctgat caagatgaat ttatggaaga aactagtgat accatcaatg   1500
```

```
atatcttcct taatgattat gaggtgaaca aacctggttg cttcaatgta actaatcctg   1560

cagtgaatga tacaggcatg tcattcatat atgagactac cttctcaaat gactcccctc   1620

ttgatttttt gggtggatca atgaccaatt tttcaaggat tgggccagtt gaaacctttg   1680

gctctgttga gaatttgtca cttgatgact tctattaa                           1718
```

```
<210> SEQ ID NO 37
<211> LENGTH: 525
<212> TYPE: DNA
<213> ORGANISM: Glycine max

<400> SEQUENCE: 37

atgatattgc caaagaaagc agcagaggct ttccttccag ctcttgaatc caaagaagga     60

attgtaatca gcatggatga tatagatggt cttcatgtat ggagtttcaa gtacaggttt    120

tggcctaaca acaacagtcg gatgtatgta cttgaaaata ctggagattt tgtcaacaca    180

catggccttc gctttggaga ttccattatg gtttaccaag atagtgaaaa caacaattat    240

gttattcagg ccaaaaaggc ttctgatcaa gatgaattta tggaagaaac tagtgatacc    300

atcaatgata tcttccttaa tgattatgag gtgaacaaac ctggttgctt caatgtaact    360

aatcctgcag tgaatgatac aggcatgtca ttcatatatg agactacctt ctcaaatgac    420

tcccctcttg atttttgggg tggatcaatg accaattttt caaggattgg gccagttgaa    480

acctttggct ctgttgagaa tttgtcactt gatgacttct attaa                    525
```

```
<210> SEQ ID NO 38
<211> LENGTH: 174
<212> TYPE: PRT
<213> ORGANISM: Glycine max

<400> SEQUENCE: 38

Met Ile Leu Pro Lys Lys Ala Ala Glu Ala Phe Leu Pro Ala Leu Glu
1               5                   10                  15

Ser Lys Glu Gly Ile Val Ile Ser Met Asp Asp Ile Asp Gly Leu His
            20                  25                  30

Val Trp Ser Phe Lys Tyr Arg Phe Trp Pro Asn Asn Asn Ser Arg Met
        35                  40                  45

Tyr Val Leu Glu Asn Thr Gly Asp Phe Val Asn Thr His Gly Leu Arg
    50                  55                  60

Phe Gly Asp Ser Ile Met Val Tyr Gln Asp Ser Glu Asn Asn Asn Tyr
65                  70                  75                  80

Val Ile Gln Ala Lys Lys Ala Ser Asp Gln Asp Glu Phe Met Glu Glu
                85                  90                  95

Thr Ser Asp Thr Ile Asn Asp Ile Phe Leu Asn Asp Tyr Glu Val Asn
            100                 105                 110

Lys Pro Gly Cys Phe Asn Val Thr Asn Pro Ala Val Asn Asp Thr Gly
        115                 120                 125

Met Ser Phe Ile Tyr Glu Thr Thr Phe Ser Asn Asp Ser Pro Leu Asp
    130                 135                 140

Phe Leu Gly Gly Ser Met Thr Asn Phe Ser Arg Ile Gly Pro Val Glu
145                 150                 155                 160

Thr Phe Gly Ser Val Glu Asn Leu Ser Leu Asp Asp Phe Tyr
                165                 170
```

```
<210> SEQ ID NO 39
<211> LENGTH: 3991
<212> TYPE: DNA
```

<213> ORGANISM: Glycine max

<400> SEQUENCE: 39
atgtttcctg tgtctttacc atccatccgt cactcactgc ttgggcaatc tctaaccacc 60
accaccaccc cgcagcacca aaccctatgc cacaaactta accctggttt gcaccacacc 120
ccctattcac acgcagccac attatcatcg atcatatcat aatgtagcca gcagaaagtg 180
ccaaatccaa aaccaaccca tgaatccaat cctcacattt ggtcaccaaa actcattaac 240
ccatatcatt tagataaagg gagagagaga gagagagaga gagagaaaga gagtgtgtgt 300
gaatgtgagt ggggggtggt gtttcaattc atttatgtta tggtaaaagt aaaaggaagc 360
aaagggagag gatggggaga ggagtgaatg caggatgcac aaatgtcata aaaaccagac 420
ccttataatc acaaaaaacc ttgctaaaaa tagaaaaaat ccaaaaaaaa aagaagaaga 480
gagagagaga gaatttggat tgagttgggt tgggggaaga gaagagtgaa tgagagttcc 540
accattgatc tcttaaacac caaaccccac acccatttcg tgagtgccga gcgtcgttct 600
atctattttt tctctgccta cacacactga tactgagaga aagagaacca actactacag 660
tcacagaaaa ccaaaaaaac actgtgttgt gtgtgtgtca aaaaaaaaac cctaagctaa 720
tgatgatgga tcagcgacag cgagagaagc tgcttcacaa aaccgaggcc tgtgctttcg 780
tggcaggtgt tgttccggag ctttcccttg tcaccgttcc agggaacaac accaacaacg 840
ttaacaacaa caacaacgtt gtttctcatt ctcaatctaa cgggtcgggt cggatccagg 900
aaaacaacca ccaccttgga ctcgttgctg ctgtcacctc cgccttcggt accgttcaaa 960
ggaagaaaag gatggcgaga caaagaagat ccactaaacc cacttcgttg atgaaccatc 1020
tcaacaacca taagcacaac aagcctcgtt ctcttccttc tcccagtgca tcctcctcgt 1080
acgtgccact ctcctccgca actctccagc ccgcacgtgt gagttccccc ttttaaatgt 1140
gtttctttct ctaaatctct catcttatat acagtcatac atagcttgat tctcaatttt 1200
gttgttgcta tatcttcgga tattgtcttt tccataaatt ttctgccccc attttttttt 1260
caatctctta ttttttggat ctttcataaa ttaagtgttt ttcgcaatct tattaaaatt 1320
tggagttttt ttttttcatg gacaaatgtt aattgttact tttaggagag atctgatcca 1380
tgatcttttt tttctttctt aactacctca tcaatcttat atcttcaagt ttcgtcatct 1440
tcataattcg cgtaataaat ggagtttcat ctatgtaatt tatattaatc tttaattcta 1500
ttctttatac gttaattatc gagataaaat tctaattctg attagaaact taaagaattg 1560
tatttaagat ttatcctttt gggtttttctt tcttttatat ggttgtgttt atttgtctcg 1620
tgattctcat acttatttaa atagttttta cgataatctt ttccgatgct aaatgtaaag 1680
ttctttaatt ctatacatat atctttattg ttgagttact ttagtaccat acctgtttaa 1740
acaaagcata atttaattgt ttgatcttca attttggtat ttctacgtgt gaaaggtggg 1800
aagggtgaga acggagggca aaagtggcac tctggtaaag aaatgaacta aaaaaaaaat 1860
ttatattaaa ttccccaccg aagaaaaaaa agactaaaag gaaacacaat atatgaagaa 1920
ctacatctag aagagaatct ctttcgaaaa caagtttttc tttttatgtg ggtttcgaaa 1980
acaagttaaa tgaaatgaag tgaagacgtc atgggctatt attttctttt aaaatttttt 2040
cgtaactcaa tttgtgttgt atattaagtc gctaaacaca agtcagacat actttgattc 2100
cctagctagc ttgcaaatct tggaacctcg tgtctgattg tgcaaccaaa aaatatatac 2160
gcttacacgt aaaaagggga agaattttat cgcgctgcta aaaggggcat gatcaatata 2220
agtacggaat tagcctcata atggatatgt gtatgtgtgt atatatatat atatatatat 2280
atatttatat atacaacttt tacatatatt aaaaacaaat tatgtggagt tacctaagtt 2340
tctatcttca aacttagtag gacattcact ttttttgttt tactttactg gggtgggaaa 2400
gagttacaag aggagttaaa ttttggttat taattgcaaa attgccaaat atagtactac 2460
tacataatac atggttactc ttattactgg tatattatct ataatgttaa tgtccatcct 2520
tttgtgtaga gaaataaaat aaaataaaaa gaaaaagaaa actgatgatt agtggttatt 2580
gacggcttca tatttgggaa attgtgtatt caagacatcc ataaagcatg ctggacatgg 2640
cagcattgat gtcttagtta tacaaaatta gcatgttttg ccacaattaa ttatattttg 2700
ctcccccttt taggtgaatg ccttagttcc atgtttttat aatgagattg ataacagaaa 2760
ttgcctaatt tcatttactt tgcttttagg aaatcgatca aagaaggttg agattccttt 2820
tccagaagga gttaaagaac agtgatgtta gctcccttag gagaatgata ttgccaaagg 2880
tttggcctat gtcaataact ctttacagta atattgtctc tacttgattt ctattccttc 2940
gtgagcctag ctataataat gaattgtgcg acaaattaca aacttgcaga aagcagcaga 3000
ggctttcctt ccagctcttg aatccaaaga aggaattgta atcagcatgg atgatataga 3060
tggtcttcat gtatggagtt tcaagtacag gtctgttata catatagttg gtttatatgc 3120
atggatggcc acaaaataaa caaaaaattg aatacatagt cacattattt taccacgacg 3180
aaaattgata ctagttgaga atatgattta agtttatttt tagttaattg atactaacaa 3240
ttcaaattta taggttattg tgtttgtatt tgaataatgc aggttttggc ctaacaacaa 3300
cagtcggatg tatgtacttg aaaatactgg taactaactc cttcatttgc taaaagtaat 3360
ggtctaacta ttgggaaagg ttatattttg gttatgaaat attcttatgc tgaatgtttt 3420
caggagattt tgtcaacaca catggccttc gctttggaga ttccattatg gtttaccaag 3480
atagtgaaaa caacaattat gtatgtctcg ccagaaagtt catttttttta aaacagtttt 3540 gaattaattt caaaatactg ttatgcacat ttttttttct gtacattctg ttaagccttt 3600
ttaattgtgc taactttcta attttatatc ggtacattct gttaagtgtt tttaattgtg 3660
caaactttct aattttgtat cgactgcgcg cgttacattt ctgcaggtta ttcaggccaa 3720
aaaggcttct gatcaagatg aatttatgga agaaactagt gataccatca atgatatctt 3780
ccttaatgat tatgaggtga acaaacctgg ttgcttcaat gtaactaatc ctgcagtgaa 3840
tgatacaggc atgtcattca tatatgagac taccttctca aatgactccc ctcttgattt 3900
tttgggtgga tcaatgacca atttttcaag gattgggcca gttgaaacct ttggctctgt 3960
tgagaatttg tcacttgatg acttctatta a 3991

<210> SEQ ID NO 40
<211> LENGTH: 40
<212> TYPE: DNA
<213> ORGANISM: artificial sequence
<220> FEATURE:
<223> OTHER INFORMATION: primer sequence

<400> SEQUENCE: 40
agcggccgca ccatgtttcc tgtgtcttta ccatccatcc 40

<210> SEQ ID NO 41
<211> LENGTH: 39
<212> TYPE: DNA
<213> ORGANISM: artificial sequence
<220> FEATURE:
<223> OTHER INFORMATION: primer sequence

<400> SEQUENCE: 41
tgcggccgct taatagaagt catcaagtga caaattctc 39

<210> SEQ ID NO 42
<211> LENGTH: 5250
<212> TYPE: DNA
<213> ORGANISM: artificial sequence
<220> FEATURE:
<223> OTHER INFORMATION: plasmid sequence

<400> SEQUENCE: 42
cctgaattcc agcacactgg cggccgttac tagtggatcc gagctcggta ccaagcttga 60
tgcatagctt gagtattcta acgcgtcacc taaatagctt ggcgtaatca tggtcatagc 120
tgtttcctgt gtgaaattgt tatccgctca caattccaca caacatacga gccggaagca 180
taaagtgtaa agcctggggt gcctaatgag tgagctaact cacattaatt gcgttgcgct 240
cactgcccgc tttccagtcg ggaaacctgt cgtgccagct gcattaatga atcggccaac 300
gcgcggggag aggcggtttg cgtattgggc gctcttccgc ttcctcgctc actgactcgc 360
tgcgctcggt cgttcggctg cggcgagcgg tatcagctca ctcaaaggcg gtaatacggt 420
tatccacaga atcaggggat aacgcaggaa agaacatgtg agcaaaaggc cagcaaaagg 480
ccaggaaccg taaaaaggcc gcgttgctgg cgtttttcca taggctccgc ccccctgacg 540
agcatcacaa aaatcgacgc tcaagtcaga ggtggcgaaa cccgacagga ctataaagat 600
accaggcgtt tccccctgga agctccctcg tgcgctctcc tgttccgacc ctgccgctta 660
ccggatacct gtccgccttt ctcccttcgg gaagcgtggc gctttctcat agctcacgct 720
gtaggtatct cagttcggtg taggtcgttc gctccaagct gggctgtgtg cacgaacccc 780
ccgttcagcc cgaccgctgc gccttatccg gtaactatcg tcttgagtcc aacccggtaa 840
gacacgactt atcgccactg gcagcagcca ctggtaacag gattagcaga gcgaggtatg 900
taggcggtgc tacagagttc ttgaagtggt ggcctaacta cggctacact agaagaacag 960
tatttggtat ctgcgctctg ctgaagccag ttaccttcgg aaaaagagtt ggtagctctt 1020
gatccggcaa acaaaccacc gctggtagcg gtggtttttt tgtttgcaag cagcagatta 1080
cgcgcagaaa aaaaggatct caagaagatc ctttgatctt ttctacgggg tctgacgctc 1140
agtggaacga aaactcacgt taagggattt tggtcatgag attatcaaaa aggatcttca 1200
cctagatcct tttaaattaa aaatgaagtt ttagcacgtg tcagtcctgc tcctcggcca 1260
cgaagtgcac gcagttgccg gccgggtcgc gcagggcgaa ctcccgcccc cacggctgct 1320
cgccgatctc ggtcatggcc ggcccggagg cgtcccggaa gttcgtggac acgacctccg 1380
accactcggc gtacagctcg tccaggccgc gcacccacac ccaggccagg gtgttgtccg 1440
gcaccacctg gtcctggacc gcgctgatga acagggtcac gtcgtcccgg accacaccgg 1500
cgaagtcgtc ctccacgaag tcccgggaga acccgagccg gtcggtccag aactcgaccg 1560
ctccggcgac gtcgcgcgcg gtgagcaccg gaacggcact ggtcaacttg gccatggtgg 1620
ccctcctcac gtgctattat tgaagcattt atcagggtta ttgtctcatg agcggataca 1680
tatttgaatg tatttagaaa aataaacaaa taggggttcc gcgcacattt ccccgaaaag 1740
tgccacctga tgcggtgtga aataccgcac agatgcgtaa ggagaaaata ccgcatcagg 1800
aaattgtaag cgttaatatt ttgttaaaat tcgcgttaaa tttttgttaa atcagctcat 1860
tgcgaatcgg gagcggcgat accgtaaagc acgaggaagc ggtcagccca ttcgccgcca 1920
agctcttcag caatatcacg ggtagccaac gctatgtcct gatagcggtc cgccacaccc 1980

-continued

```
agccggccac agtcgatgaa tccagaaaag cggccatttt ccaccatgat attcggcaag   2040
caggcatcgc catgggtcac gacgagatcc tcgccgtcgg gcatgctcgc cttgagcctg   2100
gcgaacagtt cggctggcgc gagcccctga tgctcttcgt ccagatcatc ctgatcgaca   2160
agaccggctt ccatccgagt acgtgctcgc tcgatgcgat gtttcgcttg gtggtcgaat   2220
gggcaggtag ccggatcaag cgtatgcagc cgccgcattg catcagccat gatggatact   2280
ttctcggcag gagcaaggtg agatgacagg agatcctgcc ccggcacttc gcccaatagc   2340
agccagtccc ttcccgcttc agtgacaacg tcgagcacag ctgcgcaagg aacgcccgtc   2400
gtggccagcc acgatagccg cgctgcctcg tcttgcagtt cattcagggc accggacagg   2460
tcggtcttga caaaaagaac cgggcgcccc tgcgctgaca gccggaacac ggcggcatca   2520
gagcagccga ttgtctgttg tgcccagtca tagccgaata gcctctccac ccaagcggcc   2580
ggagaacctg cgtgcaatcc atcttgttca atcatgcgaa acgatcctca tcctgtctct   2640
tgatcagagc ttgatcccct gcgccatcag atccttggcg gcaagaaagc catccagttt   2700
actttgcagg gcttcccaac cttaccagag ggcgccccag ctggcaattc cggttcgctt   2760
gctgtccata aaaccgccca gtctagctat cgccatgtaa gcccactgca agctacctgc   2820
tttctctttg cgcttgcgtt ttcccttgtc cagatagccc agtagctgac attcatccgg   2880
ggtcagcacc gtttctgcgg actggctttc tacgtgaaaa ggatctaggt gaagatcctt   2940
tttgataatc tcatgcctga catttatatt ccccagaaca tcaggttaat ggcgtttttg   3000
atgtcatttt cgcggtggct gagatcagcc acttcttccc cgataacgga gaccggcaca   3060
ctggccatat cggtggtcat catgcgccag ctttcatccc cgatatgcac caccgggtaa   3120
agttcacggg agactttatc tgacagcaga cgtgcactgg ccagggggat caccatccgt   3180
cgccccggcg tgtcaataat atcactctgt acatccacaa acagacgata acggctctct   3240
cttttatagg tgtaaacctt aaactgccgt acgtataggc tgcgcaactg ttgggaaggg   3300
cgatcggtgc gggcctcttc gctattacgc cagctggcga aagggggatg tgctgcaagg   3360
cgattaagtt gggtaacgcc agggttttcc cagtcacgac gttgtaaaac gacggccagt   3420
gaattgtaat acgactcact atagggcgaa ttgggccctc tagatgcatg ctcgagcggc   3480
cgccagtgtg atggatatct gcagaattca gggcggccgc ttaatagaag tcatcaagtg   3540
acaaattctc aacagagcca aaggtttcaa ctggcccaat ccttgaaaaa ttggtcattg   3600
atccacccaa aaaatcaaga ggggagtcat ttgagaaggt agtctcatat atgaatgaca   3660
tgcctgtatc attcactgca ggattagtta cattgaagca accaggtttg ttcacctcat   3720
aatcattaag gaagatatca ttgatggtat cactagtttc ttccataaat tcatcttgat   3780
cagaagcctt tttggcctga ataacataat tgttgttttc actatcttgg taaaccataa   3840
tggaatctcc aaagcgaagg ccatgtgtgt tgacaaaatc tccagtattt tcaagtacat   3900
acatccgact gttgttgtta ggccaaaacc tgtacttgaa actccataca tgaagaccat   3960
ctatatcatc catgctgatt acaattcctt ctttggattc aagagctgga aggaaagcct   4020
ctgctgcttt ctttggcaat atcattctcc taagggagct aacatcactg ttctttaact   4080
ccttctggaa aaggaatctc aaccttcttt gatcgatttc acgtgcgggc tggagagttg   4140
cggaggagag tggcacgtac gaggaggatg cactgggaga aggaagagaa cgaggcttgt   4200
tgtgcttatg gttgttgaga tggttcatca acgaagtggg tttagtggat cttctttgtc   4260
tcgccatcct tttcttcctt tgaacggtac cgaaggcgga ggtgacagca gcaacgagtc   4320
```

-continued

```
caaggtggtg gttgttttcc tggatccgac ccgacccgtt agattgagaa tgagaaacaa   4380

cgttgttgtt gttgttaacg ttgttggtgt tgttccctgg aacggtgaca agggaaagct   4440

ccggaacaac acctgccacg aaagcacagg cctcggtttt gtgaagcagc ttctctcgct   4500

gtcgctgatc catcatcatt agcttagggt tttttttttg acacacacac aacacagtgt   4560

tttttggtt ttctgtgact gtagtagttg gttctctttc tctcagtatc agtgtgtgta   4620

ggcagagaaa aaatagatag aacgacgctc ggcactcacg aaatgggtgt ggggtttggt   4680

gtttaagaga tcaatggtgg aactctcatt cactcttctc ttccccccaac ccaactcaat   4740

ccaaattctc tctctctctc ttcttctttt ttttttggat tttttctatt tttagcaagg   4800

tttttgtga ttataagggt ctggttttta tgacatttgt gcatcctgca ttcactcctc   4860

tccccatcct ctccctttgc ttccttttac ttttaccata acataaatga attgaaacac   4920

caccccccac tcacattcac acacactctc tttctctctc tctctctctc tctctctccc   4980

tttatctaaa tgatatgggt taatgagttt tggtgaccaa atgtgaggat tggattcatg   5040

ggttggtttt ggatttggca ctttctgctg gctacattat gatatgatcg atgataatgt   5100

ggctgcgtgt gaataggggg tgtggtgcaa accagggtta agtttgtggc atagggtttg   5160

gtgctgcggg gtggtggtgg tggttagaga ttgcccaagc agtgagtgac ggatggatgg   5220

taaagacaca ggaaacatgg tgcggccgct                                    5250
```

<210> SEQ ID NO 43
<211> LENGTH: 1718
<212> TYPE: DNA
<213> ORGANISM: Glycine max

<400> SEQUENCE: 43

```
atgtttcctg tgtctttacc atccatccgt cactcactgc ttgggcaatc tctaaccacc     60

accaccaccc cgcagcacca aaccctatgc cacaaactta accctggttt gcaccacacc    120

ccctattcac acgcagccac attatcatcg atcatatcat aatgtagcca gcagaaagtg    180

ccaaatccaa aaccaaccca tgaatccaat cctcacattt ggtcaccaaa actcattaac    240

ccatatcatt tagataaagg gagagagaga gagagagaga gagagaaaga gagtgtgtgt    300

gaatgtgagt ggggggtggt gtttcaattc atttatgtta tggtaaaagt aaaaggaagc    360

aaagggagag gatggggaga ggagtgaatg caggatgcac aaatgtcata aaaaccagac    420

ccttataatc acaaaaaacc ttgctaaaaa tagaaaaaat ccaaaaaaaa aagaagaaga    480

gagagagaga gaatttggat tgagttgggt tgggggaaga gaagagtgaa tgagagttcc    540

accattgatc tcttaaacac caaaccccac acccatttcg tgagtgccga gcgtcgttct    600

atctattttt tctctgccta cacacactga tactgagaga aagagaacca actactacag    660

tcacagaaaa ccaaaaaaac actgtgttgt gtgtgtgtca aaaaaaaaac cctaagctaa    720

tgatgatgga tcagcgacag cgagagaagc tgcttcacaa aaccgaggcc tgtgctttcg    780

tggcaggtgt tgttccggag ctttcccttg tcaccgttcc agggaacaac accaacaacg    840

ttaacaacaa caacaacgtt gtttctcatt ctcaatctaa cgggtcgggt cggatccagg    900

aaaacaacca ccaccttgga ctcgttgctg ctgtcacctc cgccttcggt accgttcaaa    960

ggaagaaaag gatggcgaga caaagaagat ccactaaacc cacttcgttg atgaaccatc   1020

tcaacaacca taagcacaac aagcctcgtt ctcttccttc tcccagtgca tcctcctcgt   1080

acgtgccact ctcctccgca actctccagc ccgcacgtga aatcgatcaa agaaggttga   1140

gattcctttt ccagaaggag ttaaagaaca gtgatgttag ctcccttagg agaatgatat   1200
```

tgccaaagaa agcagcagag gctttccttc cagctcttga atccaaagaa ggaattgtaa 1260
tcagcatgga tgatatagat ggtcttcatg tatggagttt caagtacagg ttttggccta 1320
acaacaacag tcggatgtat gtacttgaaa atactggaga ttttgtcaac acacatggcc 1380
ttcgctttgg agattccatt atggtttacc aagatagtga aaacaacaat tatgttattc 1440
aggccaaaaa ggcttctgat caagatgaat ttatggaaga aactagtgat accatcaatg 1500
atatcttcct taatgattat gaggtgaaca aacctggttg cttcaatgta actaatcctg 1560
cagtgaatga tacaggcatg tcattcatat atgagactac cttctcaaat gactcccctc 1620
ttgatttttt gggtggatca atgaccaatt tttcaaggat tgggccagtt gaaacctttg 1680
gctctgttga gaatttgtca cttgatgact tctattaa 1718

<210> SEQ ID NO 44
<211> LENGTH: 1185
<212> TYPE: DNA
<213> ORGANISM: Glycine max

<400> SEQUENCE: 44
atgtttcctg tgtcttcacc atccatccgt cactcactgc ttgggcaatc tctaaccacc 60
accaccaccc cgcagcacca aaccctatgc cacaaactta accctgaaag agaaccaact 120
actacagtca cagaaaacca aaaaaacact gtgttgtgtg tgtgtcaaaa aaaaaaccct 180
aagctaatga tgatggatca gcgacagcga gagaagctgc ttcacaaaac cgaggcctgt 240
gctttcgtgg caggtgttgt tccggagctt tcccttgtca ccgttccagg gaacaacacc 300
aacaacgtta acaacaacaa caacgttgtt tctcattctc aatctaacgg gtcgggtcgg 360
atccaggaaa acaaccacca ccttggactc gttgctgctg tcacctccgc cttcggtacc 420
gttcaaagga agaaaaggat ggcgagacaa agaagatcca ctaaacccac ttcgttgatg 480
aaccatctca acaaccataa gcacaacaag cctcgttctc ttccttctcc cagtgcatcc 540
tcctcgtacg tgccactctc ctccgcaact ctccagcccg cacgtgaaat cgatcaaaga 600
aggttgagat tccttttcca gaaggagtta aagaacagtg atgttagctc ccttaggaga 660
atgatattgc caaagaaagc agcagaggct ttccttccag ctcttgaatc caaagaagga 720
attgtaatca gcatggatga tatagatggt cttcatgtat ggagtttcaa gtacaggttt 780
tggcctaaca acaacagtcg gatgtatgta cttgaaaata ctggagattt tgtcaacaca 840
catggccttc gctttggaga ttccattatg gtttaccaag atagtgaaaa caacaattat 900
gttattcagg ccaaaaaggc ttctgatcaa gatgaattta tggaagaaac tagtgatacc 960
atcaatgata tcttccttaa tgattatgag gtgaacaaac ctggttgctt caatgtaact 1020
aatcctgcag tgaatgatac aggcatgtca ttcatatatg agactacctt ctcaaatgac 1080
tcccctcttg atttttgggg tggatcaatg accaattttt caaggattgg gccagttgaa 1140
acctttggct ctgttgagaa tttgtcactt gatgacttct attaa 1185

<210> SEQ ID NO 45
<211> LENGTH: 394
<212> TYPE: PRT
<213> ORGANISM: Glycine max

<400> SEQUENCE: 45

Met Phe Pro Val Ser Ser Pro Ser Ile Arg His Ser Leu Leu Gly Gln
1 5 10 15

Ser Leu Thr Thr Thr Thr Thr Pro Gln His Gln Thr Leu Cys His Lys

```
            20                  25                  30

Leu Asn Pro Glu Arg Glu Pro Thr Thr Thr Val Thr Glu Asn Gln Lys
        35                  40                  45

Asn Thr Val Leu Cys Val Cys Gln Lys Lys Asn Pro Lys Leu Met Met
    50                  55                  60

Met Asp Gln Arg Gln Arg Glu Lys Leu Leu His Lys Thr Glu Ala Cys
65                  70                  75                  80

Ala Phe Val Ala Gly Val Val Pro Glu Leu Ser Leu Val Thr Val Pro
                85                  90                  95

Gly Asn Asn Thr Asn Asn Val Asn Asn Asn Asn Asn Val Val Ser His
            100                 105                 110

Ser Gln Ser Asn Gly Ser Gly Arg Ile Gln Glu Asn Asn His His Leu
        115                 120                 125

Gly Leu Val Ala Ala Val Thr Ser Ala Phe Gly Thr Val Gln Arg Lys
    130                 135                 140

Lys Arg Met Ala Arg Gln Arg Arg Ser Thr Lys Pro Thr Ser Leu Met
145                 150                 155                 160

Asn His Leu Asn Asn His Lys His Asn Lys Pro Arg Ser Leu Pro Ser
                165                 170                 175

Pro Ser Ala Ser Ser Ser Tyr Val Pro Leu Ser Ser Ala Thr Leu Gln
            180                 185                 190

Pro Ala Arg Glu Ile Asp Gln Arg Arg Leu Arg Phe Leu Phe Gln Lys
        195                 200                 205

Glu Leu Lys Asn Ser Asp Val Ser Ser Leu Arg Arg Met Ile Leu Pro
    210                 215                 220

Lys Lys Ala Ala Glu Ala Phe Leu Pro Ala Leu Glu Ser Lys Glu Gly
225                 230                 235                 240

Ile Val Ile Ser Met Asp Asp Ile Asp Gly Leu His Val Trp Ser Phe
                245                 250                 255

Lys Tyr Arg Phe Trp Pro Asn Asn Asn Ser Arg Met Tyr Val Leu Glu
            260                 265                 270

Asn Thr Gly Asp Phe Val Asn Thr His Gly Leu Arg Phe Gly Asp Ser
        275                 280                 285

Ile Met Val Tyr Gln Asp Ser Glu Asn Asn Asn Tyr Val Ile Gln Ala
    290                 295                 300

Lys Lys Ala Ser Asp Gln Asp Glu Phe Met Glu Glu Thr Ser Asp Thr
305                 310                 315                 320

Ile Asn Asp Ile Phe Leu Asn Asp Tyr Glu Val Asn Lys Pro Gly Cys
                325                 330                 335

Phe Asn Val Thr Asn Pro Ala Val Asn Asp Thr Gly Met Ser Phe Ile
            340                 345                 350

Tyr Glu Thr Thr Phe Ser Asn Asp Ser Pro Leu Asp Phe Leu Gly Gly
        355                 360                 365

Ser Met Thr Asn Phe Ser Arg Ile Gly Pro Val Glu Thr Phe Gly Ser
    370                 375                 380

Val Glu Asn Leu Ser Leu Asp Asp Phe Tyr
385                 390


<210> SEQ ID NO 46
<211> LENGTH: 39
<212> TYPE: DNA
<213> ORGANISM: artificial sequence
<220> FEATURE:
<223> OTHER INFORMATION: primer sequence
```

<400> SEQUENCE: 46
agcggccgca ccatgatgat ggatcagcga cagcgagag 39

<210> SEQ ID NO 47
<211> LENGTH: 4532
<212> TYPE: DNA
<213> ORGANISM: artificial sequence
<220> FEATURE:
<223> OTHER INFORMATION: plasmid sequence

<400> SEQUENCE: 47
cctgaattcc agcacactgg cggccgttac tagtggatcc gagctcggta ccaagcttga 60
tgcatagctt gagtattcta acgcgtcacc taaatagctt ggcgtaatca tggtcatagc 120
tgtttcctgt gtgaaattgt tatccgctca caattccaca caacatacga gccggaagca 180
taaagtgtaa agcctggggt gcctaatgag tgagctaact cacattaatt gcgttgcgct 240
cactgcccgc tttccagtcg ggaaacctgt cgtgccagct gcattaatga atcggccaac 300
gcgcggggag aggcggtttg cgtattgggc gctcttccgc ttcctcgctc actgactcgc 360
tgcgctcggt cgttcggctg cggcgagcgg tatcagctca ctcaaaggcg gtaatacggt 420
tatccacaga atcaggggat aacgcaggaa agaacatgtg agcaaaaggc cagcaaaagg 480
ccaggaaccg taaaaaggcc gcgttgctgg cgtttttcca taggctccgc ccccctgacg 540
agcatcacaa aaatcgacgc tcaagtcaga ggtggcgaaa cccgacagga ctataaagat 600
accaggcgtt tccccctgga agctccctcg tgcgctctcc tgttccgacc ctgccgctta 660
ccggatacct gtccgccttt ctcccttcgg gaagcgtggc gctttctcat agctcacgct 720
gtaggtatct cagttcggtg taggtcgttc gctccaagct gggctgtgtg cacgaacccc 780
ccgttcagcc cgaccgctgc gccttatccg gtaactatcg tcttgagtcc aacccggtaa 840
gacacgactt atcgccactg gcagcagcca ctggtaacag gattagcaga gcgaggtatg 900
taggcggtgc tacagagttc ttgaagtggt ggcctaacta cggctacact agaagaacag 960
tatttggtat ctgcgctctg ctgaagccag ttaccttcgg aaaaagagtt ggtagctctt 1020
gatccggcaa acaaaccacc gctggtagcg gtggtttttt tgtttgcaag cagcagatta 1080
cgcgcagaaa aaaggatctc aagaagatcc tttgatcttt tctacggggt ctgacgctc 1140 agtggaacga aaactcacgt taagggattt tggtcatgag attatcaaaa aggatcttca 1200
cctagatcct tttaaattaa aaatgaagtt ttagcacgtg tcagtcctgc tcctcggcca 1260
cgaagtgcac gcagttgccg gccgggtcgc gcagggcgaa ctcccgcccc cacggctgct 1320
cgccgatctc ggtcatggcc ggcccggagg cgtcccggaa gttcgtggac acgacctccg 1380
accactcggc gtacagctcg tccaggccgc gcacccacac ccaggccagg gtgttgtccg 1440
gcaccacctg gtcctggacc gcgctgatga acagggtcac gtcgtcccgg accacaccgg 1500
cgaagtcgtc ctccacgaag tcccgggaga acccgagccg gtcggtccag aactcgaccg 1560
ctccggcgac gtcgcgcgcg gtgagcaccg gaacggcact ggtcaacttg gccatggtgg 1620
ccctcctcac gtgctattat tgaagcattt atcagggtta ttgtctcatg agcggataca 1680
tatttgaatg tatttagaaa aataaacaaa taggggttcc gcgcacattt ccccgaaaag 1740
tgccacctga tgcggtgtga aataccgcac agatgcgtaa ggagaaaata ccgcatcagg 1800
aaattgtaag cgttaataat tcagaagaac tcgtcaagaa ggcgatagaa ggcgatgcgc 1860
tgcgaatcgg gagcggcgat accgtaaagc acgaggaagc ggtcagccca ttcgccgcca 1920
agctcttcag caatatcacg ggtagccaac gctatgtcct gatagcggtc cgccacaccc 1980

-continued

```
agccggccac agtcgatgaa tccagaaaag cggccatttt ccaccatgat attcggcaag   2040
caggcatcgc catgggtcac gacgagatcc tcgccgtcgg gcatgctcgc cttgagcctg   2100
gcgaacagtt cggctggcgc gagcccctga tgctcttcgt ccagatcatc ctgatcgaca   2160
agaccggctt ccatccgagt acgtgctcgc tcgatgcgat gtttcgcttg gtggtcgaat   2220
gggcaggtag ccggatcaag cgtatgcagc cgccgcattg catcagccat gatggatact   2280
ttctcggcag gagcaaggtg agatgacagg agatcctgcc ccggcacttc gcccaatagc   2340
agccagtccc ttcccgcttc agtgacaacg tcgagcacag ctgcgcaagg aacgcccgtc   2400
gtggccagcc acgatagccg cgctgcctcg tcttgcagtt cattcagggc accggacagg   2460
tcggtcttga caaaaagaac cgggcgcccc tgcgctgaca gccggaacac ggcggcatca   2520
gagcagccga ttgtctgttg tgcccagtca tagccgaata gcctctccac ccaagcggcc   2580
ggagaacctg cgtgcaatcc atcttgttca atcatgcgaa acgatcctca tcctgtctct   2640
tgatcagagc ttgatcccct gcgccatcag atccttggcg gcaagaaagc catccagttt   2700
actttgcagg gcttcccaac cttaccagag ggcgccccag ctggcaattc cggttcgctt   2760
gctgtccata aaaccgccca gtctagctat cgccatgtaa gcccactgca agctacctgc   2820
tttctctttg cgcttgcgtt ttcccttgtc cagatagccc agtagctgac attcatccgg   2880
ggtcagcacc gtttctgcgg actggctttc tacgtgaaaa ggatctaggt gaagatcctt   2940
tttgataatc tcatgcctga catttatatt ccccagaaca tcaggttaat ggcgtttttg   3000
atgtcatttt cgcggtggct gagatcagcc acttcttccc cgataacgga gaccggcaca   3060
ctggccatat cggtggtcat catgcgccag ctttcatccc cgatatgcac caccgggtaa   3120
agttcacggg agactttatc tgacagcaga cgtgcactgg ccagggggat caccatccgt   3180
cgccccggcg tgtcaataat atcactctgt acatccacaa acagacgata acggctctct   3240
cttttatagg tgtaaacctt aaactgccgt acgtataggc tgcgcaactg ttgggaaggg   3300
cgatcggtgc gggcctcttc gctattacgc cagctggcga aagggggatg tgctgcaagg   3360
cgattaagtt gggtaacgcc agggttttcc cagtcacgac gttgtaaaac gacggccagt   3420
gaattgtaat acgactcact atagggcgaa ttgggccctc tagatgcatg ctcgagcggc   3480
cgccagtgtg atggatatct gcagaattca ggtgcggccg cttaatagaa gtcatcaagt   3540
gacaaattct caacagagcc aaaggtttca actggcccaa tccttgaaaa attggtcatt   3600
gatccaccca aaaaatcaag aggggagtca tttgagaagg tagtctcata tatgaatgac   3660
atgcctgtat cattcactgc aggattagtt acattgaagc aaccaggttt gttcacctca   3720
taatcattaa ggaagatatc attgatggta tcactagttt cttccataaa ttcatcttga   3780
tcagaagcct tttggcctg aataacataa ttgttgtttt cactatcttg gtaaaccata   3840
atggaatctc caaagcgaag gccatgtgtg ttgacaaaat ctccagtatt ttcaagtaca   3900
tacatccgac tgttgttgtt aggccaaaac ctgtacttga aactccatac atgaagacca   3960
tctatatcat ccatgctgat tacaattcct tctttggatt caagagctgg aaggaaagcc   4020
tctgctgctt tctttggcaa tatcattctc ctaagggagc taacatcact gttctttaac   4080
tccttctgga aaaggaatct caaccttctt tgatcgattt cacgtgcggg ctggagagtt   4140
gcggaggaga gtggcacgta cgaggaggat gcactgggag aaggaagaga acgaggcttg   4200
ttgtgcttat ggttgttgag atggttcatc aacgaagtgg gtttagtgga tcttctttgt   4260
ctcgccatcc ttttcttcct ttgaacggta ccgaaggcgg aggtgacagc agcaacgagt   4320
```

-continued

```
ccaaggtggt ggttgttttc ctggatccga cccgacccgt tagattgaga atgagaaaca   4380

acgttgttgt tgttgttaac gttgttggtg ttgttccctg gaacggtgac aagggaaagc   4440

tccggaacaa cacctgccac gaaagcacag gcctcggttt tgtgaagcag cttctctcgc   4500

tgtcgctgat ccatcatcat ggtgcggccg ct                                  4532


<210> SEQ ID NO 48
<211> LENGTH: 999
<212> TYPE: DNA
<213> ORGANISM: Glycine max

<400> SEQUENCE: 48

atgatgatgg atcagcgaca gcgagagaag ctgcttcaca aaaccgaggc ctgtgctttc     60

gtggcaggtg ttgttccgga gctttccctt gtcaccgttc cagggaacaa caccaacaac    120

gttaacaaca acaacaacgt tgtttctcat tctcaatcta acgggtcggg tcggatccag    180

gaaaacaacc accaccttgg actcgttgct gctgtcacct ccgccttcgg taccgttcaa    240

aggaagaaaa ggatggcgag acaaagaaga tccactaaac ccacttcgtt gatgaaccat    300

ctcaacaacc ataagcacaa caagcctcgt tctcttcctt ctcccagtgc atcctcctcg    360

tacgtgccac tctcctccgc aactctccag cccgcacgtg aaatcgatca aagaaggttg    420

agattccttt tccagaagga gttaaagaac agtgatgtta gctcccttag gagaatgata    480

ttgccaaaga aagcagcaga ggctttcctt ccagctcttg aatccaaaga aggaattgta    540

atcagcatgg atgatataga tggtcttcat gtatggagtt tcaagtacag gttttggcct    600

aacaacaaca gtcggatgta tgtacttgaa aatactggag attttgtcaa cacacatggc    660

cttcgctttg gagattccat tatggtttac caagatagtg aaaacaacaa ttatgttatt    720

caggccaaaa aggcttctga tcaagatgaa tttatggaag aaactagtga taccatcaat    780

gatatcttcc ttaatgatta tgaggtgaac aaacctggtt gcttcaatgt aactaatcct    840

gcagtgaatg atacaggcat gtcattcata tatgagacta ccttctcaaa tgactcccct    900

cttgattttt tgggtggatc aatgaccaat ttttcaagga ttgggccagt tgaaaccttt    960

ggctctgttg agaatttgtc acttgatgac ttctattaa                           999


<210> SEQ ID NO 49
<211> LENGTH: 332
<212> TYPE: PRT
<213> ORGANISM: Glycine max

<400> SEQUENCE: 49

Met Met Met Asp Gln Arg Gln Arg Glu Lys Leu Leu His Lys Thr Glu
1               5                   10                  15

Ala Cys Ala Phe Val Ala Gly Val Val Pro Glu Leu Ser Leu Val Thr
            20                  25                  30

Val Pro Gly Asn Asn Thr Asn Asn Val Asn Asn Asn Asn Asn Val Val
        35                  40                  45

Ser His Ser Gln Ser Asn Gly Ser Gly Arg Ile Gln Glu Asn Asn His
    50                  55                  60

His Leu Gly Leu Val Ala Ala Val Thr Ser Ala Phe Gly Thr Val Gln
65                  70                  75                  80

Arg Lys Lys Arg Met Ala Arg Gln Arg Arg Ser Thr Lys Pro Thr Ser
                85                  90                  95

Leu Met Asn His Leu Asn Asn His Lys His Asn Lys Pro Arg Ser Leu
            100                 105                 110
```

```
Pro Ser Pro Ser Ala Ser Ser Ser Tyr Val Pro Leu Ser Ser Ala Thr
        115                 120                 125

Leu Gln Pro Ala Arg Glu Ile Asp Gln Arg Arg Leu Arg Phe Leu Phe
    130                 135                 140

Gln Lys Glu Leu Lys Asn Ser Asp Val Ser Ser Leu Arg Arg Met Ile
145                 150                 155                 160

Leu Pro Lys Lys Ala Ala Glu Ala Phe Leu Pro Ala Leu Glu Ser Lys
                165                 170                 175

Glu Gly Ile Val Ile Ser Met Asp Asp Ile Asp Gly Leu His Val Trp
            180                 185                 190

Ser Phe Lys Tyr Arg Phe Trp Pro Asn Asn Asn Ser Arg Met Tyr Val
        195                 200                 205

Leu Glu Asn Thr Gly Asp Phe Val Asn Thr His Gly Leu Arg Phe Gly
    210                 215                 220

Asp Ser Ile Met Val Tyr Gln Asp Ser Glu Asn Asn Asn Tyr Val Ile
225                 230                 235                 240

Gln Ala Lys Lys Ala Ser Asp Gln Asp Glu Phe Met Glu Glu Thr Ser
                245                 250                 255

Asp Thr Ile Asn Asp Ile Phe Leu Asn Asp Tyr Glu Val Asn Lys Pro
            260                 265                 270

Gly Cys Phe Asn Val Thr Asn Pro Ala Val Asn Asp Thr Gly Met Ser
        275                 280                 285

Phe Ile Tyr Glu Thr Thr Phe Ser Asn Asp Ser Pro Leu Asp Phe Leu
    290                 295                 300

Gly Gly Ser Met Thr Asn Phe Ser Arg Ile Gly Pro Val Glu Thr Phe
305                 310                 315                 320

Gly Ser Val Glu Asn Leu Ser Leu Asp Asp Phe Tyr
                325                 330
```

<210> SEQ ID NO 50
<211> LENGTH: 9979
<212> TYPE: DNA
<213> ORGANISM: artificial sequence
<220> FEATURE:
<223> OTHER INFORMATION: plasmid sequence

<400> SEQUENCE: 50

```
ggccgcattt cgcaccaaat caatgaaagt aataatgaaa agtctgaata agaatactta     60

ggcttagatg cctttgttac ttgtgtaaaa taacttgagt catgtacctt tggcggaaac    120

agaataaata aaaggtgaaa ttccaatgct ctatgtataa gttagtaata cttaatgtgt    180

tctacggttg tttcaatatc atcaaactct aattgaaact ttagaaccac aaatctcaat    240

cttttcttaa tgaaatgaaa aatcttaatt gtaccatgtt tatgttaaac accttacaat    300

taattggttg gagaggagga ccaaccgatg ggacaacatt gggagaaaga gattcaatgg    360

agatttggat aggagaacaa cattcttttt cacttcaata caagatgagt gcaacactaa    420

ggatatgtat gagactttca gaagctacga caacatagat gagtgaggtg gtgattccta    480

gcaagaaaga cattagagga agccaaaatc gaacaaggaa gacatcaagg gcaagagaca    540

ggaccatcca tctcaggaaa aggagctttg ggatagtccg agaagttgta caagaaattt    600

tttggagggt gagtgatgca ttgctggtga ctttaactca atcaaaattg agaaagaaag    660

aaaagggagg gggctcacat gtgaatagaa gggaaacggg agaattttac agttttgatc    720

taatgggcat cccagctagt ggtaacatat tcaccatgtt taaccttcac gtacgagatc    780

cggccggcca gatcctgcag gagatccaag cttggcgcgc cgttctatag tgtcacctaa    840
```

atcgtatgtg tatgatacat aaggttatgt attaattgta gccgcgttct aacgacaata 900
tgtccatatg gtgcactctc agtacaatct gctctgatgc cgcatagtta agccagcccc 960
gacacccgcc aacacccgct gacgcgccct gacgggcttg tctgctcccg gcatccgctt 1020
acagacaagc tgtgaccgtc tccgggagct gcatgtgtca gaggttttca ccgtcatcac 1080
cgaaacgcgc gagacgaaag ggcctcgtga tacgcctatt tttataggtt aatgtcatga 1140
ccaaaatccc ttaacgtgag ttttcgttcc actgagcgtc agaccccgta gaaaagatca 1200
aaggatcttc ttgagatcct ttttttctgc gcgtaatctg ctgcttgcaa acaaaaaaac 1260
caccgctacc agcggtggtt tgtttgccgg atcaagagct accaactctt tttccgaagg 1320
taactggctt cagcagagcg cagataccaa atactgtcct tctagtgtag ccgtagttag 1380
gccaccactt caagaactct gtagcaccgc ctacatacct cgctctgcta atcctgttac 1440
cagtggctgc tgccagtggc gataagtcgt gtcttaccgg gttggactca agacgatagt 1500
taccggataa ggcgcagcgg tcgggctgaa cggggggttc gtgcacacag cccagcttgg 1560
agcgaacgac ctacaccgaa ctgagatacc tacagcgtga gcattgagaa agcgccacgc 1620
ttcccgaagg gagaaaggcg gacaggtatc cggtaagcgg cagggtcgga acaggagagc 1680
gcacgaggga gcttccaggg ggaaacgcct ggtatcttta tagtcctgtc gggtttcgcc 1740
acctctgact tgagcgtcga tttttgtgat gctcgtcagg ggggcggagc ctatggaaaa 1800
acgccagcaa cgcggccttt ttacggttcc tggccttttg ctggcctttt gctcacatgt 1860
tctttcctgc gttatcccct gattctgtgg ataaccgtat taccgccttt gagtgagctg 1920
ataccgctcg ccgcagccga acgaccgagc gcagcgagtc agtgagcgag gaagcggaag 1980
agcgcccaat acgcaaaccg cctctccccg cgcgttggcc gattcattaa tgcaggttga 2040
tcgattcgac atcgatctag taacatagat gacaccgcgc gcgataattt atcctagttt 2100
gcgcgctata ttttgttttc tatcgcgtat taaatgtata attgcgggac tctaatcata 2160
aaaacccatc tcataaataa cgtcatgcat tacatgttaa ttattacatg cttaacgtaa 2220
ttcaacagaa attatatgat aatcatcgca agaccggcaa caggattcaa tcttaagaaa 2280
ctttattgcc aaatgtttga acgatctgct tcgacgcact ccttctttag gtacctcact 2340
attcctttgc cctcggacga gtgctggggc gtcggtttcc actatcggcg agtacttcta 2400
cacagccatc ggtccagacg gccgcgcttc tgcgggcgat ttgtgtacgc ccgacagtcc 2460
cggctccgga tcggacgatt gcgtcgcatc gaccctgcgc ccaagctgca tcatcgaaat 2520
tgccgtcaac caagctctga tagagttggt caagaccaat gcggagcata tacgcccgga 2580
gccgcggcga tcctgcaagc tccggatgcc tccgctcgaa gtagcgcgtc tgctgctcca 2640
tacaagccaa ccacggcctc cagaagaaga tgttggcgac ctcgtattgg gaatccccga 2700
acatcgcctc gctccagtca atgaccgctg ttatgcggcc attgtccgtc aggacattgt 2760
tggagccgaa atccgcgtgc acgaggtgcc ggacttcggg gcagtcctcg gcccaaagca 2820
tcagctcatc gagagcctgc gcgacggacg cactgacggt gtcgtccatc acagtttgcc 2880
agtgatacac atggggatca gcaatcgcgc atatgaaatc acgccatgta gtgtattgac 2940
cgattccttg cggtccgaat gggccgaacc cgctcgtctg gctaagatcg gccgcagcga 3000
tcgcatccat ggcctccgcg accggctgca gaacagcggg cagttcggtt tcaggcaggt 3060
cttgcaacgt gacaccctgt gcacggcggg agatgcaata ggtcaggctc tcgctgaatt 3120
ccccaatgtc aagcacttcc ggaatcggga gcgcggccga tgcaaagtgc cgataaacat 3180
aacgatcttt gtagaaacca tcggcgcagc tatttacccg caggacatat ccacgccctc 3240
ctacatcgaa gctgaaagca cgagattctt cgccctccga gagctgcatc aggtcggaga 3300
cgctgtcgaa cttttcgatc agaaacttct cgacagacgt cgcggtgagt tcaggctttt 3360
tcatggttta ataagaagag aaaagagttc ttttgttatg gctgaagtaa tagagaaatg 3420
agctcgagcg tgtcctctcc aaatgaaatg aacttcctta tatagaggaa gggtcttgcg 3480
aaggatagtg ggattgtgcg tcatccctta cgtcagtgga gatgtcacat caatccactt 3540
gctttgaaga cgtggttgga acgtcttctt tttccacgat gctcctcgtg ggtgggggtc 3600
catctttggg accactgtcg gcagaggcat cttgaatgat agcctttcct ttatcgcaat 3660
gatggcattt gtaggagcca ccttcctttt ctactgtcct ttcgatgaag tgacagatag 3720
ctgggcaatg gaatccgagg aggtttcccg aaattatcct ttgttgaaaa gtctcaatag 3780
ccctttggtc ttctgagact gtatctttga catttttgga gtagaccaga gtgtcgtgct 3840
ccaccatgtt gacgaagatt ttcttcttgt cattgagtcg taaaagactc tgtatgaact 3900
gttcgccagt cttcacggcg agttctgtta gatcctcgat ttgaatctta gactccatgc 3960
atggccttag attcagtagg aactaccttt ttagagactc caatctctat tacttgcctt 4020
ggtttatgaa gcaagccttg aatcgtccat actggaatag tacttctgat cttgagaaat 4080
atgtctttct ctgtgttctt gatgcaatta gtcctgaatc ttttgactgc atctttaacc 4140
ttcttgggaa ggtatttgat ctcctggaga ttgttactcg ggtagatcgt cttgatgaga 4200
cctgctgcgt aggcctctct aaccatctgt gggtcagcat tctttctgaa attgaagagg 4260
ctaaccttct cattatcagt ggtgaacata gtgtcgtcac cttcaccttc gaacttcctt 4320
cctagatcgt aaagatagag gaaatcgtcc attgtaatct ccggggcaaa ggagatctct 4380
tttggggctg gatcactgct gggccttttg gttcctagcg tgagccagtg ggctttttgc 4440
tttggtgggc ttgttagggc cttagcaaag ctcttgggct tgagttgagc ttctcctttg 4500
gggatgaagt tcaacctgtc tgtttgctga cttgttgtgt acgcgtcagc tgctgctctt 4560
gcctctgtaa tagtggcaaa tttcttgtgt gcaactccgg gaacgccgtt tgttgccgcc 4620
tttgtacaac cccagtcatc gtatataccg gcatgtggac cgttatacac aacgtagtag 4680
ttgatatgag ggtgttgaat acccgattct gctctgagag gagcaactgt gctgttaagc 4740
tcagattttt gtgggattgg aattggatcg atctcgatcc cgcgaaatta atacgactca 4800
ctatagggag accacaacgg tttccctcta gaaataattt tgtttaactt taagaaggag 4860
atatacccat ggaaaagcct gaactcaccg cgacgtctgt cgagaagttt ctgatcgaaa 4920
agttcgacag cgtctccgac ctgatgcagc tctcggaggg cgaagaatct cgtgctttca 4980
gcttcgatgt aggagggcgt ggatatgtcc tgcgggtaaa tagctgcgcc gatggtttct 5040
acaaagatcg ttatgtttat cggcactttg catcggccgc gctcccgatt ccggaagtgc 5100
ttgacattgg ggaattcagc gagagcctga cctattgcat ctcccgccgt gcacagggtg 5160
tcacgttgca agacctgcct gaaaccgaac tgcccgctgt tctgcagccg gtcgcggagg 5220
ctatggatgc gatcgctgcg gccgatctta gccagacgag cgggttcggc ccattcggac 5280
cgcaaggaat cggtcaatac actacatggc gtgatttcat atgcgcgatt gctgatcccc 5340
atgtgtatca ctggcaaact gtgatggacg acaccgtcag tgcgtccgtc gcgcaggctc 5400
tcgatgagct gatgctttgg gccgaggact gccccgaagt ccggcacctc gtgcacgcgg 5460
atttcggctc caacaatgtc ctgacggaca atggccgcat aacagcggtc attgactgga 5520
gcgaggcgat gttcggggat tcccaatacg aggtcgccaa catcttcttc tggaggccgt 5580

```
ggttggcttg tatggagcag cagacgcgct acttcgagcg gaggcatccg gagcttgcag   5640
gatcgccgcg gctccgggcg tatatgctcc gcattggtct tgaccaactc tatcagagct   5700
tggttgacgg caatttcgat gatgcagctt gggcgcaggg tcgatgcgac gcaatcgtcc   5760
gatccggagc cgggactgtc gggcgtacac aaatcgcccg cagaagcgcg gccgtctgga   5820
ccgatggctg tgtagaagta ctcgccgata gtggaaaccg acgccccagc actcgtccga   5880
gggcaaagga atagtgaggt acagcttgga tcgatccggc tgctaacaaa gcccgaaagg   5940
aagctgagtt ggctgctgcc accgctgagc aataactagc ataacccctt ggggcctcta   6000
aacgggtctt gaggggtttt ttgctgaaag gaggaactat atccggatga tcgggcgcgc   6060
cgtcgacgga tccgtacgtc ctgcaggtaa attgcagctg aaggacagtg aagggtgaat   6120
ttatccattt aaaccatttt ctttttaaca catttcttat ggtaatctct tctcactaca   6180
ctataaaaat ggcttctcaa tcccattttc tacatcatcc cattctattg agttttgttt   6240
atttgctttc acttttttt ttatctgcct cttcccttaa tttgcttgac ttcttcttca   6300
cattttgctt tgttttctcc tccggcttcc ggtatttcaa attcaagatg agcaagttga   6360
aatttataaa tagaaataca gatattattt acaacgtcaa atctttggta ttttcaatat   6420
ttgaatgggg taaatttgtc atatagtcat catcactgac tacttatcta acctatttaa   6480
tttggagcat attctttata aggtccctct cacggccaat gtctaattat tgatatacag   6540
ctcttgtttt ctagtgctgc ttataatatt atctacacat atatatggta ctgcacacta   6600
ctactatata gtagtaagta aactagcaac agccggggcc aaactccaat aactaggcat   6660
tggggtttag ttggtaatat aaatataaca tcaaaaagtc tttgcttgtg acgaacatca   6720
caatgcaccc accattgatg ccacgacaga cattgttaat ttttttttta atttttaaaa   6780
aagaagcaat tccaatagtt ctatattaca atctcacgtg atccaagcac aacgtttcat   6840
tttttgtaca tgctcgatat ataaataata tttcatttta tagtaaaata taatgacatt   6900
ttcgaatata atttttgaaa tttcattttc caaatgaaat actaatatta atattaatga   6960
gattaccaca aatcatgtta tgaatgaaat aaagagtttt ggcattctaa ctttctttga   7020
atagaacaaa atgtatacaa cactctccat atatacacga tttattcagg gatcatatac   7080
attctctcat gattaacata gtctgctttc ttcacgtcta agcagataat ttttggtcca   7140
caagataaaa ttatcattag tcgttttaat taattccttg agcatcaagc actaaaataa   7200
ttaaacttct ccattaccaa aaaaaaaaga taggtgattc agtaacatgt agtactagta   7260
ctactgattt tttttttctt ttgattttaa tgaatggttc gtatcgagca tcgagaaatc   7320
catttattag gtgtgtaatg taatagtagt atttccttga ttttcagtaa taagatggat   7380
tcttacattt atatctgttt gacagaaaat gttgtcaatg catttcttgg gcacaaagtt   7440
ttttgaaaca tgaattaatt ttttcaaaat atttatgaca tcaaattgac cctaaaataa   7500
gtgataaagc tttaacgtgg aatgacatta atttttccat gataaataaa acacttaaaa   7560
cattttaata ttaatattat aatcagttac aactatgttc aattaatgca ataactttta   7620
aataaatatt aaaatatttt ttttctgttc tccaataaag agatcttgtt gcacggaaaa   7680
agtcacattc ttatttagta aaaaattata attattgttt gaaaaatatc attttcactg   7740
cagaaaattt gatccagctc tacagatcat acttttattg tacaataata caataaaaat   7800
attcatctgc aggaaatatc attttcattg tacaataata taaagataaa tatataccag   7860
aaaagaaaaa gaaactgatg tggcacaatg tattcactga aagaatgcat attgtatttc   7920
```

acctttcaag cagcactaag aatatacttc ttttattata cttgtgcatt tactcaacca 7980
ccctcggtgg agtaagaaag aagatagata aaagtttttt ttgacatttg gtgaatctct 8040
taattaaaaa aataaaataa tccatttcct ttatttaatt tctttttcc catctgtgaa 8100
attccaattc tgcttcgcgc tcctgtctat aaattgactt agccaccacc tcagtttcca 8160
ttcattcact tcttctcttt atacccccc tctctttttt gcgttcattc tgttttcgta 8220
agtactgttg tttttctctt ctatttcttt ttttgtttgt gttgtttttt tttcttcctt 8280
atcgttgttc tgcctctcct ctgtttcggt gctctgttca ccacttccac gtgagaatga 8340
tcttccttct ttgcatgttc attctctcgt gaccactgga tcagactcca tgttctgatc 8400
cagggtctct ctctaacgcc tgtactttca tccatgacca ccttaaaaac aacatggggg 8460
tggtgctgtt acactaactc tgtttctggg gtgctgtctt tgttcaattt tactcagaaa 8520
atatcttttc ttggattcta ttcggtgtgt gggaacatga tcctgtcggt cggttgtttt 8580
taggttaatc cttaactggt tacaaggatc taacgcttga atgcatgtcc tgagttaaag 8640
aaacaaaaga agaacacacc tagtacagcc tggcctcgaa ccaagaactt ctttgttggt 8700
ttctcattat tactaaaata aaataaagta tacgttttct tttttctttg ggatgaacgg 8760
ttcagactta tgagaagttt aagctaatcc tgtagtggag tgttcaattt attttaaact 8820
ttaaagcaat agctcaagca ctaaacttct ttttcaagtt caaccacttt ggtagcttgc 8880
taattgctgc tattgttcta attaattaat gtaattattg tttaaaaaag aaaagttggt 8940
gacactggaa taaaaaagtg tactatctgg caattattct tctgcagcaa tgtttgaggt 9000
tgaaatctta gtagaacaaa gtagaagatc tggtatttat attttttgta gacagatggt 9060
gggggtgggt ggtaggcctt gaaatccaat atagttttgt agaataattt tattattttt 9120
tttttttgct cacttgtttg tggtattgat tttgtgatga ctcaagatta atgatttacc 9180
ttcatttttt tcatggtgac atattatgta tattcttgat ctgtttctta cacttctttt 9240
tcgttgttgt agctgttgaa gtctgcggcc gcaccatgga aactggaggc tttcacggct 9300
accgcaagct ccccaacacc accgctgggt tgaagctgtc agtgtcagac atgaacatga 9360
acatgaggca gcagcaggta gcatcatcag atcagaactg cagcaaccac agtgcagcag 9420
gagaggagaa cgaatgcacg gtgagggagc aagacaggtt catgccaatc gctaacgtga 9480
tacggatcat gcgcaagatt ctccctccac acgcaaaaat ctccgatgat gcaaaggaga 9540
caatccaaga gtgcgtgtcg gagtacatca gcttcatcac cggggaggcg aacgagcgtt 9600
gccagaggga gcaacggaag accataaccg cagaggacgt gctttgggcc atgagcaagc 9660
ttggattcga cgactacatc gaaccgttga ccatgtacct tcaccgctac cgtgaacttg 9720
agggtgaccg cacctctatg aggggtgaac cactcgggaa gaggactgtg gaatacgcca 9780
cgcttggtgt tgctactgct tttgtccctc caccctatca tcaccacaat gggtactttg 9840
gtgctgccat gcccatgggg acttacgtta gggaagcgcc accaaataca gcctcctccc 9900
atcaccacca ccaccaccac caccaccatg ctcgtggaat ctccaatgct catgaaccaa 9960
atgctcgctc catataagc 9979

<210> SEQ ID NO 51
<211> LENGTH: 10513
<212> TYPE: DNA
<213> ORGANISM: artificial sequence
<220> FEATURE:
<223> OTHER INFORMATION: plasmid sequence

<400> SEQUENCE: 51

-continued ggccgcattt cgcaccaaat caatgaaagt aataatgaaa agtctgaata agaatactta 60
ggcttagatg cctttgttac ttgtgtaaaa taacttgagt catgtacctt tggcggaaac 120
agaataaata aaaggtgaaa ttccaatgct ctatgtataa gttagtaata cttaatgtgt 180
tctacggttg tttcaatatc atcaaactct aattgaaact ttagaaccac aaatctcaat 240
cttttcttaa tgaaatgaaa aatcttaatt gtaccatgtt tatgttaaac accttacaat 300
taattggttg gagaggagga ccaaccgatg ggacaacatt gggagaaaga gattcaatgg 360
agatttggat aggagaacaa cattcttttt cacttcaata caagatgagt gcaacactaa 420
ggatatgtat gagactttca gaagctacga caacatagat gagtgaggtg gtgattccta 480
gcaagaaaga cattagagga agccaaaatc gaacaaggaa gacatcaagg gcaagagaca 540
ggaccatcca tctcaggaaa aggagctttg ggatagtccg agaagttgta caagaaattt 600
tttggagggt gagtgatgca ttgctggtga ctttaactca atcaaaattg agaaagaaag 660
aaaagggagg gggctcacat gtgaatagaa gggaaacggg agaattttac agttttgatc 720
taatgggcat cccagctagt ggtaacatat tcaccatgtt taaccttcac gtacgagatc 780
cggccggcca gatcctgcag gagatccaag cttggcgcgc cgttctatag tgtcacctaa 840
atcgtatgtg tatgatacat aaggttatgt attaattgta gccgcgttct aacgacaata 900
tgtccatatg gtgcactctc agtacaatct gctctgatgc cgcatagtta agccagcccc 960
gacacccgcc aacacccgct gacgcgccct gacgggcttg tctgctcccg gcatccgctt 1020
acagacaagc tgtgaccgtc tccgggagct gcatgtgtca gaggttttca ccgtcatcac 1080
cgaaacgcgc gagacgaaag ggcctcgtga tacgcctatt tttataggtt aatgtcatga 1140
ccaaaatccc ttaacgtgag ttttcgttcc actgagcgtc agaccccgta gaaaagatca 1200
aaggatcttc ttgagatcct ttttttctgc gcgtaatctg ctgcttgcaa acaaaaaaac 1260
caccgctacc agcggtggtt tgtttgccgg atcaagagct accaactctt tttccgaagg 1320
taactggctt cagcagagcg cagataccaa atactgtcct tctagtgtag ccgtagttag 1380
gccaccactt caagaactct gtagcaccgc ctacatacct cgctctgcta atcctgttac 1440
cagtggctgc tgccagtggc gataagtcgt gtcttaccgg gttggactca agacgatagt 1500
taccggataa ggcgcagcgg tcgggctgaa cggggggttc gtgcacacag cccagcttgg 1560
agcgaacgac ctacaccgaa ctgagatacc tacagcgtga gcattgagaa agcgccacgc 1620
ttcccgaagg gagaaaggcg gacaggtatc cggtaagcgg cagggtcgga acaggagagc 1680
gcacgaggga gcttccaggg ggaaacgcct ggtatcttta tagtcctgtc gggtttcgcc 1740
acctctgact tgagcgtcga tttttgtgat gctcgtcagg ggggcggagc ctatggaaaa 1800
acgccagcaa cgcggccttt ttacggttcc tggccttttg ctggcctttt gctcacatgt 1860
tctttcctgc gttatcccct gattctgtgg ataaccgtat taccgccttt gagtgagctg 1920
ataccgctcg ccgcagccga acgaccgagc gcagcgagtc agtgagcgag gaagcggaag 1980
agcgcccaat acgcaaaccg cctctccccg cgcgttggcc gattcattaa tgcaggttga 2040
tcgattcgac atcgatctag taacatagat gacaccgcgc gcgataattt atcctagttt 2100
gcgcgctata ttttgttttc tatcgcgtat taaatgtata attgcgggac tctaatcata 2160
aaaacccatc tcataaataa cgtcatgcat tacatgttaa ttattacatg cttaacgtaa 2220
ttcaacagaa attatatgat aatcatcgca agaccggcaa caggattcaa tcttaagaaa 2280
ctttattgcc aaatgtttga acgatctgct tcgacgcact ccttctttag gtacctcact 2340

-continued

```
attcctttgc cctcggacga gtgctggggc gtcggtttcc actatcggcg agtacttcta   2400
cacagccatc ggtccagacg gccgcgcttc tgcgggcgat ttgtgtacgc ccgacagtcc   2460
cggctccgga tcggacgatt gcgtcgcatc gaccctgcgc ccaagctgca tcatcgaaat   2520
tgccgtcaac caagctctga tagagttggt caagaccaat gcggagcata tacgcccgga   2580
gccgcggcga tcctgcaagc tccggatgcc tccgctcgaa gtagcgcgtc tgctgctcca   2640
tacaagccaa ccacggcctc cagaagaaga tgttggcgac ctcgtattgg gaatccccga   2700
acatcgcctc gctccagtca atgaccgctg ttatgcggcc attgtccgtc aggacattgt   2760
tggagccgaa atccgcgtgc acgaggtgcc ggacttcggg gcagtcctcg gcccaaagca   2820
tcagctcatc gagagcctgc gcgacggacg cactgacggt gtcgtccatc acagtttgcc   2880
agtgatacac atggggatca gcaatcgcgc atatgaaatc acgccatgta gtgtattgac   2940
cgattccttg cggtccgaat gggccgaacc cgctcgtctg gctaagatcg gccgcagcga   3000
tcgcatccat ggcctccgcg accggctgca gaacagcggg cagttcggtt tcaggcaggt   3060
cttgcaacgt gacaccctgt gcacggcggg agatgcaata ggtcaggctc tcgctgaatt   3120
ccccaatgtc aagcacttcc ggaatcggga gcgcggccga tgcaaagtgc cgataaacat   3180
aacgatcttt gtagaaacca tcggcgcagc tatttacccg caggacatat ccacgccctc   3240
ctacatcgaa gctgaaagca cgagattctt cgccctccga gagctgcatc aggtcggaga   3300
cgctgtcgaa cttttcgatc agaaacttct cgacagacgt cgcggtgagt tcaggctttt   3360
tcatggttta ataagaagag aaaagagttc ttttgttatg gctgaagtaa tagagaaatg   3420
agctcgagcg tgtcctctcc aaatgaaatg aacttcctta tatagaggaa gggtcttgcg   3480
aaggatagtg ggattgtgcg tcatccctta cgtcagtgga gatgtcacat caatccactt   3540
gctttgaaga cgtggttgga acgtcttctt tttccacgat gctcctcgtg ggtgggggtc   3600
catctttggg accactgtcg gcagaggcat cttgaatgat agcctttcct ttatcgcaat   3660
gatggcattt gtaggagcca ccttcctttt ctactgtcct ttcgatgaag tgacagatag   3720
ctgggcaatg gaatccgagg aggtttcccg aaattatcct ttgttgaaaa gtctcaatag   3780
ccctttggtc ttctgagact gtatctttga catttttgga gtagaccaga gtgtcgtgct   3840
ccaccatgtt gacgaagatt ttcttcttgt cattgagtcg taaaagactc tgtatgaact   3900
gttcgccagt cttcacggcg agttctgtta gatcctcgat ttgaatctta gactccatgc   3960
atggccttag attcagtagg aactaccttt ttagagactc caatctctat tacttgcctt   4020
ggtttatgaa gcaagccttg aatcgtccat actggaatag tacttctgat cttgagaaat   4080
atgtctttct ctgtgttctt gatgcaatta gtcctgaatc ttttgactgc atctttaacc   4140
ttcttgggaa ggtatttgat ctcctggaga ttgttactcg ggtagatcgt cttgatgaga   4200
cctgctgcgt aggcctctct aaccatctgt gggtcagcat tctttctgaa attgaagagg   4260
ctaaccttct cattatcagt ggtgaacata gtgtcgtcac cttcaccttc gaacttcctt   4320
cctagatcgt aaagatagag gaaatcgtcc attgtaatct ccggggcaaa ggagatctct   4380
tttggggctg gatcactgct gggccttttg gttcctagcg tgagccagtg ggctttttgc   4440
tttggtgggc ttgttagggc cttagcaaag ctcttgggct tgagttgagc ttctcctttg   4500
gggatgaagt tcaacctgtc tgtttgctga cttgttgtgt acgcgtcagc tgctgctctt   4560
gcctctgtaa tagtggcaaa tttcttgtgt gcaactccgg gaacgccgtt tgttgccgcc   4620
tttgtacaac cccagtcatc gtatataccg gcatgtggac cgttatacac aacgtagtag   4680
ttgatatgag ggtgttgaat acccgattct gctctgagag gagcaactgt gctgttaagc   4740
```

```
tcagattttt gtgggattgg aattggatcg atctcgatcc cgcgaaatta atacgactca   4800
ctatagggag accacaacgg tttccctcta gaaataattt tgtttaactt taagaaggag   4860
atatacccat ggaaaagcct gaactcaccg cgacgtctgt cgagaagttt ctgatcgaaa   4920
agttcgacag cgtctccgac ctgatgcagc tctcggaggg cgaagaatct cgtgctttca   4980
gcttcgatgt aggagggcgt ggatatgtcc tgcgggtaaa tagctgcgcc gatggtttct   5040
acaaagatcg ttatgtttat cggcactttg catcggccgc gctcccgatt ccggaagtgc   5100
ttgacattgg ggaattcagc gagagcctga cctattgcat ctcccgccgt gcacagggtg   5160
tcacgttgca agacctgcct gaaaccgaac tgcccgctgt tctgcagccg gtcgcggagg   5220
ctatggatgc gatcgctgcg gccgatctta gccagacgag cgggttcggc ccattcggac   5280
cgcaaggaat cggtcaatac actacatggc gtgatttcat atgcgcgatt gctgatcccc   5340
atgtgtatca ctggcaaact gtgatggacg acaccgtcag tgcgtccgtc gcgcaggctc   5400
tcgatgagct gatgctttgg gccgaggact gccccgaagt ccggcacctc gtgcacgcgg   5460
atttcggctc caacaatgtc ctgacggaca atggccgcat aacagcggtc attgactgga   5520
gcgaggcgat gttcggggat tcccaatacg aggtcgccaa catcttcttc tggaggccgt   5580
ggttggcttg tatggagcag cagacgcgct acttcgagcg gaggcatccg gagcttgcag   5640
gatcgccgcg gctccgggcg tatatgctcc gcattggtct tgaccaactc tatcagagct   5700
tggttgacgg caatttcgat gatgcagctt gggcgcaggg tcgatgcgac gcaatcgtcc   5760
gatccggagc cgggactgtc gggcgtacac aaatcgcccg cagaagcgcg gccgtctgga   5820
ccgatggctg tgtagaagta ctcgccgata gtggaaaccg acgccccagc actcgtccga   5880
gggcaaagga atagtgaggt acagcttgga tcgatccggc tgctaacaaa gcccgaaagg   5940
aagctgagtt ggctgctgcc accgctgagc aataactagc ataacccctt ggggcctcta   6000
aacgggtctt gaggggtttt ttgctgaaag gaggaactat atccggatga tcgggcgcgc   6060
cgtcgacgga tccgtacgtc ctgcaggtaa attgcagctg aaggacagtg aagggtgaat   6120
ttatccattt aaaccatttt ctttttaaca catttcttat ggtaatctct tctcactaca   6180
ctataaaaat ggcttctcaa tcccattttc tacatcatcc cattctattg agttttgttt   6240
atttgctttc actttttttt ttatctgcct cttcccttaa tttgcttgac ttcttcttca   6300
cattttgctt tgttttctcc tccggcttcc ggtatttcaa attcaagatg agcaagttga   6360
aatttataaa tagaaataca gatattattt acaacgtcaa atctttggta ttttcaatat   6420
ttgaatgggg taaatttgtc atatagtcat catcactgac tacttatcta acctatttaa   6480
tttggagcat attctttata aggtccctct cacggccaat gtctaattat tgatatacag   6540
ctcttgtttt ctagtgctgc ttataatatt atctacacat atatatggta ctgcacacta   6600
ctactatata gtagtaagta aactagcaac agccggggcc aaactccaat aactaggcat   6660
tggggtttag ttggtaatat aaatataaca tcaaaaagtc tttgcttgtg acgaacatca   6720
caatgcaccc accattgatg ccacgacaga cattgttaat ttttttttta atttttaaaa   6780
aagaagcaat tccaatagtt ctatattaca atctcacgtg atccaagcac aacgtttcat   6840
tttttgtaca tgctcgatat ataaataata tttcatttta tagtaaaata taatgacatt   6900
ttcgaatata atttttgaaa tttcattttc caaatgaaat actaatatta atattaatga   6960
gattaccaca aatcatgtta tgaatgaaat aaagagtttt ggcattctaa ctttctttga   7020
atagaacaaa atgtatacaa cactctccat atatacacga tttattcagg gatcatatac   7080
```

attctctcat gattaacata gtctgctttc ttcacgtcta agcagataat ttttggtcca 7140
caagataaaa ttatcattag tcgttttaat taatttcttg agcatcaagc actaaaataa 7200
ttaaacttct ccattaccaa aaaaaaaaga taggtgattc agtaacatgt agtactagta 7260
ctactgattt ttttttcttt ttgattttaa tgaatggttc gtatcgagca tcgagaaatc 7320
catttattag gtgtgtaatg taatagtagt atttccttga ttttcagtaa taagatggat 7380
tcttacattt atatctgttt gacagaaaat gttgtcaatg catttcttgg gcacaaagtt 7440
ttttgaaaca tgaattaatt ttttcaaaat atttatgaca tcaaattgac cctaaaataa 7500
gtgataaagc tttaacgtgg aatgacatta atttttccat gataaataaa acacttaaaa 7560
cattttaata ttaatattat aatcagttac aactatgttc aattaatgca ataacttttta 7620 aataaatatt aaaatatttt ttttctgttc tccaataaag agatcttgtt gcacggaaaa 7680
agtcacattc ttatttagta aaaaattata attattgttt gaaaaatatc attttcactg 7740
cagaaaattt gatccagctc tacagatcat acttttattg tacaataata caataaaaat 7800
attcatctgc aggaaatatc attttcattg tacaataata taaagataaa tatataccag 7860
aaaagaaaaa gaaactgatg tggcacaatg tattcactga aagaatgcat attgtatttc 7920
acctttcaag cagcactaag aatatacttc ttttattata cttgtgcatt tactcaacca 7980
ccctcggtgg agtaagaaag aagatagata aaagtttttt ttgacatttg gtgaatctct 8040
taattaaaaa aataaaataa tccatttcct ttatttaatt tctttttttcc catctgtgaa 8100 attccaattc tgcttcgcgc tcctgtctat aaattgactt agccaccacc tcagtttcca 8160
ttcattcact tcttctcttt ataccccccc tctctttttt gcgttcattc tgttttcgta 8220
agtactgttg tttttctctt ctatttcttt ttttgtttgt gttgtttttt tttcttcctt 8280
atcgttgttc tgcctctcct ctgtttcggt gctctgttca ccacttccac gtgagaatga 8340
tcttccttct ttgcatgttc attctctcgt gaccactgga tcagactcca tgttctgatc 8400
cagggtctct ctctaacgcc tgtactttca tccatgacca ccttaaaaac aacatggggg 8460
tggtgctgtt acactaactc tgtttctggg gtgctgtctt tgttcaattt tactcagaaa 8520
atatcttttc ttggattcta ttcggtgtgt gggaacatga tcctgtcggt cggttgtttt 8580
taggttaatc cttaactggt tacaaggatc taacgcttga atgcatgtcc tgagttaaag 8640
aaacaaaaga agaacacacc tagtacagcc tggcctcgaa ccaagaactt ctttgttggt 8700
ttctcattat tactaaaata aaataaagta tacgttttct tttttctttg ggatgaacgg 8760
ttcagactta tgagaagttt aagctaatcc tgtagtggag tgttcaattt attttaaact 8820
ttaaagcaat agctcaagca ctaaacttct ttttcaagtt caaccacttt ggtagcttgc 8880
taattgctgc tattgttcta attaattaat gtaattattg tttaaaaaag aaaagttggt 8940
gacactggaa taaaaaagtg tactatctgg caattattct tctgcagcaa tgtttgaggt 9000
tgaaatctta gtagaacaaa gtagaagatc tggtatttat attttttgta gacagatggt 9060
gggggtgggt ggtaggcctt gaaatccaat atagttttgt agaataattt tattattttt 9120 ttttttgct cacttgtttg tggtattgat tttgtgatga ctcaagatta atgatttacc 9180
ttcatttttt tcatggtgac atattatgta tattcttgat ctgtttctta cacttctttt 9240
tcgttgttgt agctgttgaa gtctgcggcc gcatgaagag gtctccagca tcttcttgtt 9300
catcatctac ttcctctgtt gggtttgaag ctcccattga aaaaagaagg cctaagcatc 9360
caaggaggaa taatttgaag tcacaaaaat gcaagcagaa ccaaaccacc actggtggca 9420
gaagaagctc tatctataga ggagttacaa ggcataggtg gacagggagg tttgaagctc 9480
acctatggga taagagctct tggaacaaca ttcagagcaa gaagggtcga caagtttatt 9540
tgggggcata tgatactgaa gaatctgcag cccgtaccta tgaccttgca gcccttaaat 9600
actggggaaa agatgcaacc ctgaatttcc cgatagaaac ttataccaag gagctcgagg 9660
aaatggacaa ggtttcaaga gaagaatatt tggcttcttt gcggcgccaa agcagtggct 9720
tttctagagg cctgtctaag taccgtgggg ttgctaggca tcatcataat ggtcgctggg 9780
aagcacgaat tggaagagta tgcggaaaca agtacctcta cttggggaca tataaaactc 9840
aagaggaggc agcagtggca tatgacatgg cagcaataga gtaccgtgga gtcaatgcag 9900
tgaccaattt tgacataagc aactacatgg acaaaataaa gaagaaaaat gaccaaaccc 9960
aacaacaaca aacagaagca caaacggaaa cagttcctaa ctcctctgac tctgaagaag 10020
tagaagtaga acaacagaca acaacaataa ccacaccacc cccatctgaa aatctgcaca 10080
tgccaccaca gcagcaccaa gttcaataca ccccccatgt ctctccaagg gaagaagaat 10140
catcatcact gatcacaatt atggaccatg tgcttgagca ggatctgcca tggagcttca 10200
tgtacactgg cttgtctcag tttcaagatc caaacttggc tttctgcaaa ggtgatgatg 10260
acttggtggg catgtttgat agtgcagggt ttgaggaaga cattgatttt ctgttcagca 10320
ctcaacctgg tgatgagact gagagtgatg tcaacaatat gagcgcagtt ttggatagtg 10380
ttgagtgtgg agacacaaat ggggctggtg gaagcatgat gcatgtggat aacaagcaga 10440
agatagtatc atttgcttct tcaccatcat ctacaactac agtttcttgt gactatgctc 10500
tagatctatg agc 10513

<210> SEQ ID NO 52
<211> LENGTH: 10276
<212> TYPE: DNA
<213> ORGANISM: artificial sequence
<220> FEATURE:
<223> OTHER INFORMATION: plasmid sequence

<400> SEQUENCE: 52
ggccgcattt cgcaccaaat caatgaaagt aataatgaaa agtctgaata agaatactta 60
ggcttagatg cctttgttac ttgtgtaaaa taacttgagt catgtacctt tggcggaaac 120
agaataaata aaaggtgaaa ttccaatgct ctatgtataa gttagtaata cttaatgtgt 180
tctacggttg tttcaatatc atcaaactct aattgaaact ttagaaccac aaatctcaat 240
cttttcttaa tgaaatgaaa aatcttaatt gtaccatgtt tatgttaaac accttacaat 300
taattggttg gagaggagga ccaaccgatg ggacaacatt gggagaaaga gattcaatgg 360
agatttggat aggagaacaa cattcttttt cacttcaata caagatgagt gcaacactaa 420
ggatatgtat gagactttca gaagctacga caacatagat gagtgaggtg gtgattccta 480
gcaagaaaga cattagagga agccaaaatc gaacaaggaa gacatcaagg gcaagagaca 540
ggaccatcca tctcaggaaa aggagctttg ggatagtccg agaagttgta caagaaattt 600
tttggagggt gagtgatgca ttgctggtga ctttaactca atcaaaattg agaaagaaag 660
aaaagggagg gggctcacat gtgaatagaa gggaaacggg agaattttac agttttgatc 720
taatgggcat cccagctagt ggtaacatat tcaccatgtt taaccttcac gtacgagatc 780
cggccggcca gatcctgcag gagatccaag cttggcgcgc cgttctatag tgtcacctaa 840
atcgtatgtg tatgatacat aaggttatgt attaattgta gccgcgttct aacgacaata 900
tgtccatatg gtgcactctc agtacaatct gctctgatgc cgcatagtta agccagcccc 960

-continued

```
gacacccgcc aacacccgct gacgcgccct gacgggcttg tctgctcccg gcatccgctt   1020
acagacaagc tgtgaccgtc tccgggagct gcatgtgtca gaggttttca ccgtcatcac   1080
cgaaacgcgc gagacgaaag ggcctcgtga tacgcctatt tttataggtt aatgtcatga   1140
ccaaaatccc ttaacgtgag ttttcgttcc actgagcgtc agaccccgta gaaaagatca   1200
aaggatcttc ttgagatcct ttttttctgc gcgtaatctg ctgcttgcaa acaaaaaaac   1260
caccgctacc agcggtggtt tgtttgccgg atcaagagct accaactctt tttccgaagg   1320
taactggctt cagcagagcg cagataccaa atactgtcct tctagtgtag ccgtagttag   1380
gccaccactt caagaactct gtagcaccgc ctacatacct cgctctgcta atcctgttac   1440
cagtggctgc tgccagtggc gataagtcgt gtcttaccgg gttggactca agacgatagt   1500
taccggataa ggcgcagcgg tcgggctgaa cggggggttc gtgcacacag cccagcttgg   1560
agcgaacgac ctacaccgaa ctgagatacc tacagcgtga gcattgagaa agcgccacgc   1620
ttcccgaagg gagaaaggcg gacaggtatc cggtaagcgg cagggtcgga acaggagagc   1680
gcacgaggga gcttccaggg ggaaacgcct ggtatcttta tagtcctgtc gggtttcgcc   1740
acctctgact tgagcgtcga tttttgtgat gctcgtcagg ggggcggagc ctatggaaaa   1800
acgccagcaa cgcggccttt ttacggttcc tggccttttg ctggcctttt gctcacatgt   1860
tctttcctgc gttatcccct gattctgtgg ataaccgtat taccgccttt gagtgagctg   1920
ataccgctcg ccgcagccga acgaccgagc gcagcgagtc agtgagcgag gaagcggaag   1980
agcgcccaat acgcaaaccg cctctccccg cgcgttggcc gattcattaa tgcaggttga   2040
tcgattcgac atcgatctag taacatagat gacaccgcgc gcgataattt atcctagttt   2100
gcgcgctata ttttgttttc tatcgcgtat taaatgtata attgcgggac tctaatcata   2160
aaaacccatc tcataaataa cgtcatgcat tacatgttaa ttattacatg cttaacgtaa   2220
ttcaacagaa attatatgat aatcatcgca agaccggcaa caggattcaa tcttaagaaa   2280
ctttattgcc aaatgtttga acgatctgct tcgacgcact ccttctttag gtacctcact   2340
attcctttgc cctcggacga gtgctggggc gtcggtttcc actatcggcg agtacttcta   2400
cacagccatc ggtccagacg gccgcgcttc tgcgggcgat ttgtgtacgc ccgacagtcc   2460
cggctccgga tcggacgatt gcgtcgcatc gaccctgcgc ccaagctgca tcatcgaaat   2520
tgccgtcaac caagctctga tagagttggt caagaccaat gcggagcata tacgcccgga   2580
gccgcggcga tcctgcaagc tccggatgcc tccgctcgaa gtagcgcgtc tgctgctcca   2640
tacaagccaa ccacggcctc cagaagaaga tgttggcgac ctcgtattgg gaatccccga   2700
acatcgcctc gctccagtca atgaccgctg ttatgcggcc attgtccgtc aggacattgt   2760
tggagccgaa atccgcgtgc acgaggtgcc ggacttcggg gcagtcctcg gcccaaagca   2820
tcagctcatc gagagcctgc gcgacggacg cactgacggt gtcgtccatc acagtttgcc   2880
agtgatacac atggggatca gcaatcgcgc atatgaaatc acgccatgta gtgtattgac   2940
cgattccttg cggtccgaat gggccgaacc cgctcgtctg gctaagatcg gccgcagcga   3000
tcgcatccat ggcctccgcg accggctgca gaacagcggg cagttcggtt tcaggcaggt   3060
cttgcaacgt gacaccctgt gcacggcggg agatgcaata ggtcaggctc tcgctgaatt   3120
ccccaatgtc aagcacttcc ggaatcggga gcgcggccga tgcaaagtgc cgataaacat   3180
aacgatcttt gtagaaacca tcggcgcagc tatttacccg caggacatat ccacgccctc   3240
ctacatcgaa gctgaaagca cgagattctt cgccctccga gagctgcatc aggtcggaga   3300
cgctgtcgaa cttttcgatc agaaacttct cgacagacgt cgcggtgagt tcaggctttt   3360
```

```
tcatggttta ataagaagag aaaagagttc ttttgttatg gctgaagtaa tagagaaatg   3420
agctcgagcg tgtcctctcc aaatgaaatg aacttcctta tatagaggaa gggtcttgcg   3480
aaggatagtg ggattgtgcg tcatccctta cgtcagtgga gatgtcacat caatccactt   3540
gctttgaaga cgtggttgga acgtcttctt tttccacgat gctcctcgtg ggtgggggtc   3600
catctttggg accactgtcg gcagaggcat cttgaatgat agcctttcct ttatcgcaat   3660
gatggcattt gtaggagcca ccttcctttt ctactgtcct ttcgatgaag tgacagatag   3720
ctgggcaatg gaatccgagg aggtttcccg aaattatcct ttgttgaaaa gtctcaatag   3780
ccctttggtc ttctgagact gtatctttga catttttgga gtagaccaga gtgtcgtgct   3840
ccaccatgtt gacgaagatt ttcttcttgt cattgagtcg taaaagactc tgtatgaact   3900
gttcgccagt cttcacggcg agttctgtta gatcctcgat ttgaatctta gactccatgc   3960
atggccttag attcagtagg aactaccttt ttagagactc caatctctat tacttgcctt   4020
ggtttatgaa gcaagccttg aatcgtccat actggaatag tacttctgat cttgagaaat   4080
atgtctttct ctgtgttctt gatgcaatta gtcctgaatc ttttgactgc atctttaacc   4140
ttcttgggaa ggtatttgat ctcctggaga ttgttactcg ggtagatcgt cttgatgaga   4200
cctgctgcgt aggcctctct aaccatctgt gggtcagcat tctttctgaa attgaagagg   4260
ctaaccttct cattatcagt ggtgaacata gtgtcgtcac cttcaccttc gaacttcctt   4320
cctagatcgt aaagatagag gaaatcgtcc attgtaatct ccggggcaaa ggagatctct   4380
tttggggctg gatcactgct gggccttttg gttcctagcg tgagccagtg ggctttttgc   4440
tttggtgggc ttgttagggc cttagcaaag ctcttgggct tgagttgagc ttctcctttg   4500
gggatgaagt tcaacctgtc tgtttgctga cttgttgtgt acgcgtcagc tgctgctctt   4560
gcctctgtaa tagtggcaaa tttcttgtgt gcaactccgg gaacgccgtt tgttgccgcc   4620
tttgtacaac cccagtcatc gtatataccg gcatgtggac cgttatacac aacgtagtag   4680
ttgatatgag ggtgttgaat acccgattct gctctgagag gagcaactgt gctgttaagc   4740
tcagattttt gtgggattgg aattggatcg atctcgatcc cgcgaaatta atacgactca   4800
ctatagggag accacaacgg tttccctcta gaaataattt tgtttaactt taagaaggag   4860
atatacccat ggaaaagcct gaactcaccg cgacgtctgt cgagaagttt ctgatcgaaa   4920
agttcgacag cgtctccgac ctgatgcagc tctcggaggg cgaagaatct cgtgctttca   4980
gcttcgatgt aggagggcgt ggatatgtcc tgcgggtaaa tagctgcgcc gatggtttct   5040
acaaagatcg ttatgtttat cggcactttg catcggccgc gctcccgatt ccggaagtgc   5100
ttgacattgg ggaattcagc gagagcctga cctattgcat ctcccgccgt gcacagggtg   5160
tcacgttgca agacctgcct gaaaccgaac tgcccgctgt tctgcagccg gtcgcggagg   5220
ctatggatgc gatcgctgcg gccgatctta gccagacgag cgggttcggc ccattcggac   5280
cgcaaggaat cggtcaatac actacatggc gtgatttcat atgcgcgatt gctgatcccc   5340
atgtgtatca ctggcaaact gtgatggacg acaccgtcag tgcgtccgtc gcgcaggctc   5400
tcgatgagct gatgctttgg gccgaggact gccccgaagt ccggcacctc gtgcacgcgg   5460
atttcggctc caacaatgtc ctgacggaca atggccgcat aacagcggtc attgactgga   5520
gcgaggcgat gttcggggat tcccaatacg aggtcgccaa catcttcttc tggaggccgt   5580
ggttggcttg tatggagcag cagacgcgct acttcgagcg gaggcatccg gagcttgcag   5640
gatcgccgcg gctccgggcg tatatgctcc gcattggtct tgaccaactc tatcagagct   5700
```

-continued

```
tggttgacgg caatttcgat gatgcagctt gggcgcaggg tcgatgcgac gcaatcgtcc   5760
gatccggagc cgggactgtc gggcgtacac aaatcgcccg cagaagcgcg gccgtctgga   5820
ccgatggctg tgtagaagta ctcgccgata gtggaaaccg acgccccagc actcgtccga   5880
gggcaaagga atagtgaggt acagcttgga tcgatccggc tgctaacaaa gcccgaaagg   5940
aagctgagtt ggctgctgcc accgctgagc aataactagc ataacccctt ggggcctcta   6000
aacgggtctt gaggggtttt ttgctgaaag gaggaactat atccggatga tcgggcgcgc   6060
cgtcgacgga tccgtacgtc ctgcaggtaa attgcagctg aaggacagtg aagggtgaat   6120
ttatccattt aaaccatttt ctttttaaca catttcttat ggtaatctct tctcactaca   6180
ctataaaaat ggcttctcaa tcccattttc tacatcatcc cattctattg agttttgttt   6240
atttgctttc actttttttt ttatctgcct cttcccttaa tttgcttgac ttcttcttca   6300
cattttgctt tgttttctcc tccggcttcc ggtatttcaa attcaagatg agcaagttga   6360
aatttataaa tagaaataca gatattattt acaacgtcaa atctttggta ttttcaatat   6420
ttgaatgggg taaatttgtc atatagtcat catcactgac tacttatcta acctatttaa   6480
tttggagcat attctttata aggtccctct cacggccaat gtctaattat tgatatacag   6540
ctcttgtttt ctagtgctgc ttataatatt atctacacat atatatggta ctgcacacta   6600
ctactatata gtagtaagta aactagcaac agccggggcc aaactccaat aactaggcat   6660
tggggtttag ttggtaatat aaatataaca tcaaaaagtc tttgcttgtg acgaacatca   6720
caatgcaccc accattgatg ccacgacaga cattgttaat ttttttttta atttttaaaa   6780
aagaagcaat tccaatagtt ctatattaca atctcacgtg atccaagcac aacgtttcat   6840
tttttgtaca tgctcgatat ataaataata tttcatttta tagtaaaata taatgacatt   6900
ttcgaatata atttttgaaa tttcattttc caaatgaaat actaatatta atattaatga   6960
gattaccaca aatcatgtta tgaatgaaat aaagagtttt ggcattctaa ctttctttga   7020
atagaacaaa atgtatacaa cactctccat atatacacga tttattcagg gatcatatac   7080
attctctcat gattaacata gtctgctttc ttcacgtcta agcagataat tttggtccca   7140
caagataaaa ttatcattag tcgttttaat taattccttg agcatcaagc actaaaataa   7200
ttaaacttct ccattaccaa aaaaaaaaga taggtgattc agtaacatgt agtactagta   7260
ctactgattt tttttttctt ttgattttaa tgaatggttc gtatcgagca tcgagaaatc   7320
catttattag gtgtgtaatg taatagtagt atttccttga ttttcagtaa taagatggat   7380
tcttacattt atatctgttt gacagaaaat gttgtcaatg catttcttgg gcacaaagtt   7440
ttttgaaaca tgaattaatt ttttcaaaat atttatgaca tcaaattgac cctaaaataa   7500
gtgataaagc tttaacgtgg aatgacatta atttttccat gataaataaa acacttaaaa   7560
cattttaata ttaatattat aatcagttac aactatgttc aattaatgca ataactttta   7620
aataaatatt aaaatatttt ttttctgttc tccaataaag agatcttgtt gcacggaaaa   7680
agtcacattc ttatttagta aaaaattata attattgttt gaaaaatatc attttcactg   7740
cagaaaattt gatccagctc tacagatcat acttttattg tacaataata caataaaaat   7800
attcatctgc aggaaatatc attttcattg tacaataata taaagataaa tatataccag   7860
aaaagaaaaa gaaactgatg tggcacaatg tattcactga aagaatgcat attgtatttc   7920
acctttcaag cagcactaag aatatacttc ttttattata cttgtgcatt tactcaacca   7980
ccctcggtgg agtaagaaag aagatagata aaagtttttt ttgacatttg gtgaatctct   8040
taattaaaaa aataaaataa tccatttcct ttatttaatt tctttttttcc catctgtgaa   8100
```

```
attccaattc tgcttcgcgc tcctgtctat aaattgactt agccaccacc tcagtttcca   8160
ttcattcact tcttctcttt atacccccc tctcttttt gcgttcattc tgttttcgta   8220
agtactgttg tttttctctt ctatttcttt ttttgtttgt gttgtttttt tttcttcctt   8280
atcgttgttc tgcctctcct ctgtttcggt gctctgttca ccacttccac gtgagaatga   8340
tcttccttct ttgcatgttc attctctcgt gaccactgga tcagactcca tgttctgatc   8400
cagggtctct ctctaacgcc tgtactttca tccatgacca ccttaaaaac aacatggggg   8460
tggtgctgtt acactaactc tgtttctggg gtgctgtctt tgttcaattt tactcagaaa   8520
atatcttttc ttggattcta ttcggtgtgt gggaacatga tcctgtcggt cggttgtttt   8580
taggttaatc cttaactggt tacaaggatc taacgcttga atgcatgtcc tgagttaaag   8640
aaacaaaaga agaacacacc tagtacagcc tggcctcgaa ccaagaactt ctttgttggt   8700
ttctcattat tactaaaata aaataaagta tacgttttct tttttctttg ggatgaacgg   8760
ttcagactta tgagaagttt aagctaatcc tgtagtggag tgttcaattt attttaaact   8820
ttaaagcaat agctcaagca ctaaacttct ttttcaagtt caaccacttt ggtagcttgc   8880
taattgctgc tattgttcta attaattaat gtaattattg tttaaaaaag aaaagttggt   8940
gacactggaa taaaaaagtg tactatctgg caattattct tctgcagcaa tgtttgaggt   9000
tgaaatctta gtagaacaaa gtagaagatc tggtatttat attttttgta gacagatggt   9060
gggggtgggt ggtaggcctt gaaatccaat atagttttgt agaataattt tattattttt   9120
tttttttgct cacttgtttg tggtattgat tttgtgatga ctcaagatta atgatttacc   9180
ttcatttttt tcatggtgac atattatgta tattcttgat ctgtttctta cacttctttt   9240
tcgttgttgt agctgttgaa gtctgcggcc gcaccatgat gatggatcag cgacagcgag   9300
agaagctgct tcacaaaacc gaggcctgtg ctttcgtggc aggtgttgtt ccggagcttt   9360
cccttgtcac cgttccaggg aacaacacca acaacgttaa caacaacaac aacgttgttt   9420
ctcattctca atctaacggg tcgggtcgga tccaggaaaa caaccaccac cttggactcg   9480
ttgctgctgt cacctccgcc ttcggtaccg ttcaaaggaa gaaaaggatg gcgagacaaa   9540
gaagatccac taaacccact tcgttgatga accatctcaa caaccataag cacaacaagc   9600
ctcgttctct tccttctccc agtgcatcct cctcgtacgt gccactctcc tccgcaactc   9660
tccagcccgc acgtgaaatc gatcaaagaa ggttgagatt ccttttccag aaggagttaa   9720
agaacagtga tgttagctcc cttaggagaa tgatattgcc aaagaaagca gcagaggctt   9780
tccttccagc tcttgaatcc aaagaaggaa ttgtaatcag catggatgat atagatggtc   9840
ttcatgtatg gagtttcaag tacaggtttt ggcctaacaa caacagtcgg atgtatgtac   9900
ttgaaaatac tggagatttt gtcaacacac atggccttcg ctttggagat tccattatgg   9960
tttaccaaga tagtgaaaac aacaattatg ttattcaggc caaaaaggct tctgatcaag  10020
atgaatttat ggaagaaact agtgatacca tcaatgatat cttccttaat gattatgagg  10080
tgaacaaacc tggttgcttc aatgtaacta atcctgcagt gaatgataca ggcatgtcat  10140
tcatatatga gactaccttc tcaaatgact cccctcttga ttttttgggt ggatcaatga  10200
ccaatttttc aaggattggg ccagttgaaa cctttggctc tgttgagaat ttgtcacttg  10260
atgacttcta ttaagc                                                  10276
```

<210> SEQ ID NO 53
<211> LENGTH: 10995
<212> TYPE: DNA

<213> ORGANISM: artificial sequence
<220> FEATURE:
<223> OTHER INFORMATION: plasmid sequence

<400> SEQUENCE: 53
ggccgcattt cgcaccaaat caatgaaagt aataatgaaa agtctgaata agaatactta 60
ggcttagatg cctttgttac ttgtgtaaaa taacttgagt catgtacctt tggcggaaac 120
agaataaata aaaggtgaaa ttccaatgct ctatgtataa gttagtaata cttaatgtgt 180
tctacggttg tttcaatatc atcaaactct aattgaaact ttagaaccac aaatctcaat 240
cttttcttaa tgaaatgaaa aatcttaatt gtaccatgtt tatgttaaac accttacaat 300
taattggttg gagaggagga ccaaccgatg ggacaacatt gggagaaaga gattcaatgg 360
agatttggat aggagaacaa cattcttttt cacttcaata caagatgagt gcaacactaa 420
ggatatgtat gagactttca gaagctacga caacatagat gagtgaggtg gtgattccta 480
gcaagaaaga cattagagga agccaaaatc gaacaaggaa gacatcaagg gcaagagaca 540
ggaccatcca tctcaggaaa aggagctttg ggatagtccg agaagttgta caagaaattt 600
tttggagggt gagtgatgca ttgctggtga ctttaactca atcaaaattg agaaagaaag 660
aaaagggagg gggctcacat gtgaatagaa gggaaacggg agaattttac agttttgatc 720
taatgggcat cccagctagt ggtaacatat tcaccatgtt taaccttcac gtacgagatc 780
cggccggcca gatcctgcag gagatccaag cttggcgcgc cgttctatag tgtcacctaa 840
atcgtatgtg tatgatacat aaggttatgt attaattgta gccgcgttct aacgacaata 900
tgtccatatg gtgcactctc agtacaatct gctctgatgc cgcatagtta agccagcccc 960
gacacccgcc aacacccgct gacgcgccct gacgggcttg tctgctcccg gcatccgctt 1020
acagacaagc tgtgaccgtc tccgggagct gcatgtgtca gaggttttca ccgtcatcac 1080
cgaaacgcgc gagacgaaag ggcctcgtga tacgcctatt tttataggtt aatgtcatga 1140
ccaaaatccc ttaacgtgag ttttcgttcc actgagcgtc agaccccgta gaaaagatca 1200
aaggatcttc ttgagatcct ttttttctgc gcgtaatctg ctgcttgcaa acaaaaaaac 1260
caccgctacc agcggtggtt tgtttgccgg atcaagagct accaactctt tttccgaagg 1320
taactggctt cagcagagcg cagataccaa atactgtcct tctagtgtag ccgtagttag 1380
gccaccactt caagaactct gtagcaccgc ctacatacct cgctctgcta atcctgttac 1440
cagtggctgc tgccagtggc gataagtcgt gtcttaccgg gttggactca agacgatagt 1500
taccggataa ggcgcagcgg tcgggctgaa cggggggttc gtgcacacag cccagcttgg 1560
agcgaacgac ctacaccgaa ctgagatacc tacagcgtga gcattgagaa agcgccacgc 1620
ttcccgaagg gagaaaggcg gacaggtatc cggtaagcgg cagggtcgga acaggagagc 1680
gcacgaggga gcttccaggg ggaaacgcct ggtatcttta tagtcctgtc gggtttcgcc 1740
acctctgact tgagcgtcga tttttgtgat gctcgtcagg ggggcggagc ctatggaaaa 1800
acgccagcaa cgcggccttt ttacggttcc tggccttttg ctggcctttt gctcacatgt 1860
tctttcctgc gttatcccct gattctgtgg ataaccgtat taccgccttt gagtgagctg 1920
ataccgctcg ccgcagccga acgaccgagc gcagcgagtc agtgagcgag gaagcggaag 1980
agcgcccaat acgcaaaccg cctctccccg cgcgttggcc gattcattaa tgcaggttga 2040
tcgattcgac atcgatctag taacatagat gacaccgcgc gcgataattt atcctagttt 2100
gcgcgctata ttttgttttc tatcgcgtat taaatgtata attgcgggac tctaatcata 2160
aaaacccatc tcataaataa cgtcatgcat tacatgttaa ttattacatg cttaacgtaa 2220

```
ttcaacagaa attatatgat aatcatcgca agaccggcaa caggattcaa tcttaagaaa   2280
ctttattgcc aaatgtttga acgatctgct tcgacgcact ccttctttag gtacctcact   2340
attcctttgc cctcggacga gtgctggggc gtcggtttcc actatcggcg agtacttcta   2400
cacagccatc ggtccagacg gccgcgcttc tgcgggcgat ttgtgtacgc ccgacagtcc   2460
cggctccgga tcggacgatt gcgtcgcatc gaccctgcgc ccaagctgca tcatcgaaat   2520
tgccgtcaac caagctctga tagagttggt caagaccaat gcggagcata tacgcccgga   2580
gccgcggcga tcctgcaagc tccggatgcc tccgctcgaa gtagcgcgtc tgctgctcca   2640
tacaagccaa ccacggcctc cagaagaaga tgttggcgac ctcgtattgg gaatccccga   2700
acatcgcctc gctccagtca atgaccgctg ttatgcggcc attgtccgtc aggacattgt   2760
tggagccgaa atccgcgtgc acgaggtgcc ggacttcggg gcagtcctcg gcccaaagca   2820
tcagctcatc gagagcctgc gcgacggacg cactgacggt gtcgtccatc acagtttgcc   2880
agtgatacac atggggatca gcaatcgcgc atatgaaatc acgccatgta gtgtattgac   2940
cgattccttg cggtccgaat gggccgaacc cgctcgtctg gctaagatcg gccgcagcga   3000
tcgcatccat ggcctccgcg accggctgca gaacagcggg cagttcggtt tcaggcaggt   3060
cttgcaacgt gacaccctgt gcacggcggg agatgcaata ggtcaggctc tcgctgaatt   3120
ccccaatgtc aagcacttcc ggaatcggga gcgcggccga tgcaaagtgc cgataaacat   3180
aacgatcttt gtagaaacca tcggcgcagc tatttacccg caggacatat ccacgccctc   3240
ctacatcgaa gctgaaagca cgagattctt cgccctccga gagctgcatc aggtcggaga   3300
cgctgtcgaa cttttcgatc agaaacttct cgacagacgt cgcggtgagt tcaggctttt   3360
tcatggttta ataagaagag aaaagagttc ttttgttatg gctgaagtaa tagagaaatg   3420
agctcgagcg tgtcctctcc aaatgaaatg aacttcctta tatagaggaa gggtcttgcg   3480
aaggatagtg ggattgtgcg tcatccctta cgtcagtgga gatgtcacat caatccactt   3540
gctttgaaga cgtggttgga acgtcttctt tttccacgat gctcctcgtg ggtgggggtc   3600
catctttggg accactgtcg gcagaggcat cttgaatgat agcctttcct ttatcgcaat   3660
gatggcattt gtaggagcca ccttcctttt ctactgtcct ttcgatgaag tgacagatag   3720
ctgggcaatg gaatccgagg aggtttcccg aaattatcct ttgttgaaaa gtctcaatag   3780
ccctttggtc ttctgagact gtatctttga catttttgga gtagaccaga gtgtcgtgct   3840
ccaccatgtt gacgaagatt ttcttcttgt cattgagtcg taaaagactc tgtatgaact   3900
gttcgccagt cttcacggcg agttctgtta gatcctcgat ttgaatctta gactccatgc   3960
atggccttag attcagtagg aactaccttt ttagagactc caatctctat tacttgcctt   4020
ggtttatgaa gcaagccttg aatcgtccat actggaatag tacttctgat cttgagaaat   4080
atgtctttct ctgtgttctt gatgcaatta gtcctgaatc ttttgactgc atctttaacc   4140
ttcttgggaa ggtatttgat ctcctggaga ttgttactcg ggtagatcgt cttgatgaga   4200
cctgctgcgt aggcctctct aaccatctgt gggtcagcat tctttctgaa attgaagagg   4260
ctaaccttct cattatcagt ggtgaacata gtgtcgtcac cttcaccttc gaacttcctt   4320
cctagatcgt aaagatagag gaaatcgtcc attgtaatct ccggggcaaa ggagatctct   4380
tttggggctg gatcactgct gggccttttg gttcctagcg tgagccagtg ggctttttgc   4440
tttggtgggc ttgttagggc cttagcaaag ctcttgggct tgagttgagc ttctcctttg   4500
gggatgaagt tcaacctgtc tgtttgctga cttgttgtgt acgcgtcagc tgctgctctt   4560
```

gcctctgtaa tagtggcaaa tttcttgtgt gcaactccgg gaacgccgtt tgttgccgcc 4620
tttgtacaac cccagtcatc gtatataccg gcatgtggac cgttatacac aacgtagtag 4680
ttgatatgag ggtgttgaat acccgattct gctctgagag gagcaactgt gctgttaagc 4740
tcagattttt gtgggattgg aattggatcg atctcgatcc cgcgaaatta atacgactca 4800
ctatagggag accacaacgg tttccctcta gaaataattt tgtttaactt taagaaggag 4860
atatacccat ggaaaagcct gaactcaccg cgacgtctgt cgagaagttt ctgatcgaaa 4920
agttcgacag cgtctccgac ctgatgcagc tctcggaggg cgaagaatct cgtgctttca 4980
gcttcgatgt aggagggcgt ggatatgtcc tgcgggtaaa tagctgcgcc gatggtttct 5040
acaaagatcg ttatgtttat cggcactttg catcggccgc gctcccgatt ccggaagtgc 5100
ttgacattgg ggaattcagc gagagcctga cctattgcat ctcccgccgt gcacagggtg 5160
tcacgttgca agacctgcct gaaaccgaac tgcccgctgt tctgcagccg gtcgcggagg 5220
ctatggatgc gatcgctgcg gccgatctta gccagacgag cgggttcggc ccattcggac 5280
cgcaaggaat cggtcaatac actacatggc gtgatttcat atgcgcgatt gctgatcccc 5340
atgtgtatca ctggcaaact gtgatggacg acaccgtcag tgcgtccgtc gcgcaggctc 5400
tcgatgagct gatgctttgg gccgaggact gccccgaagt ccggcacctc gtgcacgcgg 5460
atttcggctc caacaatgtc ctgacggaca atggccgcat aacagcggtc attgactgga 5520
gcgaggcgat gttcggggat tcccaatacg aggtcgccaa catcttcttc tggaggccgt 5580
ggttggcttg tatggagcag cagacgcgct acttcgagcg gaggcatccg gagcttgcag 5640
gatcgccgcg gctccgggcg tatatgctcc gcattggtct tgaccaactc tatcagagct 5700
tggttgacgg caatttcgat gatgcagctt gggcgcaggg tcgatgcgac gcaatcgtcc 5760
gatccggagc cgggactgtc gggcgtacac aaatcgcccg cagaagcgcg gccgtctgga 5820
ccgatggctg tgtagaagta ctcgccgata gtggaaaccg acgccccagc actcgtccga 5880
gggcaaagga atagtgaggt acagcttgga tcgatccggc tgctaacaaa gcccgaaagg 5940
aagctgagtt ggctgctgcc accgctgagc aataactagc ataacccctt ggggcctcta 6000
aacgggtctt gaggggtttt ttgctgaaag gaggaactat atccggatga tcgggcgcgc 6060
cgtcgacgga tccgtacgtc ctgcaggtaa attgcagctg aaggacagtg aagggtgaat 6120
ttatccattt aaaccatttt ctttttaaca catttcttat ggtaatctct tctcactaca 6180
ctataaaaat ggcttctcaa tcccattttc tacatcatcc cattctattg agttttgttt 6240
atttgctttc actttttttt ttatctgcct cttcccttaa tttgcttgac ttcttcttca 6300
cattttgctt tgttttctcc tccggcttcc ggtatttcaa attcaagatg agcaagttga 6360
aatttataaa tagaaataca gatattattt acaacgtcaa atctttggta ttttcaatat 6420
ttgaatgggg taaatttgtc atatagtcat catcactgac tacttatcta acctatttaa 6480
tttggagcat attctttata aggtccctct cacggccaat gtctaattat tgatatacag 6540
ctcttgtttt ctagtgctgc ttataatatt atctacacat atatatggta ctgcacacta 6600
ctactatata gtagtaagta aactagcaac agccggggcc aaactccaat aactaggcat 6660
tggggtttag ttggtaatat aaatataaca tcaaaaagtc tttgcttgtg acgaacatca 6720
caatgcaccc accattgatg ccacgacaga cattgttaat ttttttttta atttttaaaa 6780
aagaagcaat tccaatagtt ctatattaca atctcacgtg atccaagcac aacgtttcat 6840
tttttgtaca tgctcgatat ataaataata tttcatttta tagtaaaata taatgacatt 6900
ttcgaatata atttttgaaa tttcattttc caaatgaaat actaatatta atattaatga 6960
gattaccaca aatcatgtta tgaatgaaat aaagagtttt ggcattctaa ctttctttga 7020
atagaacaaa atgtatacaa cactctccat atatacacga tttattcagg gatcatatac 7080
attctctcat gattaacata gtctgctttc ttcacgtcta agcagataat ttttggtcca 7140
caagataaaa ttatcattag tcgttttaat taattccttg agcatcaagc actaaaataa 7200
ttaaacttct ccattaccaa aaaaaaaaga taggtgattc agtaacatgt agtactagta 7260
ctactgattt ttttttcttt ttgattttaa tgaatggttc gtatcgagca tcgagaaatc 7320
catttattag gtgtgtaatg taatagtagt atttccttga ttttcagtaa taagatggat 7380
tcttacattt atatctgttt gacagaaaat gttgtcaatg catttcttgg gcacaaagtt 7440
ttttgaaaca tgaattaatt ttttcaaaat atttatgaca tcaaattgac cctaaaataa 7500
gtgataaagc tttaacgtgg aatgacatta atttttccat gataaataaa acacttaaaa 7560
cattttaata ttaatattat aatcagttac aactatgttc aattaatgca ataactttta 7620
aataaatatt aaaatatttt ttttctgttc tccaataaag agatcttgtt gcacggaaaa 7680
agtcacattc ttatttagta aaaaattata attattgttt gaaaaatatc attttcactg 7740
cagaaaattt gatccagctc tacagatcat acttttattg tacaataata caataaaaat 7800
attcatctgc aggaaatatc attttcattg tacaataata taaagataaa tatataccag 7860
aaaagaaaaa gaaactgatg tggcacaatg tattcactga aagaatgcat attgtatttc 7920
acctttcaag cagcactaag aatatacttc ttttattata cttgtgcatt tactcaacca 7980
ccctcggtgg agtaagaaag aagatagata aaagtttttt ttgacatttg gtgaatctct 8040
taattaaaaa aataaaataa tccatttcct ttatttaatt tctttttttcc catctgtgaa 8100
attccaattc tgcttcgcgc tcctgtctat aaattgactt agccaccacc tcagtttcca 8160
ttcattcact tcttctcttt atacccccc tctcttttt gcgttcattc tgttttcgta 8220
agtactgttg tttttctctt ctatttcttt ttttgtttgt gttgtttttt tttcttcctt 8280
atcgttgttc tgcctctcct ctgtttcggt gctctgttca ccacttccac gtgagaatga 8340
tcttccttct ttgcatgttc attctctcgt gaccactgga tcagactcca tgttctgatc 8400
cagggtctct ctctaacgcc tgtactttca tccatgacca ccttaaaaac aacatggggg 8460
tggtgctgtt acactaactc tgtttctggg gtgctgtctt tgttcaattt tactcagaaa 8520
atatcttttc ttggattcta ttcggtgtgt gggaacatga tcctgtcggt cggttgtttt 8580
taggttaatc cttaactggt tacaaggatc taacgcttga atgcatgtcc tgagttaaag 8640
aaacaaaaga agaacacacc tagtacagcc tggcctcgaa ccaagaactt ctttgttggt 8700
ttctcattat tactaaaata aaataaagta tacgttttct tttttctttg ggatgaacgg 8760
ttcagactta tgagaagttt aagctaatcc tgtagtggag tgttcaattt attttaaact 8820
ttaaagcaat agctcaagca ctaaacttct ttttcaagtt caaccacttt ggtagcttgc 8880
taattgctgc tattgttcta attaattaat gtaattattg tttaaaaaag aaaagttggt 8940
gacactggaa taaaaaagtg tactatctgg caattattct tctgcagcaa tgtttgaggt 9000
tgaaatctta gtagaacaaa gtagaagatc tggtatttat attttttgta gacagatggt 9060
gggggtgggt ggtaggcctt gaaatccaat atagttttgt agaataattt tattattttt 9120
tttttttgct cacttgtttg tggtattgat tttgtgatga ctcaagatta atgatttacc 9180
ttcatttttt tcatggtgac atattatgta tattcttgat ctgtttctta cacttctttt 9240
tcgttgttgt agctgttgaa gtctgcggcc gcaccatgtt tcctgtgtct ttaccatcca 9300
tccgtcactc actgcttggg caatctctaa ccaccaccac caccccgcag caccaaaccc 9360
tatgccacaa acttaaccct ggtttgcacc acacccccta ttcacacgca gccacattat 9420
catcgatcat atcataatgt agccagcaga aagtgccaaa tccaaaacca acccatgaat 9480
ccaatcctca catttggtca ccaaaactca ttaacccata tcatttagat aaagggagag 9540
agagagagag agagagagag aaagagagtg tgtgtgaatg tgagtggggg gtggtgtttc 9600
aattcattta tgttatggta aaagtaaaag gaagcaaagg gagaggatgg ggagaggagt 9660
gaatgcagga tgcacaaatg tcataaaaac cagaccctta taatcacaaa aaaccttgct 9720
aaaaatagaa aaaatccaaa aaaaaaagaa gaagagagag agagagaatt tggattgagt 9780
tgggttgggg gaagagaaga gtgaatgaga gttccaccat tgatctctta aacaccaaac 9840
cccacaccca tttcgtgagt gccgagcgtc gttctatcta ttttttctct gcctacacac 9900
actgatactg agagaaagag aaccaactac tacagtcaca gaaaaccaaa aaaacactgt 9960
gttgtgtgtg tgtcaaaaaa aaaaccctaa gctaatgatg atggatcagc gacagcgaga 10020
gaagctgctt cacaaaaccg aggcctgtgc tttcgtggca ggtgttgttc cggagctttc 10080
ccttgtcacc gttccaggga acaacaccaa caacgttaac aacaacaaca acgttgtttc 10140
tcattctcaa tctaacgggt cgggtcggat ccaggaaaac aaccaccacc ttggactcgt 10200
tgctgctgtc acctccgcct tcggtaccgt tcaaaggaag aaaaggatgg cgagacaaag 10260
aagatccact aaacccactt cgttgatgaa ccatctcaac aaccataagc acaacaagcc 10320
tcgttctctt ccttctccca gtgcatcctc ctcgtacgtg ccactctcct ccgcaactct 10380
ccagcccgca cgtgaaatcg atcaaagaag gttgagattc cttttccaga aggagttaaa 10440
gaacagtgat gttagctccc ttaggagaat gatattgcca aagaaagcag cagaggcttt 10500
ccttccagct cttgaatcca aagaaggaat tgtaatcagc atggatgata tagatggtct 10560
tcatgtatgg agtttcaagt acaggttttg gcctaacaac aacagtcgga tgtatgtact 10620
tgaaaatact ggagattttg tcaacacaca tggccttcgc tttggagatt ccattatggt 10680
ttaccaagat agtgaaaaca acaattatgt tattcaggcc aaaaaggctt ctgatcaaga 10740
tgaatttatg gaagaaacta gtgataccat caatgatatc ttccttaatg attatgaggt 10800
gaacaaacct ggttgcttca atgtaactaa tcctgcagtg aatgatacag gcatgtcatt 10860
catatatgag actaccttct caaatgactc ccctcttgat tttttgggtg gatcaatgac 10920
caatttttca aggattgggc cagttgaaac ctttggctct gttgagaatt tgtcacttga 10980
tgacttctat taagc 10995

<210> SEQ ID NO 54
<211> LENGTH: 1515
<212> TYPE: DNA
<213> ORGANISM: Glycine max

<400> SEQUENCE: 54
atggcgattt ccgatgagcc tgaaagtgta gccactgctc tcaaccactc ttccctgcgc 60
cgccgtccct ccgccacctc caccgccggc ctcttcaatt cgcctgagac aaccaccgac 120
agttccggtg atgacttggc caaggattct ggttccgacg actccatcaa caacgacgac 180
gccgccgtca attcccaaca gcaaaacgaa aaacaagaca ctgatttctc cgtcctcaaa 240
ttcgcctacc gtccttccgt ccccgctcac cgcaaagtga aggaaagtcc gctcagctcc 300
gacactattt tccgtcagag tcacgcgggc ctcttcaacc tttgtatagt agtccttgtt 360
gctgtgaata gccgactcat cattgagaat ttaatgaagt atggttggtt gatcaaatct 420

```
ggcttttggt ttagtgcaaa gtcattgaga gactggcccc ttttcatgtg ttgtctttct    480

cttgtggtat ttcctttcgc tgcctttatg gtggagaagt tggcacaacg gaagtgtata    540

cccgaaccag ttgttgttgt acttcatata atcattacct caacttcgct tttctatcca    600

gttttagtta ttctcaagtg tgattctgct tttgtatcag gtgtcacgtt aatgctgttt    660

tcttgtgttg tatggttaaa attggtgtct tttgcacata caaactatga tatgagagca    720

cttaccaaat tagttgaaaa gggagaagca ctgctcgata ctctgaacat ggagtatcct    780

tacaacgtaa ccttcaagag cttggcatat ttcctgcttg cccctacatt atgttaccag    840

ccaagctatc ctcgcacacc ttatattcga aagggttggt tgtttcgcca acttgtcaag    900

ctgatagtat ttacaggagt tatgggattt ataatagaac aatatattaa tcccatagta    960

caaaattcac agcatcctct caagggaaac cttctttacg ccaccgagag agttctgaag   1020

ctttctgttc caaatttata tgtgtggctc tgcatgttct attgcttttt ccacctttgg   1080

ttaaatatcg tggcagagct tcttcgattt ggtgatcgtg aattctacaa ggattggtgg   1140

aatgccaaaa ctgtcgaaga ttattggagg atgtggaata tgcctgttca caaatggatg   1200

atccgccacc tatattttcc atgtttaagg cacggtctac caaaggctgc tgctctttta   1260

atttccttcc tggtttctgc tttattccat gagctgtgca ttgctgttcc ttgccacatg   1320

ttcaagttgt gggctttcgg tggaattatg tttcaggttc ctttggtctt gatcactaat   1380

tatctgcaaa ataaattcaa aaactcaatg gttggaaata tgattttttg gttcatattc   1440

agtatcgttg gtcaacctat gtgtgtactg ctatactacc atgacttgat gaataggaaa   1500

ggcaaacttg actga                                                    1515
```

<210> SEQ ID NO 55
<211> LENGTH: 504
<212> TYPE: PRT
<213> ORGANISM: Glycine max

<400> SEQUENCE: 55

```
Met Ala Ile Ser Asp Glu Pro Glu Ser Val Ala Thr Ala Leu Asn His
1               5                   10                  15

Ser Ser Leu Arg Arg Arg Pro Ser Ala Thr Ser Thr Ala Gly Leu Phe
            20                  25                  30

Asn Ser Pro Glu Thr Thr Thr Asp Ser Ser Gly Asp Asp Leu Ala Lys
        35                  40                  45

Asp Ser Gly Ser Asp Asp Ser Ile Asn Asn Asp Asp Ala Ala Val Asn
    50                  55                  60

Ser Gln Gln Gln Asn Glu Lys Gln Asp Thr Asp Phe Ser Val Leu Lys
65                  70                  75                  80

Phe Ala Tyr Arg Pro Ser Val Pro Ala His Arg Lys Val Lys Glu Ser
                85                  90                  95

Pro Leu Ser Ser Asp Thr Ile Phe Arg Gln Ser His Ala Gly Leu Phe
            100                 105                 110

Asn Leu Cys Ile Val Val Leu Val Ala Val Asn Ser Arg Leu Ile Ile
        115                 120                 125

Glu Asn Leu Met Lys Tyr Gly Trp Leu Ile Lys Ser Gly Phe Trp Phe
    130                 135                 140

Ser Ala Lys Ser Leu Arg Asp Trp Pro Leu Phe Met Cys Cys Leu Ser
145                 150                 155                 160

Leu Val Val Phe Pro Phe Ala Ala Phe Met Val Glu Lys Leu Ala Gln
                165                 170                 175
```

Arg Lys Cys Ile Pro Glu Pro Val Val Val Val Leu His Ile Ile Ile
180 185 190

Thr Ser Thr Ser Leu Phe Tyr Pro Val Leu Val Ile Leu Lys Cys Asp
195 200 205

Ser Ala Phe Val Ser Gly Val Thr Leu Met Leu Phe Ser Cys Val Val
210 215 220

Trp Leu Lys Leu Val Ser Phe Ala His Thr Asn Tyr Asp Met Arg Ala
225 230 235 240

Leu Thr Lys Leu Val Glu Lys Gly Glu Ala Leu Leu Asp Thr Leu Asn
245 250 255

Met Glu Tyr Pro Tyr Asn Val Thr Phe Lys Ser Leu Ala Tyr Phe Leu
260 265 270

Leu Ala Pro Thr Leu Cys Tyr Gln Pro Ser Tyr Pro Arg Thr Pro Tyr
275 280 285

Ile Arg Lys Gly Trp Leu Phe Arg Gln Leu Val Lys Leu Ile Val Phe
290 295 300

Thr Gly Val Met Gly Phe Ile Ile Glu Gln Tyr Ile Asn Pro Ile Val
305 310 315 320

Gln Asn Ser Gln His Pro Leu Lys Gly Asn Leu Leu Tyr Ala Thr Glu
325 330 335

Arg Val Leu Lys Leu Ser Val Pro Asn Leu Tyr Val Trp Leu Cys Met
340 345 350

Phe Tyr Cys Phe Phe His Leu Trp Leu Asn Ile Val Ala Glu Leu Leu
355 360 365

Arg Phe Gly Asp Arg Glu Phe Tyr Lys Asp Trp Trp Asn Ala Lys Thr
370 375 380

Val Glu Asp Tyr Trp Arg Met Trp Asn Met Pro Val His Lys Trp Met
385 390 395 400

Ile Arg His Leu Tyr Phe Pro Cys Leu Arg His Gly Leu Pro Lys Ala
405 410 415

Ala Ala Leu Leu Ile Ser Phe Leu Val Ser Ala Leu Phe His Glu Leu
420 425 430

Cys Ile Ala Val Pro Cys His Met Phe Lys Leu Trp Ala Phe Gly Gly
435 440 445

Ile Met Phe Gln Val Pro Leu Val Leu Ile Thr Asn Tyr Leu Gln Asn
450 455 460

Lys Phe Lys Asn Ser Met Val Gly Asn Met Ile Phe Trp Phe Ile Phe
465 470 475 480

Ser Ile Val Gly Gln Pro Met Cys Val Leu Leu Tyr Tyr His Asp Leu
485 490 495

Met Asn Arg Lys Gly Lys Leu Asp
500

<210> SEQ ID NO 56
<211> LENGTH: 13304
<212> TYPE: DNA
<213> ORGANISM: artificial sequence
<220> FEATURE:
<223> OTHER INFORMATION: plasmid sequence

<400> SEQUENCE: 56
ggagatccaa gcttttgatc catgcccttc atttgccgct tattaattaa tttggtaaca 60
gtccgtacta atcagttact tatccttccc ccatcataat taatcttggt agtctcgaat 120
gccacaacac tgactagtct cttggatcat aagaaaaagc caaggaacaa aagaagacaa 180

```
aacacaatga gagtatcctt tgcatagcaa tgtctaagtt cataaaattc aaacaaaaac    240
gcaatcacac acagtggaca tcacttatcc actagctgat caggatcgcc gcgtcaagaa    300
aaaaaaactg gaccccaaaa gccatgcaca acaacacgta ctcacaaagg tgtcaatcga    360
gcagcccaaa acattcacca actcaaccca tcatgagccc tcacatttgt tgtttctaac    420
ccaacctcaa actcgtattc tcttccgcca cctcattttt gtttatttca acacccgtca    480
aactgcatgc caccccgtgg ccaaatgtcc atgcatgtta acaagaccta tgactataaa    540
tagctgcaat ctcggcccag gttttcatca tcaagaacca gttcaatatc ctagtacacc    600
gtattaaaga atttaagata tactgcggcc gcaccatggc gatttccgat gagcctgaaa    660
gtgtagccac tgctctcaac cactcttccc tgcgccgccg tccctccgcc acctccaccg    720
ccggcctctt caattcgcct gagacaacca ccgacagttc cggtgatgac ttggccaagg    780
attctggttc cgacgactcc atcaacaacg acgacgccgc cgtcaattcc caacagcaaa    840
acgaaaaaca agacactgat ttctccgtcc tcaaattcgc ctaccgtcct tccgtccccg    900
ctcaccgcaa agtgaaggaa agtccgctca gctccgacac tattttccgt cagagtcacg    960
cgggcctctt caacctttgt atagtagtcc ttgttgctgt gaatagccga ctcatcattg   1020
agaatttaat gaagtatggt tggttgatca aatctggctt ttggtttagt gcaaagtcat   1080
tgagagactg gccccttttc atgtgttgtc tttctcttgt ggtatttcct ttcgctgcct   1140
ttatggtgga gaagttggca caacggaagt gtatacccga accagttgtt gttgtacttc   1200
atataatcat tacctcaact tcgcttttct atccagtttt agttattctc aagtgtgatt   1260
ctgcttttgt atcaggtgtc acgttaatgc tgttttcttg tgttgtatgg ttaaaattgg   1320
tgtcttttgc acatacaaac tatgatatga gagcacttac caaattagtt gaaaagggag   1380
aagcactgct cgatactctg aacatggagt atccttacaa cgtaaccttc aagagcttgg   1440
catatttcct gcttgcccct acattatgtt accagccaag ctatcctcgc acaccttata   1500
ttcgaaaggg ttggttgttt cgccaacttg tcaagctgat agtatttaca ggagttatgg   1560
gatttataat agaacaatat attaatccca tagtacaaaa ttcacagcat cctctcaagg   1620
gaaaccttct ttacgccacc gagagagttc tgaagctttc tgttccaaat ttatatgtgt   1680
ggctctgcat gttctattgc tttttccacc tttggttaaa tatcgtggca gagcttcttc   1740
gatttggtga tcgtgaattc tacaaggatt ggtggaatgc caaaactgtc gaagattatt   1800
ggaggatgtg gaatatgcct gttcacaaat ggatgatccg ccacctatat tttccatgtt   1860
taaggcacgg tctaccaaag gctgctgctc ttttaatttc cttcctggtt tctgctttat   1920
tccatgagct gtgcattgct gttccttgcc acatgttcaa gttgtgggct ttcggtggaa   1980
ttatgtttca ggttcctttg gtcttgatca ctaattatct gcaaaataaa ttcaaaaact   2040
caatggttgg aaatatgatt ttttggttca tattcagtat cgttggtcaa cctatgtgtg   2100
tactgctata ctaccatgac ttgatgaata ggaaaggcaa acttgactga gcggccgcaa   2160
gtatgaacta aaatgcatgt aggtgtaaga gctcatggag agcatggaat attgtatccg   2220
accatgtaac agtataataa ctgagctcca tctcacttct tctatgaata aacaaaggat   2280
gttatgatat attaacactc tatctatgca ccttattgtt ctatgataaa tttcctctta   2340
ttattataaa tcatctgaat cgtgacggct tatggaatgc ttcaaatagt acaaaaacaa   2400
atgtgtacta taagactttc taaacaattc taaccttagc attgtgaacg agacataagt   2460
gttaagaaga cataacaatt ataatggaag aagtttgtct ccatttatat attatatatt   2520
```

```
acccacttat gtattatatt aggatgttaa ggagacataa caattataaa gagagaagtt   2580
tgtatccatt tatatattat atactaccca tttatatatt atacttatcc acttatttaa   2640
tgtctttata aggtttgatc catgatattt ctaatatttt agttgatatg tatatgaaag   2700
ggtactattt gaactctctt actctgtata aaggttggat catccttaaa gtgggtctat   2760
ttaattttat tgcttcttac agataaaaaa aaaattatga gttggtttga taaaatattg   2820
aaggatttaa aataataata aataacatat aatatatgta tataaattta ttataatata   2880
acatttatct ataaaaaagt aaatattgtc ataaatctat acaatcgttt agccttgctg   2940
gacgaatctc aattatttaa acgagagtaa acatatttga ctttttggtt atttaacaaa   3000
ttattattta acactatatg aaattttttt ttttatcagc aaagaataaa attaaattaa   3060
gaaggacaat ggtgtcccaa tccttataca accaacttcc acaagaaagt caagtcagag   3120
acaacaaaaa aacaagcaaa ggaaattttt taatttgagt tgtcttgttt gctgcataat   3180
ttatgcagta aaacactaca cataaccctt ttagcagtag agcaatggtt gaccgtgtgc   3240
ttagcttctt ttattttatt tttttatcag caaagaataa ataaaataaa atgagacact   3300
tcagggatgt ttcaacaagc ttggcgcgcc gttctatagt gtcacctaaa tcgtatgtgt   3360
atgatacata aggttatgta ttaattgtag ccgcgttcta acgacaatat gtccatatgg   3420
tgcactctca gtacaatctg ctctgatgcc gcatagttaa gccagccccg acacccgcca   3480
acacccgctg acgcgccctg acgggcttgt ctgctcccgg catccgctta cagacaagct   3540
gtgaccgtct ccgggagctg catgtgtcag aggttttcac cgtcatcacc gaaacgcgcg   3600
agacgaaagg gcctcgtgat acgcctattt ttataggtta atgtcatgac caaaatccct   3660
taacgtgagt tttcgttcca ctgagcgtca gaccccgtag aaaagatcaa aggatcttct   3720
tgagatcctt tttttctgcg cgtaatctgc tgcttgcaaa caaaaaaacc accgctacca   3780
gcggtggttt gtttgccgga tcaagagcta ccaactcttt ttccgaaggt aactggcttc   3840
agcagagcgc agataccaaa tactgtcctt ctagtgtagc cgtagttagg ccaccacttc   3900
aagaactctg tagcaccgcc tacatacctc gctctgctaa tcctgttacc agtggctgct   3960
gccagtggcg ataagtcgtg tcttaccggg ttggactcaa gacgatagtt accggataag   4020
gcgcagcggt cgggctgaac ggggggttcg tgcacacagc ccagcttgga gcgaacgacc   4080
tacaccgaac tgagatacct acagcgtgag cattgagaaa gcgccacgct tcccgaaggg   4140
agaaaggcgg acaggtatcc ggtaagcggc agggtcggaa caggagagcg cacgagggag   4200
cttccagggg gaaacgcctg gtatctttat agtcctgtcg ggtttcgcca cctctgactt   4260
gagcgtcgat ttttgtgatg ctcgtcaggg gggcggagcc tatggaaaaa cgccagcaac   4320
gcggcctttt tacggttcct ggccttttgc tggccttttg ctcacatgtt ctttcctgcg   4380
ttatcccctg attctgtgga taaccgtatt accgcctttg agtgagctga taccgctcgc   4440
cgcagccgaa cgaccgagcg cagcgagtca gtgagcgagg aagcggaaga gcgcccaata   4500
cgcaaaccgc ctctccccgc gcgttggccg attcattaat gcaggttgat cgattcgaca   4560
tcgatctagt aacatagatg acaccgcgcg cgataattta tcctagtttg cgcgctatat   4620
tttgttttct atcgcgtatt aaatgtataa ttgcgggact ctaatcataa aaacccatct   4680
cataaataac gtcatgcatt acatgttaat tattacatgc ttaacgtaat tcaacagaaa   4740
ttatatgata atcatcgcaa gaccggcaac aggattcaat cttaagaaac tttattgcca   4800
aatgtttgaa cgatctgctt cgacgcactc cttctttagg tacctcacta ttcctttgcc   4860
ctcggacgag tgctggggcg tcggtttcca ctatcggcga gtacttctac acagccatcg   4920
```

gtccagacgg ccgcgcttct gcgggcgatt tgtgtacgcc cgacagtccc ggctccggat 4980
cggacgattg cgtcgcatcg accctgcgcc caagctgcat catcgaaatt gccgtcaacc 5040
aagctctgat agagttggtc aagaccaatg cggagcatat acgcccggag ccgcggcgat 5100
cctgcaagct ccggatgcct ccgctcgaag tagcgcgtct gctgctccat acaagccaac 5160
cacggcctcc agaagaagat gttggcgacc tcgtattggg aatccccgaa catcgcctcg 5220
ctccagtcaa tgaccgctgt tatgcggcca ttgtccgtca ggacattgtt ggagccgaaa 5280
tccgcgtgca cgaggtgccg gacttcgggg cagtcctcgg cccaaagcat cagctcatcg 5340
agagcctgcg cgacggacgc actgacggtg tcgtccatca cagtttgcca gtgatacaca 5400
tggggatcag caatcgcgca tatgaaatca cgccatgtag tgtattgacc gattccttgc 5460
ggtccgaatg ggccgaaccc gctcgtctgg ctaagatcgg ccgcagcgat cgcatccatg 5520
gcctccgcga ccggctgcag aacagcgggc agttcggttt caggcaggtc ttgcaacgtg 5580
acaccctgtg cacggcggga gatgcaatag gtcaggctct cgctgaattc cccaatgtca 5640
agcacttccg gaatcgggag cgcggccgat gcaaagtgcc gataaacata acgatctttg 5700
tagaaaccat cggcgcagct atttacccgc aggacatatc cacgccctcc tacatcgaag 5760
ctgaaagcac gagattcttc gccctccgag agctgcatca ggtcggagac gctgtcgaac 5820
ttttcgatca gaaacttctc gacagacgtc gcggtgagtt caggcttttt catggtttaa 5880
taagaagaga aaagagttct tttgttatgg ctgaagtaat agagaaatga gctcgagcgt 5940
gtcctctcca aatgaaatga acttccttat atagaggaag ggtcttgcga aggatagtgg 6000
gattgtgcgt catcccttac gtcagtggag atgtcacatc aatccacttg ctttgaagac 6060
gtggttggaa cgtcttcttt ttccacgatg ctcctcgtgg gtgggggtcc atctttggga 6120
ccactgtcgg cagaggcatc ttgaatgata gcctttcctt tatcgcaatg atggcatttg 6180
taggagccac cttccttttc tactgtcctt tcgatgaagt gacagatagc tgggcaatgg 6240
aatccgagga ggtttcccga aattatcctt tgttgaaaag tctcaatagc cctttggtct 6300
tctgagactg tatctttgac atttttggag tagaccagag tgtcgtgctc caccatgttg 6360
acgaagattt tcttcttgtc attgagtcgt aaaagactct gtatgaactg ttcgccagtc 6420
ttcacggcga gttctgttag atcctcgatt tgaatcttag actccatgca tggccttaga 6480
ttcagtagga actacctttt tagagactcc aatctctatt acttgccttg gtttatgaag 6540
caagccttga atcgtccata ctggaatagt acttctgatc ttgagaaata tgtctttctc 6600
tgtgttcttg atgcaattag tcctgaatct tttgactgca tctttaacct tcttgggaag 6660
gtatttgatc tcctggagat tgttactcgg gtagatcgtc ttgatgagac ctgctgcgta 6720
ggcctctcta accatctgtg ggtcagcatt ctttctgaaa ttgaagaggc taaccttctc 6780
attatcagtg gtgaacatag tgtcgtcacc ttcaccttcg aacttccttc ctagatcgta 6840
aagatagagg aaatcgtcca ttgtaatctc cggggcaaag gagatctctt ttggggctgg 6900
atcactgctg ggccttttgg ttcctagcgt gagccagtgg gctttttgct ttggtgggct 6960
tgttagggcc ttagcaaagc tcttgggctt gagttgagct tctcctttgg ggatgaagtt 7020
caacctgtct gtttgctgac ttgttgtgta cgcgtcagct gctgctcttg cctctgtaat 7080
agtggcaaat ttcttgtgtg caactccggg aacgccgttt gttgccgcct ttgtacaacc 7140
ccagtcatcg tatataccgg catgtggacc gttatacaca acgtagtagt tgatatgagg 7200
gtgttgaata cccgattctg ctctgagagg agcaactgtg ctgttaagct cagatttttg 7260

-continued tgggattgga attggatcga tctcgatccc gcgaaattaa tacgactcac tatagggaga 7320
ccacaacggt ttccctctag aaataatttt gtttaacttt aagaaggaga tatacccatg 7380
gaaaagcctg aactcaccgc gacgtctgtc gagaagtttc tgatcgaaaa gttcgacagc 7440
gtctccgacc tgatgcagct ctcggagggc gaagaatctc gtgctttcag cttcgatgta 7500
ggagggcgtg gatatgtcct gcgggtaaat agctgcgccg atggtttcta caaagatcgt 7560
tatgtttatc ggcactttgc atcggccgcg ctcccgattc cggaagtgct tgacattggg 7620
gaattcagcg agagcctgac ctattgcatc tcccgccgtg cacagggtgt cacgttgcaa 7680
gacctgcctg aaaccgaact gcccgctgtt ctgcagccgg tcgcggaggc tatggatgcg 7740
atcgctgcgg ccgatcttag ccagacgagc gggttcggcc cattcggacc gcaaggaatc 7800
ggtcaataca ctacatggcg tgatttcata tgcgcgattg ctgatcccca tgtgtatcac 7860
tggcaaactg tgatggacga caccgtcagt gcgtccgtcg cgcaggctct cgatgagctg 7920
atgctttggg ccgaggactg ccccgaagtc cggcacctcg tgcacgcgga tttcggctcc 7980
aacaatgtcc tgacggacaa tggccgcata acagcggtca ttgactggag cgaggcgatg 8040
ttcggggatt cccaatacga ggtcgccaac atcttcttct ggaggccgtg gttggcttgt 8100
atggagcagc agacgcgcta cttcgagcgg aggcatccgg agcttgcagg atcgccgcgg 8160
ctccgggcgt atatgctccg cattggtctt gaccaactct atcagagctt ggttgacggc 8220
aatttcgatg atgcagcttg ggcgcagggt cgatgcgacg caatcgtccg atccggagcc 8280
gggactgtcg ggcgtacaca aatcgcccgc agaagcgcgg ccgtctggac cgatggctgt 8340
gtagaagtac tcgccgatag tggaaaccga cgccccagca ctcgtccgag ggcaaaggaa 8400
tagtgaggta cagcttggat cgatccggct gctaacaaag cccgaaagga agctgagttg 8460
gctgctgcca ccgctgagca ataactagca taaccccttg gggcctctaa acgggtcttg 8520
aggggttttt tgctgaaagg aggaactata tccggatgat cgggcgcgcc gtcgacggat 8580
ccgtacgaga tccggccggc cagatcctgc aggtaaattg cagctgaagg acagtgaagg 8640
gtgaatttat ccatttaaac cattttcttt ttaacacatt tcttatggta atctcttctc 8700
actacactat aaaaatggct tctcaatccc attttctaca tcatcccatt ctattgagtt 8760
ttgtttattt gctttcactt tttttttat ctgcctcttc ccttaatttg cttgacttct 8820
tcttcacatt ttgctttgtt ttctcctccg gcttccggta tttcaaattc aagatgagca 8880
agttgaaatt tataaataga aatacagata ttatttacaa cgtcaaatct ttggtatttt 8940
caatatttga atggggtaaa tttgtcatat agtcatcatc actgactact tatctaacct 9000
atttaatttg gagcatattc tttataaggt ccctctcacg gccaatgtct aattattgat 9060
atacagctct tgttttctag tgctgcttat aatattatct acacatatat atggtactgc 9120
acactactac tatatagtag taagtaaact agcaacagcc ggggccaaac tccaataact 9180
aggcattggg gtttagttgg taatataaat ataacatcaa aaagtctttg cttgtgacga 9240
acatcacaat gcacccacca ttgatgccac gacagacatt gttaattttt tttttaattt 9300
ttaaaaaaga agcaattcca atagttctat attacaatct cacgtgatcc aagcacaacg 9360
tttcattttt tgtacatgct cgatatataa ataatatttc attttatagt aaaatataat 9420
gacattttcg aatataattt ttgaaatttc attttccaaa tgaaatacta atattaatat 9480
taatgagatt accacaaatc atgttatgaa tgaaataaag agttttggca ttctaacttt 9540
ctttgaatag aacaaaatgt atacaacact ctccatatat acacgattta ttcagggatc 9600
atatacattc tctcatgatt aacatagtct gctttcttca cgtctaagca gataattttt 9660

```
ggtccacaag ataaaattat cattagtcgt tttaattaat tccttgagca tcaagcacta   9720
aaataattaa acttctccat taccaaaaaa aaaagatagg tgattcagta acatgtagta   9780
ctagtactac tgattttttt tttcttttga ttttaatgaa tggttcgtat cgagcatcga   9840
gaaatccatt tattaggtgt gtaatgtaat agtagtattt ccttgatttt cagtaataag   9900
atggattctt acatttatat ctgtttgaca gaaaatgttg tcaatgcatt tcttgggcac   9960
aaagtttttt gaaacatgaa ttaatttttt caaaatattt atgacatcaa attgacccta  10020
aaataagtga taaagcttta acgtggaatg acattaattt ttccatgata aataaaacac  10080
ttaaaacatt ttaatattaa tattataatc agttacaact atgttcaatt aatgcaataa  10140
cttttaaata aatattaaaa tatttttttt ctgttctcca ataaagagat cttgttgcac  10200
ggaaaaagtc acattcttat ttagtaaaaa attataatta ttgtttgaaa aatatcattt  10260
tcactgcaga aaatttgatc cagctctaca gatcatactt ttattgtaca ataatacaat  10320
aaaaatattc atctgcagga aatatcattt tcattgtaca ataatataaa gataaatata  10380
taccagaaaa gaaaaagaaa ctgatgtggc acaatgtatt cactgaaaga atgcatattg  10440
tatttcacct ttcaagcagc actaagaata tacttctttt attatacttg tgcatttact  10500
caaccaccct cggtggagta agaaagaaga tagataaaag ttttttttga catttggtga  10560
atctcttaat taaaaaaata aaataatcca tttcctttat ttaatttctt ttttcccatc  10620
tgtgaaattc caattctgct tcgcgctcct gtctataaat tgacttagcc accacctcag  10680
tttccattca ttcacttctt ctctttatac ccccccctctc ttttttgcgt tcattctgtt  10740
ttcgtaagta ctgttgtttt tctcttctat ttcttttttt gtttgtgttg tttttttttc  10800
ttccttatcg ttgttctgcc tctcctctgt ttcggtgctc tgttcaccac ttccacgtga  10860
gaatgatctt ccttctttgc atgttcattc tctcgtgacc actggatcag actccatgtt  10920
ctgatccagg gtctctctct aacgcctgta ctttcatcca tgaccacctt aaaaacaaca  10980
tgggggtggt gctgttacac taactctgtt tctggggtgc tgtctttgtt caattttact  11040
cagaaaatat cttttcttgg attctattcg gtgtgtggga acatgatcct gtcggtcggt  11100
tgtttttagg ttaatcctta actggttaca aggatctaac gcttgaatgc atgtcctgag  11160
ttaaagaaac aaaagaagaa cacacctagt acagcctggc ctcgaaccaa gaacttcttt  11220
gttggtttct cattattact aaaataaaat aaagtatacg ttttcttttt tctttgggat  11280
gaacggttca gacttatgag aagtttaagc taatcctgta gtggagtgtt caatttattt  11340
taaactttaa agcaatagct caagcactaa acttcttttt caagttcaac cactttggta  11400
gcttgctaat tgctgctatt gttctaatta attaatgtaa ttattgttta aaaaagaaaa  11460
gttggtgaca ctggaataaa aaagtgtact atctggcaat tattcttctg cagcaatgtt  11520
tgaggttgaa atcttagtag aacaaagtag aagatctggt atttatattt tttgtagaca  11580
gatggtgggg gtgggtggta ggccttgaaa tccaatatag ttttgtagaa taattttatt  11640
attttttttt tttgctcact tgtttgtggt attgattttg tgatgactca agattaatga  11700
tttaccttca tttttttcat ggtgacatat tatgtatatt cttgatctgt ttcttacact  11760
tctttttcgt tgttgtagct gttgaagtct gcggccgcac catggaaact ggaggctttc  11820
acggctaccg caagctcccc aacaccaccg ctgggttgaa gctgtcagtg tcagacatga  11880
acatgaacat gaggcagcag caggtagcat catcagatca gaactgcagc aaccacagtg  11940
cagcaggaga ggagaacgaa tgcacggtga gggagcaaga caggttcatg ccaatcgcta  12000
```

acgtgatacg gatcatgcgc aagattctcc ctccacacgc aaaaatctcc gatgatgcaa 12060
aggagacaat ccaagagtgc gtgtcggagt acatcagctt catcaccggg gaggcgaacg 12120
agcgttgcca gagggagcaa cggaagacca taaccgcaga ggacgtgctt tgggccatga 12180
gcaagcttgg attcgacgac tacatcgaac cgttgaccat gtaccttcac cgctaccgtg 12240
aacttgaggg tgaccgcacc tctatgaggg gtgaaccact cgggaagagg actgtggaat 12300
acgccacgct tggtgttgct actgcttttg tccctccacc ctatcatcac cacaatgggt 12360
actttggtgc tgccatgccc atggggactt acgttaggga agcgccacca aatacagcct 12420
cctcccatca ccaccaccac caccaccacc accatgctcg tggaatctcc aatgctcatg 12480
aaccaaatgc tcgctccata taagcggccg catttcgcac caaatcaatg aaagtaataa 12540
tgaaaagtct gaataagaat acttaggctt agatgccttt gttacttgtg taaaataact 12600
tgagtcatgt acctttggcg gaaacagaat aaataaaagg tgaaattcca atgctctatg 12660
tataagttag taatacttaa tgtgttctac ggttgtttca atatcatcaa actctaattg 12720
aaactttaga accacaaatc tcaatctttt cttaatgaaa tgaaaaatct taattgtacc 12780
atgtttatgt taaacacctt acaattaatt ggttggagag gaggaccaac cgatgggaca 12840
acattgggag aaagagattc aatggagatt tggataggag aacaacattc tttttcactt 12900
caatacaaga tgagtgcaac actaaggata tgtatgagac tttcagaagc tacgacaaca 12960
tagatgagtg aggtggtgat tcctagcaag aaagacatta gaggaagcca aaatcgaaca 13020
aggaagacat caagggcaag agacaggacc atccatctca ggaaaaggag ctttgggata 13080
gtccgagaag ttgtacaaga aattttttgg agggtgagtg atgcattgct ggtgacttta 13140
actcaatcaa aattgagaaa gaaagaaaag ggagggggct cacatgtgaa tagaagggaa 13200
acgggagaat tttacagttt tgatctaatg ggcatcccag ctagtggtaa catattcacc 13260
atgtttaacc ttcacgtacg agatccggcc ggccagatcc tgca 13304

<210> SEQ ID NO 57
<211> LENGTH: 13838
<212> TYPE: DNA
<213> ORGANISM: artificial sequence
<220> FEATURE:
<223> OTHER INFORMATION: plasmid sequence

<400> SEQUENCE: 57
ggagatccaa gcttttgatc catgcccttc atttgccgct tattaattaa tttggtaaca 60
gtccgtacta atcagttact tatccttccc ccatcataat taatcttggt agtctcgaat 120
gccacaacac tgactagtct cttggatcat aagaaaaagc caaggaacaa aagaagacaa 180
aacacaatga gagtatcctt tgcatagcaa tgtctaagtt cataaaattc aaacaaaaac 240
gcaatcacac acagtggaca tcacttatcc actagctgat caggatcgcc gcgtcaagaa 300
aaaaaaactg gaccccaaaa gccatgcaca acaacacgta ctcacaaagg tgtcaatcga 360
gcagcccaaa acattcacca actcaaccca tcatgagccc tcacatttgt tgtttctaac 420
ccaacctcaa actcgtattc tcttccgcca cctcattttt gtttatttca acacccgtca 480
aactgcatgc caccccgtgg ccaaatgtcc atgcatgtta acaagaccta tgactataaa 540
tagctgcaat ctcggcccag gttttcatca tcaagaacca gttcaatatc ctagtacacc 600
gtattaaaga atttaagata tactgcggcc gcaccatggc gatttccgat gagcctgaaa 660
gtgtagccac tgctctcaac cactcttccc tgcgccgccg tccctccgcc acctccaccg 720
ccggcctctt caattcgcct gagacaacca ccgacagttc cggtgatgac ttggccaagg 780

```
attctggttc cgacgactcc atcaacaacg acgacgccgc cgtcaattcc caacagcaaa    840
acgaaaaaca agacactgat ttctccgtcc tcaaattcgc ctaccgtcct tccgtccccg    900
ctcaccgcaa agtgaaggaa agtccgctca gctccgacac tattttccgt cagagtcacg    960
cgggcctctt caacctttgt atagtagtcc ttgttgctgt gaatagccga ctcatcattg   1020
agaatttaat gaagtatggt tggttgatca aatctggctt ttggtttagt gcaaagtcat   1080
tgagagactg gccccttttc atgtgttgtc tttctcttgt ggtatttcct ttcgctgcct   1140
ttatggtgga gaagttggca caacggaagt gtatacccga accagttgtt gttgtacttc   1200
atataatcat tacctcaact tcgcttttct atccagtttt agttattctc aagtgtgatt   1260
ctgcttttgt atcaggtgtc acgttaatgc tgttttcttg tgttgtatgg ttaaaattgg   1320
tgtcttttgc acatacaaac tatgatatga gagcacttac caaattagtt gaaaagggag   1380
aagcactgct cgatactctg aacatggagt atccttacaa cgtaaccttc aagagcttgg   1440
catatttcct gcttgcccct acattatgtt accagccaag ctatcctcgc acaccttata   1500
ttcgaaaggg ttggttgttt cgccaacttg tcaagctgat agtatttaca ggagttatgg   1560
gatttataat agaacaatat attaatccca tagtacaaaa ttcacagcat cctctcaagg   1620
gaaaccttct ttacgccacc gagagagttc tgaagctttc tgttccaaat ttatatgtgt   1680
ggctctgcat gttctattgc tttttccacc tttggttaaa tatcgtggca gagcttcttc   1740
gatttggtga tcgtgaattc tacaaggatt ggtggaatgc caaaactgtc gaagattatt   1800
ggaggatgtg gaatatgcct gttcacaaat ggatgatccg ccacctatat tttccatgtt   1860
taaggcacgg tctaccaaag gctgctgctc ttttaatttc cttcctggtt tctgctttat   1920
tccatgagct gtgcattgct gttccttgcc acatgttcaa gttgtgggct ttcggtggaa   1980
ttatgtttca ggttcctttg gtcttgatca ctaattatct gcaaaataaa ttcaaaaact   2040
caatggttgg aaatatgatt ttttggttca tattcagtat cgttggtcaa cctatgtgtg   2100
tactgctata ctaccatgac ttgatgaata ggaaaggcaa acttgactga gcggccgcaa   2160
gtatgaacta aaatgcatgt aggtgtaaga gctcatggag agcatggaat attgtatccg   2220
accatgtaac agtataataa ctgagctcca tctcacttct tctatgaata aacaaaggat   2280
gttatgatat attaacactc tatctatgca ccttattgtt ctatgataaa tttcctctta   2340
ttattataaa tcatctgaat cgtgacggct tatggaatgc ttcaaatagt acaaaaacaa   2400
atgtgtacta taagactttc taaacaattc taaccttagc attgtgaacg agacataagt   2460
gttaagaaga cataacaatt ataatggaag aagtttgtct ccatttatat attatatatt   2520
acccacttat gtattatatt aggatgttaa ggagacataa caattataaa gagagaagtt   2580
tgtatccatt tatatattat atactaccca tttatatatt atacttatcc acttatttaa   2640
tgtctttata aggtttgatc catgatattt ctaatatttt agttgatatg tatatgaaag   2700
ggtactattt gaactctctt actctgtata aaggttggat catccttaaa gtgggtctat   2760
ttaattttat tgcttcttac agataaaaaa aaaattatga gttggtttga taaaatattg   2820
aaggatttaa aataataata aataacatat aatatatgta tataaattta ttataatata   2880
acatttatct ataaaaaagt aaatattgtc ataaatctat acaatcgttt agccttgctg   2940
gacgaatctc aattatttaa acgagagtaa acatatttga ctttttggtt atttaacaaa   3000
ttattattta acactatatg aaattttttt ttttatcagc aaagaataaa attaaattaa   3060
gaaggacaat ggtgtcccaa tccttataca accaacttcc acaagaaagt caagtcagag   3120
```

```
acaacaaaaa aacaagcaaa ggaaattttt taatttgagt tgtcttgttt gctgcataat   3180
ttatgcagta aaacactaca cataaccctt ttagcagtag agcaatggtt gaccgtgtgc   3240
ttagcttctt ttattttatt tttttatcag caaagaataa ataaaataaa atgagacact   3300
tcagggatgt ttcaacaagc ttggcgcgcc gttctatagt gtcacctaaa tcgtatgtgt   3360
atgatacata aggttatgta ttaattgtag ccgcgttcta acgacaatat gtccatatgg   3420
tgcactctca gtacaatctg ctctgatgcc gcatagttaa gccagccccg acacccgcca   3480
acacccgctg acgcgccctg acgggcttgt ctgctcccgg catccgctta cagacaagct   3540
gtgaccgtct ccgggagctg catgtgtcag aggttttcac cgtcatcacc gaaacgcgcg   3600
agacgaaagg gcctcgtgat acgcctattt ttataggtta atgtcatgac caaaatccct   3660
taacgtgagt tttcgttcca ctgagcgtca gaccccgtag aaaagatcaa aggatcttct   3720
tgagatcctt tttttctgcg cgtaatctgc tgcttgcaaa caaaaaaacc accgctacca   3780
gcggtggttt gtttgccgga tcaagagcta ccaactcttt ttccgaaggt aactggcttc   3840
agcagagcgc agataccaaa tactgtcctt ctagtgtagc cgtagttagg ccaccacttc   3900
aagaactctg tagcaccgcc tacatacctc gctctgctaa tcctgttacc agtggctgct   3960
gccagtggcg ataagtcgtg tcttaccggg ttggactcaa gacgatagtt accggataag   4020
gcgcagcggt cgggctgaac ggggggttcg tgcacacagc ccagcttgga gcgaacgacc   4080
tacaccgaac tgagatacct acagcgtgag cattgagaaa gcgccacgct tcccgaaggg   4140
agaaaggcgg acaggtatcc ggtaagcggc agggtcggaa caggagagcg cacgagggag   4200
cttccagggg gaaacgcctg gtatctttat agtcctgtcg ggtttcgcca cctctgactt   4260
gagcgtcgat ttttgtgatg ctcgtcaggg gggcggagcc tatggaaaaa cgccagcaac   4320
gcggcctttt tacggttcct ggccttttgc tggccttttg ctcacatgtt ctttcctgcg   4380
ttatcccctg attctgtgga taaccgtatt accgcctttg agtgagctga taccgctcgc   4440
cgcagccgaa cgaccgagcg cagcgagtca gtgagcgagg aagcggaaga gcgcccaata   4500
cgcaaaccgc ctctccccgc gcgttggccg attcattaat gcaggttgat cgattcgaca   4560
tcgatctagt aacatagatg acaccgcgcg cgataattta tcctagtttg cgcgctatat   4620
tttgttttct atcgcgtatt aaatgtataa ttgcgggact ctaatcataa aaacccatct   4680
cataaataac gtcatgcatt acatgttaat tattacatgc ttaacgtaat tcaacagaaa   4740
ttatatgata atcatcgcaa gaccggcaac aggattcaat cttaagaaac tttattgcca   4800
aatgtttgaa cgatctgctt cgacgcactc cttctttagg tacctcacta ttcctttgcc   4860
ctcggacgag tgctggggcg tcggtttcca ctatcggcga gtacttctac acagccatcg   4920
gtccagacgg ccgcgcttct gcgggcgatt tgtgtacgcc cgacagtccc ggctccggat   4980
cggacgattg cgtcgcatcg accctgcgcc caagctgcat catcgaaatt gccgtcaacc   5040
aagctctgat agagttggtc aagaccaatg cggagcatat acgcccggag ccgcggcgat   5100
cctgcaagct ccggatgcct ccgctcgaag tagcgcgtct gctgctccat acaagccaac   5160
cacggcctcc agaagaagat gttggcgacc tcgtattggg aatccccgaa catcgcctcg   5220
ctccagtcaa tgaccgctgt tatgcggcca ttgtccgtca ggacattgtt ggagccgaaa   5280
tccgcgtgca cgaggtgccg gacttcgggg cagtcctcgg cccaaagcat cagctcatcg   5340
agagcctgcg cgacggacgc actgacggtg tcgtccatca cagtttgcca gtgatacaca   5400
tggggatcag caatcgcgca tatgaaatca cgccatgtag tgtattgacc gattccttgc   5460
ggtccgaatg ggccgaaccc gctcgtctgg ctaagatcgg ccgcagcgat cgcatccatg   5520
```

gcctccgcga ccggctgcag aacagcgggc agttcggttt caggcaggtc ttgcaacgtg 5580
acaccctgtg cacggcggga gatgcaatag gtcaggctct cgctgaattc cccaatgtca 5640
agcacttccg gaatcgggag cgcggccgat gcaaagtgcc gataaacata acgatctttg 5700
tagaaaccat cggcgcagct atttacccgc aggacatatc cacgccctcc tacatcgaag 5760
ctgaaagcac gagattcttc gccctccgag agctgcatca ggtcggagac gctgtcgaac 5820
ttttcgatca gaaacttctc gacagacgtc gcggtgagtt caggcttttt catggtttaa 5880
taagaagaga aaagagttct tttgttatgg ctgaagtaat agagaaatga gctcgagcgt 5940
gtcctctcca aatgaaatga acttccttat atagaggaag ggtcttgcga aggatagtgg 6000
gattgtgcgt catcccttac gtcagtggag atgtcacatc aatccacttg ctttgaagac 6060
gtggttggaa cgtcttcttt ttccacgatg ctcctcgtgg gtgggggtcc atctttggga 6120
ccactgtcgg cagaggcatc ttgaatgata gcctttcctt tatcgcaatg atggcatttg 6180
taggagccac cttccttttc tactgtcctt tcgatgaagt gacagatagc tgggcaatgg 6240
aatccgagga ggtttcccga aattatcctt tgttgaaaag tctcaatagc cctttggtct 6300
tctgagactg tatctttgac atttttggag tagaccagag tgtcgtgctc caccatgttg 6360
acgaagattt tcttcttgtc attgagtcgt aaaagactct gtatgaactg ttcgccagtc 6420
ttcacggcga gttctgttag atcctcgatt tgaatcttag actccatgca tggccttaga 6480
ttcagtagga actacctttt tagagactcc aatctctatt acttgccttg gtttatgaag 6540
caagccttga atcgtccata ctggaatagt acttctgatc ttgagaaata tgtctttctc 6600
tgtgttcttg atgcaattag tcctgaatct tttgactgca tctttaacct tcttgggaag 6660
gtatttgatc tcctggagat tgttactcgg gtagatcgtc ttgatgagac ctgctgcgta 6720
ggcctctcta accatctgtg ggtcagcatt ctttctgaaa ttgaagaggc taaccttctc 6780
attatcagtg gtgaacatag tgtcgtcacc ttcaccttcg aacttccttc ctagatcgta 6840
aagatagagg aaatcgtcca ttgtaatctc cggggcaaag gagatctctt ttggggctgg 6900
atcactgctg ggccttttgg ttcctagcgt gagccagtgg gctttttgct ttggtgggct 6960
tgttagggcc ttagcaaagc tcttgggctt gagttgagct tctcctttgg ggatgaagtt 7020
caacctgtct gtttgctgac ttgttgtgta cgcgtcagct gctgctcttg cctctgtaat 7080
agtggcaaat ttcttgtgtg caactccggg aacgccgttt gttgccgcct ttgtacaacc 7140
ccagtcatcg tatataccgg catgtggacc gttatacaca acgtagtagt tgatatgagg 7200
gtgttgaata cccgattctg ctctgagagg agcaactgtg ctgttaagct cagatttttg 7260
tgggattgga attggatcga tctcgatccc gcgaaattaa tacgactcac tatagggaga 7320
ccacaacggt ttccctctag aaataatttt gtttaacttt aagaaggaga tatacccatg 7380
gaaaagcctg aactcaccgc gacgtctgtc gagaagtttc tgatcgaaaa gttcgacagc 7440
gtctccgacc tgatgcagct ctcggagggc gaagaatctc gtgctttcag cttcgatgta 7500
ggagggcgtg gatatgtcct gcgggtaaat agctgcgccg atggtttcta caaagatcgt 7560
tatgtttatc ggcactttgc atcggccgcg ctcccgattc cggaagtgct tgacattggg 7620
gaattcagcg agagcctgac ctattgcatc tcccgccgtg cacagggtgt cacgttgcaa 7680
gacctgcctg aaaccgaact gcccgctgtt ctgcagccgg tcgcggaggc tatggatgcg 7740
atcgctgcgg ccgatcttag ccagacgagc gggttcggcc cattcggacc gcaaggaatc 7800
ggtcaataca ctacatggcg tgatttcata tgcgcgattg ctgatcccca tgtgtatcac 7860

```
tggcaaactg tgatggacga caccgtcagt gcgtccgtcg cgcaggctct cgatgagctg   7920
atgctttggg ccgaggactg ccccgaagtc cggcacctcg tgcacgcgga tttcggctcc   7980
aacaatgtcc tgacggacaa tggccgcata acagcggtca ttgactggag cgaggcgatg   8040
ttcggggatt cccaatacga ggtcgccaac atcttcttct ggaggccgtg gttggcttgt   8100
atggagcagc agacgcgcta cttcgagcgg aggcatccgg agcttgcagg atcgccgcgg   8160
ctccgggcgt atatgctccg cattggtctt gaccaactct atcagagctt ggttgacggc   8220
aatttcgatg atgcagcttg ggcgcagggt cgatgcgacg caatcgtccg atccggagcc   8280
gggactgtcg ggcgtacaca aatcgcccgc agaagcgcgg ccgtctggac cgatggctgt   8340
gtagaagtac tcgccgatag tggaaaccga cgccccagca ctcgtccgag ggcaaaggaa   8400
tagtgaggta cagcttggat cgatccggct gctaacaaag cccgaaagga agctgagttg   8460
gctgctgcca ccgctgagca ataactagca taaccccttg gggcctctaa acgggtcttg   8520
aggggttttt tgctgaaagg aggaactata tccggatgat cgggcgcgcc gtcgacggat   8580
ccgtacgaga tccggccggc cagatcctgc aggtaaattg cagctgaagg acagtgaagg   8640
gtgaatttat ccatttaaac cattttcttt ttaacacatt tcttatggta atctcttctc   8700
actacactat aaaaatggct tctcaatccc attttctaca tcatcccatt ctattgagtt   8760
ttgtttattt gctttcactt ttttttttat ctgcctcttc ccttaatttg cttgacttct   8820
tcttcacatt ttgctttgtt ttctcctccg gcttccggta tttcaaattc aagatgagca   8880
agttgaaatt tataaataga aatacagata ttatttacaa cgtcaaatct ttggtatttt   8940
caatatttga atggggtaaa tttgtcatat agtcatcatc actgactact tatctaacct   9000
atttaatttg gagcatattc tttataaggt ccctctcacg gccaatgtct aattattgat   9060
atacagctct tgttttctag tgctgcttat aatattatct acacatatat atggtactgc   9120
acactactac tatatagtag taagtaaact agcaacagcc ggggccaaac tccaataact   9180
aggcattggg gtttagttgg taatataaat ataacatcaa aaagtctttg cttgtgacga   9240
acatcacaat gcacccacca ttgatgccac gacagacatt gttaattttt tttttaattt   9300
ttaaaaaaga agcaattcca atagttctat attacaatct cacgtgatcc aagcacaacg   9360
tttcattttt tgtacatgct cgatatataa ataatatttc attttatagt aaaatataat   9420
gacattttcg aatataattt ttgaaatttc attttccaaa tgaaatacta atattaatat   9480
taatgagatt accacaaatc atgttatgaa tgaaataaag agttttggca ttctaacttt   9540
ctttgaatag aacaaaatgt atacaacact ctccatatat acacgattta ttcagggatc   9600
atatacattc tctcatgatt aacatagtct gctttcttca cgtctaagca gataattttt   9660
ggtccacaag ataaaattat cattagtcgt tttaattaat tccttgagca tcaagcacta   9720
aaataattaa acttctccat taccaaaaaa aaaagatagg tgattcagta acatgtagta   9780
ctagtactac tgattttttt tttcttttga ttttaatgaa tggttcgtat cgagcatcga   9840
gaaatccatt tattaggtgt gtaatgtaat agtagtattt ccttgatttt cagtaataag   9900
atggattctt acatttatat ctgtttgaca gaaaatgttg tcaatgcatt tcttgggcac   9960
aaagtttttt gaaacatgaa ttaatttttt caaaatattt atgacatcaa attgacccta  10020
aaataagtga taaagcttta acgtggaatg acattaattt ttccatgata aataaaacac  10080
ttaaaacatt ttaatattaa tattataatc agttacaact atgttcaatt aatgcaataa  10140
cttttaaata aatattaaaa tatttttttt ctgttctcca ataaagagat cttgttgcac  10200
ggaaaaagtc acattcttat ttagtaaaaa attataatta ttgtttgaaa aatatcattt  10260
```

-continued

```
tcactgcaga aaatttgatc cagctctaca gatcatactt ttattgtaca ataatacaat  10320
aaaaatattc atctgcagga aatatcattt tcattgtaca ataatataaa gataaatata  10380
taccagaaaa gaaaaagaaa ctgatgtggc acaatgtatt cactgaaaga atgcatattg  10440
tatttcacct ttcaagcagc actaagaata tacttctttt attatacttg tgcatttact  10500
caaccaccct cggtggagta agaaagaaga tagataaaag ttttttttga catttggtga  10560
atctcttaat taaaaaaata aaataatcca tttcctttat ttaatttctt ttttcccatc  10620
tgtgaaattc caattctgct tcgcgctcct gtctataaat tgacttagcc accacctcag  10680
tttccattca ttcacttctt ctctttatac ccccctctc tttttgcgt tcattctgtt  10740
ttcgtaagta ctgttgtttt tctcttctat ttcttttttt gtttgtgttg ttttttttc  10800
ttccttatcg ttgttctgcc tctcctctgt ttcggtgctc tgttcaccac ttccacgtga  10860
gaatgatctt ccttctttgc atgttcattc tctcgtgacc actggatcag actccatgtt  10920
ctgatccagg gtctctctct aacgcctgta ctttcatcca tgaccacctt aaaaacaaca  10980
tgggggtggt gctgttacac taactctgtt tctggggtgc tgtctttgtt caattttact  11040
cagaaaatat cttttcttgg attctattcg gtgtgtggga acatgatcct gtcggtcggt  11100
tgtttttagg ttaatcctta actggttaca aggatctaac gcttgaatgc atgtcctgag  11160
ttaaagaaac aaaagaagaa cacacctagt acagcctggc ctcgaaccaa gaacttcttt  11220
gttggtttct cattattact aaaataaaat aaagtatacg ttttcttttt tctttgggat  11280
gaacggttca gacttatgag aagtttaagc taatcctgta gtggagtgtt caatttattt  11340
taaactttaa agcaatagct caagcactaa acttcttttt caagttcaac cactttggta  11400
gcttgctaat tgctgctatt gttctaatta attaatgtaa ttattgttta aaaaagaaaa  11460
gttggtgaca ctggaataaa aaagtgtact atctggcaat tattcttctg cagcaatgtt  11520
tgaggttgaa atcttagtag aacaaagtag aagatctggt atttatattt tttgtagaca  11580
gatggtgggg gtgggtggta ggccttgaaa tccaatatag ttttgtagaa taattttatt  11640
attttttttt tttgctcact tgtttgtggt attgattttg tgatgactca agattaatga  11700
tttaccttca ttttttttcat ggtgacatat tatgtatatt cttgatctgt ttcttacact  11760
tctttttcgt tgttgtagct gttgaagtct gcggccgcat gaagaggtct ccagcatctt  11820
cttgttcatc atctacttcc tctgttgggt ttgaagctcc cattgaaaaa agaaggccta  11880
agcatccaag gaggaataat ttgaagtcac aaaaatgcaa gcagaaccaa accaccactg  11940
gtggcagaag aagctctatc tatagaggag ttacaaggca taggtggaca gggaggtttg  12000
aagctcacct atgggataag agctcttgga acaacattca gagcaagaag ggtcgacaag  12060
tttatttggg ggcatatgat actgaagaat ctgcagcccg tacctatgac cttgcagccc  12120
ttaaatactg ggaaaaagat gcaaccctga atttcccgat agaaacttat accaaggagc  12180
tcgaggaaat ggacaaggtt tcaagagaag aatatttggc ttctttgcgg cgccaaagca  12240
gtggcttttc tagaggcctg tctaagtacc gtggggttgc taggcatcat cataatggtc  12300
gctgggaagc acgaattgga agagtatgcg gaaacaagta cctctacttg gggacatata  12360
aaactcaaga ggaggcagca gtggcatatg acatggcagc aatagagtac cgtggagtca  12420
atgcagtgac caattttgac ataagcaact acatggacaa aataaagaag aaaaatgacc  12480
aaacccaaca acaacaaaca gaagcacaaa cggaaacagt tcctaactcc tctgactctg  12540
aagaagtaga agtagaacaa cagacaacaa caataaccac accaccccca tctgaaaatc  12600
```

```
tgcacatgcc accacagcag caccaagttc aatacacccc ccatgtctct ccaagggaag  12660
aagaatcatc atcactgatc acaattatgg accatgtgct tgagcaggat ctgccatgga  12720
gcttcatgta cactggcttg tctcagtttc aagatccaaa cttggctttc tgcaaaggtg  12780
atgatgactt ggtgggcatg tttgatagtg cagggtttga ggaagacatt gattttctgt  12840
tcagcactca acctggtgat gagactgaga gtgatgtcaa caatatgagc gcagttttgg  12900
atagtgttga gtgtggagac acaaatgggg ctggtggaag catgatgcat gtggataaca  12960
agcagaagat agtatcattt gcttcttcac catcatctac aactacagtt tcttgtgact  13020
atgctctaga tctatgagcg gccgcatttc gcaccaaatc aatgaaagta ataatgaaaa  13080
gtctgaataa gaatacttag gcttagatgc ctttgttact tgtgtaaaat aacttgagtc  13140
atgtaccttt ggcggaaaca gaataaataa aaggtgaaat tccaatgctc tatgtataag  13200
ttagtaatac ttaatgtgtt ctacggttgt ttcaatatca tcaaactcta attgaaactt  13260
tagaaccaca aatctcaatc ttttcttaat gaaatgaaaa atcttaattg taccatgttt  13320
atgttaaaca ccttacaatt aattggttgg agaggaggac caaccgatgg gacaacattg  13380
ggagaaagag attcaatgga gatttggata ggagaacaac attctttttc acttcaatac  13440
aagatgagtg caacactaag gatatgtatg agactttcag aagctacgac aacatagatg  13500
agtgaggtgg tgattcctag caagaaagac attagaggaa gccaaaatcg aacaaggaag  13560
acatcaaggg caagagacag gaccatccat ctcaggaaaa ggagctttgg gatagtccga  13620
gaagttgtac aagaaatttt ttggagggtg agtgatgcat tgctggtgac tttaactcaa  13680
tcaaaattga gaaagaaaga aaagggaggg ggctcacatg tgaatagaag ggaaacggga  13740
gaattttaca gttttgatct aatgggcatc ccagctagtg gtaacatatt caccatgttt  13800
aaccttcacg tacgagatcc ggccggccag atcctgca                          13838
```

<210> SEQ ID NO 58
<211> LENGTH: 13601
<212> TYPE: DNA
<213> ORGANISM: artificial sequence
<220> FEATURE:
<223> OTHER INFORMATION: plasmid sequence

<400> SEQUENCE: 58

```
ggagatccaa gcttttgatc catgcccttc atttgccgct tattaattaa tttggtaaca     60
gtccgtacta atcagttact tatccttccc ccatcataat taatcttggt agtctcgaat    120
gccacaacac tgactagtct cttggatcat aagaaaaagc caaggaacaa aagaagacaa    180
aacacaatga gagtatcctt tgcatagcaa tgtctaagtt cataaaattc aaacaaaaac    240
gcaatcacac acagtggaca tcacttatcc actagctgat caggatcgcc gcgtcaagaa    300
aaaaaaactg gaccccaaaa gccatgcaca acaacacgta ctcacaaagg tgtcaatcga    360
gcagcccaaa acattcacca actcaaccca tcatgagccc tcacatttgt tgtttctaac    420
ccaacctcaa actcgtattc tcttccgcca cctcattttt gtttatttca acacccgtca    480
aactgcatgc caccccgtgg ccaaatgtcc atgcatgtta acaagaccta tgactataaa    540
tagctgcaat ctcggcccag gttttcatca tcaagaacca gttcaatatc ctagtacacc    600
gtattaaaga atttaagata tactgcggcc gcaccatggc gatttccgat gagcctgaaa    660
gtgtagccac tgctctcaac cactcttccc tgcgccgccg tccctccgcc acctccaccg    720
ccggcctctt caattcgcct gagacaacca ccgacagttc cggtgatgac ttggccaagg    780
attctggttc cgacgactcc atcaacaacg acgacgccgc cgtcaattcc caacagcaaa    840
```

-continued

```
acgaaaaaca agacactgat ttctccgtcc tcaaattcgc ctaccgtcct tccgtccccg    900
ctcaccgcaa agtgaaggaa agtccgctca gctccgacac tattttccgt cagagtcacg    960
cgggcctctt caacctttgt atagtagtcc ttgttgctgt gaatagccga ctcatcattg   1020
agaatttaat gaagtatggt tggttgatca aatctggctt ttggtttagt gcaaagtcat   1080
tgagagactg gccccttttc atgtgttgtc tttctcttgt ggtatttcct ttcgctgcct   1140
ttatggtgga gaagttggca caacggaagt gtatacccga accagttgtt gttgtacttc   1200
atataatcat tacctcaact tcgcttttct atccagtttt agttattctc aagtgtgatt   1260
ctgcttttgt atcaggtgtc acgttaatgc tgttttcttg tgttgtatgg ttaaaattgg   1320
tgtcttttgc acatacaaac tatgatatga gagcacttac caaattagtt gaaaagggag   1380
aagcactgct cgatactctg aacatggagt atccttacaa cgtaaccttc aagagcttgg   1440
catatttcct gcttgcccct acattatgtt accagccaag ctatcctcgc acaccttata   1500
ttcgaaaggg ttggttgttt cgccaacttg tcaagctgat agtatttaca ggagttatgg   1560
gatttataat agaacaatat attaatccca tagtacaaaa ttcacagcat cctctcaagg   1620
gaaaccttct ttacgccacc gagagagttc tgaagctttc tgttccaaat ttatatgtgt   1680
ggctctgcat gttctattgc tttttccacc tttggttaaa tatcgtggca gagcttcttc   1740
gatttggtga tcgtgaattc tacaaggatt ggtggaatgc caaaactgtc gaagattatt   1800
ggaggatgtg gaatatgcct gttcacaaat ggatgatccg ccacctatat tttccatgtt   1860
taaggcacgg tctaccaaag gctgctgctc ttttaatttc cttcctggtt tctgctttat   1920
tccatgagct gtgcattgct gttccttgcc acatgttcaa gttgtgggct ttcggtggaa   1980
ttatgtttca ggttcctttg gtcttgatca ctaattatct gcaaaataaa ttcaaaaact   2040
caatggttgg aaatatgatt ttttggttca tattcagtat cgttggtcaa cctatgtgtg   2100
tactgctata ctaccatgac ttgatgaata ggaaaggcaa acttgactga gcggccgcaa   2160
gtatgaacta aaatgcatgt aggtgtaaga gctcatggag agcatggaat attgtatccg   2220
accatgtaac agtataataa ctgagctcca tctcacttct tctatgaata aacaaaggat   2280
gttatgatat attaacactc tatctatgca ccttattgtt ctatgataaa tttcctctta   2340
ttattataaa tcatctgaat cgtgacggct tatggaatgc ttcaaatagt acaaaaacaa   2400
atgtgtacta taagactttc taaacaattc taaccttagc attgtgaacg agacataagt   2460
gttaagaaga cataacaatt ataatggaag aagtttgtct ccatttatat attatatatt   2520
acccacttat gtattatatt aggatgttaa ggagacataa caattataaa gagagaagtt   2580
tgtatccatt tatatattat atactaccca tttatatatt atacttatcc acttatttaa   2640
tgtctttata aggtttgatc catgatattt ctaatatttt agttgatatg tatatgaaag   2700
ggtactattt gaactctctt actctgtata aaggttggat catccttaaa gtgggtctat   2760
ttaattttat tgcttcttac agataaaaaa aaaattatga gttggtttga taaaatattg   2820
aaggatttaa aataataata aataacatat aatatatgta tataaattta ttataatata   2880
acatttatct ataaaaaagt aaatattgtc ataaatctat acaatcgttt agccttgctg   2940
gacgaatctc aattatttaa acgagagtaa acatatttga ctttttggtt atttaacaaa   3000
ttattattta acactatatg aaattttttt ttttatcagc aaagaataaa attaaattaa   3060
gaaggacaat ggtgtcccaa tccttataca accaacttcc acaagaaagt caagtcagag   3120
acaacaaaaa aacaagcaaa ggaaattttt taatttgagt tgtcttgttt gctgcataat   3180
```

-continued

```
ttatgcagta aaacactaca cataaccctt ttagcagtag agcaatggtt gaccgtgtgc   3240
ttagcttctt ttattttatt tttttatcag caaagaataa ataaaataaa atgagacact   3300
tcagggatgt ttcaacaagc ttggcgcgcc gttctatagt gtcacctaaa tcgtatgtgt   3360
atgatacata aggttatgta ttaattgtag ccgcgttcta acgacaatat gtccatatgg   3420
tgcactctca gtacaatctg ctctgatgcc gcatagttaa gccagccccg acacccgcca   3480
acacccgctg acgcgccctg acgggcttgt ctgctcccgg catccgctta cagacaagct   3540
gtgaccgtct ccgggagctg catgtgtcag aggttttcac cgtcatcacc gaaacgcgcg   3600
agacgaaagg gcctcgtgat acgcctattt ttataggtta atgtcatgac caaaatccct   3660
taacgtgagt tttcgttcca ctgagcgtca gaccccgtag aaaagatcaa aggatcttct   3720
tgagatcctt tttttctgcg cgtaatctgc tgcttgcaaa caaaaaaacc accgctacca   3780
gcggtggttt gtttgccgga tcaagagcta ccaactcttt ttccgaaggt aactggcttc   3840
agcagagcgc agataccaaa tactgtcctt ctagtgtagc cgtagttagg ccaccacttc   3900
aagaactctg tagcaccgcc tacatacctc gctctgctaa tcctgttacc agtggctgct   3960
gccagtggcg ataagtcgtg tcttaccggg ttggactcaa gacgatagtt accggataag   4020
gcgcagcggt cgggctgaac ggggggttcg tgcacacagc ccagcttgga gcgaacgacc   4080
tacaccgaac tgagatacct acagcgtgag cattgagaaa gcgccacgct tcccgaaggg   4140
agaaaggcgg acaggtatcc ggtaagcggc agggtcggaa caggagagcg cacgagggag   4200
cttccagggg gaaacgcctg gtatctttat agtcctgtcg ggtttcgcca cctctgactt   4260
gagcgtcgat ttttgtgatg ctcgtcaggg gggcggagcc tatggaaaaa cgccagcaac   4320
gcggcctttt tacggttcct ggccttttgc tggccttttg ctcacatgtt ctttcctgcg   4380
ttatcccctg attctgtgga taaccgtatt accgcctttg agtgagctga taccgctcgc   4440
cgcagccgaa cgaccgagcg cagcgagtca gtgagcgagg aagcggaaga gcgcccaata   4500
cgcaaaccgc ctctccccgc gcgttggccg attcattaat gcaggttgat cgattcgaca   4560
tcgatctagt aacatagatg acaccgcgcg cgataattta tcctagtttg cgcgctatat   4620
tttgttttct atcgcgtatt aaatgtataa ttgcgggact ctaatcataa aaacccatct   4680
cataaataac gtcatgcatt acatgttaat tattacatgc ttaacgtaat tcaacagaaa   4740
ttatatgata atcatcgcaa gaccggcaac aggattcaat cttaagaaac tttattgcca   4800
aatgtttgaa cgatctgctt cgacgcactc cttctttagg tacctcacta ttcctttgcc   4860
ctcggacgag tgctggggcg tcggtttcca ctatcggcga gtacttctac acagccatcg   4920
gtccagacgg ccgcgcttct gcgggcgatt tgtgtacgcc cgacagtccc ggctccggat   4980
cggacgattg cgtcgcatcg accctgcgcc caagctgcat catcgaaatt gccgtcaacc   5040
aagctctgat agagttggtc aagaccaatg cggagcatat acgcccggag ccgcggcgat   5100
cctgcaagct ccggatgcct ccgctcgaag tagcgcgtct gctgctccat acaagccaac   5160
cacggcctcc agaagaagat gttggcgacc tcgtattggg aatccccgaa catcgcctcg   5220
ctccagtcaa tgaccgctgt tatgcggcca ttgtccgtca ggacattgtt ggagccgaaa   5280
tccgcgtgca cgaggtgccg gacttcgggg cagtcctcgg cccaaagcat cagctcatcg   5340
agagcctgcg cgacggacgc actgacggtg tcgtccatca cagtttgcca gtgatacaca   5400
tggggatcag caatcgcgca tatgaaatca cgccatgtag tgtattgacc gattccttgc   5460
ggtccgaatg ggccgaaccc gctcgtctgg ctaagatcgg ccgcagcgat cgcatccatg   5520
gcctccgcga ccggctgcag aacagcgggc agttcggttt caggcaggtc ttgcaacgtg   5580
```

```
acaccctgtg cacggcggga gatgcaatag gtcaggctct cgctgaattc cccaatgtca   5640
agcacttccg gaatcgggag cgcggccgat gcaaagtgcc gataaacata acgatctttg   5700
tagaaaccat cggcgcagct atttacccgc aggacatatc cacgccctcc tacatcgaag   5760
ctgaaagcac gagattcttc gccctccgag agctgcatca ggtcggagac gctgtcgaac   5820
ttttcgatca gaaacttctc gacagacgtc gcggtgagtt caggcttttt catggtttaa   5880
taagaagaga aaagagttct tttgttatgg ctgaagtaat agagaaatga gctcgagcgt   5940
gtcctctcca aatgaaatga acttccttat atagaggaag ggtcttgcga aggatagtgg   6000
gattgtgcgt catcccttac gtcagtggag atgtcacatc aatccacttg ctttgaagac   6060
gtggttggaa cgtcttcttt ttccacgatg ctcctcgtgg gtgggggtcc atctttggga   6120
ccactgtcgg cagaggcatc ttgaatgata gcctttcctt tatcgcaatg atggcatttg   6180
taggagccac cttccttttc tactgtcctt tcgatgaagt gacagatagc tgggcaatgg   6240
aatccgagga ggtttcccga aattatcctt tgttgaaaag tctcaatagc cctttggtct   6300
tctgagactg tatctttgac atttttggag tagaccagag tgtcgtgctc caccatgttg   6360
acgaagattt tcttcttgtc attgagtcgt aaaagactct gtatgaactg ttcgccagtc   6420
ttcacggcga gttctgttag atcctcgatt tgaatcttag actccatgca tggccttaga   6480
ttcagtagga actacctttt tagagactcc aatctctatt acttgccttg gtttatgaag   6540
caagccttga atcgtccata ctggaatagt acttctgatc ttgagaaata tgtctttctc   6600
tgtgttcttg atgcaattag tcctgaatct tttgactgca tctttaacct tcttgggaag   6660
gtatttgatc tcctggagat tgttactcgg gtagatcgtc ttgatgagac ctgctgcgta   6720
ggcctctcta accatctgtg ggtcagcatt ctttctgaaa ttgaagaggc taaccttctc   6780
attatcagtg gtgaacatag tgtcgtcacc ttcaccttcg aacttccttc ctagatcgta   6840
aagatagagg aaatcgtcca ttgtaatctc cggggcaaag gagatctctt ttggggctgg   6900
atcactgctg ggccttttgg ttcctagcgt gagccagtgg gctttttgct ttggtgggct   6960
tgttagggcc ttagcaaagc tcttgggctt gagttgagct tctcctttgg ggatgaagtt   7020
caacctgtct gtttgctgac ttgttgtgta cgcgtcagct gctgctcttg cctctgtaat   7080
agtggcaaat ttcttgtgtg caactccggg aacgccgttt gttgccgcct ttgtacaacc   7140
ccagtcatcg tatataccgg catgtggacc gttatacaca acgtagtagt tgatatgagg   7200
gtgttgaata cccgattctg ctctgagagg agcaactgtg ctgttaagct cagatttttg   7260
tgggattgga attggatcga tctcgatccc gcgaaattaa tacgactcac tatagggaga   7320
ccacaacggt ttccctctag aaataatttt gtttaacttt aagaaggaga tatacccatg   7380
gaaaagcctg aactcaccgc gacgtctgtc gagaagtttc tgatcgaaaa gttcgacagc   7440
gtctccgacc tgatgcagct ctcggagggc gaagaatctc gtgctttcag cttcgatgta   7500
ggagggcgtg gatatgtcct gcgggtaaat agctgcgccg atggtttcta caaagatcgt   7560
tatgtttatc ggcactttgc atcggccgcg ctcccgattc cggaagtgct tgacattggg   7620
gaattcagcg agagcctgac ctattgcatc tcccgccgtg cacagggtgt cacgttgcaa   7680
gacctgcctg aaaccgaact gcccgctgtt ctgcagccgg tcgcggaggc tatggatgcg   7740
atcgctgcgg ccgatcttag ccagacgagc gggttcggcc cattcggacc gcaaggaatc   7800
ggtcaataca ctacatggcg tgatttcata tgcgcgattg ctgatcccca tgtgtatcac   7860
tggcaaactg tgatggacga caccgtcagt gcgtccgtcg cgcaggctct cgatgagctg   7920
```

-continued

```
atgctttggg ccgaggactg ccccgaagtc cggcacctcg tgcacgcgga tttcggctcc   7980
aacaatgtcc tgacggacaa tggccgcata acagcggtca ttgactggag cgaggcgatg   8040
ttcggggatt cccaatacga ggtcgccaac atcttcttct ggaggccgtg gttggcttgt   8100
atggagcagc agacgcgcta cttcgagcgg aggcatccgg agcttgcagg atcgccgcgg   8160
ctccgggcgt atatgctccg cattggtctt gaccaactct atcagagctt ggttgacggc   8220
aatttcgatg atgcagcttg ggcgcagggt cgatgcgacg caatcgtccg atccggagcc   8280
gggactgtcg ggcgtacaca aatcgcccgc agaagcgcgg ccgtctggac cgatggctgt   8340
gtagaagtac tcgccgatag tggaaaccga cgccccagca ctcgtccgag ggcaaaggaa   8400
tagtgaggta cagcttggat cgatccggct gctaacaaag cccgaaagga agctgagttg   8460
gctgctgcca ccgctgagca ataactagca taaccccttg gggcctctaa acgggtcttg   8520
aggggttttt tgctgaaagg aggaactata tccggatgat cgggcgcgcc gtcgacggat   8580
ccgtacgaga tccggccggc cagatcctgc aggtaaattg cagctgaagg acagtgaagg   8640
gtgaatttat ccatttaaac cattttcttt ttaacacatt tcttatggta atctcttctc   8700
actacactat aaaaatggct tctcaatccc attttctaca tcatcccatt ctattgagtt   8760
ttgtttattt gctttcactt ttttttttat ctgcctcttc ccttaatttg cttgacttct   8820
tcttcacatt ttgctttgtt ttctcctccg gcttccggta tttcaaattc aagatgagca   8880
agttgaaatt tataaataga aatacagata ttatttacaa cgtcaaatct ttggtatttt   8940
caatatttga atggggtaaa tttgtcatat agtcatcatc actgactact tatctaacct   9000
atttaatttg gagcatattc tttataaggt ccctctcacg gccaatgtct aattattgat   9060
atacagctct tgttttctag tgctgcttat aatattatct acacatatat atggtactgc   9120
acactactac tatatagtag taagtaaact agcaacagcc ggggccaaac tccaataact   9180
aggcattggg gtttagttgg taatataaat ataacatcaa aaagtctttg cttgtgacga   9240
acatcacaat gcacccacca ttgatgccac gacagacatt gttaattttt tttttaattt   9300
ttaaaaaaga agcaattcca atagttctat attacaatct cacgtgatcc aagcacaacg   9360
tttcattttt tgtacatgct cgatatataa ataatatttc attttatagt aaaatataat   9420
gacattttcg aatataattt ttgaaatttc attttccaaa tgaaatacta atattaatat   9480
taatgagatt accacaaatc atgttatgaa tgaaataaag agttttggca ttctaacttt   9540
ctttgaatag aacaaaatgt atacaacact ctccatatat acacgattta ttcagggatc   9600
atatacattc tctcatgatt aacatagtct gctttcttca cgtctaagca gataattttt   9660
ggtccacaag ataaaattat cattagtcgt tttaattaat tccttgagca tcaagcacta   9720
aaataattaa acttctccat taccaaaaaa aaaagatagg tgattcagta acatgtagta   9780
ctagtactac tgattttttt tttcttttga ttttaatgaa tggttcgtat cgagcatcga   9840
gaaatccatt tattaggtgt gtaatgtaat agtagtattt ccttgatttt cagtaataag   9900
atggattctt acatttatat ctgtttgaca gaaaatgttg tcaatgcatt tcttgggcac   9960
aaagtttttt gaaacatgaa ttaatttttt caaaatattt atgacatcaa attgacccta  10020
aaataagtga taaagcttta acgtggaatg acattaattt ttccatgata aataaaacac  10080
ttaaaacatt ttaatattaa tattataatc agttacaact atgttcaatt aatgcaataa  10140
cttttaaata aatattaaaa tatttttttt ctgttctcca ataaagagat cttgttgcac  10200
ggaaaaagtc acattcttat ttagtaaaaa attataatta ttgtttgaaa aatatcattt  10260
tcactgcaga aaatttgatc cagctctaca gatcatactt ttattgtaca ataatacaat  10320
```

```
aaaaatattc atctgcagga aatatcattt tcattgtaca ataatataaa gataaatata  10380
taccagaaaa gaaaaagaaa ctgatgtggc acaatgtatt cactgaaaga atgcatattg  10440
tatttcacct ttcaagcagc actaagaata tacttctttt attatacttg tgcatttact  10500
caaccaccct cggtggagta agaaagaaga tagataaaag tttttttga catttggtga  10560
atctcttaat taaaaaaata aaataatcca tttcctttat ttaatttctt ttttcccatc  10620
tgtgaaattc caattctgct tcgcgctcct gtctataaat tgacttagcc accacctcag  10680
tttccattca ttcacttctt ctctttatac ccccctctc ttttttgcgt tcattctgtt  10740
ttcgtaagta ctgttgtttt tctcttctat ttcttttttt gtttgtgttg ttttttttc  10800
ttccttatcg ttgttctgcc tctcctctgt ttcggtgctc tgttcaccac ttccacgtga  10860
gaatgatctt ccttctttgc atgttcattc tctcgtgacc actggatcag actccatgtt  10920
ctgatccagg gtctctctct aacgcctgta ctttcatcca tgaccacctt aaaaacaaca  10980
tgggggtggt gctgttacac taactctgtt tctggggtgc tgtctttgtt caattttact  11040
cagaaaatat cttttcttgg attctattcg gtgtgtggga acatgatcct gtcggtcggt  11100
tgtttttagg ttaatcctta actggttaca aggatctaac gcttgaatgc atgtcctgag  11160
ttaaagaaac aaaagaagaa cacacctagt acagcctggc ctcgaaccaa gaacttcttt  11220
gttggtttct cattattact aaaataaaat aaagtatacg ttttcttttt tctttgggat  11280
gaacggttca gacttatgag aagtttaagc taatcctgta gtggagtgtt caatttattt  11340
taaactttaa agcaatagct caagcactaa acttcttttt caagttcaac cactttggta  11400
gcttgctaat tgctgctatt gttctaatta attaatgtaa ttattgttta aaaaagaaaa  11460
gttggtgaca ctggaataaa aaagtgtact atctggcaat tattcttctg cagcaatgtt  11520
tgaggttgaa atcttagtag aacaaagtag aagatctggt atttatattt tttgtagaca  11580
gatggtgggg gtgggtggta ggccttgaaa tccaatatag ttttgtagaa taattttatt  11640
attttttttt tttgctcact tgtttgtggt attgattttg tgatgactca agattaatga  11700
tttaccttca tttttttcat ggtgacatat tatgtatatt cttgatctgt ttcttacact  11760
tctttttcgt tgttgtagct gttgaagtct gcggccgcac catgatgatg gatcagcgac  11820
agcgagagaa gctgcttcac aaaaccgagg cctgtgcttt cgtggcaggt gttgttccgg  11880
agctttccct tgtcaccgtt ccagggaaca acaccaacaa cgttaacaac aacaacaacg  11940
ttgtttctca ttctcaatct aacgggtcgg gtcggatcca ggaaaacaac caccaccttg  12000
gactcgttgc tgctgtcacc tccgccttcg gtaccgttca aaggaagaaa aggatggcga  12060
gacaaagaag atccactaaa cccacttcgt tgatgaacca tctcaacaac cataagcaca  12120
acaagcctcg ttctcttcct tctcccagtg catcctcctc gtacgtgcca ctctcctccg  12180
caactctcca gcccgcacgt gaaatcgatc aaagaaggtt gagattcctt ttccagaagg  12240
agttaaagaa cagtgatgtt agctccctta ggagaatgat attgccaaag aaagcagcag  12300
aggctttcct tccagctctt gaatccaaag aaggaattgt aatcagcatg gatgatatag  12360
atggtcttca tgtatggagt ttcaagtaca ggttttggcc taacaacaac agtcggatgt  12420
atgtacttga aaatactgga gattttgtca acacacatgg ccttcgcttt ggagattcca  12480
ttatggttta ccaagatagt gaaaacaaca attatgttat tcaggccaaa aaggcttctg  12540
atcaagatga atttatggaa gaaactagtg ataccatcaa tgatatcttc cttaatgatt  12600
atgaggtgaa caaacctggt tgcttcaatg taactaatcc tgcagtgaat gatacaggca  12660
```

```
tgtcattcat atatgagact accttctcaa atgactcccc tcttgatttt ttgggtggat  12720

caatgaccaa tttttcaagg attgggccag ttgaaacctt tggctctgtt gagaatttgt  12780

cacttgatga cttctattaa gcggccgcat ttcgcaccaa atcaatgaaa gtaataatga  12840

aaagtctgaa taagaatact taggcttaga tgcctttgtt acttgtgtaa aataacttga  12900

gtcatgtacc tttggcggaa acagaataaa taaaaggtga aattccaatg ctctatgtat  12960

aagttagtaa tacttaatgt gttctacggt tgtttcaata tcatcaaact ctaattgaaa  13020

ctttagaacc acaaatctca atcttttctt aatgaaatga aaaatcttaa ttgtaccatg  13080

tttatgttaa acaccttaca attaattggt tggagaggag gaccaaccga tgggacaaca  13140

ttgggagaaa gagattcaat ggagatttgg ataggagaac aacattcttt ttcacttcaa  13200

tacaagatga gtgcaacact aaggatatgt atgagacttt cagaagctac gacaacatag  13260

atgagtgagg tggtgattcc tagcaagaaa gacattagag gaagccaaaa tcgaacaagg  13320

aagacatcaa gggcaagaga caggaccatc catctcagga aaaggagctt tgggatagtc  13380

cgagaagttg tacaagaaat tttttggagg gtgagtgatg cattgctggt gactttaact  13440

caatcaaaat tgagaaagaa agaaaaggga gggggctcac atgtgaatag aagggaaacg  13500

ggagaatttt acagttttga tctaatgggc atcccagcta gtggtaacat attcaccatg  13560

tttaaccttc acgtacgaga tccggccggc cagatcctgc a                     13601
```

<210> SEQ ID NO 59
<211> LENGTH: 1545
<212> TYPE: DNA
<213> ORGANISM: Yarrowia Lipolytica

<400> SEQUENCE: 59

```
atgactatcg actcacaata ctacaagtcg cgagacaaaa acgacacggc acccaaaatc     60

gcgggaatcc gatatgcccc gctatcgaca ccattactca accgatgtga gaccttctct    120

ctggtctggc acattttcag cattcccact ttcctcacaa ttttcatgct atgctgcgca    180

attccactgc tctggccatt tgtgattgcg tatgtagtgt acgctgttaa agacgactcc    240

ccgtccaacg gaggagtggt caagcgatac tcgcctattt caagaaactt cttcatctgg    300

aagctctttg gccgctactt ccccataact ctgcacaaga cggtggatct ggagcccacg    360

cacacatact accctctgga cgtccaggag tatcacctga ttgctgagag atactggccg    420

cagaacaagt acctccgagc aatcatcacc accatcgagt actttctgcc cgccttcatg    480

aaacggtctc tttctatcaa cgagcaggag cagcctgccg agcgagatcc tctcctgtct    540

cccgtttctc ccagctctcc gggttctcaa cctgacaagt ggattaacca cgacagcaga    600

tatagccgtg gagaatcatc tggctccaac ggccacgcct cgggctccga acttaacggc    660

aacggcaaca acggcaccac taaccgacga cctttgtcgt ccgcctctgc tggctccact    720

gcatctgatt ccacgcttct taacgggtcc ctcaactcct acgccaacca gatcattggc    780

gaaaacgacc cacagctgtc gcccacaaaa ctcaagccca ctggcagaaa atacatcttc    840

ggctaccacc cccacggcat tatcggcatg ggagcctttg gtggaattgc caccgaggga    900

gctggatggt ccaagctctt tccgggcatc cctgtttctc ttatgactct caccaacaac    960

ttccgagtgc ctctctacag agagtacctc atgagtctgg gagtcgcttc tgtctccaag   1020

aagtcctgca aggccctcct caagcgaaac cagtctatct gcattgtcgt tggtggagca   1080

caggaaagtc ttctggccag acccggtgtc atggacctgg tgctactcaa gcgaaagggt   1140

tttgttcgac ttggtatgga ggtcggaaat gtcgcccttg ttcccatcat ggcctttggt   1200
```

```
gagaacgacc tctatgacca ggttagcaac gacaagtcgt ccaagctgta ccgattccag   1260

cagtttgtca agaacttcct tggattcacc cttcctttga tgcatgcccg aggcgtcttc   1320

aactacgatg tcggtcttgt cccctacagg cgacccgtca acattgtggt tggttccccc   1380

attgacttgc cttatctccc acaccccacc gacgaagaag tgtccgaata ccacgaccga   1440

tacatcgccg agctgcagcg aatctacaac gagcacaagg atgaatattt catcgattgg   1500

accgaggagg gcaaaggagc cccagagttc cgaatgattg agtaa                    1545


<210> SEQ ID NO 60
<211> LENGTH: 514
<212> TYPE: PRT
<213> ORGANISM: Yarrowia lipolytica

<400> SEQUENCE: 60

Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
                85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
        115                 120                 125

Gln Glu Tyr His Leu Ile Ala Glu Arg Tyr Trp Pro Gln Asn Lys Tyr
    130                 135                 140

Leu Arg Ala Ile Ile Thr Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
    210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
        275                 280                 285

Gly Met Gly Ala Phe Gly Gly Ile Ala Thr Glu Gly Ala Gly Trp Ser
    290                 295                 300

Lys Leu Phe Pro Gly Ile Pro Val Ser Leu Met Thr Leu Thr Asn Asn
```

```
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
            340                 345                 350

Ile Cys Ile Val Val Gly Gly Ala Gln Glu Ser Leu Leu Ala Arg Pro
        355                 360                 365

Gly Val Met Asp Leu Val Leu Leu Lys Arg Lys Gly Phe Val Arg Leu
    370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                405                 410                 415

Tyr Arg Phe Gln Gln Phe Val Lys Asn Phe Leu Gly Phe Thr Leu Pro
            420                 425                 430

Leu Met His Ala Arg Gly Val Phe Asn Tyr Asp Val Gly Leu Val Pro
        435                 440                 445

Tyr Arg Arg Pro Val Asn Ile Val Val Gly Ser Pro Ile Asp Leu Pro
    450                 455                 460

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
                485                 490                 495

Phe Ile Asp Trp Thr Glu Glu Gly Lys Gly Ala Pro Glu Phe Arg Met
            500                 505                 510

Ile Glu
```

<210> SEQ ID NO 61
<211> LENGTH: 13334
<212> TYPE: DNA
<213> ORGANISM: artificial sequence
<220> FEATURE:
<223> OTHER INFORMATION: plasmid sequence

<400> SEQUENCE: 61

```
ggagatccaa gcttttgatc catgcccttc atttgccgct tattaattaa tttggtaaca     60

gtccgtacta atcagttact tatccttccc ccatcataat taatcttggt agtctcgaat    120

gccacaacac tgactagtct cttggatcat aagaaaaagc caaggaacaa aagaagacaa    180

aacacaatga gagtatcctt tgcatagcaa tgtctaagtt cataaaattc aaacaaaaac    240

gcaatcacac acagtggaca tcacttatcc actagctgat caggatcgcc gcgtcaagaa    300

aaaaaaactg gaccccaaaa gccatgcaca acaacacgta ctcacaaagg tgtcaatcga    360

gcagcccaaa acattcacca actcaaccca tcatgagccc tcacatttgt tgtttctaac    420

ccaacctcaa actcgtattc tcttccgcca cctcattttt gtttatttca acacccgtca    480

aactgcatgc caccccgtgg ccaaatgtcc atgcatgtta acaagaccta tgactataaa    540

tagctgcaat ctcggcccag gttttcatca tcaagaacca gttcaatatc ctagtacacc    600

gtattaaaga atttaagata tactgcggcc gcaacatgac tatcgactca caatactaca    660

agtcgcgaga caaaaacgac acggcaccca aaatcgcggg aatccgatat gccccgctat    720

cgacaccatt actcaaccga tgtgagacct tctctctggt ctggcacatt ttcagcattc    780

ccactttcct cacaattttc atgctatgct gcgcaattcc actgctctgg ccatttgtga    840

ttgcgtatgt agtgtacgct gttaaagacg actccccgtc caacggagga gtggtcaagc    900
```

```
gatactcgcc tatttcaaga aacttcttca tctggaagct ctttggccgc tacttcccca    960
taactctgca caagacggtg gatctggagc ccacgcacac atactaccct ctggacgtcc   1020
aggagtatca cctgattgct gagagatact ggccgcagaa caagtacctc cgagcaatca   1080
tcaccaccat cgagtacttt ctgcccgcct tcatgaaacg gtctctttct atcaacgagc   1140
aggagcagcc tgccgagcga gatcctctcc tgtctcccgt ttctcccagc tctccgggtt   1200
ctcaacctga caagtggatt aaccacgaca gcagatatag ccgtggagaa tcatctggct   1260
ccaacggcca cgcctcgggc tccgaactta acggcaacgg caacaacggc accactaacc   1320
gacgaccttt gtcgtccgcc tctgctggct ccactgcatc tgattccacg cttcttaacg   1380
ggtccctcaa ctcctacgcc aaccagatca ttggcgaaaa cgacccacag ctgtcgccca   1440
caaaactcaa gcccactggc agaaaataca tcttcggcta ccacccccac ggcattatcg   1500
gcatgggagc ctttggtgga attgccaccg agggagctgg atggtccaag ctctttccgg   1560
gcatccctgt ttctcttatg actctcacca acaacttccg agtgcctctc tacagagagt   1620
acctcatgag tctgggagtc gcttctgtct ccaagaagtc ctgcaaggcc ctcctcaagc   1680
gaaaccagtc tatctgcatt gtcgttggtg gagcacagga aagtcttctg gccagacccg   1740
gtgtcatgga cctggtgcta ctcaagcgaa agggttttgt tcgacttggt atggaggtcg   1800
gaaatgtcgc ccttgttccc atcatggcct ttggtgagaa cgacctctat gaccaggtta   1860
gcaacgacaa gtcgtccaag ctgtaccgat tccagcagtt tgtcaagaac ttccttggat   1920
tcacccttcc tttgatgcat gcccgaggcg tcttcaacta cgatgtcggt cttgtcccct   1980
acaggcgacc cgtcaacatt gtggttggtt cccccattga cttgccttat ctcccacacc   2040
ccaccgacga agaagtgtcc gaataccacg accgatacat cgccgagctg cagcgaatct   2100
acaacgagca caaggatgaa tatttcatcg attggaccga ggagggcaaa ggagccccag   2160
agttccgaat gattgagtaa gcggccgcaa gtatgaacta aaatgcatgt aggtgtaaga   2220
gctcatggag agcatggaat attgtatccg accatgtaac agtataataa ctgagctcca   2280
tctcacttct tctatgaata aacaaaggat gttatgatat attaacactc tatctatgca   2340
ccttattgtt ctatgataaa tttcctctta ttattataaa tcatctgaat cgtgacggct   2400
tatggaatgc ttcaaatagt acaaaaacaa atgtgtacta taagactttc taaacaattc   2460
taaccttagc attgtgaacg agacataagt gttaagaaga cataacaatt ataatggaag   2520
aagtttgtct ccatttatat attatatatt acccacttat gtattatatt aggatgttaa   2580
ggagacataa caattataaa gagagaagtt tgtatccatt tatatattat atactaccca   2640
tttatatatt atacttatcc acttatttaa tgtctttata aggtttgatc catgatattt   2700
ctaatatttt agttgatatg tatatgaaag ggtactattt gaactctctt actctgtata   2760
aaggttggat catccttaaa gtgggtctat ttaattttat tgcttcttac agataaaaaa   2820
aaaattatga gttggtttga taaaatattg aaggatttaa aataataata aataacatat   2880
aatatatgta tataaattta ttataaatata acatttatct ataaaaaagt aaatattgtc   2940
ataaatctat acaatcgttt agccttgctg gacgaatctc aattatttaa acgagagtaa   3000
acatatttga ctttttggtt atttaacaaa ttattattta acactatatg aaattttttt   3060
ttttatcagc aaagaataaa attaaattaa gaaggacaat ggtgtcccaa tccttataca   3120
accaacttcc acaagaaagt caagtcagag acaacaaaaa aacaagcaaa ggaaattttt   3180
taatttgagt tgtcttgttt gctgcataat ttatgcagta aaacactaca cataaccctt   3240
```

-continued ttagcagtag agcaatggtt gaccgtgtgc ttagcttctt ttattttatt tttttatcag 3300
caaagaataa ataaaataaa atgagacact tcagggatgt ttcaacaagc ttggcgcgcc 3360
gttctatagt gtcacctaaa tcgtatgtgt atgatacata aggttatgta ttaattgtag 3420
ccgcgttcta acgacaatat gtccatatgg tgcactctca gtacaatctg ctctgatgcc 3480
gcatagttaa gccagccccg acacccgcca acacccgctg acgcgccctg acgggcttgt 3540
ctgctcccgg catccgctta cagacaagct gtgaccgtct ccgggagctg catgtgtcag 3600
aggttttcac cgtcatcacc gaaacgcgcg agacgaaagg gcctcgtgat acgcctattt 3660
ttataggtta atgtcatgac caaaatccct taacgtgagt tttcgttcca ctgagcgtca 3720
gaccccgtag aaaagatcaa aggatcttct tgagatcctt tttttctgcg cgtaatctgc 3780
tgcttgcaaa caaaaaaacc accgctacca gcggtggttt gtttgccgga tcaagagcta 3840
ccaactcttt ttccgaaggt aactggcttc agcagagcgc agataccaaa tactgtcctt 3900
ctagtgtagc cgtagttagg ccaccacttc aagaactctg tagcaccgcc tacatacctc 3960
gctctgctaa tcctgttacc agtggctgct gccagtggcg ataagtcgtg tcttaccggg 4020
ttggactcaa gacgatagtt accggataag gcgcagcggt cgggctgaac ggggggttcg 4080
tgcacacagc ccagcttgga gcgaacgacc tacaccgaac tgagatacct acagcgtgag 4140
cattgagaaa gcgccacgct tcccgaaggg agaaaggcgg acaggtatcc ggtaagcggc 4200
agggtcggaa caggagagcg cacgagggag cttccagggg gaaacgcctg gtatctttat 4260
agtcctgtcg ggtttcgcca cctctgactt gagcgtcgat ttttgtgatg ctcgtcaggg 4320
gggcggagcc tatggaaaaa cgccagcaac gcggcctttt tacggttcct ggccttttgc 4380
tggccttttg ctcacatgtt ctttcctgcg ttatcccctg attctgtgga taaccgtatt 4440
accgcctttg agtgagctga taccgctcgc cgcagccgaa cgaccgagcg cagcgagtca 4500
gtgagcgagg aagcggaaga gcgcccaata cgcaaaccgc ctctccccgc gcgttggccg 4560
attcattaat gcaggttgat cgattcgaca tcgatctagt aacatagatg acaccgcgcg 4620
cgataattta tcctagtttg cgcgctatat tttgttttct atcgcgtatt aaatgtataa 4680
ttgcgggact ctaatcataa aaacccatct cataaataac gtcatgcatt acatgttaat 4740
tattacatgc ttaacgtaat tcaacagaaa ttatatgata atcatcgcaa gaccggcaac 4800
aggattcaat cttaagaaac tttattgcca aatgtttgaa cgatctgctt cgacgcactc 4860
cttctttagg tacctcacta ttcctttgcc ctcggacgag tgctggggcg tcggtttcca 4920
ctatcggcga gtacttctac acagccatcg gtccagacgg ccgcgcttct gcgggcgatt 4980
tgtgtacgcc cgacagtccc ggctccggat cggacgattg cgtcgcatcg accctgcgcc 5040
caagctgcat catcgaaatt gccgtcaacc aagctctgat agagttggtc aagaccaatg 5100
cggagcatat acgcccggag ccgcggcgat cctgcaagct ccggatgcct ccgctcgaag 5160
tagcgcgtct gctgctccat acaagccaac cacggcctcc agaagaagat gttggcgacc 5220
tcgtattggg aatccccgaa catcgcctcg ctccagtcaa tgaccgctgt tatgcggcca 5280
ttgtccgtca ggacattgtt ggagccgaaa tccgcgtgca cgaggtgccg gacttcgggg 5340
cagtcctcgg cccaaagcat cagctcatcg agagcctgcg cgacggacgc actgacggtg 5400
tcgtccatca cagtttgcca gtgatacaca tggggatcag caatcgcgca tatgaaatca 5460
cgccatgtag tgtattgacc gattccttgc ggtccgaatg ggccgaaccc gctcgtctgg 5520
ctaagatcgg ccgcagcgat cgcatccatg gcctccgcga ccggctgcag aacagcgggc 5580
agttcggttt caggcaggtc ttgcaacgtg acaccctgtg cacggcggga gatgcaatag 5640

```
gtcaggctct cgctgaattc cccaatgtca agcacttccg gaatcgggag cgcggccgat   5700
gcaaagtgcc gataaacata acgatctttg tagaaaccat cggcgcagct atttacccgc   5760
aggacatatc cacgccctcc tacatcgaag ctgaaagcac gagattcttc gccctccgag   5820
agctgcatca ggtcggagac gctgtcgaac ttttcgatca gaaacttctc gacagacgtc   5880
gcggtgagtt caggcttttt catggtttaa taagaagaga aaagagttct tttgttatgg   5940
ctgaagtaat agagaaatga gctcgagcgt gtcctctcca aatgaaatga acttccttat   6000
atagaggaag ggtcttgcga aggatagtgg gattgtgcgt catcccttac gtcagtggag   6060
atgtcacatc aatccacttg ctttgaagac gtggttggaa cgtcttcttt ttccacgatg   6120
ctcctcgtgg gtgggggtcc atctttggga ccactgtcgg cagaggcatc ttgaatgata   6180
gcctttcctt tatcgcaatg atggcatttg taggagccac cttccttttc tactgtcctt   6240
tcgatgaagt gacagatagc tgggcaatgg aatccgagga ggtttcccga aattatcctt   6300
tgttgaaaag tctcaatagc cctttggtct tctgagactg tatctttgac atttttggag   6360
tagaccagag tgtcgtgctc caccatgttg acgaagattt tcttcttgtc attgagtcgt   6420
aaaagactct gtatgaactg ttcgccagtc ttcacggcga gttctgttag atcctcgatt   6480
tgaatcttag actccatgca tggccttaga ttcagtagga actacctttt tagagactcc   6540
aatctctatt acttgccttg gtttatgaag caagccttga atcgtccata ctggaatagt   6600
acttctgatc ttgagaaata tgtctttctc tgtgttcttg atgcaattag tcctgaatct   6660
tttgactgca tctttaacct tcttgggaag gtatttgatc tcctggagat tgttactcgg   6720
gtagatcgtc ttgatgagac ctgctgcgta ggcctctcta accatctgtg ggtcagcatt   6780
ctttctgaaa ttgaagaggc taaccttctc attatcagtg gtgaacatag tgtcgtcacc   6840
ttcaccttcg aacttccttc ctagatcgta aagatagagg aaatcgtcca ttgtaatctc   6900
cggggcaaag gagatctctt ttggggctgg atcactgctg ggccttttgg ttcctagcgt   6960
gagccagtgg gctttttgct ttggtgggct tgttagggcc ttagcaaagc tcttgggctt   7020
gagttgagct tctcctttgg ggatgaagtt caacctgtct gtttgctgac ttgttgtgta   7080
cgcgtcagct gctgctcttg cctctgtaat agtggcaaat ttcttgtgtg caactccggg   7140
aacgccgttt gttgccgcct ttgtacaacc ccagtcatcg tatataccgg catgtggacc   7200
gttatacaca acgtagtagt tgatatgagg gtgttgaata cccgattctg ctctgagagg   7260
agcaactgtg ctgttaagct cagatttttg tgggattgga attggatcga tctcgatccc   7320
gcgaaattaa tacgactcac tatagggaga ccacaacggt ttccctctag aaataatttt   7380
gtttaacttt aagaaggaga tatacccatg gaaaagcctg aactcaccgc gacgtctgtc   7440
gagaagtttc tgatcgaaaa gttcgacagc gtctccgacc tgatgcagct ctcggagggc   7500
gaagaatctc gtgctttcag cttcgatgta ggagggcgtg gatatgtcct gcgggtaaat   7560
agctgcgccg atggtttcta caaagatcgt tatgtttatc ggcactttgc atcggccgcg   7620
ctcccgattc cggaagtgct tgacattggg gaattcagcg agagcctgac ctattgcatc   7680
tcccgccgtg cacagggtgt cacgttgcaa gacctgcctg aaaccgaact gcccgctgtt   7740
ctgcagccgg tcgcggaggc tatggatgcg atcgctgcgg ccgatcttag ccagacgagc   7800
gggttcggcc cattcggacc gcaaggaatc ggtcaataca ctacatggcg tgatttcata   7860
tgcgcgattg ctgatcccca tgtgtatcac tggcaaactg tgatggacga caccgtcagt   7920
gcgtccgtcg cgcaggctct cgatgagctg atgctttggg ccgaggactg ccccgaagtc   7980
```

```
cggcacctcg tgcacgcgga tttcggctcc aacaatgtcc tgacggacaa tggccgcata   8040
acagcggtca ttgactggag cgaggcgatg ttcggggatt cccaatacga ggtcgccaac   8100
atcttcttct ggaggccgtg gttggcttgt atggagcagc agacgcgcta cttcgagcgg   8160
aggcatccgg agcttgcagg atcgccgcgg ctccgggcgt atatgctccg cattggtctt   8220
gaccaactct atcagagctt ggttgacggc aatttcgatg atgcagcttg ggcgcagggt   8280
cgatgcgacg caatcgtccg atccggagcc gggactgtcg ggcgtacaca aatcgcccgc   8340
agaagcgcgg ccgtctggac cgatggctgt gtagaagtac tcgccgatag tggaaaccga   8400
cgccccagca ctcgtccgag ggcaaaggaa tagtgaggta cagcttggat cgatccggct   8460
gctaacaaag cccgaaagga agctgagttg gctgctgcca ccgctgagca ataactagca   8520
taaccccttg gggcctctaa acgggtcttg aggggttttt tgctgaaagg aggaactata   8580
tccggatgat cgggcgcgcc gtcgacggat ccgtacgaga tccggccggc cagatcctgc   8640
aggtaaattg cagctgaagg acagtgaagg gtgaatttat ccatttaaac cattttcttt   8700
ttaacacatt tcttatggta atctcttctc actacactat aaaaatggct tctcaatccc   8760
attttctaca tcatcccatt ctattgagtt ttgtttattt gctttcactt ttttttttat   8820
ctgcctcttc ccttaatttg cttgacttct tcttcacatt ttgctttgtt ttctcctccg   8880
gcttccggta tttcaaattc aagatgagca agttgaaatt tataaataga aatacagata   8940
ttatttacaa cgtcaaatct ttggtatttt caatatttga atggggtaaa tttgtcatat   9000
agtcatcatc actgactact tatctaacct atttaatttg gagcatattc tttataaggt   9060
ccctctcacg gccaatgtct aattattgat atacagctct tgttttctag tgctgcttat   9120
aatattatct acacatatat atggtactgc acactactac tatatagtag taagtaaact   9180
agcaacagcc ggggccaaac tccaataact aggcattggg gtttagttgg taatataaat   9240
ataacatcaa aaagtctttg cttgtgacga acatcacaat gcacccacca ttgatgccac   9300
gacagacatt gttaattttt tttttaattt ttaaaaaaga agcaattcca atagttctat   9360
attacaatct cacgtgatcc aagcacaacg tttcattttt tgtacatgct cgatatataa   9420
ataatatttc attttatagt aaaatataat gacattttcg aatataattt ttgaaatttc   9480
attttccaaa tgaaatacta atattaatat taatgagatt accacaaatc atgttatgaa   9540
tgaaataaag agttttggca ttctaacttt ctttgaatag aacaaaatgt atacaacact   9600
ctccatatat acacgattta ttcagggatc atatacattc tctcatgatt aacatagtct   9660
gctttcttca cgtctaagca gataattttt ggtccacaag ataaaattat cattagtcgt   9720
tttaattaat tccttgagca tcaagcacta aaataattaa acttctccat taccaaaaaa   9780
aaaagatagg tgattcagta acatgtagta ctagtactac tgattttttt tttcttttga   9840
ttttaatgaa tggttcgtat cgagcatcga gaaatccatt tattaggtgt gtaatgtaat   9900
agtagtattt ccttgatttt cagtaataag atggattctt acatttatat ctgtttgaca   9960
gaaaatgttg tcaatgcatt tcttgggcac aaagtttttt gaaacatgaa ttaatttttt  10020
caaaatattt atgacatcaa attgacccta aaataagtga taaagcttta acgtggaatg  10080
acattaattt ttccatgata aataaaacac ttaaaacatt ttaatattaa tattataatc  10140
agttacaact atgttcaatt aatgcaataa cttttaaata aatattaaaa tattttttttt  10200
ctgttctcca ataaagagat cttgttgcac ggaaaaagtc acattcttat ttagtaaaaa  10260
attataatta ttgtttgaaa aatatcattt tcactgcaga aaatttgatc cagctctaca  10320
gatcatactt ttattgtaca ataatacaat aaaaatattc atctgcagga aatatcattt  10380
```

tcattgtaca ataatataaa gataaatata taccagaaaa gaaaaagaaa ctgatgtggc 10440
acaatgtatt cactgaaaga atgcatattg tatttcacct ttcaagcagc actaagaata 10500
tacttctttt attatacttg tgcatttact caaccaccct cggtggagta agaaagaaga 10560
tagataaaag ttttttttga catttggtga atctcttaat taaaaaaata aaataatcca 10620
tttcctttat ttaatttctt ttttcccatc tgtgaaattc caattctgct tcgcgctcct 10680
gtctataaat tgacttagcc accacctcag tttccattca ttcacttctt ctctttatac 10740 ccccccctctc ttttttgcgt tcattctgtt ttcgtaagta ctgttgtttt tctcttctat 10800
ttcttttttt gtttgtgttg ttttttttttc ttccttatcg ttgttctgcc tctcctctgt 10860
ttcggtgctc tgttcaccac ttccacgtga gaatgatctt ccttctttgc atgttcattc 10920
tctcgtgacc actggatcag actccatgtt ctgatccagg gtctctctct aacgcctgta 10980
ctttcatcca tgaccacctt aaaaacaaca tgggggtggt gctgttacac taactctgtt 11040
tctggggtgc tgtctttgtt caattttact cagaaaatat cttttcttgg attctattcg 11100
gtgtgtggga acatgatcct gtcggtcggt tgtttttagg ttaatcctta actggttaca 11160
aggatctaac gcttgaatgc atgtcctgag ttaaagaaac aaaagaagaa cacacctagt 11220
acagcctggc ctcgaaccaa gaacttcttt gttggtttct cattattact aaaataaaat 11280
aaagtatacg ttttcttttt tctttgggat gaacggttca gacttatgag aagtttaagc 11340
taatcctgta gtggagtgtt caatttattt taaactttaa agcaatagct caagcactaa 11400
acttcttttt caagttcaac cactttggta gcttgctaat tgctgctatt gttctaatta 11460
attaatgtaa ttattgttta aaaaagaaaa gttggtgaca ctggaataaa aaagtgtact 11520
atctggcaat tattcttctg cagcaatgtt tgaggttgaa atcttagtag aacaaagtag 11580
aagatctggt atttatattt tttgtagaca gatggtgggg gtgggtggta ggccttgaaa 11640
tccaatatag ttttgtagaa taattttatt attttttttt tttgctcact tgtttgtggt 11700
attgattttg tgatgactca agattaatga tttaccttca tttttttcat ggtgacatat 11760
tatgtatatt cttgatctgt ttcttacact tctttttcgt tgttgtagct gttgaagtct 11820
gcggccgcac catggaaact ggaggctttc acggctaccg caagctcccc aacaccaccg 11880
ctgggttgaa gctgtcagtg tcagacatga acatgaacat gaggcagcag caggtagcat 11940
catcagatca gaactgcagc aaccacagtg cagcaggaga ggagaacgaa tgcacggtga 12000
gggagcaaga caggttcatg ccaatcgcta acgtgatacg gatcatgcgc aagattctcc 12060
ctccacacgc aaaaatctcc gatgatgcaa aggagacaat ccaagagtgc gtgtcggagt 12120
acatcagctt catcaccggg gaggcgaacg agcgttgcca gagggagcaa cggaagacca 12180
taaccgcaga ggacgtgctt tggccatga gcaagcttgg attcgacgac tacatcgaac 12240
cgttgaccat gtaccttcac cgctaccgtg aacttgaggg tgaccgcacc tctatgaggg 12300
gtgaaccact cgggaagagg actgtggaat acgccacgct tggtgttgct actgcttttg 12360
tccctccacc ctatcatcac cacaatgggt actttggtgc tgccatgccc atggggactt 12420
acgttaggga agcgccacca aatacagcct cctcccatca ccaccaccac caccaccacc 12480
accatgctcg tggaatctcc aatgctcatg aaccaaatgc tcgctccata taagcggccg 12540
catttcgcac caaatcaatg aaagtaataa tgaaaagtct gaataagaat acttaggctt 12600
agatgccttt gttacttgtg taaaataact tgagtcatgt acctttggcg gaaacagaat 12660
aaataaaagg tgaaattcca atgctctatg tataagttag taatacttaa tgtgttctac 12720
ggttgtttca atatcatcaa actctaattg aaactttaga accacaaatc tcaatctttt 12780
cttaatgaaa tgaaaaatct taattgtacc atgtttatgt taaacacctt acaattaatt 12840
ggttggagag gaggaccaac cgatgggaca acattgggag aaagagattc aatggagatt 12900
tggataggag aacaacattc tttttcactt caatacaaga tgagtgcaac actaaggata 12960
tgtatgagac tttcagaagc tacgacaaca tagatgagtg aggtggtgat tcctagcaag 13020
aaagacatta gaggaagcca aaatcgaaca aggaagacat caagggcaag agacaggacc 13080
atccatctca ggaaaaggag ctttgggata gtccgagaag ttgtacaaga aatttttttgg 13140 agggtgagtg atgcattgct ggtgacttta actcaatcaa aattgagaaa gaaagaaaag 13200 ggaggggct cacatgtgaa tagaagggaa acgggagaat tttacagttt tgatctaatg 13260
ggcatcccag ctagtggtaa catattcacc atgtttaacc ttcacgtacg agatccggcc 13320
ggccagatcc tgca 13334

<210> SEQ ID NO 62
<211> LENGTH: 13868
<212> TYPE: DNA
<213> ORGANISM: artificial sequence
<220> FEATURE:
<223> OTHER INFORMATION: plasmid sequence

<400> SEQUENCE: 62
ggagatccaa gcttttgatc catgcccttc atttgccgct tattaattaa tttggtaaca 60
gtccgtacta atcagttact tatccttccc ccatcataat taatcttggt agtctcgaat 120
gccacaacac tgactagtct cttggatcat aagaaaaagc caaggaacaa aagaagacaa 180
aacacaatga gagtatcctt tgcatagcaa tgtctaagtt cataaaattc aaacaaaaac 240
gcaatcacac acagtggaca tcacttatcc actagctgat caggatcgcc gcgtcaagaa 300
aaaaaaactg gaccccaaaa gccatgcaca acaacacgta ctcacaaagg tgtcaatcga 360
gcagcccaaa acattcacca actcaaccca tcatgagccc tcacatttgt tgtttctaac 420
ccaacctcaa actcgtattc tcttccgcca cctcattttt gtttatttca acacccgtca 480
aactgcatgc caccccgtgg ccaaatgtcc atgcatgtta acaagaccta tgactataaa 540
tagctgcaat ctcggcccag gttttcatca tcaagaacca gttcaatatc ctagtacacc 600
gtattaaaga atttaagata tactgcggcc gcaacatgac tatcgactca caatactaca 660
agtcgcgaga caaaaacgac acggcaccca aaatcgcggg aatccgatat gccccgctat 720
cgacaccatt actcaaccga tgtgagacct tctctctggt ctggcacatt ttcagcattc 780
ccactttcct cacaatttc atgctatgct gcgcaattcc actgctctgg ccatttgtga 840
ttgcgtatgt agtgtacgct gttaaagacg actccccgtc caacggagga gtggtcaagc 900
gatactcgcc tatttcaaga aacttcttca tctggaagct ctttggccgc tacttcccca 960
taactctgca caagacggtg gatctggagc ccacgcacac atactaccct ctggacgtcc 1020
aggagtatca cctgattgct gagagatact ggccgcagaa caagtacctc cgagcaatca 1080
tcaccaccat cgagtacttt ctgcccgcct tcatgaaacg gtctctttct atcaacgagc 1140
aggagcagcc tgccgagcga gatcctctcc tgtctcccgt ttctcccagc tctccgggtt 1200
ctcaacctga caagtggatt aaccacgaca gcagatatag ccgtggagaa tcatctggct 1260
ccaacggcca cgcctcgggc tccgaactta acggcaacgg caacaacggc accactaacc 1320
gacgaccttt gtcgtccgcc tctgctggct ccactgcatc tgattccacg cttcttaacg 1380
ggtccctcaa ctcctacgcc aaccagatca ttggcgaaaa cgacccacag ctgtcgccca 1440
caaaactcaa gcccactggc agaaaataca tcttcggcta ccaccccccac ggcattatcg 1500
gcatgggagc ctttggtgga attgccaccg agggagctgg atggtccaag ctctttccgg 1560
gcatccctgt ttctcttatg actctcacca acaacttccg agtgcctctc tacagagagt 1620
acctcatgag tctgggagtc gcttctgtct ccaagaagtc ctgcaaggcc ctcctcaagc 1680
gaaaccagtc tatctgcatt gtcgttggtg gagcacagga aagtcttctg gccagacccg 1740
gtgtcatgga cctggtgcta ctcaagcgaa agggttttgt tcgacttggt atggaggtcg 1800
gaaatgtcgc ccttgttccc atcatggcct ttggtgagaa cgacctctat gaccaggtta 1860
gcaacgacaa gtcgtccaag ctgtaccgat tccagcagtt tgtcaagaac ttccttggat 1920
tcacccttcc tttgatgcat gcccgaggcg tcttcaacta cgatgtcggt cttgtcccct 1980
acaggcgacc cgtcaacatt gtggttggtt cccccattga cttgccttat ctcccacacc 2040
ccaccgacga agaagtgtcc gaataccacg accgatacat cgccgagctg cagcgaatct 2100
acaacgagca caaggatgaa tatttcatcg attggaccga ggagggcaaa ggagccccag 2160
agttccgaat gattgagtaa gcggccgcaa gtatgaacta aaatgcatgt aggtgtaaga 2220
gctcatggag agcatggaat attgtatccg accatgtaac agtataataa ctgagctcca 2280
tctcacttct tctatgaata aacaaaggat gttatgatat attaacactc tatctatgca 2340
ccttattgtt ctatgataaa tttcctctta ttattataaa tcatctgaat cgtgacggct 2400
tatggaatgc ttcaaatagt acaaaaacaa atgtgtacta taagactttc taaacaattc 2460
taaccttagc attgtgaacg agacataagt gttaagaaga cataacaatt ataatggaag 2520
aagtttgtct ccatttatat attatatatt acccacttat gtattatatt aggatgttaa 2580
ggagacataa caattataaa gagagaagtt tgtatccatt tatatattat atactaccca 2640
tttatatatt atacttatcc acttatttaa tgtctttata aggtttgatc catgatattt 2700
ctaatatttt agttgatatg tatatgaaag ggtactattt gaactctctt actctgtata 2760
aaggttggat catccttaaa gtgggtctat ttaattttat tgcttcttac agataaaaaa 2820
aaaattatga gttggtttga taaaatattg aaggatttaa aataataata aataacatat 2880
aatatatgta tataaattta ttataatata acatttatct ataaaaaagt aaatattgtc 2940
ataaatctat acaatcgttt agccttgctg gacgaatctc aattatttaa acgagagtaa 3000
acatatttga ctttttggtt atttaacaaa ttattattta acactatatg aaattttttt 3060
ttttatcagc aaagaataaa attaaattaa gaaggacaat ggtgtcccaa tccttataca 3120
accaacttcc acaagaaagt caagtcagag acaacaaaaa aacaagcaaa ggaaattttt 3180
taatttgagt tgtcttgttt gctgcataat ttatgcagta aaacactaca cataaccctt 3240
ttagcagtag agcaatggtt gaccgtgtgc ttagcttctt ttattttatt tttttatcag 3300
caaagaataa ataaaataaa atgagacact tcagggatgt ttcaacaagc ttggcgcgcc 3360
gttctatagt gtcacctaaa tcgtatgtgt atgatacata aggttatgta ttaattgtag 3420
ccgcgttcta acgacaatat gtccatatgg tgcactctca gtacaatctg ctctgatgcc 3480
gcatagttaa gccagccccg acacccgcca acacccgctg acgcgccctg acgggcttgt 3540
ctgctcccgg catccgctta cagacaagct gtgaccgtct ccgggagctg catgtgtcag 3600
aggttttcac cgtcatcacc gaaacgcgcg agacgaaagg gcctcgtgat acgcctattt 3660
ttataggtta atgtcatgac caaaatccct taacgtgagt tttcgttcca ctgagcgtca 3720
gaccccgtag aaaagatcaa aggatcttct tgagatcctt tttttctgcg cgtaatctgc 3780

```
tgcttgcaaa caaaaaaacc accgctacca gcggtggttt gtttgccgga tcaagagcta   3840
ccaactcttt ttccgaaggt aactggcttc agcagagcgc agataccaaa tactgtcctt   3900
ctagtgtagc cgtagttagg ccaccacttc aagaactctg tagcaccgcc tacatacctc   3960
gctctgctaa tcctgttacc agtggctgct gccagtggcg ataagtcgtg tcttaccggg   4020
ttggactcaa gacgatagtt accggataag gcgcagcggt cgggctgaac ggggggttcg   4080
tgcacacagc ccagcttgga gcgaacgacc tacaccgaac tgagatacct acagcgtgag   4140
cattgagaaa gcgccacgct tcccgaaggg agaaaggcgg acaggtatcc ggtaagcggc   4200
agggtcggaa caggagagcg cacgagggag cttccagggg gaaacgcctg gtatctttat   4260
agtcctgtcg ggtttcgcca cctctgactt gagcgtcgat ttttgtgatg ctcgtcaggg   4320
gggcggagcc tatggaaaaa cgccagcaac gcggcctttt tacggttcct ggccttttgc   4380
tggccttttg ctcacatgtt ctttcctgcg ttatcccctg attctgtgga taaccgtatt   4440
accgcctttg agtgagctga taccgctcgc cgcagccgaa cgaccgagcg cagcgagtca   4500
gtgagcgagg aagcggaaga gcgcccaata cgcaaaccgc ctctccccgc gcgttggccg   4560
attcattaat gcaggttgat cgattcgaca tcgatctagt aacatagatg acaccgcgcg   4620
cgataattta tcctagtttg cgcgctatat tttgttttct atcgcgtatt aaatgtataa   4680
ttgcgggact ctaatcataa aaacccatct cataaataac gtcatgcatt acatgttaat   4740
tattacatgc ttaacgtaat tcaacagaaa ttatatgata atcatcgcaa gaccggcaac   4800
aggattcaat cttaagaaac tttattgcca aatgtttgaa cgatctgctt cgacgcactc   4860
cttctttagg tacctcacta ttcctttgcc ctcggacgag tgctggggcg tcggtttcca   4920
ctatcggcga gtacttctac acagccatcg gtccagacgg ccgcgcttct gcgggcgatt   4980
tgtgtacgcc cgacagtccc ggctccggat cggacgattg cgtcgcatcg accctgcgcc   5040
caagctgcat catcgaaatt gccgtcaacc aagctctgat agagttggtc aagaccaatg   5100
cggagcatat acgcccggag ccgcggcgat cctgcaagct ccggatgcct ccgctcgaag   5160
tagcgcgtct gctgctccat acaagccaac cacggcctcc agaagaagat gttggcgacc   5220
tcgtattggg aatccccgaa catcgcctcg ctccagtcaa tgaccgctgt tatgcggcca   5280
ttgtccgtca ggacattgtt ggagccgaaa tccgcgtgca cgaggtgccg gacttcgggg   5340
cagtcctcgg cccaaagcat cagctcatcg agagcctgcg cgacggacgc actgacggtg   5400
tcgtccatca cagtttgcca gtgatacaca tggggatcag caatcgcgca tatgaaatca   5460
cgccatgtag tgtattgacc gattccttgc ggtccgaatg ggccgaaccc gctcgtctgg   5520
ctaagatcgg ccgcagcgat cgcatccatg gcctccgcga ccggctgcag aacagcgggc   5580
agttcggttt caggcaggtc ttgcaacgtg acaccctgtg cacggcggga gatgcaatag   5640
gtcaggctct cgctgaattc cccaatgtca agcacttccg gaatcgggag cgcggccgat   5700
gcaaagtgcc gataaacata acgatctttg tagaaaccat cggcgcagct atttacccgc   5760
aggacatatc cacgccctcc tacatcgaag ctgaaagcac gagattcttc gccctccgag   5820
agctgcatca ggtcggagac gctgtcgaac ttttcgatca gaaacttctc gacagacgtc   5880
gcggtgagtt caggcttttt catggtttaa taagaagaga aaagagttct tttgttatgg   5940
ctgaagtaat agagaaatga gctcgagcgt gtcctctcca aatgaaatga acttccttat   6000
atagaggaag ggtcttgcga aggatagtgg gattgtgcgt catcccttac gtcagtggag   6060
atgtcacatc aatccacttg ctttgaagac gtggttggaa cgtcttcttt ttccacgatg   6120
ctcctcgtgg gtgggggtcc atctttggga ccactgtcgg cagaggcatc ttgaatgata   6180
```

```
gcctttcctt tatcgcaatg atggcatttg taggagccac cttccttttc tactgtcctt   6240
tcgatgaagt gacagatagc tgggcaatgg aatccgagga ggtttcccga aattatcctt   6300
tgttgaaaag tctcaatagc cctttggtct tctgagactg tatctttgac atttttggag   6360
tagaccagag tgtcgtgctc caccatgttg acgaagattt tcttcttgtc attgagtcgt   6420
aaaagactct gtatgaactg ttcgccagtc ttcacggcga gttctgttag atcctcgatt   6480
tgaatcttag actccatgca tggccttaga ttcagtagga actacctttt tagagactcc   6540
aatctctatt acttgccttg gtttatgaag caagccttga atcgtccata ctggaatagt   6600
acttctgatc ttgagaaata tgtctttctc tgtgttcttg atgcaattag tcctgaatct   6660
tttgactgca tctttaacct tcttgggaag gtatttgatc tcctggagat tgttactcgg   6720
gtagatcgtc ttgatgagac ctgctgcgta ggcctctcta accatctgtg ggtcagcatt   6780
ctttctgaaa ttgaagaggc taaccttctc attatcagtg gtgaacatag tgtcgtcacc   6840
ttcaccttcg aacttccttc ctagatcgta aagatagagg aaatcgtcca ttgtaatctc   6900
cggggcaaag gagatctctt ttggggctgg atcactgctg ggccttttgg ttcctagcgt   6960
gagccagtgg gctttttgct ttggtgggct tgttagggcc ttagcaaagc tcttgggctt   7020
gagttgagct tctcctttgg ggatgaagtt caacctgtct gtttgctgac ttgttgtgta   7080
cgcgtcagct gctgctcttg cctctgtaat agtggcaaat ttcttgtgtg caactccggg   7140
aacgccgttt gttgccgcct ttgtacaacc ccagtcatcg tatataccgg catgtggacc   7200
gttatacaca acgtagtagt tgatatgagg gtgttgaata cccgattctg ctctgagagg   7260
agcaactgtg ctgttaagct cagatttttg tgggattgga attggatcga tctcgatccc   7320
gcgaaattaa tacgactcac tatagggaga ccacaacggt ttccctctag aaataatttt   7380
gtttaacttt aagaaggaga tatacccatg gaaaagcctg aactcaccgc gacgtctgtc   7440
gagaagtttc tgatcgaaaa gttcgacagc gtctccgacc tgatgcagct ctcggagggc   7500
gaagaatctc gtgctttcag cttcgatgta ggagggcgtg gatatgtcct gcgggtaaat   7560
agctgcgccg atggtttcta caaagatcgt tatgtttatc ggcactttgc atcggccgcg   7620
ctcccgattc cggaagtgct tgacattggg gaattcagcg agagcctgac ctattgcatc   7680
tcccgccgtg cacagggtgt cacgttgcaa gacctgcctg aaaccgaact gcccgctgtt   7740
ctgcagccgg tcgcggaggc tatggatgcg atcgctgcgg ccgatcttag ccagacgagc   7800
gggttcggcc cattcggacc gcaaggaatc ggtcaataca ctacatggcg tgatttcata   7860
tgcgcgattg ctgatcccca tgtgtatcac tggcaaactg tgatggacga caccgtcagt   7920
gcgtccgtcg cgcaggctct cgatgagctg atgctttggg ccgaggactg ccccgaagtc   7980
cggcacctcg tgcacgcgga tttcggctcc aacaatgtcc tgacggacaa tggccgcata   8040
acagcggtca ttgactggag cgaggcgatg ttcggggatt cccaatacga ggtcgccaac   8100
atcttcttct ggaggccgtg gttggcttgt atggagcagc agacgcgcta cttcgagcgg   8160
aggcatccgg agcttgcagg atcgccgcgg ctccgggcgt atatgctccg cattggtctt   8220
gaccaactct atcagagctt ggttgacggc aatttcgatg atgcagcttg ggcgcagggt   8280
cgatgcgacg caatcgtccg atccggagcc gggactgtcg ggcgtacaca aatcgcccgc   8340
agaagcgcgg ccgtctggac cgatggctgt gtagaagtac tcgccgatag tggaaaccga   8400
cgccccagca ctcgtccgag ggcaaaggaa tagtgaggta cagcttggat cgatccggct   8460
gctaacaaag cccgaaagga agctgagttg gctgctgcca ccgctgagca ataactagca   8520
```

-continued

```
taacccttg gggcctctaa acgggtcttg aggggttttt tgctgaaagg aggaactata   8580
tccggatgat cgggcgcgcc gtcgacggat ccgtacgaga tccggccggc cagatcctgc   8640
aggtaaattg cagctgaagg acagtgaagg gtgaatttat ccatttaaac cattttcttt   8700
ttaacacatt tcttatggta atctcttctc actacactat aaaaatggct tctcaatccc   8760
attttctaca tcatcccatt ctattgagtt ttgtttattt gctttcactt ttttttttat   8820
ctgcctcttc ccttaatttg cttgacttct tcttcacatt ttgctttgtt ttctcctccg   8880
gcttccggta tttcaaattc aagatgagca agttgaaatt tataaataga aatacagata   8940
ttatttacaa cgtcaaatct ttggtatttt caatatttga atggggtaaa tttgtcatat   9000
agtcatcatc actgactact tatctaacct atttaatttg gagcatattc tttataaggt   9060
ccctctcacg gccaatgtct aattattgat atacagctct tgttttctag tgctgcttat   9120
aatattatct acacatatat atggtactgc acactactac tatatagtag taagtaaact   9180
agcaacagcc ggggccaaac tccaataact aggcattggg gtttagttgg taatataaat   9240
ataacatcaa aaagtctttg cttgtgacga acatcacaat gcacccacca ttgatgccac   9300
gacagacatt gttaattttt tttttaattt ttaaaaaaga agcaattcca atagttctat   9360
attacaatct cacgtgatcc aagcacaacg tttcattttt tgtacatgct cgatatataa   9420
ataatatttc attttatagt aaaatataat gacattttcg aatataattt ttgaaatttc   9480
attttccaaa tgaaatacta atattaatat taatgagatt accacaaatc atgttatgaa   9540
tgaaataaag agttttggca ttctaacttt ctttgaatag aacaaaatgt atacaacact   9600
ctccatatat acacgattta ttcagggatc atatacattc tctcatgatt aacatagtct   9660
gctttcttca cgtctaagca gataattttt ggtccacaag ataaaattat cattagtcgt   9720
tttaattaat tccttgagca tcaagcacta aaataattaa acttctccat taccaaaaaa   9780
aaaagatagg tgattcagta acatgtagta ctagtactac tgattttttt tttcttttga   9840
ttttaatgaa tggttcgtat cgagcatcga gaaatccatt tattaggtgt gtaatgtaat   9900
agtagtattt ccttgatttt cagtaataag atggattctt acatttatat ctgtttgaca   9960
gaaaatgttg tcaatgcatt tcttgggcac aaagtttttt gaaacatgaa ttaatttttt  10020
caaaatattt atgacatcaa attgacccta aaataagtga taaagcttta acgtggaatg  10080
acattaattt ttccatgata aataaaacac ttaaaacatt ttaatattaa tattataatc  10140
agttacaact atgttcaatt aatgcaataa cttttaaata aatattaaaa tatttttttt  10200
ctgttctcca ataaagagat cttgttgcac ggaaaaagtc acattcttat ttagtaaaaa  10260
attataatta ttgtttgaaa aatatcattt tcactgcaga aaatttgatc cagctctaca  10320
gatcatactt ttattgtaca ataatacaat aaaaatattc atctgcagga aatatcattt  10380
tcattgtaca ataatataaa gataaatata taccagaaaa gaaaaagaaa ctgatgtggc  10440
acaatgtatt cactgaaaga atgcatattg tatttcacct ttcaagcagc actaagaata  10500
tacttctttt attatacttg tgcatttact caaccaccct cggtggagta agaaagaaga  10560
tagataaaag tttttttga catttggtga atctcttaat taaaaaaata aaataatcca  10620
tttcctttat ttaatttctt ttttcccatc tgtgaaattc caattctgct tcgcgctcct  10680
gtctataaat tgacttagcc accacctcag tttccattca ttcacttctt ctctttatac  10740
ccccctctc ttttttgcgt tcattctgtt ttcgtaagta ctgttgtttt tctcttctat  10800
ttcttttttt gtttgtgttg ttttttttc ttccttatcg ttgttctgcc tctcctctgt  10860
ttcggtgctc tgttcaccac ttccacgtga gaatgatctt ccttctttgc atgttcattc  10920
```

```
tctcgtgacc actggatcag actccatgtt ctgatccagg gtctctctct aacgcctgta  10980
ctttcatcca tgaccacctt aaaaacaaca tgggggtggt gctgttacac taactctgtt  11040
tctggggtgc tgtctttgtt caattttact cagaaaatat cttttcttgg attctattcg  11100
gtgtgtggga acatgatcct gtcggtcggt tgtttttagg ttaatcctta actggttaca  11160
aggatctaac gcttgaatgc atgtcctgag ttaaagaaac aaaagaagaa cacacctagt  11220
acagcctggc ctcgaaccaa gaacttcttt gttggtttct cattattact aaaataaaat  11280
aaagtatacg ttttcttttt tctttgggat gaacggttca gacttatgag aagtttaagc  11340
taatcctgta gtggagtgtt caatttattt taaactttaa agcaatagct caagcactaa  11400
acttcttttt caagttcaac cactttggta gcttgctaat tgctgctatt gttctaatta  11460
attaatgtaa ttattgttta aaaaagaaaa gttggtgaca ctggaataaa aaagtgtact  11520
atctggcaat tattcttctg cagcaatgtt tgaggttgaa atcttagtag aacaaagtag  11580
aagatctggt atttatattt tttgtagaca gatggtgggg gtgggtggta ggccttgaaa  11640
tccaatatag ttttgtagaa taattttatt attttttttt tttgctcact tgtttgtggt  11700
attgattttg tgatgactca agattaatga tttaccttca ttttttttcat ggtgacatat  11760
tatgtatatt cttgatctgt ttcttacact tctttttcgt tgttgtagct gttgaagtct  11820
gcggccgcat gaagaggtct ccagcatctt cttgttcatc atctacttcc tctgttgggt  11880
ttgaagctcc cattgaaaaa agaaggccta agcatccaag gaggaataat ttgaagtcac  11940
aaaaatgcaa gcagaaccaa accaccactg gtggcagaag aagctctatc tatagaggag  12000
ttacaaggca taggtggaca gggaggtttg aagctcacct atgggataag agctcttgga  12060
acaacattca gagcaagaag ggtcgacaag tttatttggg ggcatatgat actgaagaat  12120
ctgcagcccg tacctatgac cttgcagccc ttaaatactg ggaaaaagat gcaaccctga  12180
atttcccgat agaaacttat accaaggagc tcgaggaaat ggacaaggtt tcaagagaag  12240
aatatttggc ttctttgcgg cgccaaagca gtggcttttc tagaggcctg tctaagtacc  12300
gtggggttgc taggcatcat cataatggtc gctgggaagc acgaattgga agagtatgcg  12360
gaaacaagta cctctacttg ggacatata aaactcaaga ggaggcagca gtggcatatg  12420
acatggcagc aatagagtac cgtggagtca atgcagtgac caattttgac ataagcaact  12480
acatggacaa aataaagaag aaaaatgacc aaacccaaca acaacaaaca gaagcacaaa  12540
cggaaacagt tcctaactcc tctgactctg aagaagtaga agtagaacaa cagacaacaa  12600
caataaccac accaccccca tctgaaaatc tgcacatgcc accacagcag caccaagttc  12660
aatacacccc ccatgtctct ccaagggaag aagaatcatc atcactgatc acaattatgg  12720
accatgtgct tgagcaggat ctgccatgga gcttcatgta cactggcttg tctcagtttc  12780
aagatccaaa cttggctttc tgcaaaggtg atgatgactt ggtgggcatg tttgatagtg  12840
cagggtttga ggaagacatt gattttctgt tcagcactca acctggtgat gagactgaga  12900
gtgatgtcaa caatatgagc gcagttttgg atagtgttga gtgtggagac acaaatgggg  12960
ctggtggaag catgatgcat gtggataaca agcagaagat agtatcattt gcttcttcac  13020
catcatctac aactacagtt tcttgtgact atgctctaga tctatgagcg gccgcatttc  13080
gcaccaaatc aatgaaagta ataatgaaaa gtctgaataa gaatacttag gcttagatgc  13140
ctttgttact tgtgtaaaat aacttgagtc atgtaccttt ggcggaaaca gaataaataa  13200
aaggtgaaat tccaatgctc tatgtataag ttagtaatac ttaatgtgtt ctacggttgt  13260
```

ttcaatatca tcaaactcta attgaaactt tagaaccaca aatctcaatc ttttcttaat 13320
gaaatgaaaa atcttaattg taccatgttt atgttaaaca ccttacaatt aattggttgg 13380
agaggaggac caaccgatgg gacaacattg ggagaaagag attcaatgga gatttggata 13440
ggagaacaac attctttttc acttcaatac aagatgagtg caacactaag gatatgtatg 13500
agactttcag aagctacgac aacatagatg agtgaggtgg tgattcctag caagaaagac 13560
attagaggaa gccaaaatcg aacaaggaag acatcaaggg caagagacag gaccatccat 13620
ctcaggaaaa ggagctttgg gatagtccga gaagttgtac aagaaatttt ttggagggtg 13680
agtgatgcat tgctggtgac tttaactcaa tcaaaattga gaaagaaaga aaagggaggg 13740
ggctcacatg tgaatagaag ggaaacggga gaattttaca gttttgatct aatgggcatc 13800
ccagctagtg gtaacatatt caccatgttt aaccttcacg tacgagatcc ggccggccag 13860
atcctgca 13868

<210> SEQ ID NO 63
<211> LENGTH: 13631
<212> TYPE: DNA
<213> ORGANISM: artificial sequence
<220> FEATURE:
<223> OTHER INFORMATION: plasmid sequence

<400> SEQUENCE: 63
ggagatccaa gcttttgatc catgcccttc atttgccgct tattaattaa tttggtaaca 60
gtccgtacta atcagttact tatccttccc ccatcataat taatcttggt agtctcgaat 120
gccacaacac tgactagtct cttggatcat aagaaaaagc caaggaacaa aagaagacaa 180
aacacaatga gagtatcctt tgcatagcaa tgtctaagtt cataaaattc aaacaaaaac 240
gcaatcacac acagtggaca tcacttatcc actagctgat caggatcgcc gcgtcaagaa 300
aaaaaaactg gaccccaaaa gccatgcaca acaacacgta ctcacaaagg tgtcaatcga 360
gcagcccaaa acattcacca actcaaccca tcatgagccc tcacatttgt tgtttctaac 420
ccaacctcaa actcgtattc tcttccgcca cctcattttt gtttatttca acacccgtca 480
aactgcatgc caccccgtgg ccaaatgtcc atgcatgtta acaagaccta tgactataaa 540
tagctgcaat ctcggcccag gttttcatca tcaagaacca gttcaatatc ctagtacacc 600
gtattaaaga atttaagata tactgcggcc gcaacatgac tatcgactca caatactaca 660
agtcgcgaga caaaaacgac acggcaccca aaatcgcggg aatccgatat gccccgctat 720
cgacaccatt actcaaccga tgtgagacct tctctctggt ctggcacatt ttcagcattc 780
ccactttcct cacaattttc atgctatgct gcgcaattcc actgctctgg ccatttgtga 840
ttgcgtatgt agtgtacgct gttaaagacg actccccgtc caacggagga gtggtcaagc 900
gatactcgcc tatttcaaga aacttcttca tctggaagct ctttggccgc tacttcccca 960
taactctgca caagacggtg gatctggagc ccacgcacac atactaccct ctggacgtcc 1020
aggagtatca cctgattgct gagagatact ggccgcagaa caagtacctc cgagcaatca 1080
tcaccaccat cgagtacttt ctgcccgcct tcatgaaacg gtctctttct atcaacgagc 1140
aggagcagcc tgccgagcga gatcctctcc tgtctcccgt ttctcccagc tctccgggtt 1200
ctcaacctga caagtggatt aaccacgaca gcagatatag ccgtggagaa tcatctggct 1260
ccaacggcca cgcctcgggc tccgaactta acggcaacgg caacaacggc accactaacc 1320
gacgaccttt gtcgtccgcc tctgctggct ccactgcatc tgattccacg cttcttaacg 1380
ggtccctcaa ctcctacgcc aaccagatca ttggcgaaaa cgacccacag ctgtcgccca 1440

-continued

```
caaaactcaa gcccactggc agaaaataca tcttcggcta ccaccccccac ggcattatcg   1500
gcatgggagc ctttggtgga attgccaccg agggagctgg atggtccaag ctctttccgg   1560
gcatccctgt ttctcttatg actctcacca acaacttccg agtgcctctc tacagagagt   1620
acctcatgag tctgggagtc gcttctgtct ccaagaagtc ctgcaaggcc ctcctcaagc   1680
gaaaccagtc tatctgcatt gtcgttggtg gagcacagga aagtcttctg gccagacccg   1740
gtgtcatgga cctggtgcta ctcaagcgaa agggttttgt tcgacttggt atggaggtcg   1800
gaaatgtcgc ccttgttccc atcatggcct ttggtgagaa cgacctctat gaccaggtta   1860
gcaacgacaa gtcgtccaag ctgtaccgat tccagcagtt tgtcaagaac ttccttggat   1920
tcacccttcc tttgatgcat gcccgaggcg tcttcaacta cgatgtcggt cttgtcccct   1980
acaggcgacc cgtcaacatt gtggttggtt cccccattga cttgccttat ctcccacacc   2040
ccaccgacga agaagtgtcc gaataccacg accgatacat cgccgagctg cagcgaatct   2100
acaacgagca caaggatgaa tatttcatcg attggaccga ggagggcaaa ggagccccag   2160
agttccgaat gattgagtaa gcggccgcaa gtatgaacta aaatgcatgt aggtgtaaga   2220
gctcatggag agcatggaat attgtatccg accatgtaac agtataataa ctgagctcca   2280
tctcacttct tctatgaata aacaaaggat gttatgatat attaacactc tatctatgca   2340
ccttattgtt ctatgataaa tttcctctta ttattataaa tcatctgaat cgtgacggct   2400
tatggaatgc ttcaaatagt acaaaaacaa atgtgtacta taagactttc taaacaattc   2460
taaccttagc attgtgaacg agacataagt gttaagaaga cataacaatt ataatggaag   2520
aagtttgtct ccatttatat attatatatt acccacttat gtattatatt aggatgttaa   2580
ggagacataa caattataaa gagagaagtt tgtatccatt tatatattat atactaccca   2640
tttatatatt atacttatcc acttatttaa tgtctttata aggtttgatc catgatattt   2700
ctaatatttt agttgatatg tatatgaaag ggtactattt gaactctctt actctgtata   2760
aaggttggat catccttaaa gtgggtctat ttaattttat tgcttcttac agataaaaaa   2820
aaaattatga gttggtttga taaaatattg aaggatttaa aataataata aataacatat   2880
aatatatgta tataaattta ttataatata acatttatct ataaaaaagt aaatattgtc   2940
ataaatctat acaatcgttt agccttgctg gacgaatctc aattatttaa acgagagtaa   3000
acatatttga ctttttggtt atttaacaaa ttattattta acactatatg aaattttttt   3060
ttttatcagc aaagaataaa attaaattaa gaaggacaat ggtgtcccaa tccttataca   3120
accaacttcc acaagaaagt caagtcagag acaacaaaaa aacaagcaaa ggaaattttt   3180
taatttgagt tgtcttgttt gctgcataat ttatgcagta aaacactaca cataaccctt   3240
ttagcagtag agcaatggtt gaccgtgtgc ttagcttctt ttattttatt tttttatcag   3300
caaagaataa ataaaataaa atgagacact tcagggatgt ttcaacaagc ttggcgcgcc   3360
gttctatagt gtcacctaaa tcgtatgtgt atgatacata aggttatgta ttaattgtag   3420
ccgcgttcta acgacaatat gtccatatgg tgcactctca gtacaatctg ctctgatgcc   3480
gcatagttaa gccagccccg acacccgcca acacccgctg acgcgccctg acgggcttgt   3540
ctgctcccgg catccgctta cagacaagct gtgaccgtct ccgggagctg catgtgtcag   3600
aggttttcac cgtcatcacc gaaacgcgcg agacgaaagg gcctcgtgat acgcctattt   3660
ttataggtta atgtcatgac caaaatccct taacgtgagt tttcgttcca ctgagcgtca   3720
gaccccgtag aaaagatcaa aggatcttct tgagatcctt tttttctgcg cgtaatctgc   3780
```

```
tgcttgcaaa caaaaaaacc accgctacca gcggtggttt gtttgccgga tcaagagcta   3840
ccaactcttt ttccgaaggt aactggcttc agcagagcgc agataccaaa tactgtcctt   3900
ctagtgtagc cgtagttagg ccaccacttc aagaactctg tagcaccgcc tacatacctc   3960
gctctgctaa tcctgttacc agtggctgct gccagtggcg ataagtcgtg tcttaccggg   4020
ttggactcaa gacgatagtt accggataag gcgcagcggt cgggctgaac ggggggttcg   4080
tgcacacagc ccagcttgga gcgaacgacc tacaccgaac tgagatacct acagcgtgag   4140
cattgagaaa gcgccacgct tcccgaaggg agaaaggcgg acaggtatcc ggtaagcggc   4200
agggtcggaa caggagagcg cacgagggag cttccagggg gaaacgcctg gtatctttat   4260
agtcctgtcg ggtttcgcca cctctgactt gagcgtcgat ttttgtgatg ctcgtcaggg   4320
gggcggagcc tatggaaaaa cgccagcaac gcggcctttt tacggttcct ggccttttgc   4380
tggccttttg ctcacatgtt ctttcctgcg ttatcccctg attctgtgga taaccgtatt   4440
accgcctttg agtgagctga taccgctcgc cgcagccgaa cgaccgagcg cagcgagtca   4500
gtgagcgagg aagcggaaga gcgcccaata cgcaaaccgc ctctccccgc gcgttggccg   4560
attcattaat gcaggttgat cgattcgaca tcgatctagt aacatagatg acaccgcgcg   4620
cgataattta tcctagtttg cgcgctatat tttgttttct atcgcgtatt aaatgtataa   4680
ttgcgggact ctaatcataa aaacccatct cataaataac gtcatgcatt acatgttaat   4740
tattacatgc ttaacgtaat tcaacagaaa ttatatgata atcatcgcaa gaccggcaac   4800
aggattcaat cttaagaaac tttattgcca aatgtttgaa cgatctgctt cgacgcactc   4860
cttctttagg tacctcacta ttcctttgcc ctcggacgag tgctggggcg tcggtttcca   4920
ctatcggcga gtacttctac acagccatcg gtccagacgg ccgcgcttct gcgggcgatt   4980
tgtgtacgcc cgacagtccc ggctccggat cggacgattg cgtcgcatcg accctgcgcc   5040
caagctgcat catcgaaatt gccgtcaacc aagctctgat agagttggtc aagaccaatg   5100
cggagcatat acgcccggag ccgcggcgat cctgcaagct ccggatgcct ccgctcgaag   5160
tagcgcgtct gctgctccat acaagccaac cacggcctcc agaagaagat gttggcgacc   5220
tcgtattggg aatccccgaa catcgcctcg ctccagtcaa tgaccgctgt tatgcggcca   5280
ttgtccgtca ggacattgtt ggagccgaaa tccgcgtgca cgaggtgccg gacttcgggg   5340
cagtcctcgg cccaaagcat cagctcatcg agagcctgcg cgacggacgc actgacggtg   5400
tcgtccatca cagtttgcca gtgatacaca tggggatcag caatcgcgca tatgaaatca   5460
cgccatgtag tgtattgacc gattccttgc ggtccgaatg ggccgaaccc gctcgtctgg   5520
ctaagatcgg ccgcagcgat cgcatccatg gcctccgcga ccggctgcag aacagcgggc   5580
agttcggttt caggcaggtc ttgcaacgtg acaccctgtg cacggcggga gatgcaatag   5640
gtcaggctct cgctgaattc cccaatgtca agcacttccg gaatcgggag cgcggccgat   5700
gcaaagtgcc gataaacata acgatctttg tagaaaccat cggcgcagct atttacccgc   5760
aggacatatc cacgccctcc tacatcgaag ctgaaagcac gagattcttc gccctccgag   5820
agctgcatca ggtcggagac gctgtcgaac ttttcgatca gaaacttctc gacagacgtc   5880
gcggtgagtt caggcttttt catggtttaa taagaagaga aaagagttct tttgttatgg   5940
ctgaagtaat agagaaatga gctcgagcgt gtcctctcca aatgaaatga acttccttat   6000
atagaggaag ggtcttgcga aggatagtgg gattgtgcgt catcccttac gtcagtggag   6060
atgtcacatc aatccacttg ctttgaagac gtggttggaa cgtcttcttt ttccacgatg   6120
ctcctcgtgg gtgggggtcc atctttggga ccactgtcgg cagaggcatc ttgaatgata   6180
```

-continued gcctttcctt tatcgcaatg atggcatttg taggagccac cttccttttc tactgtcctt 6240
tcgatgaagt gacagatagc tgggcaatgg aatccgagga ggtttcccga aattatcctt 6300
tgttgaaaag tctcaatagc cctttggtct tctgagactg tatctttgac atttttggag 6360
tagaccagag tgtcgtgctc caccatgttg acgaagattt tcttcttgtc attgagtcgt 6420
aaaagactct gtatgaactg ttcgccagtc ttcacggcga gttctgttag atcctcgatt 6480
tgaatcttag actccatgca tggccttaga ttcagtagga actacctttt tagagactcc 6540
aatctctatt acttgccttg gtttatgaag caagccttga atcgtccata ctggaatagt 6600
acttctgatc ttgagaaata tgtctttctc tgtgttcttg atgcaattag tcctgaatct 6660
tttgactgca tctttaacct tcttgggaag gtatttgatc tcctggagat tgttactcgg 6720
gtagatcgtc ttgatgagac ctgctgcgta ggcctctcta accatctgtg ggtcagcatt 6780
ctttctgaaa ttgaagaggc taaccttctc attatcagtg gtgaacatag tgtcgtcacc 6840
ttcaccttcg aacttccttc ctagatcgta aagatagagg aaatcgtcca ttgtaatctc 6900
cggggcaaag gagatctctt ttggggctgg atcactgctg ggccttttgg ttcctagcgt 6960
gagccagtgg gctttttgct ttggtgggct tgttagggcc ttagcaaagc tcttgggctt 7020
gagttgagct tctcctttgg ggatgaagtt caacctgtct gtttgctgac ttgttgtgta 7080
cgcgtcagct gctgctcttg cctctgtaat agtggcaaat ttcttgtgtg caactccggg 7140
aacgccgttt gttgccgcct ttgtacaacc ccagtcatcg tatataccgg catgtggacc 7200
gttatacaca acgtagtagt tgatatgagg gtgttgaata cccgattctg ctctgagagg 7260
agcaactgtg ctgttaagct cagatttttg tgggattgga attggatcga tctcgatccc 7320
gcgaaattaa tacgactcac tatagggaga ccacaacggt ttccctctag aaataatttt 7380
gtttaacttt aagaaggaga tatacccatg gaaaagcctg aactcaccgc gacgtctgtc 7440
gagaagtttc tgatcgaaaa gttcgacagc gtctccgacc tgatgcagct ctcggagggc 7500
gaagaatctc gtgctttcag cttcgatgta ggagggcgtg gatatgtcct gcgggtaaat 7560
agctgcgccg atggtttcta caaagatcgt tatgtttatc ggcactttgc atcggccgcg 7620
ctcccgattc cggaagtgct tgacattggg gaattcagcg agagcctgac ctattgcatc 7680
tcccgccgtg cacagggtgt cacgttgcaa gacctgcctg aaaccgaact gcccgctgtt 7740
ctgcagccgg tcgcggaggc tatggatgcg atcgctgcgg ccgatcttag ccagacgagc 7800
gggttcggcc cattcggacc gcaaggaatc ggtcaataca ctacatggcg tgatttcata 7860
tgcgcgattg ctgatcccca tgtgtatcac tggcaaactg tgatggacga caccgtcagt 7920
gcgtccgtcg cgcaggctct cgatgagctg atgctttggg ccgaggactg ccccgaagtc 7980
cggcacctcg tgcacgcgga tttcggctcc aacaatgtcc tgacggacaa tggccgcata 8040
acagcggtca ttgactggag cgaggcgatg ttcggggatt cccaatacga ggtcgccaac 8100
atcttcttct ggaggccgtg gttggcttgt atggagcagc agacgcgcta cttcgagcgg 8160
aggcatccgg agcttgcagg atcgccgcgg ctccgggcgt atatgctccg cattggtctt 8220
gaccaactct atcagagctt ggttgacggc aatttcgatg atgcagcttg ggcgcagggt 8280
cgatgcgacg caatcgtccg atccggagcc gggactgtcg ggcgtacaca aatcgcccgc 8340
agaagcgcgg ccgtctggac cgatggctgt gtagaagtac tcgccgatag tggaaaccga 8400
cgccccagca ctcgtccgag ggcaaaggaa tagtgaggta cagcttggat cgatccggct 8460
gctaacaaag cccgaaagga agctgagttg gctgctgcca ccgctgagca ataactagca 8520
taaccccttg gggcctctaa acgggtcttg aggggttttt tgctgaaagg aggaactata 8580
tccggatgat cgggcgcgcc gtcgacggat ccgtacgaga tccggccggc cagatcctgc 8640
aggtaaattg cagctgaagg acagtgaagg gtgaatttat ccatttaaac cattttcttt 8700
ttaacacatt tcttatggta atctcttctc actacactat aaaaatggct tctcaatccc 8760
attttctaca tcatcccatt ctattgagtt ttgtttattt gctttcactt ttttttttat 8820
ctgcctcttc ccttaatttg cttgacttct tcttcacatt ttgctttgtt ttctcctccg 8880
gcttccggta tttcaaattc aagatgagca agttgaaatt tataaataga aatacagata 8940
ttatttacaa cgtcaaatct ttggtatttt caatatttga atggggtaaa tttgtcatat 9000
agtcatcatc actgactact tatctaacct atttaatttg gagcatattc tttataaggt 9060
ccctctcacg gccaatgtct aattattgat atacagctct tgttttctag tgctgcttat 9120
aatattatct acacatatat atggtactgc acactactac tatatagtag taagtaaact 9180
agcaacagcc ggggccaaac tccaataact aggcattggg gtttagttgg taatataaat 9240
ataacatcaa aaagtctttg cttgtgacga acatcacaat gcacccacca ttgatgccac 9300
gacagacatt gttaattttt tttttaattt ttaaaaaaga agcaattcca atagttctat 9360
attacaatct cacgtgatcc aagcacaacg tttcattttt tgtacatgct cgatatataa 9420
ataatatttc attttatagt aaaatataat gacattttcg aatataattt ttgaaatttc 9480
attttccaaa tgaaatacta atattaatat taatgagatt accacaaatc atgttatgaa 9540
tgaaataaag agttttggca ttctaacttt ctttgaatag aacaaaatgt atacaacact 9600
ctccatatat acacgattta ttcagggatc atatacattc tctcatgatt aacatagtct 9660
gctttcttca cgtctaagca gataattttt ggtccacaag ataaaattat cattagtcgt 9720
tttaattaat tccttgagca tcaagcacta aaataattaa acttctccat taccaaaaaa 9780
aaaagatagg tgattcagta acatgtagta ctagtactac tgattttttt tttcttttga 9840
ttttaatgaa tggttcgtat cgagcatcga gaaatccatt tattaggtgt gtaatgtaat 9900
agtagtattt ccttgatttt cagtaataag atggattctt acatttatat ctgtttgaca 9960
gaaaatgttg tcaatgcatt tcttgggcac aaagtttttt gaaacatgaa ttaatttttt 10020
caaaatattt atgacatcaa attgacccta aaataagtga taaagcttta acgtggaatg 10080
acattaattt ttccatgata aataaaacac ttaaaacatt ttaatattaa tattataatc 10140
agttacaact atgttcaatt aatgcaataa cttttaaata aatattaaaa tatttttttt 10200
ctgttctcca ataaagagat cttgttgcac ggaaaaagtc acattcttat ttagtaaaaa 10260
attataatta ttgtttgaaa aatatcattt tcactgcaga aaatttgatc cagctctaca 10320
gatcatactt ttattgtaca ataatacaat aaaaatattc atctgcagga aatatcattt 10380
tcattgtaca ataatataaa gataaatata taccagaaaa gaaaaagaaa ctgatgtggc 10440
acaatgtatt cactgaaaga atgcatattg tatttcacct ttcaagcagc actaagaata 10500
tacttctttt attatacttg tgcatttact caaccaccct cggtggagta agaaagaaga 10560
tagataaaag tttttttttga catttggtga atctcttaat taaaaaaata aaataatcca 10620
tttcctttat ttaatttctt ttttcccatc tgtgaaattc caattctgct tcgcgctcct 10680
gtctataaat tgacttagcc accacctcag tttccattca ttcacttctt ctctttatac 10740 ccccccctctc ttttttgcgt tcattctgtt ttcgtaagta ctgttgtttt tctcttctat 10800
ttcttttttt gtttgtgttg tttttttttc ttccttatcg ttgttctgcc tctcctctgt 10860
ttcggtgctc tgttcaccac ttccacgtga gaatgatctt ccttctttgc atgttcattc 10920

-continued

```
tctcgtgacc actggatcag actccatgtt ctgatccagg gtctctctct aacgcctgta  10980
ctttcatcca tgaccacctt aaaaacaaca tgggggtggt gctgttacac taactctgtt  11040
tctggggtgc tgtctttgtt caattttact cagaaaatat cttttcttgg attctattcg  11100
gtgtgtggga acatgatcct gtcggtcggt tgtttttagg ttaatcctta actggttaca  11160
aggatctaac gcttgaatgc atgtcctgag ttaaagaaac aaaagaagaa cacacctagt  11220
acagcctggc ctcgaaccaa gaacttcttt gttggtttct cattattact aaaataaaat  11280
aaagtatacg ttttcttttt tctttgggat gaacggttca gacttatgag aagtttaagc  11340
taatcctgta gtggagtgtt caatttattt taaactttaa agcaatagct caagcactaa  11400
acttcttttt caagttcaac cactttggta gcttgctaat tgctgctatt gttctaatta  11460
attaatgtaa ttattgttta aaaaagaaaa gttggtgaca ctggaataaa aaagtgtact  11520
atctggcaat tattcttctg cagcaatgtt tgaggttgaa atcttagtag aacaaagtag  11580
aagatctggt atttatattt tttgtagaca gatggtgggg gtgggtggta ggccttgaaa  11640
tccaatatag ttttgtagaa taattttatt attttttttt tttgctcact tgtttgtggt  11700
attgattttg tgatgactca agattaatga tttaccttca ttttttttcat ggtgacatat  11760
tatgtatatt cttgatctgt ttcttacact tctttttcgt tgttgtagct gttgaagtct  11820
gcggccgcac catgatgatg gatcagcgac agcgagagaa gctgcttcac aaaaccgagg  11880
cctgtgcttt cgtggcaggt gttgttccgg agctttccct tgtcaccgtt ccagggaaca  11940
acaccaacaa cgttaacaac aacaacaacg ttgtttctca ttctcaatct aacgggtcgg  12000
gtcggatcca ggaaaacaac caccaccttg gactcgttgc tgctgtcacc tccgccttcg  12060
gtaccgttca aaggaagaaa aggatggcga gacaaagaag atccactaaa cccacttcgt  12120
tgatgaacca tctcaacaac cataagcaca acaagcctcg ttctcttcct tctcccagtg  12180
catcctcctc gtacgtgcca ctctcctccg caactctcca gcccgcacgt gaaatcgatc  12240
aaagaaggtt gagattcctt ttccagaagg agttaaagaa cagtgatgtt agctccctta  12300
ggagaatgat attgccaaag aaagcagcag aggctttcct tccagctctt gaatccaaag  12360
aaggaattgt aatcagcatg gatgatatag atggtcttca tgtatggagt ttcaagtaca  12420
ggttttggcc taacaacaac agtcggatgt atgtacttga aaatactgga gattttgtca  12480
acacacatgg ccttcgcttt ggagattcca ttatggttta ccaagatagt gaaaacaaca  12540
attatgttat tcaggccaaa aaggcttctg atcaagatga atttatggaa gaaactagtg  12600
ataccatcaa tgatatcttc cttaatgatt atgaggtgaa caaacctggt tgcttcaatg  12660
taactaatcc tgcagtgaat gatacaggca tgtcattcat atatgagact accttctcaa  12720
atgactcccc tcttgatttt ttgggtggat caatgaccaa tttttcaagg attgggccag  12780
ttgaaacctt tggctctgtt gagaatttgt cacttgatga cttctattaa gcggccgcat  12840
ttcgcaccaa atcaatgaaa gtaataatga aaagtctgaa taagaatact taggcttaga  12900
tgcctttgtt acttgtgtaa aataacttga gtcatgtacc tttggcggaa acagaataaa  12960
taaaaggtga aattccaatg ctctatgtat aagttagtaa tacttaatgt gttctacggt  13020
tgtttcaata tcatcaaact ctaattgaaa ctttagaacc acaaatctca atcttttctt  13080
aatgaaatga aaaatcttaa ttgtaccatg tttatgttaa acaccttaca attaattggt  13140
tggagaggag gaccaaccga tgggacaaca ttgggagaaa gagattcaat ggagatttgg  13200
ataggagaac aacattcttt ttcacttcaa tacaagatga gtgcaacact aaggatatgt  13260
```

-continued

```
atgagacttt cagaagctac gacaacatag atgagtgagg tggtgattcc tagcaagaaa  13320

gacattagag gaagccaaaa tcgaacaagg aagacatcaa gggcaagaga caggaccatc  13380

catctcagga aaaggagctt tgggatagtc cgagaagttg tacaagaaat tttttggagg  13440

gtgagtgatg cattgctggt gactttaact caatcaaaat tgagaaagaa agaaaaggga  13500

gggggctcac atgtgaatag aagggaaacg ggagaatttt acagttttga tctaatgggc  13560

atcccagcta gtggtaacat attcaccatg tttaaccttc acgtacgaga tccggccggc  13620

cagatcctgc a                                                        13631
```

<210> SEQ ID NO 64
<211> LENGTH: 837
<212> TYPE: DNA
<213> ORGANISM: Zea mays

<400> SEQUENCE: 64

```
atggactcca gcagcttcct ccctgccgcc ggcgcggaga atggctcggc ggcgggcggc     60

gccaacaatg gcggcgctgc tcagcagcat gcggcgccgg cgatccgcga gcaggaccgg    120

ctgatgccga tcgcgaacgt gatccgcatc atgcggcgcg tgctgccggc gcacgccaag    180

atctcggacg acgccaagga gacgatccag gagtgcgtgt cggagtacat cagcttcatc    240

acgggggagg ccaacgagcg gtgccagcgg gagcagcgca agaccatcac cgccgaggac    300

gtgctgtggg ccatgagccg cctcggcttc gacgactacg tcgagccgct cggcgcctac    360

ctccaccgct accgcgagtt cgagggcgac gcgcgcggcg tcgggctcgt cccgggggcc    420

gccccatcgc gcggcggcga ccaccacccg cactccatgt cgccagcggc gatgctcaag    480

tcccgcgggc cagtctccgg agccgccatg ctaccgcacc accaccacca ccacgacatg    540

cagatgcacg ccgccatgta cgggggaacg gccgtgcccc cgccggccgg gcctcctcac    600

cacggcgggt tcctcatgcc acacccacag ggtagtagcc actacctgcc ttacgcgtac    660

gagcccacgt acggcggtga gcacgccatg gctgcatact atggaggcgc cgcgtacgcg    720

cccggcaacg gcgggagcgg cgacggcagt ggcagtggcg gcggtggcgg gagcgcgtcg    780

cacacaccgc agggcagcgg cggcttggag cacccgcacc cgttcgcgta caagtag       837
```

<210> SEQ ID NO 65
<211> LENGTH: 278
<212> TYPE: PRT
<213> ORGANISM: Zea mays

<400> SEQUENCE: 65

```
Met Asp Ser Ser Ser Phe Leu Pro Ala Ala Gly Ala Glu Asn Gly Ser
1               5                   10                  15

Ala Ala Gly Gly Ala Asn Asn Gly Gly Ala Ala Gln Gln His Ala Ala
            20                  25                  30

Pro Ala Ile Arg Glu Gln Asp Arg Leu Met Pro Ile Ala Asn Val Ile
        35                  40                  45

Arg Ile Met Arg Arg Val Leu Pro Ala His Ala Lys Ile Ser Asp Asp
    50                  55                  60

Ala Lys Glu Thr Ile Gln Glu Cys Val Ser Glu Tyr Ile Ser Phe Ile
65                  70                  75                  80

Thr Gly Glu Ala Asn Glu Arg Cys Gln Arg Glu Gln Arg Lys Thr Ile
                85                  90                  95

Thr Ala Glu Asp Val Leu Trp Ala Met Ser Arg Leu Gly Phe Asp Asp
            100                 105                 110
```

```
Tyr Val Glu Pro Leu Gly Ala Tyr Leu His Arg Tyr Arg Glu Phe Glu
        115                 120                 125

Gly Asp Ala Arg Gly Val Gly Leu Val Pro Gly Ala Ala Pro Ser Arg
    130                 135                 140

Gly Gly Asp His His Pro His Ser Met Ser Pro Ala Ala Met Leu Lys
145                 150                 155                 160

Ser Arg Gly Pro Val Ser Gly Ala Ala Met Leu Pro His His His His
                165                 170                 175

His His Asp Met Gln Met His Ala Ala Met Tyr Gly Gly Thr Ala Val
            180                 185                 190

Pro Pro Pro Ala Gly Pro Pro His His Gly Gly Phe Leu Met Pro His
        195                 200                 205

Pro Gln Gly Ser Ser His Tyr Leu Pro Tyr Ala Tyr Glu Pro Thr Tyr
    210                 215                 220

Gly Gly Glu His Ala Met Ala Ala Tyr Tyr Gly Gly Ala Ala Tyr Ala
225                 230                 235                 240

Pro Gly Asn Gly Gly Ser Gly Asp Gly Ser Gly Ser Gly Gly Gly Gly
                245                 250                 255

Gly Ser Ala Ser His Thr Pro Gln Gly Ser Gly Gly Leu Glu His Pro
            260                 265                 270

His Pro Phe Ala Tyr Lys
        275


<210> SEQ ID NO 66
<211> LENGTH: 28
<212> TYPE: DNA
<213> ORGANISM: artificial sequence
<220> FEATURE:
<223> OTHER INFORMATION: primer sequence

<400> SEQUENCE: 66

tgcggccgca aaccatggac tccagcag                                        28


<210> SEQ ID NO 67
<211> LENGTH: 27
<212> TYPE: DNA
<213> ORGANISM: artificial sequence
<220> FEATURE:
<223> OTHER INFORMATION: primer sequence

<400> SEQUENCE: 67

agcggccgct acttgtacgc gaacggg                                         27


<210> SEQ ID NO 68
<211> LENGTH: 4372
<212> TYPE: DNA
<213> ORGANISM: artificial sequence
<220> FEATURE:
<223> OTHER INFORMATION: plasmid sequence

<400> SEQUENCE: 68

aattctgcag atatccatca cactggcggc cgctcgagca tgcatctaga gggcccaatt      60

cgccctatag tgagtcgtat tacaattcac tggccgtcgt tttacaacgt cgtgactggg     120

aaaaccctgg cgttacccaa cttaatcgcc ttgcagcaca tccccctttc gccagctggc     180

gtaatagcga agaggcccgc accgatcgcc cttcccaaca gttgcgcagc ctatacgtac     240

ggcagtttaa ggtttacacc tataaaagag agagccgtta tcgtctgttt gtggatgtac     300

agagtgatat tattgacacg ccggggcgac ggatggtgat ccccctggcc agtgcacgtc     360
```

-continued

```
tgctgtcaga taaagtctcc cgtgaacttt acccggtggt gcatatcggg gatgaaagct    420
ggcgcatgat gaccaccgat atggccagtg tgccggtctc cgttatcggg gaagaagtgg    480
ctgatctcag ccaccgcgaa aatgacatca aaaacgccat taacctgatg ttctggggaa    540
tataaatgtc aggcatgaga ttatcaaaaa ggatcttcac ctagatcctt ttcacgtaga    600
aagccagtcc gcagaaacgg tgctgacccc ggatgaatgt cagctactgg gctatctgga    660
caagggaaaa cgcaagcgca aagagaaagc aggtagcttg cagtgggctt acatggcgat    720
agctagactg ggcggtttta tggacagcaa gcgaaccgga attgccagct ggggcgccct    780
ctggtaaggt tgggaagccc tgcaaagtaa actggatggc tttctcgccg ccaaggatct    840
gatggcgcag gggatcaagc tctgatcaag agacaggatg aggatcgttt cgcatgattg    900
aacaagatgg attgcacgca ggttctccgg ccgcttgggt ggagaggcta ttcggctatg    960
actgggcaca acagacaatc ggctgctctg atgccgccgt gttccggctg tcagcgcagg   1020
ggcgcccggt tctttttgtc aagaccgacc tgtccggtgc cctgaatgaa ctgcaagacg   1080
aggcagcgcg gctatcgtgg ctggccacga cgggcgttcc ttgcgcagct gtgctcgacg   1140
ttgtcactga agcgggaagg gactggctgc tattgggcga agtgccgggg caggatctcc   1200
tgtcatctca ccttgctcct gccgagaaag tatccatcat ggctgatgca atgcggcggc   1260
tgcatacgct tgatccggct acctgcccat tcgaccacca agcgaaacat cgcatcgagc   1320
gagcacgtac tcggatggaa gccggtcttg tcgatcagga tgatctggac gaagagcatc   1380
aggggctcgc gccagccgaa ctgttcgcca ggctcaaggc gagcatgccc gacggcgagg   1440
atctcgtcgt gacccatggc gatgcctgct tgccgaatat catggtggaa aatggccgct   1500
tttctggatt catcgactgt ggccggctgg gtgtggcgga ccgctatcag gacatagcgt   1560
tggctacccg tgatattgct gaagagcttg gcggcgaatg ggctgaccgc ttcctcgtgc   1620
tttacggtat cgccgctccc gattcgcagc gcatcgcctt ctatcgcctt cttgacgagt   1680
tcttctgaat tattaacgct tacaatttcc tgatgcggta ttttctcctt acgcatctgt   1740
gcggtatttc acaccgcata caggtggcac ttttcgggga aatgtgcgcg gaacccctat   1800
ttgtttattt ttctaaatac attcaaatat gtatccgctc atgagacaat aaccctgata   1860
aatgcttcaa taatagcacg tgaggagggc caccatggcc aagttgacca gtgccgttcc   1920
ggtgctcacc gcgcgcgacg tcgccggagc ggtcgagttc tggaccgacc ggctcgggtt   1980
ctcccgggac ttcgtggagg acgacttcgc cggtgtggtc cgggacgacg tgaccctgtt   2040
catcagcgcg gtccaggacc aggtggtgcc ggacaacacc ctggcctggg tgtgggtgcg   2100
cggcctggac gagctgtacg ccgagtggtc ggaggtcgtg tccacgaact tccgggacgc   2160
ctccgggccg gccatgaccg agatcggcga gcagccgtgg gggcgggagt tcgccctgcg   2220
cgacccggcc ggcaactgcg tgcacttcgt ggccgaggag caggactgac acgtgctaaa   2280
acttcatttt taatttaaaa ggatctaggt gaagatcctt tttgataatc tcatgaccaa   2340
aatcccttaa cgtgagtttt cgttccactg agcgtcagac cccgtagaaa agatcaaagg   2400
atcttcttga gatccttttt ttctgcgcgt aatctgctgc ttgcaaacaa aaaaaccacc   2460
gctaccagcg gtggtttgtt tgccggatca agagctacca actctttttc cgaaggtaac   2520
tggcttcagc agagcgcaga taccaaatac tgtccttcta gtgtagccgt agttaggcca   2580
ccacttcaag aactctgtag caccgcctac atacctcgct ctgctaatcc tgttaccagt   2640
ggctgctgcc agtggcgata agtcgtgtct taccgggttg gactcaagac gatagttacc   2700
ggataaggcg cagcggtcgg gctgaacggg gggttcgtgc acacagccca gcttggagcg   2760
```

aacgacctac accgaactga gatacctaca gcgtgagcta tgagaaagcg ccacgcttcc 2820
cgaagggaga aaggcggaca ggtatccggt aagcggcagg gtcggaacag gagagcgcac 2880
gagggagctt ccagggggaa acgcctggta tctttatagt cctgtcgggt ttcgccacct 2940
ctgacttgag cgtcgatttt tgtgatgctc gtcagggggg cggagcctat ggaaaaacgc 3000
cagcaacgcg gcctttttac ggttcctggg cttttgctgg ccttttgctc acatgttctt 3060
tcctgcgtta tcccctgatt ctgtggataa ccgtattacc gcctttgagt gagctgatac 3120
cgctcgccgc agccgaacga ccgagcgcag cgagtcagtg agcgaggaag cggaagagcg 3180
cccaatacgc aaaccgcctc tccccgcgcg ttggccgatt cattaatgca gctggcacga 3240
caggtttccc gactggaaag cgggcagtga gcgcaacgca attaatgtga gttagctcac 3300
tcattaggca ccccaggctt tacactttat gcttccggct cgtatgttgt gtggaattgt 3360
gagcggataa caatttcaca caggaaacag ctatgaccat gattacgcca agctatttag 3420
gtgacgcgtt agaatactca agctatgcat caagcttggt accgagctcg gatccactag 3480
taacggccgc cagtgtgctg gaattcaggt gcggccgcaa accatggact ccagcagctt 3540
cctccctgcc gccggcgcgg agaatggctc ggcggcgggc ggcgccaaca atggcggcgc 3600
tgctcagcag catgcggcgc cggcgatccg cgagcaggac cggctgatgc cgatcgcgaa 3660
cgtgatccgc atcatgcggc gcgtgctgcc ggcgcacgcc aagatctcgg acgacgccaa 3720
ggagacgatc caggagtgcg tgtcggagta catcagcttc atcacggggg aggccaacga 3780
gcggtgccag cgggagcagc gcaagaccat caccgccgag gacgtgctgt gggccatgag 3840
ccgcctcggc ttcgacgact acgtcgagcc gctcggcgcc tacctccacc gctaccgcga 3900
gttcgagggc gacgcgcgcg gcgtcgggct cgtcccgggg gccgccccat cgcgcggcgg 3960
cgaccaccac ccgcactcca tgtcgccagc ggcgatgctc aagtcccgcg ggccagtctc 4020
cggagccgcc atgctaccgc accaccacca ccaccacgac atgcagatgc acgccgccat 4080 gtacgggggga acggccgtgc cccgccggc cgggcctcct caccacggcg ggttcctcat 4140
gccacaccca cagggtagta gccactacct gccttacgcg tacgagccca cgtacggcgg 4200
tgagcacgcc atggctgcat actatggagg cgccgcgtac gcgcccggca acggcgggag 4260
cggcgacggc agtggcagtg gcggcggtgg cgggagcgcg tcgcacacac cgcagggcag 4320
cggcggcttg gagcacccgc acccgttcgc gtacaagtag cggccgctcc tg 4372

<210> SEQ ID NO 69
<211> LENGTH: 1188
<212> TYPE: DNA
<213> ORGANISM: Zea mays

<400> SEQUENCE: 69
atggagagat ctcaacggca gtctcctccg ccaccgtcgc cgtcctcctc ctcgtcctcc 60
gtctccgcgg acaccgtcct cgtccctccc ggaaagaggc ggagggcggc gacggccaag 120
gccggcgccg agcctaataa gaggatccgc aaggaccccg ccgccgccgc cgcggggaag 180
aggagctccg tctacagggg agtcaccagg cacaggtgga cgggcaggtt cgaggcgcat 240
ctctgggaca agcactgcct cgccgcgctc cacaacaaga agaaaggcag gcaagtctac 300
ctgggggcgt atgacagcga ggaggcagct gctcgtgcct atgacctcgc agctctcaag 360
tactggggtc ctgagactct gctcaacttc cctgtggagg attactccag cgagatgccg 420
gagatggagg ccgtgtcccg ggaggagtac ctggcctccc tccgccgcag gagcagcggc 480

```
ttctccaggg gcgtctccaa gtacagaggc gtcgccaggc atcaccacaa cgggaggtgg    540

gaggcacgga ttgggcgagt ctttgggaac aagtacctct acttgggaac atttgacact    600

caagaagagg cagccaaggc ctatgacctt gcggccattg aataccgtgg cgtcaatgct    660

gtaaccaact tcgacatcag ctgctacctg gaccacccgc tgttcctggc acagctccaa    720

caggagccac aggtggtgcc ggcactcaac caagaacctc aacctgatca gagcgaaacc    780

ggaactacag agcaagagcc ggagtcaagc gaagccaaga caccggatgg cagtgcagaa    840

cccgatgaga acgcggtgcc tgacgacacc gcggagcccc tcaccacagt cgacgacagc    900

atcgaagagg gcttgtggag cccttgcatg gattacgagc tagacaccat gtcgagacca    960

aactttggca gctcaatcaa tctgagcgag tggttcgctg acgcagactt cgactgcaac   1020

atcggatgcc tgttcgatgg gtgttctgcg gctgacgaag gaagcaagga tggtgtaggt   1080

ctggcagatt tcagtctgtt tgaggcaggt gatgtccagc tgaaggatgt tctttcggat   1140

atggaagagg ggatacaacc tccagcgatg atcagtgtgt gcaactaa                1188
```

<210> SEQ ID NO 70
<211> LENGTH: 395
<212> TYPE: PRT
<213> ORGANISM: Zea mays

<400> SEQUENCE: 70

```
Met Glu Arg Ser Gln Arg Gln Ser Pro Pro Pro Pro Ser Pro Ser Ser
1               5                   10                  15

Ser Ser Ser Ser Val Ser Ala Asp Thr Val Leu Val Pro Pro Gly Lys
            20                  25                  30

Arg Arg Arg Ala Ala Thr Ala Lys Ala Gly Ala Glu Pro Asn Lys Arg
        35                  40                  45

Ile Arg Lys Asp Pro Ala Ala Ala Ala Ala Gly Lys Arg Ser Ser Val
    50                  55                  60

Tyr Arg Gly Val Thr Arg His Arg Trp Thr Gly Arg Phe Glu Ala His
65                  70                  75                  80

Leu Trp Asp Lys His Cys Leu Ala Ala Leu His Asn Lys Lys Lys Gly
                85                  90                  95

Arg Gln Val Tyr Leu Gly Ala Tyr Asp Ser Glu Glu Ala Ala Ala Arg
            100                 105                 110

Ala Tyr Asp Leu Ala Ala Leu Lys Tyr Trp Gly Pro Glu Thr Leu Leu
        115                 120                 125

Asn Phe Pro Val Glu Asp Tyr Ser Ser Glu Met Pro Glu Met Glu Ala
    130                 135                 140

Val Ser Arg Glu Glu Tyr Leu Ala Ser Leu Arg Arg Arg Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Phe Asp Thr Gln Glu Glu Ala Ala Lys Ala Tyr
        195                 200                 205

Asp Leu Ala Ala Ile Glu Tyr Arg Gly Val Asn Ala Val Thr Asn Phe
    210                 215                 220

Asp Ile Ser Cys Tyr Leu Asp His Pro Leu Phe Leu Ala Gln Leu Gln
225                 230                 235                 240

Gln Glu Pro Gln Val Val Pro Ala Leu Asn Gln Glu Pro Gln Pro Asp
                245                 250                 255
```

```
Gln Ser Glu Thr Gly Thr Thr Glu Gln Glu Pro Glu Ser Ser Glu Ala
            260                 265                 270

Lys Thr Pro Asp Gly Ser Ala Glu Pro Asp Glu Asn Ala Val Pro Asp
        275                 280                 285

Asp Thr Ala Glu Pro Leu Thr Thr Val Asp Asp Ser Ile Glu Glu Gly
    290                 295                 300

Leu Trp Ser Pro Cys Met Asp Tyr Glu Leu Asp Thr Met Ser Arg Pro
305                 310                 315                 320

Asn Phe Gly Ser Ser Ile Asn Leu Ser Glu Trp Phe Ala Asp Ala Asp
                325                 330                 335

Phe Asp Cys Asn Ile Gly Cys Leu Phe Asp Gly Cys Ser Ala Ala Asp
            340                 345                 350

Glu Gly Ser Lys Asp Gly Val Gly Leu Ala Asp Phe Ser Leu Phe Glu
        355                 360                 365

Ala Gly Asp Val Gln Leu Lys Asp Val Leu Ser Asp Met Glu Glu Gly
    370                 375                 380

Ile Gln Pro Pro Ala Met Ile Ser Val Cys Asn
385                 390                 395


<210> SEQ ID NO 71
<211> LENGTH: 10115
<212> TYPE: DNA
<213> ORGANISM: artificial sequence
<220> FEATURE:
<223> OTHER INFORMATION: plasmid sequence

<400> SEQUENCE: 71

ggccgcattt cgcaccaaat caatgaaagt aataatgaaa agtctgaata agaatactta      60

ggcttagatg cctttgttac ttgtgtaaaa taacttgagt catgtacctt tggcggaaac     120

agaataaata aaaggtgaaa ttccaatgct ctatgtataa gttagtaata cttaatgtgt     180

tctacggttg tttcaatatc atcaaactct aattgaaact ttagaaccac aaatctcaat     240

cttttcttaa tgaaatgaaa aatcttaatt gtaccatgtt tatgttaaac accttacaat     300

taattggttg gagaggagga ccaaccgatg ggacaacatt gggagaaaga gattcaatgg     360

agatttggat aggagaacaa cattcttttt cacttcaata caagatgagt gcaacactaa     420

ggatatgtat gagactttca gaagctacga caacatagat gagtgaggtg gtgattccta     480

gcaagaaaga cattagagga agccaaaatc gaacaaggaa gacatcaagg gcaagagaca     540

ggaccatcca tctcaggaaa aggagctttg ggatagtccg agaagttgta caagaaattt     600

tttggagggt gagtgatgca ttgctggtga ctttaactca atcaaaattg agaaagaaag     660

aaaagggagg gggctcacat gtgaatagaa gggaaacggg agaattttac agttttgatc     720

taatgggcat cccagctagt ggtaacatat tcaccatgtt taaccttcac gtacgagatc     780

cggccggcca gatcctgcag gagatccaag cttggcgcgc cgttctatag tgtcacctaa     840

atcgtatgtg tatgatacat aaggttatgt attaattgta gccgcgttct aacgacaata     900

tgtccatatg gtgcactctc agtacaatct gctctgatgc cgcatagtta agccagcccc     960

gacacccgcc aacacccgct gacgcgccct gacgggcttg tctgctcccg gcatccgctt    1020

acagacaagc tgtgaccgtc tccgggagct gcatgtgtca gaggttttca ccgtcatcac    1080

cgaaacgcgc gagacgaaag ggcctcgtga tacgcctatt tttataggtt aatgtcatga    1140

ccaaaatccc ttaacgtgag ttttcgttcc actgagcgtc agaccccgta gaaaagatca    1200

aaggatcttc ttgagatcct ttttttctgc gcgtaatctg ctgcttgcaa acaaaaaaac    1260
```

```
caccgctacc agcggtggtt tgtttgccgg atcaagagct accaactctt tttccgaagg   1320
taactggctt cagcagagcg cagataccaa atactgtcct tctagtgtag ccgtagttag   1380
gccaccactt caagaactct gtagcaccgc ctacatacct cgctctgcta atcctgttac   1440
cagtggctgc tgccagtggc gataagtcgt gtcttaccgg gttggactca agacgatagt   1500
taccggataa ggcgcagcgg tcgggctgaa cggggggttc gtgcacacag cccagcttgg   1560
agcgaacgac ctacaccgaa ctgagatacc tacagcgtga gcattgagaa agcgccacgc   1620
ttcccgaagg gagaaaggcg gacaggtatc cggtaagcgg cagggtcgga acaggagagc   1680
gcacgaggga gcttccaggg ggaaacgcct ggtatcttta tagtcctgtc gggtttcgcc   1740
acctctgact tgagcgtcga tttttgtgat gctcgtcagg ggggcggagc ctatggaaaa   1800
acgccagcaa cgcggccttt ttacggttcc tggccttttg ctggcctttt gctcacatgt   1860
tctttcctgc gttatcccct gattctgtgg ataaccgtat taccgccttt gagtgagctg   1920
ataccgctcg ccgcagccga acgaccgagc gcagcgagtc agtgagcgag gaagcggaag   1980
agcgcccaat acgcaaaccg cctctccccg cgcgttggcc gattcattaa tgcaggttga   2040
tcgattcgac atcgatctag taacatagat gacaccgcgc gcgataattt atcctagttt   2100
gcgcgctata ttttgttttc tatcgcgtat taaatgtata attgcgggac tctaatcata   2160
aaaacccatc tcataaataa cgtcatgcat tacatgttaa ttattacatg cttaacgtaa   2220
ttcaacagaa attatatgat aatcatcgca agaccggcaa caggattcaa tcttaagaaa   2280
ctttattgcc aaatgtttga acgatctgct tcgacgcact ccttctttag gtacctcact   2340
attcctttgc cctcggacga gtgctggggc gtcggtttcc actatcggcg agtacttcta   2400
cacagccatc ggtccagacg gccgcgcttc tgcgggcgat ttgtgtacgc ccgacagtcc   2460
cggctccgga tcggacgatt gcgtcgcatc gaccctgcgc ccaagctgca tcatcgaaat   2520
tgccgtcaac caagctctga tagagttggt caagaccaat gcggagcata tacgcccgga   2580
gccgcggcga tcctgcaagc tccggatgcc tccgctcgaa gtagcgcgtc tgctgctcca   2640
tacaagccaa ccacggcctc cagaagaaga tgttggcgac ctcgtattgg gaatccccga   2700
acatcgcctc gctccagtca atgaccgctg ttatgcggcc attgtccgtc aggacattgt   2760
tggagccgaa atccgcgtgc acgaggtgcc ggacttcggg gcagtcctcg gcccaaagca   2820
tcagctcatc gagagcctgc gcgacggacg cactgacggt gtcgtccatc acagtttgcc   2880
agtgatacac atggggatca gcaatcgcgc atatgaaatc acgccatgta gtgtattgac   2940
cgattccttg cggtccgaat gggccgaacc cgctcgtctg gctaagatcg gccgcagcga   3000
tcgcatccat ggcctccgcg accggctgca gaacagcggg cagttcggtt tcaggcaggt   3060
cttgcaacgt gacaccctgt gcacggcggg agatgcaata ggtcaggctc tcgctgaatt   3120
ccccaatgtc aagcacttcc ggaatcggga gcgcggccga tgcaaagtgc cgataaacat   3180
aacgatcttt gtagaaacca tcggcgcagc tatttacccg caggacatat ccacgccctc   3240
ctacatcgaa gctgaaagca cgagattctt cgccctccga gagctgcatc aggtcggaga   3300
cgctgtcgaa cttttcgatc agaaacttct cgacagacgt cgcggtgagt tcaggctttt   3360
tcatggttta ataagaagag aaaagagttc ttttgttatg gctgaagtaa tagagaaatg   3420
agctcgagcg tgtcctctcc aaatgaaatg aacttcctta tatagaggaa gggtcttgcg   3480
aaggatagtg ggattgtgcg tcatccctta cgtcagtgga gatgtcacat caatccactt   3540
gctttgaaga cgtggttgga acgtcttctt tttccacgat gctcctcgtg ggtgggggtc   3600
```

catctttggg accactgtcg gcagaggcat cttgaatgat agcctttcct ttatcgcaat 3660
gatggcattt gtaggagcca ccttcctttt ctactgtcct ttcgatgaag tgacagatag 3720
ctgggcaatg gaatccgagg aggtttcccg aaattatcct ttgttgaaaa gtctcaatag 3780
ccctttggtc ttctgagact gtatctttga catttttgga gtagaccaga gtgtcgtgct 3840
ccaccatgtt gacgaagatt ttcttcttgt cattgagtcg taaaagactc tgtatgaact 3900
gttcgccagt cttcacggcg agttctgtta gatcctcgat ttgaatctta gactccatgc 3960
atggccttag attcagtagg aactaccttt ttagagactc caatctctat tacttgcctt 4020
ggtttatgaa gcaagccttg aatcgtccat actggaatag tacttctgat cttgagaaat 4080
atgtctttct ctgtgttctt gatgcaatta gtcctgaatc ttttgactgc atctttaacc 4140
ttcttgggaa ggtatttgat ctcctggaga ttgttactcg ggtagatcgt cttgatgaga 4200
cctgctgcgt aggcctctct aaccatctgt gggtcagcat tctttctgaa attgaagagg 4260
ctaaccttct cattatcagt ggtgaacata gtgtcgtcac cttcaccttc gaacttcctt 4320
cctagatcgt aaagatagag gaaatcgtcc attgtaatct ccggggcaaa ggagatctct 4380
tttggggctg gatcactgct gggccttttg gttcctagcg tgagccagtg ggctttttgc 4440
tttggtgggc ttgttagggc cttagcaaag ctcttgggct tgagttgagc ttctcctttg 4500
gggatgaagt tcaacctgtc tgtttgctga cttgttgtgt acgcgtcagc tgctgctctt 4560
gcctctgtaa tagtggcaaa tttcttgtgt gcaactccgg gaacgccgtt tgttgccgcc 4620
tttgtacaac cccagtcatc gtatataccg gcatgtggac cgttatacac aacgtagtag 4680
ttgatatgag ggtgttgaat acccgattct gctctgagag gagcaactgt gctgttaagc 4740
tcagattttt gtgggattgg aattggatcg atctcgatcc cgcgaaatta atacgactca 4800
ctatagggag accacaacgg tttccctcta gaaataattt tgtttaactt taagaaggag 4860
atatacccat ggaaaagcct gaactcaccg cgacgtctgt cgagaagttt ctgatcgaaa 4920
agttcgacag cgtctccgac ctgatgcagc tctcggaggg cgaagaatct cgtgctttca 4980
gcttcgatgt aggagggcgt ggatatgtcc tgcgggtaaa tagctgcgcc gatggtttct 5040
acaaagatcg ttatgtttat cggcactttg catcggccgc gctcccgatt ccggaagtgc 5100
ttgacattgg ggaattcagc gagagcctga cctattgcat ctcccgccgt gcacagggtg 5160
tcacgttgca agacctgcct gaaaccgaac tgcccgctgt tctgcagccg gtcgcggagg 5220
ctatggatgc gatcgctgcg gccgatctta gccagacgag cgggttcggc ccattcggac 5280
cgcaaggaat cggtcaatac actacatggc gtgatttcat atgcgcgatt gctgatcccc 5340
atgtgtatca ctggcaaact gtgatggacg acaccgtcag tgcgtccgtc gcgcaggctc 5400
tcgatgagct gatgctttgg gccgaggact gccccgaagt ccggcacctc gtgcacgcgg 5460
atttcggctc caacaatgtc ctgacggaca atggccgcat aacagcggtc attgactgga 5520
gcgaggcgat gttcggggat tcccaatacg aggtcgccaa catcttcttc tggaggccgt 5580
ggttggcttg tatggagcag cagacgcgct acttcgagcg gaggcatccg gagcttgcag 5640
gatcgccgcg gctccgggcg tatatgctcc gcattggtct tgaccaactc tatcagagct 5700
tggttgacgg caatttcgat gatgcagctt gggcgcaggg tcgatgcgac gcaatcgtcc 5760
gatccggagc cgggactgtc gggcgtacac aaatcgcccg cagaagcgcg gccgtctgga 5820
ccgatggctg tgtagaagta ctcgccgata gtggaaaccg acgccccagc actcgtccga 5880
gggcaaagga atagtgaggt acagcttgga tcgatccggc tgctaacaaa gcccgaaagg 5940
aagctgagtt ggctgctgcc accgctgagc aataactagc ataacccctt ggggcctcta 6000

```
aacgggtctt gaggggtttt ttgctgaaag gaggaactat atccggatga tcgggcgcgc   6060
cgtcgacgga tccgtacgtc ctgcaggtaa attgcagctg aaggacagtg aagggtgaat   6120
ttatccattt aaaccatttt ctttttaaca catttcttat ggtaatctct tctcactaca   6180
ctataaaaat ggcttctcaa tcccattttc tacatcatcc cattctattg agttttgttt   6240
atttgctttc acttttttt ttatctgcct cttcccttaa tttgcttgac ttcttcttca   6300
cattttgctt tgttttctcc tccggcttcc ggtatttcaa attcaagatg agcaagttga   6360
aatttataaa tagaaataca gatattattt acaacgtcaa atctttggta ttttcaatat   6420
ttgaatgggg taaatttgtc atatagtcat catcactgac tacttatcta acctatttaa   6480
tttggagcat attctttata aggtccctct cacggccaat gtctaattat tgatatacag   6540
ctcttgtttt ctagtgctgc ttataatatt atctacacat atatatggta ctgcacacta   6600
ctactatata gtagtaagta aactagcaac agccggggcc aaactccaat aactaggcat   6660
tggggtttag ttggtaatat aaatataaca tcaaaaagtc tttgcttgtg acgaacatca   6720
caatgcaccc accattgatg ccacgacaga cattgttaat ttttttttta atttttaaaa   6780
aagaagcaat tccaatagtt ctatattaca atctcacgtg atccaagcac aacgtttcat   6840
tttttgtaca tgctcgatat ataaataata tttcatttta tagtaaaata taatgacatt   6900
ttcgaatata atttttgaaa tttcattttc caaatgaaat actaatatta atattaatga   6960
gattaccaca aatcatgtta tgaatgaaat aaagagtttt ggcattctaa ctttctttga   7020
atagaacaaa atgtatacaa cactctccat atatacacga tttattcagg gatcatatac   7080
attctctcat gattaacata gtctgctttc ttcacgtcta agcagataat ttttggtcca   7140
caagataaaa ttatcattag tcgttttaat taattccttg agcatcaagc actaaaataa   7200
ttaaacttct ccattaccaa aaaaaaaaga taggtgattc agtaacatgt agtactagta   7260
ctactgattt ttttttcttt ttgattttaa tgaatggttc gtatcgagca tcgagaaatc   7320
catttattag gtgtgtaatg taatagtagt atttccttga ttttcagtaa taagatggat   7380
tcttacattt atatctgttt gacagaaaat gttgtcaatg catttcttgg gcacaaagtt   7440
ttttgaaaca tgaattaatt ttttcaaaat atttatgaca tcaaattgac cctaaaataa   7500
gtgataaagc tttaacgtgg aatgacatta atttttccat gataaataaa acacttaaaa   7560
cattttaata ttaatattat aatcagttac aactatgttc aattaatgca ataactttta   7620
aataaatatt aaaatatttt ttttctgttc tccaataaag agatcttgtt gcacggaaaa   7680
agtcacattc ttatttagta aaaaattata attattgttt gaaaaatatc attttcactg   7740
cagaaaattt gatccagctc tacagatcat acttttattg tacaataata caataaaaat   7800
attcatctgc aggaaatatc attttcattg tacaataata taaagataaa tatataccag   7860
aaaagaaaaa gaaactgatg tggcacaatg tattcactga aagaatgcat attgtatttc   7920
acctttcaag cagcactaag aatatacttc ttttattata cttgtgcatt tactcaacca   7980
ccctcggtgg agtaagaaag aagatagata aaagtttttt ttgacatttg gtgaatctct   8040
taattaaaaa aataaaataa tccatttcct ttatttaatt tctttttttcc catctgtgaa   8100
attccaattc tgcttcgcgc tcctgtctat aaattgactt agccaccacc tcagtttcca   8160
ttcattcact tcttctcttt atacccccccc tctcttttttt gcgttcattc tgttttcgta   8220
agtactgttg tttttctctt ctatttcttt ttttgtttgt gttgtttttt tttcttcctt   8280
atcgttgttc tgcctctcct ctgtttcggt gctctgttca ccacttccac gtgagaatga   8340
```

```
tcttccttct ttgcatgttc attctctcgt gaccactgga tcagactcca tgttctgatc   8400

cagggtctct ctctaacgcc tgtactttca tccatgacca ccttaaaaac aacatggggg   8460

tggtgctgtt acactaactc tgtttctggg gtgctgtctt tgttcaattt tactcagaaa   8520

atatcttttc ttggattcta ttcggtgtgt gggaacatga tcctgtcggt cggttgtttt   8580

taggttaatc cttaactggt tacaaggatc taacgcttga atgcatgtcc tgagttaaag   8640

aaacaaaaga agaacacacc tagtacagcc tggcctcgaa ccaagaactt ctttgttggt   8700

ttctcattat tactaaaata aaataaagta tacgttttct tttttctttg ggatgaacgg   8760

ttcagactta tgagaagttt aagctaatcc tgtagtggag tgttcaattt attttaaact   8820

ttaaagcaat agctcaagca ctaaacttct ttttcaagtt caaccacttt ggtagcttgc   8880

taattgctgc tattgttcta attaattaat gtaattattg tttaaaaaag aaaagttggt   8940

gacactggaa taaaaaagtg tactatctgg caattattct tctgcagcaa tgtttgaggt   9000

tgaaatctta gtagaacaaa gtagaagatc tggtatttat attttttgta gacagatggt   9060

gggggtgggt ggtaggcctt gaaatccaat atagttttgt agaataattt tattattttt   9120

tttttttgct cacttgtttg tggtattgat tttgtgatga ctcaagatta atgatttacc   9180

ttcatttttt tcatggtgac atattatgta tattcttgat ctgtttctta cacttctttt   9240

tcgttgttgt agctgttgaa gtctgcggcc gcaaaccatg gactccagca gcttcctccc   9300

tgccgccggc gcggagaatg gctcggcggc gggcggcgcc aacaatggcg gcgctgctca   9360

gcagcatgcg gcgccggcga tccgcgagca ggaccggctg atgccgatcg cgaacgtgat   9420

ccgcatcatg cggcgcgtgc tgccggcgca cgccaagatc tcggacgacg ccaaggagac   9480

gatccaggag tgcgtgtcgg agtacatcag cttcatcacg ggggaggcca acgagcggtg   9540

ccagcgggag cagcgcaaga ccatcaccgc cgaggacgtg ctgtgggcca tgagccgcct   9600

cggcttcgac gactacgtcg agccgctcgg cgcctacctc caccgctacc gcgagttcga   9660

gggcgacgcg cgcggcgtcg ggctcgtccc gggggccgcc ccatcgcgcg gcggcgacca   9720

ccacccgcac tccatgtcgc cagcggcgat gctcaagtcc cgcgggccag tctccggagc   9780

cgccatgcta ccgcaccacc accaccacca cgacatgcag atgcacgccg ccatgtacgg   9840

gggaacggcc gtgcccccgc cggccgggcc tcctcaccac ggcgggttcc tcatgccaca   9900

cccacagggt agtagccact acctgcctta cgcgtacgag cccacgtacg gcggtgagca   9960

cgccatggct gcatactatg gaggcgccgc gtacgcgccc ggcaacggcg ggagcggcga  10020

cggcagtggc agtggcggcg gtggcgggag cgcgtcgcac acaccgcagg gcagcggcgg  10080

cttggagcac ccgcacccgt tcgcgtacaa gtagc                             10115
```

<210> SEQ ID NO 72
<211> LENGTH: 10462
<212> TYPE: DNA
<213> ORGANISM: artificial sequence
<220> FEATURE:
<223> OTHER INFORMATION: plasmid sequence

<400> SEQUENCE: 72

```
ggccgcattt cgcaccaaat caatgaaagt aataatgaaa agtctgaata agaatactta     60

ggcttagatg cctttgttac ttgtgtaaaa taacttgagt catgtacctt tggcggaaac    120

agaataaata aaaggtgaaa ttccaatgct ctatgtataa gttagtaata cttaatgtgt    180

tctacggttg tttcaatatc atcaaactct aattgaaact ttagaaccac aaatctcaat    240

cttttcttaa tgaaatgaaa aatcttaatt gtaccatgtt tatgttaaac accttacaat    300
```

```
taattggttg gagaggagga ccaaccgatg ggacaacatt gggagaaaga gattcaatgg    360
agatttggat aggagaacaa cattcttttt cacttcaata caagatgagt gcaacactaa    420
ggatatgtat gagactttca gaagctacga caacatagat gagtgaggtg gtgattccta    480
gcaagaaaga cattagagga agccaaaatc gaacaaggaa gacatcaagg gcaagagaca    540
ggaccatcca tctcaggaaa aggagctttg ggatagtccg agaagttgta caagaaattt    600
tttggagggt gagtgatgca ttgctggtga ctttaactca atcaaaattg agaaagaaag    660
aaaagggagg gggctcacat gtgaatagaa gggaaacggg agaattttac agttttgatc    720
taatgggcat cccagctagt ggtaacatat tcaccatgtt taaccttcac gtacgagatc    780
cggccggcca gatcctgcag gagatccaag cttggcgcgc cgttctatag tgtcacctaa    840
atcgtatgtg tatgatacat aaggttatgt attaattgta gccgcgttct aacgacaata    900
tgtccatatg gtgcactctc agtacaatct gctctgatgc cgcatagtta agccagcccc    960
gacacccgcc aacacccgct gacgcgccct gacgggcttg tctgctcccg gcatccgctt   1020
acagacaagc tgtgaccgtc tccgggagct gcatgtgtca gaggttttca ccgtcatcac   1080
cgaaacgcgc gagacgaaag ggcctcgtga tacgcctatt tttataggtt aatgtcatga   1140
ccaaaatccc ttaacgtgag ttttcgttcc actgagcgtc agaccccgta gaaaagatca   1200
aaggatcttc ttgagatcct ttttttctgc gcgtaatctg ctgcttgcaa acaaaaaaac   1260
caccgctacc agcggtggtt tgtttgccgg atcaagagct accaactctt tttccgaagg   1320
taactggctt cagcagagcg cagataccaa atactgtcct tctagtgtag ccgtagttag   1380
gccaccactt caagaactct gtagcaccgc ctacatacct cgctctgcta atcctgttac   1440
cagtggctgc tgccagtggc gataagtcgt gtcttaccgg gttggactca agacgatagt   1500
taccggataa ggcgcagcgg tcgggctgaa cggggggttc gtgcacacag cccagcttgg   1560
agcgaacgac ctacaccgaa ctgagatacc tacagcgtga gcattgagaa agcgccacgc   1620
ttcccgaagg gagaaaggcg gacaggtatc cggtaagcgg cagggtcgga acaggagagc   1680
gcacgaggga gcttccaggg ggaaacgcct ggtatcttta tagtcctgtc gggtttcgcc   1740
acctctgact tgagcgtcga tttttgtgat gctcgtcagg ggggcggagc ctatggaaaa   1800
acgccagcaa cgcggccttt ttacggttcc tggccttttg ctggcctttt gctcacatgt   1860
tctttcctgc gttatcccct gattctgtgg ataaccgtat taccgccttt gagtgagctg   1920
ataccgctcg ccgcagccga acgaccgagc gcagcgagtc agtgagcgag gaagcggaag   1980
agcgcccaat acgcaaaccg cctctccccg cgcgttggcc gattcattaa tgcaggttga   2040
tcgattcgac atcgatctag taacatagat gacaccgcgc gcgataattt atcctagttt   2100
gcgcgctata ttttgttttc tatcgcgtat taaatgtata attgcgggac tctaatcata   2160
aaaacccatc tcataaataa cgtcatgcat tacatgttaa ttattacatg cttaacgtaa   2220
ttcaacagaa attatatgat aatcatcgca agaccggcaa caggattcaa tcttaagaaa   2280
ctttattgcc aaatgtttga acgatctgct tcgacgcact ccttctttag gtacctcact   2340
attcctttgc cctcggacga gtgctggggc gtcggtttcc actatcggcg agtacttcta   2400
cacagccatc ggtccagacg gccgcgcttc tgcgggcgat ttgtgtacgc ccgacagtcc   2460
cggctccgga tcggacgatt gcgtcgcatc gaccctgcgc ccaagctgca tcatcgaaat   2520
tgccgtcaac caagctctga tagagttggt caagaccaat gcggagcata tacgcccgga   2580
gccgcggcga tcctgcaagc tccggatgcc tccgctcgaa gtagcgcgtc tgctgctcca   2640
```

-continued

```
tacaagccaa ccacggcctc cagaagaaga tgttggcgac ctcgtattgg gaatccccga   2700
acatcgcctc gctccagtca atgaccgctg ttatgcggcc attgtccgtc aggacattgt   2760
tggagccgaa atccgcgtgc acgaggtgcc ggacttcggg gcagtcctcg gcccaaagca   2820
tcagctcatc gagagcctgc gcgacggacg cactgacggt gtcgtccatc acagtttgcc   2880
agtgatacac atggggatca gcaatcgcgc atatgaaatc acgccatgta gtgtattgac   2940
cgattccttg cggtccgaat gggccgaacc cgctcgtctg gctaagatcg gccgcagcga   3000
tcgcatccat ggcctccgcg accggctgca gaacagcggg cagttcggtt tcaggcaggt   3060
cttgcaacgt gacaccctgt gcacggcggg agatgcaata ggtcaggctc tcgctgaatt   3120
ccccaatgtc aagcacttcc ggaatcggga gcgcggccga tgcaaagtgc cgataaacat   3180
aacgatcttt gtagaaacca tcggcgcagc tatttacccg caggacatat ccacgccctc   3240
ctacatcgaa gctgaaagca cgagattctt cgccctccga gagctgcatc aggtcggaga   3300
cgctgtcgaa cttttcgatc agaaacttct cgacagacgt cgcggtgagt tcaggctttt   3360
tcatggttta ataagaagag aaaagagttc ttttgttatg gctgaagtaa tagagaaatg   3420
agctcgagcg tgtcctctcc aaatgaaatg aacttcctta tatagaggaa gggtcttgcg   3480
aaggatagtg ggattgtgcg tcatccctta cgtcagtgga gatgtcacat caatccactt   3540
gctttgaaga cgtggttgga acgtcttctt tttccacgat gctcctcgtg ggtgggggtc   3600
catctttggg accactgtcg gcagaggcat cttgaatgat agcctttcct ttatcgcaat   3660
gatggcattt gtaggagcca ccttcctttt ctactgtcct ttcgatgaag tgacagatag   3720
ctgggcaatg gaatccgagg aggtttcccg aaattatcct ttgttgaaaa gtctcaatag   3780
ccctttggtc ttctgagact gtatctttga catttttgga gtagaccaga gtgtcgtgct   3840
ccaccatgtt gacgaagatt ttcttcttgt cattgagtcg taaaagactc tgtatgaact   3900
gttcgccagt cttcacggcg agttctgtta gatcctcgat ttgaatctta gactccatgc   3960
atggccttag attcagtagg aactaccttt ttagagactc caatctctat tacttgcctt   4020
ggtttatgaa gcaagccttg aatcgtccat actggaatag tacttctgat cttgagaaat   4080
atgtctttct ctgtgttctt gatgcaatta gtcctgaatc ttttgactgc atctttaacc   4140
ttcttgggaa ggtatttgat ctcctggaga ttgttactcg ggtagatcgt cttgatgaga   4200
cctgctgcgt aggcctctct aaccatctgt gggtcagcat tctttctgaa attgaagagg   4260
ctaaccttct cattatcagt ggtgaacata gtgtcgtcac cttcaccttc gaacttcctt   4320
cctagatcgt aaagatagag gaaatcgtcc attgtaatct ccggggcaaa ggagatctct   4380
tttggggctg gatcactgct gggccttttg gttcctagcg tgagccagtg ggctttttgc   4440
tttggtgggc ttgttagggc cttagcaaag ctcttgggct tgagttgagc ttctcctttg   4500
gggatgaagt tcaacctgtc tgtttgctga cttgttgtgt acgcgtcagc tgctgctctt   4560
gcctctgtaa tagtggcaaa tttcttgtgt gcaactccgg gaacgccgtt tgttgccgcc   4620
tttgtacaac cccagtcatc gtatataccg gcatgtggac cgttatacac aacgtagtag   4680
ttgatatgag ggtgttgaat acccgattct gctctgagag gagcaactgt gctgttaagc   4740
tcagattttt gtgggattgg aattggatcg atctcgatcc cgcgaaatta atacgactca   4800
ctatagggag accacaacgg tttccctcta gaaataattt tgtttaactt taagaaggag   4860
atatacccat ggaaaagcct gaactcaccg cgacgtctgt cgagaagttt ctgatcgaaa   4920
agttcgacag cgtctccgac ctgatgcagc tctcggaggg cgaagaatct cgtgctttca   4980
gcttcgatgt aggagggcgt ggatatgtcc tgcgggtaaa tagctgcgcc gatggtttct   5040
```

acaaagatcg ttatgtttat cggcactttg catcggccgc gctcccgatt ccggaagtgc 5100
ttgacattgg ggaattcagc gagagcctga cctattgcat ctcccgccgt gcacagggtg 5160
tcacgttgca agacctgcct gaaaccgaac tgcccgctgt tctgcagccg gtcgcggagg 5220
ctatggatgc gatcgctgcg gccgatctta gccagacgag cgggttcggc ccattcggac 5280
cgcaaggaat cggtcaatac actacatggc gtgatttcat atgcgcgatt gctgatcccc 5340
atgtgtatca ctggcaaact gtgatggacg acaccgtcag tgcgtccgtc gcgcaggctc 5400
tcgatgagct gatgctttgg gccgaggact gccccgaagt ccggcacctc gtgcacgcgg 5460
atttcggctc caacaatgtc ctgacggaca atggccgcat aacagcggtc attgactgga 5520
gcgaggcgat gttcggggat tcccaatacg aggtcgccaa catcttcttc tggaggccgt 5580
ggttggcttg tatggagcag cagacgcgct acttcgagcg gaggcatccg gagcttgcag 5640
gatcgccgcg gctccgggcg tatatgctcc gcattggtct tgaccaactc tatcagagct 5700
tggttgacgg caatttcgat gatgcagctt gggcgcaggg tcgatgcgac gcaatcgtcc 5760
gatccggagc cgggactgtc gggcgtacac aaatcgcccg cagaagcgcg gccgtctgga 5820
ccgatggctg tgtagaagta ctcgccgata gtggaaaccg acgccccagc actcgtccga 5880
gggcaaagga atagtgaggt acagcttgga tcgatccggc tgctaacaaa gcccgaaagg 5940
aagctgagtt ggctgctgcc accgctgagc aataactagc ataacccctt ggggcctcta 6000
aacgggtctt gaggggtttt ttgctgaaag gaggaactat atccggatga tcgggcgcgc 6060
cgtcgacgga tccgtacgtc ctgcaggtaa attgcagctg aaggacagtg aagggtgaat 6120
ttatccattt aaaccatttt ctttttaaca catttcttat ggtaatctct tctcactaca 6180
ctataaaaat ggcttctcaa tcccattttc tacatcatcc cattctattg agttttgttt 6240
atttgctttc actttttttt ttatctgcct cttcccttaa tttgcttgac ttcttcttca 6300
cattttgctt tgttttctcc tccggcttcc ggtatttcaa attcaagatg agcaagttga 6360
aatttataaa tagaaataca gatattattt acaacgtcaa atctttggta ttttcaatat 6420
ttgaatgggg taaatttgtc atatagtcat catcactgac tacttatcta acctatttaa 6480
tttggagcat attctttata aggtccctct cacggccaat gtctaattat tgatatacag 6540
ctcttgtttt ctagtgctgc ttataatatt atctacacat atatatggta ctgcacacta 6600
ctactatata gtagtaagta aactagcaac agccggggcc aaactccaat aactaggcat 6660
tggggtttag ttggtaatat aaatataaca tcaaaaagtc tttgcttgtg acgaacatca 6720
caatgcaccc accattgatg ccacgacaga cattgttaat tttttttta atttttaaaa 6780
aagaagcaat tccaatagtt ctatattaca atctcacgtg atccaagcac aacgtttcat 6840
tttttgtaca tgctcgatat ataaataata tttcatttta tagtaaaata taatgacatt 6900
ttcgaatata atttttgaaa tttcattttc caaatgaaat actaatatta atattaatga 6960
gattaccaca aatcatgtta tgaatgaaat aaagagtttt ggcattctaa ctttctttga 7020
atagaacaaa atgtatacaa cactctccat atatacacga tttattcagg gatcatatac 7080
attctctcat gattaacata gtctgctttc ttcacgtcta agcagataat ttttggtcca 7140
caagataaaa ttatcattag tcgttttaat taattccttg agcatcaagc actaaaataa 7200
ttaaacttct ccattaccaa aaaaaaaaga taggtgattc agtaacatgt agtactagta 7260
ctactgattt tttttttctt ttgattttaa tgaatggttc gtatcgagca tcgagaaatc 7320
catttattag gtgtgtaatg taatagtagt atttccttga ttttcagtaa taagatggat 7380

-continued

```
tcttacattt atatctgttt gacagaaaat gttgtcaatg catttcttgg gcacaaagtt   7440
ttttgaaaca tgaattaatt ttttcaaaat atttatgaca tcaaattgac cctaaaataa   7500
gtgataaagc tttaacgtgg aatgacatta atttttccat gataaataaa acacttaaaa   7560
cattttaata ttaatattat aatcagttac aactatgttc aattaatgca ataactttta   7620
aataaatatt aaaatatttt ttttctgttc tccaataaag agatcttgtt gcacggaaaa   7680
agtcacattc ttatttagta aaaaattata attattgttt gaaaaaatatc attttcactg   7740
cagaaaattt gatccagctc tacagatcat acttttattg tacaataata caataaaaat   7800
attcatctgc aggaaatatc attttcattg tacaataata taaagataaa tatataccag   7860
aaaagaaaaa gaaactgatg tggcacaatg tattcactga aagaatgcat attgtatttc   7920
acctttcaag cagcactaag aatatacttc ttttattata cttgtgcatt tactcaacca   7980
ccctcggtgg agtaagaaag aagatagata aaagtttttt ttgacatttg gtgaatctct   8040
taattaaaaa aataaaataa tccatttcct ttatttaatt tctttttttcc catctgtgaa   8100
attccaattc tgcttcgcgc tcctgtctat aaattgactt agccaccacc tcagtttcca   8160
ttcattcact tcttctcttt ataccccccc tctcttttttt gcgttcattc tgttttcgta   8220
agtactgttg tttttctctt ctatttcttt ttttgtttgt gttgtttttt tttcttcctt   8280
atcgttgttc tgcctctcct ctgtttcggt gctctgttca ccacttccac gtgagaatga   8340
tcttccttct ttgcatgttc attctctcgt gaccactgga tcagactcca tgttctgatc   8400
cagggtctct ctctaacgcc tgtactttca tccatgacca ccttaaaaac aacatggggg   8460
tggtgctgtt acactaactc tgtttctggg gtgctgtctt tgttcaattt tactcagaaa   8520
atatcttttc ttggattcta ttcggtgtgt gggaacatga tcctgtcggt cggttgtttt   8580
taggttaatc cttaactggt tacaaggatc taacgcttga atgcatgtcc tgagttaaag   8640
aaacaaaaga agaacacacc tagtacagcc tggcctcgaa ccaagaactt ctttgttggt   8700
ttctcattat tactaaaata aaataaagta tacgttttct tttttctttg ggatgaacgg   8760
ttcagactta tgagaagttt aagctaatcc tgtagtggag tgttcaattt attttaaact   8820
ttaaagcaat agctcaagca ctaaacttct ttttcaagtt caaccacttt ggtagcttgc   8880
taattgctgc tattgttcta attaattaat gtaattattg tttaaaaaag aaaagttggt   8940
gacactggaa taaaaaagtg tactatctgg caattattct tctgcagcaa tgtttgaggt   9000
tgaaatctta gtagaacaaa gtagaagatc tggtatttat attttttgta gacagatggt   9060
gggggtgggt ggtaggcctt gaaatccaat atagttttgt agaataattt tattattttt   9120
ttttttgct cacttgtttg tggtattgat tttgtgatga ctcaagatta atgatttacc   9180
ttcatttttt tcatggtgac atattatgta tattcttgat ctgtttctta cacttctttt   9240
tcgttgttgt agctgttgaa gtctgcggcc gcatggagag atctcaacgg cagtctcctc   9300
cgccaccgtc gccgtcctcc tcctcgtcct ccgtctccgc ggacaccgtc ctcgtccctc   9360
ccggaaagag gcggagggcg gcgacggcca aggccggcgc cgagcctaat aagaggatcc   9420
gcaaggaccc cgccgccgcc gccgcgggga agaggagctc cgtctacagg ggagtcacca   9480
ggcacaggtg gacgggcagg ttcgaggcgc atctctggga caagcactgc ctcgccgcgc   9540
tccacaacaa gaagaaaggc aggcaagtct acctgggggc gtatgacagc gaggaggcag   9600
ctgctcgtgc ctatgacctc gcagctctca agtactgggg tcctgagact ctgctcaact   9660
tccctgtgga ggattactcc agcgagatgc cggagatgga ggccgtgtcc cgggaggagt   9720
acctggcctc cctccgccgc aggagcagcg gcttctccag ggcgtctcc aagtacagag   9780
```

gcgtcgccag gcatcaccac aacgggaggt gggaggcacg gattgggcga gtctttggga 9840
acaagtacct ctacttggga acatttgaca ctcaagaaga ggcagccaag gcctatgacc 9900
ttgcggccat tgaataccgt ggcgtcaatg ctgtaaccaa cttcgacatc agctgctacc 9960
tggaccaccc gctgttcctg gcacagctcc aacaggagcc acaggtggtg ccggcactca 10020
accaagaacc tcaacctgat cagagcgaaa ccggaactac agagcaagag ccggagtcaa 10080
gcgaagccaa gacaccggat ggcagtgcag aacccgatga gaacgcggtg cctgacgaca 10140
ccgcggagcc cctcaccaca gtcgacgaca gcatcgaaga gggcttgtgg agcccttgca 10200
tggattacga gctagacacc atgtcgagac caaactttgg cagctcaatc aatctgagcg 10260
agtggttcgc tgacgcagac ttcgactgca acatcggatg cctgttcgat gggtgttctg 10320
cggctgacga aggaagcaag gatggtgtag gtctggcaga tttcagtctg tttgaggcag 10380
gtgatgtcca gctgaaggat gttctttcgg atatggaaga ggggatacaa cctccagcga 10440
tgatcagtgt gtgcaactaa gc 10462

<210> SEQ ID NO 73
<211> LENGTH: 13440
<212> TYPE: DNA
<213> ORGANISM: artificial sequence
<220> FEATURE:
<223> OTHER INFORMATION: plasmid sequence

<400> SEQUENCE: 73
ggagatccaa gcttttgatc catgcccttc atttgccgct tattaattaa tttggtaaca 60
gtccgtacta atcagttact tatccttccc ccatcataat taatcttggt agtctcgaat 120
gccacaacac tgactagtct cttggatcat aagaaaaagc caaggaacaa aagaagacaa 180
aacacaatga gagtatcctt tgcatagcaa tgtctaagtt cataaaattc aaacaaaaac 240
gcaatcacac acagtggaca tcacttatcc actagctgat caggatcgcc gcgtcaagaa 300
aaaaaaactg gaccccaaaa gccatgcaca acaacacgta ctcacaaagg tgtcaatcga 360
gcagcccaaa acattcacca actcaaccca tcatgagccc tcacatttgt tgtttctaac 420
ccaacctcaa actcgtattc tcttccgcca cctcattttt gtttatttca acacccgtca 480
aactgcatgc caccccgtgg ccaaatgtcc atgcatgtta acaagaccta tgactataaa 540
tagctgcaat ctcggcccag gttttcatca tcaagaacca gttcaatatc ctagtacacc 600
gtattaaaga atttaagata tactgcggcc gcaccatggc gatttccgat gagcctgaaa 660
gtgtagccac tgctctcaac cactcttccc tgcgccgccg tccctccgcc acctccaccg 720
ccggcctctt caattcgcct gagacaacca ccgacagttc cggtgatgac ttggccaagg 780
attctggttc cgacgactcc atcaacaacg acgacgccgc cgtcaattcc caacagcaaa 840
acgaaaaaca agacactgat ttctccgtcc tcaaattcgc ctaccgtcct tccgtccccg 900
ctcaccgcaa agtgaaggaa agtccgctca gctccgacac tattttccgt cagagtcacg 960
cgggcctctt caacctttgt atagtagtcc ttgttgctgt gaatagccga ctcatcattg 1020
agaatttaat gaagtatggt tggttgatca aatctggctt ttggtttagt gcaaagtcat 1080
tgagagactg gccccttttc atgtgttgtc tttctcttgt ggtatttcct ttcgctgcct 1140
ttatggtgga gaagttggca caacggaagt gtatacccga accagttgtt gttgtacttc 1200
atataatcat tacctcaact tcgcttttct atccagtttt agttattctc aagtgtgatt 1260
ctgcttttgt atcaggtgtc acgttaatgc tgttttcttg tgttgtatgg ttaaaattgg 1320

-continued

```
tgtcttttgc acatacaaac tatgatatga gagcacttac caaattagtt gaaaagggag   1380
aagcactgct cgatactctg aacatggagt atccttacaa cgtaaccttc aagagcttgg   1440
catatttcct gcttgcccct acattatgtt accagccaag ctatcctcgc acaccttata   1500
ttcgaaaggg ttggttgttt cgccaacttg tcaagctgat agtatttaca ggagttatgg   1560
gatttataat agaacaatat attaatccca tagtacaaaa ttcacagcat cctctcaagg   1620
gaaaccttct ttacgccacc gagagagttc tgaagctttc tgttccaaat ttatatgtgt   1680
ggctctgcat gttctattgc tttttccacc tttggttaaa tatcgtggca gagcttcttc   1740
gatttggtga tcgtgaattc tacaaggatt ggtggaatgc caaaactgtc gaagattatt   1800
ggaggatgtg gaatatgcct gttcacaaat ggatgatccg ccacctatat tttccatgtt   1860
taaggcacgg tctaccaaag gctgctgctc ttttaatttc cttcctggtt tctgctttat   1920
tccatgagct gtgcattgct gttccttgcc acatgttcaa gttgtgggct ttcggtggaa   1980
ttatgtttca ggttcctttg gtcttgatca ctaattatct gcaaaataaa ttcaaaaact   2040
caatggttgg aaatatgatt ttttggttca tattcagtat cgttggtcaa cctatgtgtg   2100
tactgctata ctaccatgac ttgatgaata ggaaaggcaa acttgactga gcggccgcaa   2160
gtatgaacta aaatgcatgt aggtgtaaga gctcatggag agcatggaat attgtatccg   2220
accatgtaac agtataataa ctgagctcca tctcacttct tctatgaata aacaaaggat   2280
gttatgatat attaacactc tatctatgca ccttattgtt ctatgataaa tttcctctta   2340
ttattataaa tcatctgaat cgtgacggct tatggaatgc ttcaaatagt acaaaaacaa   2400
atgtgtacta taagactttc taaacaattc taaccttagc attgtgaacg agacataagt   2460
gttaagaaga cataacaatt ataatggaag aagtttgtct ccatttatat attatatatt   2520
acccacttat gtattatatt aggatgttaa ggagacataa caattataaa gagagaagtt   2580
tgtatccatt tatatattat atactaccca tttatatatt atacttatcc acttatttaa   2640
tgtctttata aggtttgatc catgatattt ctaatatttt agttgatatg tatatgaaag   2700
ggtactattt gaactctctt actctgtata aaggttggat catccttaaa gtgggtctat   2760
ttaattttat tgcttcttac agataaaaaa aaaattatga gttggtttga taaaatattg   2820
aaggatttaa aataataata aataacatat aatatatgta tataaattta ttataatata   2880
acatttatct ataaaaaagt aaatattgtc ataaatctat acaatcgttt agccttgctg   2940
gacgaatctc aattatttaa acgagagtaa acatatttga ctttttggtt atttaacaaa   3000
ttattattta acactatatg aaattttttt ttttatcagc aaagaataaa attaaattaa   3060
gaaggacaat ggtgtcccaa tccttataca accaacttcc acaagaaagt caagtcagag   3120
acaacaaaaa aacaagcaaa ggaaattttt taatttgagt tgtcttgttt gctgcataat   3180
ttatgcagta aaacactaca cataaccctt ttagcagtag agcaatggtt gaccgtgtgc   3240
ttagcttctt ttattttatt tttttatcag caaagaataa ataaaataaa atgagacact   3300
tcagggatgt ttcaacaagc ttggcgcgcc gttctatagt gtcacctaaa tcgtatgtgt   3360
atgatacata aggttatgta ttaattgtag ccgcgttcta acgacaatat gtccatatgg   3420
tgcactctca gtacaatctg ctctgatgcc gcatagttaa gccagccccg acacccgcca   3480
acacccgctg acgcgccctg acgggcttgt ctgctcccgg catccgctta cagacaagct   3540
gtgaccgtct ccgggagctg catgtgtcag aggttttcac cgtcatcacc gaaacgcgcg   3600
agacgaaagg gcctcgtgat acgcctattt ttataggtta atgtcatgac caaaatccct   3660
taacgtgagt tttcgttcca ctgagcgtca gaccccgtag aaaagatcaa aggatcttct   3720
```

tgagatcctt tttttctgcg cgtaatctgc tgcttgcaaa caaaaaaacc accgctacca 3780
gcggtggttt gtttgccgga tcaagagcta ccaactcttt ttccgaaggt aactggcttc 3840
agcagagcgc agataccaaa tactgtcctt ctagtgtagc cgtagttagg ccaccacttc 3900
aagaactctg tagcaccgcc tacatacctc gctctgctaa tcctgttacc agtggctgct 3960
gccagtggcg ataagtcgtg tcttaccggg ttggactcaa gacgatagtt accggataag 4020
gcgcagcggt cgggctgaac ggggggttcg tgcacacagc ccagcttgga gcgaacgacc 4080
tacaccgaac tgagatacct acagcgtgag cattgagaaa gcgccacgct tcccgaaggg 4140
agaaaggcgg acaggtatcc ggtaagcggc agggtcggaa caggagagcg cacgagggag 4200
cttccagggg gaaacgcctg gtatctttat agtcctgtcg ggtttcgcca cctctgactt 4260
gagcgtcgat ttttgtgatg ctcgtcaggg gggcggagcc tatggaaaaa cgccagcaac 4320
gcggcctttt tacggttcct ggccttttgc tggccttttg ctcacatgtt ctttcctgcg 4380
ttatcccctg attctgtgga taaccgtatt accgcctttg agtgagctga taccgctcgc 4440
cgcagccgaa cgaccgagcg cagcgagtca gtgagcgagg aagcggaaga gcgcccaata 4500
cgcaaaccgc ctctccccgc gcgttggccg attcattaat gcaggttgat cgattcgaca 4560
tcgatctagt aacatagatg acaccgcgcg cgataattta tcctagtttg cgcgctatat 4620
tttgttttct atcgcgtatt aaatgtataa ttgcgggact ctaatcataa aaacccatct 4680
cataaataac gtcatgcatt acatgttaat tattacatgc ttaacgtaat tcaacagaaa 4740
ttatatgata atcatcgcaa gaccggcaac aggattcaat cttaagaaac tttattgcca 4800
aatgtttgaa cgatctgctt cgacgcactc cttctttagg tacctcacta ttcctttgcc 4860
ctcggacgag tgctggggcg tcggtttcca ctatcggcga gtacttctac acagccatcg 4920
gtccagacgg ccgcgcttct gcgggcgatt tgtgtacgcc cgacagtccc ggctccggat 4980
cggacgattg cgtcgcatcg accctgcgcc caagctgcat catcgaaatt gccgtcaacc 5040
aagctctgat agagttggtc aagaccaatg cggagcatat acgcccggag ccgcggcgat 5100
cctgcaagct ccggatgcct ccgctcgaag tagcgcgtct gctgctccat acaagccaac 5160
cacggcctcc agaagaagat gttggcgacc tcgtattggg aatccccgaa catcgcctcg 5220
ctccagtcaa tgaccgctgt tatgcggcca ttgtccgtca ggacattgtt ggagccgaaa 5280
tccgcgtgca cgaggtgccg gacttcgggg cagtcctcgg cccaaagcat cagctcatcg 5340
agagcctgcg cgacggacgc actgacggtg tcgtccatca cagtttgcca gtgatacaca 5400
tggggatcag caatcgcgca tatgaaatca cgccatgtag tgtattgacc gattccttgc 5460
ggtccgaatg ggccgaaccc gctcgtctgg ctaagatcgg ccgcagcgat cgcatccatg 5520
gcctccgcga ccggctgcag aacagcgggc agttcggttt caggcaggtc ttgcaacgtg 5580
acaccctgtg cacggcggga gatgcaatag gtcaggctct cgctgaattc cccaatgtca 5640
agcacttccg gaatcgggag cgcggccgat gcaaagtgcc gataaacata acgatctttg 5700
tagaaaccat cggcgcagct atttacccgc aggacatatc cacgccctcc tacatcgaag 5760
ctgaaagcac gagattcttc gccctccgag agctgcatca ggtcggagac gctgtcgaac 5820
ttttcgatca gaaacttctc gacagacgtc gcggtgagtt caggcttttt catggtttaa 5880
taagaagaga aaagagttct tttgttatgg ctgaagtaat agagaaatga gctcgagcgt 5940
gtcctctcca aatgaaatga acttccttat atagaggaag ggtcttgcga aggatagtgg 6000
gattgtgcgt catcccttac gtcagtggag atgtcacatc aatccacttg ctttgaagac 6060
gtggttggaa cgtcttcttt ttccacgatg ctcctcgtgg gtgggggtcc atctttggga 6120
ccactgtcgg cagaggcatc ttgaatgata gcctttcctt tatcgcaatg atggcatttg 6180
taggagccac cttccttttc tactgtcctt tcgatgaagt gacagatagc tgggcaatgg 6240
aatccgagga ggtttcccga aattatcctt tgttgaaaag tctcaatagc cctttggtct 6300
tctgagactg tatctttgac atttttggag tagaccagag tgtcgtgctc caccatgttg 6360
acgaagattt tcttcttgtc attgagtcgt aaaagactct gtatgaactg ttcgccagtc 6420
ttcacggcga gttctgttag atcctcgatt tgaatcttag actccatgca tggccttaga 6480
ttcagtagga actacctttt tagagactcc aatctctatt acttgccttg gtttatgaag 6540
caagccttga atcgtccata ctggaatagt acttctgatc ttgagaaata tgtctttctc 6600
tgtgttcttg atgcaattag tcctgaatct tttgactgca tctttaacct tcttgggaag 6660
gtatttgatc tcctggagat tgttactcgg gtagatcgtc ttgatgagac ctgctgcgta 6720
ggcctctcta accatctgtg ggtcagcatt ctttctgaaa ttgaagaggc taaccttctc 6780
attatcagtg gtgaacatag tgtcgtcacc ttcaccttcg aacttccttc ctagatcgta 6840
aagatagagg aaatcgtcca ttgtaatctc cggggcaaag gagatctctt ttggggctgg 6900
atcactgctg ggccttttgg ttcctagcgt gagccagtgg gctttttgct ttggtgggct 6960
tgttagggcc ttagcaaagc tcttggcctt gagttgagct tctcctttgg ggatgaagtt 7020
caacctgtct gtttgctgac ttgttgtgta cgcgtcagct gctgctcttg cctctgtaat 7080
agtggcaaat ttcttgtgtg caactccggg aacgccgttt gttgccgcct ttgtacaacc 7140
ccagtcatcg tatataccgg catgtggacc gttatacaca acgtagtagt tgatatgagg 7200
gtgttgaata cccgattctg ctctgagagg agcaactgtg ctgttaagct cagatttttg 7260
tgggattgga attggatcga tctcgatccc gcgaaattaa tacgactcac tatagggaga 7320
ccacaacggt ttccctctag aaataatttt gtttaacttt aagaaggaga tatacccatg 7380
gaaaagcctg aactcaccgc gacgtctgtc gagaagtttc tgatcgaaaa gttcgacagc 7440
gtctccgacc tgatgcagct ctcggagggc gaagaatctc gtgctttcag cttcgatgta 7500
ggagggcgtg gatatgtcct gcgggtaaat agctgcgccg atggtttcta caaagatcgt 7560
tatgtttatc ggcactttgc atcggccgcg ctcccgattc cggaagtgct tgacattggg 7620
gaattcagcg agagcctgac ctattgcatc tcccgccgtg cacagggtgt cacgttgcaa 7680
gacctgcctg aaaccgaact gcccgctgtt ctgcagccgg tcgcggaggc tatggatgcg 7740
atcgctgcgg ccgatcttag ccagacgagc gggttcggcc cattcggacc gcaaggaatc 7800
ggtcaataca ctacatggcg tgatttcata tgcgcgattg ctgatcccca tgtgtatcac 7860
tggcaaactg tgatggacga caccgtcagt gcgtccgtcg cgcaggctct cgatgagctg 7920
atgctttggg ccgaggactg ccccgaagtc cggcacctcg tgcacgcgga tttcggctcc 7980
aacaatgtcc tgacggacaa tggccgcata acagcggtca ttgactggag cgaggcgatg 8040
ttcggggatt cccaatacga ggtcgccaac atcttcttct ggaggccgtg gttggcttgt 8100
atggagcagc agacgcgcta cttcgagcgg aggcatccgg agcttgcagg atcgccgcgg 8160
ctccgggcgt atatgctccg cattggtctt gaccaactct atcagagctt ggttgacggc 8220
aatttcgatg atgcagcttg ggcgcagggt cgatgcgacg caatcgtccg atccggagcc 8280
gggactgtcg ggcgtacaca aatcgcccgc agaagcgcgg ccgtctggac cgatggctgt 8340
gtagaagtac tcgccgatag tggaaaccga cgccccagca ctcgtccgag ggcaaaggaa 8400
tagtgaggta cagcttggat cgatccggct gctaacaaag cccgaaagga agctgagttg 8460

```
gctgctgcca ccgctgagca ataactagca taaccccttg gggcctctaa acgggtcttg   8520
aggggttttt tgctgaaagg aggaactata tccggatgat cgggcgcgcc gtcgacggat   8580
ccgtacgaga tccggccggc cagatcctgc aggtaaattg cagctgaagg acagtgaagg   8640
gtgaatttat ccatttaaac cattttcttt ttaacacatt tcttatggta atctcttctc   8700
actacactat aaaaatggct tctcaatccc attttctaca tcatcccatt ctattgagtt   8760
ttgtttattt gctttcactt tttttttat ctgcctcttc ccttaatttg cttgacttct   8820
tcttcacatt ttgctttgtt ttctcctccg gcttccggta tttcaaattc aagatgagca   8880
agttgaaatt tataaataga aatacagata ttatttacaa cgtcaaatct ttggtatttt   8940
caatatttga atggggtaaa tttgtcatat agtcatcatc actgactact tatctaacct   9000
atttaatttg gagcatattc tttataaggt ccctctcacg gccaatgtct aattattgat   9060
atacagctct tgttttctag tgctgcttat aatattatct acacatatat atggtactgc   9120
acactactac tatatagtag taagtaaact agcaacagcc ggggccaaac tccaataact   9180
aggcattggg gtttagttgg taatataaat ataacatcaa aaagtctttg cttgtgacga   9240
acatcacaat gcacccacca ttgatgccac gacagacatt gttaattttt tttttaattt   9300
ttaaaaaaga agcaattcca atagttctat attacaatct cacgtgatcc aagcacaacg   9360
tttcattttt tgtacatgct cgatatataa ataatatttc attttatagt aaaatataat   9420
gacattttcg aatataattt ttgaaatttc attttccaaa tgaaatacta atattaatat   9480
taatgagatt accacaaatc atgttatgaa tgaaataaag agttttggca ttctaacttt   9540
ctttgaatag aacaaaatgt atacaacact ctccatatat acacgattta ttcagggatc   9600
atatacattc tctcatgatt aacatagtct gctttcttca cgtctaagca gataattttt   9660
ggtccacaag ataaaattat cattagtcgt tttaattaat tccttgagca tcaagcacta   9720
aaataattaa acttctccat taccaaaaaa aaaagatagg tgattcagta acatgtagta   9780
ctagtactac tgattttttt tttcttttga ttttaatgaa tggttcgtat cgagcatcga   9840
gaaatccatt tattaggtgt gtaatgtaat agtagtattt ccttgatttt cagtaataag   9900
atggattctt acatttatat ctgtttgaca gaaaatgttg tcaatgcatt tcttgggcac   9960
aaagtttttt gaaacatgaa ttaatttttt caaaatattt atgacatcaa attgacccta  10020
aaataagtga taaagcttta acgtggaatg acattaattt ttccatgata aataaaacac  10080
ttaaaacatt ttaatattaa tattataatc agttacaact atgttcaatt aatgcaataa  10140
cttttaaata aatattaaaa tattttttt ctgttctcca ataaagagat cttgttgcac  10200
ggaaaaagtc acattcttat ttagtaaaaa attataatta ttgtttgaaa aatatcattt  10260
tcactgcaga aaatttgatc cagctctaca gatcatactt ttattgtaca ataatacaat  10320
aaaaatattc atctgcagga aatatcattt tcattgtaca ataatataaa gataaatata  10380
taccagaaaa gaaaaagaaa ctgatgtggc acaatgtatt cactgaaaga atgcatattg  10440
tatttcacct ttcaagcagc actaagaata tacttctttt attatacttg tgcatttact  10500
caaccaccct cggtggagta agaaagaaga tagataaaag tttttttga catttggtga  10560
atctcttaat taaaaaaata aaataatcca tttcctttat ttaatttctt ttttcccatc  10620
tgtgaaattc caattctgct tcgcgctcct gtctataaat tgacttagcc accacctcag  10680
tttccattca ttcacttctt ctctttatac ccccctctc ttttttgcgt tcattctgtt  10740
ttcgtaagta ctgttgtttt tctcttctat ttcttttttt gtttgtgttg ttttttttc  10800
```

```
ttccttatcg ttgttctgcc tctcctctgt ttcggtgctc tgttcaccac ttccacgtga  10860
gaatgatctt ccttctttgc atgttcattc tctcgtgacc actggatcag actccatgtt  10920
ctgatccagg gtctctctct aacgcctgta ctttcatcca tgaccacctt aaaaacaaca  10980
tgggggtggt gctgttacac taactctgtt tctggggtgc tgtctttgtt caattttact  11040
cagaaaatat cttttcttgg attctattcg gtgtgtggga acatgatcct gtcggtcggt  11100
tgtttttagg ttaatcctta actggttaca aggatctaac gcttgaatgc atgtcctgag  11160
ttaaagaaac aaaagaagaa cacacctagt acagcctggc ctcgaaccaa gaacttcttt  11220
gttggtttct cattattact aaaataaaat aaagtatacg ttttcttttt tctttgggat  11280
gaacggttca gacttatgag aagtttaagc taatcctgta gtggagtgtt caatttattt  11340
taaactttaa agcaatagct caagcactaa acttcttttt caagttcaac cactttggta  11400
gcttgctaat tgctgctatt gttctaatta attaatgtaa ttattgttta aaaaagaaaa  11460
gttggtgaca ctggaataaa aaagtgtact atctggcaat tattcttctg cagcaatgtt  11520
tgaggttgaa atcttagtag aacaaagtag aagatctggt atttatattt tttgtagaca  11580
gatggtgggg gtgggtggta ggccttgaaa tccaatatag ttttgtagaa taattttatt  11640
attttttttt tttgctcact tgtttgtggt attgattttg tgatgactca agattaatga  11700
tttaccttca tttttttcat ggtgacatat tatgtatatt cttgatctgt ttcttacact  11760
tctttttcgt tgttgtagct gttgaagtct gcggccgcaa accatggact ccagcagctt  11820
cctccctgcc gccggcgcgg agaatggctc ggcggcgggc ggcgccaaca atggcggcgc  11880
tgctcagcag catgcggcgc cggcgatccg cgagcaggac cggctgatgc cgatcgcgaa  11940
cgtgatccgc atcatgcggc gcgtgctgcc ggcgcacgcc aagatctcgg acgacgccaa  12000
ggagacgatc caggagtgcg tgtcggagta catcagcttc atcacggggg aggccaacga  12060
gcggtgccag cgggagcagc gcaagaccat caccgccgag gacgtgctgt gggccatgag  12120
ccgcctcggc ttcgacgact acgtcgagcc gctcggcgcc tacctccacc gctaccgcga  12180
gttcgagggc gacgcgcgcg gcgtcgggct cgtcccgggg gccgccccat cgcgcggcgg  12240
cgaccaccac ccgcactcca tgtcgccagc ggcgatgctc aagtcccgcg ggccagtctc  12300
cggagccgcc atgctaccgc accaccacca ccaccacgac atgcagatgc acgccgccat  12360
gtacgggggga acggccgtgc ccccgccggc cgggcctcct caccacggcg ggttcctcat  12420
gccacaccca cagggtagta gccactacct gccttacgcg tacgagccca cgtacggcgg  12480
tgagcacgcc atggctgcat actatggagg cgccgcgtac gcgcccggca acggcgggag  12540
cggcgacggc agtggcagtg gcggcggtgg cgggagcgcg tcgcacacac cgcagggcag  12600
cggcggcttg gagcacccgc acccgttcgc gtacaagtag cggccgcatt tcgcaccaaa  12660
tcaatgaaag taataatgaa aagtctgaat aagaatactt aggcttagat gcctttgtta  12720
cttgtgtaaa ataacttgag tcatgtacct ttggcggaaa cagaataaat aaaaggtgaa  12780
attccaatgc tctatgtata agttagtaat acttaatgtg ttctacggtt gtttcaatat  12840
catcaaactc taattgaaac tttagaacca caaatctcaa tcttttctta atgaaatgaa  12900
aaatcttaat tgtaccatgt ttatgttaaa caccttacaa ttaattggtt ggagaggagg  12960
accaaccgat gggacaacat tgggagaaag agattcaatg gagatttgga taggagaaca  13020
acattctttt tcacttcaat acaagatgag tgcaacacta aggatatgta tgagactttc  13080
agaagctacg acaacataga tgagtgaggt ggtgattcct agcaagaaag acattagagg  13140
aagccaaaat cgaacaagga agacatcaag ggcaagagac aggaccatcc atctcaggaa  13200
```

aaggagcttt gggatagtcc gagaagttgt acaagaaatt ttttggaggg tgagtgatgc 13260
attgctggtg actttaactc aatcaaaatt gagaaagaaa gaaaagggag ggggctcaca 13320
tgtgaataga agggaaacgg gagaatttta cagttttgat ctaatgggca tcccagctag 13380
tggtaacata ttcaccatgt ttaaccttca cgtacgagat ccggccggcc agatcctgca 13440

<210> SEQ ID NO 74
<211> LENGTH: 13787
<212> TYPE: DNA
<213> ORGANISM: artificial sequence
<220> FEATURE:
<223> OTHER INFORMATION: plasmid sequence

<400> SEQUENCE: 74
ggagatccaa gcttttgatc catgcccttc atttgccgct tattaattaa tttggtaaca 60
gtccgtacta atcagttact tatccttccc ccatcataat taatcttggt agtctcgaat 120
gccacaacac tgactagtct cttggatcat aagaaaaagc caaggaacaa aagaagacaa 180
aacacaatga gagtatcctt tgcatagcaa tgtctaagtt cataaaattc aaacaaaaac 240
gcaatcacac acagtggaca tcacttatcc actagctgat caggatcgcc gcgtcaagaa 300
aaaaaaactg gaccccaaaa gccatgcaca acaacacgta ctcacaaagg tgtcaatcga 360
gcagcccaaa acattcacca actcaaccca tcatgagccc tcacatttgt tgtttctaac 420
ccaacctcaa actcgtattc tcttccgcca cctcattttt gtttatttca acacccgtca 480
aactgcatgc caccccgtgg ccaaatgtcc atgcatgtta acaagaccta tgactataaa 540
tagctgcaat ctcggcccag gttttcatca tcaagaacca gttcaatatc ctagtacacc 600
gtattaaaga atttaagata tactgcggcc gcaccatggc gatttccgat gagcctgaaa 660
gtgtagccac tgctctcaac cactcttccc tgcgccgccg tccctccgcc acctccaccg 720
ccggcctctt caattcgcct gagacaacca ccgacagttc cggtgatgac ttggccaagg 780
attctggttc cgacgactcc atcaacaacg acgacgccgc cgtcaattcc caacagcaaa 840
acgaaaaaca agacactgat ttctccgtcc tcaaattcgc ctaccgtcct tccgtccccg 900
ctcaccgcaa agtgaaggaa agtccgctca gctccgacac tattttccgt cagagtcacg 960
cgggcctctt caacctttgt atagtagtcc ttgttgctgt gaatagccga ctcatcattg 1020
agaatttaat gaagtatggt tggttgatca aatctggctt ttggtttagt gcaaagtcat 1080
tgagagactg gcccctttc atgtgttgtc tttctcttgt ggtatttcct ttcgctgcct 1140
ttatggtgga gaagttggca caacggaagt gtatacccga accagttgtt gttgtacttc 1200
atataatcat tacctcaact tcgcttttct atccagtttt agttattctc aagtgtgatt 1260
ctgcttttgt atcaggtgtc acgttaatgc tgttttcttg tgttgtatgg ttaaaattgg 1320
tgtcttttgc acatacaaac tatgatatga gagcacttac caaattagtt gaaaagggag 1380
aagcactgct cgatactctg aacatggagt atccttacaa cgtaaccttc aagagcttgg 1440
catatttcct gcttgcccct acattatgtt accagccaag ctatcctcgc acaccttata 1500
ttcgaaaggg ttggttgttt cgccaacttg tcaagctgat agtatttaca ggagttatgg 1560
gatttataat agaacaatat attaatccca tagtacaaaa ttcacagcat cctctcaagg 1620
gaaaccttct ttacgccacc gagagagttc tgaagctttc tgttccaaat ttatatgtgt 1680
ggctctgcat gttctattgc tttttccacc tttggttaaa tatcgtggca gagcttcttc 1740
gatttggtga tcgtgaattc tacaaggatt ggtggaatgc caaaactgtc gaagattatt 1800

-continued

```
ggaggatgtg gaatatgcct gttcacaaat ggatgatccg ccacctatat tttccatgtt   1860
taaggcacgg tctaccaaag gctgctgctc ttttaatttc cttcctggtt tctgctttat   1920
tccatgagct gtgcattgct gttccttgcc acatgttcaa gttgtgggct ttcggtggaa   1980
ttatgtttca ggttcctttg gtcttgatca ctaattatct gcaaaataaa ttcaaaaact   2040
caatggttgg aaatatgatt ttttggttca tattcagtat cgttggtcaa cctatgtgtg   2100
tactgctata ctaccatgac ttgatgaata ggaaaggcaa acttgactga gcggccgcaa   2160
gtatgaacta aaatgcatgt aggtgtaaga gctcatggag agcatggaat attgtatccg   2220
accatgtaac agtataataa ctgagctcca tctcacttct tctatgaata aacaaaggat   2280
gttatgatat attaacactc tatctatgca ccttattgtt ctatgataaa tttcctctta   2340
ttattataaa tcatctgaat cgtgacggct tatggaatgc ttcaaatagt acaaaaacaa   2400
atgtgtacta taagactttc taaacaattc taaccttagc attgtgaacg agacataagt   2460
gttaagaaga cataacaatt ataatggaag aagtttgtct ccatttatat attatatatt   2520
acccacttat gtattatatt aggatgttaa ggagacataa caattataaa gagagaagtt   2580
tgtatccatt tatatattat atactaccca tttatatatt atacttatcc acttatttaa   2640
tgtctttata aggtttgatc catgatattt ctaatatttt agttgatatg tatatgaaag   2700
ggtactattt gaactctctt actctgtata aaggttggat catccttaaa gtgggtctat   2760
ttaattttat tgcttcttac agataaaaaa aaaattatga gttggtttga taaaatattg   2820
aaggatttaa aataataata aataacatat aatatatgta tataaattta ttataatata   2880
acatttatct ataaaaaagt aaatattgtc ataaatctat acaatcgttt agccttgctg   2940
gacgaatctc aattatttaa acgagagtaa acatatttga ctttttggtt atttaacaaa   3000
ttattattta acactatatg aaattttttt ttttatcagc aaagaataaa attaaattaa   3060
gaaggacaat ggtgtcccaa tccttataca accaacttcc acaagaaagt caagtcagag   3120
acaacaaaaa aacaagcaaa ggaaattttt taatttgagt tgtcttgttt gctgcataat   3180
ttatgcagta aaacactaca cataaccctt ttagcagtag agcaatggtt gaccgtgtgc   3240
ttagcttctt ttattttatt tttttatcag caaagaataa ataaaataaa atgagacact   3300
tcagggatgt ttcaacaagc ttggcgcgcc gttctatagt gtcacctaaa tcgtatgtgt   3360
atgatacata aggttatgta ttaattgtag ccgcgttcta acgacaatat gtccatatgg   3420
tgcactctca gtacaatctg ctctgatgcc gcatagttaa gccagccccg acacccgcca   3480
acacccgctg acgcgccctg acgggcttgt ctgctcccgg catccgctta cagacaagct   3540
gtgaccgtct ccgggagctg catgtgtcag aggttttcac cgtcatcacc gaaacgcgcg   3600
agacgaaagg gcctcgtgat acgcctattt ttataggtta atgtcatgac caaaatccct   3660
taacgtgagt tttcgttcca ctgagcgtca gaccccgtag aaaagatcaa aggatcttct   3720
tgagatcctt tttttctgcg cgtaatctgc tgcttgcaaa caaaaaaacc accgctacca   3780
gcggtggttt gtttgccgga tcaagagcta ccaactcttt ttccgaaggt aactggcttc   3840
agcagagcgc agataccaaa tactgtcctt ctagtgtagc cgtagttagg ccaccacttc   3900
aagaactctg tagcaccgcc tacatacctc gctctgctaa tcctgttacc agtggctgct   3960
gccagtggcg ataagtcgtg tcttaccggg ttggactcaa gacgatagtt accggataag   4020
gcgcagcggt cgggctgaac ggggggttcg tgcacacagc ccagcttgga gcgaacgacc   4080
tacaccgaac tgagatacct acagcgtgag cattgagaaa gcgccacgct tcccgaaggg   4140
agaaaggcgg acaggtatcc ggtaagcggc agggtcggaa caggagagcg cacgagggag   4200
```

```
cttccagggg gaaacgcctg gtatctttat agtcctgtcg ggtttcgcca cctctgactt   4260
gagcgtcgat ttttgtgatg ctcgtcaggg gggcggagcc tatggaaaaa cgccagcaac   4320
gcggcctttt tacggttcct ggccttttgc tggccttttg ctcacatgtt ctttcctgcg   4380
ttatcccctg attctgtgga taaccgtatt accgcctttg agtgagctga taccgctcgc   4440
cgcagccgaa cgaccgagcg cagcgagtca gtgagcgagg aagcggaaga gcgcccaata   4500
cgcaaaccgc ctctccccgc gcgttggccg attcattaat gcaggttgat cgattcgaca   4560
tcgatctagt aacatagatg acaccgcgcg cgataattta tcctagtttg cgcgctatat   4620
tttgttttct atcgcgtatt aaatgtataa ttgcgggact ctaatcataa aaacccatct   4680
cataaataac gtcatgcatt acatgttaat tattacatgc ttaacgtaat tcaacagaaa   4740
ttatatgata atcatcgcaa gaccggcaac aggattcaat cttaagaaac tttattgcca   4800
aatgtttgaa cgatctgctt cgacgcactc cttctttagg tacctcacta ttcctttgcc   4860
ctcggacgag tgctggggcg tcggtttcca ctatcggcga gtacttctac acagccatcg   4920
gtccagacgg ccgcgcttct gcgggcgatt tgtgtacgcc cgacagtccc ggctccggat   4980
cggacgattg cgtcgcatcg accctgcgcc caagctgcat catcgaaatt gccgtcaacc   5040
aagctctgat agagttggtc aagaccaatg cggagcatat acgcccggag ccgcggcgat   5100
cctgcaagct ccggatgcct ccgctcgaag tagcgcgtct gctgctccat acaagccaac   5160
cacggcctcc agaagaagat gttggcgacc tcgtattggg aatccccgaa catcgcctcg   5220
ctccagtcaa tgaccgctgt tatgcggcca ttgtccgtca ggacattgtt ggagccgaaa   5280
tccgcgtgca cgaggtgccg gacttcgggg cagtcctcgg cccaaagcat cagctcatcg   5340
agagcctgcg cgacggacgc actgacggtg tcgtccatca cagtttgcca gtgatacaca   5400
tggggatcag caatcgcgca tatgaaatca cgccatgtag tgtattgacc gattccttgc   5460
ggtccgaatg ggccgaaccc gctcgtctgg ctaagatcgg ccgcagcgat cgcatccatg   5520
gcctccgcga ccggctgcag aacagcgggc agttcggttt caggcaggtc ttgcaacgtg   5580
acaccctgtg cacggcggga gatgcaatag gtcaggctct cgctgaattc cccaatgtca   5640
agcacttccg gaatcgggag cgcggccgat gcaaagtgcc gataaacata acgatctttg   5700
tagaaaccat cggcgcagct atttacccgc aggacatatc cacgccctcc tacatcgaag   5760
ctgaaagcac gagattcttc gccctccgag agctgcatca ggtcggagac gctgtcgaac   5820
ttttcgatca gaaacttctc gacagacgtc gcggtgagtt caggcttttt catggtttaa   5880
taagaagaga aaagagttct tttgttatgg ctgaagtaat agagaaatga gctcgagcgt   5940
gtcctctcca aatgaaatga acttccttat atagaggaag ggtcttgcga aggatagtgg   6000
gattgtgcgt catcccttac gtcagtggag atgtcacatc aatccacttg ctttgaagac   6060
gtggttggaa cgtcttcttt ttccacgatg ctcctcgtgg gtgggggtcc atctttggga   6120
ccactgtcgg cagaggcatc ttgaatgata gcctttcctt tatcgcaatg atggcatttg   6180
taggagccac cttccttttc tactgtcctt tcgatgaagt gacagatagc tgggcaatgg   6240
aatccgagga ggtttcccga aattatcctt tgttgaaaag tctcaatagc cctttggtct   6300
tctgagactg tatctttgac atttttggag tagaccagag tgtcgtgctc caccatgttg   6360
acgaagattt tcttcttgtc attgagtcgt aaaagactct gtatgaactg ttcgccagtc   6420
ttcacggcga gttctgttag atcctcgatt tgaatcttag actccatgca tggccttaga   6480
ttcagtagga actacctttt tagagactcc aatctctatt acttgccttg gtttatgaag   6540
```

-continued

```
caagccttga atcgtccata ctggaatagt acttctgatc ttgagaaata tgtctttctc   6600
tgtgttcttg atgcaattag tcctgaatct tttgactgca tctttaacct tcttgggaag   6660
gtatttgatc tcctggagat tgttactcgg gtagatcgtc ttgatgagac ctgctgcgta   6720
ggcctctcta accatctgtg ggtcagcatt ctttctgaaa ttgaagaggc taaccttctc   6780
attatcagtg gtgaacatag tgtcgtcacc ttcaccttcg aacttccttc ctagatcgta   6840
aagatagagg aaatcgtcca ttgtaatctc cggggcaaag gagatctctt ttggggctgg   6900
atcactgctg ggccttttgg ttcctagcgt gagccagtgg gctttttgct ttggtgggct   6960
tgttagggcc ttagcaaagc tcttgggctt gagttgagct tctcctttgg ggatgaagtt   7020
caacctgtct gtttgctgac ttgttgtgta cgcgtcagct gctgctcttg cctctgtaat   7080
agtggcaaat ttcttgtgtg caactccggg aacgccgttt gttgccgcct ttgtacaacc   7140
ccagtcatcg tatataccgg catgtggacc gttatacaca acgtagtagt tgatatgagg   7200
gtgttgaata cccgattctg ctctgagagg agcaactgtg ctgttaagct cagatttttg   7260
tgggattgga attggatcga tctcgatccc gcgaaattaa tacgactcac tatagggaga   7320
ccacaacggt ttccctctag aaataatttt gtttaacttt aagaaggaga tatacccatg   7380
gaaaagcctg aactcaccgc gacgtctgtc gagaagtttc tgatcgaaaa gttcgacagc   7440
gtctccgacc tgatgcagct ctcggagggc gaagaatctc gtgctttcag cttcgatgta   7500
ggagggcgtg gatatgtcct gcgggtaaat agctgcgccg atggtttcta caaagatcgt   7560
tatgtttatc ggcactttgc atcggccgcg ctcccgattc cggaagtgct tgacattggg   7620
gaattcagcg agagcctgac ctattgcatc tcccgccgtg cacagggtgt cacgttgcaa   7680
gacctgcctg aaaccgaact gcccgctgtt ctgcagccgg tcgcggaggc tatggatgcg   7740
atcgctgcgg ccgatcttag ccagacgagc gggttcggcc cattcggacc gcaaggaatc   7800
ggtcaataca ctacatggcg tgatttcata tgcgcgattg ctgatcccca tgtgtatcac   7860
tggcaaactg tgatggacga caccgtcagt gcgtccgtcg cgcaggctct cgatgagctg   7920
atgctttggg ccgaggactg ccccgaagtc cggcacctcg tgcacgcgga tttcggctcc   7980
aacaatgtcc tgacggacaa tggccgcata acagcggtca ttgactggag cgaggcgatg   8040
ttcggggatt cccaatacga ggtcgccaac atcttcttct ggaggccgtg gttggcttgt   8100
atggagcagc agacgcgcta cttcgagcgg aggcatccgg agcttgcagg atcgccgcgg   8160
ctccgggcgt atatgctccg cattggtctt gaccaactct atcagagctt ggttgacggc   8220
aatttcgatg atgcagcttg ggcgcagggt cgatgcgacg caatcgtccg atccggagcc   8280
gggactgtcg ggcgtacaca aatcgcccgc agaagcgcgg ccgtctggac cgatggctgt   8340
gtagaagtac tcgccgatag tggaaaccga cgccccagca ctcgtccgag ggcaaaggaa   8400
tagtgaggta cagcttggat cgatccggct gctaacaaag cccgaaagga agctgagttg   8460
gctgctgcca ccgctgagca ataactagca taaccccttg gggcctctaa acgggtcttg   8520
aggggttttt tgctgaaagg aggaactata tccggatgat cgggcgcgcc gtcgacggat   8580
ccgtacgaga tccggccggc cagatcctgc aggtaaattg cagctgaagg acagtgaagg   8640
gtgaatttat ccatttaaac cattttcttt ttaacacatt tcttatggta atctcttctc   8700
actacactat aaaaatggct tctcaatccc attttctaca tcatcccatt ctattgagtt   8760
ttgtttattt gctttcactt ttttttttat ctgcctcttc ccttaatttg cttgacttct   8820
tcttcacatt ttgctttgtt ttctcctccg gcttccggta tttcaaattc aagatgagca   8880
agttgaaatt tataaataga aatacagata ttatttacaa cgtcaaatct ttggtatttt   8940
```

caatatttga atggggtaaa tttgtcatat agtcatcatc actgactact tatctaacct 9000
atttaatttg gagcatattc tttataaggt ccctctcacg gccaatgtct aattattgat 9060
atacagctct tgttttctag tgctgcttat aatattatct acacatatat atggtactgc 9120
acactactac tatatagtag taagtaaact agcaacagcc ggggccaaac tccaataact 9180
aggcattggg gtttagttgg taatataaat ataacatcaa aaagtctttg cttgtgacga 9240
acatcacaat gcacccacca ttgatgccac gacagacatt gttaattttt tttttaattt 9300
ttaaaaaaga agcaattcca atagttctat attacaatct cacgtgatcc aagcacaacg 9360
tttcattttt tgtacatgct cgatatataa ataatatttc attttatagt aaaatataat 9420
gacattttcg aatataattt ttgaaatttc attttccaaa tgaaatacta atattaatat 9480
taatgagatt accacaaatc atgttatgaa tgaaataaag agttttggca ttctaacttt 9540
ctttgaatag aacaaaatgt atacaacact ctccatatat acacgattta ttcagggatc 9600
atatacattc tctcatgatt aacatagtct gctttcttca cgtctaagca gataattttt 9660
ggtccacaag ataaaattat cattagtcgt tttaattaat tccttgagca tcaagcacta 9720
aaataattaa acttctccat taccaaaaaa aaaagatagg tgattcagta acatgtagta 9780
ctagtactac tgattttttt tttcttttga ttttaatgaa tggttcgtat cgagcatcga 9840
gaaatccatt tattaggtgt gtaatgtaat agtagtattt ccttgatttt cagtaataag 9900
atggattctt acatttatat ctgtttgaca gaaaatgttg tcaatgcatt tcttgggcac 9960
aaagtttttt gaaacatgaa ttaatttttt caaaatattt atgacatcaa attgacccta 10020
aaataagtga taaagcttta acgtggaatg acattaattt ttccatgata aataaaacac 10080
ttaaaacatt ttaatattaa tattataatc agttacaact atgttcaatt aatgcaataa 10140
cttttaaata aatattaaaa tatttttttt ctgttctcca ataaagagat cttgttgcac 10200
ggaaaaagtc acattcttat ttagtaaaaa attataatta ttgtttgaaa aatatcattt 10260
tcactgcaga aaatttgatc cagctctaca gatcatactt ttattgtaca ataatacaat 10320
aaaaatattc atctgcagga aatatcattt tcattgtaca ataatataaa gataaatata 10380
taccagaaaa gaaaaagaaa ctgatgtggc acaatgtatt cactgaaaga atgcatattg 10440
tatttcacct ttcaagcagc actaagaata tacttctttt attatacttg tgcatttact 10500
caaccaccct cggtggagta agaaagaaga tagataaaag tttttttga catttggtga 10560
atctcttaat taaaaaaata aaataatcca tttcctttat ttaatttctt ttttcccatc 10620
tgtgaaattc caattctgct tcgcgctcct gtctataaat tgacttagcc accacctcag 10680
tttccattca ttcacttctt ctctttatac ccccctctc tttttgcgt tcattctgtt 10740
ttcgtaagta ctgttgtttt tctcttctat ttctttttt gtttgtgttg ttttttttc 10800
ttccttatcg ttgttctgcc tctcctctgt ttcggtgctc tgttcaccac ttccacgtga 10860
gaatgatctt ccttctttgc atgttcattc tctcgtgacc actggatcag actccatgtt 10920
ctgatccagg gtctctctct aacgcctgta ctttcatcca tgaccacctt aaaaacaaca 10980
tgggggtggt gctgttacac taactctgtt tctggggtgc tgtctttgtt caattttact 11040
cagaaaatat cttttcttgg attctattcg gtgtgtggga acatgatcct gtcggtcggt 11100
tgtttttagg ttaatcctta actggttaca aggatctaac gcttgaatgc atgtcctgag 11160
ttaaagaaac aaaagaagaa cacacctagt acagcctggc ctcgaaccaa gaacttcttt 11220
gttggtttct cattattact aaaataaaat aaagtatacg ttttcttttt tctttgggat 11280

```
gaacggttca gacttatgag aagtttaagc taatcctgta gtggagtgtt caatttattt  11340
taaactttaa agcaatagct caagcactaa acttcttttt caagttcaac cactttggta  11400
gcttgctaat tgctgctatt gttctaatta attaatgtaa ttattgttta aaaaagaaaa  11460
gttggtgaca ctggaataaa aaagtgtact atctggcaat tattcttctg cagcaatgtt  11520
tgaggttgaa atcttagtag aacaaagtag aagatctggt atttatattt tttgtagaca  11580
gatggtgggg gtgggtggta ggccttgaaa tccaatatag ttttgtagaa taattttatt  11640
attttttttt tttgctcact tgtttgtggt attgattttg tgatgactca agattaatga  11700
tttaccttca ttttttttcat ggtgacatat tatgtatatt cttgatctgt ttcttacact  11760
tctttttcgt tgttgtagct gttgaagtct gcggccgcat ggagagatct caacggcagt  11820
ctcctccgcc accgtcgccg tcctcctcct cgtcctccgt ctccgcggac accgtcctcg  11880
tccctcccgg aaagaggcgg agggcggcga cggccaaggc cggcgccgag cctaataaga  11940
ggatccgcaa ggaccccgcc gccgccgccg cggggaagag gagctccgtc tacaggggag  12000
tcaccaggca caggtggacg ggcaggttcg aggcgcatct ctgggacaag cactgcctcg  12060
ccgcgctcca caacaagaag aaaggcaggc aagtctacct gggggcgtat gacagcgagg  12120
aggcagctgc tcgtgcctat gacctcgcag ctctcaagta ctggggtcct gagactctgc  12180
tcaacttccc tgtggaggat tactccagcg agatgccgga gatggaggcc gtgtcccggg  12240
aggagtacct ggcctccctc cgccgcagga gcagcggctt ctccaggggc gtctccaagt  12300
acagaggcgt cgccaggcat caccacaacg ggaggtggga ggcacggatt gggcgagtct  12360
ttgggaacaa gtacctctac ttgggaacat ttgacactca agaagaggca gccaaggcct  12420
atgaccttgc ggccattgaa taccgtggcg tcaatgctgt aaccaacttc gacatcagct  12480
gctacctgga ccacccgctg ttcctggcac agctccaaca ggagccacag gtggtgccgg  12540
cactcaacca agaacctcaa cctgatcaga gcgaaaccgg aactacagag caagagccgg  12600
agtcaagcga agccaagaca ccggatggca gtgcagaacc cgatgagaac gcggtgcctg  12660
acgacaccgc ggagcccctc accacagtcg acgacagcat cgaagagggc ttgtggagcc  12720
cttgcatgga ttacgagcta gacaccatgt cgagaccaaa ctttggcagc tcaatcaatc  12780
tgagcgagtg gttcgctgac gcagacttcg actgcaacat cggatgcctg ttcgatgggt  12840
gttctgcggc tgacgaagga agcaaggatg gtgtaggtct ggcagatttc agtctgtttg  12900
aggcaggtga tgtccagctg aaggatgttc tttcggatat ggaagagggg atacaacctc  12960
cagcgatgat cagtgtgtgc aactaagcgg ccgcatttcg caccaaatca atgaaagtaa  13020
taatgaaaag tctgaataag aatacttagg cttagatgcc tttgttactt gtgtaaaata  13080
acttgagtca tgtacctttg gcggaaacag aataaataaa aggtgaaatt ccaatgctct  13140
atgtataagt tagtaatact taatgtgttc tacggttgtt tcaatatcat caaactctaa  13200
ttgaaacttt agaaccacaa atctcaatct tttcttaatg aaatgaaaaa tcttaattgt  13260
accatgttta tgttaaacac cttacaatta attggttgga gaggaggacc aaccgatggg  13320
acaacattgg gagaaagaga ttcaatggag atttggatag gagaacaaca ttctttttca  13380
cttcaataca agatgagtgc aacactaagg atatgtatga gactttcaga agctacgaca  13440
acatagatga gtgaggtggt gattcctagc aagaaagaca ttagaggaag ccaaaatcga  13500
acaaggaaga catcaagggc aagagacagg accatccatc tcaggaaaag gagctttggg  13560
atagtccgag aagttgtaca agaaattttt tggagggtga gtgatgcatt gctggtgact  13620
ttaactcaat caaaattgag aaagaaagaa aagggagggg gctcacatgt gaatagaagg  13680
```

gaaacgggag aattttacag ttttgatcta atgggcatcc cagctagtgg taacatattc 13740
accatgttta accttcacgt acgagatccg gccggccaga tcctgca 13787

<210> SEQ ID NO 75
<211> LENGTH: 13470
<212> TYPE: DNA
<213> ORGANISM: artificial sequence
<220> FEATURE:
<223> OTHER INFORMATION: plasmid sequence

<400> SEQUENCE: 75
ggagatccaa gcttttgatc catgcccttc atttgccgct tattaattaa tttggtaaca 60
gtccgtacta atcagttact tatccttccc ccatcataat taatcttggt agtctcgaat 120
gccacaacac tgactagtct cttggatcat aagaaaaagc caaggaacaa aagaagacaa 180
aacacaatga gagtatcctt tgcatagcaa tgtctaagtt cataaaattc aaacaaaaac 240
gcaatcacac acagtggaca tcacttatcc actagctgat caggatcgcc gcgtcaagaa 300
aaaaaaactg gaccccaaaa gccatgcaca acaacacgta ctcacaaagg tgtcaatcga 360
gcagcccaaa acattcacca actcaaccca tcatgagccc tcacatttgt tgtttctaac 420
ccaacctcaa actcgtattc tcttccgcca cctcattttt gtttatttca acacccgtca 480
aactgcatgc caccccgtgg ccaaatgtcc atgcatgtta acaagaccta tgactataaa 540
tagctgcaat ctcggcccag gttttcatca tcaagaacca gttcaatatc ctagtacacc 600
gtattaaaga atttaagata tactgcggcc gcaacatgac tatcgactca caatactaca 660
agtcgcgaga caaaaacgac acggcaccca aaatcgcggg aatccgatat gccccgctat 720
cgacaccatt actcaaccga tgtgagacct tctctctggt ctggcacatt ttcagcattc 780
ccactttcct cacaatttc atgctatgct gcgcaattcc actgctctgg ccatttgtga 840
ttgcgtatgt agtgtacgct gttaaagacg actccccgtc caacggagga gtggtcaagc 900
gatactcgcc tatttcaaga aacttcttca tctggaagct ctttggccgc tacttcccca 960
taactctgca caagacggtg gatctggagc ccacgcacac atactaccct ctggacgtcc 1020
aggagtatca cctgattgct gagagatact ggccgcagaa caagtacctc cgagcaatca 1080
tcaccaccat cgagtacttt ctgcccgcct tcatgaaacg gtctctttct atcaacgagc 1140
aggagcagcc tgccgagcga gatcctctcc tgtctcccgt ttctcccagc tctccgggtt 1200
ctcaacctga caagtggatt aaccacgaca gcagatatag ccgtggagaa tcatctggct 1260
ccaacggcca cgcctcgggc tccgaactta acggcaacgg caacaacggc accactaacc 1320
gacgaccttt gtcgtccgcc tctgctggct ccactgcatc tgattccacg cttcttaacg 1380
ggtccctcaa ctcctacgcc aaccagatca ttggcgaaaa cgacccacag ctgtcgccca 1440
caaaactcaa gcccactggc agaaaataca tcttcggcta ccaccccccac ggcattatcg 1500 gcatgggagc ctttggtgga attgccaccg agggagctgg atggtccaag ctctttccgg 1560
gcatccctgt ttctcttatg actctcacca acaacttccg agtgcctctc tacagagagt 1620
acctcatgag tctgggagtc gcttctgtct ccaagaagtc ctgcaaggcc ctcctcaagc 1680
gaaaccagtc tatctgcatt gtcgttggtg gagcacagga aagtcttctg gccagacccg 1740
gtgtcatgga cctggtgcta ctcaagcgaa agggttttgt tcgacttggt atggaggtcg 1800
gaaatgtcgc ccttgttccc atcatggcct ttggtgagaa cgacctctat gaccaggtta 1860
gcaacgacaa gtcgtccaag ctgtaccgat tccagcagtt tgtcaagaac ttccttggat 1920

```
tcacccttcc tttgatgcat gcccgaggcg tcttcaacta cgatgtcggt cttgtcccct   1980
acaggcgacc cgtcaacatt gtggttggtt cccccattga cttgccttat ctcccacacc   2040
ccaccgacga agaagtgtcc gaataccacg accgatacat cgccgagctg cagcgaatct   2100
acaacgagca caaggatgaa tatttcatcg attggaccga ggagggcaaa ggagccccag   2160
agttccgaat gattgagtaa gcggccgcaa gtatgaacta aaatgcatgt aggtgtaaga   2220
gctcatggag agcatggaat attgtatccg accatgtaac agtataataa ctgagctcca   2280
tctcacttct tctatgaata aacaaaggat gttatgatat attaacactc tatctatgca   2340
ccttattgtt ctatgataaa tttcctctta ttattataaa tcatctgaat cgtgacggct   2400
tatggaatgc ttcaaatagt acaaaaacaa atgtgtacta taagactttc taaacaattc   2460
taaccttagc attgtgaacg agacataagt gttaagaaga cataacaatt ataatggaag   2520
aagtttgtct ccatttatat attatatatt acccacttat gtattatatt aggatgttaa   2580
ggagacataa caattataaa gagagaagtt tgtatccatt tatatattat atactaccca   2640
tttatatatt atacttatcc acttatttaa tgtctttata aggtttgatc catgatattt   2700
ctaatatttt agttgatatg tatatgaaag ggtactattt gaactctctt actctgtata   2760
aaggttggat catccttaaa gtgggtctat ttaattttat tgcttcttac agataaaaaa   2820
aaaattatga gttggtttga taaaatattg aaggatttaa aataataata aataacatat   2880
aatatatgta tataaattta ttataaatata acatttatct ataaaaaagt aaatattgtc   2940
ataaatctat acaatcgttt agccttgctg gacgaatctc aattatttaa acgagagtaa   3000
acatatttga ctttttggtt atttaacaaa ttattattta acactatatg aaattttttt   3060
ttttatcagc aaagaataaa attaaattaa gaaggacaat ggtgtcccaa tccttataca   3120
accaacttcc acaagaaagt caagtcagag acaacaaaaa aacaagcaaa ggaaattttt   3180
taatttgagt tgtcttgttt gctgcataat ttatgcagta aaacactaca cataaccctt   3240
ttagcagtag agcaatggtt gaccgtgtgc ttagcttctt ttattttatt tttttatcag   3300
caaagaataa ataaaataaa atgagacact tcagggatgt ttcaacaagc ttggcgcgcc   3360
gttctatagt gtcacctaaa tcgtatgtgt atgatacata aggttatgta ttaattgtag   3420
ccgcgttcta acgacaatat gtccatatgg tgcactctca gtacaatctg ctctgatgcc   3480
gcatagttaa gccagccccg acacccgcca acacccgctg acgcgccctg acgggcttgt   3540
ctgctcccgg catccgctta cagacaagct gtgaccgtct ccgggagctg catgtgtcag   3600
aggttttcac cgtcatcacc gaaacgcgcg agacgaaagg gcctcgtgat acgcctattt   3660
ttataggtta atgtcatgac caaaatccct taacgtgagt tttcgttcca ctgagcgtca   3720
gaccccgtag aaaagatcaa aggatcttct tgagatcctt tttttctgcg cgtaatctgc   3780
tgcttgcaaa caaaaaaacc accgctacca gcggtggttt gtttgccgga tcaagagcta   3840
ccaactcttt ttccgaaggt aactggcttc agcagagcgc agataccaaa tactgtcctt   3900
ctagtgtagc cgtagttagg ccaccacttc aagaactctg tagcaccgcc tacatacctc   3960
gctctgctaa tcctgttacc agtggctgct gccagtggcg ataagtcgtg tcttaccggg   4020
ttggactcaa gacgatagtt accggataag gcgcagcggt cgggctgaac ggggggttcg   4080
tgcacacagc ccagcttgga gcgaacgacc tacaccgaac tgagatacct acagcgtgag   4140
cattgagaaa gcgccacgct tcccgaaggg agaaaggcgg acaggtatcc ggtaagcggc   4200
agggtcggaa caggagagcg cacgagggag cttccagggg gaaacgcctg gtatctttat   4260
agtcctgtcg ggtttcgcca cctctgactt gagcgtcgat ttttgtgatg ctcgtcaggg   4320
```

```
gggcggagcc tatggaaaaa cgccagcaac gcggcctttt tacggttcct ggccttttgc   4380
tggccttttg ctcacatgtt ctttcctgcg ttatcccctg attctgtgga taaccgtatt   4440
accgcctttg agtgagctga taccgctcgc cgcagccgaa cgaccgagcg cagcgagtca   4500
gtgagcgagg aagcggaaga gcgcccaata cgcaaaccgc ctctccccgc gcgttggccg   4560
attcattaat gcaggttgat cgattcgaca tcgatctagt aacatagatg acaccgcgcg   4620
cgataattta tcctagtttg cgcgctatat tttgttttct atcgcgtatt aaatgtataa   4680
ttgcgggact ctaatcataa aaacccatct cataaataac gtcatgcatt acatgttaat   4740
tattacatgc ttaacgtaat tcaacagaaa ttatatgata atcatcgcaa gaccggcaac   4800
aggattcaat cttaagaaac tttattgcca aatgtttgaa cgatctgctt cgacgcactc   4860
cttctttagg tacctcacta ttcctttgcc ctcggacgag tgctggggcg tcggtttcca   4920
ctatcggcga gtacttctac acagccatcg gtccagacgg ccgcgcttct gcgggcgatt   4980
tgtgtacgcc cgacagtccc ggctccggat cggacgattg cgtcgcatcg accctgcgcc   5040
caagctgcat catcgaaatt gccgtcaacc aagctctgat agagttggtc aagaccaatg   5100
cggagcatat acgcccggag ccgcggcgat cctgcaagct ccggatgcct ccgctcgaag   5160
tagcgcgtct gctgctccat acaagccaac cacggcctcc agaagaagat gttggcgacc   5220
tcgtattggg aatccccgaa catcgcctcg ctccagtcaa tgaccgctgt tatgcggcca   5280
ttgtccgtca ggacattgtt ggagccgaaa tccgcgtgca cgaggtgccg gacttcgggg   5340
cagtcctcgg cccaaagcat cagctcatcg agagcctgcg cgacggacgc actgacggtg   5400
tcgtccatca cagtttgcca gtgatacaca tggggatcag caatcgcgca tatgaaatca   5460
cgccatgtag tgtattgacc gattccttgc ggtccgaatg ggccgaaccc gctcgtctgg   5520
ctaagatcgg ccgcagcgat cgcatccatg gcctccgcga ccggctgcag aacagcgggc   5580
agttcggttt caggcaggtc ttgcaacgtg acaccctgtg cacggcggga gatgcaatag   5640
gtcaggctct cgctgaattc cccaatgtca agcacttccg gaatcgggag cgcggccgat   5700
gcaaagtgcc gataaacata acgatctttg tagaaaccat cggcgcagct atttacccgc   5760
aggacatatc cacgccctcc tacatcgaag ctgaaagcac gagattcttc gccctccgag   5820
agctgcatca ggtcggagac gctgtcgaac ttttcgatca gaaacttctc gacagacgtc   5880
gcggtgagtt caggcttttt catggtttaa taagaagaga aaagagttct tttgttatgg   5940
ctgaagtaat agagaaatga gctcgagcgt gtcctctcca aatgaaatga acttccttat   6000
atagaggaag ggtcttgcga aggatagtgg gattgtgcgt catcccttac gtcagtggag   6060
atgtcacatc aatccacttg ctttgaagac gtggttggaa cgtcttcttt ttccacgatg   6120
ctcctcgtgg gtgggggtcc atctttggga ccactgtcgg cagaggcatc ttgaatgata   6180
gcctttcctt tatcgcaatg atggcatttg taggagccac cttccttttc tactgtcctt   6240
tcgatgaagt gacagatagc tgggcaatgg aatccgagga ggtttcccga aattatcctt   6300
tgttgaaaag tctcaatagc cctttggtct tctgagactg tatctttgac atttttggag   6360
tagaccagag tgtcgtgctc caccatgttg acgaagattt tcttcttgtc attgagtcgt   6420
aaaagactct gtatgaactg ttcgccagtc ttcacggcga gttctgttag atcctcgatt   6480
tgaatcttag actccatgca tggccttaga ttcagtagga actacctttt tagagactcc   6540
aatctctatt acttgccttg gtttatgaag caagccttga atcgtccata ctggaatagt   6600
acttctgatc ttgagaaata tgtctttctc tgtgttcttg atgcaattag tcctgaatct   6660
```

```
tttgactgca tctttaacct tcttgggaag gtatttgatc tcctggagat tgttactcgg   6720
gtagatcgtc ttgatgagac ctgctgcgta ggcctctcta accatctgtg ggtcagcatt   6780
ctttctgaaa ttgaagaggc taaccttctc attatcagtg gtgaacatag tgtcgtcacc   6840
ttcaccttcg aacttccttc ctagatcgta aagatagagg aaatcgtcca ttgtaatctc   6900
cggggcaaag gagatctctt ttggggctgg atcactgctg ggccttttgg ttcctagcgt   6960
gagccagtgg gctttttgct ttggtgggct tgttagggcc ttagcaaagc tcttgggctt   7020
gagttgagct tctcctttgg ggatgaagtt caacctgtct gtttgctgac ttgttgtgta   7080
cgcgtcagct gctgctcttg cctctgtaat agtggcaaat ttcttgtgtg caactccggg   7140
aacgccgttt gttgccgcct ttgtacaacc ccagtcatcg tatataccgg catgtggacc   7200
gttatacaca acgtagtagt tgatatgagg gtgttgaata cccgattctg ctctgagagg   7260
agcaactgtg ctgttaagct cagatttttg tgggattgga attggatcga tctcgatccc   7320
gcgaaattaa tacgactcac tatagggaga ccacaacggt ttccctctag aaataatttt   7380
gtttaacttt aagaaggaga tatacccatg gaaaagcctg aactcaccgc gacgtctgtc   7440
gagaagtttc tgatcgaaaa gttcgacagc gtctccgacc tgatgcagct ctcggagggc   7500
gaagaatctc gtgctttcag cttcgatgta ggagggcgtg gatatgtcct gcgggtaaat   7560
agctgcgccg atggtttcta caaagatcgt tatgtttatc ggcactttgc atcggccgcg   7620
ctcccgattc cggaagtgct tgacattggg gaattcagcg agagcctgac ctattgcatc   7680
tcccgccgtg cacagggtgt cacgttgcaa gacctgcctg aaaccgaact gcccgctgtt   7740
ctgcagccgg tcgcggaggc tatggatgcg atcgctgcgg ccgatcttag ccagacgagc   7800
gggttcggcc cattcggacc gcaaggaatc ggtcaataca ctacatggcg tgatttcata   7860
tgcgcgattg ctgatcccca tgtgtatcac tggcaaactg tgatggacga caccgtcagt   7920
gcgtccgtcg cgcaggctct cgatgagctg atgctttggg ccgaggactg ccccgaagtc   7980
cggcacctcg tgcacgcgga tttcggctcc aacaatgtcc tgacggacaa tggccgcata   8040
acagcggtca ttgactggag cgaggcgatg ttcggggatt cccaatacga ggtcgccaac   8100
atcttcttct ggaggccgtg gttggcttgt atggagcagc agacgcgcta cttcgagcgg   8160
aggcatccgg agcttgcagg atcgccgcgg ctccgggcgt atatgctccg cattggtctt   8220
gaccaactct atcagagctt ggttgacggc aatttcgatg atgcagcttg ggcgcagggt   8280
cgatgcgacg caatcgtccg atccggagcc gggactgtcg ggcgtacaca aatcgcccgc   8340
agaagcgcgg ccgtctggac cgatggctgt gtagaagtac tcgccgatag tggaaaccga   8400
cgccccagca ctcgtccgag ggcaaaggaa tagtgaggta cagcttggat cgatccggct   8460
gctaacaaag cccgaaagga agctgagttg gctgctgcca ccgctgagca ataactagca   8520
taaccccttg gggcctctaa acgggtcttg aggggttttt tgctgaaagg aggaactata   8580
tccggatgat cgggcgcgcc gtcgacggat ccgtacgaga tccggccggc cagatcctgc   8640
aggtaaattg cagctgaagg acagtgaagg gtgaatttat ccatttaaac cattttcttt   8700
ttaacacatt tcttatggta atctcttctc actacactat aaaaatggct tctcaatccc   8760
attttctaca tcatcccatt ctattgagtt ttgtttattt gctttcactt ttttttttat   8820
ctgcctcttc ccttaatttg cttgacttct tcttcacatt ttgctttgtt ttctcctccg   8880
gcttccggta tttcaaattc aagatgagca agttgaaatt tataaataga aatacagata   8940
ttatttacaa cgtcaaatct ttggtatttt caatatttga atggggtaaa tttgtcatat   9000
agtcatcatc actgactact tatctaacct atttaatttg gagcatattc tttataaggt   9060
```

```
ccctctcacg gccaatgtct aattattgat atacagctct tgttttctag tgctgcttat   9120
aatattatct acacatatat atggtactgc acactactac tatatagtag taagtaaact   9180
agcaacagcc ggggccaaac tccaataact aggcattggg gtttagttgg taatataaat   9240
ataacatcaa aaagtctttg cttgtgacga acatcacaat gcacccacca ttgatgccac   9300
gacagacatt gttaattttt tttttaattt ttaaaaaaga agcaattcca atagttctat   9360
attacaatct cacgtgatcc aagcacaacg tttcattttt tgtacatgct cgatatataa   9420
ataatatttc attttatagt aaaatataat gacattttcg aatataattt ttgaaatttc   9480
attttccaaa tgaaatacta atattaatat taatgagatt accacaaatc atgttatgaa   9540
tgaaataaag agttttggca ttctaacttt ctttgaatag aacaaaatgt atacaacact   9600
ctccatatat acacgattta ttcagggatc atatacattc tctcatgatt aacatagtct   9660
gctttcttca cgtctaagca gataattttt ggtccacaag ataaaattat cattagtcgt   9720
tttaattaat tccttgagca tcaagcacta aaataattaa acttctccat taccaaaaaa   9780
aaaagatagg tgattcagta acatgtagta ctagtactac tgattttttt tttcttttga   9840
ttttaatgaa tggttcgtat cgagcatcga gaaatccatt tattaggtgt gtaatgtaat   9900
agtagtattt ccttgatttt cagtaataag atggattctt acatttatat ctgtttgaca   9960
gaaaatgttg tcaatgcatt tcttgggcac aaagtttttt gaaacatgaa ttaatttttt  10020
caaaatattt atgacatcaa attgacccta aaataagtga taaagcttta acgtggaatg  10080
acattaattt ttccatgata aataaaacac ttaaaacatt ttaatattaa tattataatc  10140
agttacaact atgttcaatt aatgcaataa cttttaaata aatattaaaa tatttttttt  10200
ctgttctcca ataaagagat cttgttgcac ggaaaaagtc acattcttat ttagtaaaaa  10260
attataatta ttgtttgaaa aatatcattt tcactgcaga aaatttgatc cagctctaca  10320
gatcatactt ttattgtaca ataatacaat aaaaatattc atctgcagga aatatcattt  10380
tcattgtaca ataatataaa gataaatata taccagaaaa gaaaaagaaa ctgatgtggc  10440
acaatgtatt cactgaaaga atgcatattg tatttcacct ttcaagcagc actaagaata  10500
tacttctttt attatacttg tgcatttact caaccaccct cggtggagta agaaagaaga  10560
tagataaaag tttttttga catttggtga atctcttaat taaaaaaata aaataatcca  10620
tttcctttat ttaatttctt ttttcccatc tgtgaaattc caattctgct tcgcgctcct  10680
gtctataaat tgacttagcc accacctcag tttccattca ttcacttctt ctctttatac  10740
ccccctctc tttttgcgt tcattctgtt ttcgtaagta ctgttgtttt tctcttctat  10800
ttcttttttt gtttgtgttg tttttttttc ttccttatcg ttgttctgcc tctcctctgt  10860
ttcggtgctc tgttcaccac ttccacgtga gaatgatctt ccttctttgc atgttcattc  10920
tctcgtgacc actggatcag actccatgtt ctgatccagg gtctctctct aacgcctgta  10980
ctttcatcca tgaccacctt aaaaacaaca tgggggtggt gctgttacac taactctgtt  11040
tctggggtgc tgtctttgtt caattttact cagaaaatat cttttcttgg attctattcg  11100
gtgtgtggga acatgatcct gtcggtcggt tgtttttagg ttaatcctta actggttaca  11160
aggatctaac gcttgaatgc atgtcctgag ttaaagaaac aaaagaagaa cacacctagt  11220
acagcctggc ctcgaaccaa gaacttcttt gttggtttct cattattact aaaataaaat  11280
aaagtatacg ttttcttttt tctttgggat gaacggttca gacttatgag aagtttaagc  11340
taatcctgta gtggagtgtt caatttattt taaactttaa agcaatagct caagcactaa  11400
```

acttcttttt caagttcaac cactttggta gcttgctaat tgctgctatt gttctaatta 11460
attaatgtaa ttattgttta aaaaagaaaa gttggtgaca ctggaataaa aaagtgtact 11520
atctggcaat tattcttctg cagcaatgtt tgaggttgaa atcttagtag aacaaagtag 11580
aagatctggt atttatattt tttgtagaca gatggtgggg gtgggtggta ggccttgaaa 11640
tccaatatag ttttgtagaa taattttatt attttttttt tttgctcact tgtttgtggt 11700
attgattttg tgatgactca agattaatga tttaccttca tttttttcat ggtgacatat 11760
tatgtatatt cttgatctgt ttcttacact tctttttcgt tgttgtagct gttgaagtct 11820
gcggccgcaa accatggact ccagcagctt cctccctgcc gccggcgcgg agaatggctc 11880
ggcggcgggc ggcgccaaca atggcggcgc tgctcagcag catgcggcgc cggcgatccg 11940
cgagcaggac cggctgatgc cgatcgcgaa cgtgatccgc atcatgcggc gcgtgctgcc 12000
ggcgcacgcc aagatctcgg acgacgccaa ggagacgatc caggagtgcg tgtcggagta 12060
catcagcttc atcacggggg aggccaacga gcggtgccag cgggagcagc gcaagaccat 12120
caccgccgag gacgtgctgt gggccatgag ccgcctcggc ttcgacgact acgtcgagcc 12180
gctcggcgcc tacctccacc gctaccgcga gttcgagggc gacgcgcgcg gcgtcgggct 12240
cgtcccgggg gccgccccat cgcgcggcgg cgaccaccac ccgcactcca tgtcgccagc 12300
ggcgatgctc aagtcccgcg ggccagtctc cggagccgcc atgctaccgc accaccacca 12360
ccaccacgac atgcagatgc acgccgccat gtacgggga acggccgtgc ccccgccggc 12420
cgggcctcct caccacggcg ggttcctcat gccacaccca cagggtagta gccactacct 12480
gccttacgcg tacgagccca cgtacggcgg tgagcacgcc atggctgcat actatggagg 12540
cgccgcgtac gcgcccggca acggcgggag cggcgacggc agtggcagtg gcggcggtgg 12600
cgggagcgcg tcgcacacac cgcagggcag cggcggcttg gagcacccgc acccgttcgc 12660
gtacaagtag cggccgcatt tcgcaccaaa tcaatgaaag taataatgaa aagtctgaat 12720
aagaatactt aggcttagat gcctttgtta cttgtgtaaa ataacttgag tcatgtacct 12780
ttggcggaaa cagaataaat aaaaggtgaa attccaatgc tctatgtata agttagtaat 12840
acttaatgtg ttctacggtt gtttcaatat catcaaactc taattgaaac tttagaacca 12900
caaatctcaa tcttttctta atgaaatgaa aaatcttaat tgtaccatgt ttatgttaaa 12960
caccttacaa ttaattggtt ggagaggagg accaaccgat gggacaacat tgggagaaag 13020
agattcaatg gagatttgga taggagaaca acattctttt tcacttcaat acaagatgag 13080
tgcaacacta aggatatgta tgagactttc agaagctacg acaacataga tgagtgaggt 13140
ggtgattcct agcaagaaag acattagagg aagccaaaat cgaacaagga agacatcaag 13200
ggcaagagac aggaccatcc atctcaggaa aaggagcttt gggatagtcc gagaagttgt 13260
acaagaaatt ttttggaggg tgagtgatgc attgctggtg actttaactc aatcaaaatt 13320
gagaaagaaa gaaaagggag ggggctcaca tgtgaataga agggaaacgg gagaatttta 13380
cagttttgat ctaatgggca tcccagctag tggtaacata ttcaccatgt ttaaccttca 13440
cgtacgagat ccggccggcc agatcctgca 13470

<210> SEQ ID NO 76
<211> LENGTH: 13817
<212> TYPE: DNA
<213> ORGANISM: artificial sequence
<220> FEATURE:
<223> OTHER INFORMATION: plasmid sequence

<400> SEQUENCE: 76

```
ggagatccaa gcttttgatc catgcccttc atttgccgct tattaattaa tttggtaaca     60
gtccgtacta atcagttact tatccttccc ccatcataat taatcttggt agtctcgaat    120
gccacaacac tgactagtct cttggatcat aagaaaaagc caaggaacaa aagaagacaa    180
aacacaatga gagtatcctt tgcatagcaa tgtctaagtt cataaaattc aaacaaaaac    240
gcaatcacac acagtggaca tcacttatcc actagctgat caggatcgcc gcgtcaagaa    300
aaaaaaactg gaccccaaaa gccatgcaca acaacacgta ctcacaaagg tgtcaatcga    360
gcagcccaaa acattcacca actcaaccca tcatgagccc tcacatttgt tgtttctaac    420
ccaacctcaa actcgtattc tcttccgcca cctcattttt gtttatttca acacccgtca    480
aactgcatgc caccccgtgg ccaaatgtcc atgcatgtta acaagaccta tgactataaa    540
tagctgcaat ctcggcccag gttttcatca tcaagaacca gttcaatatc ctagtacacc    600
gtattaaaga atttaagata tactgcggcc gcaacatgac tatcgactca caatactaca    660
agtcgcgaga caaaaacgac acggcaccca aaatcgcggg aatccgatat gccccgctat    720
cgacaccatt actcaaccga tgtgagacct tctctctggt ctggcacatt ttcagcattc    780
ccactttcct cacaattttc atgctatgct gcgcaattcc actgctctgg ccatttgtga    840
ttgcgtatgt agtgtacgct gttaaagacg actccccgtc caacggagga gtggtcaagc    900
gatactcgcc tatttcaaga aacttcttca tctggaagct ctttggccgc tacttcccca    960
taactctgca caagacggtg gatctggagc ccacgcacac atactaccct ctggacgtcc   1020
aggagtatca cctgattgct gagagatact ggccgcagaa caagtacctc cgagcaatca   1080
tcaccaccat cgagtacttt ctgcccgcct tcatgaaacg gtctctttct atcaacgagc   1140
aggagcagcc tgccgagcga gatcctctcc tgtctcccgt ttctcccagc tctccgggtt   1200
ctcaacctga caagtggatt aaccacgaca gcagatatag ccgtggagaa tcatctggct   1260
ccaacggcca cgcctcgggc tccgaactta acggcaacgg caacaacggc accactaacc   1320
gacgaccttt gtcgtccgcc tctgctggct ccactgcatc tgattccacg cttcttaacg   1380
ggtccctcaa ctcctacgcc aaccagatca ttggcgaaaa cgacccacag ctgtcgccca   1440
caaaactcaa gcccactggc agaaaataca tcttcggcta ccaccccccac ggcattatcg   1500
gcatgggagc ctttggtgga attgccaccg agggagctgg atggtccaag ctctttccgg   1560
gcatccctgt ttctcttatg actctcacca acaacttccg agtgcctctc tacagagagt   1620
acctcatgag tctgggagtc gcttctgtct ccaagaagtc ctgcaaggcc ctcctcaagc   1680
gaaaccagtc tatctgcatt gtcgttggtg gagcacagga aagtcttctg gccagacccg   1740
gtgtcatgga cctggtgcta ctcaagcgaa agggttttgt tcgacttggt atggaggtcg   1800
gaaatgtcgc ccttgttccc atcatggcct ttggtgagaa cgacctctat gaccaggtta   1860
gcaacgacaa gtcgtccaag ctgtaccgat tccagcagtt tgtcaagaac ttccttggat   1920
tcacccttcc tttgatgcat gcccgaggcg tcttcaacta cgatgtcggt cttgtcccct   1980
acaggcgacc cgtcaacatt gtggttggtt cccccattga cttgccttat ctcccacacc   2040
ccaccgacga agaagtgtcc gaataccacg accgatacat cgccgagctg cagcgaatct   2100
acaacgagca caaggatgaa tatttcatcg attggaccga ggagggcaaa ggagccccag   2160
agttccgaat gattgagtaa gcggccgcaa gtatgaacta aaatgcatgt aggtgtaaga   2220
gctcatggag agcatggaat attgtatccg accatgtaac agtataataa ctgagctcca   2280
tctcacttct tctatgaata aacaaaggat gttatgatat attaacactc tatctatgca   2340
```

```
ccttattgtt ctatgataaa tttcctctta ttattataaa tcatctgaat cgtgacggct   2400
tatggaatgc ttcaaatagt acaaaaacaa atgtgtacta taagactttc taaacaattc   2460
taaccttagc attgtgaacg agacataagt gttaagaaga cataacaatt ataatggaag   2520
aagtttgtct ccatttatat attatatatt acccacttat gtattatatt aggatgttaa   2580
ggagacataa caattataaa gagagaagtt tgtatccatt tatatattat atactaccca   2640
tttatatatt atacttatcc acttatttaa tgtctttata aggtttgatc catgatattt   2700
ctaatatttt agttgatatg tatatgaaag ggtactattt gaactctctt actctgtata   2760
aaggttggat catccttaaa gtgggtctat ttaattttat tgcttcttac agataaaaaa   2820
aaaattatga gttggtttga taaaatattg aaggatttaa aataataata aataacatat   2880
aatatatgta tataaattta ttataatata acatttatct ataaaaaagt aaatattgtc   2940
ataaatctat acaatcgttt agccttgctg gacgaatctc aattatttaa acgagagtaa   3000
acatatttga ctttttggtt atttaacaaa ttattattta acactatatg aaattttttt   3060
ttttatcagc aaagaataaa attaaattaa gaaggacaat ggtgtcccaa tccttataca   3120
accaacttcc acaagaaagt caagtcagag acaacaaaaa aacaagcaaa ggaaattttt   3180
taatttgagt tgtcttgttt gctgcataat ttatgcagta aaacactaca cataaccctt   3240
ttagcagtag agcaatggtt gaccgtgtgc ttagcttctt ttattttatt tttttatcag   3300
caaagaataa ataaaataaa atgagacact tcagggatgt ttcaacaagc ttggcgcgcc   3360
gttctatagt gtcacctaaa tcgtatgtgt atgatacata aggttatgta ttaattgtag   3420
ccgcgttcta acgacaatat gtccatatgg tgcactctca gtacaatctg ctctgatgcc   3480
gcatagttaa gccagccccg acacccgcca acacccgctg acgcgccctg acgggcttgt   3540
ctgctcccgg catccgctta cagacaagct gtgaccgtct ccgggagctg catgtgtcag   3600
aggttttcac cgtcatcacc gaaacgcgcg agacgaaagg gcctcgtgat acgcctattt   3660
ttataggtta atgtcatgac caaaatccct taacgtgagt tttcgttcca ctgagcgtca   3720
gaccccgtag aaaagatcaa aggatcttct tgagatcctt tttttctgcg cgtaatctgc   3780
tgcttgcaaa caaaaaaacc accgctacca gcggtggttt gtttgccgga tcaagagcta   3840
ccaactcttt ttccgaaggt aactggcttc agcagagcgc agataccaaa tactgtcctt   3900
ctagtgtagc cgtagttagg ccaccacttc aagaactctg tagcaccgcc tacatacctc   3960
gctctgctaa tcctgttacc agtggctgct gccagtggcg ataagtcgtg tcttaccggg   4020
ttggactcaa gacgatagtt accggataag gcgcagcggt cgggctgaac ggggggttcg   4080
tgcacacagc ccagcttgga gcgaacgacc tacaccgaac tgagatacct acagcgtgag   4140
cattgagaaa gcgccacgct tcccgaaggg agaaaggcgg acaggtatcc ggtaagcggc   4200
agggtcggaa caggagagcg cacgagggag cttccagggg gaaacgcctg gtatctttat   4260
agtcctgtcg ggtttcgcca cctctgactt gagcgtcgat ttttgtgatg ctcgtcaggg   4320
gggcggagcc tatggaaaaa cgccagcaac gcggcctttt tacggttcct ggccttttgc   4380
tggccttttg ctcacatgtt ctttcctgcg ttatcccctg attctgtgga taaccgtatt   4440
accgcctttg agtgagctga taccgctcgc cgcagccgaa cgaccgagcg cagcgagtca   4500
gtgagcgagg aagcggaaga gcgcccaata cgcaaaccgc ctctccccgc gcgttggccg   4560
attcattaat gcaggttgat cgattcgaca tcgatctagt aacatagatg acaccgcgcg   4620
cgataattta tcctagtttg cgcgctatat tttgttttct atcgcgtatt aaatgtataa   4680
ttgcgggact ctaatcataa aaacccatct cataaataac gtcatgcatt acatgttaat   4740
```

tattacatgc ttaacgtaat tcaacagaaa ttatatgata atcatcgcaa gaccggcaac 4800
aggattcaat cttaagaaac tttattgcca aatgtttgaa cgatctgctt cgacgcactc 4860
cttctttagg tacctcacta ttcctttgcc ctcggacgag tgctggggcg tcggtttcca 4920
ctatcggcga gtacttctac acagccatcg gtccagacgg ccgcgcttct gcgggcgatt 4980
tgtgtacgcc cgacagtccc ggctccggat cggacgattg cgtcgcatcg accctgcgcc 5040
caagctgcat catcgaaatt gccgtcaacc aagctctgat agagttggtc aagaccaatg 5100
cggagcatat acgcccggag ccgcggcgat cctgcaagct ccggatgcct ccgctcgaag 5160
tagcgcgtct gctgctccat acaagccaac cacggcctcc agaagaagat gttggcgacc 5220
tcgtattggg aatccccgaa catcgcctcg ctccagtcaa tgaccgctgt tatgcggcca 5280
ttgtccgtca ggacattgtt ggagccgaaa tccgcgtgca cgaggtgccg gacttcgggg 5340
cagtcctcgg cccaaagcat cagctcatcg agagcctgcg cgacggacgc actgacggtg 5400
tcgtccatca cagtttgcca gtgatacaca tggggatcag caatcgcgca tatgaaatca 5460
cgccatgtag tgtattgacc gattccttgc ggtccgaatg ggccgaaccc gctcgtctgg 5520
ctaagatcgg ccgcagcgat cgcatccatg gcctccgcga ccggctgcag aacagcgggc 5580
agttcggttt caggcaggtc ttgcaacgtg acaccctgtg cacggcggga gatgcaatag 5640
gtcaggctct cgctgaattc cccaatgtca agcacttccg gaatcgggag cgcggccgat 5700
gcaaagtgcc gataaacata acgatctttg tagaaaccat cggcgcagct atttacccgc 5760
aggacatatc cacgccctcc tacatcgaag ctgaaagcac gagattcttc gccctccgag 5820
agctgcatca ggtcggagac gctgtcgaac ttttcgatca gaaacttctc gacagacgtc 5880
gcggtgagtt caggcttttt catggtttaa taagaagaga aaagagttct tttgttatgg 5940
ctgaagtaat agagaaatga gctcgagcgt gtcctctcca aatgaaatga acttccttat 6000
atagaggaag ggtcttgcga aggatagtgg gattgtgcgt catcccttac gtcagtggag 6060
atgtcacatc aatccacttg ctttgaagac gtggttggaa cgtcttcttt ttccacgatg 6120
ctcctcgtgg gtgggggtcc atctttggga ccactgtcgg cagaggcatc ttgaatgata 6180
gcctttcctt tatcgcaatg atggcatttg taggagccac cttccttttc tactgtcctt 6240
tcgatgaagt gacagatagc tgggcaatgg aatccgagga ggtttcccga aattatcctt 6300
tgttgaaaag tctcaatagc cctttggtct tctgagactg tatctttgac atttttggag 6360
tagaccagag tgtcgtgctc caccatgttg acgaagattt tcttcttgtc attgagtcgt 6420
aaaagactct gtatgaactg ttcgccagtc ttcacggcga gttctgttag atcctcgatt 6480
tgaatcttag actccatgca tggccttaga ttcagtagga actacctttt tagagactcc 6540
aatctctatt acttgccttg gtttatgaag caagccttga atcgtccata ctggaatagt 6600
acttctgatc ttgagaaata tgtctttctc tgtgttcttg atgcaattag tcctgaatct 6660
tttgactgca tctttaacct tcttgggaag gtatttgatc tcctggagat tgttactcgg 6720
gtagatcgtc ttgatgagac ctgctgcgta ggcctctcta accatctgtg ggtcagcatt 6780
ctttctgaaa ttgaagaggc taaccttctc attatcagtg gtgaacatag tgtcgtcacc 6840
ttcaccttcg aacttccttc ctagatcgta aagatagagg aaatcgtcca ttgtaatctc 6900
cggggcaaag gagatctctt ttggggctgg atcactgctg ggccttttgg ttcctagcgt 6960
gagccagtgg gctttttgct ttggtgggct tgttagggcc ttagcaaagc tcttgggctt 7020
gagttgagct tctcctttgg ggatgaagtt caacctgtct gtttgctgac ttgttgtgta 7080

-continued

```
cgcgtcagct gctgctcttg cctctgtaat agtggcaaat ttcttgtgtg caactccggg   7140
aacgccgttt gttgccgcct ttgtacaacc ccagtcatcg tatataccgg catgtggacc   7200
gttatacaca acgtagtagt tgatatgagg gtgttgaata cccgattctg ctctgagagg   7260
agcaactgtg ctgttaagct cagatttttg tgggattgga attggatcga tctcgatccc   7320
gcgaaattaa tacgactcac tatagggaga ccacaacggt ttccctctag aaataatttt   7380
gtttaacttt aagaaggaga tatacccatg gaaaagcctg aactcaccgc gacgtctgtc   7440
gagaagtttc tgatcgaaaa gttcgacagc gtctccgacc tgatgcagct ctcggagggc   7500
gaagaatctc gtgctttcag cttcgatgta ggagggcgtg gatatgtcct gcgggtaaat   7560
agctgcgccg atggtttcta caaagatcgt tatgtttatc ggcactttgc atcggccgcg   7620
ctcccgattc cggaagtgct tgacattggg gaattcagcg agagcctgac ctattgcatc   7680
tcccgccgtg cacagggtgt cacgttgcaa gacctgcctg aaaccgaact gcccgctgtt   7740
ctgcagccgg tcgcggaggc tatggatgcg atcgctgcgg ccgatcttag ccagacgagc   7800
gggttcggcc cattcggacc gcaaggaatc ggtcaataca ctacatggcg tgatttcata   7860
tgcgcgattg ctgatcccca tgtgtatcac tggcaaactg tgatggacga caccgtcagt   7920
gcgtccgtcg cgcaggctct cgatgagctg atgctttggg ccgaggactg ccccgaagtc   7980
cggcacctcg tgcacgcgga tttcggctcc aacaatgtcc tgacggacaa tggccgcata   8040
acagcggtca ttgactggag cgaggcgatg ttcggggatt cccaatacga ggtcgccaac   8100
atcttcttct ggaggccgtg gttggcttgt atggagcagc agacgcgcta cttcgagcgg   8160
aggcatccgg agcttgcagg atcgccgcgg ctccgggcgt atatgctccg cattggtctt   8220
gaccaactct atcagagctt ggttgacggc aatttcgatg atgcagcttg ggcgcagggt   8280
cgatgcgacg caatcgtccg atccggagcc gggactgtcg ggcgtacaca aatcgcccgc   8340
agaagcgcgg ccgtctggac cgatggctgt gtagaagtac tcgccgatag tggaaaccga   8400
cgccccagca ctcgtccgag ggcaaaggaa tagtgaggta cagcttggat cgatccggct   8460
gctaacaaag cccgaaagga agctgagttg gctgctgcca ccgctgagca ataactagca   8520
taaccccttg gggcctctaa acgggtcttg aggggttttt tgctgaaagg aggaactata   8580
tccggatgat cgggcgcgcc gtcgacggat ccgtacgaga tccggccggc cagatcctgc   8640
aggtaaattg cagctgaagg acagtgaagg gtgaatttat ccatttaaac cattttcttt   8700
ttaacacatt tcttatggta atctcttctc actacactat aaaaatggct tctcaatccc   8760
attttctaca tcatcccatt ctattgagtt ttgtttattt gctttcactt ttttttttat   8820
ctgcctcttc ccttaatttg cttgacttct tcttcacatt ttgctttgtt ttctcctccg   8880
gcttccggta tttcaaattc aagatgagca agttgaaatt tataaataga aatacagata   8940
ttatttacaa cgtcaaatct ttggtatttt caatatttga atggggtaaa tttgtcatat   9000
agtcatcatc actgactact tatctaacct atttaatttg gagcatattc tttataaggt   9060
ccctctcacg gccaatgtct aattattgat atacagctct tgttttctag tgctgcttat   9120
aatattatct acacatatat atggtactgc acactactac tatatagtag taagtaaact   9180
agcaacagcc ggggccaaac tccaataact aggcattggg gtttagttgg taatataaat   9240
ataacatcaa aaagtctttg cttgtgacga acatcacaat gcacccacca ttgatgccac   9300
gacagacatt gttaattttt tttttaattt ttaaaaaaga agcaattcca atagttctat   9360
attacaatct cacgtgatcc aagcacaacg tttcattttt tgtacatgct cgatatataa   9420
ataatatttc attttatagt aaaatataat gacattttcg aatataattt ttgaaatttc   9480
```

-continued

```
attttccaaa tgaaatacta atattaatat taatgagatt accacaaatc atgttatgaa   9540
tgaaataaag agttttggca ttctaacttt ctttgaatag aacaaaatgt atacaacact   9600
ctccatatat acacgattta ttcagggatc atatacattc tctcatgatt aacatagtct   9660
gctttcttca cgtctaagca gataattttt ggtccacaag ataaaattat cattagtcgt   9720
tttaattaat tccttgagca tcaagcacta aaataattaa acttctccat taccaaaaaa   9780
aaaagatagg tgattcagta acatgtagta ctagtactac tgattttttt tttcttttga   9840
ttttaatgaa tggttcgtat cgagcatcga gaaatccatt tattaggtgt gtaatgtaat   9900
agtagtattt ccttgatttt cagtaataag atggattctt acatttatat ctgtttgaca   9960
gaaaatgttg tcaatgcatt tcttgggcac aaagtttttt gaaacatgaa ttaatttttt  10020
caaaatattt atgacatcaa attgacccta aaataagtga taaagcttta acgtggaatg  10080
acattaattt ttccatgata aataaaacac ttaaaacatt ttaatattaa tattataatc  10140
agttacaact atgttcaatt aatgcaataa cttttaaata aatattaaaa tatttttttt  10200
ctgttctcca ataaagagat cttgttgcac ggaaaaagtc acattcttat ttagtaaaaa  10260
attataatta ttgtttgaaa aatatcattt tcactgcaga aaatttgatc cagctctaca  10320
gatcatactt ttattgtaca ataatacaat aaaaatattc atctgcagga aatatcattt  10380
tcattgtaca ataatataaa gataaatata taccagaaaa gaaaaagaaa ctgatgtggc  10440
acaatgtatt cactgaaaga atgcatattg tatttcacct ttcaagcagc actaagaata  10500
tacttctttt attatacttg tgcatttact caaccaccct cggtggagta agaaagaaga  10560
tagataaaag ttttttttga catttggtga atctcttaat taaaaaaata aaataatcca  10620
tttcctttat ttaatttctt ttttcccatc tgtgaaattc caattctgct tcgcgctcct  10680
gtctataaat tgacttagcc accacctcag tttccattca ttcacttctt ctctttatac  10740
ccccccctctc ttttttgcgt tcattctgtt ttcgtaagta ctgttgtttt tctcttctat  10800
ttcttttttt gtttgtgttg ttttttttc ttccttatcg ttgttctgcc tctcctctgt  10860
ttcggtgctc tgttcaccac ttccacgtga gaatgatctt ccttctttgc atgttcattc  10920
tctcgtgacc actggatcag actccatgtt ctgatccagg gtctctctct aacgcctgta  10980
ctttcatcca tgaccacctt aaaaacaaca tgggggtggt gctgttacac taactctgtt  11040
tctggggtgc tgtctttgtt caattttact cagaaaatat cttttcttgg attctattcg  11100
gtgtgtggga acatgatcct gtcggtcggt tgtttttagg ttaatcctta actggttaca  11160
aggatctaac gcttgaatgc atgtcctgag ttaaagaaac aaaagaagaa cacacctagt  11220
acagcctggc ctcgaaccaa gaacttcttt gttggtttct cattattact aaaataaaat  11280
aaagtatacg ttttcttttt tctttgggat gaacggttca gacttatgag aagtttaagc  11340
taatcctgta gtggagtgtt caatttattt taaactttaa agcaatagct caagcactaa  11400
acttcttttt caagttcaac cactttggta gcttgctaat tgctgctatt gttctaatta  11460
attaatgtaa ttattgttta aaaaagaaaa gttggtgaca ctggaataaa aaagtgtact  11520
atctggcaat tattcttctg cagcaatgtt tgaggttgaa atcttagtag aacaaagtag  11580
aagatctggt atttatattt tttgtagaca gatggtgggg gtgggtggta ggccttgaaa  11640
tccaatatag ttttgtagaa taattttatt attttttttt tttgctcact tgtttgtggt  11700
attgattttg tgatgactca agattaatga tttaccttca tttttttcat ggtgacatat  11760
tatgtatatt cttgatctgt ttcttacact tctttttcgt tgttgtagct gttgaagtct  11820
```

-continued

```
gcggccgcat ggagagatct caacggcagt ctcctccgcc accgtcgccg tcctcctcct  11880

cgtcctccgt ctccgcggac accgtcctcg tccctcccgg aaagaggcgg agggcggcga  11940

cggccaaggc cggcgccgag cctaataaga ggatccgcaa ggaccccgcc gccgccgccg  12000

cggggaagag gagctccgtc tacaggggag tcaccaggca caggtggacg ggcaggttcg  12060

aggcgcatct ctgggacaag cactgcctcg ccgcgctcca caacaagaag aaaggcaggc  12120

aagtctacct gggggcgtat gacagcgagg aggcagctgc tcgtgcctat gacctcgcag  12180

ctctcaagta ctggggtcct gagactctgc tcaacttccc tgtggaggat tactccagcg  12240

agatgccgga gatggaggcc gtgtcccggg aggagtacct ggcctccctc cgccgcagga  12300

gcagcggctt ctccaggggc gtctccaagt acagaggcgt cgccaggcat caccacaacg  12360

ggaggtggga ggcacggatt gggcgagtct ttgggaacaa gtacctctac ttgggaacat  12420

ttgacactca agaagaggca gccaaggcct atgaccttgc ggccattgaa taccgtggcg  12480

tcaatgctgt aaccaacttc gacatcagct gctacctgga ccacccgctg ttcctggcac  12540

agctccaaca ggagccacag gtggtgccgg cactcaacca agaacctcaa cctgatcaga  12600

gcgaaaccgg aactacagag caagagccgg agtcaagcga agccaagaca ccggatggca  12660

gtgcagaacc cgatgagaac gcggtgcctg acgacaccgc ggagcccctc accacagtcg  12720

acgacagcat cgaagagggc ttgtggagcc cttgcatgga ttacgagcta gacaccatgt  12780

cgagaccaaa ctttggcagc tcaatcaatc tgagcgagtg gttcgctgac gcagacttcg  12840

actgcaacat cggatgcctg ttcgatgggt gttctgcggc tgacgaagga agcaaggatg  12900

gtgtaggtct ggcagatttc agtctgtttg aggcaggtga tgtccagctg aaggatgttc  12960

tttcggatat ggaagagggg atacaacctc cagcgatgat cagtgtgtgc aactaagcgg  13020

ccgcatttcg caccaaatca atgaaagtaa taatgaaaag tctgaataag aatacttagg  13080

cttagatgcc tttgttactt gtgtaaaata acttgagtca tgtacctttg gcggaaacag  13140

aataaataaa aggtgaaatt ccaatgctct atgtataagt tagtaatact taatgtgttc  13200

tacggttgtt tcaatatcat caaactctaa ttgaaacttt agaaccacaa atctcaatct  13260

tttcttaatg aaatgaaaaa tcttaattgt accatgttta tgttaaacac cttacaatta  13320

attggttgga gaggaggacc aaccgatggg acaacattgg gagaaagaga ttcaatggag  13380

atttggatag gagaacaaca ttctttttca cttcaataca agatgagtgc aacactaagg  13440

atatgtatga gactttcaga agctacgaca acatagatga gtgaggtggt gattcctagc  13500

aagaaagaca ttagaggaag ccaaaatcga acaaggaaga catcaagggc aagagacagg  13560

accatccatc tcaggaaaag gagctttggg atagtccgag aagttgtaca agaaattttt  13620

tggagggtga gtgatgcatt gctggtgact ttaactcaat caaaattgag aaagaaagaa  13680

aagggagggg gctcacatgt gaatagaagg gaaacgggag aattttacag ttttgatcta  13740

atgggcatcc cagctagtgg taacatattc accatgttta accttcacgt acgagatccg  13800

gccggccaga tcctgca                                                 13817
```

<210> SEQ ID NO 77
<211> LENGTH: 64
<212> TYPE: PRT
<213> ORGANISM: Artificial Sequence
<220> FEATURE:
<223> OTHER INFORMATION: Lec1 conserved amino acid sequence motif
<220> FEATURE:
<221> NAME/KEY: misc_feature
<222> LOCATION: (5)..(6)
<223> OTHER INFORMATION: Xaa can be any naturally occurring amino acid

```
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (54)..(57)
<223> OTHER INFORMATION: Xaa can be any naturally occurring amino acid
<220> FEATURE:
<221> NAME/KEY: misc_feature
<222> LOCATION: (61)..(63)
<223> OTHER INFORMATION: Xaa can be any naturally occurring amino acid

<400> SEQUENCE: 77

Arg Glu Gln Asp Xaa Xaa Met Pro Xaa Ala Asn Val Xaa Arg Ile Met
1               5                   10                  15

Arg Xaa Xaa Leu Pro Xaa Xaa Ala Lys Ile Ser Asp Asp Ala Lys Glu
            20                  25                  30

Xaa Ile Gln Glu Cys Val Ser Glu Xaa Ile Ser Phe Xaa Thr Xaa Glu
        35                  40                  45

Ala Asn Xaa Arg Cys Xaa Xaa Xaa Xaa Arg Lys Thr Xaa Xaa Xaa Glu
    50                  55                  60


<210> SEQ ID NO 78
<211> LENGTH: 14
<212> TYPE: DNA
<213> ORGANISM: Artificial Sequence
<220> FEATURE:
<223> OTHER INFORMATION: AW Box sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(12)
<223> OTHER INFORMATION: n is a, c, g, or t
```

<400> SEQUENCE: 78
cntngnnnnn nncg 14

<210> SEQ ID NO 79
<211> LENGTH: 2418
<212> TYPE: DNA
<213> ORGANISM: Medicago truncatula

<400> SEQUENCE: 79
atggctaccg aacgtttgac tcgtgttcat agcctcaagg agaggcttga tgaaacctta 60
actgctaata ggaatgaaat tttggccctt ctttcaaggc ttgaagcaaa gggaaaggga 120
attttgcaac accatcaagt gattgctgag tttgaggaaa ttcctgaaga tagtagacag 180
aagttgactg atggtgcatt tggtgaagtt ttgagatcca cacaggaagc aatagttttg 240
ccaccatggg ttgcacttgc tgttcgtcca aggccaggta tttgggagta tctgagagta 300
aatgtgcatg ctcttgttgt tgaaaatttg caacctgctg agtttctcaa attcaaggaa 360
gaacttgttg atggaagtgc taatggaaac tttgtgcttg agttggactt tgaaccattt 420
actgcatctt tccctcgtcc tactctcaac aagtcaattg gaaatggtgt gcaattcctt 480
aatcgccacc tttctgctaa actcttccat gacaaggaga gtttacatcc acttttggaa 540
tttctcagac ttcacagcta caagggaaag acattgatgt tgaatgacag aattcaaaac 600
cctgattctc ttcaacatgt tctgaggaaa gctgaagagt atctaagcac aattgatcct 660
gaaacaccat actcagaatt tgaacacagg ttccaggaga ttggtttgga gagaggttgg 720
ggagacaccg cagagcgcgt cctcgagtcc atccaacttc tcttggatct tctcgaggct 780
cccgaccctt gcacccttga gactttcctt gatagaatcc ccatggtctt taatgttgtc 840
atcctttctc ctcatggtta ctttgctcaa gatgatgtct tgggataccc tgatactgga 900
ggccaggttg tttacatctt ggatcaagtt cgtgccttgg agagcgagat gctcagtcgc 960
attaagaaac aaggcttgga tatcatccct cgcattctca ttatcacccg tcttctcccc 1020
gatgcagtcg gaacgacttg tggccaacga cttgagaagg tctacggaac tgagcattgc 1080
cacattcttc gagttccctt cagagatacg aagggaattg tccgcaagtg gatctcacga 1140
tttgaagtct ggccatatct agaaacttac actgaggatg ttgctcatga gcttgccaaa 1200
gagttgcaag gcaaaccaga tctgattgtt ggaaactaca gtgatggaaa cattgttgcc 1260
tctttgttgg cacataaatt aggtgtcact cagtgtacca ttgctcatgc actcgagaag 1320
actaagtacc ccgaatccga catttactgg aaaaaattcg aagagaagta tcacttctcc 1380
tgccaattta ccgctgatct tttcgcaatg aaccacacag atttcatcat cactagtacc 1440
ttccaagaga ttgctggaag caaggacaag gttggacagt atgagagtca cactgccttt 1500
actcttccag gactctaccg tgtcgtgcac ggtattgatg tctttgatcc aaagttcaac 1560
attgtatctc caggagctga tcagaccatt tacttccctt acaccgaaac tagccgccga 1620
ttgacatcct tctaccctga aatcgaagag cttctttaca gctcagttga gaatgaagag 1680
cacatatgtg tgctgaagga ccgcaacaag ccaattatct tcaccatggc aaggttggac 1740
cgtgtgaaga acattacagg acttgttgag tggtacggca agaatgccaa gcttcgtgag 1800
ttggtgaacc ttgttgttgt tgccggagac aggaggaagg agtcaaagga cttggaagag 1860
atagctgaga tgaagaagat gtatggccta atcgagacct acaagttgaa tggccaattc 1920
agatggattt cctctcagat gaaccgtgtc agaaacggag agctgtaccg tgtgatttgt 1980
gacaccaagg gagctttcgt gcaacctgct gtgtatgaag ctttcggttt gacagttgtt 2040

```
gaggccatgg ctactggatt accaacattt gcaactctta atggtggccc tgctgagatc   2100

attgtccatg gcaaatctgg attccacatt gatccttacc atggcgaccg tgctgctgat   2160

ctcctcgttg aattctttga gaaggtcaag gttgatccat ctcactggga caagatctct   2220

caaggtggtc tccaacgtat tgaagagaag tacacatgga caatatactc tcagaggctt   2280

cttacactca ctggtgtcta tggcttctgg aagcatgtgt ctaacctcga ccgtcttgag   2340

agccgccgct atcttgagat gttctatgct ctcaagtacc gcaaattggc tgagtctgtg   2400

cccctagctg ttgagtaa                                                  2418


<210> SEQ ID NO 80
<211> LENGTH: 805
<212> TYPE: PRT
<213> ORGANISM: Medicago truncatula

<400> SEQUENCE: 80

Met Ala Thr Glu Arg Leu Thr Arg Val His Ser Leu Lys Glu Arg Leu
1               5                   10                  15

Asp Glu Thr Leu Thr Ala Asn Arg Asn Glu Ile Leu Ala Leu Leu Ser
            20                  25                  30

Arg Leu Glu Ala Lys Gly Lys Gly Ile Leu Gln His His Gln Val Ile
        35                  40                  45

Ala Glu Phe Glu Glu Ile Pro Glu Asp Ser Arg Gln Lys Leu Thr Asp
    50                  55                  60

Gly Ala Phe Gly Glu Val Leu Arg Ser Thr Gln Glu Ala Ile Val Leu
65                  70                  75                  80

Pro Pro Trp Val Ala Leu Ala Val Arg Pro Arg Pro Gly Ile Trp Glu
                85                  90                  95

Tyr Leu Arg Val Asn Val His Ala Leu Val Val Glu Asn Leu Gln Pro
            100                 105                 110

Ala Glu Phe Leu Lys Phe Lys Glu Glu Leu Val Asp Gly Ser Ala Asn
        115                 120                 125

Gly Asn Phe Val Leu Glu Leu Asp Phe Glu Pro Phe Thr Ala Ser Phe
    130                 135                 140

Pro Arg Pro Thr Leu Asn Lys Ser Ile Gly Asn Gly Val Gln Phe Leu
145                 150                 155                 160

Asn Arg His Leu Ser Ala Lys Leu Phe His Asp Lys Glu Ser Leu His
                165                 170                 175

Pro Leu Leu Glu Phe Leu Arg Leu His Ser Tyr Lys Gly Lys Thr Leu
            180                 185                 190

Met Leu Asn Asp Arg Ile Gln Asn Pro Asp Ser Leu Gln His Val Leu
        195                 200                 205

Arg Lys Ala Glu Glu Tyr Leu Ser Thr Ile Asp Pro Glu Thr Pro Tyr
    210                 215                 220

Ser Glu Phe Glu His Arg Phe Gln Glu Ile Gly Leu Glu Arg Gly Trp
225                 230                 235                 240

Gly Asp Thr Ala Glu Arg Val Leu Glu Ser Ile Gln Leu Leu Leu Asp
                245                 250                 255

Leu Leu Glu Ala Pro Asp Pro Cys Thr Leu Glu Thr Phe Leu Asp Arg
            260                 265                 270

Ile Pro Met Val Phe Asn Val Val Ile Leu Ser Pro His Gly Tyr Phe
        275                 280                 285

Ala Gln Asp Asp Val Leu Gly Tyr Pro Asp Thr Gly Gly Gln Val Val
    290                 295                 300
```

```
Tyr Ile Leu Asp Gln Val Arg Ala Leu Glu Ser Glu Met Leu Ser Arg
305                 310                 315                 320

Ile Lys Lys Gln Gly Leu Asp Ile Ile Pro Arg Ile Leu Ile Ile Thr
                325                 330                 335

Arg Leu Leu Pro Asp Ala Val Gly Thr Thr Cys Gly Gln Arg Leu Glu
            340                 345                 350

Lys Val Tyr Gly Thr Glu His Cys His Ile Leu Arg Val Pro Phe Arg
        355                 360                 365

Asp Thr Lys Gly Ile Val Arg Lys Trp Ile Ser Arg Phe Glu Val Trp
    370                 375                 380

Pro Tyr Leu Glu Thr Tyr Thr Glu Asp Val Ala His Glu Leu Ala Lys
385                 390                 395                 400

Glu Leu Gln Gly Lys Pro Asp Leu Ile Val Gly Asn Tyr Ser Asp Gly
                405                 410                 415

Asn Ile Val Ala Ser Leu Leu Ala His Lys Leu Gly Val Thr Gln Cys
            420                 425                 430

Thr Ile Ala His Ala Leu Glu Lys Thr Lys Tyr Pro Glu Ser Asp Ile
        435                 440                 445

Tyr Trp Lys Lys Phe Glu Glu Lys Tyr His Phe Ser Cys Gln Phe Thr
    450                 455                 460

Ala Asp Leu Phe Ala Met Asn His Thr Asp Phe Ile Ile Thr Ser Thr
465                 470                 475                 480

Phe Gln Glu Ile Ala Gly Ser Lys Asp Lys Val Gly Gln Tyr Glu Ser
                485                 490                 495

His Thr Ala Phe Thr Leu Pro Gly Leu Tyr Arg Val Val His Gly Ile
            500                 505                 510

Asp Val Phe Asp Pro Lys Phe Asn Ile Val Ser Pro Gly Ala Asp Gln
        515                 520                 525

Thr Ile Tyr Phe Pro Tyr Thr Glu Thr Ser Arg Arg Leu Thr Ser Phe
    530                 535                 540

Tyr Pro Glu Ile Glu Glu Leu Leu Tyr Ser Ser Val Glu Asn Glu Glu
545                 550                 555                 560

His Ile Cys Val Leu Lys Asp Arg Asn Lys Pro Ile Ile Phe Thr Met
                565                 570                 575

Ala Arg Leu Asp Arg Val Lys Asn Ile Thr Gly Leu Val Glu Trp Tyr
            580                 585                 590

Gly Lys Asn Ala Lys Leu Arg Glu Leu Val Asn Leu Val Val Val Ala
        595                 600                 605

Gly Asp Arg Arg Lys Glu Ser Lys Asp Leu Glu Glu Ile Ala Glu Met
    610                 615                 620

Lys Lys Met Tyr Gly Leu Ile Glu Thr Tyr Lys Leu Asn Gly Gln Phe
625                 630                 635                 640

Arg Trp Ile Ser Ser Gln Met Asn Arg Val Arg Asn Gly Glu Leu Tyr
                645                 650                 655

Arg Val Ile Cys Asp Thr Lys Gly Ala Phe Val Gln Pro Ala Val Tyr
            660                 665                 670

Glu Ala Phe Gly Leu Thr Val Val Glu Ala Met Ala Thr Gly Leu Pro
        675                 680                 685

Thr Phe Ala Thr Leu Asn Gly Gly Pro Ala Glu Ile Ile Val His Gly
    690                 695                 700

Lys Ser Gly Phe His Ile Asp Pro Tyr His Gly Asp Arg Ala Ala Asp
705                 710                 715                 720
```

```
Leu Leu Val Glu Phe Phe Glu Lys Val Lys Val Asp Pro Ser His Trp
                725                 730                 735

Asp Lys Ile Ser Gln Gly Gly Leu Gln Arg Ile Glu Glu Lys Tyr Thr
            740                 745                 750

Trp Thr Ile Tyr Ser Gln Arg Leu Leu Thr Leu Thr Gly Val Tyr Gly
        755                 760                 765

Phe Trp Lys His Val Ser Asn Leu Asp Arg Leu Glu Ser Arg Arg Tyr
    770                 775                 780

Leu Glu Met Phe Tyr Ala Leu Lys Tyr Arg Lys Leu Ala Glu Ser Val
785                 790                 795                 800

Pro Leu Ala Val Glu
                805


<210> SEQ ID NO 81
<211> LENGTH: 3265
<212> TYPE: DNA
<213> ORGANISM: Medicago truncatula

<400> SEQUENCE: 81

cagatccgaa gacatgggta ttccagagac ttaaatatag tcatatgtgt aggctttaat     60

actttgccgt tttatgctat taacatggat gctgtgagtt tgttcacaga ttcatccttt    120

ttgtttttgg cgaattttca ttgcatcgat ctatcaattt gaatgaatga atatcactta    180

tttttgtaaa aaaaagaaga taaaaaaaat taattatatt cttaataata ctcttattta    240

attattgtat ctcaattatt ctaattattc tatctatata aatatattag ttattgaaac    300

ttatttataa taaaaagcat gacattttgg aatttttctta aaatgtaagc ataactacaa    360

acgagactaa gacgtagaaa tagctagaag ttaggaacaa gagaagggtt aattgcatta    420

tcatgaattc tacattgaag tgtctcatac tctcatctca tataataaga tagacttaga    480

aaataagtac tgtactaata ataatatgta ttgttataag attatctcgt ctaaagaact    540

agcatttttt ttttgttttt tcataattaa gttatctcaa ttggaggtta tgtgtatcag    600

acattaaata taaataaatt aatggtcagt ttgagatctt ggaatgtgtt tctttaaaga    660

ttttatgttc aatttttttt tgtgtgtcaa attcggtgga caagttcata ctgagctttg    720

ctctggctta gaacgggacc tcgcaaatgg gcagtgggat gaggctactc taattagtcg    780

gtcatagatc ggatatcgaa ttttataaaa ataatataaa taaacgattc aaatgaaatc    840

gaaatattag ttcctcaagt tgtaaatgtc tagctccctt atatttcatc taatcttgtt    900

gataggactg atattttaaa atgagttctg tttgttttta tttaattatt tctaaaatga    960

gttttgtttg cttgacttcg tttacctcgt tttcttctcc gggttcgggc atttcaaaaa   1020

taaggtatat caacttgatg tttatttata aattgaagtt catagtatac gatttttttt   1080

tgtaatataa agttccatat atgatttatc gccaggtctt ggtattttcg acatttgcat   1140

ggggttaaaa taaatgtcac atatagtcac atattttttt ttgatgaaat gtcacatagt   1200

catcatcatt gtctagtttg ctgacttatt taattaggag catattcttt attaagtacc   1260

ccttacggtt gcattatcta attattgata tgttcaattt gtttcttagt gctgttttgt   1320

ttataatatt atccgaacac tatacactac aatcatcgta cataaattac tcaattgcaa   1380

caaaaaacaa gaggggtcag tctctgttga tgcattatcc aataacaaga ggaattagag   1440

gattagtagg taaaccaaag ttaaataaat ataacaacag gaaaaaagtc tttgcttgtg   1500

acgaacacca ccataatgca cccccacaat ttaatttttt caccaagaaa aaatcattat   1560

agacaactac actcatgaca catatttaac ttctgtgcat tgctgctaat cagtttattt   1620
```

aaatcactat tccctcaaca aaaaaaaagt ttatttaaat cactagatta attgtaataa 1680
aaagtcactt taataattaa tttatgcaat gtctctatca attgaactaa acttacggag 1740
ataaatatgt agtatttttg aattcaacat tctttatcga aagatgaatt ttattttaaa 1800
tttattttgt aatgtactag taatttaatt tcaaaacata ttaatgaatt aaattgtcct 1860
aatacaaata tattgaaaat tgttaggttg gacacatgat caaaattcaa acccaactca 1920
cctatttaca aaagaaaaat tcttaaagaa aaacattact atccatatag gaaaaagtat 1980
aatttttatt atcagagtaa atcctatcca gataaaaaaa aaaactgaac cgcactttaa 2040
gtaattgcta aaagtatgca tattctagct ttatttcaat ttttaagcaa catttagaat 2100
tttgtcaaaa aagataaagc aacatttaaa aaagaatata cttcttatat tcgctatgca 2160
tttatttaac tttaggcttg aggaataaga taagacttgt caaaaaaaaa aaaaaacaaa 2220
agattgggaa gtaagaaaaa gataggtaaa gatttttgac ctttggtgaa cgtcttaaac 2280
taaaataaaa taaaataaaa caaaataaat aaatttcatt ggtcaatctt ttttccttta 2340
actaattaat taatataagt gccacatcag catgtgaaat tcccattatg tatctccttt 2400
cttgtctata aattgagtta gccaccacct tattttccat tcattcatcc cttctcttta 2460
cacccccccc tctttttgc gttcactctg ttttcttttc ataggtattc tattctattc 2520
tttctttatt atttttcttt ctttgttact ctgtttttcc cctgtttctc catcaccact 2580
gccacgtcac tattccacca cctctgcatg ttctttcttt tgtgatcata agatcaaaca 2640
ctataccatg attctgatct catgatatga gtcacacatg ttttcctctg catgaaaaaa 2700
tagtgctgag tttttttttt tagtatagtt ctgtttttgt tgaattttat tcatgttctg 2760
ttcttgtgac actatacacg gtttcacttt gaagaacaag gttctgtcgt tattattcaa 2820
gatacttgtt caagaaactt catgacacaa catgcacggc cttgattaaa taaaaaacaa 2880
aaacaaaaac aaaactttat acagcctggc atagaacaaa gagattcttt ctttgttcgt 2940
ttcttaaata aattttgttt ttaattttat ggataaacaa acactaactt atgaggttta 3000
gtaatgttaa aattctaaaa ggaaattatt attctcatgc actgtttatg gttgaaatct 3060
tagttgaaaa aagtggaaga tttggtatta atattttatt tgacaggtgg ttggtcatgg 3120
tgggtcgtag gtctttgttg aaaattcata aaccaattca gttttttaa atgtttgttt 3180 aattgattaa tttttgtact atgatgttga tctgttactt aaagtgatga tgaattattt 3240
ttgttgttgc agttgaagat tttca 3265

<210> SEQ ID NO 82
<211> LENGTH: 32
<212> TYPE: DNA
<213> ORGANISM: Artificial sequence
<220> FEATURE:
<223> OTHER INFORMATION: oMDSP-1F forward primer

<400> SEQUENCE: 82
acgtacgcct gcaggcagat ccgaagacat gg 32

<210> SEQ ID NO 83
<211> LENGTH: 29
<212> TYPE: DNA
<213> ORGANISM: Artificial sequence
<220> FEATURE:
<223> OTHER INFORMATION: oMDSP-1R reverse primer

<400> SEQUENCE: 83
tgcggccgct gaaaatcttc aactgcaac 29

<210> SEQ ID NO 84
<211> LENGTH: 6850
<212> TYPE: DNA
<213> ORGANISM: Artificial sequence
<220> FEATURE:
<223> OTHER INFORMATION: Plasmid pKR2434

<400> SEQUENCE: 84
aattctgcag atatccatca cactggcggc cgctcgagca tgcatctaga gggcccaatt 60
cgccctatag tgagtcgtat tacaattcac tggccgtcgt tttacaacgt cgtgactggg 120
aaaaccctgg cgttacccaa cttaatcgcc ttgcagcaca tccccctttc gccagctggc 180
gtaatagcga agaggcccgc accgatcgcc cttcccaaca gttgcgcagc ctatacgtac 240
ggcagtttaa ggtttacacc tataaaagag agagccgtta tcgtctgttt gtggatgtac 300
agagtgatat tattgacacg ccggggcgac ggatggtgat ccccctggcc agtgcacgtc 360
tgctgtcaga taaagtctcc cgtgaacttt acccggtggt gcatatcggg gatgaaagct 420
ggcgcatgat gaccaccgat atggccagtg tgccggtctc cgttatcggg gaagaagtgg 480
ctgatctcag ccaccgcgaa aatgacatca aaaacgccat taacctgatg ttctggggaa 540
tataaatgtc aggcatgaga ttatcaaaaa ggatcttcac ctagatcctt ttcacgtaga 600
aagccagtcc gcagaaacgg tgctgacccc ggatgaatgt cagctactgg gctatctgga 660
caagggaaaa cgcaagcgca aagagaaagc aggtagcttg cagtgggctt acatggcgat 720
agctagactg ggcggtttta tggacagcaa gcgaaccgga attgccagct ggggcgccct 780
ctggtaaggt tgggaagccc tgcaaagtaa actggatggc tttctcgccg ccaaggatct 840
gatggcgcag gggatcaagc tctgatcaag agacaggatg aggatcgttt cgcatgattg 900
aacaagatgg attgcacgca ggttctccgg ccgcttgggt ggagaggcta ttcggctatg 960
actgggcaca acagacaatc ggctgctctg atgccgccgt gttccggctg tcagcgcagg 1020
ggcgcccggt tctttttgtc aagaccgacc tgtccggtgc cctgaatgaa ctgcaagacg 1080
aggcagcgcg gctatcgtgg ctggccacga cgggcgttcc ttgcgcagct gtgctcgacg 1140
ttgtcactga agcgggaagg gactggctgc tattgggcga agtgccgggg caggatctcc 1200
tgtcatctca ccttgctcct gccgagaaag tatccatcat ggctgatgca atgcggcggc 1260
tgcatacgct tgatccggct acctgcccat tcgaccacca agcgaaacat cgcatcgagc 1320
gagcacgtac tcggatggaa gccggtcttg tcgatcagga tgatctggac gaagagcatc 1380
aggggctcgc gccagccgaa ctgttcgcca ggctcaaggc gagcatgccc gacggcgagg 1440
atctcgtcgt gacccatggc gatgcctgct tgccgaatat catggtggaa aatggccgct 1500
tttctggatt catcgactgt ggccggctgg gtgtggcgga ccgctatcag gacatagcgt 1560
tggctacccg tgatattgct gaagagcttg gcggcgaatg ggctgaccgc ttcctcgtgc 1620
tttacggtat cgccgctccc gattcgcagc gcatcgcctt ctatcgcctt cttgacgagt 1680
tcttctgaat tattaacgct tacaatttcc tgatgcggta ttttctcctt acgcatctgt 1740
gcggtatttc acaccgcata caggtggcac ttttcgggga aatgtgcgcg gaacccctat 1800
ttgtttattt ttctaaatac attcaaatat gtatccgctc atgagacaat aaccctgata 1860
aatgcttcaa taatagcacg tgaggagggc caccatggcc aagttgacca gtgccgttcc 1920
ggtgctcacc gcgcgcgacg tcgccggagc ggtcgagttc tggaccgacc ggctcgggtt 1980
ctcccgggac ttcgtggagg acgacttcgc cggtgtggtc cgggacgacg tgaccctgtt 2040
catcagcgcg gtccaggacc aggtggtgcc ggacaacacc ctggcctggg tgtgggtgcg 2100
cggcctggac gagctgtacg ccgagtggtc ggaggtcgtg tccacgaact tccgggacgc 2160
ctccgggccg gccatgaccg agatcggcga gcagccgtgg gggcgggagt tcgccctgcg 2220
cgacccggcc ggcaactgcg tgcacttcgt ggccgaggag caggactgac acgtgctaaa 2280
acttcatttt taatttaaaa ggatctaggt gaagatcctt tttgataatc tcatgaccaa 2340
aatcccttaa cgtgagtttt cgttccactg agcgtcagac cccgtagaaa agatcaaagg 2400
atcttcttga gatccttttt ttctgcgcgt aatctgctgc ttgcaaacaa aaaaaccacc 2460
gctaccagcg gtggtttgtt tgccggatca agagctacca actctttttc cgaaggtaac 2520
tggcttcagc agagcgcaga taccaaatac tgtccttcta gtgtagccgt agttaggcca 2580
ccacttcaag aactctgtag caccgcctac atacctcgct ctgctaatcc tgttaccagt 2640
ggctgctgcc agtggcgata agtcgtgtct taccgggttg gactcaagac gatagttacc 2700
ggataaggcg cagcggtcgg gctgaacggg gggttcgtgc acacagccca gcttggagcg 2760
aacgacctac accgaactga gatacctaca gcgtgagcta tgagaaagcg ccacgcttcc 2820
cgaagggaga aaggcggaca ggtatccggt aagcggcagg gtcggaacag gagagcgcac 2880
gagggagctt ccagggggaa acgcctggta tctttatagt cctgtcgggt ttcgccacct 2940
ctgacttgag cgtcgatttt tgtgatgctc gtcagggggg cggagcctat ggaaaaacgc 3000
cagcaacgcg gcctttttac ggttcctggg cttttgctgg ccttttgctc acatgttctt 3060
tcctgcgtta tcccctgatt ctgtggataa ccgtattacc gcctttgagt gagctgatac 3120
cgctcgccgc agccgaacga ccgagcgcag cgagtcagtg agcgaggaag cggaagagcg 3180
cccaatacgc aaaccgcctc tccccgcgcg ttggccgatt cattaatgca gctggcacga 3240
caggtttccc gactggaaag cgggcagtga gcgcaacgca attaatgtga gttagctcac 3300
tcattaggca ccccaggctt tacactttat gcttccggct cgtatgttgt gtggaattgt 3360
gagcggataa caatttcaca caggaaacag ctatgaccat gattacgcca agctatttag 3420
gtgacgcgtt agaatactca agctatgcat caagcttggt accgagctcg gatccactag 3480
taacggccgc cagtgtgctg gaattcagga cgtacgcctg caggcagatc cgaagacatg 3540
ggtattccag agacttaaat atagtcatat gtgtaggctt taatactttg tcgttttatg 3600
ctattaacat ggatgctgtg agtttgttca cagattcatc ctttttgttt ttggcgaatt 3660
ttcattgcat cgatctatca atttgaatga atgaatatca cttatttttg taaaaaaaag 3720
aagataaaaa aaattaatta tattcttaat aatactctta tttaattatt gtatctcaat 3780
tattctaatt attctatcta tataaatata ttagttattg aaacttattt ataataaaaa 3840
gcatgacatt ttggaatttt cttaaaatgt aagcataact acaaacgaga ctaagacgta 3900
gaaatagcta gaagttagga acaagagaag ggttaattgc attatcatga attctacatt 3960
gaagtgtctc atactctcat ctcatataat aagatagact tagaaaataa gtcctgtact 4020
aataataata tgtattgtta taagattatc tcgtctaaag aactagcatt tttttttttt 4080
ttcataatta agttatctca attggaggtt atgtgtatca gacattaaat ataaataaat 4140
taatggtcaa tttgagatct tggaatgtgc ttctttaaag attttatgtt caattttttt 4200
ttgtgtgtca aattcggtgg acaagttcat actgaacttt gctctggctt agaacgggac 4260
ctcgcaaatg ggcagtggga tgaggctact ctaattagtc ggtcctagat cggatatcga 4320
gttttataaa aataatataa ataaacgatt caaatgaaat cgaaatatta gttcctcaag 4380

-continued

```
ttgtaaatgt ctagctccct tatatttcat ctagtcttgt tgataggact gatattttaa   4440
aatgagttct gtttgttttt atttaattat ttctaaaatg agttttgttt gcttgacttc   4500
gtttacctcg ttttcttctc cgggttcggg catttcaaaa ataaggtata tcaacttgat   4560
gtttatttat aaattgaagt tcatagtata cgattttttt ttgtaatata aagttccata   4620
tatgatttat cgccaggtct tggtattttc gacatttgca tggggttaaa ataaatgtca   4680
catataatca catatttttt tttgatgaaa tgtcacatag tcatcatcat tgtctagttt   4740
gctgacttat ttaattagga gcatattctt tattaagtac cccttacggt tgcattatct   4800
aattattgat atgttcaatt tgtttcttag tgctgttttg tttataatat tatccgaaca   4860
ctatacacta caatcatcgt acataaatta ctcaattgca acaaaaaaca agaggggtca   4920
gtctctgttg atgcattatc caataacaag aggaattaga ggattagtag gtaaaccaaa   4980
gttaaataaa tataacaaca ggaaaaaagt ctttgcttgt gacgaacacc accataatgc   5040
acccccacaa tttaattttt caccaagaaa aaatcattat agacaactac actcatgaca   5100
catatttaac ttctgtgcat tgctgctaat cagtttattt aaatcactat tccctcaaca   5160
aaaaaaaagt ttatttaaat cactagatta attgtaataa aaagtcactt taataattag   5220
tttatgcaat gtctctacca attgaactaa acttacggag ataaatatgt agtatttttg   5280
aattcaacat tctttatcga aagatgaatt ttattttaaa tttattttgt aatgtactag   5340
taatttaatt tcaaaacata ttaatgaatt aaattgattt tagaatatgc aataaaattg   5400
tcctaataca aatatattga aaattgttag gttggacaca tgatcaaaat tcaaacccaa   5460
ctcacctatt tagaaaagaa aaattcttaa agaaaaacat tactatccat ataggaaaaa   5520
gtataatttt tattatcaga gtaaatccta tccagataaa aaaaaaactg aaccgcactt   5580
taagtaattg ctaaaagtat gcatattcta gctttatttc aatttttaag caacatttag   5640
aattttgtca aaaaagataa agcaacattt aaaaaagaat atacttctta tattcgctat   5700
gcatttattt aactttaggc ttgaggaata agataagact tgtaggcttg aggaataaga   5760
taagacttgt caaaaaaaaa aaaaaaacaa aagattggga agtaagaaaa agataggtaa   5820
agatttttga cctttggtga acgtcttaaa ctaaaataaa ataaaataaa acaaaataaa   5880
taaatttcat tggtcaatct tttttccttt aactaattaa ttaatataag tgccacatca   5940
gcatgtgaaa ttcccattat gtatctcgtt tcttgtctat aaattgagtt agccaccacc   6000
ttattttcca ttcattcatc ccttctcttt acaccccccc ctctttttg cgttcactct   6060
gttttctttt catagtgtatt ctattctatt ctttctttat tatttttctt tctttgttac   6120
tctgtttttc ccctgtttct ccatcaccac tgccacgtca ctattccacc acctctgcat   6180
gttctttctt ttgtgatcat aagatcaaac actataccat gattctgatc tcatgatatg   6240
agtcacacat gttttcctct gcatgaaaaa atagtgctga gttttttttt tttagtatag   6300
ttctgttttt gttgaatttt attcatgttc tgttcttgtg acactataca cggtttcact   6360
ttgaagaaca aggttctgtc gttattattc aagatacttg ttcaagaaac ttcatgacac   6420
aacatgcatg gccttgatta aataaaaaac aaaaacaaaa acaaaacttt atacagcctg   6480
gcatagaaca aagagattct ttctttgttc gtttcttaaa taaattttgt ttttaatttt   6540
atggataaac aaacactaac ttatgaggtt tagtaatgtt aaaattctaa aaggaaatta   6600
ttattctcat gcactgttta tggttgaaat cttagttgaa aaaagtggaa gatttggtat   6660
taatatttta tttgacaggt ggttggtcat ggtgggtcgt aggtctttgt tgaaaattca   6720
taaaccaatt cagttttttt aaatgtttgt ttaattgatt aatttttgta ctatgatgtt   6780
```

gatctgttac ttaaagtgat gatgaattat ttttgttgtt gcagttgaag attttcagcg 6840
gccgcacctg 6850

<210> SEQ ID NO 85
<211> LENGTH: 3313
<212> TYPE: DNA
<213> ORGANISM: Medicago truncatula

<400> SEQUENCE: 85
cagatccgaa gacatgggta ttccagagac ttaaatatag tcatatgtgt aggctttaat 60
actttgtcgt tttatgctat taacatggat gctgtgagtt tgttcacaga ttcatccttt 120
ttgtttttgg cgaattttca ttgcatcgat ctatcaattt gaatgaatga atatcactta 180
tttttgtaaa aaaaagaaga taaaaaaaat taattatatt cttaataata ctcttattta 240
attattgtat ctcaattatt ctaattattc tatctatata aatatattag ttattgaaac 300
ttatttataa taaaaagcat gacattttgg aattttctta aaatgtaagc ataactacaa 360
acgagactaa gacgtagaaa tagctagaag ttaggaacaa gagaagggtt aattgcatta 420
tcatgaattc tacattgaag tgtctcatac tctcatctca tataataaga tagacttaga 480
aaataagtcc tgtactaata ataaatatgta ttgttataag attatctcgt ctaaagaact 540
agcatttttt tttttttca taattaagtt atctcaattg gaggttatgt gtatcagaca 600
ttaaatataa ataaattaat ggtcaatttg agatcttgga atgtgcttct ttaaagattt 660
tatgttcaat tttttttgt gtgtcaaatt cggtggacaa gttcatactg aactttgctc 720
tggcttagaa cgggacctcg caaatgggca gtgggatgag gctactctaa ttagtcggtc 780
ctagatcgga tatcgagttt tataaaaata atataaataa acgattcaaa tgaaatcgaa 840
atattagttc ctcaagttgt aaatgtctag ctcccttata tttcatctag tcttgttgat 900
aggactgata ttttaaaatg agttctgttt gtttttattt aattatttct aaaatgagtt 960
ttgtttgctt gacttcgttt acctcgtttt cttctccggg ttcgggcatt tcaaaaataa 1020
ggtatatcaa cttgatgttt atttataaat tgaagttcat agtatacgat tttttttgt 1080 aatataaagt tccatatatg atttatcgcc aggtcttggt attttcgaca tttgcatggg 1140
gttaaaataa atgtcacata taatcacata tttttttttg atgaaatgtc acatagtcat 1200
catcattgtc tagtttgctg acttatttaa ttaggagcat attctttatt aagtacccct 1260
tacggttgca ttatctaatt attgatatgt tcaatttgtt tcttagtgct gttttgttta 1320
taatattatc cgaacactat acactacaat catcgtacat aaattactca attgcaacaa 1380
aaaacaagag gggtcagtct ctgttgatgc attatccaat aacaagagga attagaggat 1440
tagtaggtaa accaaagtta aataaatata acaacaggaa aaaagtcttt gcttgtgacg 1500
aacaccacca taatgcaccc ccacaattta atttttcacc aagaaaaaat cattatagac 1560
aactacactc atgacacata tttaacttct gtgcattgct gctaatcagt ttatttaaat 1620
cactattccc tcaacaaaaa aaaagtttat ttaaatcact agattaattg taataaaaag 1680
tcactttaat aattagttta tgcaatgtct ctaccaattg aactaaactt acggagataa 1740
atatgtagta tttttgaatt caacattctt tatcgaaaga tgaattttat tttaaattta 1800
ttttgtaatg tactagtaat ttaatttcaa aacatattaa tgaattaaat tgattttaga 1860
atatgcaata aaattgtcct aatacaaata tattgaaaat tgttaggttg gacacatgat 1920
caaaattcaa acccaactca cctatttaga aaagaaaaat tcttaaagaa aaacattact 1980
atccatatag gaaaaagtat aatttttatt atcagagtaa atcctatcca gataaaaaaa 2040
aaactgaacc gcactttaag taattgctaa aagtatgcat attctagctt tatttcaatt 2100
tttaagcaac atttagaatt ttgtcaaaaa agataaagca acatttaaaa aagaatatac 2160
ttcttatatt cgctatgcat ttatttaact ttaggcttga ggaataagat aagacttgta 2220
ggcttgagga ataagataag acttgtcaaa aaaaaaaaaa aaacaaaaga ttgggaagta 2280
agaaaaagat aggtaaagat ttttgacctt tggtgaacgt cttaaactaa aataaaataa 2340
aataaaacaa aataaataaa tttcattggt caatcttttt tcctttaact aattaattaa 2400
tataagtgcc acatcagcat gtgaaattcc cattatgtat ctcgtttctt gtctataaat 2460
tgagttagcc accaccttat tttccattca ttcatccctt ctctttacac ccccccctct 2520
tttttgcgtt cactctgttt tcttttcata ggtattctat tctattcttt ctttattatt 2580
tttctttctt tgttactctg tttttcccct gtttctccat caccactgcc acgtcactat 2640
tccaccacct ctgcatgttc tttcttttgt gatcataaga tcaaacacta taccatgatt 2700
ctgatctcat gatatgagtc acacatgttt tcctctgcat gaaaaaatag tgctgagttt 2760
ttttttttta gtatagttct gtttttgttg aattttattc atgttctgtt cttgtgacac 2820
tatacacggt ttcactttga agaacaaggt tctgtcgtta ttattcaaga tacttgttca 2880
agaaacttca tgacacaaca tgcatggcct tgattaaata aaaaacaaaa acaaaaacaa 2940
aactttatac agcctggcat agaacaaaga gattctttct ttgttcgttt cttaaataaa 3000
ttttgttttt aattttatgg ataaacaaac actaacttat gaggtttagt aatgttaaaa 3060
ttctaaaagg aaattattat tctcatgcac tgtttatggt tgaaatctta gttgaaaaaa 3120
gtggaagatt tggtattaat attttatttg acaggtggtt ggtcatggtg ggtcgtaggt 3180
ctttgttgaa aattcataaa ccaattcagt ttttttaaat gtttgtttaa ttgattaatt 3240
tttgtactat gatgttgatc tgttacttaa agtgatgatg aattattttt gttgttgcag 3300
ttgaagattt tca 3313

<210> SEQ ID NO 86
<211> LENGTH: 7588
<212> TYPE: DNA
<213> ORGANISM: Artificial sequence
<220> FEATURE:
<223> OTHER INFORMATION: Plasmid pKR2446

<400> SEQUENCE: 86
tcgagcatgc atctagaggg cccaattcgc cctatagtga gtcgtattac aattcactgg 60
ccgtcgtttt acaacgtcgt gactgggaaa accctggcgt tacccaactt aatcgccttg 120
cagcacatcc ccctttcgcc agctggcgta atagcgaaga ggcccgcacc gatcgccctt 180
cccaacagtt gcgcagccta tacgtacggc agtttaaggt ttacacctat aaaagagaga 240
gccgttatcg tctgtttgtg gatgtacaga gtgatattat tgacacgccg gggcgacgga 300
tggtgatccc cctggccagt gcacgtctgc tgtcagataa agtctcccgt gaactttacc 360
cggtggtgca tatcggggat gaaagctggc gcatgatgac caccgatatg gccagtgtgc 420
cggtctccgt tatcggggaa gaagtggctg atctcagcca ccgcgaaaat gacatcaaaa 480
acgccattaa cctgatgttc tggggaatat aaatgtcagg catgagatta tcaaaaagga 540
tcttcaccta gatccttttc acgtagaaag ccagtccgca gaaacggtgc tgaccccgga 600
tgaatgtcag ctactgggct atctggacaa gggaaaacgc aagcgcaaag agaaagcagg 660
tagcttgcag tgggcttaca tggcgatagc tagactgggc ggttttatgg acagcaagcg 720
aaccggaatt gccagctggg gcgccctctg gtaaggttgg gaagccctgc aaagtaaact 780
ggatggcttt ctcgccgcca aggatctgat ggcgcagggg atcaagctct gatcaagaga 840
caggatgagg atcgtttcgc atgattgaac aagatggatt gcacgcaggt tctccggccg 900
cttgggtgga gaggctattc ggctatgact gggcacaaca gacaatcggc tgctctgatg 960
ccgccgtgtt ccggctgtca gcgcaggggc gcccggttct ttttgtcaag accgacctgt 1020
ccggtgccct gaatgaactg caagacgagg cagcgcggct atcgtggctg gccacgacgg 1080
gcgttccttg cgcagctgtg ctcgacgttg tcactgaagc gggaagggac tggctgctat 1140
tgggcgaagt gccggggcag gatctcctgt catctcacct tgctcctgcc gagaaagtat 1200
ccatcatggc tgatgcaatg cggcggctgc atacgcttga tccggctacc tgcccattcg 1260
accaccaagc gaaacatcgc atcgagcgag cacgtactcg gatggaagcc ggtcttgtcg 1320
atcaggatga tctggacgaa gagcatcagg ggctcgcgcc agccgaactg ttcgccaggc 1380
tcaaggcgag catgcccgac ggcgaggatc tcgtcgtgac ccatggcgat gcctgcttgc 1440
cgaatatcat ggtggaaaat ggccgctttt ctggattcat cgactgtggc cggctgggtg 1500
tggcggaccg ctatcaggac atagcgttgg ctacccgtga tattgctgaa gagcttggcg 1560
gcgaatgggc tgaccgcttc ctcgtgcttt acggtatcgc cgctcccgat tcgcagcgca 1620
tcgccttcta tcgccttctt gacgagttct tctgaattat taacgcttac aatttcctga 1680
tgcggtattt tctccttacg catctgtgcg gtatttcaca ccgcatacag gtggcacttt 1740
tcggggaaat gtgcgcggaa cccctatttg tttatttttc taaatacatt caaatatgta 1800
tccgctcatg agacaataac cctgataaat gcttcaataa tagcacgtga ggagggccac 1860
catggccaag ttgaccagtg ccgttccggt gctcaccgcg cgcgacgtcg ccggagcggt 1920
cgagttctgg accgaccggc tcgggttctc ccgggacttc gtggaggacg acttcgccgg 1980
tgtggtccgg gacgacgtga ccctgttcat cagcgcggtc caggaccagg tggtgccgga 2040
caacaccctg gcctgggtgt gggtgcgcgg cctggacgag ctgtacgccg agtggtcgga 2100
ggtcgtgtcc acgaacttcc gggacgcctc cgggccggcc atgaccgaga tcggcgagca 2160
gccgtggggg cgggagttcg ccctgcgcga cccggccggc aactgcgtgc acttcgtggc 2220
cgaggagcag gactgacacg tgctaaaact tcatttttaa tttaaaagga tctaggtgaa 2280
gatccttttt gataatctca tgaccaaaat cccttaacgt gagttttcgt tccactgagc 2340
gtcagacccc gtagaaaaga tcaaaggatc ttcttgagat cctttttttc tgcgcgtaat 2400
ctgctgcttg caaacaaaaa aaccaccgct accagcggtg gtttgtttgc cggatcaaga 2460
gctaccaact ctttttccga aggtaactgg cttcagcaga gcgcagatac caaatactgt 2520
ccttctagtg tagccgtagt taggccacca cttcaagaac tctgtagcac cgcctacata 2580
cctcgctctg ctaatcctgt taccagtggc tgctgccagt ggcgataagt cgtgtcttac 2640
cgggttggac tcaagacgat agttaccgga taaggcgcag cggtcgggct gaacgggggg 2700
ttcgtgcaca cagcccagct tggagcgaac gacctacacc gaactgagat acctacagcg 2760
tgagctatga gaaagcgcca cgcttcccga agggagaaag gcggacaggt atccggtaag 2820
cggcagggtc ggaacaggag agcgcacgag ggagcttcca gggggaaacg cctggtatct 2880
ttatagtcct gtcgggtttc gccacctctg acttgagcgt cgatttttgt gatgctcgtc 2940
aggggggcgg agcctatgga aaaacgccag caacgcggcc tttttacggt tcctgggctt 3000
ttgctggcct tttgctcaca tgttctttcc tgcgttatcc cctgattctg tggataaccg 3060

```
tattaccgcc tttgagtgag ctgataccgc tcgccgcagc cgaacgaccg agcgcagcga   3120
gtcagtgagc gaggaagcgg aagagcgccc aatacgcaaa ccgcctctcc ccgcgcgttg   3180
gccgattcat taatgcagct ggcacgacag gtttcccgac tggaaagcgg gcagtgagcg   3240
caacgcaatt aatgtgagtt agctcactca ttaggcaccc caggctttac actttatgct   3300
tccggctcgt atgttgtgtg gaattgtgag cggataacaa tttcacacag gaaacagcta   3360
tgaccatgat tacgccaagc tatttaggtg acgcgttaga atactcaagc tatgcatcaa   3420
gcttggtacc gagctcggat ccactagtaa cggccgccag tgtgctggaa ttcaggacgt   3480
acgcctgcag gcagatccga agacatgggt attccagaga cttaaatata gtcatatgtg   3540
taggctttaa tactttgtcg ttttatgcta ttaacatgga tgctgtgagt ttgttcacag   3600
attcatcctt tttgtttttg gcgaattttc attgcatcga tctatcaatt tgaatgaatg   3660
aatatcactt atttttgtaa aaaaaagaag ataaaaaaaa ttaattatat tcttaataat   3720
actcttattt aattattgta tctcaattat tctaattatt ctatctatat aaatatatta   3780
gttattgaaa cttatttata ataaaaagca tgacattttg gaattttctt aaaatgtaag   3840
cataactaca aacgagacta agacgtagaa atagctagaa gttaggaaca agagaagggt   3900
taattgcatt atcatgaatt ctacattgaa gtgtctcata ctctcatctc atataataag   3960
atagacttag aaaataagtc ctgtactaat aataatatgt attgttataa gattatctcg   4020
tctaaagaac tagcattttt tttttttttc ataattaagt tatctcaatt ggaggttatg   4080
tgtatcagac attaaatata aataaattaa tggtcaattt gagatcttgg aatgtgcttc   4140
tttaaagatt ttatgttcaa tttttttttg tgtgtcaaat tcggtggaca agttcatact   4200
gaactttgct ctggcttaga acgggacctc gcaaatgggc agtgggatga ggctactcta   4260
attagtcggt cctagatcgg atatcgagtt ttataaaaat aatataaata aacgattcaa   4320
atgaaatcga aatattagtt cctcaagttg taaatgtcta gctcccttat atttcatcta   4380
gtcttgttga taggactgat attttaaaat gagttctgtt tgtttttatt taattatttc   4440
taaaatgagt tttgtttgct tgacttcgtt tacctcgttt tcttctccgg gttcgggcat   4500
ttcaaaaata aggtatatca acttgatgtt tatttataaa ttgaagttca tagtatacga   4560
tttttttttg taatataaag ttccatatat gatttatcgc caggtcttgg tattttcgac   4620
atttgcatgg ggttaaaata aatgtcacat ataatcacat atttttttttt gatgaaatgt   4680
cacatagtca tcatcattgt ctagtttgct gacttattta attaggagca tattctttat   4740
taagtacccc ttacggttgc attatctaat tattgatatg ttcaatttgt ttcttagtgc   4800
tgttttgttt ataatattat ccgaacacta tacactacaa tcatcgtaca taaattactc   4860
aattgcaaca aaaaacaaga ggggtcagtc tctgttgatg cattatccaa taacaagagg   4920
aattagagga ttagtaggta aaccaaagtt aaataaatat aacaacagga aaaaagtctt   4980
tgcttgtgac gaacaccacc ataatgcacc cccacaattt aatttttcac caagaaaaaa   5040
tcattataga caactacact catgacacat atttaacttc tgtgcattgc tgctaatcag   5100
tttatttaaa tcactattcc ctcaacaaaa aaaaagttta tttaaatcac tagattaatt   5160
gtaataaaaa gtcactttaa taattagttt atgcaatgtc tctaccaatt gaactaaact   5220
tacggagata aatatgtagt atttttgaat tcaacattct ttatcgaaag atgaatttta   5280
ttttaaattt attttgtaat gtactagtaa tttaatttca aaacatatta atgaattaaa   5340
ttgattttag aatatgcaat aaaattgtcc taatacaaat atattgaaaa ttgttaggtt   5400
ggacacatga tcaaaattca aacccaactc acctatttag aaaagaaaaa ttcttaaaga   5460
```

aaaacattac tatccatata ggaaaaagta taatttttat tatcagagta aatcctatcc 5520
agataaaaaa aaaactgaac cgcactttaa gtaattgcta aaagtatgca tattctagct 5580
ttatttcaat ttttaagcaa catttagaat tttgtcaaaa aagataaagc aacatttaaa 5640
aaagaatata cttcttatat tcgctatgca tttatttaac tttaggcttg aggaataaga 5700
taagacttgt aggcttgagg aataagataa gacttgtcaa aaaaaaaaaa aaaacaaaag 5760
attgggaagt aagaaaaaga taggtaaaga tttttgacct ttggtgaacg tcttaaacta 5820
aaataaaata aaataaaaca aaataaataa atttcattgg tcaatctttt ttcctttaac 5880
taattaatta atataagtgc cacatcagca tgtgaaattc ccattatgta tctcgtttct 5940
tgtctataaa ttgagttagc caccacctta ttttccattc attcatccct tctctttaca 6000
cccccccctc ttttttgcgt tcactctgtt ttcttttcat aggtattcta ttctattctt 6060
tctttattat ttttctttct ttgttactct gtttttcccc tgtttctcca tcaccactgc 6120
cacgtcacta ttccaccacc tctgcatgtt ctttctttg tgatcataag atcaaacact 6180
ataccatgat tctgatctca tgatatgagt cacacatgtt ttcctctgca tgaaaaaata 6240
gtgctgagtt tttttttttt agtatagttc tgtttttgtt gaattttatt catgttctgt 6300
tcttgtgaca ctatacacgg tttcactttg aagaacaagg ttctgtcgtt attattcaag 6360
atacttgttc aagaaacttc atgacacaac atgcatggcc ttgattaaat aaaaaacaaa 6420
aacaaaaaca aaactttata cagcctggca tagaacaaag agattctttc tttgttcgtt 6480
tcttaaataa attttgtttt taattttatg gataaacaaa cactaactta tgaggtttag 6540
taatgttaaa attctaaaag gaaattatta ttctcatgca ctgtttatgg ttgaaatctt 6600
agttgaaaaa agtggaagat ttggtattaa tattttattt gacaggtggt tggtcatggt 6660
gggtcgtagg tctttgttga aaattcataa accaattcag tttttttaaa tgtttgttta 6720
attgattaat ttttgtacta tgatgttgat ctgttactta aagtgatgat gaattatttt 6780
tgttgttgca gttgaagatt ttcagcggcc gcatttcgca ccaaatcaat gaaagtaata 6840
atgaaaagtc tgaataagaa tacttaggct tagatgcctt tgttacttgt gtaaaataac 6900
ttgagtcatg tacctttggc ggaaacagaa taaataaaag gtgaaattcc aatgctctat 6960
gtataagtta gtaatactta atgtgttcta cggttgtttc aatatcatca aactctaatt 7020
gaaactttag aaccacaaat ctcaatcttt tcttaatgaa atgaaaaatc ttaattgtac 7080
catgtttatg ttaaacacct tacaattaat tggttggaga ggaggaccaa ccgatgggac 7140
aacattggga gaaagagatt caatggagat ttggatagga gaacaacatt ctttttcact 7200
tcaatacaag atgagtgcaa cactaaggat atgtatgaga ctttcagaag ctacgacaac 7260
atagatgagt gaggtggtga ttcctagcaa gaaagacatt agaggaagcc aaaatcgaac 7320
aaggaagaca tcaagggcaa gagacaggac catccatctc aggaaaagga gctttgggat 7380
agtccgagaa gttgtacaag aaattttttg gagggtgagt gatgcattgc tggtgacttt 7440
aactcaatca aaattgagaa agaaagaaaa gggagggggc tcacatgtga atagaaggga 7500
aacgggagaa ttttacagtt ttgatctaat gggcatccca gctagtggta acatattcac 7560
catgtttaac cttcacgtac gtctagag 7588

<210> SEQ ID NO 87
<211> LENGTH: 9401
<212> TYPE: DNA
<213> ORGANISM: Artificial sequence
<220> FEATURE:

<223> OTHER INFORMATION: Plasmid pKR2457

<400> SEQUENCE: 87
gtacgagatc cggccggcca gatcctgcag gagatccaag cttggcgcgc cgttctatag 60
tgtcacctaa atcgtatgtg tatgatacat aaggttatgt attaattgta gccgcgttct 120
aacgacaata tgtccatatg gtgcactctc agtacaatct gctctgatgc cgcatagtta 180
agccagcccc gacacccgcc aacacccgct gacgcgccct gacgggcttg tctgctcccg 240
gcatccgctt acagacaagc tgtgaccgtc tccgggagct gcatgtgtca gaggttttca 300
ccgtcatcac cgaaacgcgc gagacgaaag ggcctcgtga tacgcctatt tttataggtt 360
aatgtcatga ccaaaatccc ttaacgtgag ttttcgttcc actgagcgtc agaccccgta 420
gaaaagatca aaggatcttc ttgagatcct ttttttctgc gcgtaatctg ctgcttgcaa 480
acaaaaaaac caccgctacc agcggtggtt tgtttgccgg atcaagagct accaactctt 540
tttccgaagg taactggctt cagcagagcg cagataccaa atactgtcct tctagtgtag 600
ccgtagttag gccaccactt caagaactct gtagcaccgc ctacatacct cgctctgcta 660
atcctgttac cagtggctgc tgccagtggc gataagtcgt gtcttaccgg gttggactca 720
agacgatagt taccggataa ggcgcagcgg tcgggctgaa cggggggttc gtgcacacag 780
cccagcttgg agcgaacgac ctacaccgaa ctgagatacc tacagcgtga gcattgagaa 840
agcgccacgc ttcccgaagg gagaaaggcg gacaggtatc cggtaagcgg cagggtcgga 900
acaggagagc gcacgaggga gcttccaggg ggaaacgcct ggtatcttta tagtcctgtc 960
gggtttcgcc acctctgact tgagcgtcga tttttgtgat gctcgtcagg ggggcggagc 1020
ctatggaaaa acgccagcaa cgcggccttt ttacggttcc tggccttttg ctggcctttt 1080
gctcacatgt tctttcctgc gttatcccct gattctgtgg ataaccgtat taccgccttt 1140
gagtgagctg ataccgctcg ccgcagccga acgaccgagc gcagcgagtc agtgagcgag 1200
gaagcggaag agcgcccaat acgcaaaccg cctctccccg cgcgttggcc gattcattaa 1260
tgcaggttga tcgattcgac atcgatctag taacatagat gacaccgcgc gcgataattt 1320
atcctagttt gcgcgctata ttttgttttc tatcgcgtat taaatgtata attgcgggac 1380
tctaatcata aaaacccatc tcataaataa cgtcatgcat tacatgttaa ttattacatg 1440
cttaacgtaa ttcaacagaa attatatgat aatcatcgca agaccggcaa caggattcaa 1500
tcttaagaaa ctttattgcc aaatgtttga acgatctgct tcgacgcact ccttctttag 1560
gtacctcact attcctttgc cctcggacga gtgctggggc gtcggtttcc actatcggcg 1620
agtacttcta cacagccatc ggtccagacg gccgcgcttc tgcgggcgat ttgtgtacgc 1680
ccgacagtcc cggctccgga tcggacgatt gcgtcgcatc gaccctgcgc ccaagctgca 1740
tcatcgaaat tgccgtcaac caagctctga tagagttggt caagaccaat gcggagcata 1800
tacgcccgga gccgcggcga tcctgcaagc tccggatgcc tccgctcgaa gtagcgcgtc 1860
tgctgctcca tacaagccaa ccacggcctc cagaagaaga tgttggcgac ctcgtattgg 1920
gaatccccga acatcgcctc gctccagtca atgaccgctg ttatgcggcc attgtccgtc 1980
aggacattgt tggagccgaa atccgcgtgc acgaggtgcc ggacttcggg gcagtcctcg 2040
gcccaaagca tcagctcatc gagagcctgc gcgacggacg cactgacggt gtcgtccatc 2100
acagtttgcc agtgatacac atggggatca gcaatcgcgc atatgaaatc acgccatgta 2160
gtgtattgac cgattccttg cggtccgaat gggccgaacc cgctcgtctg gctaagatcg 2220
gccgcagcga tcgcatccat ggcctccgcg accggctgca gaacagcggg cagttcggtt 2280
tcaggcaggt cttgcaacgt gacaccctgt gcacggcggg agatgcaata ggtcaggctc 2340
tcgctgaatt ccccaatgtc aagcacttcc ggaatcggga gcgcggccga tgcaaagtgc 2400
cgataaacat aacgatcttt gtagaaacca tcggcgcagc tatttacccg caggacatat 2460
ccacgccctc ctacatcgaa gctgaaagca cgagattctt cgccctccga gagctgcatc 2520
aggtcggaga cgctgtcgaa cttttcgatc agaaacttct cgacagacgt cgcggtgagt 2580
tcaggctttt tcatggttta ataagaagag aaaagagttc ttttgttatg gctgaagtaa 2640
tagagaaatg agctcgagcg tgtcctctcc aaatgaaatg aacttcctta tatagaggaa 2700
gggtcttgcg aaggatagtg ggattgtgcg tcatccctta cgtcagtgga gatgtcacat 2760
caatccactt gctttgaaga cgtggttgga acgtcttctt tttccacgat gctcctcgtg 2820
ggtgggggtc catctttggg accactgtcg gcagaggcat cttgaatgat agcctttcct 2880
ttatcgcaat gatggcattt gtaggagcca ccttcctttt ctactgtcct ttcgatgaag 2940
tgacagatag ctgggcaatg gaatccgagg aggtttcccg aaattatcct ttgttgaaaa 3000
gtctcaatag ccctttggtc ttctgagact gtatctttga catttttgga gtagaccaga 3060
gtgtcgtgct ccaccatgtt gacgaagatt ttcttcttgt cattgagtcg taaaagactc 3120
tgtatgaact gttcgccagt cttcacggcg agttctgtta gatcctcgat ttgaatctta 3180
gactccatgc atggccttag attcagtagg aactaccttt ttagagactc caatctctat 3240
tacttgcctt ggtttatgaa gcaagccttg aatcgtccat actggaatag tacttctgat 3300
cttgagaaat atgtctttct ctgtgttctt gatgcaatta gtcctgaatc ttttgactgc 3360
atctttaacc ttcttgggaa ggtatttgat ctcctggaga ttgttactcg ggtagatcgt 3420
cttgatgaga cctgctgcgt aggcctctct aaccatctgt gggtcagcat tctttctgaa 3480
attgaagagg ctaaccttct cattatcagt ggtgaacata gtgtcgtcac cttcaccttc 3540
gaacttcctt cctagatcgt aaagatagag gaaatcgtcc attgtaatct ccggggcaaa 3600
ggagatctct tttggggctg gatcactgct gggccttttg gttcctagcg tgagccagtg 3660
ggctttttgc tttggtgggc ttgttagggc cttagcaaag ctcttgggct tgagttgagc 3720
ttctcctttg ggatgaagt tcaacctgtc tgtttgctga cttgttgtgt acgcgtcagc 3780
tgctgctctt gcctctgtaa tagtggcaaa tttcttgtgt gcaactccgg gaacgccgtt 3840
tgttgccgcc tttgtacaac cccagtcatc gtatataccg gcatgtggac cgttatacac 3900
aacgtagtag ttgatatgag ggtgttgaat acccgattct gctctgagag gagcaactgt 3960
gctgttaagc tcagattttt gtgggattgg aattggatcg atctcgatcc cgcgaaatta 4020
atacgactca ctatagggag accacaacgg tttccctcta gaaataattt tgtttaactt 4080
taagaaggag atatacccat ggaaaagcct gaactcaccg cgacgtctgt cgagaagttt 4140
ctgatcgaaa agttcgacag cgtctccgac ctgatgcagc tctcggaggg cgaagaatct 4200
cgtgctttca gcttcgatgt aggagggcgt ggatatgtcc tgcgggtaaa tagctgcgcc 4260
gatggtttct acaaagatcg ttatgtttat cggcactttg catcggccgc gctcccgatt 4320
ccggaagtgc ttgacattgg ggaattcagc gagagcctga cctattgcat ctcccgccgt 4380
gcacagggtg tcacgttgca agacctgcct gaaaccgaac tgcccgctgt tctgcagccg 4440
gtcgcggagg ctatggatgc gatcgctgcg gccgatctta gccagacgag cgggttcggc 4500
ccattcggac cgcaaggaat cggtcaatac actacatggc gtgatttcat atgcgcgatt 4560
gctgatcccc atgtgtatca ctggcaaact gtgatggacg acaccgtcag tgcgtccgtc 4620

-continued gcgcaggctc tcgatgagct gatgctttgg gccgaggact gccccgaagt ccggcacctc 4680
gtgcacgcgg atttcggctc caacaatgtc ctgacggaca atggccgcat aacagcggtc 4740
attgactgga gcgaggcgat gttcggggat tcccaatacg aggtcgccaa catcttcttc 4800
tggaggccgt ggttggcttg tatggagcag cagacgcgct acttcgagcg gaggcatccg 4860
gagcttgcag gatcgccgcg gctccgggcg tatatgctcc gcattggtct tgaccaactc 4920
tatcagagct tggttgacgg caatttcgat gatgcagctt gggcgcaggg tcgatgcgac 4980
gcaatcgtcc gatccggagc cgggactgtc gggcgtacac aaatcgcccg cagaagcgcg 5040
gccgtctgga ccgatggctg tgtagaagta ctcgccgata gtggaaaccg acgccccagc 5100
actcgtccga gggcaaagga atagtgaggt acagcttgga tcgatccggc tgctaacaaa 5160
gcccgaaagg aagctgagtt ggctgctgcc accgctgagc aataactagc ataacccctt 5220
ggggcctcta aacgggtctt gaggggtttt ttgctgaaag gaggaactat atccggatga 5280
tcgggcgcgc cgtcgacgga tccgtacgcc tgcaggcaga tccgaagaca tgggtattcc 5340
agagacttaa atatagtcat atgtgtaggc tttaatactt tgtcgtttta tgctattaac 5400
atggatgctg tgagtttgtt cacagattca tcctttttgt tttggcgaa ttttcattgc 5460 atcgatctat caatttgaat gaatgaatat cacttatttt tgtaaaaaaa agaagataaa 5520
aaaaattaat tatattctta ataatactct tatttaatta ttgtatctca attattctaa 5580
ttattctatc tatataaata tattagttat tgaaacttat ttataataaa aagcatgaca 5640
ttttggaatt ttcttaaaat gtaagcataa ctacaaacga gactaagacg tagaaatagc 5700
tagaagttag gaacaagaga agggttaatt gcattatcat gaattctaca ttgaagtgtc 5760
tcatactctc atctcatata ataagataga cttagaaaat aagtcctgta ctaataataa 5820
tatgtattgt tataagatta tctcgtctaa agaactagca tttttttttt ttttcataat 5880
taagttatct caattggagg ttatgtgtat cagacattaa atataaataa attaatggtc 5940
aatttgagat cttggaatgt gcttctttaa agattttatg ttcaattttt ttttgtgtgt 6000
caaattcggt ggacaagttc atactgaact ttgctctggc ttagaacggg acctcgcaaa 6060
tgggcagtgg gatgaggcta ctctaattag tcggtcctag atcggatatc gagttttata 6120
aaaataatat aaataaacga ttcaaatgaa atcgaaatat tagttcctca agttgtaaat 6180
gtctagctcc cttatatttc atctagtctt gttgatagga ctgatatttt aaaatgagtt 6240
ctgtttgttt ttatttaatt atttctaaaa tgagttttgt ttgcttgact tcgtttacct 6300
cgttttcttc tccgggttcg ggcatttcaa aaataaggta tatcaacttg atgtttattt 6360
ataaattgaa gttcatagta tacgattttt ttttgtaata taaagttcca tatatgattt 6420
atcgccaggt cttggtattt tcgacatttg catggggtta aaataaatgt cacatataat 6480
cacatatttt tttttgatga aatgtcacat agtcatcatc attgtctagt ttgctgactt 6540
atttaattag gagcatattc tttattaagt accccttacg gttgcattat ctaattattg 6600
atatgttcaa tttgtttctt agtgctgttt tgtttataat attatccgaa cactatacac 6660
tacaatcatc gtacataaat tactcaattg caacaaaaaa caagaggggt cagtctctgt 6720
tgatgcatta tccaataaca agaggaatta gaggattagt aggtaaacca aagttaaata 6780
aatataacaa caggaaaaaa gtctttgctt gtgacgaaca ccaccataat gcaccccccac 6840 aatttaattt ttcaccaaga aaaaatcatt atagacaact acactcatga cacatattta 6900
acttctgtgc attgctgcta atcagtttat ttaaatcact attccctcaa caaaaaaaaa 6960
gtttatttaa atcactagat taattgtaat aaaaagtcac tttaataatt agtttatgca 7020
atgtctctac caattgaact aaacttacgg agataaatat gtagtatttt tgaattcaac 7080
attctttatc gaaagatgaa ttttatttta aatttatttt gtaatgtact agtaatttaa 7140
tttcaaaaca tattaatgaa ttaaattgat tttagaatat gcaataaaat tgtcctaata 7200
caaatatatt gaaaattgtt aggttggaca catgatcaaa attcaaaccc aactcaccta 7260
tttagaaaag aaaaattctt aaagaaaaac attactatcc atataggaaa aagtataatt 7320
tttattatca gagtaaatcc tatccagata aaaaaaaaac tgaaccgcac tttaagtaat 7380
tgctaaaagt atgcatattc tagctttatt tcaattttta agcaacattt agaattttgt 7440
caaaaaagat aaagcaacat ttaaaaaaga atatacttct tatattcgct atgcatttat 7500
ttaactttag gcttgaggaa taagataaga cttgtaggct tgaggaataa gataagactt 7560
gtcaaaaaaa aaaaaaaaac aaaagattgg gaagtaagaa aaagataggt aaagattttt 7620
gacctttggt gaacgtctta aactaaaata aaataaaata aaacaaaata aataaatttc 7680
attggtcaat ctttttttcct ttaactaatt aattaatata agtgccacat cagcatgtga 7740
aattcccatt atgtatctcg tttcttgtct ataaattgag ttagccacca ccttattttc 7800
cattcattca tcccttctct ttacaccccc ccctcttttt tgcgttcact ctgttttctt 7860
ttcataggta ttctattcta ttctttcttt attattttc tttctttgtt actctgtttt 7920
tcccctgttt ctccatcacc actgccacgt cactattcca ccacctctgc atgttctttc 7980
ttttgtgatc ataagatcaa acactatacc atgattctga tctcatgata tgagtcacac 8040
atgttttcct ctgcatgaaa aaatagtgct gagttttttt tttttagtat agttctgttt 8100
ttgttgaatt ttattcatgt tctgttcttg tgacactata cacggtttca ctttgaagaa 8160
caaggttctg tcgttattat tcaagatact tgttcaagaa acttcatgac acaacatgca 8220
tggccttgat taaataaaaa acaaaaacaa aaacaaaact ttatacagcc tggcatagaa 8280
caaagagatt ctttctttgt tcgtttctta aataaatttt gtttttaatt tttatggataa 8340
acaaacacta acttatgagg tttagtaatg ttaaaattct aaaaggaaat tattattctc 8400
atgcactgtt tatggttgaa atcttagttg aaaaaagtgg aagatttggt attaatattt 8460
tatttgacag gtggttggtc atggtgggtc gtaggtcttt gttgaaaatt cataaaccaa 8520
ttcagttttt ttaaatgttt gtttaattga ttaatttttg tactatgatg ttgatctgtt 8580
acttaaagtg atgatgaatt atttttgttg ttgcagttga agattttcag cggccgcatt 8640
tcgcaccaaa tcaatgaaag taataatgaa aagtctgaat aagaatactt aggcttagat 8700
gcctttgtta cttgtgtaaa ataacttgag tcatgtacct ttggcggaaa cagaataaat 8760
aaaaggtgaa attccaatgc tctatgtata agttagtaat acttaatgtg ttctacggtt 8820
gtttcaatat catcaaactc taattgaaac tttagaacca caaatctcaa tcttttctta 8880
atgaaatgaa aaatcttaat tgtaccatgt ttatgttaaa caccttacaa ttaattggtt 8940
ggagaggagg accaaccgat gggacaacat tgggagaaag agattcaatg gagatttgga 9000
taggagaaca acattctttt tcacttcaat acaagatgag tgcaacacta aggatatgta 9060
tgagactttc agaagctacg acaacataga tgagtgaggt ggtgattcct agcaagaaag 9120
acattagagg aagccaaaat cgaacaagga agacatcaag ggcaagagac aggaccatcc 9180
atctcaggaa aaggagcttt gggatagtcc gagaagttgt acaagaaatt ttttggaggg 9240
tgagtgatgc attgctggtg actttaactc aatcaaaatt gagaaagaaa gaaaagggag 9300
ggggctcaca tgtgaataga agggaaacgg gagaatttta cagttttgat ctaatgggca 9360
tcccagctag tggtaacata ttcaccatgt ttaaccttca c 9401

<210> SEQ ID NO 88
<211> LENGTH: 10648
<212> TYPE: DNA
<213> ORGANISM: Artificial sequence
<220> FEATURE:
<223> OTHER INFORMATION: Plasmid pKR2461

<400> SEQUENCE: 88
ggccgcattt cgcaccaaat caatgaaagt aataatgaaa agtctgaata agaatactta 60
ggcttagatg cctttgttac ttgtgtaaaa taacttgagt catgtacctt tggcggaaac 120
agaataaata aaaggtgaaa ttccaatgct ctatgtataa gttagtaata cttaatgtgt 180
tctacggttg tttcaatatc atcaaactct aattgaaact ttagaaccac aaatctcaat 240
cttttcttaa tgaaatgaaa aatcttaatt gtaccatgtt tatgttaaac accttacaat 300
taattggttg gagaggagga ccaaccgatg ggacaacatt gggagaaaga gattcaatgg 360
agatttggat aggagaacaa cattcttttt cacttcaata caagatgagt gcaacactaa 420
ggatatgtat gagactttca gaagctacga caacatagat gagtgaggtg gtgattccta 480
gcaagaaaga cattagagga agccaaaatc gaacaaggaa gacatcaagg gcaagagaca 540
ggaccatcca tctcaggaaa aggagctttg ggatagtccg agaagttgta caagaaattt 600
tttggagggt gagtgatgca ttgctggtga ctttaactca atcaaaattg agaaagaaag 660
aaaagggagg gggctcacat gtgaatagaa gggaaacggg agaattttac agttttgatc 720
taatgggcat cccagctagt ggtaacatat tcaccatgtt taaccttcac gtacgagatc 780
cggccggcca gatcctgcag gagatccaag cttggcgcgc cgttctatag tgtcacctaa 840
atcgtatgtg tatgatacat aaggttatgt attaattgta gccgcgttct aacgacaata 900
tgtccatatg gtgcactctc agtacaatct gctctgatgc cgcatagtta agccagcccc 960
gacacccgcc aacacccgct gacgcgccct gacgggcttg tctgctcccg gcatccgctt 1020
acagacaagc tgtgaccgtc tccgggagct gcatgtgtca gaggttttca ccgtcatcac 1080
cgaaacgcgc gagacgaaag ggcctcgtga tacgcctatt tttataggtt aatgtcatga 1140
ccaaaatccc ttaacgtgag ttttcgttcc actgagcgtc agaccccgta gaaaagatca 1200
aaggatcttc ttgagatcct ttttttctgc gcgtaatctg ctgcttgcaa acaaaaaaac 1260
caccgctacc agcggtggtt tgtttgccgg atcaagagct accaactctt tttccgaagg 1320
taactggctt cagcagagcg cagataccaa atactgtcct tctagtgtag ccgtagttag 1380
gccaccactt caagaactct gtagcaccgc ctacatacct cgctctgcta atcctgttac 1440
cagtggctgc tgccagtggc gataagtcgt gtcttaccgg gttggactca agacgatagt 1500
taccggataa ggcgcagcgg tcgggctgaa cggggggttc gtgcacacag cccagcttgg 1560
agcgaacgac ctacaccgaa ctgagatacc tacagcgtga gcattgagaa agcgccacgc 1620
ttcccgaagg gagaaaggcg gacaggtatc cggtaagcgg cagggtcgga acaggagagc 1680
gcacgaggga gcttccaggg ggaaacgcct ggtatcttta tagtcctgtc gggtttcgcc 1740
acctctgact tgagcgtcga tttttgtgat gctcgtcagg ggggcggagc ctatggaaaa 1800
acgccagcaa cgcggccttt ttacggttcc tggccttttg ctggcctttt gctcacatgt 1860
tctttcctgc gttatcccct gattctgtgg ataaccgtat taccgccttt gagtgagctg 1920
ataccgctcg ccgcagccga acgaccgagc gcagcgagtc agtgagcgag gaagcggaag 1980
agcgcccaat acgcaaaccg cctctccccg cgcgttggcc gattcattaa tgcaggttga 2040

-continued

```
tcgattcgac atcgatctag taacatagat gacaccgcgc gcgataattt atcctagttt   2100
gcgcgctata ttttgttttc tatcgcgtat taaatgtata attgcgggac tctaatcata   2160
aaaacccatc tcataaataa cgtcatgcat tacatgttaa ttattacatg cttaacgtaa   2220
ttcaacagaa attatatgat aatcatcgca agaccggcaa caggattcaa tcttaagaaa   2280
ctttattgcc aaatgtttga acgatctgct tcgacgcact ccttctttag gtacctcact   2340
attcctttgc cctcggacga gtgctggggc gtcggtttcc actatcggcg agtacttcta   2400
cacagccatc ggtccagacg gccgcgcttc tgcgggcgat ttgtgtacgc ccgacagtcc   2460
cggctccgga tcggacgatt gcgtcgcatc gaccctgcgc ccaagctgca tcatcgaaat   2520
tgccgtcaac caagctctga tagagttggt caagaccaat gcggagcata tacgcccgga   2580
gccgcggcga tcctgcaagc tccggatgcc tccgctcgaa gtagcgcgtc tgctgctcca   2640
tacaagccaa ccacggcctc cagaagaaga tgttggcgac ctcgtattgg gaatccccga   2700
acatcgcctc gctccagtca atgaccgctg ttatgcggcc attgtccgtc aggacattgt   2760
tggagccgaa atccgcgtgc acgaggtgcc ggacttcggg gcagtcctcg gcccaaagca   2820
tcagctcatc gagagcctgc gcgacggacg cactgacggt gtcgtccatc acagtttgcc   2880
agtgatacac atggggatca gcaatcgcgc atatgaaatc acgccatgta gtgtattgac   2940
cgattccttg cggtccgaat gggccgaacc cgctcgtctg gctaagatcg gccgcagcga   3000
tcgcatccat ggcctccgcg accggctgca gaacagcggg cagttcggtt tcaggcaggt   3060
cttgcaacgt gacaccctgt gcacggcggg agatgcaata ggtcaggctc tcgctgaatt   3120
ccccaatgtc aagcacttcc ggaatcggga gcgcggccga tgcaaagtgc cgataaacat   3180
aacgatcttt gtagaaacca tcggcgcagc tatttacccg caggacatat ccacgccctc   3240
ctacatcgaa gctgaaagca cgagattctt cgccctccga gagctgcatc aggtcggaga   3300
cgctgtcgaa cttttcgatc agaaacttct cgacagacgt cgcggtgagt tcaggctttt   3360
tcatggttta ataagaagag aaaagagttc ttttgttatg gctgaagtaa tagagaaatg   3420
agctcgagcg tgtcctctcc aaatgaaatg aacttcctta tatagaggaa gggtcttgcg   3480
aaggatagtg ggattgtgcg tcatccctta cgtcagtgga gatgtcacat caatccactt   3540
gctttgaaga cgtggttgga acgtcttctt tttccacgat gctcctcgtg ggtgggggtc   3600
catctttggg accactgtcg gcagaggcat cttgaatgat agcctttcct ttatcgcaat   3660
gatggcattt gtaggagcca ccttcctttt ctactgtcct ttcgatgaag tgacagatag   3720
ctgggcaatg gaatccgagg aggtttcccg aaattatcct ttgttgaaaa gtctcaatag   3780
ccctttggtc ttctgagact gtatctttga catttttgga gtagaccaga gtgtcgtgct   3840
ccaccatgtt gacgaagatt ttcttcttgt cattgagtcg taaaagactc tgtatgaact   3900
gttcgccagt cttcacggcg agttctgtta gatcctcgat ttgaatctta gactccatgc   3960
atggccttag attcagtagg aactaccttt ttagagactc caatctctat tacttgcctt   4020
ggtttatgaa gcaagccttg aatcgtccat actggaatag tacttctgat cttgagaaat   4080
atgtctttct ctgtgttctt gatgcaatta gtcctgaatc ttttgactgc atctttaacc   4140
ttcttgggaa ggtatttgat ctcctggaga ttgttactcg ggtagatcgt cttgatgaga   4200
cctgctgcgt aggcctctct aaccatctgt gggtcagcat tctttctgaa attgaagagg   4260
ctaaccttct cattatcagt ggtgaacata gtgtcgtcac cttcaccttc gaacttcctt   4320
cctagatcgt aaagatagag gaaatcgtcc attgtaatct ccggggcaaa ggagatctct   4380
```

```
tttggggctg gatcactgct gggccttttg gttcctagcg tgagccagtg ggctttttgc   4440
tttggtgggc ttgttagggc cttagcaaag ctcttgggct tgagttgagc ttctcctttg   4500
gggatgaagt tcaacctgtc tgtttgctga cttgttgtgt acgcgtcagc tgctgctctt   4560
gcctctgtaa tagtggcaaa tttcttgtgt gcaactccgg gaacgccgtt tgttgccgcc   4620
tttgtacaac cccagtcatc gtatataccg gcatgtggac cgttatacac aacgtagtag   4680
ttgatatgag ggtgttgaat acccgattct gctctgagag gagcaactgt gctgttaagc   4740
tcagattttt gtgggattgg aattggatcg atctcgatcc cgcgaaatta atacgactca   4800
ctatagggag accacaacgg tttccctcta gaaataattt tgtttaactt taagaaggag   4860
atatacccat ggaaaagcct gaactcaccg cgacgtctgt cgagaagttt ctgatcgaaa   4920
agttcgacag cgtctccgac ctgatgcagc tctcggaggg cgaagaatct cgtgctttca   4980
gcttcgatgt aggagggcgt ggatatgtcc tgcgggtaaa tagctgcgcc gatggtttct   5040
acaaagatcg ttatgtttat cggcactttg catcggccgc gctcccgatt ccggaagtgc   5100
ttgacattgg ggaattcagc gagagcctga cctattgcat ctcccgccgt gcacagggtg   5160
tcacgttgca agacctgcct gaaaccgaac tgcccgctgt tctgcagccg gtcgcggagg   5220
ctatggatgc gatcgctgcg gccgatctta gccagacgag cgggttcggc ccattcggac   5280
cgcaaggaat cggtcaatac actacatggc gtgatttcat atgcgcgatt gctgatcccc   5340
atgtgtatca ctggcaaact gtgatggacg acaccgtcag tgcgtccgtc gcgcaggctc   5400
tcgatgagct gatgctttgg gccgaggact gccccgaagt ccggcacctc gtgcacgcgg   5460
atttcggctc caacaatgtc ctgacggaca atggccgcat aacagcggtc attgactgga   5520
gcgaggcgat gttcggggat tcccaatacg aggtcgccaa catcttcttc tggaggccgt   5580
ggttggcttg tatggagcag cagacgcgct acttcgagcg gaggcatccg gagcttgcag   5640
gatcgccgcg gctccgggcg tatatgctcc gcattggtct tgaccaactc tatcagagct   5700
tggttgacgg caatttcgat gatgcagctt gggcgcaggg tcgatgcgac gcaatcgtcc   5760
gatccggagc cgggactgtc gggcgtacac aaatcgcccg cagaagcgcg gccgtctgga   5820
ccgatggctg tgtagaagta ctcgccgata gtggaaaccg acgccccagc actcgtccga   5880
gggcaaagga atagtgaggt acagcttgga tcgatccggc tgctaacaaa gcccgaaagg   5940
aagctgagtt ggctgctgcc accgctgagc aataactagc ataacccctt ggggcctcta   6000
aacgggtctt gaggggtttt ttgctgaaag gaggaactat atccggatga tcgggcgcgc   6060
cgtcgacgga tccgtacgcc tgcaggcaga tccgaagaca tgggtattcc agagacttaa   6120
atatagtcat atgtgtaggc tttaatactt tgtcgtttta tgctattaac atggatgctg   6180
tgagtttgtt cacagattca tcctttttgt tttggcgaa ttttcattgc atcgatctat   6240
caatttgaat gaatgaatat cacttatttt tgtaaaaaaa agaagataaa aaaaattaat   6300
tatattctta ataatactct tatttaatta ttgtatctca attattctaa ttattctatc   6360
tatataaata tattagttat tgaaacttat ttataataaa aagcatgaca ttttggaatt   6420
ttcttaaaat gtaagcataa ctacaaacga gactaagacg tagaaatagc tagaagttag   6480
gaacaagaga agggttaatt gcattatcat gaattctaca ttgaagtgtc tcatactctc   6540
atctcatata ataagataga cttagaaaat aagtcctgta ctaataataa tatgtattgt   6600
tataagatta tctcgtctaa agaactagca tttttttttt ttttcataat taagttatct   6660
caattggagg ttatgtgtat cagacattaa atataaataa attaatggtc aatttgagat   6720
cttggaatgt gcttctttaa agattttatg ttcaattttt ttttgtgtgt caaattcggt   6780
```

```
ggacaagttc atactgaact ttgctctggc ttagaacggg acctcgcaaa tgggcagtgg   6840
gatgaggcta ctctaattag tcggtcctag atcggatatc gagttttata aaaataatat   6900
aaataaacga ttcaaatgaa atcgaaatat tagttcctca agttgtaaat gtctagctcc   6960
cttatatttc atctagtctt gttgatagga ctgatatttt aaaatgagtt ctgtttgttt   7020
ttatttaatt atttctaaaa tgagttttgt ttgcttgact tcgtttacct cgttttcttc   7080
tccgggttcg ggcatttcaa aaataaggta tatcaacttg atgtttattt ataaattgaa   7140
gttcatagta tacgattttt ttttgtaata taaagttcca tatatgattt atcgccaggt   7200
cttggtattt tcgacatttg catggggtta aaataaatgt cacatataat cacatatttt   7260
tttttgatga aatgtcacat agtcatcatc attgtctagt ttgctgactt atttaattag   7320
gagcatattc tttattaagt accccttacg gttgcattat ctaattattg atatgttcaa   7380
tttgtttctt agtgctgttt tgtttataat attatccgaa cactatacac tacaatcatc   7440
gtacataaat tactcaattg caacaaaaaa caagaggggt cagtctctgt tgatgcatta   7500
tccaataaca agaggaatta gaggattagt aggtaaacca aagttaaata aatataacaa   7560
caggaaaaaa gtctttgctt gtgacgaaca ccaccataat gcaccccccac aatttaattt   7620
ttcaccaaga aaaaatcatt atagacaact acactcatga cacatattta acttctgtgc   7680
attgctgcta atcagtttat ttaaatcact attccctcaa caaaaaaaaa gtttatttaa   7740
atcactagat taattgtaat aaaaagtcac tttaataatt agtttatgca atgtctctac   7800
caattgaact aaacttacgg agataaatat gtagtatttt tgaattcaac attctttatc   7860
gaaagatgaa ttttatttta aatttatttt gtaatgtact agtaatttaa tttcaaaaca   7920
tattaatgaa ttaaattgat tttagaatat gcaataaaat tgtcctaata caaatatatt   7980
gaaaattgtt aggttggaca catgatcaaa attcaaaccc aactcaccta tttagaaaag   8040
aaaaattctt aaagaaaaac attactatcc atataggaaa aagtataatt tttattatca   8100
gagtaaatcc tatccagata aaaaaaaaac tgaaccgcac tttaagtaat tgctaaaagt   8160
atgcatattc tagctttatt tcaattttta agcaacattt agaattttgt caaaaaagat   8220
aaagcaacat ttaaaaaaga atatacttct tatattcgct atgcatttat ttaactttag   8280
gcttgaggaa taagataaga cttgtaggct tgaggaataa gataagactt gtcaaaaaaa   8340
aaaaaaaaac aaaagattgg gaagtaagaa aaagataggt aaagattttt gacctttggt   8400
gaacgtctta aactaaaata aaataaaata aaacaaaata aataaatttc attggtcaat   8460
ctttttttcct ttaactaatt aattaatata agtgccacat cagcatgtga aattcccatt   8520
atgtatctcg tttcttgtct ataaattgag ttagccacca ccttattttc cattcattca   8580
tcccttctct ttacacccccc ccctcttttt tgcgttcact ctgttttctt ttcataggta   8640
ttctattcta ttctttcttt attatttttc tttctttgtt actctgtttt tcccctgttt   8700
ctccatcacc actgccacgt cactattcca ccacctctgc atgttctttc ttttgtgatc   8760
ataagatcaa acactatacc atgattctga tctcatgata tgagtcacac atgttttcct   8820
ctgcatgaaa aaatagtgct gagttttttt tttttagtat agttctgttt ttgttgaatt   8880
ttattcatgt tctgttcttg tgacactata cacggtttca ctttgaagaa caaggttctg   8940
tcgttattat tcaagatact tgttcaagaa acttcatgac acaacatgca tggccttgat   9000
taaataaaaa acaaaaacaa aaacaaaact ttatacagcc tggcatagaa caaagagatt   9060
ctttctttgt tcgtttctta aataaatttt gtttttaatt ttatggataa acaaacacta   9120
```

```
acttatgagg tttagtaatg ttaaaattct aaaaggaaat tattattctc atgcactgtt   9180
tatggttgaa atcttagttg aaaaaagtgg aagatttggt attaatattt tatttgacag   9240
gtggttggtc atggtgggtc gtaggtcttt gttgaaaatt cataaaccaa ttcagttttt   9300
ttaaatgttt gtttaattga ttaatttttg tactatgatg ttgatctgtt acttaaagtg   9360
atgatgaatt atttttgttg ttgcagttga agattttcag cggccgcatg aagaggtctc   9420
cagcatcttc ttgttcatca tctacttcct ctgttgggtt tgaagctccc attgaaaaaa   9480
gaaggcctaa gcatccaagg aggaataatt tgaagtcaca aaaatgcaag cagaaccaaa   9540
ccaccactgg tggcagaaga agctctatct atagaggagt tacaaggcat aggtggacag   9600
ggaggtttga agctcaccta tgggataaga gctcttggaa caacattcag agcaagaagg   9660
gtcgacaagt ttatttgggg gcatatgata ctgaagaatc tgcagcccgt acctatgacc   9720
ttgcagccct taaatactgg ggaaaagatg caaccctgaa tttcccgata gaaacttata   9780
ccaaggagct cgaggaaatg gacaaggttt caagagaaga atatttggct tctttgcggc   9840
gccaaagcag tggcttttct agaggcctgt ctaagtaccg tggggttgct aggcatcatc   9900
ataatggtcg ctgggaagca cgaattggaa gagtatgcgg aaacaagtac ctctacttgg   9960
ggacatataa aactcaagag gaggcagcag tggcatatga catggcagca atagagtacc  10020
gtggagtcaa tgcagtgacc aattttgaca taagcaacta catggacaaa ataaagaaga  10080
aaaatgacca aacccaacaa caacaaacag aagcacaaac ggaaacagtt cctaactcct  10140
ctgactctga agaagtagaa gtagaacaac agacaacaac aataaccaca ccaccccccat  10200
ctgaaaatct gcacatgcca ccacagcagc accaagttca atacaccccc catgtctctc  10260
caagggaaga agaatcatca tcactgatca caattatgga ccatgtgctt gagcaggatc  10320
tgccatggag cttcatgtac actggcttgt ctcagtttca agatccaaac ttggctttct  10380
gcaaaggtga tgatgacttg gtgggcatgt ttgatagtgc agggtttgag gaagacattg  10440
attttctgtt cagcactcaa cctggtgatg agactgagag tgatgtcaac aatatgagcg  10500
cagttttgga tagtgttgag tgtggagaca caaatggggc tggtggaagc atgatgcatg  10560
tggataacaa gcagaagata gtatcatttg cttcttcacc atcatctaca actacagttt  10620
cttgtgacta tgctctagat ctatgagc                                     10648
```

<210> SEQ ID NO 89
<211> LENGTH: 14004
<212> TYPE: DNA
<213> ORGANISM: Artificial sequence
<220> FEATURE:
<223> OTHER INFORMATION: Plasmid pKR2465

<400> SEQUENCE: 89

```
ggagatccaa gcttttgatc catgcccttc atttgccgct tattaattaa tttggtaaca     60
gtccgtacta atcagttact tatccttccc ccatcataat taatcttggt agtctcgaat    120
gccacaacac tgactagtct cttggatcat aagaaaaagc caaggaacaa aagaagacaa    180
aacacaatga gagtatcctt tgcatagcaa tgtctaagtt cataaaattc aaacaaaaac    240
gcaatcacac acagtggaca tcacttatcc actagctgat caggatcgcc gcgtcaagaa    300
aaaaaaactg gaccccaaaa gccatgcaca acaacacgta ctcacaaagg tgtcaatcga    360
gcagcccaaa acattcacca actcaaccca tcatgagccc tcacatttgt tgtttctaac    420
ccaacctcaa actcgtattc tcttccgcca cctcattttt gtttatttca acacccgtca    480
aactgcatgc caccccgtgg ccaaatgtcc atgcatgtta acaagaccta tgactataaa    540
```

```
tagctgcaat ctcggcccag gttttcatca tcaagaacca gttcaatatc ctagtacacc    600
gtattaaaga atttaagata tactgcggcc gcaacatgac tatcgactca caatactaca    660
agtcgcgaga caaaaacgac acggcaccca aaatcgcggg aatccgatat gccccgctat    720
cgacaccatt actcaaccga tgtgagacct tctctctggt ctggcacatt ttcagcattc    780
ccactttcct cacaattttc atgctatgct gcgcaattcc actgctctgg ccatttgtga    840
ttgcgtatgt agtgtacgct gttaaagacg actccccgtc caacggagga gtggtcaagc    900
gatactcgcc tatttcaaga aacttcttca tctggaagct ctttggccgc tacttcccca    960
taactctgca caagacggtg gatctggagc ccacgcacac atactaccct ctggacgtcc   1020
aggagtatca cctgattgct gagagatact ggccgcagaa caagtacctc cgagcaatca   1080
tcaccaccat cgagtacttt ctgcccgcct tcatgaaacg gtctctttct atcaacgagc   1140
aggagcagcc tgccgagcga gatcctctcc tgtctcccgt ttctcccagc tctccgggtt   1200
ctcaacctga caagtggatt aaccacgaca gcagatatag ccgtggagaa tcatctggct   1260
ccaacggcca cgcctcgggc tccgaactta acggcaacgg caacaacggc accactaacc   1320
gacgaccttt gtcgtccgcc tctgctggct ccactgcatc tgattccacg cttcttaacg   1380
ggtccctcaa ctcctacgcc aaccagatca ttggcgaaaa cgacccacag ctgtcgccca   1440
caaaactcaa gcccactggc agaaaataca tcttcggcta ccacccccac ggcattatcg   1500
gcatgggagc ctttggtgga attgccaccg agggagctgg atggtccaag ctctttccgg   1560
gcatccctgt ttctcttatg actctcacca acaacttccg agtgcctctc tacagagagt   1620
acctcatgag tctgggagtc gcttctgtct ccaagaagtc ctgcaaggcc ctcctcaagc   1680
gaaaccagtc tatctgcatt gtcgttggtg gagcacagga aagtcttctg gccagacccg   1740
gtgtcatgga cctggtgcta ctcaagcgaa agggttttgt tcgacttggt atggaggtcg   1800
gaaatgtcgc ccttgttccc atcatggcct ttggtgagaa cgacctctat gaccaggtta   1860
gcaacgacaa gtcgtccaag ctgtaccgat tccagcagtt tgtcaagaac ttccttggat   1920
tcacccttcc tttgatgcat gcccgaggcg tcttcaacta cgatgtcggt cttgtcccct   1980
acaggcgacc cgtcaacatt gtggttggtt cccccattga cttgccttat ctcccacacc   2040
ccaccgacga agaagtgtcc gaataccacg accgatacat cgccgagctg cagcgaatct   2100
acaacgagca caaggatgaa tatttcatcg attggaccga ggagggcaaa ggagccccag   2160
agttccgaat gattgagtaa gcggccgcaa gtatgaacta aaatgcatgt aggtgtaaga   2220
gctcatggag agcatggaat attgtatccg accatgtaac agtataataa ctgagctcca   2280
tctcacttct tctatgaata aacaaaggat gttatgatat attaacactc tatctatgca   2340
ccttattgtt ctatgataaa tttcctctta ttattataaa tcatctgaat cgtgacggct   2400
tatggaatgc ttcaaatagt acaaaaacaa atgtgtacta taagactttc taaacaattc   2460
taaccttagc attgtgaacg agacataagt gttaagaaga cataacaatt ataatggaag   2520
aagtttgtct ccatttatat attatatatt acccacttat gtattatatt aggatgttaa   2580
ggagacataa caattataaa gagagaagtt tgtatccatt tatatattat atactaccca   2640
tttatatatt atacttatcc acttatttaa tgtctttata aggtttgatc catgatattt   2700
ctaatatttt agttgatatg tatatgaaag ggtactattt gaactctctt actctgtata   2760
aaggttggat catccttaaa gtgggtctat ttaattttat tgcttcttac agataaaaaa   2820
aaaattatga gttggtttga taaaatattg aaggatttaa aataataata aataacatat   2880
```

```
aatatatgta tataaattta ttataatata acatttatct ataaaaaagt aaatattgtc   2940
ataaatctat acaatcgttt agccttgctg gacgaatctc aattatttaa acgagagtaa   3000
acatatttga ctttttggtt atttaacaaa ttattattta acactatatg aaattttttt   3060
ttttatcagc aaagaataaa attaaattaa gaaggacaat ggtgtcccaa tccttataca   3120
accaacttcc acaagaaagt caagtcagag acaacaaaaa aacaagcaaa ggaaattttt   3180
taatttgagt tgtcttgttt gctgcataat ttatgcagta aaacactaca cataaccctt   3240
ttagcagtag agcaatggtt gaccgtgtgc ttagcttctt ttattttatt tttttatcag   3300
caaagaataa ataaaataaa atgagacact tcagggatgt ttcaacaagc ttggcgcgcc   3360
gttctatagt gtcacctaaa tcgtatgtgt atgatacata aggttatgta ttaattgtag   3420
ccgcgttcta acgacaatat gtccatatgg tgcactctca gtacaatctg ctctgatgcc   3480
gcatagttaa gccagccccg acacccgcca acacccgctg acgcgccctg acgggcttgt   3540
ctgctcccgg catccgctta cagacaagct gtgaccgtct ccgggagctg catgtgtcag   3600
aggttttcac cgtcatcacc gaaacgcgcg agacgaaagg gcctcgtgat acgcctattt   3660
ttataggtta atgtcatgac caaaatccct taacgtgagt tttcgttcca ctgagcgtca   3720
gaccccgtag aaaagatcaa aggatcttct tgagatcctt tttttctgcg cgtaatctgc   3780
tgcttgcaaa caaaaaaacc accgctacca gcggtggttt gtttgccgga tcaagagcta   3840
ccaactcttt ttccgaaggt aactggcttc agcagagcgc agataccaaa tactgtcctt   3900
ctagtgtagc cgtagttagg ccaccacttc aagaactctg tagcaccgcc tacatacctc   3960
gctctgctaa tcctgttacc agtggctgct gccagtggcg ataagtcgtg tcttaccggg   4020
ttggactcaa gacgatagtt accggataag gcgcagcggt cgggctgaac ggggggttcg   4080
tgcacacagc ccagcttgga gcgaacgacc tacaccgaac tgagatacct acagcgtgag   4140
cattgagaaa gcgccacgct tcccgaaggg agaaaggcgg acaggtatcc ggtaagcggc   4200
agggtcggaa caggagagcg cacgagggag cttccagggg gaaacgcctg gtatctttat   4260
agtcctgtcg ggtttcgcca cctctgactt gagcgtcgat ttttgtgatg ctcgtcaggg   4320
gggcggagcc tatggaaaaa cgccagcaac gcggcctttt tacggttcct ggccttttgc   4380
tggccttttg ctcacatgtt ctttcctgcg ttatcccctg attctgtgga taaccgtatt   4440
accgcctttg agtgagctga taccgctcgc cgcagccgaa cgaccgagcg cagcgagtca   4500
gtgagcgagg aagcggaaga gcgcccaata cgcaaaccgc ctctccccgc gcgttggccg   4560
attcattaat gcaggttgat cgattcgaca tcgatctagt aacatagatg acaccgcgcg   4620
cgataattta tcctagtttg cgcgctatat tttgttttct atcgcgtatt aaatgtataa   4680
ttgcgggact ctaatcataa aaacccatct cataaataac gtcatgcatt acatgttaat   4740
tattacatgc ttaacgtaat tcaacagaaa ttatatgata atcatcgcaa gaccggcaac   4800
aggattcaat cttaagaaac tttattgcca aatgtttgaa cgatctgctt cgacgcactc   4860
cttctttagg tacctcacta ttcctttgcc ctcggacgag tgctggggcg tcggtttcca   4920
ctatcggcga gtacttctac acagccatcg gtccagacgg ccgcgcttct gcgggcgatt   4980
tgtgtacgcc cgacagtccc ggctccggat cggacgattg cgtcgcatcg accctgcgcc   5040
caagctgcat catcgaaatt gccgtcaacc aagctctgat agagttggtc aagaccaatg   5100
cggagcatat acgcccggag ccgcggcgat cctgcaagct ccggatgcct ccgctcgaag   5160
tagcgcgtct gctgctccat acaagccaac cacggcctcc agaagaagat gttggcgacc   5220
tcgtattggg aatccccgaa catcgcctcg ctccagtcaa tgaccgctgt tatgcggcca   5280
```

-continued ttgtccgtca ggacattgtt ggagccgaaa tccgcgtgca cgaggtgccg gacttcgggg 5340
cagtcctcgg cccaaagcat cagctcatcg agagcctgcg cgacggacgc actgacggtg 5400
tcgtccatca cagtttgcca gtgatacaca tggggatcag caatcgcgca tatgaaatca 5460
cgccatgtag tgtattgacc gattccttgc ggtccgaatg ggccgaaccc gctcgtctgg 5520
ctaagatcgg ccgcagcgat cgcatccatg gcctccgcga ccggctgcag aacagcgggc 5580
agttcggttt caggcaggtc ttgcaacgtg acaccctgtg cacggcggga gatgcaatag 5640
gtcaggctct cgctgaattc cccaatgtca agcacttccg gaatcgggag cgcggccgat 5700
gcaaagtgcc gataaacata acgatctttg tagaaaccat cggcgcagct atttacccgc 5760
aggacatatc cacgccctcc tacatcgaag ctgaaagcac gagattcttc gccctccgag 5820
agctgcatca ggtcggagac gctgtcgaac ttttcgatca gaaacttctc gacagacgtc 5880
gcggtgagtt caggcttttt catggtttaa taagaagaga aaagagttct tttgttatgg 5940
ctgaagtaat agagaaatga gctcgagcgt gtcctctcca aatgaaatga acttccttat 6000
atagaggaag ggtcttgcga aggatagtgg gattgtgcgt catcccttac gtcagtggag 6060
atgtcacatc aatccacttg ctttgaagac gtggttggaa cgtcttcttt ttccacgatg 6120
ctcctcgtgg gtgggggtcc atctttggga ccactgtcgg cagaggcatc ttgaatgata 6180
gcctttcctt tatcgcaatg atggcatttg taggagccac cttccttttc tactgtcctt 6240
tcgatgaagt gacagatagc tgggcaatgg aatccgagga ggtttcccga aattatcctt 6300
tgttgaaaag tctcaatagc cctttggtct tctgagactg tatctttgac atttttggag 6360
tagaccagag tgtcgtgctc caccatgttg acgaagattt tcttcttgtc attgagtcgt 6420
aaaagactct gtatgaactg ttcgccagtc ttcacggcga gttctgttag atcctcgatt 6480
tgaatcttag actccatgca tggccttaga ttcagtagga actacctttt tagagactcc 6540
aatctctatt acttgccttg gtttatgaag caagccttga atcgtccata ctggaatagt 6600
acttctgatc ttgagaaata tgtctttctc tgtgttcttg atgcaattag tcctgaatct 6660
tttgactgca tctttaacct tcttgggaag gtatttgatc tcctggagat tgttactcgg 6720
gtagatcgtc ttgatgagac ctgctgcgta ggcctctcta accatctgtg ggtcagcatt 6780
ctttctgaaa ttgaagaggc taaccttctc attatcagtg gtgaacatag tgtcgtcacc 6840
ttcaccttcg aacttccttc ctagatcgta aagatagagg aaatcgtcca ttgtaatctc 6900
cggggcaaag gagatctctt ttggggctgg atcactgctg ggccttttgg ttcctagcgt 6960
gagccagtgg gctttttgct ttggtgggct tgttagggcc ttagcaaagc tcttgggctt 7020
gagttgagct tctcctttgg ggatgaagtt caacctgtct gtttgctgac ttgttgtgta 7080
cgcgtcagct gctgctcttg cctctgtaat agtggcaaat ttcttgtgtg caactccggg 7140
aacgccgttt gttgccgcct ttgtacaacc ccagtcatcg tatataccgg catgtggacc 7200
gttatacaca acgtagtagt tgatatgagg gtgttgaata cccgattctg ctctgagagg 7260
agcaactgtg ctgttaagct cagatttttg tgggattgga attggatcga tctcgatccc 7320
gcgaaattaa tacgactcac tatagggaga ccacaacggt ttccctctag aaataatttt 7380
gtttaacttt aagaaggaga tatacccatg gaaaagcctg aactcaccgc gacgtctgtc 7440
gagaagtttc tgatcgaaaa gttcgacagc gtctccgacc tgatgcagct ctcggagggc 7500
gaagaatctc gtgctttcag cttcgatgta ggagggcgtg gatatgtcct gcgggtaaat 7560
agctgcgccg atggtttcta caaagatcgt tatgtttatc ggcactttgc atcggccgcg 7620

-continued

```
ctcccgattc cggaagtgct tgacattggg gaattcagcg agagcctgac ctattgcatc   7680
tcccgccgtg cacagggtgt cacgttgcaa gacctgcctg aaaccgaact gcccgctgtt   7740
ctgcagccgg tcgcggaggc tatggatgcg atcgctgcgg ccgatcttag ccagacgagc   7800
gggttcggcc cattcggacc gcaaggaatc ggtcaataca ctacatggcg tgatttcata   7860
tgcgcgattg ctgatcccca tgtgtatcac tggcaaactg tgatggacga caccgtcagt   7920
gcgtccgtcg cgcaggctct cgatgagctg atgctttggg ccgaggactg ccccgaagtc   7980
cggcacctcg tgcacgcgga tttcggctcc aacaatgtcc tgacggacaa tggccgcata   8040
acagcggtca ttgactggag cgaggcgatg ttcggggatt cccaatacga ggtcgccaac   8100
atcttcttct ggaggccgtg gttggcttgt atggagcagc agacgcgcta cttcgagcgg   8160
aggcatccgg agcttgcagg atcgccgcgg ctccgggcgt atatgctccg cattggtctt   8220
gaccaactct atcagagctt ggttgacggc aatttcgatg atgcagcttg ggcgcagggt   8280
cgatgcgacg caatcgtccg atccggagcc gggactgtcg ggcgtacaca aatcgcccgc   8340
agaagcgcgg ccgtctggac cgatggctgt gtagaagtac tcgccgatag tggaaaccga   8400
cgccccagca ctcgtccgag ggcaaaggaa tagtgaggta cagcttggat cgatccggct   8460
gctaacaaag cccgaaagga agctgagttg gctgctgcca ccgctgagca ataactagca   8520
taaccccttg gggcctctaa acgggtcttg aggggttttt tgctgaaagg aggaactata   8580
tccggatgat cgggcgcgcc gtcgacggat ccgtacgaga tccggccggc cagatcctgc   8640
aggcagatcc gaagacatgg gtattccaga gacttaaata tagtcatatg tgtaggcttt   8700
aatactttgt cgttttatgc tattaacatg gatgctgtga gtttgttcac agattcatcc   8760
tttttgtttt tggcgaattt tcattgcatc gatctatcaa tttgaatgaa tgaatatcac   8820
ttatttttgt aaaaaaaaga agataaaaaa aattaattat attcttaata atactcttat   8880
ttaattattg tatctcaatt attctaatta ttctatctat ataaatatat tagttattga   8940
aacttattta taataaaaag catgacattt tggaattttc ttaaaatgta agcataacta   9000
caaacgagac taagacgtag aaatagctag aagttaggaa caagagaagg gttaattgca   9060
ttatcatgaa ttctacattg aagtgtctca tactctcatc tcatataata agatagactt   9120
agaaaataag tcctgtacta ataataatat gtattgttat aagattatct cgtctaaaga   9180
actagcattt tttttttttt tcataattaa gttatctcaa ttggaggtta tgtgtatcag   9240
acattaaata taaataaatt aatggtcaat ttgagatctt ggaatgtgct tctttaaaga   9300
ttttatgttc aatttttttt tgtgtgtcaa attcggtgga caagttcata ctgaactttg   9360
ctctggctta gaacgggacc tcgcaaatgg gcagtgggat gaggctactc taattagtcg   9420
gtcctagatc ggatatcgag ttttataaaa ataatataaa taaacgattc aaatgaaatc   9480
gaaatattag ttcctcaagt tgtaaatgtc tagctccctt atatttcatc tagtcttgtt   9540
gataggactg atattttaaa atgagttctg tttgttttta tttaattatt tctaaaatga   9600
gttttgtttg cttgacttcg tttacctcgt tttcttctcc gggttcgggc atttcaaaaa   9660
taaggtatat caacttgatg tttatttata aattgaagtt catagtatac gatttttttt   9720
tgtaatataa agttccatat atgatttatc gccaggtctt ggtattttcg acatttgcat   9780
ggggttaaaa taaatgtcac atataatcac atattttttt ttgatgaaat gtcacatagt   9840
catcatcatt gtctagtttg ctgacttatt taattaggag catattcttt attaagtacc   9900
ccttacggtt gcattatcta attattgata tgttcaattt gtttcttagt gctgttttgt   9960
ttataatatt atccgaacac tatacactac aatcatcgta cataaattac tcaattgcaa  10020
```

caaaaaacaa gaggggtcag tctctgttga tgcattatcc aataacaaga ggaattagag 10080
gattagtagg taaaccaaag ttaaataaat ataacaacag gaaaaaagtc tttgcttgtg 10140
acgaacacca ccataatgca cccccacaat ttaatttttc accaagaaaa aatcattata 10200
gacaactaca ctcatgacac atatttaact tctgtgcatt gctgctaatc agtttattta 10260
aatcactatt ccctcaacaa aaaaaaagtt tatttaaatc actagattaa ttgtaataaa 10320
aagtcacttt aataattagt ttatgcaatg tctctaccaa ttgaactaaa cttacggaga 10380
taaatatgta gtatttttga attcaacatt ctttatcgaa agatgaattt tattttaaat 10440
ttattttgta atgtactagt aatttaattt caaaacatat taatgaatta aattgatttt 10500
agaatatgca ataaaattgt cctaatacaa atatattgaa aattgttagg ttggacacat 10560
gatcaaaatt caaacccaac tcacctattt agaaaagaaa aattcttaaa gaaaaacatt 10620
actatccata taggaaaaag tataattttt attatcagag taaatcctat ccagataaaa 10680
aaaaaactga accgcacttt aagtaattgc taaaagtatg catattctag ctttatttca 10740
atttttaagc aacatttaga attttgtcaa aaaagataaa gcaacattta aaaaagaata 10800
tacttcttat attcgctatg catttattta actttaggct tgaggaataa gataagactt 10860
gtaggcttga ggaataagat aagacttgtc aaaaaaaaaa aaaaaacaaa agattgggaa 10920
gtaagaaaaa gataggtaaa gatttttgac ctttggtgaa cgtcttaaac taaaataaaa 10980
taaaataaaa caaaataaat aaatttcatt ggtcaatctt ttttccttta actaattaat 11040
taatataagt gccacatcag catgtgaaat tcccattatg tatctcgttt cttgtctata 11100
aattgagtta gccaccacct tattttccat tcattcatcc cttctcttta cacccccccc 11160
tctttttgc gttcactctg ttttcttttc ataggtattc tattctattc tttctttatt 11220
atttttcttt ctttgttact ctgtttttcc cctgtttctc catcaccact gccacgtcac 11280
tattccacca cctctgcatg ttctttcttt tgtgatcata agatcaaaca ctataccatg 11340
attctgatct catgatatga gtcacacatg ttttcctctg catgaaaaaa tagtgctgag 11400
ttttttttt ttagtatagt tctgtttttg ttgaatttta ttcatgttct gttcttgtga 11460
cactatacac ggtttcactt tgaagaacaa ggttctgtcg ttattattca agatacttgt 11520
tcaagaaact tcatgacaca acatgcatgg ccttgattaa ataaaaaaca aaaacaaaaa 11580
caaaacttta tacagcctgg catagaacaa agagattctt tctttgttcg tttcttaaat 11640
aaattttgtt tttaatttta tggataaaca aacactaact tatgaggttt agtaatgtta 11700
aaattctaaa aggaaattat tattctcatg cactgtttat ggttgaaatc ttagttgaaa 11760
aaagtggaag atttggtatt aatattttat ttgacaggtg gttggtcatg gtgggtcgta 11820
ggtctttgtt gaaaattcat aaaccaattc agttttttta aatgtttgtt taattgatta 11880
atttttgtac tatgatgttg atctgttact taaagtgatg atgaattatt tttgttgttg 11940
cagttgaaga ttttcagcgg ccgcatgaag aggtctccag catcttcttg ttcatcatct 12000
acttcctctg ttgggtttga agctcccatt gaaaaaagaa ggcctaagca tccaaggagg 12060
aataatttga agtcacaaaa atgcaagcag aaccaaacca ccactggtgg cagaagaagc 12120
tctatctata gaggagttac aaggcatagg tggacaggga ggtttgaagc tcacctatgg 12180
gataagagct cttggaacaa cattcagagc aagaagggtc gacaagttta tttgggggca 12240
tatgatactg aagaatctgc agcccgtacc tatgaccttg cagcccttaa atactgggga 12300
aaagatgcaa ccctgaattt cccgatagaa acttatacca aggagctcga ggaaatggac 12360

-continued aaggtttcaa gagaagaata tttggcttct ttgcggcgcc aaagcagtgg cttttctaga 12420
ggcctgtcta agtaccgtgg ggttgctagg catcatcata atggtcgctg ggaagcacga 12480
attggaagag tatgcggaaa caagtacctc tacttgggga catataaaac tcaagaggag 12540
gcagcagtgg catatgacat ggcagcaata gagtaccgtg gagtcaatgc agtgaccaat 12600
tttgacataa gcaactacat ggacaaaata aagaagaaaa atgaccaaac ccaacaacaa 12660
caaacagaag cacaaacgga aacagttcct aactcctctg actctgaaga agtagaagta 12720
gaacaacaga caacaacaat aaccacacca cccccatctg aaaatctgca catgccacca 12780
cagcagcacc aagttcaata cacccccat gtctctccaa gggaagaaga atcatcatca 12840
ctgatcacaa ttatggacca tgtgcttgag caggatctgc catggagctt catgtacact 12900
ggcttgtctc agtttcaaga tccaaacttg gctttctgca aaggtgatga tgacttggtg 12960
ggcatgtttg atagtgcagg gtttgaggaa gacattgatt ttctgttcag cactcaacct 13020
ggtgatgaga ctgagagtga tgtcaacaat atgagcgcag ttttggatag tgttgagtgt 13080
ggagacacaa atggggctgg tggaagcatg atgcatgtgg ataacaagca gaagatagta 13140
tcatttgctt cttcaccatc atctacaact acagtttctt gtgactatgc tctagatcta 13200
tgagcggccg catttcgcac caaatcaatg aaagtaataa tgaaaagtct gaataagaat 13260
acttaggctt agatgccttt gttacttgtg taaaataact tgagtcatgt acctttggcg 13320
gaaacagaat aaataaaagg tgaaattcca atgctctatg tataagttag taatacttaa 13380
tgtgttctac ggttgtttca atatcatcaa actctaattg aaactttaga accacaaatc 13440
tcaatctttt cttaatgaaa tgaaaaatct taattgtacc atgtttatgt taaacacctt 13500
acaattaatt ggttggagag gaggaccaac cgatgggaca acattgggag aaagagattc 13560
aatggagatt tggataggag aacaacattc tttttcactt caatacaaga tgagtgcaac 13620
actaaggata tgtatgagac tttcagaagc tacgacaaca tagatgagtg aggtggtgat 13680
tcctagcaag aaagacatta gaggaagcca aaatcgaaca aggaagacat caagggcaag 13740
agacaggacc atccatctca ggaaaaggag ctttgggata gtccgagaag ttgtacaaga 13800
aattttttgg agggtgagtg atgcattgct ggtgacttta actcaatcaa aattgagaaa 13860
gaaagaaaag ggagggggct cacatgtgaa tagaagggaa acgggagaat tttacagttt 13920
tgatctaatg ggcatcccag ctagtggtaa catattcacc atgtttaacc ttcacgtacg 13980
agatccggcc ggccagatcc tgca 14004

<210> SEQ ID NO 90
<211> LENGTH: 21
<212> TYPE: DNA
<213> ORGANISM: Artificial sequence
<220> FEATURE:
<223> OTHER INFORMATION: amiRNA GM-MFAD2-1B

<400> SEQUENCE: 90
tgagggaaaa gggttgagga a 21

<210> SEQ ID NO 91
<211> LENGTH: 21
<212> TYPE: DNA
<213> ORGANISM: Artificial sequence
<220> FEATURE:
<223> OTHER INFORMATION: amiRNA Star Sequence 396b-GM-MFAD2-1

<400> SEQUENCE: 91
ttactcaacc cttttccctc a 21

<210> SEQ ID NO 92
<211> LENGTH: 21
<212> TYPE: DNA
<213> ORGANISM: Artificial sequence
<220> FEATURE:
<223> OTHER INFORMATION: amiRNA GM-MFAD2-2

<400> SEQUENCE: 92
tccacataaa tacactctct t 21

<210> SEQ ID NO 93
<211> LENGTH: 21
<212> TYPE: DNA
<213> ORGANISM: Artificial sequence
<220> FEATURE:
<223> OTHER INFORMATION: amiRNA Star Sequence 159-GM-MFAD2-2

<400> SEQUENCE: 93
aagagagtgt acctatgtgg t 21

<210> SEQ ID NO 94
<211> LENGTH: 958
<212> TYPE: DNA
<213> ORGANISM: Glycine max

<400> SEQUENCE: 94
ttctagctag ctagggtttg ggtagtgagt gtaataaagt tgcaaagttt ttggttaggt 60
tacgttttga ccttattatt atagttcaaa gggaaacatt aattaaaggg gattatgaag 120
tggagctcct tgaagtccaa ttgaggatct tactgggtga attgagctgc ttagctatgg 180
atcccacagt tctacccatc aataagtgct tttgtggtag tcttgtggct tccatatctg 240
gggagcttca tttgccttta tagtattaac cttctttgga ttgaagggag ctctacaccc 300
ttctcttctt ttctctcata ataatttaaa tttgttatag actctaaact ttaaatgttt 360
tttttgaagt ttttccgttt ttctcttttg ccatgatccc gttcttgctg tggagtaacc 420
ttgtccgagg tatgtgcatg attagatcca tacttaattt gtgtgcatca cgaaggtgag 480
gttgaaatga actttgcttt tttgaccttt taggaaagtt cttttgttgc agtaatcaat 540
tttaattagt tttaattgac actattactt ttattgtcat ctttgttagt tttattgttg 600
aattgagtgc atatttccta ggaaattctc ttacctaaca ttttttatac agatctatgc 660
tcttggctct tgcccttact cttggccttg tgttggttat ttgtctacat atttattgac 720
tggtcgatga gacatgtcac aattcttggg cttatttgtt ggtctaataa aaggagtgct 780
tattgaaaga tcaagacgga gattcggttt tatataaata aactaaagat gacatattag 840
tgtgttgatg tctcttcagg ataattttttg tttgaaataa tatggtaatg tcttgtctaa 900
atttgtgtac ataattctta ctgatttttt ggattgttgg atttttataa acaaatct 958

<210> SEQ ID NO 95
<211> LENGTH: 574
<212> TYPE: DNA
<213> ORGANISM: Glycine max

<400> SEQUENCE: 95
gcgagaaact ttgtatgggc atggttattt ctcacttctc accctccttt actttcttat 60
gctaaatcct ccttccccta tatctccacc ctcaacccct ttttctcatt ataacttttg 120
gtgcctagat ggtgtgtgtg tgtgcgcgcg agagatctga gctcaatttt cctctctcaa 180

```
gtcctggtca tgcttttcca cagctttctt gaacttctta tgcatcttat atctctccac    240

ctccaggatt ttaagcccta gaagctcaag aaagctgtgg gagaatatgg caattcaggc    300

ttttaattgc tttcatttgg taccatcact tgcaagattt cagagtacaa ggtgaacaca    360

cacatcttcc tcttcatcaa ttctctagtt tcatccttat cttttcattc acggtaactc    420

tcactaccct ctttcatctt ataagttata ccgggggtgt gatgttgatg agtgtaaatt    480

aaatatatgt gatctctttc tctggaaaaa ttttcagtgt gatatacata ataatctctt    540

aatctagaga ttttatggct ttgttatata taag                                574


<210> SEQ ID NO 96
<211> LENGTH: 1577
<212> TYPE: DNA
<213> ORGANISM: Artificial sequence
<220> FEATURE:
<223> OTHER INFORMATION: amiRNA precursor 396b-fad2-1b/159-fad2-2

<400> SEQUENCE: 96

gcgagaaact ttgtatgggc atggttattt ctcacttctc accctccttt actttcttat     60

gctaaatcct ccttccccta tatctccacc ctcaacccct ttttctcatt ataacttttg    120

gtgcctagat ggtgtgtgtg tgtgcgcgcg agagatctga gctcaatttt cctctctcaa    180

gtcctggtca tgctttgagg gaaaagggtt gaggaactta tgcatcttat atctctccac    240

ctccaggatt ttaagcccta gttactcaac ccttttccct cagaatatgg caattcaggc    300

ttttaattgc tttcatttgg taccatcact tgcaagattt cagagtacaa ggtgaacaca    360

cacatcttcc tcttcatcaa ttctctagtt tcatccttat cttttcattc acggtaactc    420

tcactaccct ctttcatctt ataagttata ccgggggtgt gatgttgatg agtgtaaatt    480

aaatatatgt gatctctttc tctggaaaaa ttttcagtgt gatatacata ataatctctt    540

aatctagaga ttttatggct ttgttatata taagcggcgc aagggcgaat tctgcagata    600

tccatcacac ttgggccgct tctagctagc tagggtttgg gtagtgagtg taataaagtt    660

gcaaagtttt tggttaggtt acgttttgac cttattatta tagttcaaag ggaaacatta    720

attaaagggg attatgaaga agagagtgta cctatgtggt tgaggatctt actgggtgaa    780

ttgagctgct tagctatgga tcccacagtt ctacccatca ataagtgctt ttgtggtagt    840

cttgtggctt ccatatctgg ggagcttcat ttgcctttat agtattaacc ttctccacat    900

aaatacactc tcttcaccct tctcttcttt tctctcataa taatttaaat ttgttataga    960

ctctaaactt taaatgtttt ttttgaagtt tttccgtttt tctcttttgc catgatcccg   1020

ttcttgctgt ggagtaacct tgtccgaggt atgtgcatga ttagatccat acttaatttg   1080

tgtgcatcac gaaggtgagg ttgaaatgaa ctttgctttt ttgacctttt aggaaagttc   1140

ttttgttgca gtaatcaatt ttaattagtt ttaattgaca ctattacttt tattgtcatc   1200

tttgttagtt ttattgttga attgagtgca tatttcctag gaaattctct tacctaacat   1260

tttttataca gatctatgct cttggctctt gcccttactc ttggccttgt gttggttatt   1320

tgtctacata tttattgact ggtcgatgag acatgtcaca attcttgggc ttatttgttg   1380

gtctaataaa aggagtgctt attgaaagat caagacggag attcggtttt atataaataa   1440

actaaagatg acatattagt gtgttgatgt ctcttcagga taatttttgt ttgaaataat   1500

atggtaatgt cttgtctaaa tttgtgtaca taattcttac tgattttttg gattgttgga   1560

tttttataaa caaatct                                                  1577
```

<210> SEQ ID NO 97
<211> LENGTH: 8095
<212> TYPE: DNA
<213> ORGANISM: Artificial sequence
<220> FEATURE:
<223> OTHER INFORMATION: Plasmid pKR2109

<400> SEQUENCE: 97
gtacgaacgg ccgcgcatgc tgacttaatc agctaacgcc actcgagggg gggcccggta 60
ccggcgcgcc gttctatagt gtcacctaaa tcgtatgtgt atgatacata aggttatgta 120
ttaattgtag ccgcgttcta acgacaatat gtccatatgg tgcactctca gtacaatctg 180
ctctgatgcc gcatagttaa gccagccccg acacccgcca acacccgctg acgcgccctg 240
acgggcttgt ctgctcccgg catccgctta cagacaagct gtgaccgtct ccgggagctg 300
catgtgtcag aggttttcac cgtcatcacc gaaacgcgcg agacgaaagg gcctcgtgat 360
acgcctattt ttataggtta atgtcatgac caaaatccct taacgtgagt tttcgttcca 420
ctgagcgtca gaccccgtag aaaagatcaa aggatcttct tgagatcctt tttttctgcg 480
cgtaatctgc tgcttgcaaa caaaaaaacc accgctacca gcggtggttt gtttgccgga 540
tcaagagcta ccaactcttt ttccgaaggt aactggcttc agcagagcgc agataccaaa 600
tactgtcctt ctagtgtagc cgtagttagg ccaccacttc aagaactctg tagcaccgcc 660
tacatacctc gctctgctaa tcctgttacc agtggctgct gccagtggcg ataagtcgtg 720
tcttaccggg ttggactcaa gacgatagtt accggataag gcgcagcggt cgggctgaac 780
ggggggttcg tgcacacagc ccagcttgga gcgaacgacc tacaccgaac tgagatacct 840
acagcgtgag cattgagaaa gcgccacgct tcccgaaggg agaaaggcgg acaggtatcc 900
ggtaagcggc agggtcggaa caggagagcg cacgagggag cttccagggg gaaacgcctg 960
gtatctttat agtcctgtcg ggtttcgcca cctctgactt gagcgtcgat ttttgtgatg 1020
ctcgtcaggg gggcggagcc tatggaaaaa cgccagcaac gcggcctttt tacggttcct 1080
ggccttttgc tggccttttg ctcacatgtt ctttcctgcg ttatcccctg attctgtgga 1140
taaccgtatt accgcctttg agtgagctga taccgctcgc cgcagccgaa cgaccgagcg 1200
cagcgagtca gtgagcgagg aagcggaaga gcgcccaata cgcaaaccgc ctctccccgc 1260
gcgttggccg attcattaat gcaggttgat cagatctcga tcccgcgaaa ttaatacgac 1320
tcactatagg gagaccacaa cggtttccct ctagaaataa ttttgtttaa ctttaagaag 1380
gagatatacc catggaaaag cctgaactca ccgcgacgtc tgtcgagaag tttctgatcg 1440
aaaagttcga cagcgtctcc gacctgatgc agctctcgga gggcgaagaa tctcgtgctt 1500
tcagcttcga tgtaggaggg cgtggatatg tcctgcgggt aaatagctgc gccgatggtt 1560
tctacaaaga tcgttatgtt tatcggcact ttgcatcggc cgcgctcccg attccggaag 1620
tgcttgacat tggggaattc agcgagagcc tgacctattg catctcccgc cgtgcacagg 1680
gtgtcacgtt gcaagacctg cctgaaaccg aactgcccgc tgttctgcag ccggtcgcgg 1740
aggctatgga tgcgatcgct gcggccgatc ttagccagac gagcgggttc ggcccattcg 1800
gaccgcaagg aatcggtcaa tacactacat ggcgtgattt catatgcgcg attgctgatc 1860
cccatgtgta tcactggcaa actgtgatgg acgacaccgt cagtgcgtcc gtcgcgcagg 1920
ctctcgatga gctgatgctt tgggccgagg actgccccga agtccggcac ctcgtgcacg 1980
cggatttcgg ctccaacaat gtcctgacgg acaatggccg cataacagcg gtcattgact 2040
ggagcgaggc gatgttcggg gattcccaat acgaggtcgc caacatcttc ttctggaggc 2100

```
cgtggttggc ttgtatggag cagcagacgc gctacttcga gcggaggcat ccggagcttg   2160
caggatcgcc gcggctccgg gcgtatatgc tccgcattgg tcttgaccaa ctctatcaga   2220
gcttggttga cggcaatttc gatgatgcag cttgggcgca gggtcgatgc gacgcaatcg   2280
tccgatccgg agccgggact gtcgggcgta cacaaatcgc ccgcagaagc gcggccgtct   2340
ggaccgatgg ctgtgtagaa gtactcgccg atagtggaaa ccgacgcccc agcactcgtc   2400
cgagggcaaa ggaatagtga ggtacagctt ggatcgatcc ggctgctaac aaagcccgaa   2460
aggaagctga gttggctgct gccaccgctg agcaataact agcataaccc cttggggcct   2520
ctaaacgggt cttgaggggt tttttgctga aaggaggaac tatatccgga tgctcgggcg   2580
cgccggtacc cgggtaccga gctcactaga cgcggtgaaa ttacctaatt aacaccggtg   2640
tttaaacact agtaacggcc gccagtgtgc tggaattcgc ccttcccaag ctttgctcta   2700
gatcaaactc acatccaaac ataacatgga tatcttcctt accaatcata ctaattattt   2760
tgggttaaat attaatcatt atttttaaga tattaattaa gaaattaaaa gatttttttaa   2820
aaaaatgtat aaaattatat tattcatgat ttttcataca tttgattttg ataataaata   2880
tatttttttt aatttcttaa aaaatgttgc aagacactta ttagacatag tcttgttctg   2940
tttacaaaag cattcatcat ttaatacatt aaaaaatatt taatactaac agtagaatct   3000
tcttgtgagt ggtgtgggag taggcaacct ggcattgaaa cgagagaaag agagtcagaa   3060
ccagaagaca aataaaaagt atgcaacaaa caaatcaaaa tcaaagggca aaggctgggg   3120
ttggctcaat tggttgctac attcaatttt caactcagtc aacggttgag attcactctg   3180
acttccccaa tctaagccgc ggatgcaaac ggttgaatct aacccacaat ccaatctcgt   3240
tacttagggg cttttccgtc attaactcac ccctgccacc cggtttccct ataaattgga   3300
actcaatgct cccctctaaa ctcgtatcgc ttcagagttg agaccaagac acactcgttc   3360
atatatctct ctgctcttct cttctcttct acctctcaag gtacttttct tctccctcta   3420
ccaaatccta gattccgtgg ttcaatttcg gatcttgcac ttctggtttg ctttgccttg   3480
ctttttcctc aactgggtcc atctaggatc catgtgaaac tctactcttt ctttaatatc   3540
tgcggaatac gcgtttgact ttcagatcta gtcgaaatca tttcataatt gcctttcttt   3600
cttttagctt atgagaaata aaatcacttt ttttttattt caaaataaac cttgggcctt   3660
gtgctgactg agatggggtt tggtgattac agaattttag cgaattttgt aattgtactt   3720
gtttgtctgt agttttgttt tgttttcttg tttctcatac attccttagg cttcaatttt   3780
attcgagtat aggtcacaat aggaattcaa actttgagca ggggaattaa tcccttcctt   3840
caaatccagt ttgtttgtat atatgtttaa aaaatgaaac ttttgcttta aattctatta   3900
taactttttt tatggctgaa atttttgcat gtgtctttgc tctctgttgt aaatttactg   3960
tttaggtact aactctaggc ttgttgtgca gtttttgaag tataacaaca gaagttccta   4020
ttccgaagtt cctattctct agaaagtata ggaacttcca ctagtccatg aaaaagcctg   4080
aactcaccgc gacgtctgtc gagaagtttc tgatcgaaaa gttcgacagc gtctccgacc   4140
tgatgcagct ctcggagggc gaagaatctc gtgctttcag cttcgatgta ggagggcgtg   4200
gatatgtcct gcgggtaaat agctgcgccg atggtttcta caaagatcgt tatgtttatc   4260
ggcactttgc atcggccgcg ctcccgattc cggaagtgct tgacattggg gaattcagcg   4320
agagcctgac ctattgcatc tcccgccgtg cacagggtgt cacgttgcaa gacctgcctg   4380
aaaccgaact gcccgctgtt ctgcagccgg tcgcggaggc catggatgcg atcgctgcgg   4440
ccgatcttag ccagacgagc gggttcggcc cattcggacc gcaaggaatc ggtcaataca   4500
```

```
ctacatggcg tgatttcata tgcgcgattg ctgatcccca tgtgtatcac tggcaaactg   4560
tgatggacga caccgtcagt gcgtccgtcg cgcaggctct cgatgagctg atgctttggg   4620
ccgaggactg ccccgaagtc cggcacctcg tgcacgcgga tttcggctcc aacaatgtcc   4680
tgacggacaa tggccgcata acagcggtca ttgactggag cgaggcgatg ttcggggatt   4740
cccaatacga ggtcgccaac atcttcttct ggaggccgtg gttggcttgt atggagcagc   4800
agacgcgcta cttcgagcgg aggcatccgg agcttgcagg atcgccgcgg ctccgggcgt   4860
atatgctccg cattggtctt gaccaactct atcagagctt ggttgacggc aatttcgatg   4920
atgcagcttg ggcgcagggt cgatgcgacg caatcgtccg atccggagcc gggactgtcg   4980
ggcgtacaca aatcgcccgc agaagcgcgg ccgtctggac cgatggctgt gtagaagtac   5040
tcgccgatag tggaaaccga cgccccagca ctcgtccgag ggcaaaggaa tagtgaggta   5100
cctaaagaag gagtgcgtcg aagcagatcg ttcaaacatt tggcaataaa gtttcttaag   5160
attgaatcct gttgccggtc ttgcgatgat tatcatataa tttctgttga attacgttaa   5220
gcatgtaata attaacatgt aatgcatgac gttatttatg agatgggttt ttatgattag   5280
agtcccgcaa ttatacattt aatacgcgat agaaaacaaa atatagcgcg caaactagga   5340
taaattatcg cgcgcggtgt catctatgtt actagatcga tgtcgacccg ggccctaggc   5400
gtctttccac aatacataac tattaattaa tcttaaataa ataaaggata aaatattttt   5460
ttttcttcat aaagttaaaa tatgttattt tttgtttaga tgtatattcg aataaatcta   5520
aatatatgat aatgattttt tatattgatt aaacatataa tcaatattaa atatgatatt   5580
tttttatata ggttgtacac ataattttat aaggataaaa aatatgataa aaataaattt   5640
taaatatttt tatatttacg agaaaaaaaa atattttagc cataaataaa tgaccagcat   5700
attttacaac cttagtaatt cataaattcc tatatgtata tttgaaatta aaaacagata   5760
atcgttaagg gaaggaatcc tacgtcatct cttgccattt gtttttcatg caaacagaaa   5820
gggacgaaaa accacctcac catgaatcac tcttcacacc atttttacta gcaaacaagt   5880
ctcaacaact gaagccagct ctctttccgt ttctttttac aacactttct ttgaaatagt   5940
agtatttttt ttcacatgat ttattaacgt gccaaaagat gcttattgaa tagagtgcac   6000
atttgtaatg tactactaat tagaacatga aaaagcattg ttctaacacg ataatcctgt   6060
gaaggcgtta actccaaaga tccaatttca ctatataaat tgtgacgaaa gcaaaatgaa   6120
ttcacatagc tgagagagaa aggaaaggtt aactaagaag caatacttca gcggccgcgc   6180
gagaaacttt gtatgggcat ggttatttct cacttctcac cctcctttac tttcttatgc   6240
taaatcctcc ttcccctata tctccaccct caacccccttt ttctcattat aacttttggt   6300
gcctagatgg tgtgtgtgtg tgcgcgcgag agatctgagc tcaattttcc tctctcaagt   6360
cctggtcatg ctttgaggga aaagggttga ggaacttatg catcttatat ctctccacct   6420
ccaggatttt aagccctagt tactcaaccc ttttccctca gaatatggca attcaggctt   6480
ttaattgctt tcatttggta ccatcacttg caagatttca gagtacaagg tgaacacaca   6540
catcttcctc ttcatcaatt ctctagtttc atccttatct tttcattcac ggtaactctc   6600
actaccctct ttcatcttat aagttatacc gggggtgtga tgttgatgag tgtaaattaa   6660
atatatgtga tctctttctc tggaaaaatt ttcagtgtga tatacataat aatctcttaa   6720
tctagagatt ttatggcttt gttatatata agcggcgcaa gggcgaattc tgcagatatc   6780
catcacactt gggccgcttc tagctagcta gggtttgggt agtgagtgta ataaagttgc   6840
```

aaagtttttg gttaggttac gttttgacct tattattata gttcaaaggg aaacattaat 6900
taaaggggat tatgaagaag agagtgtacc tatgtggttg aggatcttac tgggtgaatt 6960
gagctgctta gctatggatc ccacagttct acccatcaat aagtgctttt gtggtagtct 7020
tgtggcttcc atatctgggg agcttcattt gcctttatag tattaacctt ctccacataa 7080
atacactctc ttcacccttc tcttcttttc tctcataata atttaaattt gttatagact 7140
ctaaacttta aatgtttttt ttgaagtttt tccgtttttc tcttttgcca tgatcccgtt 7200
cttgctgtgg agtaaccttg tccgaggtat gtgcatgatt agatccatac ttaatttgtg 7260
tgcatcacga aggtgaggtt gaaatgaact ttgctttttt gacctttag gaaagttctt 7320 ttgttgcagt aatcaatttt aattagtttt aattgacact attactttta ttgtcatctt 7380
tgttagtttt attgttgaat tgagtgcata tttcctagga aattctctta cctaacattt 7440
tttatacaga tctatgctct tggctcttgc ccttactctt ggccttgtgt tggttatttg 7500
tctacatatt tattgactgg tcgatgagac atgtcacaat tcttgggctt atttgttggt 7560
ctaataaaag gagtgcttat tgaaagatca agacggagat tcggttttat ataaataaac 7620
taaagatgac atattagtgt gttgatgtct cttcaggata atttttgttt gaaataatat 7680
ggtaatgtct tgtctaaatt tgtgtacata attcttactg attttttgga ttgttggatt 7740
tttataaaca aatctggggc ccaagcggcc gcatgagccg taaaggttca atacaacgag 7800
tgcttgtttt cttagggaca agcattgtac ttatgtatga ttctgtgtaa ccatgagtct 7860
tccacgttgt actaatgtga agggcaaaaa taaaacacag aacaagttcg tttttctcaa 7920
ataatgtgaa ggtagaaaat ggaaccatgc ctcctctctt gcatgtgatt taaaatatta 7980
gcagatgacc taggaggccg gcccagctga tgatcccggt gaagttccta ttccgaagtt 8040
cctattctcc agaaagtata ggaacttcac tagagcttgc ggccgacctg caggc 8095

<210> SEQ ID NO 98
<211> LENGTH: 12788
<212> TYPE: DNA
<213> ORGANISM: Artificial sequence
<220> FEATURE:
<223> OTHER INFORMATION: Plasmid pKR2118

<400> SEQUENCE: 98
ggcgtacgaa cggccgcgca tgctgactta atcagctaac gccactcgag ggggggcccg 60
gtaccggcgc gccgttctat agtgtcacct aaatcgtatg tgtatgatac ataaggttat 120
gtattaattg tagccgcgtt ctaacgacaa tatgtccata tggtgcactc tcagtacaat 180
ctgctctgat gccgcatagt taagccagcc ccgacacccg ccaacacccg ctgacgcgcc 240
ctgacgggct tgtctgctcc cggcatccgc ttacagacaa gctgtgaccg tctccgggag 300
ctgcatgtgt cagaggtttt caccgtcatc accgaaacgc gcgagacgaa agggcctcgt 360
gatacgccta tttttatagg ttaatgtcat gaccaaaatc ccttaacgtg agttttcgtt 420
ccactgagcg tcagaccccg tagaaaagat caaaggatct tcttgagatc cttttttct 480 gcgcgtaatc tgctgcttgc aaacaaaaaa accaccgcta ccagcggtgg tttgtttgcc 540
ggatcaagag ctaccaactc tttttccgaa ggtaactggc ttcagcagag cgcagatacc 600
aaatactgtc cttctagtgt agccgtagtt aggccaccac ttcaagaact ctgtagcacc 660
gcctacatac ctcgctctgc taatcctgtt accagtggct gctgccagtg gcgataagtc 720
gtgtcttacc gggttggact caagacgata gttaccggat aaggcgcagc ggtcgggctg 780
aacggggggt tcgtgcacac agcccagctt ggagcgaacg acctacaccg aactgagata 840

```
cctacagcgt gagcattgag aaagcgccac gcttcccgaa gggagaaagg cggacaggta    900
tccggtaagc ggcagggtcg gaacaggaga gcgcacgagg gagcttccag ggggaaacgc    960
ctggtatctt tatagtcctg tcgggtttcg ccacctctga cttgagcgtc gatttttgtg   1020
atgctcgtca ggggggcgga gcctatggaa aaacgccagc aacgcggcct ttttacggtt   1080
cctggccttt tgctggcctt ttgctcacat gttctttcct gcgttatccc ctgattctgt   1140
ggataaccgt attaccgcct ttgagtgagc tgataccgct cgccgcagcc gaacgaccga   1200
gcgcagcgag tcagtgagcg aggaagcgga agagcgccca atacgcaaac cgcctctccc   1260
cgcgcgttgg ccgattcatt aatgcaggtt gatcagatct cgatcccgcg aaattaatac   1320
gactcactat agggagacca caacggtttc cctctagaaa taattttgtt taactttaag   1380
aaggagatat acccatggaa aagcctgaac tcaccgcgac gtctgtcgag aagtttctga   1440
tcgaaaagtt cgacagcgtc tccgacctga tgcagctctc ggagggcgaa gaatctcgtg   1500
ctttcagctt cgatgtagga gggcgtggat atgtcctgcg ggtaaatagc tgcgccgatg   1560
gtttctacaa agatcgttat gtttatcggc actttgcatc ggccgcgctc ccgattccgg   1620
aagtgcttga cattggggaa ttcagcgaga gcctgaccta ttgcatctcc cgccgtgcac   1680
agggtgtcac gttgcaagac ctgcctgaaa ccgaactgcc cgctgttctg cagccggtcg   1740
cggaggctat ggatgcgatc gctgcggccg atcttagcca gacgagcggg ttcggcccat   1800
tcggaccgca aggaatcggt caatacacta catggcgtga tttcatatgc gcgattgctg   1860
atccccatgt gtatcactgg caaactgtga tggacgacac cgtcagtgcg tccgtcgcgc   1920
aggctctcga tgagctgatg ctttgggccg aggactgccc cgaagtccgg cacctcgtgc   1980
acgcggattt cggctccaac aatgtcctga cggacaatgg ccgcataaca gcggtcattg   2040
actggagcga ggcgatgttc ggggattccc aatacgaggt cgccaacatc ttcttctgga   2100
ggccgtggtt ggcttgtatg gagcagcaga cgcgctactt cgagcggagg catccggagc   2160
ttgcaggatc gccgcggctc cgggcgtata tgctccgcat tggtcttgac caactctatc   2220
agagcttggt tgacggcaat ttcgatgatg cagcttgggc gcagggtcga tgcgacgcaa   2280
tcgtccgatc cggagccggg actgtcgggc gtacacaaat cgcccgcaga agcgcggccg   2340
tctggaccga tggctgtgta gaagtactcg ccgatagtgg aaaccgacgc cccagcactc   2400
gtccgagggc aaaggaatag tgaggtacag cttggatcga tccggctgct aacaaagccc   2460
gaaaggaagc tgagttggct gctgccaccg ctgagcaata actagcataa ccccttgggg   2520
cctctaaacg ggtcttgagg ggttttttgc tgaaaggagg aactatatcc ggatgctcgg   2580
gcgcgccggt acccgggtac cgagctcact agacgcggtg aaattaccta attaacaccg   2640
gtgtttaaac actagtaacg gccgccagtg tgctggaatt cgcccttccc aagctttgct   2700
ctagatcaaa ctcacatcca aacataacat ggatatcttc cttaccaatc atactaatta   2760
ttttgggtta aatattaatc attattttta agatattaat taagaaatta aaagattttt   2820
taaaaaaatg tataaaatta tattattcat gatttttcat acatttgatt ttgataataa   2880
atatattttt tttaatttct taaaaaatgt tgcaagacac ttattagaca tagtcttgtt   2940
ctgtttacaa aagcattcat catttaatac attaaaaaat atttaatact aacagtagaa   3000
tcttcttgtg agtggtgtgg gagtaggcaa cctggcattg aaacgagaga aagagagtca   3060
gaaccagaag acaaataaaa agtatgcaac aaacaaatca aaatcaaagg gcaaaggctg   3120
gggttggctc aattggttgc tacattcaat tttcaactca gtcaacggtt gagattcact   3180
```

ctgacttccc caatctaagc cgcggatgca aacggttgaa tctaacccac aatccaatct 3240
cgttacttag ggcttttcc gtcattaact caccctgcc acccggtttc cctataaatt 3300
ggaactcaat gctcccctct aaactcgtat cgcttcagag ttgagaccaa gacacactcg 3360
ttcatatatc tctctgctct tctcttctct tctacctctc aaggtacttt tcttctccct 3420
ctaccaaatc ctagattccg tggttcaatt tcggatcttg cacttctggt ttgctttgcc 3480
ttgctttttc ctcaactggg tccatctagg atccatgtga aactctactc tttctttaat 3540
atctgcggaa tacgcgtttg actttcagat ctagtcgaaa tcatttcata attgcctttc 3600
tttcttttag cttatgagaa ataaaatcac ttttttttta tttcaaaata aaccttgggc 3660
cttgtgctga ctgagatggg gtttggtgat tacagaattt tagcgaattt tgtaattgta 3720
cttgtttgtc tgtagttttg ttttgttttc ttgtttctca tacattcctt aggcttcaat 3780
tttattcgag tataggtcac aataggaatt caaactttga gcaggggaat taatcccttc 3840
cttcaaatcc agtttgtttg tatatatgtt taaaaaatga aacttttgct ttaaattcta 3900
ttataacttt ttttatggct gaaatttttg catgtgtctt tgctctctgt tgtaaattta 3960
ctgtttaggt actaactcta ggcttgttgt gcagtttttg aagtataaca acagaagttc 4020
ctattccgaa gttcctattc tctagaaagt ataggaactt ccactagtcc atgaaaaagc 4080
ctgaactcac cgcgacgtct gtcgagaagt ttctgatcga aaagttcgac agcgtctccg 4140
acctgatgca gctctcggag ggcgaagaat ctcgtgcttt cagcttcgat gtaggagggc 4200
gtggatatgt cctgcgggta aatagctgcg ccgatggttt ctacaaagat cgttatgttt 4260
atcggcactt tgcatcggcc gcgctcccga ttccggaagt gcttgacatt ggggaattca 4320
gcgagagcct gacctattgc atctcccgcc gtgcacaggg tgtcacgttg caagacctgc 4380
ctgaaaccga actgcccgct gttctgcagc cggtcgcgga ggccatggat gcgatcgctg 4440
cggccgatct tagccagacg agcgggttcg gcccattcgg accgcaagga atcggtcaat 4500
acactacatg gcgtgatttc atatgcgcga ttgctgatcc ccatgtgtat cactggcaaa 4560
ctgtgatgga cgacaccgtc agtgcgtccg tcgcgcaggc tctcgatgag ctgatgcttt 4620
gggccgagga ctgccccgaa gtccggcacc tcgtgcacgc ggatttcggc tccaacaatg 4680
tcctgacgga caatggccgc ataacagcgg tcattgactg gagcgaggcg atgttcgggg 4740
attcccaata cgaggtcgcc aacatcttct tctggaggcc gtggttggct tgtatggagc 4800
agcagacgcg ctacttcgag cggaggcatc cggagcttgc aggatcgccg cggctccggg 4860
cgtatatgct ccgcattggt cttgaccaac tctatcagag cttggttgac ggcaatttcg 4920
atgatgcagc ttgggcgcag ggtcgatgcg acgcaatcgt ccgatccgga gccgggactg 4980
tcgggcgtac acaaatcgcc cgcagaagcg cggccgtctg gaccgatggc tgtgtagaag 5040
tactcgccga tagtggaaac cgacgcccca gcactcgtcc gagggcaaag gaatagtgag 5100
gtacctaaag aaggagtgcg tcgaagcaga tcgttcaaac atttggcaat aaagtttctt 5160
aagattgaat cctgttgccg gtcttgcgat gattatcata taatttctgt tgaattacgt 5220
taagcatgta ataattaaca tgtaatgcat gacgttattt atgagatggg tttttatgat 5280
tagagtcccg caattataca tttaatacgc gatagaaaac aaaatatagc gcgcaaacta 5340
ggataaatta tcgcgcgcgg tgtcatctat gttactagat cgatgtcgac ccgggcccta 5400
ggcgtctttc cacaatacat aactattaat taatcttaaa taaataaagg ataaaatatt 5460
tttttttctt cataaagtta aaatatgtta ttttttgttt agatgtatat tcgaataaat 5520
ctaaatatat gataatgatt ttttatattg attaaacata taatcaatat taaatatgat 5580

```
atttttttat ataggttgta cacataattt tataaggata aaaaatatga taaaaataaa   5640
ttttaaatat ttttatattt acgagaaaaa aaaatatttt agccataaat aaatgaccag   5700
catattttac aaccttagta attcataaat tcctatatgt atatttgaaa ttaaaaacag   5760
ataatcgtta agggaaggaa tcctacgtca tctcttgcca tttgtttttc atgcaaacag   5820
aaagggacga aaaaccacct caccatgaat cactcttcac accattttta ctagcaaaca   5880
agtctcaaca actgaagcca gctctctttc cgtttctttt tacaacactt tctttgaaat   5940
agtagtattt tttttcacat gatttattaa cgtgccaaaa gatgcttatt gaatagagtg   6000
cacatttgta atgtactact aattagaaca tgaaaaagca ttgttctaac acgataatcc   6060
tgtgaaggcg ttaactccaa agatccaatt tcactatata aattgtgacg aaagcaaaat   6120
gaattcacat agctgagaga gaaaggaaag gttaactaag aagcaatact tcagcggccg   6180
cgcgagaaac tttgtatggg catggttatt tctcacttct caccctcctt tactttctta   6240
tgctaaatcc tccttcccct atatctccac cctcaacccc tttttctcat tataactttt   6300
ggtgcctaga tggtgtgtgt gtgtgcgcgc gagagatctg agctcaattt tcctctctca   6360
agtcctggtc atgctttgag ggaaaagggt tgaggaactt atgcatctta tatctctcca   6420
cctccaggat tttaagccct agttactcaa ccccttttccc tcagaatatg gcaattcagg   6480
cttttaattg ctttcatttg gtaccatcac ttgcaagatt tcagagtaca aggtgaacac   6540
acacatcttc ctcttcatca attctctagt ttcatcctta tcttttcatt cacggtaact   6600
ctcactaccc tctttcatct tataagttat accgggggtg tgatgttgat gagtgtaaat   6660
taaatatatg tgatctcttt ctctggaaaa attttcagtg tgatatacat aataatctct   6720
taatctagag attttatggc tttgttatat ataagcggcg caagggcgaa ttctgcagat   6780
atccatcaca cttgggccgc ttctagctag ctagggtttg ggtagtgagt gtaataaagt   6840
tgcaaagttt ttggttaggt tacgttttga ccttattatt atagttcaaa gggaaacatt   6900
aattaaaggg gattatgaag aagagagtgt acctatgtgg ttgaggatct tactgggtga   6960
attgagctgc ttagctatgg atcccacagt tctacccatc aataagtgct tttgtggtag   7020
tcttgtggct tccatatctg gggagcttca tttgccttta tagtattaac cttctccaca   7080
taaatacact ctcttcaccc ttctcttctt ttctctcata ataatttaaa tttgttatag   7140
actctaaact ttaaatgttt tttttgaagt ttttccgttt ttctcttttg ccatgatccc   7200
gttcttgctg tggagtaacc ttgtccgagg tatgtgcatg attagatcca tacttaattt   7260
gtgtgcatca cgaaggtgag gttgaaatga actttgcttt tttgaccttt taggaaagtt   7320
cttttgttgc agtaatcaat tttaattagt tttaattgac actattactt ttattgtcat   7380
ctttgttagt tttattgttg aattgagtgc atatttccta ggaaattctc ttacctaaca   7440
ttttttatac agatctatgc tcttggctct tgcccttact cttggccttg tgttggttat   7500
ttgtctacat atttattgac tggtcgatga gacatgtcac aattcttggg cttatttgtt   7560
ggtctaataa aaggagtgct tattgaaaga tcaagacgga gattcggttt tatataaata   7620
aactaaagat gacatattag tgtgttgatg tctcttcagg ataatttttg tttgaaataa   7680
tatggtaatg tcttgtctaa atttgtgtac ataattctta ctgatttttt ggattgttgg   7740
atttttataa acaaatctgg ggcccaagcg gccgcatgag ccgtaaaggt tcaatacaac   7800
gagtgcttgt tttcttaggg acaagcattg tacttatgta tgattctgtg taaccatgag   7860
tcttccacgt tgtactaatg tgaagggcaa aaataaaaca cagaacaagt tcgtttttct   7920
```

caaataatgt gaaggtagaa aatggaacca tgcctcctct cttgcatgtg atttaaaata 7980
ttagcagatg acctaggagg ccggcccagc tgatgatccc ggtgaagttc ctattccgaa 8040
gttcctattc tccagaaagt ataggaactt cactagagct tgcggccgac ctgcaggtaa 8100
attgcagctg aaggacagtg aagggtgaat ttatccattt aaaccatttt ctttttaaca 8160
catttcttat ggtaatctct tctcactaca ctataaaaat ggcttctcaa tcccattttc 8220
tacatcatcc cattctattg agttttgttt atttgctttc actttttttt ttatctgcct 8280
cttcccttaa tttgcttgac ttcttcttca cattttgctt tgttttctcc tccggcttcc 8340
ggtatttcaa attcaagatg agcaagttga aatttataaa tagaaataca gatattattt 8400
acaacgtcaa atctttggta ttttcaatat ttgaatgggg taaatttgtc atatagtcat 8460
catcactgac tacttatcta acctatttaa tttggagcat attctttata aggtccctct 8520
cacggccaat gtctaattat tgatatacag ctcttgtttt ctagtgctgc ttataatatt 8580
atctacacat atatatggta ctgcacacta ctactatata gtagtaagta aactagcaac 8640
agccggggcc aaactccaat aactaggcat tggggtttag ttggtaatat aaatataaca 8700
tcaaaaagtc tttgcttgtg acgaacatca caatgcaccc accattgatg ccacgacaga 8760
cattgttaat ttttttttta atttttaaaa aagaagcaat tccaatagtt ctatattaca 8820
atctcacgtg atccaagcac aacgtttcat tttttgtaca tgctcgatat ataaataata 8880
tttcatttta tagtaaaata taatgacatt ttcgaatata atttttgaaa tttcattttc 8940
caaatgaaat actaatatta atattaatga gattaccaca aatcatgtta tgaatgaaat 9000
aaagagtttt ggcattctaa ctttctttga atagaacaaa atgtatacaa cactctccat 9060
atatacacga tttattcagg gatcatatac attctctcat gattaacata gtctgctttc 9120
ttcacgtcta agcagataat tttggtccca caagataaaa ttatcattag tcgttttaat 9180
taattccttg agcatcaagc actaaaataa ttaaacttct ccattaccaa aaaaaaaaga 9240
taggtgattc agtaacatgt agtactagta ctactgattt ttttttcttt ttgattttaa 9300
tgaatggttc gtatcgagca tcgagaaatc catttattag gtgtgtaatg taatagtagt 9360
atttccttga ttttcagtaa taagatggat tcttacattt atatctgttt gacagaaaat 9420
gttgtcaatg catttcttgg gcacaaagtt ttttgaaaca tgaattaatt ttttcaaaat 9480
atttatgaca tcaaattgac cctaaaataa gtgataaagc tttaacgtgg aatgacatta 9540
atttttccat gataaataaa acacttaaaa cattttaata ttaatattat aatcagttac 9600
aactatgttc aattaatgca ataactttta aataaatatt aaaatatttt ttttctgttc 9660
tccaataaag agatcttgtt gcacggaaaa agtcacattc ttatttagta aaaaattata 9720
attattgttt gaaaaatatc attttcactg cagaaaattt gatccagctc tacagatcat 9780
acttttattg tacaataata caataaaaat attcatctgc aggaaatatc attttcattg 9840
tacaataata taaagataaa tatataccag aaaagaaaaa gaaactgatg tggcacaatg 9900
tattcactga aagaatgcat attgtatttc acctttcaag cagcactaag aatatacttc 9960
ttttattata cttgtgcatt tactcaacca ccctcggtgg agtaagaaag aagatagata 10020
aaagtttttt ttgacatttg gtgaatctct taattaaaaa aataaaataa tccatttcct 10080
ttatttaatt tcttttttcc catctgtgaa attccaattc tgcttcgcgc tcctgtctat 10140
aaattgactt agccaccacc tcagtttcca ttcattcact tcttctcttt ataccccccc 10200
tctctttttt gcgttcattc tgttttcgta agtactgttg tttttctctt ctatttcttt 10260
ttttgtttgt gttgtttttt tttcttcctt atcgttgttc tgcctctcct ctgtttcggt 10320

```
gctctgttca ccacttccac gtgagaatga tcttccttct ttgcatgttc attctctcgt  10380
gaccactgga tcagactcca tgttctgatc cagggtctct ctctaacgcc tgtactttca  10440
tccatgacca ccttaaaaac aacatggggg tggtgctgtt acactaactc tgtttctggg  10500
gtgctgtctt tgttcaattt tactcagaaa atatcttttc ttggattcta ttcggtgtgt  10560
gggaacatga tcctgtcggt cggttgtttt taggttaatc cttaactggt tacaaggatc  10620
taacgcttga atgcatgtcc tgagttaaag aaacaaaaga agaacacacc tagtacagcc  10680
tggcctcgaa ccaagaactt ctttgttggt ttctcattat tactaaaata aaataaagta  10740
tacgttttct tttttctttg ggatgaacgg ttcagactta tgagaagttt aagctaatcc  10800
tgtagtggag tgttcaattt attttaaact ttaaagcaat agctcaagca ctaaacttct  10860
ttttcaagtt caaccacttt ggtagcttgc taattgctgc tattgttcta attaattaat  10920
gtaattattg tttaaaaaag aaaagttggt gacactggaa taaaaaagtg tactatctgg  10980
caattattct tctgcagcaa tgtttgaggt tgaaatctta gtagaacaaa gtagaagatc  11040
tggtatttat attttttgta gacagatggt gggggtgggt ggtaggcctt gaaatccaat  11100
atagttttgt agaataattt tattattttt ttttttgct cacttgtttg tggtattgat  11160
tttgtgatga ctcaagatta atgatttacc ttcatttttt tcatggtgac atattatgta  11220
tattcttgat ctgtttctta cacttctttt tcgttgttgt agctgttgaa gtctgcggcc  11280
gcaccatgga aactggaggc tttcacggct accgcaagct ccccaacacc accgctgggt  11340
tgaagctgtc agtgtcagac atgaacatga acatgaggca gcagcaggta gcatcatcag  11400
atcagaactg cagcaaccac agtgcagcag gagaggagaa cgaatgcacg gtgagggagc  11460
aagacaggtt catgccaatc gctaacgtga tacggatcat gcgcaagatt ctccctccac  11520
acgcaaaaat ctccgatgat gcaaaggaga caatccaaga gtgcgtgtcg gagtacatca  11580
gcttcatcac cggggaggcg aacgagcgtt gccagaggga gcaacggaag accataaccg  11640
cagaggacgt gctttgggcc atgagcaagc ttggattcga cgactacatc gaaccgttga  11700
ccatgtacct tcaccgctac cgtgaacttg agggtgaccg cacctctatg aggggtgaac  11760
cactcgggaa gaggactgtg gaatacgcca cgcttggtgt tgctactgct tttgtccctc  11820
caccctatca tcaccacaat gggtactttg gtgctgccat gcccatgggg acttacgtta  11880
gggaagcgcc accaaataca gcctcctccc atcaccacca ccaccaccac caccaccatg  11940
ctcgtggaat ctccaatgct catgaaccaa atgctcgctc catataagcg gccgcatttc  12000
gcaccaaatc aatgaaagta ataatgaaaa gtctgaataa gaatacttag gcttagatgc  12060
ctttgttact tgtgtaaaat aacttgagtc atgtaccttt ggcggaaaca gaataaataa  12120
aaggtgaaat tccaatgctc tatgtataag ttagtaatac ttaatgtgtt ctacggttgt  12180
ttcaatatca tcaaactcta attgaaactt tagaaccaca aatctcaatc ttttcttaat  12240
gaaatgaaaa atcttaattg taccatgttt atgttaaaca ccttacaatt aattggttgg  12300
agaggaggac caaccgatgg gacaacattg ggagaaagag attcaatgga gatttggata  12360
ggagaacaac attctttttc acttcaatac aagatgagtg caacactaag gatatgtatg  12420
agactttcag aagctacgac aacatagatg agtgaggtgg tgattcctag caagaaagac  12480
attagaggaa gccaaaatcg aacaaggaag acatcaaggg caagagacag gaccatccat  12540
ctcaggaaaa ggagctttgg gatagtccga gaagttgtac aagaaatttt ttggagggtg  12600
agtgatgcat tgctggtgac tttaactcaa tcaaaattga gaaagaaaga aaagggaggg  12660
```

| | | |
|---|---|---|
| ggctcacatg tgaatagaag ggaaacggga gaattttaca gttttgatct aatgggcatc | 12720 |
| ccagctagtg gtaacatatt caccatgttt aaccttcacg tacgagatcc ggccggccag | 12780 |
| atcctgca | 12788 |

<210> SEQ ID NO 99
<211> LENGTH: 13319
<212> TYPE: DNA
<213> ORGANISM: Artificial sequence
<220> FEATURE:
<223> OTHER INFORMATION: Plasmid pKR2120

<400> SEQUENCE: 99

| | |
|---|---|
| ggcgtacgaa cggccgcgca tgctgactta atcagctaac gccactcgag ggggggcccg | 60 |
| gtaccggcgc gccgttctat agtgtcacct aaatcgtatg tgtatgatac ataaggttat | 120 |
| gtattaattg tagccgcgtt ctaacgacaa tatgtccata tggtgcactc tcagtacaat | 180 |
| ctgctctgat gccgcatagt taagccagcc ccgacacccg ccaacacccg ctgacgcgcc | 240 |
| ctgacgggct tgtctgctcc cggcatccgc ttacagacaa gctgtgaccg tctccgggag | 300 |
| ctgcatgtgt cagaggtttt caccgtcatc accgaaacgc gcgagacgaa agggcctcgt | 360 |
| gatacgccta tttttatagg ttaatgtcat gaccaaaatc ccttaacgtg agttttcgtt | 420 |
| ccactgagcg tcagaccccg tagaaaagat caaaggatct tcttgagatc ctttttttct | 480 |
| gcgcgtaatc tgctgcttgc aaacaaaaaa accaccgcta ccagcggtgg tttgtttgcc | 540 |
| ggatcaagag ctaccaactc tttttccgaa ggtaactggc ttcagcagag cgcagatacc | 600 |
| aaatactgtc cttctagtgt agccgtagtt aggccaccac ttcaagaact ctgtagcacc | 660 |
| gcctacatac ctcgctctgc taatcctgtt accagtggct gctgccagtg gcgataagtc | 720 |
| gtgtcttacc gggttggact caagacgata gttaccggat aaggcgcagc ggtcgggctg | 780 |
| aacggggggt tcgtgcacac agcccagctt ggagcgaacg acctacaccg aactgagata | 840 |
| cctacagcgt gagcattgag aaagcgccac gcttcccgaa gggagaaagg cggacaggta | 900 |
| tccggtaagc ggcagggtcg gaacaggaga gcgcacgagg gagcttccag ggggaaacgc | 960 |
| ctggtatctt tatagtcctg tcgggtttcg ccacctctga cttgagcgtc gatttttgtg | 1020 |
| atgctcgtca ggggggcgga gcctatggaa aaacgccagc aacgcggcct ttttacggtt | 1080 |
| cctggccttt tgctggcctt ttgctcacat gttctttcct gcgttatccc ctgattctgt | 1140 |
| ggataaccgt attaccgcct ttgagtgagc tgataccgct cgccgcagcc gaacgaccga | 1200 |
| gcgcagcgag tcagtgagcg aggaagcgga agagcgccca atacgcaaac cgcctctccc | 1260 |
| cgcgcgttgg ccgattcatt aatgcaggtt gatcagatct cgatcccgcg aaattaatac | 1320 |
| gactcactat agggagacca caacggtttc cctctagaaa taattttgtt taactttaag | 1380 |
| aaggagatat acccatggaa aagcctgaac tcaccgcgac gtctgtcgag aagtttctga | 1440 |
| tcgaaaagtt cgacagcgtc tccgacctga tgcagctctc ggagggcgaa gaatctcgtg | 1500 |
| ctttcagctt cgatgtagga gggcgtggat atgtcctgcg ggtaaatagc tgcgccgatg | 1560 |
| gtttctacaa agatcgttat gtttatcggc actttgcatc ggccgcgctc ccgattccgg | 1620 |
| aagtgcttga cattggggaa ttcagcgaga gcctgaccta ttgcatctcc cgccgtgcac | 1680 |
| agggtgtcac gttgcaagac ctgcctgaaa ccgaactgcc cgctgttctg cagccggtcg | 1740 |
| cggaggctat ggatgcgatc gctgcggccg atcttagcca gacgagcggg ttcggcccat | 1800 |
| tcggaccgca aggaatcggt caatacacta catggcgtga tttcatatgc gcgattgctg | 1860 |
| atccccatgt gtatcactgg caaactgtga tggacgacac cgtcagtgcg tccgtcgcgc | 1920 |

```
aggctctcga tgagctgatg ctttgggccg aggactgccc cgaagtccgg cacctcgtgc   1980
acgcggattt cggctccaac aatgtcctga cggacaatgg ccgcataaca gcggtcattg   2040
actggagcga ggcgatgttc ggggattccc aatacgaggt cgccaacatc ttcttctgga   2100
ggccgtggtt ggcttgtatg gagcagcaga cgcgctactt cgagcggagg catccggagc   2160
ttgcaggatc gccgcggctc cgggcgtata tgctccgcat tggtcttgac caactctatc   2220
agagcttggt tgacggcaat ttcgatgatg cagcttgggc gcagggtcga tgcgacgcaa   2280
tcgtccgatc cggagccggg actgtcgggc gtacacaaat cgcccgcaga agcgcggccg   2340
tctggaccga tggctgtgta gaagtactcg ccgatagtgg aaaccgacgc cccagcactc   2400
gtccgagggc aaaggaatag tgaggtacag cttggatcga tccggctgct aacaaagccc   2460
gaaaggaagc tgagttggct gctgccaccg ctgagcaata actagcataa ccccttgggg   2520
cctctaaacg ggtcttgagg ggttttttgc tgaaaggagg aactatatcc ggatgctcgg   2580
gcgcgccggt acccgggtac cgagctcact agacgcggtg aaattaccta attaacaccg   2640
gtgtttaaac actagtaacg gccgccagtg tgctggaatt cgcccttccc aagctttgct   2700
ctagatcaaa ctcacatcca aacataacat ggatatcttc cttaccaatc atactaatta   2760
ttttgggtta aatattaatc attattttta agatattaat taagaaatta aaagattttt   2820
taaaaaaatg tataaaatta tattattcat gatttttcat acatttgatt ttgataataa   2880
atatattttt tttaatttct taaaaaatgt tgcaagacac ttattagaca tagtcttgtt   2940
ctgtttacaa aagcattcat catttaatac attaaaaaat atttaatact aacagtagaa   3000
tcttcttgtg agtggtgtgg gagtaggcaa cctggcattg aaacgagaga aagagagtca   3060
gaaccagaag acaaataaaa agtatgcaac aaacaaatca aaatcaaagg gcaaaggctg   3120
gggttggctc aattggttgc tacattcaat tttcaactca gtcaacggtt gagattcact   3180
ctgacttccc caatctaagc cgcggatgca aacggttgaa tctaacccac aatccaatct   3240
cgttacttag ggcttttcc gtcattaact caccccctgcc acccggtttc cctataaatt   3300
ggaactcaat gctcccctct aaactcgtat cgcttcagag ttgagaccaa gacacactcg   3360
ttcatatatc tctctgctct tctcttctct tctacctctc aaggtacttt tcttctccct   3420
ctaccaaatc ctagattccg tggttcaatt tcggatcttg cacttctggt ttgctttgcc   3480
ttgctttttc ctcaactggg tccatctagg atccatgtga aactctactc tttctttaat   3540
atctgcggaa tacgcgtttg actttcagat ctagtcgaaa tcatttcata attgcctttc   3600
tttcttttag cttatgagaa ataaaatcac tttttttta tttcaaaata aaccttgggc   3660
cttgtgctga ctgagatggg gtttggtgat tacagaattt tagcgaattt tgtaattgta   3720
cttgtttgtc tgtagtttg ttttgtttc ttgtttctca tacattcctt aggcttcaat   3780
tttattcgag tataggtcac aataggaatt caaactttga gcaggggaat taatcccttc   3840
cttcaaatcc agtttgtttg tatatatgtt taaaaaatga aacttttgct ttaaattcta   3900
ttataacttt ttttatggct gaaatttttg catgtgtctt tgctctctgt tgtaaattta   3960
ctgtttaggt actaactcta ggcttgttgt gcagtttttg aagtataaca acagaagttc   4020
ctattccgaa gttcctattc tctagaaagt ataggaactt ccactagtcc atgaaaaagc   4080
ctgaactcac cgcgacgtct gtcgagaagt ttctgatcga aaagttcgac agcgtctccg   4140
acctgatgca gctctcggag ggcgaagaat ctcgtgcttt cagcttcgat gtaggagggc   4200
gtggatatgt cctgcgggta aatagctgcg ccgatggttt ctacaaagat cgttatgttt   4260
```

atcggcactt tgcatcggcc gcgctcccga ttccggaagt gcttgacatt ggggaattca 4320
gcgagagcct gacctattgc atctcccgcc gtgcacaggg tgtcacgttg caagacctgc 4380
ctgaaaccga actgcccgct gttctgcagc cggtcgcgga ggccatggat gcgatcgctg 4440
cggccgatct tagccagacg agcgggttcg gcccattcgg accgcaagga atcggtcaat 4500
acactacatg gcgtgatttc atatgcgcga ttgctgatcc ccatgtgtat cactggcaaa 4560
ctgtgatgga cgacaccgtc agtgcgtccg tcgcgcaggc tctcgatgag ctgatgcttt 4620
gggccgagga ctgccccgaa gtccggcacc tcgtgcacgc ggatttcggc tccaacaatg 4680
tcctgacgga caatggccgc ataacagcgg tcattgactg gagcgaggcg atgttcgggg 4740
attcccaata cgaggtcgcc aacatcttct tctggaggcc gtggttggct tgtatggagc 4800
agcagacgcg ctacttcgag cggaggcatc cggagcttgc aggatcgccg cggctccggg 4860
cgtatatgct ccgcattggt cttgaccaac tctatcagag cttggttgac ggcaatttcg 4920
atgatgcagc ttgggcgcag ggtcgatgcg acgcaatcgt ccgatccgga gccgggactg 4980
tcgggcgtac acaaatcgcc cgcagaagcg cggccgtctg gaccgatggc tgtgtagaag 5040
tactcgccga tagtggaaac cgacgcccca gcactcgtcc gagggcaaag gaatagtgag 5100
gtacctaaag aaggagtgcg tcgaagcaga tcgttcaaac atttggcaat aaagtttctt 5160
aagattgaat cctgttgccg gtcttgcgat gattatcata taatttctgt tgaattacgt 5220
taagcatgta ataattaaca tgtaatgcat gacgttattt atgagatggg tttttatgat 5280
tagagtcccg caattataca tttaatacgc gatagaaaac aaaatatagc gcgcaaacta 5340
ggataaatta tcgcgcgcgg tgtcatctat gttactagat cgatgtcgac ccgggcccta 5400
ggcgtctttc cacaatacat aactattaat taatcttaaa taaataaagg ataaaatatt 5460
ttttttcttt cataaagtta aaatatgtta tttttgttt agatgtatat tcgaataaat 5520
ctaaatatat gataatgatt ttttatattg attaaacata taatcaatat taaatatgat 5580
atttttttat ataggttgta cacataattt tataaggata aaaaatatga taaaaataaa 5640
ttttaaatat ttttatattt acgagaaaaa aaaatatttt agccataaat aaatgaccag 5700
catattttac aaccttagta attcataaat tcctatatgt atatttgaaa ttaaaaacag 5760
ataatcgtta agggaaggaa tcctacgtca tctcttgcca tttgtttttc atgcaaacag 5820
aaagggacga aaaaccacct caccatgaat cactcttcac accattttta ctagcaaaca 5880
agtctcaaca actgaagcca gctctctttc cgtttctttt tacaacactt tctttgaaat 5940
agtagtattt tttttcacat gatttattaa cgtgccaaaa gatgcttatt gaatagagtg 6000
cacatttgta atgtactact aattagaaca tgaaaaagca ttgttctaac acgataatcc 6060
tgtgaaggcg ttaactccaa agatccaatt tcactatata aattgtgacg aaagcaaaat 6120
gaattcacat agctgagaga gaaaggaaag gttaactaag aagcaatact tcagcggccg 6180
cgcgagaaac tttgtatggg catggttatt tctcacttct caccctcctt tactttctta 6240
tgctaaatcc tccttcccct atatctccac cctcaacccc tttttctcat tataactttt 6300
ggtgcctaga tggtgtgtgt gtgtgcgcgc gagagatctg agctcaattt tcctctctca 6360
agtcctggtc atgctttgag ggaaaagggt tgaggaactt atgcatctta tatctctcca 6420
cctccaggat tttaagccct agttactcaa ccctttttccc tcagaatatg gcaattcagg 6480
cttttaattg ctttcatttg gtaccatcac ttgcaagatt tcagagtaca aggtgaacac 6540
acacatcttc ctcttcatca attctctagt ttcatcctta tcttttcatt cacggtaact 6600
ctcactaccc tctttcatct tataagttat accgggggtg tgatgttgat gagtgtaaat 6660

```
taaatatatg tgatctcttt ctctggaaaa attttcagtg tgatatacat aataatctct   6720
taatctagag attttatggc tttgttatat ataagcggcg caagggcgaa ttctgcagat   6780
atccatcaca cttgggccgc ttctagctag ctagggtttg ggtagtgagt gtaataaagt   6840
tgcaaagttt ttggttaggt tacgttttga ccttattatt atagttcaaa gggaaacatt   6900
aattaaaggg gattatgaag aagagagtgt acctatgtgg ttgaggatct tactgggtga   6960
attgagctgc ttagctatgg atcccacagt tctacccatc aataagtgct tttgtggtag   7020
tcttgtggct tccatatctg gggagcttca tttgccttta tagtattaac cttctccaca   7080
taaatacact ctcttcaccc ttctcttctt ttctctcata ataatttaaa tttgttatag   7140
actctaaact ttaaatgttt tttttgaagt ttttccgttt ttctcttttg ccatgatccc   7200
gttcttgctg tggagtaacc ttgtccgagg tatgtgcatg attagatcca tacttaattt   7260
gtgtgcatca cgaaggtgag gttgaaatga actttgcttt tttgaccttt taggaaagtt   7320
cttttgttgc agtaatcaat tttaattagt tttaattgac actattactt ttattgtcat   7380
ctttgttagt tttattgttg aattgagtgc atatttccta ggaaattctc ttacctaaca   7440
ttttttatac agatctatgc tcttggctct tgcccttact cttggccttg tgttggttat   7500
ttgtctacat atttattgac tggtcgatga gacatgtcac aattcttggg cttatttgtt   7560
ggtctaataa aaggagtgct tattgaaaga tcaagacgga gattcggttt tatataaata   7620
aactaaagat gacatattag tgtgttgatg tctcttcagg ataatttttg tttgaaataa   7680
tatggtaatg tcttgtctaa atttgtgtac ataattctta ctgatttttt ggattgttgg   7740
atttttataa acaaatctgg ggcccaagcg gccgcatgag ccgtaaaggt tcaatacaac   7800
gagtgcttgt tttcttaggg acaagcattg tacttatgta tgattctgtg taaccatgag   7860
tcttccacgt tgtactaatg tgaagggcaa aaataaaaca cagaacaagt tcgtttttct   7920
caaataatgt gaaggtagaa aatggaacca tgcctcctct cttgcatgtg atttaaaata   7980
ttagcagatg acctaggagg ccggcccagc tgatgatccc ggtgaagttc ctattccgaa   8040
gttcctattc tccagaaagt ataggaactt cactagagct tgcggccgac ctgcaggtaa   8100
attgcagctg aaggacagtg aagggtgaat ttatccattt aaaccatttt ctttttaaca   8160
catttcttat ggtaatctct tctcactaca ctataaaaat ggcttctcaa tcccattttc   8220
tacatcatcc cattctattg agttttgttt atttgctttc actttttttt ttatctgcct   8280
cttcccttaa tttgcttgac ttcttcttca cattttgctt tgttttctcc tccggcttcc   8340
ggtatttcaa attcaagatg agcaagttga aatttataaa tagaaataca gatattattt   8400
acaacgtcaa atctttggta ttttcaatat ttgaatgggg taaatttgtc atatagtcat   8460
catcactgac tacttatcta acctatttaa tttggagcat attctttata aggtccctct   8520
cacggccaat gtctaattat tgatatacag ctcttgtttt ctagtgctgc ttataatatt   8580
atctacacat atatatggta ctgcacacta ctactatata gtagtaagta aactagcaac   8640
agccggggcc aaactccaat aactaggcat tggggtttag ttggtaatat aaatataaca   8700
tcaaaaagtc tttgcttgtg acgaacatca caatgcaccc accattgatg ccacgacaga   8760
cattgttaat ttttttttta atttttaaaa aagaagcaat tccaatagtt ctatattaca   8820
atctcacgtg atccaagcac aacgtttcat tttttgtaca tgctcgatat ataaataata   8880
tttcatttta tagtaaaata taatgacatt ttcgaatata atttttgaaa tttcattttc   8940
caaatgaaat actaatatta atattaatga gattaccaca aatcatgtta tgaatgaaat   9000
```

```
aaagagtttt ggcattctaa ctttctttga atagaacaaa atgtatacaa cactctccat   9060
atatacacga tttattcagg gatcatatac attctctcat gattaacata gtctgctttc   9120
ttcacgtcta agcagataat ttttggtcca caagataaaa ttatcattag tcgttttaat   9180
taattccttg agcatcaagc actaaaataa ttaaacttct ccattaccaa aaaaaaaaga   9240
taggtgattc agtaacatgt agtactagta ctactgattt ttttttcttt ttgattttaa   9300
tgaatggttc gtatcgagca tcgagaaatc catttattag gtgtgtaatg taatagtagt   9360
atttccttga ttttcagtaa taagatggat tcttacattt atatctgttt gacagaaaat   9420
gttgtcaatg catttcttgg gcacaaagtt ttttgaaaca tgaattaatt ttttcaaaat   9480
atttatgaca tcaaattgac cctaaaataa gtgataaagc tttaacgtgg aatgacatta   9540
atttttccat gataaataaa acacttaaaa cattttaata ttaatattat aatcagttac   9600
aactatgttc aattaatgca ataactttta aataaatatt aaaatatttt ttttctgttc   9660
tccaataaag agatcttgtt gcacggaaaa agtcacattc ttatttagta aaaaattata   9720
attattgttt gaaaaatatc attttcactg cagaaaattt gatccagctc tacagatcat   9780
acttttattg tacaataata caataaaaat attcatctgc aggaaatatc attttcattg   9840
tacaataata taaagataaa tatataccag aaaagaaaaa gaaactgatg tggcacaatg   9900
tattcactga aagaatgcat attgtatttc acctttcaag cagcactaag aatatacttc   9960
ttttattata cttgtgcatt tactcaacca ccctcggtgg agtaagaaag aagatagata  10020
aaagtttttt ttgacatttg gtgaatctct taattaaaaa aataaaataa tccatttcct  10080
ttatttaatt tctttttttcc catctgtgaa attccaattc tgcttcgcgc tcctgtctat  10140
aaattgactt agccaccacc tcagtttcca ttcattcact tcttctcttt atacccccccc  10200
tctcttttt gcgttcattc tgttttcgta agtactgttg tttttctctt ctatttcttt  10260
ttttgtttgt gttgtttttt tttcttcctt atcgttgttc tgcctctcct ctgtttcggt  10320
gctctgttca ccacttccac gtgagaatga tcttccttct ttgcatgttc attctctcgt  10380
gaccactgga tcagactcca tgttctgatc cagggtctct ctctaacgcc tgtactttca  10440
tccatgacca ccttaaaaac aacatggggg tggtgctgtt acactaactc tgtttctggg  10500
gtgctgtctt tgttcaattt tactcagaaa atatcttttc ttggattcta ttcggtgtgt  10560
gggaacatga tcctgtcggt cggttgtttt taggttaatc cttaactggt tacaaggatc  10620
taacgcttga atgcatgtcc tgagttaaag aaacaaaaga agaacacacc tagtacagcc  10680
tggcctcgaa ccaagaactt ctttgttggt ttctcattat tactaaaata aaataaagta  10740
tacgttttct tttttctttg ggatgaacgg ttcagactta tgagaagttt aagctaatcc  10800
tgtagtggag tgttcaattt attttaaact ttaaagcaat agctcaagca ctaaacttct  10860
ttttcaagtt caaccacttt ggtagcttgc taattgctgc tattgttcta attaattaat  10920
gtaattattg tttaaaaaag aaaagttggt gacactggaa taaaaaagtg tactatctgg  10980
caattattct tctgcagcaa tgtttgaggt tgaaatctta gtagaacaaa gtagaagatc  11040
tggtatttat attttttgta gacagatggt gggggtgggt ggtaggcctt gaaatccaat  11100
atagttttgt agaataattt tattattttt tttttttgct cacttgtttg tggtattgat  11160
tttgtgatga ctcaagatta atgatttacc ttcatttttt tcatggtgac atattatgta  11220
tattcttgat ctgtttctta cacttctttt tcgttgttgt agctgttgaa gtctgcggcc  11280
gcatgaagag gtctccagca tcttcttgtt catcatctac ttcctctgtt gggtttgaag  11340
ctcccattga aaaaagaagg cctaagcatc caaggaggaa taatttgaag tcacaaaaat  11400
```

gcaagcagaa ccaaaccacc actggtggca gaagaagctc tatctataga ggagttacaa 11460
ggcataggtg gacagggagg tttgaagctc acctatggga taagagctct tggaacaaca 11520
ttcagagcaa gaagggtcga caagtttatt tgggggcata tgatactgaa gaatctgcag 11580
cccgtaccta tgaccttgca gcccttaaat actggggaaa agatgcaacc ctgaatttcc 11640
cgatagaaac ttataccaag gagctcgagg aaatggacaa ggtttcaaga gaagaatatt 11700
tggcttcttt gcggcgccaa agcagtggct tttctagagg cctgtctaag taccgtgggg 11760
ttgctaggca tcatcataat ggtcgctggg aagcacgaat tggaagagta tgcggaaaca 11820
agtacctcta cttggggaca tataaaactc aagaggaggc agcagtggca tatgacatgg 11880
cagcaataga gtaccgtgga gtcaatgcag tgaccaattt tgacataagc aactacatgg 11940
acaaaataaa gaagaaaaat gaccaaaccc aacaacaaca aacagaagca caaacggaaa 12000
cagttcctaa ctcctctgac tctgaagaag tagaagtaga acaacagaca acaacaataa 12060
ccacaccacc cccatctgaa aatctgcaca tgccaccaca gcagcaccaa gttcaataca 12120
ccccccatgt ctctccaagg gaagaagaat catcatcact gatcacaatt atggaccatg 12180
tgcttgagca ggatctgcca tggagcttca tgtacactgg cttgtctcag tttcaagatc 12240
caaacttggc tttctgcaaa ggtgatgatg acttggtggg catgtttgat agtgcagggt 12300
ttgaggaaga cattgatttt ctgttcagca ctcaacctgg tgatgagact gagagtgatg 12360
tcaacaatat gagcgcagtt ttggatagtg ttgagtgtgg agacacaaat ggggctggtg 12420
gaagcatgat gcatgtggat aacaagcaga agatagtatc atttgcttct tcaccatcat 12480
ctacaactac agtttcttgt gactatgctc tagatctagc ggccgcattt cgcaccaaat 12540
caatgaaagt aataatgaaa agtctgaata agaatactta ggcttagatg cctttgttac 12600
ttgtgtaaaa taacttgagt catgtacctt tggcggaaac agaataaata aaaggtgaaa 12660
ttccaatgct ctatgtataa gttagtaata cttaatgtgt tctacggttg tttcaatatc 12720
atcaaactct aattgaaact ttagaaccac aaatctcaat cttttcttaa tgaaatgaaa 12780
aatcttaatt gtaccatgtt tatgttaaac accttacaat taattggttg gagaggagga 12840
ccaaccgatg ggacaacatt gggagaaaga gattcaatgg agatttggat aggagaacaa 12900
cattcttttt cacttcaata caagatgagt gcaacactaa ggatatgtat gagactttca 12960
gaagctacga caacatagat gagtgaggtg gtgattccta gcaagaaaga cattagagga 13020
agccaaaatc gaacaaggaa gacatcaagg gcaagagaca ggaccatcca tctcaggaaa 13080
aggagctttg ggatagtccg agaagttgta caagaaattt tttggagggt gagtgatgca 13140
ttgctggtga ctttaactca atcaaaattg agaaagaaag aaaagggagg gggctcacat 13200
gtgaatagaa gggaaacggg agaattttac agttttgatc taatgggcat cccagctagt 13260
ggtaacatat tcaccatgtt taaccttcac gtacgagatc cggccggcca gatcctgca 13319

<210> SEQ ID NO 100
<211> LENGTH: 13085
<212> TYPE: DNA
<213> ORGANISM: Artificial sequence
<220> FEATURE:
<223> OTHER INFORMATION: Plasmid pKR2119

<400> SEQUENCE: 100
ggcgtacgaa cggccgcgca tgctgactta atcagctaac gccactcgag ggggggcccg 60
gtaccggcgc gccgttctat agtgtcacct aaatcgtatg tgtatgatac ataaggttat 120

```
gtattaattg tagccgcgtt ctaacgacaa tatgtccata tggtgcactc tcagtacaat    180
ctgctctgat gccgcatagt taagccagcc ccgacacccg ccaacacccg ctgacgcgcc    240
ctgacgggct tgtctgctcc cggcatccgc ttacagacaa gctgtgaccg tctccgggag    300
ctgcatgtgt cagaggtttt caccgtcatc accgaaacgc gcgagacgaa agggcctcgt    360
gatacgccta tttttatagg ttaatgtcat gaccaaaatc ccttaacgtg agttttcgtt    420
ccactgagcg tcagaccccg tagaaaagat caaaggatct tcttgagatc cttttttct     480
gcgcgtaatc tgctgcttgc aaacaaaaaa accaccgcta ccagcggtgg tttgtttgcc    540
ggatcaagag ctaccaactc tttttccgaa ggtaactggc ttcagcagag cgcagatacc    600
aaatactgtc cttctagtgt agccgtagtt aggccaccac ttcaagaact ctgtagcacc    660
gcctacatac ctcgctctgc taatcctgtt accagtggct gctgccagtg gcgataagtc    720
gtgtcttacc gggttggact caagacgata gttaccggat aaggcgcagc ggtcgggctg    780
aacggggggt tcgtgcacac agcccagctt ggagcgaacg acctacaccg aactgagata    840
cctacagcgt gagcattgag aaagcgccac gcttcccgaa gggagaaagg cggacaggta    900
tccggtaagc ggcagggtcg gaacaggaga gcgcacgagg gagcttccag ggggaaacgc    960
ctggtatctt tatagtcctg tcgggtttcg ccacctctga cttgagcgtc gatttttgtg   1020
atgctcgtca ggggggcgga gcctatggaa aaacgccagc aacgcggcct ttttacggtt   1080
cctggccttt tgctggcctt ttgctcacat gttctttcct gcgttatccc ctgattctgt   1140
ggataaccgt attaccgcct ttgagtgagc tgataccgct cgccgcagcc gaacgaccga   1200
gcgcagcgag tcagtgagcg aggaagcgga agagcgccca atacgcaaac cgcctctccc   1260
cgcgcgttgg ccgattcatt aatgcaggtt gatcagatct cgatcccgcg aaattaatac   1320
gactcactat agggagacca caacggtttc cctctagaaa taattttgtt taactttaag   1380
aaggagatat acccatggaa aagcctgaac tcaccgcgac gtctgtcgag aagtttctga   1440
tcgaaaagtt cgacagcgtc tccgacctga tgcagctctc ggagggcgaa gaatctcgtg   1500
ctttcagctt cgatgtagga gggcgtggat atgtcctgcg ggtaaatagc tgcgccgatg   1560
gtttctacaa agatcgttat gtttatcggc actttgcatc ggccgcgctc ccgattccgg   1620
aagtgcttga cattggggaa ttcagcgaga gcctgaccta ttgcatctcc cgccgtgcac   1680
agggtgtcac gttgcaagac ctgcctgaaa ccgaactgcc cgctgttctg cagccggtcg   1740
cggaggctat ggatgcgatc gctgcggccg atcttagcca gacgagcggg ttcggcccat   1800
tcggaccgca aggaatcggt caatacacta catggcgtga tttcatatgc gcgattgctg   1860
atccccatgt gtatcactgg caaactgtga tggacgacac cgtcagtgcg tccgtcgcgc   1920
aggctctcga tgagctgatg ctttgggccg aggactgccc cgaagtccgg cacctcgtgc   1980
acgcggattt cggctccaac aatgtcctga cggacaatgg ccgcataaca gcggtcattg   2040
actggagcga ggcgatgttc ggggattccc aatacgaggt cgccaacatc ttcttctgga   2100
ggccgtggtt ggcttgtatg gagcagcaga cgcgctactt cgagcggagg catccggagc   2160
ttgcaggatc gccgcggctc cgggcgtata tgctccgcat tggtcttgac caactctatc   2220
agagcttggt tgacggcaat ttcgatgatg cagcttgggc gcagggtcga tgcgacgcaa   2280
tcgtccgatc cggagccggg actgtcgggc gtacacaaat cgcccgcaga agcgcggccg   2340
tctggaccga tggctgtgta gaagtactcg ccgatagtgg aaaccgacgc cccagcactc   2400
gtccgagggc aaaggaatag tgaggtacag cttggatcga tccggctgct aacaaagccc   2460
gaaaggaagc tgagttggct gctgccaccg ctgagcaata actagcataa ccccttgggg   2520
```

-continued

```
cctctaaacg ggtcttgagg ggttttttgc tgaaaggagg aactatatcc ggatgctcgg    2580

gcgcgccggt acccgggtac cgagctcact agacgcggtg aaattaccta attaacaccg    2640

gtgtttaaac actagtaacg gccgccagtg tgctggaatt cgcccttccc aagctttgct    2700

ctagatcaaa ctcacatcca aacataacat ggatatcttc cttaccaatc atactaatta    2760

ttttgggtta aatattaatc attattttta agatattaat taagaaatta aaagattttt    2820

taaaaaaatg tataaaatta tattattcat gattttcat acatttgatt ttgataataa    2880

atatattttt tttaatttct taaaaaatgt tgcaagacac ttattagaca tagtcttgtt    2940

ctgtttacaa aagcattcat catttaatac attaaaaaat atttaatact aacagtagaa    3000

tcttcttgtg agtggtgtgg gagtaggcaa cctggcattg aaacgagaga aagagagtca    3060

gaaccagaag acaaataaaa agtatgcaac aaacaaatca aaatcaaagg gcaaaggctg    3120

gggttggctc aattggttgc tacattcaat tttcaactca gtcaacggtt gagattcact    3180

ctgacttccc caatctaagc cgcggatgca aacggttgaa tctaacccac aatccaatct    3240

cgttacttag gggcttttcc gtcattaact caccccctgcc acccggtttc cctataaatt    3300

ggaactcaat gctcccctct aaactcgtat cgcttcagag ttgagaccaa gacacactcg    3360

ttcatatatc tctctgctct tctcttctct tctacctctc aaggtacttt tcttctccct    3420

ctaccaaatc ctagattccg tggttcaatt tcggatcttg cacttctggt ttgctttgcc    3480

ttgcttttc ctcaactggg tccatctagg atccatgtga aactctactc tttctttaat    3540

atctgcggaa tacgcgtttg actttcagat ctagtcgaaa tcatttcata attgcctttc    3600

tttcttttag cttatgagaa ataaaatcac ttttttttta tttcaaaata aaccttgggc    3660

cttgtgctga ctgagatggg gtttggtgat tacagaattt tagcgaattt tgtaattgta    3720

cttgtttgtc tgtagttttg ttttgttttc ttgtttctca tacattcctt aggcttcaat    3780

tttattcgag tataggtcac aataggaatt caaactttga gcaggggaat taatcccttc    3840

cttcaaatcc agtttgtttg tatatatgtt taaaaaatga aacttttgct ttaaattcta    3900

ttataacttt ttttatggct gaaattttg catgtgtctt tgctctctgt tgtaaattta    3960

ctgtttaggt actaactcta ggcttgttgt gcagtttttg aagtataaca acagaagttc    4020

ctattccgaa gttcctattc tctagaaagt ataggaactt ccactagtcc atgaaaaagc    4080

ctgaactcac cgcgacgtct gtcgagaagt ttctgatcga aaagttcgac agcgtctccg    4140

acctgatgca gctctcggag ggcgaagaat ctcgtgcttt cagcttcgat gtaggagggc    4200

gtggatatgt cctgcgggta aatagctgcg ccgatggttt ctacaaagat cgttatgttt    4260

atcggcactt tgcatcggcc gcgctcccga ttccggaagt gcttgacatt ggggaattca    4320

gcgagagcct gacctattgc atctcccgcc gtgcacaggg tgtcacgttg caagacctgc    4380

ctgaaaccga actgcccgct gttctgcagc cggtcgcgga ggccatggat gcgatcgctg    4440

cggccgatct tagccagacg agcgggttcg gcccattcgg accgcaagga atcggtcaat    4500

acactacatg gcgtgatttc atatgcgcga ttgctgatcc ccatgtgtat cactggcaaa    4560

ctgtgatgga cgacaccgtc agtgcgtccg tcgcgcaggc tctcgatgag ctgatgcttt    4620

gggccgagga ctgccccgaa gtccggcacc tcgtgcacgc ggatttcggc tccaacaatg    4680

tcctgacgga caatggccgc ataacagcgg tcattgactg gagcgaggcg atgttcgggg    4740

attcccaata cgaggtcgcc aacatcttct tctggaggcc gtggttggct tgtatggagc    4800

agcagacgcg ctacttcgag cggaggcatc cggagcttgc aggatcgccg cggctccggg    4860
```

```
cgtatatgct ccgcattggt cttgaccaac tctatcagag cttggttgac ggcaatttcg   4920
atgatgcagc ttgggcgcag ggtcgatgcg acgcaatcgt ccgatccgga gccgggactg   4980
tcgggcgtac acaaatcgcc cgcagaagcg cggccgtctg gaccgatggc tgtgtagaag   5040
tactcgccga tagtggaaac cgacgcccca gcactcgtcc gagggcaaag gaatagtgag   5100
gtacctaaag aaggagtgcg tcgaagcaga tcgttcaaac atttggcaat aaagtttctt   5160
aagattgaat cctgttgccg gtcttgcgat gattatcata taatttctgt tgaattacgt   5220
taagcatgta ataattaaca tgtaatgcat gacgttattt atgagatggg tttttatgat   5280
tagagtcccg caattataca tttaatacgc gatagaaaac aaaatatagc gcgcaaacta   5340
ggataaatta tcgcgcgcgg tgtcatctat gttactagat cgatgtcgac ccgggcccta   5400
ggcgtctttc cacaatacat aactattaat taatcttaaa taaataaagg ataaaatatt   5460
ttttttctt cataaagtta aaatatgtta tttttgttt agatgtatat tcgaataaat   5520
ctaaatatat gataatgatt ttttatattg attaaacata taatcaatat taaatatgat   5580
attttttat ataggttgta cacataattt tataaggata aaaaatatga taaaaataaa   5640
ttttaaatat ttttatattt acgagaaaaa aaaatatttt agccataaat aaatgaccag   5700
catattttac aaccttagta attcataaat tcctatatgt atatttgaaa ttaaaaacag   5760
ataatcgtta agggaaggaa tcctacgtca tctcttgcca tttgtttttc atgcaaacag   5820
aaagggacga aaaaccacct caccatgaat cactcttcac accattttta ctagcaaaca   5880
agtctcaaca actgaagcca gctctctttc cgtttctttt tacaacactt tctttgaaat   5940
agtagtattt tttttcacat gatttattaa cgtgccaaaa gatgcttatt gaatagagtg   6000
cacatttgta atgtactact aattagaaca tgaaaaagca ttgttctaac acgataatcc   6060
tgtgaaggcg ttaactccaa agatccaatt tcactatata aattgtgacg aaagcaaaat   6120
gaattcacat agctgagaga gaaaggaaag gttaactaag aagcaatact tcagcggccg   6180
cgcgagaaac tttgtatggg catggttatt tctcacttct caccctcctt tactttctta   6240
tgctaaatcc tccttcccct atatctccac cctcaacccc tttttctcat tataactttt   6300
ggtgcctaga tggtgtgtgt gtgtgcgcgc gagagatctg agctcaattt tcctctctca   6360
agtcctggtc atgctttgag ggaaaagggt tgaggaactt atgcatctta tatctctcca   6420
cctccaggat tttaagccct agttactcaa ccctttttccc tcagaatatg gcaattcagg   6480
cttttaattg ctttcatttg gtaccatcac ttgcaagatt tcagagtaca aggtgaacac   6540
acacatcttc ctcttcatca attctctagt ttcatcctta tcttttcatt cacggtaact   6600
ctcactaccc tctttcatct tataagttat accgggggtg tgatgttgat gagtgtaaat   6660
taaatatatg tgatctcttt ctctggaaaa attttcagtg tgatatacat aataatctct   6720
taatctagag attttatggc tttgttatat ataagcggcg caagggcgaa ttctgcagat   6780
atccatcaca cttgggccgc ttctagctag ctagggtttg ggtagtgagt gtaataaagt   6840
tgcaaagttt ttggttaggt tacgttttga ccttattatt atagttcaaa gggaaacatt   6900
aattaaaggg gattatgaag aagagagtgt acctatgtgg ttgaggatct tactgggtga   6960
attgagctgc ttagctatgg atcccacagt tctacccatc aataagtgct tttgtggtag   7020
tcttgtggct tccatatctg gggagcttca tttgccttta tagtattaac cttctccaca   7080
taaatacact ctcttcaccc ttctcttctt ttctctcata ataatttaaa tttgttatag   7140
actctaaact ttaaatgttt tttttgaagt ttttccgttt ttctcttttg ccatgatccc   7200
gttcttgctg tggagtaacc ttgtccgagg tatgtgcatg attagatcca tacttaattt   7260
```

gtgtgcatca cgaaggtgag gttgaaatga actttgcttt tttgaccttt taggaaagtt 7320
cttttgttgc agtaatcaat tttaattagt tttaattgac actattactt ttattgtcat 7380
ctttgttagt tttattgttg aattgagtgc atatttccta ggaaattctc ttacctaaca 7440
ttttttatac agatctatgc tcttggctct tgcccttact cttggccttg tgttggttat 7500
ttgtctacat atttattgac tggtcgatga gacatgtcac aattcttggg cttatttgtt 7560
ggtctaataa aaggagtgct tattgaaaga tcaagacgga gattcggttt tatataaata 7620
aactaaagat gacatattag tgtgttgatg tctcttcagg ataatttttg tttgaaataa 7680
tatggtaatg tcttgtctaa atttgtgtac ataattctta ctgatttttt ggattgttgg 7740
atttttataa acaaatctgg ggcccaagcg gccgcatgag ccgtaaaggt tcaatacaac 7800
gagtgcttgt tttcttaggg acaagcattg tacttatgta tgattctgtg taaccatgag 7860
tcttccacgt tgtactaatg tgaagggcaa aaataaaaca cagaacaagt tcgttttttct 7920 caaataatgt gaaggtagaa aatggaacca tgcctcctct cttgcatgtg atttaaaata 7980
ttagcagatg acctaggagg ccggcccagc tgatgatccc ggtgaagttc ctattccgaa 8040
gttcctattc tccagaaagt ataggaactt cactagagct tgcggccgac ctgcaggtaa 8100
attgcagctg aaggacagtg aagggtgaat ttatccattt aaaccatttt ctttttaaca 8160
catttcttat ggtaatctct tctcactaca ctataaaaat ggcttctcaa tcccattttc 8220
tacatcatcc cattctattg agttttgttt atttgctttc acttttttttt ttatctgcct 8280 cttcccttaa tttgcttgac ttcttcttca cattttgctt tgttttctcc tccggcttcc 8340
ggtatttcaa attcaagatg agcaagttga aatttataaa tagaaataca gatattattt 8400
acaacgtcaa atctttggta ttttcaatat ttgaatgggg taaatttgtc atatagtcat 8460
catcactgac tacttatcta acctatttaa tttggagcat attctttata aggtccctct 8520
cacggccaat gtctaattat tgatatacag ctcttgtttt ctagtgctgc ttataatatt 8580
atctacacat atatatggta ctgcacacta ctactatata gtagtaagta aactagcaac 8640
agccggggcc aaactccaat aactaggcat tggggtttag ttggtaatat aaatataaca 8700
tcaaaaagtc tttgcttgtg acgaacatca caatgcaccc accattgatg ccacgacaga 8760
cattgttaat ttttttttta atttttaaaa aagaagcaat tccaatagtt ctatattaca 8820
atctcacgtg atccaagcac aacgtttcat tttttgtaca tgctcgatat ataaataata 8880
tttcatttta tagtaaaata taatgacatt ttcgaatata atttttgaaa tttcattttc 8940
caaatgaaat actaatatta atattaatga gattaccaca aatcatgtta tgaatgaaat 9000
aaagagtttt ggcattctaa ctttctttga atagaacaaa atgtatacaa cactctccat 9060
atatacacga tttattcagg gatcatatac attctctcat gattaacata gtctgctttc 9120
ttcacgtcta agcagataat ttttggtcca caagataaaa ttatcattag tcgttttaat 9180
taattccttg agcatcaagc actaaaataa ttaaacttct ccattaccaa aaaaaaaaga 9240
taggtgattc agtaacatgt agtactagta ctactgattt tttttttctt ttgattttaa 9300
tgaatggttc gtatcgagca tcgagaaatc catttattag gtgtgtaatg taatagtagt 9360
atttccttga ttttcagtaa taagatggat tcttacattt atatctgttt gacagaaaat 9420
gttgtcaatg catttcttgg gcacaaagtt ttttgaaaca tgaattaatt ttttcaaaat 9480
atttatgaca tcaaattgac cctaaaataa gtgataaagc tttaacgtgg aatgacatta 9540
atttttccat gataaataaa acacttaaaa cattttaata ttaatattat aatcagttac 9600

-continued

```
aactatgttc aattaatgca ataactttta aataaatatt aaaatatttt ttttctgttc   9660
tccaataaag agatcttgtt gcacggaaaa agtcacattc ttatttagta aaaaattata   9720
attattgttt gaaaaatatc attttcactg cagaaaattt gatccagctc tacagatcat   9780
acttttattg tacaataata caataaaaat attcatctgc aggaaatatc attttcattg   9840
tacaataata taaagataaa tatataccag aaaagaaaaa gaaactgatg tggcacaatg   9900
tattcactga aagaatgcat attgtatttc acctttcaag cagcactaag aatatacttc   9960
ttttattata cttgtgcatt tactcaacca ccctcggtgg agtaagaaag aagatagata  10020
aaagtttttt ttgacatttg gtgaatctct taattaaaaa aataaaataa tccatttcct  10080
ttatttaatt tctttttttcc catctgtgaa attccaattc tgcttcgcgc tcctgtctat  10140
aaattgactt agccaccacc tcagtttcca ttcattcact tcttctcttt atacccccccc  10200
tctctttttt gcgttcattc tgttttcgta agtactgttg tttttctctt ctatttcttt  10260
ttttgtttgt gttgtttttt tttcttcctt atcgttgttc tgcctctcct ctgtttcggt  10320
gctctgttca ccacttccac gtgagaatga tcttccttct ttgcatgttc attctctcgt  10380
gaccactgga tcagactcca tgttctgatc cagggtctct ctctaacgcc tgtactttca  10440
tccatgacca ccttaaaaac aacatggggg tggtgctgtt acactaactc tgtttctggg  10500
gtgctgtctt tgttcaattt tactcagaaa atatcttttc ttggattcta ttcggtgtgt  10560
gggaacatga tcctgtcggt cggttgtttt taggttaatc cttaactggt tacaaggatc  10620
taacgcttga atgcatgtcc tgagttaaag aaacaaaaga agaacacacc tagtacagcc  10680
tggcctcgaa ccaagaactt ctttgttggt ttctcattat tactaaaata aaataaagta  10740
tacgttttct tttttctttg ggatgaacgg ttcagactta tgagaagttt aagctaatcc  10800
tgtagtggag tgttcaattt attttaaact ttaaagcaat agctcaagca ctaaacttct  10860
ttttcaagtt caaccacttt ggtagcttgc taattgctgc tattgttcta attaattaat  10920
gtaattattg tttaaaaaag aaaagttggt gacactggaa taaaaaagtg tactatctgg  10980
caattattct tctgcagcaa tgtttgaggt tgaaatctta gtagaacaaa gtagaagatc  11040
tggtatttat attttttgta gacagatggt gggggtgggt ggtaggcctt gaaatccaat  11100
atagttttgt agaataattt tattattttt tttttttgct cacttgtttg tggtattgat  11160
tttgtgatga ctcaagatta atgatttacc ttcatttttt tcatggtgac atattatgta  11220
tattcttgat ctgtttctta cacttctttt tcgttgttgt agctgttgaa gtctgcggcc  11280
gcaccatgat gatggatcag cgacagcgag agaagctgct tcacaaaacc gaggcctgtg  11340
ctttcgtggc aggtgttgtt ccggagcttt cccttgtcac cgttccaggg aacaacacca  11400
acaacgttaa caacaacaac aacgttgttt ctcattctca atctaacggg tcgggtcgga  11460
tccaggaaaa caaccaccac cttggactcg ttgctgctgt cacctccgcc ttcggtaccg  11520
ttcaaaggaa gaaaaggatg gcgagacaaa gaagatccac taaacccact tcgttgatga  11580
accatctcaa caaccataag cacaacaagc ctcgttctct tccttctccc agtgcatcct  11640
cctcgtacgt gccactctcc tccgcaactc tccagcccgc acgtgaaatc gatcaaagaa  11700
ggttgagatt ccttttccag aaggagttaa agaacagtga tgttagctcc cttaggagaa  11760
tgatattgcc aaagaaagca gcagaggctt tccttccagc tcttgaatcc aaagaaggaa  11820
ttgtaatcag catggatgat atagatggtc ttcatgtatg gagtttcaag tacaggtttt  11880
ggcctaacaa caacagtcgg atgtatgtac ttgaaaatac tggagatttt gtcaacacac  11940
atggccttcg ctttggagat tccattatgg tttaccaaga tagtgaaaac aacaattatg  12000
```

ttattcaggc caaaaaggct tctgatcaag atgaatttat ggaagaaact agtgatacca 12060
tcaatgatat cttccttaat gattatgagg tgaacaaacc tggttgcttc aatgtaacta 12120
atcctgcagt gaatgataca ggcatgtcat tcatatatga gactaccttc tcaaatgact 12180
cccctcttga tttttgggt ggatcaatga ccaatttttc aaggattggg ccagttgaaa 12240
cctttggctc tgttgagaat ttgtcacttg atgacttcta ttaagcggcc gcatttcgca 12300
ccaaatcaat gaaagtaata atgaaaagtc tgaataagaa tacttaggct tagatgcctt 12360
tgttacttgt gtaaaataac ttgagtcatg tacctttggc ggaaacagaa taaataaaag 12420
gtgaaattcc aatgctctat gtataagtta gtaatactta atgtgttcta cggttgtttc 12480
aatatcatca aactctaatt gaaactttag aaccacaaat ctcaatcttt tcttaatgaa 12540
atgaaaaatc ttaattgtac catgtttatg ttaaacacct tacaattaat tggttggaga 12600
ggaggaccaa ccgatgggac aacattggga gaaagagatt caatggagat ttggatagga 12660
gaacaacatt ctttttcact tcaatacaag atgagtgcaa cactaaggat atgtatgaga 12720
ctttcagaag ctacgacaac atagatgagt gaggtggtga ttcctagcaa gaaagacatt 12780
agaggaagcc aaaatcgaac aaggaagaca tcaagggcaa gagacaggac catccatctc 12840
aggaaaagga gctttgggat agtccgagaa gttgtacaag aaattttttg gagggtgagt 12900
gatgcattgc tggtgacttt aactcaatca aaattgagaa agaaagaaaa gggagggggc 12960
tcacatgtga atagaaggga aacgggagaa ttttacagtt ttgatctaat gggcatccca 13020
gctagtggta acatattcac catgtttaac cttcacgtac gagatccggc cggccagatc 13080
ctgca 13085

<210> SEQ ID NO 101
<211> LENGTH: 24
<212> TYPE: DNA
<213> ORGANISM: Medicago truncatula

<400> SEQUENCE: 101
attttagaat atgcaataaa attg 24

<210> SEQ ID NO 102
<211> LENGTH: 27
<212> TYPE: DNA
<213> ORGANISM: Medicago truncatula

<400> SEQUENCE: 102
aggcttgagg aataagataa gacttgt 27

<210> SEQ ID NO 103
<211> LENGTH: 401
<212> TYPE: PRT
<213> ORGANISM: Artificial Sequence
<220> FEATURE:
<223> OTHER INFORMATION: Majority sequence presented in FIG. 3A-3B
<220> FEATURE:
<221> NAME/KEY: misc_feature
<222> LOCATION: (1)..(65)
<223> OTHER INFORMATION: Xaa can be any naturally occurring amino acid
<220> FEATURE:
<221> NAME/KEY: misc_feature
<222> LOCATION: (103)..(104)
<223> OTHER INFORMATION: Xaa can be any naturally occurring amino acid
<220> FEATURE:
<221> NAME/KEY: misc_feature
<222> LOCATION: (121)..(146)
<223> OTHER INFORMATION: Xaa can be any naturally occurring amino acid
<220> FEATURE:

```
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid

<400> SEQUENCE: 103

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Met Met Met Asp Gln Arg Gln Arg Glu Lys Leu Leu His Lys Thr
65                  70                  75                  80

Glu Ala Cys Ala Phe Val Ala Gly Val Val Pro Glu Leu Ser Leu Val
                85                  90                  95

Thr Val Pro Gly Asn Asn Xaa Xaa Thr Asn Asn Val Asn Asn Asn Asn
            100                 105                 110

Asn Val Val Ser His Ser Gln Ser Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Gln Arg Lys Lys Arg Met Ala Arg Gln Arg Arg Ser Thr Lys
145                 150                 155                 160

Pro Thr Ser Leu Met Asn His Leu Asn Asn His Lys His Asn Lys Pro
                165                 170                 175

Xaa Arg Ser Leu Pro Ser Pro Ser Xaa Ala Ser Ser Ser Tyr Val Pro
            180                 185                 190

Leu Ser Ser Ala Thr Leu Gln Pro Ala Arg Glu Ile Asp Gln Arg Arg
        195                 200                 205

Leu Arg Phe Leu Phe Gln Lys Glu Leu Lys Asn Ser Asp Val Ser Ser
    210                 215                 220

Leu Arg Arg Met Ile Leu Pro Lys Lys Ala Ala Glu Ala Phe Leu Pro
225                 230                 235                 240

Ala Leu Glu Ser Lys Glu Gly Ile Val Ile Ser Met Asp Asp Ile Asp
                245                 250                 255

Gly Leu His Val Trp Ser Phe Lys Tyr Arg Phe Trp Pro Asn Asn Asn
            260                 265                 270

Ser Arg Met Tyr Val Leu Glu Asn Thr Gly Asp Phe Val Asn Thr His
        275                 280                 285

Gly Leu Arg Phe Gly Asp Ser Ile Met Val Tyr Gln Asp Ser Glu Asn
    290                 295                 300

Asn Asn Tyr Val Ile Gln Ala Lys Lys Ala Ser Asp Gln Asp Glu Phe
305                 310                 315                 320

Met Glu Glu Thr Ser Asp Thr Ile Asn Asp Ile Phe Leu Asn Asp Tyr
                325                 330                 335

Glu Val Asn Lys Pro Gly Cys Phe Asn Val Thr Asn Pro Ala Val Asn
            340                 345                 350

Asp Thr Gly Met Ser Phe Ile Tyr Glu Thr Thr Phe Ser Asn Asp Ser
        355                 360                 365
```

Pro Leu Asp Phe Leu Gly Gly Ser Met Thr Asn Phe Ser Arg Ile Gly
    370                 375                 380

Pro Val Glu Thr Phe Gly Ser Val Glu Asn Leu Ser Leu Asp Asp Phe
385                 390                 395                 400

Tyr

<210> SEQ ID NO 104
<211> LENGTH: 11
<212> TYPE: DNA
<213> ORGANISM: Glycine max

<400> SEQUENCE: 104
gtctaattat t 11

<210> SEQ ID NO 105
<211> LENGTH: 12
<212> TYPE: DNA
<213> ORGANISM: Glycine max

<400> SEQUENCE: 105
tgtctaatta gt 12

<210> SEQ ID NO 106
<211> LENGTH: 10
<212> TYPE: DNA
<213> ORGANISM: Glycine max

<400> SEQUENCE: 106
tctaattatt 10

<210> SEQ ID NO 107
<211> LENGTH: 13
<212> TYPE: DNA
<213> ORGANISM: Glycine max

<400> SEQUENCE: 107
ctaattattg ttt 13

<210> SEQ ID NO 108
<211> LENGTH: 233
<212> TYPE: PRT
<213> ORGANISM: Artificial Sequence
<220> FEATURE:
<223> OTHER INFORMATION: Majority sequence presented in FIG. 2

<400> SEQUENCE: 108

Met Glu Thr Gly Gly Phe His Gly Tyr Arg Lys Leu Pro Asn Thr Thr
1               5                   10                  15

Ala Gly Leu Lys Leu Ser Val Ser Asp Met Asn Met Asn Met Arg Gln
            20                  25                  30

Gln Gln Val Ala Ser Ser Asp Gln Asn Cys Ser Asn His Ser Ala Ala
        35                  40                  45

Gly Glu Glu Asn Glu Cys Thr Val Arg Glu Gln Asp Arg Phe Met Pro
    50                  55                  60

Ile Ala Asn Val Ile Arg Ile Met Arg Lys Ile Leu Pro Pro His Ala
65                  70                  75                  80

Lys Ile Ser Asp Asp Ala Lys Glu Thr Ile Gln Glu Cys Val Ser Glu
                85                  90                  95

Tyr Ile Ser Phe Ile Thr Gly Glu Ala Asn Glu Arg Cys Gln Arg Glu
            100                 105                 110

-continued

```
Gln Arg Lys Thr Ile Thr Ala Glu Asp Val Leu Trp Ala Met Ser Lys
        115                 120                 125

Leu Gly Phe Asp Asp Tyr Ile Glu Pro Leu Thr Met Tyr Leu His Arg
    130                 135                 140

Tyr Arg Glu Leu Glu Gly Asp Arg Thr Ser Met Arg Gly Glu Pro Leu
145                 150                 155                 160

Gly Lys Arg Thr Val Glu Tyr Ala Thr Leu Gly Val Ala Thr Ala Phe
                165                 170                 175

Val Pro Pro Pro Tyr His His His Asn Gly Tyr Phe Gly Ala Ala Met
            180                 185                 190

Pro Met Gly Thr Tyr Val Arg Glu Ala Pro Pro Asn Thr Ala Ser Ser
        195                 200                 205

His His His His His His His His His His Ala Arg Gly Ile Ser Asn
    210                 215                 220

Ala His Glu Pro Asn Ala Arg Ser Ile
225                 230
```